(12) United States Patent
Zechel et al.

(10) Patent No.: US 7,125,883 B1
(45) Date of Patent: Oct. 24, 2006

(54) INTEGRIN RECEPTOR LIGANDS

(75) Inventors: Johann-Christian Zechel, Nussloch (DE); Andreas Kling, Mannheim (DE); Herve Geneste, Neuhofen (DE); Udo Lange, Mannheim (DE); Arnulf Lauterbach, Ludwigshafen (DE); Claudia Isabella Graef, Mannheim (DE); Thomas Subkowski, Ladenburg (DE); Jens Sadowski, Limburgerhof (DE); Wilfried Hornberger, Neustadt (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 0 days.

(21) Appl. No.: 09/958,491

(22) PCT Filed: Mar. 29, 2000

(86) PCT No.: PCT/EP00/02746

§ 371 (c)(1),
(2), (4) Date: Jun. 18, 2002

(87) PCT Pub. No.: WO00/61551

PCT Pub. Date: Oct. 19, 2000

(30) Foreign Application Priority Data

| Apr. 13, 1999 | (DE) | 199 16 719 |
| Dec. 24, 1999 | (DE) | 199 62 998 |

(51) Int. Cl.
*C07D 401/14* (2006.01)
*A61K 31/505* (2006.01)

(52) U.S. Cl. ................... 514/275; 544/297
(58) Field of Classification Search ............. 544/297; 514/275

See application file for complete search history.

(56) References Cited

FOREIGN PATENT DOCUMENTS

| EP | 0 710 657 | 5/1996 |
| EP | 0 741 133 | 11/1996 |
| WO | WO 97/23451 | 7/1997 |
| WO | WO 97/37655 | 10/1997 |
| WO | WO 98/00395 | 1/1998 |
| WO | WO 98/08840 | 3/1998 |
| WO | WO 98/18461 | 5/1998 |
| WO | WO 98/35949 | 8/1998 |
| WO | WO 98/43972 | 10/1998 |
| WO | WO 99/30713 | 6/1999 |
| WO | WO 99/31099 | 6/1999 |
| WO | WO 00/10980 | 3/2000 |

*Primary Examiner*—Bruck Kifle
(74) *Attorney, Agent, or Firm*—Wood, Phillips, Katz, Clark & Mortimer

(57) ABSTRACT

The invention relates to novel compounds which bind to integrin receptors, to their preparation, to their use as integrin receptor ligands and for treating diseases, to pharmaceutical preparations comprising these compounds, and to pharmaceutical preparations comprising at least one other active compound.

2 Claims, No Drawings ately. To date, 16 different α and 8 different β subunits and 22 different combinations have been identified.
INTEGRIN RECEPTOR LIGANDS The invention relates to novel compounds which bind to integrin receptors, and to their preparation and use.

Integrins are cell surface glycoprotein receptors which mediate interactions between cells of the same and different types, and between cells and extracellular matrix proteins. They are involved in physiological processes such as, for example, embryogenesis, hemostasis, wound healing, immune response and formation/maintenance of tissue architecture.

Disturbances of the expression of cell adhesion molecule genes, and disturbances of receptor function may contribute to the pathogenesis of a large number of disorders such as, for example, tumors, thromboembolic events, cardiovascular disorders, pulmonary diseases, disorders of the CNS, of the kidney, of the gastrointestinal tract or inflammations.

Integrins are heterodimers each consisting of an α and β transmembrane subunit, which are connected non-covalently. To date, 16 different α and 8 different β subunits and 22 different combinations have been identified.

Integrin $\alpha_v\beta_3$, also called vitronectin receptor, mediates adhesion to a large number of ligands—plasma proteins, extracellular matrix proteins, cell surface proteins—most of which contain the amino acid sequence RGD (Cell, 1986, 44, 517–518; Science 1987, 238, 491–497), such as, for example, vitronectin, fibrinogen, fibronectin, von Willebrand factor, thrombospondin, osteopontin, laminin, collagen, thrombin, tenascin, MMP-2, bone sialoprotein II, various viral, fungal, parasitic and bacterial proteins, natural integrin antagonists such as disintegrins, neurotoxins—mambin—and leech proteins—decorsin, ornatin—and some non-RGD ligands such as, for example, Cyr-61 and PECAM-1 (L. Piali, J. Cell Biol. 1995, 130, 451–460; Buckley, J. Cell Science 1996, 109, 437–445, J. Biol. Chem. 1998, 273, 3090–3096).

Several integrin receptors show cross-reactivity with ligands containing the RGD motif. Thus, integrin $\alpha_{IIb}\beta_3$, also called platelet fibrinogen receptor, recognizes fibronectin, vitronectin, thrombospondin, von Willebrand factor and fibrinogen.

Integrin $\alpha_v\beta_3$ is expressed inter alia on endothelial cells, blood platelets, monocytes/macrophages, smooth muscle cells, some B cells, fibroblasts, osteoclasts and various tumor cells such as, for example, malanomas, glioblastomas, carcinomas of the lung, breast, prostate and bladder, osteosarcomas or neuroblastomas.

Increased expression is observed under various pathological conditions, such as, for example, the prothrombotic state, in cases of vessel injury, tumor growth or metastasis or reperfusion, and on activated cells, in particular on endothelial cells, smooth muscle cells or macrophages.

Involvement of integrin $\alpha_v\beta_3$ has been detected inter alia in the following pathological states:

Cardiovascular disorders such as atherosclerosis, restenosis after vessel injury, and angioplasty (neointima formation, smooth muscle cell migration and proliferation) (J. Vasc. Surg. 1994, 19, 125–134; Circulation 1994, 90, 2203–2206), acute kidney failure (Kidney Int. 1994, 46, 1050–1058; Proc. Natl. Acad. Sci. 1993, 90, 5700–5704; Kidney Int. 1995, 48, 1375–1385), angiogenesis-associated microangiopathies such as, for example, diabetic retinopathy or rheumatoid arthritis (Ann. Rev. Physiol 1987, 49, 453–464; Int. Ophthalmol. 1987, 11, 41–50; Cell 1994, 79, 1157–1164; J. Biol. Chem. 1992, 267, 10931–10934), arterial thrombosis, stroke (phase II studies with ReoPro, Centocor Inc., 8th annual European Stroke Meeting), cancers such as, for example, in tumor metastasis or tumor growth (tumor-induced angiogenesis) (Cell 1991, 64, 327–336; Nature 1989, 339, 58–61; Science 1995, 270, 1500–1502), osteoporosis (bone resorption after proliferation, chemotaxis and adhesion of osteoclasts to bone matrix) (FASEB J. 1993, 7, 1475–1482; Exp. Cell Res. 1991, 195, 368–375, Cell 1991, 64, 327–336), high blood pressure (Am. J. Physiol. 1998, 275, H1499–H1454), psoriasis (Am. J. Pathol. 1995, 147, 1661–1667), hyperparathyroidism, Paget's disease (J. Clin. Endocrinol. Metab. 1996, 81, 1810–1820), malignant hypercalcemia (Cancer Res. 1998, 58, 1930–1935), metastatic osteolytic lesions (Am. J. Pathol. 1997, 150, 1383–1393), pathogen protein (for example HIV-1 tat)-induced processes (for example angiogenesis, Kaposi's sarcoma) (Blood 1999, 94, 663–672)

inflammation (J. Allergy Clin. Immunol. 1998, 102, 376–381), heart failure, CHF, and for antiviral, antiparasitic, antifungal or antibacterial therapy and prophylaxis (adhesion and internalization) (J. Infect. Dis. 199, 180, 156–166; J. Virology 1995, 69, 2664–2666; Cell 1993, 73, 309–319).

Because of its key role, pharmaceutical preparations which contain low molecular weight integrin $\alpha_v\beta_3$ ligands are of great therapeutic and diagnostic value and are used inter alia for the indications mentioned.

Advantageous $\alpha_v\beta_3$ integrin receptor ligands bind to the integrin $\alpha_v\beta_3$ receptor with increased affinity.

Particularly advantageous $\alpha_v\beta_3$ integrin receptor ligands additionally have increased selectivity for the integrin $\alpha_v\beta_3$ and have less effect on the integrin $\alpha_{IIb}\beta_3$ by a factor of at least 10, preferably by a factor of at least 100.

An integrin $\alpha_v\beta_3$ antagonistic effect has been shown, and a beneficial in vivo effect has been demonstrated, for a large number of compounds such as anti-$\alpha_v\beta_3$ monoclonal antibodies, peptides containing the RGD binding sequence, natural RGD-containing proteins (for example disintegrins) and low molecular weight compounds (FEBS Letts 1991, 291, 50–54; J. Biol. Chem. 1990, 265, 12267–12271; J. Biol. Chem. 1994, 269, 20233–20238; J. Cell Biol 1993, 51, 206–218; J. Biol. Chem. 1987, 262, 17703–17711; Bioorg. Med. Chem. 1998, 6, 1185–1208).

WO 99/30713 describes 1,3-substituted tetrahydropyrimidin-2(1H)one derivatives and piperidin-2-one derivatives, WO 99/31099 describes 1,3-substituted imidazolin-2-one derivatives, WO 98/35949 describes 2,6-substituted 2H-1, 4-benzoxazin-3(4H)one derivatives, WO 9800395 and WO 9723451 describe O-substituted tyrosine derivatives, EP 710657 and EP 741133 describe 3,5-substituted 1,3-oxazolidin-2-ones and WO 97/37655 describes isoindoles as antagonists of the $\alpha_v\beta_3$ integrin receptor.

It is an object of the present invention to provide novel integrin receptor ligands with advantageous properties.

We have found that this object is achieved by compounds of the formula I where B, G and L have the following meanings:

L is a structural element of the formula $I_L$ $$-U-T \qquad I_L$$

where

T is a COOH group or a radical which can be hydrolyzed to COOH and

—U— is —$(CR_L^1R_L^2)_a$-$(V_L)_b$-$(CR_L^3R_L^4)_c$-$(W_L)_d$-$(CR_L^5R_6)_E$-$(X_L)_f$-$(CR_L^7R_L^8)_g$— where a, c, e, g are, independently of one another, 0, 1, 2 or 3, b, d, f are, independently of one another, 0 or 1, $R_L^1$, $R_L^2$, $R_L^3$, $R_L^4$, $R_L^5$, $R_L^6$, $R_L^7$, $R_L^8$ are, independently of one another, hydrogen, halogen, a hydroxyl group, a branched or unbranched, optionally substituted $C_1$–$C_6$-alkyl, $C_2$–$C_6$-alkenyl, $C_2$–$C_6$-alkynyl or $C_1$–$C_6$-alkylene-$C_3$–$C_7$-cycloalkyl radical, a radical —$(CH_2)_w$-$(Y_L)_y$-$R_L^9$, an optionally substituted $C_3$–$C_7$-cycloalkyl, aryl, arylalkyl, hetaryl or hetarylalkyl radical or, in each case independently of one another, two radicals $R_L^1$ and $R_L^2$ or $R_L^3$ and $R_L^4$ or $R_L^5$ and $R_L^6$ or $R_L^7$ and $R_L^8$ together are a 3- to 7-membered, optionally substituted, saturated or unsaturated carbocyclic or heterocyclic system which may contain up to three heteroatoms from the group of O, N or S, w is 0, 1, 2, 3 or 4, y is 0 or 1

$y_L$ is —CO—, —CO—N($R_Y^1$)—, —N($R_Y^1$)—CO—, —N($R_Y^1$)—CO—N($R_Y^{1*}$)—, —N($R_Y^1$)—CO—O—, —O—, —S—, —SO$_2$—, —SO$_2$—N($R_Y^1$)—, —SO$_2$—O—, —CO—O—, —O—CO—, —O—CO—N($R_y^1$)—, —N($R_{y'}^1$)— or —N($R_{y'}^1$)—SO$_2$—, $R_Y^1$, $R_{Y'}^{1*}$ are independently of one another, hydrogen, a branched or unbranched, optionally substituted $C_1$–$C_6$-alkyl, $C_1$–$C_6$-alkoxyalkyl, $C_2$–$C_6$-alkenyl, $C_3$–$C_{12}$-alkynyl, CO—$C_1$–$C_6$-alkyl, CO—O—$C_1$–$C_6$-alkyl or SO$_2$—$C_1$–$C_6$-alkyl radical or an optionally substituted $C_3$–$C_7$-cycloalkyl, aryl, arylalkyl, CO—O-alkylene-aryl, CO-alkylene-aryl, CO-aryl, SO$_2$-aryl, hetaryl, CO-hetaryl or SO$_2$-alkylene-aryl radical, $R_L^9$ is hydrogen, or a hydroxyl group, CN, halogen, a branched or unbranched, optionally substituted $C_1$–$C_6$-alkyl radical, an optionally substituted $C_3$–$C_7$-cycloalkyl, aryl, heteroaryl or arylalkyl radical, an optionally $C_1$–$C_4$-alkyl- or aryl-substituted $C_2$–$C_6$-alkynyl or $C_2$–$C_6$-alkenyl radical, an optionally substituted $C_6$–$C_{12}$-bicycloalkyl, $C_1$–$C_6$-alkylene-$C_6$–$C_{12}$-bicyclo-alkyl, $C_7$–$C_{20}$-tricycloalkyl or $C_1$–$C_6$-alkylene-$C_7$–$C_{20}$-tricycloalkyl radical, or a 3- to 8-membered, saturated or unsaturated heterocyclic system which is substituted by up to three identical or different radicals and which may contain up to three different or identical heteroatoms O, N, S, it being possible for two radicals together to be a fused, saturated, unsaturated or aromatic carbocyclic or heterocyclic system which may contain up to three different or identical heteroatoms O, N, S, and it being possible for the cyclic system to be optionally substituted, or for another, optionally substituted, saturated, unsaturated or aromatic cyclic system to be fused to this cyclic system, or the radical $R_L^9$ forms together with $R_y^1$ or $R_y^{1*}$ a saturated or unsaturated $C_3$–$C_7$-heterocycle which may optionally contain up to two further heteroatoms selected from the group of O, S or N, $W_L$ is an optionally substituted 4- to 11-membered mono- or polycyclic aliphatic or aromatic hydrocarbon which may contain up to 6 double bonds and up to 6 heteroatoms selected from the group of N, O, S, $V_L$, $X_L$, are, independently of one another, —CO—, —CO—NR$_L^{10}$—, —NR$_L^{10}$—CO—, —S—, —SO—, —SO$_2$—, —SO$_2$—NR$_L^{10}$—, —NR$_L^{10}$—SO$_2$—, —CS—, —CS—NR$_L^{10}$—, —NR$_L^{10}$—CS—, —CS—O—, —O—CS—, —CO—O—, —O—CO—, —O—, ethylene, —CHR$_L^{11}$—O—CHR$_L^{12}$—, —C(=CR$_L^{11}$R$_L^{12}$)—, —CR$_L^{11}$=CR$_L^{12}$—, —CR$_L^{11}$=CR$_L^{12}$—, —CR$_L^{11}$(OR$_L^{13}$)—CHR$_L^{12}$—, —CHR$_L^{11}$—CR$_L^{12}$(OR$_L^{13}$)—, —CH(NR$_L^{14}$—SO$_2$—R$_L^{15}$)—, —CH(NR$_L^{14}$—CO—R$_L^{15}$)—, —CH(NR$_L^{14}$—CO—OR$_L^{16}$)—, CH(NR$_L^{14}$—CO—NR$_L^{14'}$R$_L^{15}$)—, —CH(CO—R$_L^{15}$)—, —CH(CO—OR$_L^{16}$)— or CH(CO—NR$_L^{14}$R$_L^{15}$)—, $R_L^{10}$ is hydrogen, a branched or unbranched, optionally substituted $C_1$–$C_6$-alkyl, $C_1$–$C_6$-alkoxyalkyl, $C_2$–$C_6$-alkenyl, $C_3$–$C_{12}$-alkynyl, CO—$C_1$–$C_6$-alkyl, CO—O—$C_1$–$C_6$-alkyl or SO$_2$—$C_1$–$C_6$-alkyl radical or an optionally substituted $C_3$–$C_7$-cycloalkyl, CO—O-alkylene-aryl, CO-alkylene-aryl, arylalkyl-, CO-aryl, SO$_2$-aryl, hetaryl, CO-hetaryl, hetarylalkyl or SO$_2$-alkylene-aryl radical, or $R_L^{10}$ and a radical selected from the group of $R_L^1$, $R_L^2$, $R_L^3$, $R_L^4$, $R_L^5$, $R_L^6$, $R_L^7$ or $R_L^8$ together are an optionally substituted 4- to 8-membered heterocycle which may contain up to five identical or different heteroatoms O, N or S, $R_L^{11}$, $R_L^{12}$ are, independently of one another, hydrogen, a hydroxyl group, a branched or unbranched, optionally substituted $C_1$–$C_6$-alkyl, $C_1$–$C_4$-alkoxy, $C_2$–$C_6$-alkenyl, $C_2$–$C_6$-alkynyl or alkylene-cycloalkyl radical or an optionally substituted $C_3$–$C_7$-cycloalkyl, aryl, arylalkyl, hetaryl or hetarylalkyl radical, $R_L^{13}$ is hydrogen, a branched or unbranched, optionally substituted $C_1$–$C_6$-alkyl, $C_2$–$C_6$-alkenyl, $C_2$–$C_6$-alkynyl or alkylene-cycloalkyl radical or an optionally substituted $C_3$–$C_7$-cycloalkyl, aryl, arylalkyl, hetaryl or hetarylalkyl radical, $R_L^{14}$, $R_L^{14'}$ are, independently of one another, hydrogen, a branched or unbranched, optionally substituted $C_1$–$C_6$-alkyl, $C_1$–$C_6$-alkoxyalkyl, $C_2$–$C_6$-alkenyl, $C_3$–$C_{12}$-alkynyl, CO-$C_1$–$C_6$-alkyl, CO—O—$C_1$–$C_6$-alkyl, $C_1$–$C_6$-alkylene-$C_3$–$C_7$-cycloalkyl, or SO$_2$-$C_1$–$C_6$-alkyl radical or an optionally substituted $C_3$–$C_7$-cycloalkyl, CO—O-alkylene-aryl, CO-alkylene-aryl, aryl, CO-aryl, SO$_2$-aryl, hetaryl, CO-hetaryl, hetarylalkyl, arylalkyl or SO$_2$-alkylene-aryl radical, $R_L^{15}$ is a branched or unbranched, optionally substituted $C_1$–$C_6$-alkyl, alkoxyalkyl, $C_1$–$C_6$-alkylene-$C_3$–$C_7$-cycloalkyl radical, $C_6$–$C_{12}$-bicycloalkyl, $C_1$–$C_8$-alkylene-$C_6$–$C_{12}$-bicycloalkyl, $C_7$–$C_{20}$-tricycloalkyl or $C_1$–$C_6$-alkylene-$C_7$–$C_{20}$-tricycloalkyl radical, a $C_3$–$C_7$-cycloalkyl, aryl, arylalkyl, hetarylalkyl or 3- to 8-membered, saturated, unsaturated or aromatic heterocyclic radical which may be substituted by up to three identical or different radicals and which may contain up to three different or identical heteroatoms O, N, S, it being possible for two radicals together to be a fused, saturated, unsaturated or aromatic carbocyclic or heterocyclic system which may contain up to three different or identical heteroatoms O, N, S, and it being possible for this cyclic system to be optionally substituted, or for another, optionally substituted, saturated, unsaturated or aromatic cyclic system to be fused to this cyclic system, or the radical $R_L^{15}$ forms together with $R_L^{14}$ or $R_L^*$ a saturated or unsaturated $C_3$–$C_7$ heterocycle which may optionally contain up to two further heteroatoms selected from the group of O, S or N, and $R_L^{16}$ is a branched or unbranched, optionally saturated $C_1$–$C_6$-alkyl, alkoxyalkyl or $C_1$–$C_6$-alkylene-$C_3$–$C_7$-cycloalkyl radical or an optionally substituted $C_3$–$C_7$-cycloalkyl, aryl, arylalkyl, hetaryl or hetarylalkyl radical, G is a structural element of the formula $I_G$

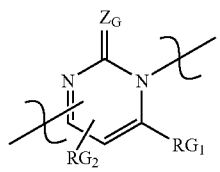

where the structural element G can be incorporated in both orientations, and $Z_G$ is oxygen, sulfur or $NR_G^3$, $R_G^1 R_G^2$ are, independently of one another, hydrogen, CN, $NO_2$, halogen, a branched or unbranched, optionally substituted $C_1$–$C_6$-alkyl, $C_2$–$C_6$-alkenyl or $C_2$–$C_6$-alkynyl radical, a branched or unbranched, optionally substituted $C_1$–$C_4$-alkylene-$OR_G^4$, $C_1$–$C_4$-alkylene-CO—$OR_G^4$, $C_1$–$C_4$-alkylene-$OR_G^4$, $C_1$–$C_4$-alkylene-$SO_2$—$NR_G^5 R_G^6$, $C_1$–$C_4$-alkylene-CO-$NR_G^5 R_G^6$, $C_1$–$C_4$-alkylene-$NR_G^5 R_G^6$ or $C_1$–$C_4$-alkylene-$SR_G^4$ radical, an optionally substituted $C_3$–$C_7$-cycloalkyl, $C_3$–$C_7$-heterocycloalkyl, $C_3$–$C_7$-heterocycloalkenyl, $C_1$–$C_4$-alkylene-$C_3$–$C_7$-cycloalkyl, $C_1$–$C_4$-alkylene-$C_3$–$C_7$-heterocycloalkyl or $C_1$–$C_4$-alkylene-$C_3$–$C_7$-heterocycloalkenyl radial, an optionally substituted aryl, arylalkyl, hetaryl or hetarylalkyl radical, an —S—$R_G^4$, —O—$R_G^4$, —SO—$R_G^4$, —$SO_2$—$R_G^4$, —CO—$OR_G^4$, —O—CO—$R_G^4$, —O—CO—$NR_G^5 R_G^6$, —$SO_2$—$NR_G^5 R_G^6$, —CO—$NR_G^5 R_G^6$, —$NR_G^5 R_G^6$, CO—$R_G^4$ radical, or $R_G^1$ and $R_G^2$ together are an optionally substituted, saturated, unsaturated or aromatic 3- to 9-membered carbocyclic, polycarbocyclic, heterocyclic or polyheterocyclic system which may contain up to 4 heteroatoms selected from the group of O, N, S, $R_G^3$ is hydrogen, a hydroxyl, CN, a branched or unbranched, optionally substituted $C_1$–$C_6$-alkyl or $C_1$–$C_4$-alkoxy radical or an optionally substituted $C_3$–$C_7$-cycloalkyl, —O—$C_3$–$C_7$-cycloalkyl radical, aryl-, —O-aryl, arylalkyl or —O-alkylene-aryl radical, $R_G^4$ is hydrogen, a branched or unbranched, optionally substituted $C_1$–$C_8$-alkyl, $C_2$–$C_6$-alkenyl, $C_2$–$C_6$-alkynyl, $C_1$–$C_5$-alkylene-$C_1$–$C_4$-alkoxy-, mono- and bisalkylaminoalkylene or acylaminoalkylene radical or an optionally substituted aryl, heterocycloalkyl, heterocycloalkenyl, hetaryl, $C_3$–$C_7$-cycloalkyl, $C_1$–$C_4$-alkylene-$C_3$–$C_7$-cycloalkyl, arylalkyl, $C_1$–$C_4$-alkylene-heterocycloalkyl, $C_1$–$C_4$-alkylene-heterocycloalkenyl or hetarylalkyl radical, $R_G^5$, $R_G^6$ are, independently of one another, hydrogen, a branched or unbranched, optionally substituted $C_1$–$C_8$-alkyl, $C_2$–$C_6$-alkenyl, $C_2$–$C_6$-alkynyl, $C_1$–$C_5$-alkylene-$C_1$–$C_4$-alkoxy, mono- and bisalkylaminoalkylene or acylaminoalkylene radical or an optionally substituted aryl, heterocycloalkyl, heterocycloalkenyl, hetaryl, $C_3$–$C_7$-cycloalkyl, $C_1$–$C_4$-alkylene-$C_3$–$C_7$-cycloalkyl, arylalkyl, $C_1$–$C_4$-alkylene-heterocycloalkyl, $C_1$–$C_4$-alkylene-heterocycloalkenyl or hetarylalkyl radical, or an —$SO_2$—$R_G^4$, —CO—$OR_G^4$, —CO—$NR_G^4 R_G^{4*}$ or —CO—$R_G^4$ radical, and $R_G^{4*}$ is an $R_G^4$ radical independent of $R_G^4$, B is a structural element containing at least one atom which can, under physiological conditions, form hydrogen bonds as hydrogen acceptor, where the distance between at least one hydrogen acceptor atom and structural element G along the shortest possible route along the structural element framework is from 4 to 13 atomic linkages, and the physiologically tolerated salts, prodrugs and enantiomerically pure or diasteromerically pure and tautomeric forms.

A halogen radical means for all radicals and substituents in the present invention for example F, Cl, Br or I, unless mentioned otherwise.

Optionally substituted radicals mean the corresponding unsubstituted and substituted radicals. For all substituted radicals in the present invention if the substituents are not specified in detail then, independently of one another, up to 5 substituents are suitable, for example selected from the following group:

—$NO_2$, —$NH_2$, —OH, —CN, —COOH, —O—$CH_2$—COOH, halogen, a branched or unbranched, optionally substituted $C_1$–$C_4$-alkyl radical such as, for example, methyl, $CF_3$, $C_2F_5$ or $CH_2F$, a branched or unbranched, optionally substituted —CO—O—$C_1$–$C_4$-alkyl, $C_3$–$C_7$-cycloalkyl, $C_1$–$C_4$-alkoxy, $C_1$–$C_4$-thioalkyl, —NH—CO—O—$C_1$–$C_4$-alkyl, —O—$CH_2$—COO—$C_1$–$C_4$-alkyl, —NH—CO—$C_1$–$C_4$-alkyl, —CO—NH—$C_1$–$C_4$-alkyl, —NH—$SO_2$—$C_1$–$C_4$-alkyl, —$SO_2$—NH—$C_1$–$C_4$-alkyl, —N($C_1$–$C_4$-alkyl)$_2$, —NH—$C_1$–$C_4$-alkoxy, or —$SO_2$—$C_1$–$C_4$-alkyl radical, such as, for example, —$SO_2$—$CF_3$, an optionally substituted —NH—CO-aryl, —CO—NH-aryl, —NH—CO—O-aryl, —NH—CO—O-alkylene-aryl, —NH—$SO_2$-aryl, —$SO_2$-NH-Aryl, —CO—NH-benzyl, —NH—$SO_2$-benzyl or —$SO_2$—NH-benzyl radical, an optionally substituted —$SO^2$—$NR^4 R^5$ or —CO—$NR^4 R^5$ radical, it being possible for $R^4$ and $R^5$ radicals independently of one another to have the meaning as $R_L^{14}$ hereinafter, or the two $R^4$ and $R^5$ radicals together being a 3- to 6-membered, optionally substituted, saturated, unsaturated or aromatic heterocycle which, in addition to the ring nitrogen, may contain up to three other different or identical heteroatoms O, N, S and optionally two radicals substituted on this heterocycle together are a fused, saturated, unsaturated or aromatic carbocyclic or heterocyclic system which may contain up to three different or identical heteroatoms O, N, S, and it being possible for the cyclic system optionally to be substituted, or for another, optionally substituted cyclic system to be fused to this cyclic system.

With all terminally bonded, substituted hetaryl and hetarylalkyl radicals in the present invention it is possible, in addition to the aforementioned list of substituents, for two substituents in the hetaryl moiety to form a fused 5- to 7-membered, unsaturated or aromatic carbocyclic system.

T in the structural element L means a COOH group or a radical which can be hydrolyzed in COOH. A radical which can be hydrolyzed to COOH means a radical which is converted into a COOH group after hydrolysis.

A group which may be mentioned as an example of a radical T which can be hydrolyzed to COOH is

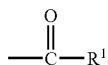

in which $R^1$ has the following meaning:
a) CM, where M can be a metal cation such as an alkali metal cation such as lithium, sodium, potassium, the equivalent of an alkaline earth metal cation such as calcium, magnesium and barium, or an environmentally compatible organic ammonium ion such as primary, secondary, tertiary or quaternary $C_1$–$C_4$-alkylammonium or an ammonium ion, such as, for example, ONa, OK or OLi,
b) a branched or unbranched, optionally halogen-substituted $C_1$–$C_8$-alkoxy radical such as, for example, methoxy, ethoxy, propoxy, 1-methylethoxy, butoxy, 1-methylpropoxy, 2-methylpropoxy, 1,1-dimethylethoxy, in particular methoxy, ethoxy, 1-methylethoxy, pentoxy, hexoxy, heptoxy, octoxy, difluoromethoxy, trifluoromethoxy, chlorodifluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy
c) a branched or unbranched, optionally halogen-substituted $C_1$–$C_4$-alkylthio radical such as methylthio, ethylthio, propylthio, 1-methylethylthio, butylthio, 1-methylpropylthio, 2-methylpropylthio or 1,1-dimethylethylthio radical
d) an optionally substituted —O-alkylene-aryl radical such as, for example, —O-benzyl
e) $R^1$ also a radical —$(O)_{m1}$—$N(R^2)(R^3)$, in which m1 is 0 or 1, and $R^2$ and $R^3$, which may be identical or different, have the following meaning:
hydrogen,
a branched or unbranched, optionally substituted $C_1$–$C_6$-alkyl radical, such as, for example, methyl, ethyl, propyl, 1-methylethyl, butyl, 1-methylpropyl, 2-methylpropyl, 1,1-dimethylethyl, pentyl, 1-methylbutyl, 2-methylbutyl, 1,2-dimethylpropyl, 1,1-dimethylpropyl, 2,2-dimethylpropyl, 1-ethylpropyl, hexyl, 1-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl or 1-ethyl-2-methylpropyl or the corresponding substituted radicals, preferably methyl, ethyl, propyl, butyl or i-butyl,
$C_2$–$C_6$-alkenyl radical such as, for example, vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, in particular 2-propenyl, 2-butenyl, 3-methyl-2-butenyl and 3-methyl-2-pentenyl or the corresponding substituted radicals,
$C_2$–$C_6$-alkynyl radical such as, for example, ethynyl, 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2propynyl, preferably 2-propynyl, 2-butynyl, 1-methyl-2-propynyl or 1-methyl-2-butynyl, or the corresponding substituted radicals,
$C_3$–$C_8$-cycloalkyl, such as, for example, cyclopropyl, cyclobutyl, cyclopentyl, cyclohexyl and cycloheptyl, cyclooctyl or the corresponding substituted radicals,
or a phenyl radical, optionally substituted one or more times, for example one to three times, by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, such as, for example, 2-fluorophenyl, 3-chlorophenyl, 4-bromophenyl, 2-methylphenyl, 3-nitrophenyl, 4-cyanophenyl, 2-trifluoromethylphenyl, 3-methoxyphenyl, 4-trifluoroethoxyphenyl, 2-methylthiophenyl, 2,4-dichlorophenyl, 2-methoxy-3-methylphenyl, 2,4-dimethoxyphenyl, 2-nitro-5-cyanophenyl, 2,6-difluorophenyl,
or $R^2$ and $R^3$ together form a $C_4$–$C_7$-alkylene chain which is closed to a ring, is optionally substituted, for example by $C_1$–$C_4$-alkyl and may contain a heteroatom selected from the group of oxygen, sulfur or nitrogen, such as, for example, —$(CH_2)_4$—, —$(CH_2)_5$—, —$(CH_2)_6$—, —$(CH_2)_7$—, —$CH_2$—O—$(CH_2)_2$—, —$CH_2S$—$(CH_2)_3$—, —$(CH_2)_2$—O—$(CH_2)_3$—, —NH—$(CH_2)_3$—, —$CH_2$—NH—$(CH_2)_2$—, —$CH_2$—CH=CH—$CH_2$—, —CH=CH—$(CH_2)_3$—, —CO—$(CH_2)_2$—CO— or —CO—$(CH_2)_3$—CO—.

Preferred T radicals are —COOH, —CO—O—$C_1$–$C_8$-alkyl or —CO—O-benzyl.

The coefficients a, c, e and g in structural element —U— are, independently of one another, 0, 1, 2 or 3, preferably 0, 1 or 2.

In further, preferred structural elements —U— the total of the coefficients a, c, e and g is less than 7.

In particularly preferred structural elements —U— the coefficients a, c, e and g are, independently of one another, 0 or 1.

The preferred halogen radical for $R_L^1$, $R_L^2$, $R_L^3$, $R_L^4$, $R_L^5$, $R_L^6$, $R_L^7$ or $R_L^8$ is F.

Examples of branched or unbranched $C_1$–$C_6$-alkyl radicals for $R_L^1$, $R_L^2$, $R_L^3$, $R_L^4$, $R_L^5$, $R_L^6$, $R_L^7$ or $R_L^8$ in structural element L are, independently of one another, methyl, ethyl, propyl, 1-methylethyl, butyl, 1-methoxypropyl, 2-methylpropyl, 1,1-dimethylethyl, pentyl, 1-methylbutyl, 2-methylbutyl, 1,2-dimethylpropyl, 1,1-dimethylpropyl, 2,2-dimethylpropyl, 1-ethoxypropyl, hexyl, 1-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2,-trimethylpropyl, 1-ethoxybutyl, 2-ethylbutyl or 1-ethyl-2-methylpropyl, preferably branched or unbranched $C_1$–$C_4$-alkyl radicals such as, for example, methyl, ethyl, propyl, 1-methylethyl, butyl, 1-methylpropyl, 2-methylpropyl or 1,1-dimethylethyl, particularly preferably methyl.

A branched or unbranched $C_2$–$C_6$-alkenyl radical for $R_L^1$, $R_L^2$, $R_L^3$, $R_L^4$, $R_L^5$, $R_L^6$, $R_L^7$ or $R_L^8$ in structural element L means, independently of one another, for example vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl or 1-ethyl-2-methyl-2-propenyl.

A branched or unbranched $C_2$–$C_6$-alkynyl radical for $R_L^1$, $R_L^2$, $R_L^3$, $R_L^4$, $R_L^5$, $R_L^6$, $R_L^7$ or $R_L^8$ in structural element L means, independently of one another, for example ethynyl, 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl, preferably ethynyl, 2-propynyl, 2-butynyl, 1-methyl-2-propynyl or 1-methyl-2-butynyl, particularly preferably ethynyl.

A $C_3$–$C_7$-cycloalkyl radical for $R_L^1$, $R_L^2$, $R_L^3$, $R_L^4$, $R_L^5$, $R_L^6$, $R_L^7$ or $R_L^8$ in structural element L means, independently of one another, for example cyclopropyl, cyclobutyl, cyclopentyl, cyclohexyl or cycloheptyl.

Branched or unbranched $C_1$–$C_6$-alkylene-$C_3$–$C_7$-cycloalkyl radicals are composed, for example, of branched or unbranched $C_1$–$C_6$-alkylene radicals and the aforementioned $C_3$–$C_7$-cycloalkyl radicals.

Preferred optionally substituted aryl radicals for $R_L^1$, $R_L^2$, $R_L^3$, $R_L^4$, $R_L^5$, $R_L^6$, $R_L^7$ or $R_L^8$ in structural element L are, independently of one another, optionally substituted phenyl, 1-naphthyl or 2-naphthyl.

Preferred optionally substituted arylalkyl radicals for $R_L^1$, $R_L^2$, $R_L^3$, $R_L^4$, $R_L^5$, $R_L^6$, $R_L^7$ or $R_L^8$ in structural element L are, independently of one another, optionally substituted benzyl or phenethyl.

Hetaryl radicals for $R_L^1$, $R_L^2$, $R_L^3$, $R_L^4$, $R_L^5$, $R_L^6$, $R_L^7$ or $R_L^8$ in structural element L mean, independently of one another, for example radicals such as 2-pyridyl, 3-pyridyl, 4-pyridyl, 2-furyl, 3-furyl, 2-pyrrolyl, 3-pyrrolyl, 2-thienyl, 3-thienyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 3-pyrazolyl, 4-pyrazolyl, 5-pyrazolyl, 3-isothiazolyl, 4-isothiazolyl, 5-isothiazolyl, 2-imidazolyl, 4-imidazolyl, 5-imidazolyl, 3-pyridazinyl, 4-pyridazinyl, 5-pyridazinyl, 6-pyridazinyl, 3-isoxazolyl, 4-isoxazolyl, 5-isoxazolyl, thiadiazolyl, oxadiazolyl or triazinyl.

Substituted hetaryl radicals for $R_L^1$, $R_L^2$, $R_L^3$, $R_L^4$, $R_L^5$, $R_L^6$, $R_L^7$ or $R_L^8$ in structural element L mean, as described above generally for terminal substituted hetaryl radicals, also fused derivatives of the aforementioned hetaryl radicals, such as, for example, indazole, indole, benzothiophene, benzofuran, indoline, benzimidazole, benzothiazole, benzoxazole, quinoline, 2,3-dihydro-1-benzofuran, furo[2,3]pyridine, furo[3,2]pyridine or isoquinoline.

Hetarylalkyl radicals for $R_L^1$, $R_L^2$, $R_L^3$, $R_L^4$, $R_L^5$, $R_L^6$, $R_L^7$ or $R_L^8$ in structural element L mean radicals which are composed, for example, of $C_1$–$C_6$-alkylene radicals and of the hetaryl radicals described above, such as, for example, the radicals —$CH_2$-2-pyridyl, —$CH_2$-3-pyridyl, —$CH_2$-4-pyridyl, —$CH_2$-2-thienyl, —$CH_2$-3-thienyl, —$CH_2$-2-thiazolyl, —$CH_2$-4-thiazolyl, $CH_2$-5-thiazolyl, —$CH_2$—$CH_2$-2-pyridyl, —$CH_2$—$CH_2$-3-pyridyl, —$CH_2$—$CH_2$-4-pyridyl, —$CH_2$—$CH_2$-2-thienyl, —$CH_2$—$CH_3$-3-thienyl, —$CH_2$—$CH_2$-2-thiazolyl, —$CH_2$—$CH_2$-4-thiazolyl, or —$CH_2$—$CH_2$-5-thiazolyl.

It is further possible for two radicals $R_L^1$ and $R_L^2$ or $R_L^3$ and $R_L^4$ or $R_L^5$ or $R_L^6$ or $R_L^7$ and $R_L^8$ in each case independently of one another together to be a 3- to 7-membered, optionally substituted, saturated or unsaturated carbocyclic or heterocyclic system which may contain up to three heteroatoms from the group of O, N or S.

The —$(CH_2)_w$—$(Y_L)_y$—$R_L^9$ radical is composed of a $C_0$–$C_4$-alkylene radical, optionally a linking element $Y_L$ selected from the group of —CO—, —CO—N($R_Y^1$)—, —N($R_Y^1$)—CO—, —N($R_Y^1$)—CO—N($R_Y^{1*}$)—, —N($R_Y^1$)—CO—O—, —O—, —S—, —$SO_2$—, —$SO_2$—N($R_Y^1$)—, —$SO_2$—O—, —CO—O—, —O—CO, —O—CO—N($R_Y^1$)—, —N($R_Y^1$)— or N($R_Y^1$)—$SO_2$— and the $R_L^9$ radical, where $R_Y^1$, $R_Y^{1*}$ are, independently of one another, hydrogen, a branched or unbranched, optionally substituted $C_1$–$C_6$-alkyl, $C_1$–$C_6$-alkoxyalkyl, $C_2$–$C_6$-alkenyl, $C_3$–$C_{12}$-alkynyl, CO—$C_1$–$C_6$-alkyl, CO—O—$C_1$–$C_6$-alkyl or $SO_2$—$C_1$–$C_6$-alkyl radical or an optionally substituted $C_3$–$C_7$-cycloalkyl, aryl, arylalkyl, CO—O-alkylene-aryl, CO-alkylene-aryl, CO-aryl, $SO_2$-aryl, hetaryl, CO-hetaryl or $SO_2$-alkylene-aryl radical, preferably hydrogen, methyl, cyclopropyl, allyl or propargyl, particularly preferably hydrogen or methyl, and $R_L^9$ is hydrogen, a hydroxyl group, CN, halogen, a branched or unbranched, optionally substituted $C_1$–$C_6$-alkyl radical, an optionally substituted $C_3$–$C_7$-cycloalkyl, aryl, heteroaryl or arylalkyl radical, an optionally $C_1$–$C_4$-alkyl- or aryl-substituted $C_2$–$C_6$-alkynyl or $C_2$–$C_6$-alkenyl radical, an optionally substituted $C_6$–$C_{12}$-bicycloalkyl, $C_1$–$C_6$-alkylene-$C_6$–$C_{12}$-bicycloalkyl, $C_7$–$C_{20}$-tricycloalkyl or $C_1$–$C_6$-alkylene-$C_7$–$C_{20}$-tricycloalkyl radical, or a 3- to 8-membered, saturated or unsaturated heterocycle which is substituted by up to three identical or different radicals and which may contain up to three different or identical heteroatoms O, N, S, it being possible for two radicals together to be a fused, saturated, unsaturated or aromatic carbocyclic or heterocyclic system which may contain up to three different or identical heteroatoms O, N, S, and it being possible for the cyclic system optionally to be substituted, or for another, optionally substituted, saturated, unsaturated or aromatic cyclic system to be fused to this cyclic system, such as, for example, optionally substituted 2-pyridyl, 3-pyridyl, 4-pyridyl, 2-furyl, 3-furyl, 2-pyrrolyl, 3-pyrrolyl, 2-thienyl, 3-thienyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 3-pyrazolyl, 4-pyrazolyl, 5-pyrazolyl, 3-isothiazolyl, 4-isothiazolyl, 5-isothiazolyl, 2-imidazolyl, 4-imidazolyl, 5-imidazolyl, 3-pyridazinyl, 4-pyridazinyl, 5-pyridazinyl, 6-pyridazinyl, 2-(1,3,4)-thiadiazolyl, 2-(1,3,4)-oxadiazolyl, 3-isoxazolyl, 4-isoxazolyl, 5-isoxazolyl or triazinyl.

It is also possible for $R_L^9$ and $R_y^1$ or $R_y^{1*}$ together to form a saturated or unsaturated $C_3$–$C_7$-heterocycle which may optionally contain up to two other heteroatoms selected from the group of O, S or N.

The radicals $R_L^9$ and $R_y^1$ or $R_y^{1*}$ preferably together form a cyclic amine as $C_3$–$C_7$-heterocycle in the case where the radicals are bonded to the same nitrogen atom, such as, for example, N-pyrrolidinyl, N-piperidinyl, N-hexahydroazepinyl, N-morpholinyl or N-piperazinyl, it being possible for the free amine protons on heterocycles having free amine protons, such as, for example, N-piperazinyl, to be replaced by conventional amine protective groups such as, for example, methyl, benzyl, Boc (tert-butoxy-carbonyl), Z (benzyloxycarbonyl), tosyl, —$SO_2$—$C_1$–$C_4$-alkyl, —$SO_2$-phenyl or —$SO_2$-benzyl.

Preferred —$(CH_2)_w$—$(Y_L)$—$R_L^9$ radicals for $R_L^1$, $R_L^3$, $R_L^5$ or $R_L^7$ in structural element L are optionally substituted side chains of natural amino acids, preferably optionally substituted side chains of the amino acids Ser, Thr, Tyr, Asp, Asn, Glu, Gln, Cys, Met, Lys or Orn, optionally substituted side chains of unnatural amino acids as described, for example, in catalogs of the companies Bachem 1999, Novabiochem 1999, Neosystem 1997/98 and Advanced ChemTech 1999.

Side chains of natural α-amino acids mean the side chains including the β carbon atom. Examples of unnatural amino acids are β-amino acids. In this case, side chains mean the side chains including the γ carbon atom. Substituted side chains also mean, for example, side chains which have a protective group on a functional group in the side chain such as, for example, —$NH_2$, —SH, —OH or —COOH.

In particularly preferred radicals for $R_L^1$, $R_L^2$, $R_L^3$, $R_L^4$, $R_L^5$, $R_L^6$, $R_L^7$ or $R_L^8$ in structural element L, in each case independently of one another one of the radicals $R_L^1$ and $R_L^2$ or $R_L^3$ and $R_L^4$ or $R_L^5$ and $R_L^6$ or $R_L^7$ and $R_L^8$ is hydrogen or methyl.

In another preferred embodiment of the structural element —U—, the $R_L^1$, $R_L^2$, $R_L^3$, $R_L^4$, $R_L^5$, $R_L^6$, $R_L^7$ or $R_L^8$ radicals are, independently of one another, hydrogen or methyl, with the proviso that the $V_L$ or $X_L$ radicals are, independently of one another, a radical —$CH(NR_L^{14}$—$SO_2$—$R_L^{15})$—, —$CH(NR_L^{14}$—CO—$R_L^{15})$—, —$CH(NR_L^{14}$—CO—$OR_L^{16})$—, —$CH(NR_L^{14}$—CO—$NR_L^{14'}R_L^{15})$—, —$CH(CO$—$OR_L^{16})$— or —$CH(CO$—$NR_L^{14}R_L^{15})$—.

An optionally substituted 4- to 11-membered mono- or polycyclic aliphatic or aromatic hydrocarbon which may contain up to 6 double bonds and up to 6 heteroatoms selected from the group of N, O, S for $W_L$ preferably means optionally substituted arylene such as, for example, optionally substituted phenylene or naphthylene, optionally substituted hetarylene such as, for example, the radicals

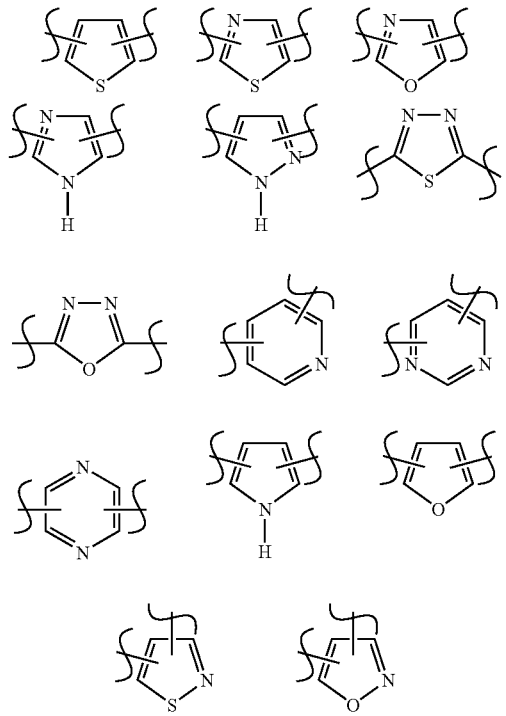

and their substituted or fused derivatives, or radicals of the formula $I_{WL}$ to $III_{WL}$,

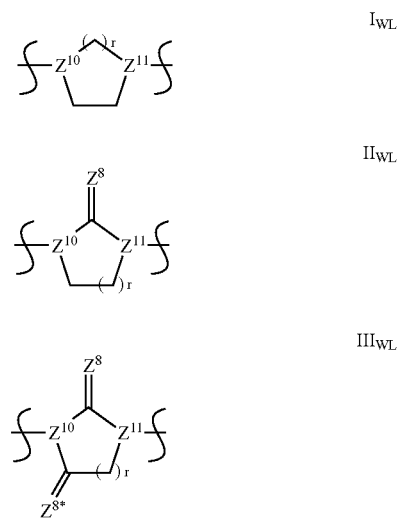

where the radicals can be incorporated in both orientations, the coefficient r is 0, 1, 2 or 3, and $Z^{10}$ and $Z^{11}$ are, independently of one another, CH or nitrogen, and $Z^8$ and $Z^{8*}$, independently of one another, are oxygen, sulfur or NH.

$W_L$ is preferably an optionally substituted phenylene radical, a radical

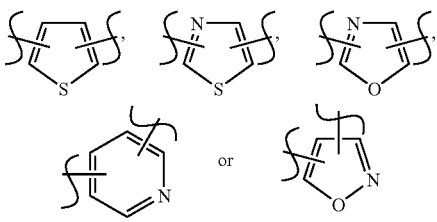

or their substituted or fused derivatives, or radicals of the formula $I_{WL}$ to $III_{WL}$,

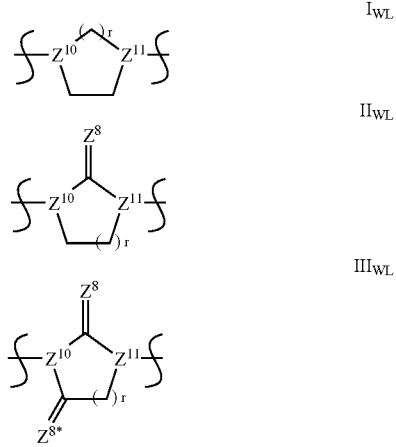

where the radicals can be incorporated in both orientations, the coefficient r is 0, 1, 2 or 3, and $Z^{10}$ and $Z^{11}$ are, independently of one another, CH or nitrogen and $Z^8$ and $Z^{8*}$, are independently of one another, are oxygen, sulfur or NH.

$Z^8$ in preferred radicals of the formula $II_{WL}$ or $III_{WL}$ for $W_L$ is oxygen.

Preferred radicals for $V_L$ and $X_L$ are, independently of one another, —CO—$NR_L^{10}$—, —$NR_L^{10}$—CO—, —$SO_2$—$NR_L^{10}$—, —$NR_L^{10}$—$SO_2$—, —O—, —CH($NR_L^{14}$—$SO_2$—$R_L^{15}$)—, —CH($NR_L^{14}$—CO—$R_L^{15}$)—, —CH($NR_L^{14}$—CO—$OR_L^{16}$)—, CH($NR_L^{14}$—CO—$NR_L^{14'}R_L^{15}$)—, —CH(CO—$R_L^{15}$)—, —CH(CO—$OR_L^{16}$)— and CH(CO—$NR_L^{14}R_L^{15}$)—.

Particularly preferred radicals for $V_L$ and $X_L$ are, independently of one another, —CH($NR_L^{14}$—$SO_2$—$R_L^{15}$)—, —CH($NR_L^{14}$—CO—$R_L^{15}$)—, —CH($NR_L^{14}$—CO—$OR_L^{16}$)—, CH($NR_L^{14}$—CO—$NR_L^{14'}R_L^{15}$)—, —CH(CO—$R_L^{15}$)—, —CH(CO—$OR_L^{16}$)— and CH(CO—$NR_L^{14}R_L^{15}$)—.

The $RL_{10}$ radical in structural element L is hydrogen,
a branched or unbranched, optionally substituted $C_1$–$C_6$-alkyl radical, for example as described above for $R_L^1$, preferably methyl,
$C_1$–$C_6$-alkoxyalkyl radical, for example methoxymethyl, ethoxymethyl, t-butoxymethyl, methoxyethyl or ethoxyethyl,
$C_2$–$C_6$-alkenyl radical, for example as described above for $R_L^1$, preferably allyl,
$C_3$–$C_{12}$-alkynyl radical, for example 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl, preferably propargyl,
or CO—$C_1$–$C_6$-alkyl, CO—O—$C_1$–$C_6$-alkyl or $SO_2$—$C_1$–$C_6$-alkyl radical which is composed in each case of the corresponding CO—, CO—O— or $SO_2$— group, and, for example, of the $C_1$–$C_6$-alkyl radicals described above, an optionally substituted
$C_3$–$C_7$-cycloalkyl, arylalkyl, hetaryl or hetarylalkyl radical as described, for example, in each case for $R_L^1$ above,
an optionally substituted CO—O-alkylene-aryl-, CO-alkylene-aryl, CO-aryl, $SO_2$—aryl, CO-hetaryl or $SO_2$-alkylene-aryl radical which is composed in each case of the corresponding CO—, CO—O— or $SO_2$— group and, for example, of the corresponding arylalkyl, aryl, hetarylalkyl and hetaryl radicals as described for $R_L^1$.

It is also possible for $R_L^{10}$ and a radical selected from the group of $R_L^1$, $R_L^2$, $R_L^3$, $R_L^4$, $R_L^5$, $R_L^6$, $R_L^7$ or $R_L^8$ together to form an optionally substituted 4- to 8-membered heterocycle which may contain up to five identical or different heteroatoms O, N or S.

Particularly preferred radicals for $R_L^{10}$ are hydrogen, methyl, cyclopropyl, allyl and propargyl.

A branched or unbranched $C_1$–$C_6$-alkyl, $C_2$–$C_6$-alkenyl, $C_2$–$C_6$-alkynyl or $C_1$–$C_6$-alkylene-$C_3$–$C_7$-cycloalkyl radical or an optionally substituted $C_3$–$C_7$-cycloalkyl, aryl, arylalkyl, hetaryl or hetarylakyl radical for $R_L^{11}$ or $R_L^{12}$ means, independently of one another, for example the corresponding radicals mentioned above for $R_L^1$.

A branched or unbranched $C_1$–$C_4$-alkoxy radical for $R_L^{11}$ or $R_L^{12}$ means, independently of one another, for example the radicals methoxy, ethoxy, propoxy, 1-methylethoxy, butoxy, 1-methylpropoxy, 2-methoxypropoxy or 1,1-dimethylethoxy.

A branched or unbranched $C_1$–$C_6$-alkyl, $C_2$–$C_6$-alkenyl, $C_2$–$C_6$-alkynyl or $C_1$–$C_6$-alkylene-$C_3$–$C_7$-cycloalkyl radical or an optionally substituted $C_3$–$C_7$-cycloalkyl, aryl, arylalkyl, hetaryl or hetarylalkyl radical for $R_L^{13}$ mean, for example, the corresponding radicals mentioned above for $R_L^1$.

Preferred radicals for $R_L^{14}$ and $R_L^{14'}$ are, independently of one another, hydrogen, a branched or unbranched, optionally substituted $C_1$–$C_6$-alkyl or $C_3$–$C_{12}$-alkynyl radical or an optionally substituted $C_3$–$C_7$-cycloalkyl, aryl, hetaryl or arylalkyl radical.

Particularly preferred radicals for $R_L^{14}$ and $R_L^{14'}$ are, independently of one another, hydrogen, methyl, cyclopropyl, allyl or propargyl.

$R_L^{15}$ is a branched or unbranched, optionally substituted $C_1$–$C_6$-alkyl radical as described above for $R_L^1$, preferably a branched or unbranched, optionally substituted $C_1$–$C_4$-alkyl radical, particularly preferably n-butyl, 2-methylpropyl, 1-methylethyl,
alkoxyalkyl radical as described above for $R_L^{10}$,
$C_1$–$C_6$-alkylene-$C_3$–$C_7$-cycloalkyl radical as described, above for $R_L^1$, preferably —$CH_2$—$C_3$–$C_7$-cycloalkyl or —$CH_2$—$CH_2$—$C_3$–$C_7$-cycloalkyl,
$C_6$–$C_{12}$-bicycloalkyl or $C_7$–$C_{20}$-tricycloalkyl radical such as, for example, bicyclo[4.4.0]decanyl, bicyclo[2.2.2]octanyl, bicyclo[3.2.1]octanyl, indanyl, adamantyl, norbornyl, noradamantyl or camphor-10-yl, $C_1$–$C_6$-alkylene-$C_6$–$C_{12}$-bicycloalkyl or $C_1$–$C_6$-alkylene-$C_7$–$C_{20}$-tricycloalkyl radical, such as, for example, —$CH_2$-bicyclo[4.4.0]decanyl, —$CH_2$-bicyclo[2.2.2]octanyl, —$CH_2$-bicyclo[3.2.1]octanyl, —$CH_2$-indanyl, —$CH_2$-adamantyl, —$CH_2$-norbornyl, —$CH_2$-noradamantyl or —$CH_2$-camphor-10-yl, a $C_3$–$C_7$-cycloalkyl, aryl, arylalkyl or hetarylalkyl radical as described above for $R_L^1$, which is substituted by up to three identical or different radicals, or a 3- to 8-membered, saturated, unsaturated or aromatic heterocyclic radical which is substituted by up to three identical or different radicals and which may contain up to three different or identical heteroatoms O, N, S, it being possible for two radicals together to be a fused, saturated, unsaturated or aromatic carbocyclic or heterocyclic system which may contain up to three different or identical heteroatoms O, N, S, and it being possible for this cyclic system optionally to be substituted, or for another, optionally substituted, saturated, unsaturated or aromatic cyclic system to be fused to this cyclic system.

It is furthermore possible for $R_L^{15}$ and $R_L^{14}$ or $R_L^{14*}$ together to form a saturated or unsaturated $C_3$–$C_7$-heterocycle which may optionally contain up to two other heteroatoms selected from the group O, S or N.

The radicals $R_L^{15}$ and $R_L^{14}$ and $R_L^{14*}$ preferably together form a cyclic amine residue as $C_3$–$C_7$-heterocycle in the case where the radicals are bonded to the same nitrogen atom, such as, for example, N-pyrrolidinyl, N-piperidinyl, N-hexahydroazepinyl, N-morpholinyl or N-piperazinyl, it being possible for the free amine protons on heterocycles having free amine protons, such as, for example, N-piperazinyl, to be replaced by conventional amine protective groups such as, for example, methyl, benzyl, Boc (tert-butoxy-carbonyl), Z (benzyloxycarbonyl), tosyl, —$SO_2$—$C_1$–$C_4$-alkyl, —$SO_2$-phenyl or —$SO_2$-benzyl. The cyclic amine residue $NR_L^{15}R_L^{14}$ or $NR_L^{15}R_L^{14*}$ may also, depending on the structural element $V_L$ or $X_L$, be a constituent of an amide, sulfonamide, urethane or other possible structural element.

Preferred radicals for $R_L^{15}$ are a branched or unbranched, optionally substituted $C_1$–$C_4$-alkyl or —CH—$C_5$–$C_7$-cycloalkyl radical, an optionally substituted $C_5$–$C_7$-cycloalkyl, phenyl, 1-naphthyl, 2-naphthyl, —$CH_2$-naphthyl, pyridyl, —$CH_2$-pyridyl, phenethyl, thienyl, —$CH_2$-thienyl, oxazolyl, —$CH_2$-oxazolyl, isoxazolyl, —$CH_2$-isoxazolyl, quinolinyl, isoquinolinyl, —$CH_2$-quinolinyl, —$CH_2$-isoquinolinyl, adamantyl, —$CH_2$-adamantyl, norbornyl, —$CH_2$-norbonyl, camphor-10-yl or —$CH_3$-camphor-10-yl radical.

A branched or unbranched, optionally substituted $C_1$–$C_6$-alkyl, alkoxyalkyl or $C_1$–$C_6$-alkylene-$C_3$–$C_7$-cycloalkyl radical or an optionally substituted $C_3$–$C_7$-cycloalkyl, aryl, arylalkyl, hetaryl or hetarylalkyl radical for $R_L^{16}$ means, for example, the corresponding radicals mentioned above for $R_L^{15}$, preferably hydrogen, a branched or unbranched, optionally substituted $C_1$–$C_4$-alkyl or —$CH_2$–$C_5$–$C_7$-cycloalkyl radical, an optionally substituted $C_5$–$C_7$-cycloalkyl, phenyl, 1-naphthyl, 2-naphthyl, —$CH_2$-naphthyl, benzyl, pyridyl, —$CH_2$-pyridyl, phenethyl, thienyl, —$CH_2$-thienyl, oxazolyl, —$CH_2$-oxazolyl, isoxazolyl, —$CH_2$-isoxazolyl, adamanthyl or —$CH_2$-adamantyl radical.

Particularly preferred radicals for $R_L^{16}$ are a branched or unbranched, optionally substituted $C_1$–$C_4$-alkyl radical and optionally substituted benzyl.

Preferred structural elements L are compared of at least one preferred radical of the radicals belonging to structural element L, while the remaining radicals may vary widely.

Particularly preferred structural elements L are composed of the preferred radicals of the structural element L.

G is a structural element of the formula $I_G$

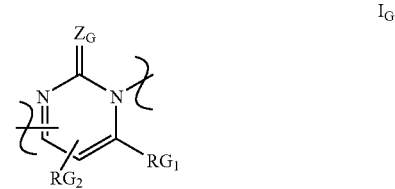

where the structural element G can be incorporated in both orientations.

$Z_G$ is oxygen, sulfur or $NR_G^3$, preferably oxygen.

In a preferred embodiment of the structural element G, the substitution pattern is fixed as in formula $I_{GB}$

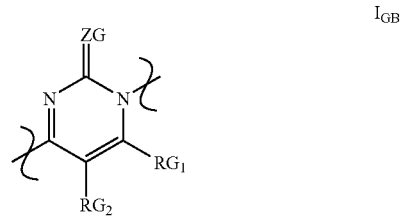

where the structural element G can be incorporated in both orientations in this case too.

In a particularly preferred embodiment of the structural element G, the substitution pattern is fixed as in formula $I_{GB}$, and the structural element G is incorporated so that the structural element E is connected to the position 4 carbon and the structural element L is connected to the position 1 nitrogen.

$R_G^1$ and $R_G^2$ in structural element G are, independently of one another, hydrogen, CN, $NO_2$, halogen, a branched or unbranched, optionally substituted $C_1$–$C_6$-alkyl radical such as, for example, optionally substituted methyl, ethyl, propyl, 1-methylethyl, butyl, 1-methylpropyl, 2-methylpropyl, 1,1-dimethylethyl, pentyl, 1-methylbutyl, 2-methylbutyl, 1,2-dimethylpropyl, 1,1-dimethylpropyl, 2,2-dimethylpropyl, 1-ethylpropyl, hexyl, 1-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl or 1-ethyl-2-methylpropyl, $C_2$–$C_6$-alkenyl radical such as, for example, optionally substituted vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-propenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3- butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl or 1-ethyl-2-methyl-2-propenyl, $C_2$–$C_6$-alkynyl radical such as, for example, optionally substituted ethynyl, 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl or 1-ethyl-1-methyl-2-propynyl, a branched or unbranched, optionally substituted $C_1$–$C_4$-alkylene-O—$R_G^4$, $C_1$–$C_4$-alkylene-CO—$OR_G^4$, $C_1$–$C_4$-alkylene-CO—$R_G^4$, $C_1$–$C_4$-alkylene-$SO_2$—$NR_G^5R_G^6$, $C_1$–$C_4$-alkylene-CO—$NR_G^5R_G^6$, $C^1$–$C_4$-alkylene-$NR_G^5R_G^6$ or $C_1$–$C_4$-alkylene—$SR_G^4$ radical, which are composed of branched or unbranched, optionally substituted $C_1$–$C_4$-alkylene radicals such as, for example, methylene, ethylene, propylene, n-butylene, isobutylene or t-butylene, the appropriate —O—, —CO—, —S—, —N groups and the terminal $R_G^4$, $R_G^5$ and $R_G^6$ radicals described below, an optionally substituted $C_3$–$C_7$-cycloalkyl radical such as, for example, optionally substituted cyclopropyl, cyclobutyl, cyclopentyl, cyclohexyl or cycloheptyl, $C_3$–$C_7$-heterocycloalkyl radical such as, for example, optionally substituted aziridinyl, diaziridinyl, oxiranyl, oxaziridinyl, oxetanyl, thiiranyl, thietanyl, pyrrolidinyl, piperazinyl, morpholinyl, piperidinyl, tetrahydrofuranyl, tetrahydropyranyl, 1,4-dioxanyl, hexahydroazepinyl, oxepanyl, 1,2-oxathiolanyl or oxazolidinyl, $C_3$–$C_7$-heterocycloalkenyl radical such as, for example, optionally substituted azirinyl, diazirinyl, thiirenyl, thietyl, pyrrolinyls, oxazolinyls, azepinyl, oxepinyl, α-pyranyl, β-pyranyl, γ-pyranyl, dihydropyranyls, 2,5-dihydropyrrolinyl or 4,5-dihydrooxazolyl, a branched or unbranched, optionally substituted $C_1$–$C_4$-alkylene-$C_3$–$C_7$-cycloalkyl radical which is composed, for example, of branched or unbranched C–$C_4$-alkylene radicals such as, for example, methylene, ethylene, propylene, n-butylene, isobutylene or t-butylene and, for example, the aforementioned $C_3$–$C_7$-cycloalkyl radicals, a branched or unbranched, optionally substituted $C_1$–$C_4$-alkylene-$C_3$–$C_7$-heterocycloalkyl or $C_1$–$C_4$-alkylene-$C_3$–$C_7$-heterocycloalkenyl radical, which are composed of optionally substituted $C_1$–$C_4$-alkylene radicals such as, for example, methylene, ethylene, propylene, n-butylene, isobutylene or t-butylene and, for example, the aforementioned $C_3$–$C_7$-heterocycloalkyl or $C_3$–$C_7$-heterocycloalkenyl radicals, preferred radicals being those containing in the cyclic moiety one or two heteroatoms selected from the group of N, O or S and up to two double bonds, an optionally substituted aryl radical, preferably optionally substituted phenyl, 1-naphthyl or 2-naphthyl, arylalkyl radical, preferably optionally substituted benzyl or phenethyl, hetaryl radical, preferably optionally substituted 2-pyridyl, 3-pyridyl, 4-pyridyl, 2-furyl, 3-furyl, 2-pyrrolyl, 3-pyrrolyl, 2-thienyl, 3-thienyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 3-pyrzolyl, 4-pyrazolyl, 5-pyrazolyl, 3-isothiazolyl, 4-isothiazolyl, 5-isothiazolyl, 2-imidazolyl, 4-imidazolyl, 5-imidazolyl, 3-pyridazinyl, 4-pyridazinyl, 5-pyridazinyl, 6-pyridazinyl, 3-isoxazolyl, 4-isoxazolyl, 5-isoxazolyl, thiadiazolyl, oxadiazolyl or triazinyl or their fused derivatives such as, for example, indazolyl, indolyl, benzothienyl, benzofuranyl, indolinyl, benzimidazolyl, benzothiazolyl, benzoxazolyl, quinolinyl or isoquinolinyl, hetarylalkyl radical, preferably optionally substituted —$CH_2$-2-pyridyl, —$CH_2$-3-pyridyl, —$CH_2$-4-pyridyl, —$CH_2$-2-thienyl, —$CH_2$-3-thienyl, —$CH_2$-2-thiazolyl, —$CH_2$-4-thiazolyl, $CH_2$-5-thiazolyl, —$CH_2$-$CH_2$-2-pyridyl, —$CH_2$—$CH_2$-3-pyridyl, —$CH_2$—$CH_2$-4-pyridyl, —$CH_2$—$CH_2$-2-thienyl, —$CH_2$—$CH_2$-3-thienyl, —$CH_2$—$CH_2$-2-thiazolyl, —$CH_2$—$CH_2$-4-thiazolyl or —$CH_2$—$CH_2$-5-thiazolyl or a radical —S—$R_G^4$, —O—$R_G^4$, —SO—$R_G^4$, —$SO_2$—$R_G^4$, —CO—$OR_G^4$, —O—CO—$R_G^4$, —O—CO—$NR_G^5R_G^6$, —$SO_2$—$NR_G^5R_G^6$, —CO—$NR_G^5R_G^6$, —$NR_G^5R_G^6$, CO—$R_G^4$.

It is also possible for the $R_G^1$ and $R_G^2$ radicals together to form an optionally substituted, saturated, unsaturated or aromatic 3- to 9-membered carbocycle, polycarbonate, heterocycle or polyheterocycle which may contain up to 4 heteroatoms selected from the group of O, N, S.

Preferred radicals for $R_G^1$ in the structural element G are hydrogen, a branched or unbranched, optionally substituted $C_1$–$C_6$-alkyl radical, preferably $CF_3$, $C_2$–$C_6$-alkenyl, $C_2$–$C_6$-alkynyl radical, $C_1$–$C_4$-alkylene-$OR_G^4$, optionally substituted aryl, arylalkyl, hetaryl or hetarylalkyl or a radical —O—$R_G^4$.

Preferred radicals for $R_G^2$ in the structural element G are hydrogen, CN, halogen, a branched or unbranched, optionally substituted $C_1$–$C_6$-alkyl radical, preferably $CF_3$, an optionally substituted $C_3$–$C_7$-cycloalkyl, aryl, arylalkyl, hetaryl or hetarylalkyl radical, an —SO—$R_G^4$, —$SO_2$—$R_G^4$, —CO—$OR_G^4$, —$SO_2$—$NR_G^5R_G^6$, —CO—$NR_G^5R_G^6$, —$NR_G^5R_G^6$, CO—$R_G^4$, $C_1$–$C_4$-alkylene-CO—$OR_G^4$, $C_1$–$C_4$-alkylene-$SO_2$—$NR_G^5R_G^6$, $C^1$–$C_4$-alkylene-CO—$NR_G^5R_G^6$ or $C_1$–$C_4$-alkylene-$NR_G^5R_G^6$ radical or an optionally substituted $C_1$–$C_4$-alkylene-$C_3$–$C_7$-cycloalkyl, $C_3$–$C_7$-heterocycloalkyl, $C_3$–$C_7$-heterocycloalkenyl, $C_1$–$C_4$-alkylene-$C_3$–$C_7$-heterocycloalkyl or $C_1$–$C_4$-alkylene-$C_3$–$C_7$-heterocycloalkenyl radical, the radicals preferred for the at last for radicals being those containing in the cyclic moiety one or two heteroatoms selected from the group of N, O or S and up to two double bonds.

$R_G^2$ in the structural element G is particularly preferably a branched or unbranched, optionally substituted $C_1$–$C_6$-alkyl radical, an optionally substituted $C_3$–$C_7$-cycloalkyl, aryl, arylalkyl, hetaryl or hetarylalkyl radical, a —CO—$OR_G^4$, —CO—$NR_G^5R_G^6$, —$NR_G^5R_G^6$, $C^1$–$C_4$-alkylene-CO—$NR_G^5R_G^6$ or $C_1$–$C_4$-alkylene-$NR_G^5R_G^6$ or an optionally substituted $C_3$–$C_7$-heterocycloalkyl, $C_3$–$C_7$-heterocycloalkenyl, $C_1$–$C_4$-alkylene-$C_3$–$C_7$-heterocycloalkyl or $C_1$–$C_4$-alkylene-$C_3$–$C_7$-heterocycloalkenyl radical, the radicals preferred for the last four radicals being those containing in the cyclic moiety one or two heteroatoms selected from the group of N, O or S and up to two double bonds.

$R_G^3$ is hydrogen, a hydroxyl group, CN, a branched or unbranched, optionally substituted $C_1$–$C_6$-alkyl radical as described, for example, for $R_G^1$ above, $C_1$–$C_4$-alkoxy radical as described, for example, for $R_L^{11}$ above, an optionally substituted $C_3$–$C_7$-cycloalkyl, aryl or arylalkyl radical as in each case described, for example, for $R_G^1$ above, or an optionally substituted —O—$C_3$–$C_7$-cycloalkyl radical, —O-aryl or —O-alkylene-aryl radical which is composed, for example, in each case of the group —O— and the corresponding radicals described above for $R_G^1$.

A branched or unbranched, optionally substituted $C_1$–$C_8$-alkyl radical for $R_G^4$, $R_G^{4*}$, $R_G^5$ and $R_G^6$ means, independently of one another, for example the $C_1$–$C_6$-alkyl radicals mentioned above for $R_G^1$ plus the radicals heptyl and octyl.

Preferred substituents of the branched or unbranched, optionally substituted $C_1$–$C_8$-alkyl radicals for $R_G^4$, $R_G^{4*}$, $R^{G5}$ and $R_G^6$ are, independently of one another, the radicals halogen, hydroxyl, $C_1$–$C_4$-alkoxy, —CN, —COOH and —CO—$C_1$–$C_4$-alkyl.

A branched or unbranched, optionally substituted $C_2$–$C_6$-alkenyl, $C_2$–$C_6$-alkynyl or $C_1$–$C_4$-alkylene-$C_3$–$C_7$-cycloalkyl radical, an optionally substituted $C_3$–$C_7$-cycloalkyl, aryl, arylalkyl, hetaryl or hetarylalkyl radical for $R_G^4$, $R_G^{4*}$, $R_G^5$ and $R_G^6$ means, independently of one another, for example the corresponding radicals mentioned above for $R_G^1$.

Preferred branched or unbranched, optionally substituted —$C_1$–$C_5$-alkylene-$C_1$–$C_4$-alkoxy radicals for $R_G^4$, $R_G^{4*}$, $R^{G5}$ and $R_G^6$ are, independently of one another, methoxymethylene, ethoxymethylene, t-butoxymethylene, methoxyethylene or ethoxyethylene.

Preferred branched or unbranched, optionally substituted mono- and bisalklaminoalkylene or acylaminoalkylene radicals for $R_G^4$, $R_G^{4*}$, $R_G^5$ and $R_G^6$ are, independently of one another, branched or unbranched, optionally substituted —$C_1$–$C_4$-alkylene-NH($C_1$–$C_4$-alkyl), —$C_1$–$C_4$-alkylene-N($C_1$–$C_4$-alkyl); and —$C_1$–$C_4$-alkylene-NH—CO—$C_1$–$C_4$-alkyl radicals.

Preferred optionally substituted heterocycloalkyl, heterocycloalkenyl, $C_1$–$C_4$-alkylene-heterocycloalkyl or $C_1$–$C_4$-alkylene-heterocycloalkenyl radicals for $R_G^4$, $R_G^{4*}$, $R_G^5$ and $R_G^6$ are, independently of one another, the $C_3$–$C_7$-heterocycloalkyl, $C_3$–$C_7$-heterocycloalkenyl, $C_1$–$C_4$-alkylene-$C_3$–$C_7$-heterocycloalkyl or $C_1$–$C_4$-alkylene-$C_3$–$C_7$-heterocycloalkenyl radicals described above for $R_G^1$.

Particularly preferred optionally substituted heterocycloalkyl, heterocycloalkenyl, $C_1$–$C_4$-alkylene-heterocycloalkyl or $C_1$–$C_4$-alkylene-heterocycloalkenyl radicals for $R_G^4$, $R_G^{4*}$, $R_G^5$ and $R_G^6$ are, independently of one another, the $C_3$–$C_7$-heterocycloalkyl, $C_3$–$C_7$-heterocycloalkenyl, $C_1$–$C_4$-alkylene-$C_3$–$C_7$-heterocycloalkyl or $C_1$–$C_4$-alkylene-$C_3$–$C_7$-heterocycloalkenyl radicals described above for $R_G^1$, the cyclic moiety containing one or two heteroatoms selected from the group of N, O or S and up to two double bonds.

It is also possible for $R_G^5$ and $R_G^6$ independently of one another to be an —$SO_2$—$R_G^4$, —CO—O—$R_G^4$, —CO—$NR_G^4R_G^{4*}$ or —CO—$R_G^4$ radical, where $R_G^{4*}$ gives an $R^{G4}$ radical independent of $R_G^4$.

Preferred structural elements G are compared of at least one preferred radical of the radicals belonging to structural element G, or the preferred substitution pattern of structural element G, while the remaining radicals may vary widely.

Particularly preferred structural elements G are compared of the preferred radicals of the structural element G.

Very particularly preferred structural elements G are composed of the preferred radicals of the structural element G and the preferred substitution pattern of the structural element G.

Structural element B means a structural element containing at least one atom which can, under physiological conditions, form hydrogen bonds as hydrogen acceptor, where the distance between at least one hydrogen acceptor atom and structural element G along the shortest possible route along the structural element framework is from 4 to 13 atomic linkages. The arrangement of the structural framework of structural element B may vary widely.

Examples of suitable atoms which, under physiological conditions, are able to form hydrogen bonds as hydrogen acceptors are atoms with Lewis base properties such as, for example, the heteroatoms nitrogen, oxygen or sulfur.

Physiological conditions mean a pH prevailing at the site in an organism at which the ligands interact with the receptors. In the present case, the pH under physiological conditions is, for example, from 5 to 9.

In a preferred embodiment, the structural element B is a structural element of the formula Ia $$A\text{—}E\text{—} \qquad \qquad Ia$$

where A and E have the following meanings:

A is a structural element selected from the group:

a 4- to 8-membered monocyclic saturated, unsaturated or aromatic hydrocarbon which may contain up to 4 heteroatoms selected from the group of O, N or S, it being possible in each case, independently of one another, for the ring nitrogen which is present where appropriate or the carbons to be substituted, with the proviso that at least one heteroatom selected from the group of O, N or S is present in the structural element A, or a 9- to 14-membered polycyclic saturated, unsaturated or aromatic hydrocarbon which may contain up to 6 -heteroatoms selected from the group of N, O or S, it being possible in each case, independently of one another, for the ring nitrogen which is present where appropriate or the carbons to be substituted, with the proviso that at least one heteroatom selected from the group of O, N or S is present in the structural element A, a radical

where $Z_A^1$ is oxygen, sulfur or optionally substituted nitrogen, preferably oxygen or nitrogen and $Z_A^2$ is optionally substituted nitrogen, oxygen or sulfur, preferably nitrogen, or a radical

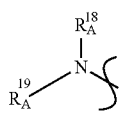   $I_A^5$ where $R_A^{18}$, $R_A^{19}$ are, independently of one another, hydrogen, a branched or unbranched, optionally substituted $C_1$–$C_8$-alkyl, $C_2$–$C_6$-alkenyl, $C_2$–$C_6$-alkynyl, $C_1$–$C_5$-alkylene-$C_1$–$C_4$-alkoxy, mono- and bisalkylaminoalkylene or acylaminoalkylene radical or an optionally substituted aryl, heterocycloalkyl, heterocycloalkenyl, hetaryl, $C_3$–$C_7$-cycloalkyl, $C_1$–$C_4$-alkylene-$C_3$–$C_7$-cycloalkyl, arylalkyl, $C_1$–$C_4$-alkylene-heterocycloalkyl, $C_1$–$C_4$-alkylene-heterocycloalkenyl or hetarylalkyl radical, or an —$SO_2$—$R_G^4$, —CO—$OR_G^4$, —CO—$NR_G^{4*}$ or —CO—$R^{G4}$ radical, and E a spacer structural element which covalently connects structural element A to structural element G, where the number of atomic linkages along the shortest possible route along the structural element framework E is from 3 to 12.

In a particularly preferred embodiment, the structural element A is a structural element selected from the group of structural elements of the formulae $I_A^1$ to $I_A^{19}$,

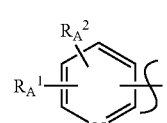   $I_A^1$

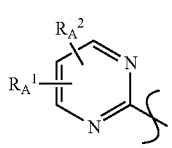   $I_A^2$

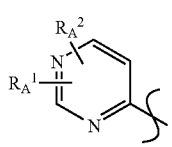   $I_A^3$

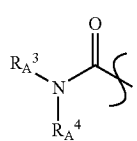   $I_A^4$

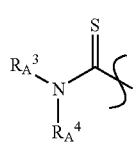   $I_A^5$

-continued

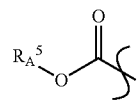   $I_A^6$

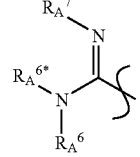   $I_A^7$

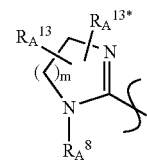   $I_A^8$

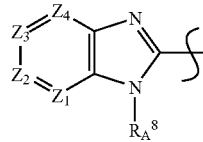   $I_A^9$

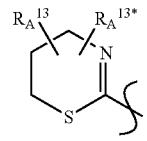   $I_A^{10}$

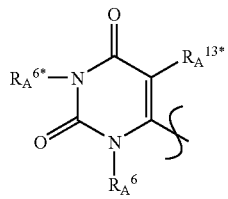   $I_A^{11}$

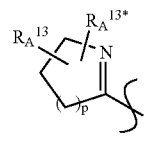   $I_A^{12}$

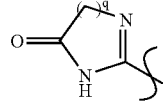   $I_A^{13}$

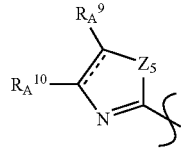   $I_A^{14}$

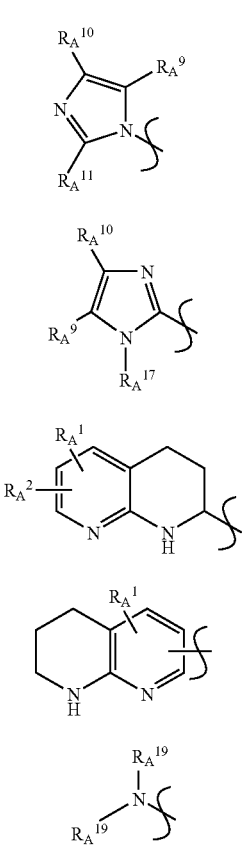

where
m,p,q are, independently of one another, 1, 2 or 3.

$R_A^1$, $R_A^2$ are, independently of one another, hydrogen, CN, halogen, a branched or unbranched, optionally substituted $C_1$–$C_6$-alkyl or CO—$C_1$–$C_6$-alkyl radical or an optionally substituted aryl, arylalkyl, hetaryl, hetarylalkyl or $C_3$–$C_7$-cycloalkyl radical or a CO—O—$R_A^{14}$, O—$R_A^{14}$, S—$R_A^{14}$, $NR_A^{15}R_A^{16}$, CO—$NR_A^{15}R_A^{16}$ or $SO_2NR_A^{15}R_A^{16}$ radical or the two radicals $R_A^1$ and $R_A^2$ together are a fused, optionally substituted, 5- or 6-membered, unsaturated or aromatic carbocyclic or heterocyclic system which may contain up to three heteroatoms selected from the group of O, N or S, $R_A^{13}$, $R_A^{13*}$ are, independently of one another, hydrogen, CN, halogen, a branched or unbranched, optionally substituted $C_1$–$C_6$-alkyl radical or an optionally substituted aryl, arylalyl, hetaryl, $C_3$–$C_7$-cycloalkyl radical or a CO—O—$R_A^{14}$, O—$R_A^{14}$, S—$R_A^{14}$, $NR_A^{15}R_A^{16}$, $SO_2$—$NR_A^{15}R_A^{16}$ or CO—$NR_A^{15}R_A^{16}$ radical, where
$R_A^{14}$ is hydrogen, a branched or unbranched, optionally substituted $C_1$–$C_6$-alkyl, alkylene-$C_1$–$C_4$-alkoxy, $C_2$–$C_6$-alkenyl, $C_2$–$C_6$-alkynyl or $C_1$–$C_6$-alkylene-$C_3$–$C_7$-cycloalkyl radical or an optionally substituted $C_3$–$C_7$-cycloalkyl, aryl, arylalkyl, hetaryl or hetarylalkyl radical, $R_A^{15}$, $R_A^{16}$, are, independently of one another, hydrogen, a branched or unbranched, optionally substituted $C_1$–$C_6$-alkyl, CO—$C_1$–$C_6$-alkyl, $SO_2$-$C_1$–$C_6$-alkyl, COO—$C_1$–$C_6$-alkyl, CO—NH—$C_1$–$C_6$-alkyl, arylalkyl, COO-alkylene-aryl, $SO_2$-alkylene-aryl, CO—NH-alkylene-aryl, CO—NH-alkylene-hetaryl or hetarylalkyl radical or an optionally substituted $C_3$–$C_7$-cycloalkyl, aryl, CO-aryl, CO—NH-aryl, $SO_2$-aryl, hetaryl, CO—NH-hetaryl, or CO-hetaryl radical, $R_A^3$, $R_A^4$ are, independently of one another, hydrogen, —$(CH_2)_n$—$(X)_j$—$R_A^{12}$, or the two radicals together are a 3- to 8-membered, saturated, unsaturated or aromatic N heterocyclic system which may additionally contain two other, identical or different heteroatoms O, N or S, it being possible for the cyclic system optionally to be substituted, or for another, optionally substituted, saturated, unsaturated or aromatic cyclic system to be fused to this cyclic system, where
n is 0, 1, 2 or 3,
j is 0 or 1,
$X_A$ is —CO—, —CO—N($R_X^1$), —N($R_X^1$)—CO—, —N($R_X^1$)—CO—N($R_X^{1*}$)—, —N($R_X^1$)—CO—, —O—, —S—, —$SO_2$—, —$SO_2$—N($R_X^1$)—, —$SO_2$—O—, —CO—O—, —O—CO—N($R_X^1$)—, —N($R_X^1$)— or —N($R_X^1$)—$SO_2$—, $R_A^{12}$ is hydrogen, a branched or unbranched, optionally substituted $C_1$–$C_6$-alkyl radical, an optionally $C_1$–$C_4$-alkyl- or aryl-substituted $C_2$–$C_6$-alkynyl or $C_2$–$C_6$-alkenyl radical or a 3- to 6-membered, saturated or unsaturated heterocyclic system which is substituted by up to three identical or different radicals and which may contain up to three different or identical heteroatoms O, N, S, or $C_3$–$C_7$-cycloalkyl, aryl or heteroaryl radical, it being possible for two radicals together to be a fused, saturated, unsaturated or aromatic carbocyclic or heterocyclic system which may contain up to three different or identical heteroatoms O, N, S, and it being possible for the cyclic system optionally to be substituted or for another, optionally substituted, saturated, unsaturated or aromatic cyclic system to be fused to this cyclic system, or the $R_A^{12}$ radical forms together with $R_X^1$ or $R_X^{1*}$ a saturated or unsaturated $C_3$–$C_7$-heterocycle which may optionally contain up to two other heteroatoms selected from the group of O, S or N, $R_X^1$, $R_X^{1*}$ are independently of one another, hydrogen, a branched or unbranched, optionally substituted $C_1$–$C_6$-alkyl, $C_1$–$C_6$-alkoxyalkyl, $C_2$–$C_6$-alkenyl, $C_2$–$C_{12}$-alkynyl, CO—$C_1$–$C_6$-alkyl, CO—O—$C_1$–$C_6$-alkyl or $SO_2$—$C_1$–$C_6$-alkyl radical or an optionally substituted $C_3$–$C_7$-cycloalkyl, aryl, arylalkyl, CO—O-alkylene-aryl, CO-alkylene-aryl, CO-aryl, $SO_2$-aryl, hetaryl, CO-hetaryl or $SO_2$-alkylene-aryl radical, $R_A^5$ is branched or unbranched, optionally substituted $C_1$–$C_6$-alkyl, arylalkyl, $C_3$–$C_7$-cycloalkyl or $C_1$–$C_4$-alkylene-$C_3$–$C_7$-cycloalkyl radical or an optionally substituted aryl, hetaryl, heterocycloalkyl or heterocycloalkenyl radical, $R_A^6$, $R_A^{6*}$ are hydrogen, a branched or unbranched, optionally substituted $C_1$–$C_4$-alkyl, —CO—O—$C_1$–$C_4$-alkyl, arylalkyl, —CO—O-alkylene-aryl, —CO—O-allyl, —CO—$C_1$–$C_4$-alkyl, —CO-alkylene-aryl, $C_3$–$C_7$-cycloalkyl or —CO-allyl radical or the two radicals $R_A^6$ and $R_A^{6*}$ in the structural element $I_A^7$ together are an optionally substituted, saturated, unsaturated or aromatic heterocyclic system which, in addition to the ring nitrogen, may contain up to two other different or identical heteroatoms O, N, S, $R_A^7$ is hydrogen, —OH, —CN, —$CONH_2$, a branched or unbranched, optionally substituted $C_1$–$C_4$-alkyl, $C_1$–$C_4$-alkoxy, $C_3$–$C_7$-cycloalkyl or —O—CO—

$C_1$–$C_4$-alkyl radical or an optionally substituted arylalkyl, —O-alkylene-aryl, —O—CO-aryl, —O—CO-alkylene-aryl or —O—CO-allyl radical, or the two radicals $R_A^6$ and $R_A^7$ together are an optionally substituted, unsaturated or aromatic heterocyclic system which, in addition to the ring nitrogen, may contain up to two other different or identical heteroatoms O, N, S, $R_A^8$ is hydrogen, a branched or unbranched, optionally substituted $C_1$–$C_4$-alkyl, CO—$C_1$–$C_4$-alkyl, $SO_2$—$C_1$–$C_4$-alkyl or CO—O—$C_1$–$C_4$-alkyl radical or an optionally substituted aryl, CO-aryl, $SO_2$-aryl, CO—O-aryl, CO-alkylene-aryl, $SO_2$-alkylene-aryl, CO—O-alkylene-aryl or alkylene-aryl radical, $R_A^9$, $R_A^{10}$ are, independently of one another, hydrogen, —CN, halogen, a branched or unbranched, optionally substituted $C_1$–$C_6$-alkyl radical or an optionally substituted aryl, arylalkyl, hetaryl, $C_3$–$C_7$-cycloalkyl radical or a CO—O—$R_A^{14}$, O—$R_A^{14}$, S—$R_A^{14}$, $NR_A^{15}R_A^{16}$, $SO_2$—$NR_A^{15}R_A^{16}$ or CO—$NR_A^{15}R_A^{16}$ radical, or the two radicals $R_A^9$ and $R_A^{10}$ in the structural element $I_A^{14}$ together are a 5- to 7-membered saturated, unsaturated or aromatic carbocyclic or heterocyclic system which may contain up to three different or identical heteroatoms O, N, S and is optionally substituted by up to three identical or different radicals, $R_A^{11}$ is hydrogen, —CN, halogen, a branched or unbranched, optionally substituted $C_1$–$C_6$-alkyl radical or an optionally substituted aryl, arylalkyl, hetaryl, $C_3$–$C_7$-cycloalkyl radical or a CO—O—$R_A^{14}$, O—$R_A^{14}$, S—$R_A^{14}$, $NR_A^{15}R_A^{16}$, $SO_2$—$NR_A^{15}R_A^{16}$ or CO—$NR^{415}R_A^{16}$ radical, $R_A^{17}$ is hydrogen or the two radicals $R_A^9$ and $R_A^{17}$ in the structural element $I_A^{16}$ together are a 5- to 7-membered saturated, unsaturated or aromatic heterocycle which, in addition to the ring nitrogen, may contain up to three different or identical heteroatoms O, N, S and is optionally substituted by up to three identical or different radicals, $R_A^{18}$, $R_A^{19}$ are, independently of one another, hydrogen, a branched or unbranched, optionally substituted $C_1$–$C_8$-alkyl, $C_2$–$C_6$-alkenyl, $C_2$–$C_6$-akynyl-, $C_1$–$C_5$-alkylene-$C_1$–$C_4$-alkoxy, mono- and bisalkylaminoalkylene or acylaminoalkylene radical or an optionally substituted aryl, heterocycloalkyl, heterocycloalkenyl, hetaryl, $C_3$–$C_7$-cycloalkyl, $C_1$–$C_4$-alkylene-$C_3$–$C_7$-cycloalkyl, arylalkyl, $C_1$–$C_4$-alkylene-heterocycloalkyl, $C_1$–$C_4$-alkylene-heterocycloalkenyl or hetarylalkyl radical, or an —$SO_2$—$R_G^4$, —CO—$OR_G^4$, —CO—$NR_G^4R_G^{4*}$ or —CO—$R_G^4$ radical, $Z^1$, $Z^2$, $Z^3$, $Z^4$ are, independently of one another, nitrogen, C—H, C-halogen or a branched or unbranched, optionally substituted C—$C_1$–$C_4$-alkyl or C—$C_1$–$C_4$-alkoxy radical, $Z^5$ is $NR_A^8$ oxygen or sulfur.

In a further very particularly preferred embodiment, the structural element A is a structural element of the formula $I_A^1$, $I_A^4$, $I_A^7$, $I_A^8$, $I_A^9$, $I_A^{14}$ or $I_A^{15}$.

A branched or unbranched, optionally substituted $C_1$–$C_6$-alkyl radical for $R_A^1$ or $R_A^2$ means, independently of one another, for example the corresponding radicals described above for $R_G^1$, preferably methyl or trifluoromethyl.

The branched or unbranched, optionally substituted CO—$C_1$–$C_6$-alkyl radical for $R_A^1$ or $R_A^2$ in the structural elements $I_A^1$, $I_A^2$, $I_A^3$ or $I_A^{17}$ is composed, for example, of the CO group and the branched or unbranched, optionally substituted $C_1$–$C_6$-alkyl radicals described above for $R_A^1$ or $R_A^2$.

Optionally substituted hetaryl, hetarylalkyl, aryl, arylalkyl or $C_3$–$C_7$-cycloalkyl radicals for $R_A^1$ or $R_A^2$ mean, independently of one another, for example the corresponding radicals described above for $R_G^1$.

The optionally substituted CO—O—$R_A^{14}$, O—$R_A^{14}$, S—$R_A^{14}$, $NR_A^{15}R_A^{16}$, CO—$NR_A^{15}R_A^{16}$ or $SO_2NR_A^{15}R_A^{16}$ radicals for $R_A^1$ or $R_A^2$ are composed, for example, of the groups CO—O, O, S, N, CO—N or $SO_2$—N and the radicals $R_A^{14}$, $R_A^{15}$ and $R_A^{16}$ which are described in detail below.

It is also possible for the two radicals $R_A^1$ and $R_A^2$ together to form a fused, optionally substituted, 5- or 6-membered, unsaturated or aromatic carbocyclic or heterocyclic system which may contain up to three heteroatoms selected from the group of O, N or S.

$R_A^{13}$ and $R_A^{13*}$ are, independently of one another, hydrogen, CN,
  halogen such as, for example, fluorine, chlorine, bromine or iodine,
  a branched or unbranched, optionally substituted $C_1$–$C_6$-alkyl radical, for example as described above for $R_G^1$, preferably methyl or trifluoromethyl or
  an optionally substituted aryl, arylalkyl, hetaryl or $C_3$–$C_7$-cycloalkyl radical or a CO—O—$R_A^{14}$, O—$R_A^{14}$, S—$R_A^{14}$, $NR_A^{15}R_A^{16}$, $SO_2NR_A^{15}R_A^{16}$ or CO—$NR^{415}R_A^{16}$ radical as in each case described above for $R_A^1$.

Preferred radicals for $R_A^{13}$ and $R_A^{13*}$ are the radicals hydrogen, F, Cl or a branched or unbranched, optionally substituted $C_1$–$C_6$-alkyl radical, optionally substituted aryl or arylalkyl or a CO—O—$R_A^{14}$, O—$R_A^{14}$, $NR_A^{15}R_A^{16}$, $SO^2$—$NR_A^{15}R_A^{16}$ or CO—$NR_A^{15}R_A^{16}$ radical.

A branched or unbranched, optionally substituted $C_1$–$C_6$-alkyl, $C_3$–$C_7$-cycloalkyl, alkylene-cycloalkyl, alkylene-$C_1$–$C_4$-alkoxy, $C_2$–$C_6$-alkenyl or $C_2$–$C_6$-alkynyl radical for $R_A^{14}$ in structural element A mean, for example, the corresponding radicals described above for $R_G^1$.

Optionally substituted aryl, arylalkyl, hetaryl or alkylhetaryl radicals for $R_A^{14}$ in structural element A mean, for example, the corresponding radicals described above for $R_G^1$.

Preferred radicals for $R_A^{14}$ are hydrogen, a branched or unbranched, optionally substituted $C_1$–$C_6$-alkyl radical and optionally substituted benzyl.

A branched or unbranched, optionally substituted $C_1$–$C_6$-alkyl or arylalkyl radical or an optionally substituted $C_3$–$C_7$-cycloalkyl, aryl, hetaryl or hetarylalkyl radical for $R_A^{15}$ or $R^{416}$ mean, independently of one another, for example the corresponding radicals described above for $R_A^{14}$.

The branched or unbranched, optionally substituted CO—$C_1$–$C_6$-alkyl, $SO_2$—$C_1$–$C_6$-alkyl, COO—$C_1$–$C_6$-alkyl, CO—NH—$C_1$–$C_6$-alkyl, COO-alkylene-aryl, CO—NH-alkylene-aryl, CO—NH-alkylene-hetaryl or $SO_2$-alkylene-aryl radicals or the optionally substituted CO-aryl, $SO_2$-aryl, CO—NH-aryl, CO—NH-hetaryl or CO-hetaryl radicals for $R_A^{15}$ or $R_A^{16}$ are composed, for example, of the appropriate groups —CO—, —$SO_2$—, —CO—O—, —CO—NH— and the appropriate branched or unbranched, optionally substituted $C_1$–$C_6$-alkyl, hetarylalkyl or arylalkyl radicals described above or the appropriate optionally substituted aryl or hetaryl radicals.

A radical —$(CH_2)_n$—$(X_A)_j$—$R_A^{12}$ for $R_A^3$ or $R_A^4$ means, independently of one another, a radical which is composed of the appropriate —$(CH_2)_n$—, $(X_A)_j$ and $R_A^{12}$ radicals. In these cases, n can be 0, 1, 2 or 3 and j can be 0 or 1.

$X_A$ is a doubly radical selected from the group of —CO—, —CO—N($R_X^1$)—, —N($R_X^1$)—CO—, —N($R_X^1$)—CO—N($R_X^{1*}$)—, —N($R_X^1$)—CO—O—, —O—, —S—, —$SO_2$—, —SO$_2$—N(R$_X^1$)—, —SO$_2$—O—, —CO—O—, —O—CO—, —O—CO—N(R$_X^1$)—, —N(R$_X^1$)— or —N(R$_X^1$)—SO$_2$—.

R$_A^{12}$ is hydrogen, a branched or unbranched, optionally substituted C$_1$–C$_6$ alkyl radical as described for R$_G^1$, an optionally C$_1$–C$_4$-alkyl- or aryl-substituted C$_2$–C$_6$-alkynyl or C$_2$–C$_6$-alkenyl radical, for example as described above for R$_L^9$, or a 3- to 6-membered, saturated or unsaturated heterocycle which is substituted by up to three identical or different radicals and which may contain up to three different or identical heteroatoms O, N, S, such as, for example, optionally substituted 2-pyridyl, 3-pyridyl, 4-pyridyl, 2-furyl, 3-furyl, 2-pyrrolyl, 3-pyrrolyl, 2-thienyl, 3-thienyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 3-pyrazolyl, 4-pyrazolyl, 5-pyrazolyl, 3-isothiazolyl, 4-isothiazolyl, 5-isothiazolyl, 2-imidazolyl, 4-imidazolyl, 5-imidazolyl, 3-pyridazinyl, 4-pyridazinyl, 5-pyridazinyl, 6-pyridazinyl, 2-(1,3,4)-thiadiazolyl, 2-(1,3,4)-oxadiazolyl, 3-isoxazolyl, 4-isoxazolyl, 5-isoxazolyl, triazinyl.

It is also possible for R$_A^{12}$ and R$_X^1$ and R$_X^{1*}$ together to form a saturated or unsaturated C$_3$–C$_7$-heterocycle which may optionally contain up to two other heteroatoms selected from the group O, S or N.

The R$_A^{12}$ radical preferably forms together with the R$_X^1$ and R$_X^{1*}$ radical a cyclic amine as C$_3$–C$_7$-heterocycle in the case where the radicals are bonded to the same nitrogen atom, such as, for example, N-pyrrolidinyl, N-piperidinyl, N-hexahydroazepinyl, N-morpholinyl or N-piperazinyl, it being possible for the free amine protons on heterocycles having free amine protons, such as, for example, N-piperazinyl, to be replaced by conventional amine protective groups such as, for example, methyl, benzyl, Boc (tert-butoxycarbonyl), Z (benzyloxycarbonyl), tosyl, —SO$_2$—C$_1$–C$_4$-alkyl, —SO$_2$-phenyl or —SO$_2$-benzyl.

A branched or unbranched, optionally substituted C$_1$–C$_6$-alkyl, C$_1$–C$_6$-alkoxyalkyl, C$_2$–C$_6$-alkenyl, C$_2$–C$_{12}$-alkynyl, CO—C$_1$–C$_6$-alkyl, CO—O—C$_1$–C$_6$-alkyl or SO$_2$—C$_1$–C$_6$-alkyl radical or an optionally substituted C$_3$–C$_7$-cycloalkyl, aryl, arylalkyl, CO—O—alkylene-aryl, CO-alkylene-aryl, CO-aryl, SO$_2$-aryl, hetaryl, CO-hetaryl or SO$_2$-alkylene-aryl radical for R$_X^1$ and R$_X^{1*}$ mean, independently of one another, for example the radicals described above for R$_L^{14}$ and R$_L^{14*}$.

Preferred radicals for R$_X^1$ and R$_X^{1*}$ are, independently of one another, hydrogen, methyl, cyclopropyl, allyl and propargyl.

R$_A^3$ and R$_A^4$ may also together form a 3- to 8-membered, saturated, unsaturated or aromatic N heterocycle which may additionally contain two other identical or different heteroatoms O, N or S, it being possible for the cyclic system optionally to be substituted or for another, optionally substituted, saturated, unsaturated or aromatic cyclic system to be fused to this cyclic system, R$_A^5$ is a branched or unbranched, optionally substituted C$_1$–C$_6$-alkyl, arylalkyl, C$_1$–C$_4$-alkyl-C$_3$–C$_7$-cycloalkyl or C$_3$–C$_7$-cycloalkyl radical or an optionally substituted aryl, hetaryl, heterocycloalkyl or heterocycloalkenyl radical, for example as described above for R$_G^4$, R$_G^5$ and R$_G^6$.

R$_A^6$ and R$_A^{6*}$ are, independently of one another, hydrogen, a branched or unbranched, optionally substituted C$_1$–C$_4$-alkyl radical such as, for example, optionally substituted methyl, ethyl, propyl, 1-methylethyl, butyl, 1-methylpropyl, 2-methylpropyl or 1,1-dimethylethyl, —CO—O—C$_1$–C$_4$-alkyl or —CO—C$_1$–C$_4$-alkyl radical such as, for example, composed of the group —CO—O— or —CO— and the C$_1$–C$_4$-alkyl radicals described above, arylalkyl radical as described above for R$_G^1$, —CO—O-alkylene-aryl or —CO-alkylene-aryl radical such as, for example, composed of the group —CO—O— or —CO— and the arylalkyl radicals described above, —CO—O-allyl or —CO-allyl radical, or C$_3$–C$_7$-cycloalkyl radical, for example as described above for R$_G^1$.

It is also possible for the two radicals R$_A^6$ and R$_A^{6*}$ in structural element I$_A^7$ together to form an optionally substituted, saturated or aromatic heterocycle which, in addition to the ring nitrogen, may contain up to two other different or identical heteroatoms O, N, S.

R$_A^7$ is hydrogen, —OH, —CN, —CONH$_2$, a branched or unbranched, optionally substituted C$_1$–C$_4$-alkyl radical, for example as described above for R$_A^6$, C$_1$–C$_4$-alkoxy, arylalkyl or C$_3$–C$_7$-cycloalkyl radical, for example as described above for R$_L^{14}$, a branched or unbranched, optionally substituted —O—CO—C$_1$–C$_4$-alkyl radical which is composed of the group —O—CO— and, for example, of the C$_1$–C$_4$-alkyl radicals described above, or an optionally substituted —O-alkylene-aryl, —O—CO-aryl, —O—CO-alkylene-aryl or —O—CO-allyl radical which is composed of the groups —O— or —O—CO— and, for example, of the corresponding radicals described above for R$_G^1$.

It is also possible for the two radicals R$_A^6$ and R$_A^7$ together to form an optionally substituted, unsaturated or aromatic heterocycle which, in addition to the ring nitrogen, may contain up to two other different or identical heteroatoms O, N, S.

A branched or unbranched, optionally substituted C$_1$–C$_4$-alkyl radical or an optionally substituted aryl or arylalkyl radical for R$_A^8$ in structural element A means, for example, the corresponding radicals described above for R$_A^{15}$, where the CO—C$_1$–C$_4$-alkyl, SO$_2$—C$_1$–C$_4$-alkyl, CO—O—C$_1$–C$_4$-alkyl, CO-aryl, SO$_2$-aryl, CO—O-aryl, CO-alkylene-aryl, SO$_2$-alkylene-aryl or CO—O-alkylene-aryl radicals for composed, in analogy to the other radicals, of the groups CO, SO$_2$ or COO and, for example, of the corresponding C$_1$–C$_4$-alkyl, aryl or arylalkyl radicals described above for R$_A^{15}$, and these radicals may optionally be substituted.

A branched or unbranched, optionally substituted C$_1$–C$_6$-alkyl radical or an optionally substituted aryl, arylalkyl, hetaryl or C$_3$–C$_7$-cycloalkyl radical in each case for R$_A^9$ or R$_A^{10}$ means, independently of one another, for example, the corresponding radicals described above for R$_A^{14}$, preferably methyl or trifluoromethyl.

A CO—O—R$_A^{14}$, O—R$_A^{14}$, S—R$_A^{14}$, SO$_2$—NR$_A^{15}$R$_A^{16}$, NR$_A^{15}$R$_A^{16}$ or CO—NR$_A^{15}$R$_A^{16}$ radical means in each case for R$_A^9$ or R$_A^{10}$, independently of one another, for example, the corresponding radicals discussed above for R$_A^{13}$.

It is also possible for the two radicals R$_A^9$ and R$_A^{10}$ together in the structural element I$_A^{14}$ to form a 5- to 7-membered saturated, unsaturated or aromatic carbocyclic or heterocyclic system which may contain up to three different or identical heteroatoms O, N, S and is optionally substituted by up to three identical or different radicals.

Substituents mean in this case in particular halogen, CN, a branched or unbranched, optionally substituted C$_1$–C$_4$-alkyl radical such as, for example, methyl or trifluoromethyl or the radicals O—$R_A^{14}$, S—$R_A^{14}$, $NR_A^{15}R_A^{16}$, CO—$NR^{A15}R_A^{16}$ or —$((R_A^8)HN)C=N—R_A^7$.

A branched or unbranched, optionally substituted $C_1$–$C_6$-alkyl radical or an optionally substituted aryl, arylalkyl, hetaryl, $C_3$–$C_7$-cycloalkyl radical or a CO—O—$R_A^{14}$, O—$R_A^{14}$, S—$R_A^{14}$, $NR_A^{15}R_A^{16}$, $SO_2$—$NR_A^{15}R_A^{16}$ or CO—$NR^{A15}R_A^{16}$ for $R_A^{11}$ means, for example, the corresponding radicals described above for $R_A^9$.

It is also possible for the two radicals $R_A^9$ and $R_A^{17}$ in the structural element $I_A^{16}$ together to form a 5- to 7-membered saturated, unsaturated or aromatic heterocycle which, in addition to the ring nitrogen, may contain up to three different or identical heteroatoms O, N, S and is optionally substituted by up to three identical or different radicals.

A branched or unbranched, optionally substituted $C_1$–$C_8$-alkyl, $C_2$–$C_6$-alkenyl, $C_2$–$C_6$-alkynyl, $C_1$–$C_5$-alkylene-$C_1$–$C_4$-alkoxy, mono- and bisalkylaminoalkylene or acylaminoalkylene radical or an optionally substituted aryl, heterocycloalkyl, heterocycloalkenyl, hetaryl, $C_3$–$C_7$-cycloalkyl, $C_1$–$C_4$-alkylene-$C_3$–$C_7$-cycloalkyl, arylalkyl, $C_1$–$C_4$-alkylene-heterocycloalkyl, $C_1$–$C_4$-alkylene-heterocycloalkenyl or hetarylalkyl radical or an —$SO_2$—$R_G^4$, —CO—$OR_G^4$, —CO—$NR_G^4R_G^{4*}$ or —CO—$R_G^4$ radical for $R_A^{18}$ and $R_A^{19}$ means, independently of one another, for example the radicals described above for $R_G^5$, preferably hydrogen or a branched or unbranched, optionally substituted $C_1$–$C_8$-alkyl radical.

$Z^1$, $Z^2$, $Z^3$, $Z^4$ are, independently of one another, nitrogen, C—H, C-halogen such as, for example, C—F, C—Cl, C—Br or C—I or a branched or unbranched, optionally substituted C—$C_1$–$C_4$-alkyl radical which is composed of a carbon radical and, for example, a $C_1$–$C_4$-alkyl radical described above for $R_A^6$, or a branched or unbranched, optionally substituted C—$C_1$–$C_4$-alkoxyl radical which is composed of a carbon radical and, for example, a $C_1$–$C_4$-alkoxy radical described above for $R_A^7$.

$Z^5$ is oxygen, sulfur or an $NR_A^8$ radical.

Preferred structural elements A are composed of at least one preferred radical of the radicals belonging to structural element A, while the remaining radicals may vary widely.

Particularly preferred structural elements A are composed of the preferred radicals of the structural element A.

In a preferred embodiment, the spacer structural element E means a structural element which consists of a branched or unbranched, optionally substituted and heteroatom-containing aliphatic $C_2$–$C_{30}$-hydrocarbon radical and/or of a 4- to 20-membered, optionally substituted and heteroatom-containing, aliphatic or aromatic mono- or polycyclic hydrocarbon radical.

In a particularly preferred embodiment, the spacer structural element E is a structural element of the formula $I_E$

   $I_E$ where $U_E$ is oxygen, sulfur or $NR_E^2$, h is 0 or 1, i is 0 or 1, $R_E^1$, $R_E^2$ are, independently of one another, hydrogen, a branched or branched, optionally substituted $C_1$–$C_6$-alkyl, $C_1$–$C_6$-alkoxyalkyl, $C_2$–$C_6$-alkenyl, $C_2$–$C_{12}$-alkynyl, CO—$C_1$–$C_6$-alkyl, CO—O—$C_1$–$C_6$-alkyl, CO—NH—$C_1$–$C_6$-alkoxyalkyl, CO—NH—$C_1$–$C_6$-alkyl or $SO_2$—$C_1$–$C_6$-alkyl radical or an optionally substituted hetaryl, arylalkyl, $C_3$–$C_7$-cycloalkyl, CO—O-alkylene-aryl, CO—NH-alkylene-aryl, CO-alkylene-aryl, CO-aryl, CO—NH-aryl, $SO_2$-aryl, CO-hetaryl, $SO_2$-alkylene-aryl, $SO_2$-hetaryl or $SO_2$-alkylene-hetaryl radical, $E_1$ is a structural element of the formula $I_{E1}$

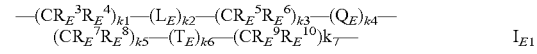   $I_{E1}$ where k2, k4, k6 are 0 or 1, k1, k3, k5, k7 are 0, 1 or 2, $R_E^3$, $R_E^4$, $R_{E5}$, $R_E^6$, $R_E^7$, $R_E^8$, $R_E^9$, $R_E^{10}$ are, independently of one another, hydrogen, halogen, a hydroxyl group, a branched or unbranched, optionally substituted $C_1$–$C_6$-alkyl, $C_2$–$C_6$-alkenyl, $C_2$–$C_6$-alkynyl or alkylene-cycloalkyl radical, a —$(CH_2)_x$—$(Y_E)_z$$R_E^{11}$ radical, an optionally substituted $C_3$–$C_7$-cycloalkyl, aryl, arylalkyl, hetaryl or hetarylalkyl radical or, independently of one another, in each case two radicals $R_E^3$ and $R_E^4$ or $R_E^5$ and $R_E^6$ or $R_E^7$ and $R_E^8$ or $R_E^9$ and $R_E^{10}$ together are a 3- to 7-membered, optionally substituted, saturated or unsaturated carbo- or heterocyclic system which may contain up to three heteroatoms from the group of O, N or S, x is 0, 1, 2, 3 or 4, z is 0 or 1, $Y_E$ is —CO—, —CO—N($R_y^2$)—, —N($R_y^2$)—CO—, —N($R_y^2$)—CO—N($R_y^{2*}$)—, —N($R_y^2$)—CO—O—, —O—, —S—, —$SO_2$—, —$SO_2$—N($R_y^2$)—, —$SO_2$—O—, —CO—O—, —O—CO—, —O—CO—N($R_y^2$)—, —N($R_y^2$)— or —N($R_y^2$)—$SO_2$—, $R_y^2$, $R_y^{2*}$ are, independently of one another, hydrogen, a branched or unbranched, optionally substituted $C_1$–$C_6$-alkyl, $C_2$–$C_8$-alkynyl, $C_2$–$C_6$-alkenyl, CO—$C_1$–$C_6$-alkyl, CO—O—$C_1$–$C_6$-alkyl or $SO_2$—$C_1$–$C_6$-alkyl radical or an optionally substituted hetaryl, hetarylalkyl, arylalkyl, $C_3$–$C_7$-cycloalkyl, CO—O-alkylene-aryl, CO-alkylene-aryl, CO-aryl, $SO_2$-aryl, CO-hetaryl or $SO_2$-alkylene-aryl radical, $R_E^{11}$ is hydrogen, a hydroxyl group, CN, halogen, a branched or unbranched, optionally substituted $C_1$–$C_6$-alkyl radical, an optionally substituted $C_3$–$C_7$-cycloalkyl, aryl, hetaryl or arylalkyl radical, an optionally $C_1$–$C_4$-alkyl- or aryl-substituted $C_2$–$C_6$-alkynyl or $C_2$–$C_6$-alkenyl radical, an optionally substituted $C_6$–$C_{12}$-bicycloalkyl, $C_1$–$C_6$-alkylene-$C_6$–$C_{12}$-bicycloalkyl, $C_7$–$C_{20}$-tricycloalkyl or $C_1$–$C_6$-alkylene-$C_7$–$C_{20}$-tricycloalkyl radical, or a 3- to 8-membered, saturated or unsaturated heterocyclic system which is substituted by up to three identical or different radicals and which may contain up to three different or identical heteroatoms O, N, S, it being possible for two radicals together to be a fused, saturated, unsaturated or aromatic carbocyclic or heterocyclic system which may contain up to three different or identical heteroatoms O, N, S, and it being possible for the cyclic system optionally to be substituted or for another, optionally substituted, saturated, unsaturated or aromatic cyclic system to be fused to this cyclic system, or the $R_E^{11}$ radical forms together with $R_y^2$ or $R_y^{2*}$ a saturated or unsaturated $C_3$–$C_7$-heterocyclic system which may optionally contain up to two other heteroatoms selected from the group of O, S or N, $L_E$, $T_E$ are, independently of one another, CO, CO—$NR_E^{12}$, $NR_E^{12}$—CO, sulfur, SO, $SO_2$, $SO_2$—$NR_E^{12}$, $NR_E^{12}$—$SO_2$, CS, CS—$NR_E^{12}$, $NR_E^{12}$—CS, CS—O, O—CS, CO—O, O—CO, oxygen, ethynylene, $CR_E^{13}$—O—$CR_E^{14}$, $C(=CR_E^{13}R_E^{14})$, $CR_E^{13}=CR_E^{14}$, —$CR_E^{13}(OR_E^{15})$—$CHR_E^{14}$—, —$CHR_E^{13}$—$CR_E^{14}(OR_E^{15})$—, $R_E^{12}$ is hydrogen, a branched or unbranched, optionally substituted $C_1$–$C_6$-alkyl, $C_2$–$C_6$-alkenyl, $C_2$–$C_8$-alkynyl, an optionally substituted $C_3$–$C_7$-cycloalkyl, hetaryl, arylalkyl or hetarylalkyl radical or a CO—$R_E^{16}$, COOR$_E^{16}$ or $SO_2$—$R_E^{16}$ radical, $R_E^{13}$, $R_E^{14}$ are, independently of one another, hydrogen, a hydroxyl group, a branched or unbranched, optionally substituted $C_1$–$C_6$-alkyl, $C_1$–$C_4$-alkoxy, $C_2$–$C_6$-alkenyl, $C_2$–$C_6$-alkynyl or alkylene-cycloalkyl radical or an optionally substituted $C_3$–$C_7$-cycloalkyl, aryl, arylalkyl, hetaryl or hetarylalkyl radical, $R_E^{15}$ is hydrogen, a branched or unbranched, optionally substituted $C_1$–$C_6$-alkyl, $C_2$–$C_6$-alkenyl, $C_2$–$C_6$-alkynyl or alkylene-cycloalkyl radical or an optionally substituted $C_3$–$C_7$-cycloalkyl, aryl, arylalkyl, hetaryl or hetarylalkyl radical, $R_E^{16}$ is hydrogen, a hydroxyl group, a branched or unbranched, optionally substituted $C_1$–$C_6$-alkyl, $C_2$–$C_6$-alkenyl, $C_2$–$C_6$-alkynyl or $C_1$–$C_5$-alkylene-$C_1$–$C_4$-alkoxy radical, or an optionally substituted aryl, heterocycloalkyl, heterocycloalkenyl, hetaryl, $C_3$–$C_7$-cycloalkyl-, $C_1$–$C_4$-alkylene-$C_3$–$C_7$-cycloalkyl, arylalkyl, $C_1$–$C_4$-alkylene-$C_3$–$C_7$-heterocycloalkyl, $C_1$–$C_4$-alkylene-$C_3$–$C_7$-heterocycloalkenyl or hetarylalkyl radical and $Q_E$ is an optionally substituted 4- to 11-membered mono- or polycyclic aliphatic or aromatic hydrocarbon which may contain up to 6 double bonds and up to 6 identical or different heteroatoms selected from the group N, O or S, it being possible for the ring carbons or ring nitrogens optionally to be substituted.

$U_E$ in structural element E is oxygen, sulfur or $NR_E^2$, with sulfur or $NR_E^2$ being preferred and $NR_E^2$ being particularly preferred.

The coefficients h and i are, independently of one another, 0 or 1.

In a preferred embodiment, the coefficient i is 1.

A branched or unbranched, optionally substituted $C_1$–$C_6$-alkyl, $C_1$–$C_6$-alkoxyalkyl, $C_2$–$C_6$-alkenyl, $C_2$–$C_{12}$-alkynyl or arylalkyl radical or an optionally substituted aryl, hetaryl or $C_3$–$C_7$-cycloalkyl for $R_E^1$ and $R_E^2$ in structural element E means, independently of one another, for example the corresponding radicals described above for $R_L^{14}$.

The branched or unbranched, optionally substituted CO—$C_1$–$C_6$-alkyl, CO—O—$C_1$–$C_6$-alkyl, CO—NH—$C_1$–$C_6$-alkoxyalkyl, CO—NH—$C_1$–$C_6$-alkyl or $SO_2$—$C_1$–$C_6$-alkyl radicals or the optionally substituted CO—O-alkylene-aryl, CO—NH-alkylene-aryl, CO-alkylene-aryl, CO-aryl, CO—NH-aryl, $SO_2$-aryl, CO-hetaryl, $SO_2$-alkylene-aryl, $SO_2$-hetaryl or $SO_2$-alkylene-hetaryl radicals for $R^{E1}$ and $R_E^2$ are composed, independently of one another, for example of the appropriate groups CO, COO, CONH or $SO_2$ and the appropriate radicals mentioned above.

Preferred radicals for $R_E^1$ or $R_E^2$ are, independently of one another, hydrogen, a branched or unbranched, optionally substituted $C_1$–$C_6$-alkyl, $C_1$–$C_6$-alkoxy, $C_2$–$C_6$-alkenyl, $C_2$–$C_{12}$-alkynyl or arylalkyl radical, or an optionally substituted hetaryl or $C_3$–$C_7$-cycloalkyl radical.

Particularly preferred radicals for $R_E^1$ or $R_E^2$ are hydrogen, methyl, cyclopropyl, allyl or propargyl.

$E_1$ means a structural element of the formula $I_{E1}$

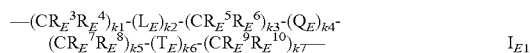

where the coefficients k2, k4, or k6 can be 0 or 1 and k1, k3, k5 or k7 can be 0, 1 or 2.

A branched or unbranched, optionally substituted $C_1$–$C_6$-alkyl, $C_2$–$C_6$-alkenyl, $C_2$–$C_6$-alkynyl or alkylene-cycloalkyl radical or an optionally substituted $C_3$–$C_7$-cycloalkyl, aryl, arylalkyl, hetaryl or hetarylalkyl radical for $R_E^3$, $R_E^4$, $R_E^5$, $R_E^6$, $R_E^7$, $R_E^8$, $R_E^9$ or $R_E^{10}$ mean, independently of one another, for example the corresponding radicals mentioned above for $R_L^1$.

It is also possible in each case independently of one another for two radicals $R_E^3$ and $R_E^4$ or $R_E^5$ and $R_E^6$ or $R_E^7$ and $R_E^8$ or $R_E^9$ and $R_E^{10}$ together to form a 3- to 7-membered, optionally substituted, saturated or unsaturated carbo- or heterocyclic system which may contain up to three heteroatoms from the group of O, N or S.

The —$(CH_2)_x$-$(Y_E)_z$—$R_E^{11}$ radical is composed of a $C_0$–$C_4$-alkylene radical, optionally a linking element $Y_E$ selected from the group of —CO—, —CO—$N(R_y^2)$—, —$N(R_y^2)$—CO—, —$N(R_y^2)$—CO—$N(R_y^{2*})$—, —$N(R_y^2)$—CO—O—, —O—, —S—, —$SO_2$—, —$SO_2$—$N(R_y^2)$—, —$SO_2$—O—, —CO—O—, —O—CO—, —O—CO—$N(R_y^2)$—, —$N(R_y^2)$— or —$N(R_y^2)$—$SO_2$—, preferably selected from the group of —CO—$N(R_y^2)$—, —$N(R_y^2)$—CO—, —O—, —$SO_2$—$N(R_y^2)$—, —$N(R_y^2)$— or —$N(R_y^2)$—$SO_2$—, and the radical $R_E^{11}$, where $R_y^2$ and $R_y^{2*}$ are, independently of one another, hydrogen, a branched or unbranched, optionally substituted $C_1$–$C_6$-alkyl, $C_2$–$C_6$-alkenyl, $C_2$–$C_8$-alkynyl, CO—$C_1$–$C_6$-alkyl, CO—O—$C_1$–$C_6$-alkyl or $SO_2$—$C_1$–$C_6$-alkyl radical or an optionally substituted hetaryl, hetarylalkyl, arylalkyl, $C_3$–$C_7$-cycloalkyl, CO—O-alkylene-aryl, CO-alkylene-aryl, CO-aryl, $SO_2$-aryl, CO-hetaryl or $SO_2$-alkylene-aryl radical, preferably independently of one another hydrogen, methyl, cyclopropyl, allyl, propargyl, and $R_E^{11}$ is hydrogen, a hydroxyl group, CN, halogen, a branched or unbranched, optionally substituted $C_1$–$C_6$-alkyl radical, an optionally substituted $C_3$–$C_7$-cycloalkyl, aryl, hetaryl or arylalkyl radical, an optionally $C_1$–$C_4$-alkyl- or aryl-substituted $C_2$–$C_6$-alkynyl or $C_2$–$C_6$-alkenyl radical, an optionally substituted $C_6$–$C_{12}$-bicycloalkyl, $C_1$–$C_6$-alkylene-$C_6$–$C_{12}$-bicycloalkyl, $C_7$–$C_{20}$-tricycloalkyl or $C_1$–$C_6$-alkylene-$C_7$–$C_{20}$-tricycloalkyl radical, or a 3- to 8-membered, saturated or unsaturated heterocyclic system which is substituted by up to three identical or different radicals and which may contain up to three different or identical heteroatoms O, N, S, it being possible for two radicals together to be a fused, saturated, unsaturated or aromatic carbocyclic or heterocyclic system which may contain up to three different or identical heteroatoms O, N, S, and it being possible for the cyclic system optionally to be substituted or for another, optionally substituted, saturated, unsaturated or aromatic cyclic system to be fused to this cyclic system, such as, for example, optionally substituted 2-pyridyl, 3-pyridyl, 4-pyridyl, 2-furyl, 3-furyl, 2-pyrrolyl, 3-pyrrolyl, 2-thienyl, 3-thienyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 3-pyrazolyl, 4-pyrazolyl, 5-pyrazolyl, 3-isothiazolyl, 4-isothiazolyl, 5-isothiazolyl, 2-imidazolyl, 4-imidazolyl, 5-imidazolyl, 3-pyridazinyl, 4-pyridazinyl, 5-pyridazinyl, 6-pyridazinyl, 2-(1,3,4)-thiadiazolyl, 2-(1,3,4)-oxadiazolyl, 3-isoxazolyl, 4-isoxazolyl, 5-isoxazolyl or triazinyl.

It is also possible for $R_E^{11}$ and $R_y^2$ or $R_y^{2*}$ together to form a saturated or unsaturated $C_3$–$C_7$-heterocycle which may optionally contain up to two other heteroatoms selected from the group of O, S or N.

The $R_E^{11}$ and $R_y^2$ or $R_y^{2*}$ radicals preferably together form a cyclic amine as $C_3$–$C_7$-heterocycle in the case where the radicals are bonded to the same nitrogen atom, such as, for example, N-pyrrolidinyl, N-piperidinyl, N-hexahydroazepinyl, N-morpholinyl or N-piperazinyl, it being possible for the free amine protons on heterocycles having free amine protons, such as, for example, N-piperazinyl, to be replaced by conventional amine protective groups such as, for example, methyl, benzyl, Boc (tert-butoxycarbonyl), Z (benzyloxycarbonyl), tosyl, —$SO_2$—$C_1$–$C_4$-alkyl, —$SO_2$-phenyl or —$SO_2$-benzyl.

Preferred radicals for $R_E^3$, $R_E^4$, $R_E^5$, $R_E^6$, $R_E^7$, $R_E^8$, $R_E^9$ or $R_E^{10}$ are, independently of one another, hydrogen, a branched or unbranched, optionally substituted $C_1$–$C_6$-alkyl radical, optionally substituted aryl or the —$(CH^2)_x$-$(Y_E)_z$— $R_E^{11}$ radical.

In a preferred embodiment of the structural element $E_1$, one radical of $R_E^3$ and $R_E^4$ or $R_E^5$ and $R_E^6$ or $R_E^7$ and $R_E^8$ or $R_E^9$ and $R_E^{10}$ is, independently of one another, hydrogen or methyl.

In a particularly preferred embodiment of the structural element $E_1$, the $R_E^3$, $R_E^4$, $R_E^5$, $R_E^6$, $R_E^7$, $R_E^8$, $R_E^9$ or $R_E^{10}$ radicals are, independently of one another, hydrogen or methyl.

$L_E$ and $T_E$ are, independently of one another, CO, CO—$NR_E^{12}$, $NR_E^{12}$—CO, sulfur, SO, $SO_2$, $SO_2$—$NR_E^{12}$, $NR_E^{12}$—$SO_2$, CS, CS—$NR_E^{12}$, $NR_E^{12}$—CS, CS—O, O—CS, CO—O, O—CO, oxygen, ethynylene, $CR_E^{13}$—O—$CR_E^{14}$, C(=$CR_E^{13}R_E^{14}$), $CR_E^{13}$=$CR_E^{14}$, —$CR_E^{13}$($OR_E^{15}$)—$CHR_E^{14}$— or —$CHR_E^{13}$—$CR_E^{14}(OR_E^{15})$—, preferably CO—$NR_E^{12}$, $NR_E^{12}$—CO, $SO_2$—$NR_E^{12}$, $NR_E^{12}$—$SO_2$ and oxygen.

$R_E^{12}$ is hydrogen, a branched or unbranched, optionally substituted $C_1$–$C_6$-alkyl, $C_2$–$C_6$-alkenyl or $C_2$–$C_8$-alkynyl radical or an optionally substituted $C_3$–$C_7$-cycloalkyl, hetaryl, arylalkyl or hetarylalkyl radical, for example as described above in each case for $R_L^1$, or CO—$R_E^{16}$, COOR$^{E16}$ or $SO_2$—$R_E^{16}$ radical, preferably hydrogen, methyl, allyl, propargyl and cyclopropyl.

A branched or unbranched, optionally saturated $C_1$–$C_6$-alkyl, $C_2$–$C_6$-alkenyl or $C_2$–$C_6$-alkynyl radical or an optionally substituted $C_3$–$C_7$-cycloalkyl, aryl, arylalkyl, hetaryl or hetarylalkyl radical for $R_E^{13}$, $R_E^{14}$ or $R_E^{15}$ means, independently of one another, for example the corresponding radicals described above for $R_L^1$.

A branched or unbranched, optionally substituted $C_1$–$C_4$-alkoxy radical for $R_E^{13}$ or $R_E^{14}$ means, independently of one another, for example the $C_1$–$C_4$-alkoxy radicals described for $R_A^{14}$.

Preferred alkylene-cycloalkyl radicals for $R_E^{13}$, $R_E^{14}$ or $R^{E15}$ are, independently of one another, for example the $C_1$–$C_4$-alkylene-$C_3$–$C_7$-cycloalkyl radicals described above for $R_L^1$.

A branched or unbranched, optionally substituted $C_1$–$C_6$-alkyl, $C_2$–$C_6$-alkenyl, $C_2$–$C_6$-alkynyl or $C_1$–$C_5$-alkylene-$C_1$–$C_4$-alkoxy radical, or an optionally substituted aryl, heterocycloalkyl, heterocycloalkenyl, hetaryl, $C_3$–$C_7$-cycloalkyl, $C_1$–$C_4$-alkylene-$C_3$–$C_7$-cycloalkyl, arylalkyl, $C_1$–$C_4$-alkylene-$C_3$–$C_7$-heterocycloalkyl, $C_1$–$C_4$-alkylene-$C_3$–$C_7$-heterocycloalkenyl or hetarylalkyl radical for $R_E^{16}$ means, for example, the corresponding radicals described above for $R_G^4$.

An optionally substituted 4- to 11-membered mono- or polycyclic aliphatic or aromatic hydrocarbon which may contain up to 6 double bonds and up to 6 identical or different heteroatoms selected from the group of N, O, S, it being possible for the ring carbons or ring nitrogens optionally to be substituted, for $Q_E$ preferably means optionally substituted arylene such as, for example, optionally substituted phenylene or naphthylene, optionally substituted hetarylene such as, for example, the radicals

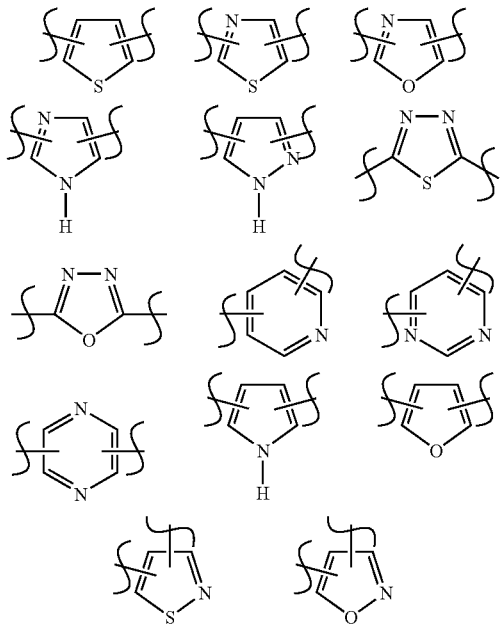

and their substituted or fused derivatives, or radicals of the formulae $I_E^1$ to $I_E^{11}$

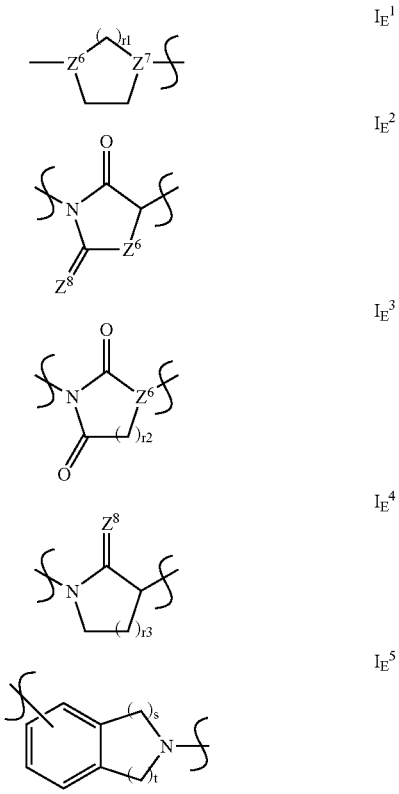

it being possible for the radicals to be incorporated in both orientations.

$Z^6$ and $Z^7$ are, independently of one another, CH or nitrogen.

$Z^8$ is oxygen, sulfur or NH $Z^9$ is oxygen, sulfur or $NR_E^{19}$.

r1, r2, r3 and t are, independently of one another, 0, 1, 2 or 3.

s and u are, independently of one another, 0, 1 or 2.

$Q_E$ is particularly preferably optionally substituted phenylene, a radical and their substituted or fused derivatives, or radicals of the formulae $I_E^1$, $I_E^2$, $I_E^3$, $I_E^4$ and $I_E^7$, it being possible for the radicals to be incorporated in both orientations.

$R_E^{17}$ and $R_E^{18}$ are, independently of one another, hydrogen, —NO$_2$, —NH$_2$, —CN, —COOH, a hydroxyl group, halogen, a branched or unbranched, optionally substituted $C_1$–$C_6$-alkyl, $C_1$–$C_4$-alkoxy, $C_2$–$C_6$-alkenyl, $C_2$–$C_6$-alkynyl or alkylene-cycloalkyl radical or an optionally substituted $C_3$–$C_7$-cycloalkyl, aryl, arylalkyl, hetaryl or hetarylalkyl radical as described above in each case.

$R_E^{19}$ is, independently of one another, hydrogen, a branched or unbranched, optionally substituted $C_1$–$C_6$-alkyl, $C_1$–$C_6$-alkoxyalkyl, $C_3$–$C_{12}$-alkynyl, CO—$C_1$–$C_6$-alkyl, CO—O—$C_1$–$C_6$-alkyl or SO$_2$—$C_1$–$C_6$-alkyl radical or an optionally substituted $C_3$–$C_7$-cycloalkyl, aryl, arylalkyl, CO—O-alkylene-aryl, CO-alkylene-aryl, CO-aryl, SO$_2$-aryl, hetaryl, CO-hetaryl or SO$_2$-alkylene-aryl radical, preferably hydrogen or a branched or unbranched, optionally substituted $C_1$–$C_6$-alkyl radical.

Preferred structural elements E are composed of at least one preferred radical of the radicals belonging to the structural element E, while the remaining radicals may vary widely.

Particularly preferred structural elements E are composed of the preferred radicals of the structural element E.

Preferred structural elements B are composed either of the preferred structural element A, while E may vary widely, or of the preferred structural element E, while A may vary widely.

The compounds of the formula I and the intermediates for preparing them may have one or more asymmetric substituted carbon atoms. The compounds may be in the form of pure enantiomers or pure diastereomers or a mixture thereof. The use of an enantiomerically pure compound as active substance is preferred.

The compounds of the formula I may also exist in other tautomeric forms.

The compounds of the formula I may also be in the form of physiologically tolerated salts.

The compounds of the formula I may also be in a form as prodrugs in which the compounds of the formula I are liberated under physiological conditions. Reference may be made here by way of example to group T in the structural element L, which in some cases contains groups which can be hydrolyzed under physiological conditions to a free carboxyl group. Derivatized structural elements B and A which release the structural element B or A under physiological conditions are also suitable.

In preferred compounds of the formula I, in each case one of the three structural elements B, G or L has the preferred range, while the remaining structural elements may vary widely.

In particularly preferred compounds of the formula I, in each case two of the three structural elements B, G or L have the preferred range, while the remaining structural elements may vary widely.

In very particularly preferred compounds of the formula I, in each case all three structural elements B, G or L have the preferred range, while the remaining structural element may vary widely.

Preferred compounds of the formula I have, for example, the preferred structural element G, while the structural elements B and L may vary widely.

In particularly preferred compounds of the formula I, for example B is replaced by the structural element A-E-, and the compounds have, for example, the preferred structural element G and the preferred structural element A, while the structural elements E and L may vary widely.

Further particularly preferred compounds have, for example, the preferred structural element G and the preferred structural element A, while the structural elements E and L may vary widely. Very particularly preferred compounds of the formula I in which A-E- is B- are listed below, where the number in front of the block of text is the number of an individualized compound of the formula I, and in the A-E-G-L block of text the abbreviations separated by a dash in each case represent a single structural element A, E, G or L, and the meaning of the abbreviations of the structural elements is explained after the table.

1 imhs-m24thizman2-mes-oxal
2 dmam-ams2-5pho-zlys
3 pyr-dimephmep-eoco-psdab
4 imhs-diphmem-baeo-betadcph
5 imhs-24thizman2-men-zdabs
6 piraz-dis-5pho-aspbzla
7 pippy-m24thizman2-eoco-betadcph
8 2py-eta-no1-psdap
9 bim-pazin-oem-zdapee
10 chmhs-dimephmep-5pho-psdap
11 2py-mepipen2-imo-zdabs
12 bimhs-m24thiman2-hso-zdap
13 pippy-din-meo-bsdap
14 2py-mepipe-meo-psdab
15 2py-m25thiz-meo-betapy
16 amim-dis-ocho-osdap
17 imhs-dimephmep-5amo-aspbzla
18 me2py-eta-meo-mezphe
19 bzl-pazin-men-mezphe
20 dpam-mepipe2-sem-nbetabnaphth
21 2py-25oxman2-emo-aspibua
22 2pmhs-din-paco-psdab
23 mam2py-dimephmep-pyo-dfzdap
24 mam2py-m24thiz-no2-aspibua
25 imhs-thizn-men-betadcph
26 phpip-din-no2-betapy
27 tolhs-mepipe-mmen-betadcph
28 mam2py-dis-no2-psdab
29 amim-pazin-meteto-oxal
30 bim-pazin-no1-zdap
31 impy-pyma2-chexo-betainyl
32 mam2py-trias-eoco-aspibua
33 imhs-diphmem-imo-csdap
34 imhs-props-chexo-bhsdab
35 ec-diaz-emo-bsdap
36 mam2py-tetradi-oem-bsdap
37 imhs-diphmem-5-pho-csdap
38 thpym-mepazin-eoco-asppha
39 bimhs-m25thiman2-men-dfzdap
40 me2py-diphmep-fo-bphabs
41 ibhs-pazin-ocho-bphabs
42 bhs-pipmea-ocho-tsdap
43 morhs-diphmem-cnmo-betadcph
44 ppy-dimen-oem-betainyl
45 impy-din-no1-aspibua
46 menim-ams2-eoco-zdab
47 mam2py-amo3-baeo-glupha
48 bhs-edian2-no2-psdab
49 am4py-am2-sem-nbeta34dimeoph
50 pippy-pyma2-imo-bphabs
51 me2py-pymea-oem-zlys
52 imhs-edian2-ocho-psdap
53 piraz-dis-ocho-osdap
54 me2py-dis-napo-betaet
55 thpym-diphmep-emo-betapy
56 thpym-25thiman2-aco-zorn
57 bzl-m24thizman2-ocho-psdap
58 bzl-pipa-meo-zdab
59 tolhs-edian2-chexo-zdapee
60 piraz-25oxman2-imo-ibsdap
61 bim-amn2-5pho-betapy
62 bimhs-mepazin-meo-aspibua
63 2py-pazin-5pho-bsdap
64 amim-ams2-meto-aspibua
65 bhs-diphmem-emo-bsdap
66 morhs-pazin-eoco-bhsdab
67 phhs-dis-fo-mezphe
68 am2py-mepipen2-oeto-aspaba
69 me2py-2pazin-fo-zdab
70 chmhs-pipmea-napo-asppha
71 piraz-eta2s-5pho-bhsdap
72 pippy-pazi2n-hso-csdap
73 pippy-tetradi-meo-betadcph
74 am2py-pyma2-5amo-aspbzla
75 2py-edia2-sem-nbetabnaphth
76 amim-mepipe2-sem-nzdap
77 bim-amn3-fo-zlys
78 mam2py-amn2-5amo-bphabs
79 dmam-ams2-cnmo-zdabs
80 thpym-mepipe-4amo-zlys
81 impy-24thiz-mmen-thizzdap
82 bhs-edian2-oem-bnsdap
83 4pmhs-edia2-oem-nbetameph
84 hythpym-24thiz-meo-zlys
85 bhs-pazin-oem-bhsdap
86 piraz-25oxman2-no1-oxal
87 im-pipa-ocho-betapy
88 im-mea2s-napo-csdap
89 imhs-amn2-meo-bnsdap
90 2py-tridi-5amo-bsdap
91 pippy-m24thizman2-oem-bhsdap
92 im-pnymea-5pho-asppha
93 mam2py-m24thizman2-no2-ppsdap
94 chmhs-thizn-napo-psdapee
95 amim-diphmep-5amo-bhsdap
96 Amim-amn3-napo-betainyl
97 morhs-amn3-ocho-zlys
98 am2py-tetradi-eoco-zdabs
99 amim-25thizman2-napo-aspbzla
100 bim-m24oxman2-mmen-zdabs
101 imhs-24thizman2-emo-asppha
102 bim-25oxman2-mecpo-glyzdap
103 thpym-mepipe-meo-zdap
104 mam2py-pyma2-meto-bhsdab
105 am-25thizman2-napo-zdab
106 piraz-24thiz-baeo-psdab
107 ibhs-propa2s-5amo-glubzla 108 cl3pyme-diphmem-chexo-betaet
109 2py-edian2-eoco-bnsdap
110 prhs-dimephmep-no2-zdap
111 amthiaz-pipmea-emo-glyzdap betainyl
112 me2py-mepipe-eoco-bnsdap
113 amim-diphmem-meo-bhsdab
114 dmam-amn3-mes-betainyl
115 piraz-dimephmep-ocho-zlys
116 im-2pazin-mes-bphabs
117 impy-ams2-napo-tsdap
118 piraz-pipa-5amo-betaet
119 bzl-edia2-oem-npsdap
120 bhs-mepipe-no2-psdap
121 hythpym-24thiman-napo-aspibua
122 hythpym-dich-mes-psdab
123 gua-24thizman2-imo-aspibua
124 imhs-din-pro-csdap
125 bhs-pymea-meo-aspibua
126 me2py-24thiz-fo-bhsdap
127 dhim-eta-emo-betapy
128 hythpym-am3-sem-nzdab
129 phhs-dimephmep-oem-tsdap
130 bim-tetradi-chexo-zlys
131 bimhs-pnymea-ocho-zdap
132 thpym-dimephmem-men-betaet
133 bhs-dimen-chexo-betadcph
134 imhs-n2nme2n-hso-zlys
135 2pmhs-am2-oem-nbeta34dimeoph
136 deam-dis-5amo-aspibua
137 bhs-edian2-no2-bphabs
138 2py-mepipe-eoco-zdap
139 me2py-m24oxman2-5amo-bphabs
140 impy-mepazin-emo-betaet
141 tolhs-edia2-sem-nbeta34dimeoph
142 bim-eta-no2-psdap
143 im-pipmes-cpeo-zdap
144 pyraz-n2o2n-ocho-aspibua
145 amim-pipa-mecpo-zdap
146 bhs-am2-oem-npsdap
147 deam-edian2-mes-psdap
148 me2py-eta2s-meo-bhsdab
149 bimhs-25thiz-cpro-aspibua
150 hythpym-amn3-eoco-asppha
151 bhs-tetradi-4amo-zdabs
152 2py-dimephmem-chexo-glyzdap
153 bimhs-ams2-imo-ibsdap
154 imhs-pazin-ocho-bsdap
155 dmam-pipa-mecpo-betainyl
156 me2py-24thiz-oem-betapy
157 bim-pyma2-mes-dfzdap
158 mam2py-pipmeo-5amo-bhsdab
159 amim-am3diaz-cnmo-aspbzla
160 am2py-amn3-oem-ppsdap
161 edothpym-dis-meto-bphabs
162 amthiaz-dimephmem-eocobetainyl
163 2py-m25thiz-mes-aspbzla
164 piraz-trias-napo-zdab
165 mepip-pymea-no1-psdab
166 pippy-tridi-no2-betadcph
167 bhs-edian2-no2-bhsdap
168 pyraz-din-meo-betapy
169 pyraz-dimen-paco-bsdap
170 chhs-mepipe-fo-mezphe
171 hythpym-tetradi-ocho-betainyl
172 dhim-24thizman2-pro-bnsdap
173 me2py-amn3-napo-aspbzla
174 am2py-mepipe-5pho-bnsdap
175 amim-ams2-no2-betapy
176 mam2py-dich-oem-betapy
177 inhs-25thiz-pheo-glyzdap
178 thpym-amn2-mes-zdab
179 nmhs-amn2-mmen-asppha
180 dmam-tetradi-imo-glubzla
181 me2py-24thizman2-ocho-bhsdap
182 bhs-pazin-ocho-zdab
183 dmbim-pnymea-no2-mezphe
184 hythpym-pnymea-5pho-csdap
185 dhim-pnymea-meto-zlys
186 bim-tetradi-cpro-osdap
187 cl3pyme-mepipen2-meo-aspbzla
188 am4py-pentadi-mes-zdapee
189 impy-m25thiz-mes-zdab
190 prhs-thizo-aco-betadcph
191 piraz-m25thiz-oem-bsdap
192 pippy-n2o2n-mmen-psdap
193 tolhs-amo2-meo-glupha
194 impy-butn-pheo-csdap
195 thpym-25oxman2-men-aspibua
196 bim-edian2-mes-bnsdap
197 amim-tetradi-eoco-aspbzla
198 tolhs-m25oxman2-4amo-aspbzla
199 im-m24thiman2-chexo-zdap
200 me2py-amo2-mes-bhsdap
201 am2py-mepipen2-5pho-psdab
202 piraz-edian2-eoco-zdap
203 dhim-pipa-meo-aspibua
204 ec-eta2s-ocho-glyzdap
205 hythpym-am3-sem-nzdab
206 pippy-24oxman2-imo-bhsdap
207 pippy-24thizman2-emo-betadcph
208 bzl-din-fo-betapy
209 imhs-diphmep-men-asppha
210 thpym-edian2-no1-psdab
211 impy-mepipen2-napo-glupha
212 moegua-mepipe-pro-bhsdab
213 hythpym-amn3-chexo-bhsdab
214 piraz-eta-no1-betapy
215 imhs-ams2-eoco-csdap
216 hythpym-mepipe-aco-aval
217 bim-amn2-no1-zdap
218 bzl-pnymea-imo-bhsdap
219 thpym-edian2-ocho-psdab
220 bhs-m24thizman2-5amo-csdap
221 bz-dimephmem-4pho-aval
222 dhim-25thiz-hso-aspibua
223 2py-edian2-eoco-bsdap
224 thpym-pazin-no1-betapy
225 bhs-m24thiz-daco-mezphe
226 bim-edian2-meo-zdab
227 emnim-pymea-mes-bphabs
228 impy-mea-meo-ibsdap
229 impy-dimen-mes-mezphe
230 imhs-amn2-mes-zdab
231 piraz-diaz-cno-betainyl
232 impy-m24thizman2-emo-bsdap
233 amim-24thiz-meo-bhsdap
234 am2py-mepipe-5amo-basdap
235 amim-trias-paco-psdap
236 imhs-edian2-mes-bsdap
237 bim-dis-emo-asppha
238 bim-24thiman-5pho-aspibua
239 bhs-edian2-oem-psdab
240 2py-pyma2-chexo-psdapee
241 emnim-am2-oem-nbeta34dimeoph 242 pippy-m25thiz-meo-dfzdap
243 am2py-amo2-napo-bhsdap
244 deam-am3-oem-npsdap
245 2pmhs-pymea-ocho-bhsdap
246 thpym-dipch-chexo-glyzdap
247 bim-mepipe-ocho-betapy
248 dhim-pipa-aco-zdabs
249 am2py-ams2-5pho-zdap
250 bim-propn-eoco-aspibua
251 imhs-ams2-men-aspbzla
252 piraz-pymea-chexo-csdap
253 tolhs-mepazin-oeto-zdab
254 bim-diphmep-5amo-bsdap
255 bimhs-propa2s-cpeo-csdap
256 thpym-pazin-no2-bhsdap
257 bhs-thizn-cno-bsdap
258 amim-tetradi-napo-aspaba
259 am4py-din-oem-zdap
260 deam-24thiz-cpro-mezphe
261 thpym-pazin-eoco-bsdap
262 piraz-pyma2-no2-bhsdap
263 me2py-24thiman2-meo-bhsdab
264 2py-mepazin-mes-psdab
265 mam2py-mepipe2-oem-nbetapy
266 imhs-24thiman-fo-betapy
267 bim-eta-mes-betapy
268 bim-24thiz-meto-bhsdap
269 thpym-pazin-no2-zdab
270 mam2py-dimephmep-mes-betadcph
271 2py-amn3-men-glyzdap
272 bimhs-diaz-no2-zdapee
273 pippy-amn3-men-psdap
274 impy-pyma2-imo-aspibua
275 bimhs-pipmeo-fo-bhsdap
276 am4py-tridi-daco-ibsdap
277 thpym-mepipe-ocho-zdab
278 hythpym-eta2s-5pho-dfzdap
279 chmhs-amn2-men-mezphe
280 thpym-pipa-4pho-zdap
281 pippy-pymea-4pho-betapy
282 thpym-mepipe-ocho-glupha
283 impy-24thizman2-mes-mezphe
284 bimhs-tridi-eoco-aspibua
285 bimhs-dis-mes-bphabs
286 bhs-am3diaz-5amo-mezphe
287 cl3pyme-amn3-daco-psdapee
288 bhs-pipmea-cpro-asppha
289 amim-pnymea-oem-bhsdap
290 bhs-edian2-no2-zdab
291 bz-eta-emo-aspbzla
292 dpam-dio-eoco-bhsdab
293 imhs-24thizman2-cno-aspibua
294 piraz-trias-meo-zlys
295 ibhs-pipa-meto-csdap
296 ec-am3diaz-ocho-dfzdap
297 bhs-mepazin-meo-betadcph
298 pyraz-pipmea-mes-psdap
299 me2py-amo2-mes-asppha
300 tolhs-am2-sem-nbeta34dimeoph
301 bhs-amn3-imo-osdap
302 n2py-dimephmem-pro-betainyl
303 bhs-trias-napo-dfzdap
304 thpym-dimen-men-dfzdap
305 thpym-thizn-cpeo-ibsdap
306 imhs-eta-chexo-tsdap
307 piraz-thizn-paco-glyzdap
308 pyraz-diphmep-5amo-aval
309 piraz-pyma2-napo-betadcph
310 2py-pipmea-eoco-zdap
311 bhs-mepipe-meo-psdab
312 piraz-trias-emo-bhsdap
313 amim-edia2-oem-nbeta34dimeoph
314 nmor-mepazin-no1-bhsdab
315 impy-mepipe-chexo-bphabs
316 dmam-am3diaz-no1-glyzdap
317 bim-mepipe-meo-bsdap
318 piraz-mepazin-chexo-psdap
319 moegua-mepazin-fo-csdap
320 imhs-25thiman2-eoco-bphabs
321 me2py-m25thiz-chexo-zorn
322 mam2py-tridi-men-mezphe
323 morhs-am3-oem-nbetameph
324 pyrhs-m25thiz-oem-glupha
325 me2py-pnymea-mes-betainyl
326 mam2py-amo2-no1-zdab
327 2py-mepipe-mes-bsdap
328 impy-diphmep-ocho-asppha
329 nmor-hexas-chexo-psdap
330 me2py-pipmea-ocho-asppha
331 imhs-pazin-no1-psdap
332 2py-mepipe-5pho-zdab
333 fthpym-am3-sem-nbetabnaphth
334 bhs-amn2-oem-psdap
335 piraz-pazi2n-ocho-aspibua
336 emnim-24thizman2-imo-bhsdab
337 nim-diphmem-oem-zdab
338 2py-ms-mes-zdap
339 2py-edian2-ocho-bsdap
340 nmor-diphmep-no1-bsdap
341 amim-25oxman2-nmo-betadcph
342 mam2py-edian2-5pho-osdap
343 pyr-n2o2n-cno-betapy
344 phpip-pipmes-fo-mezphe
345 bhs-24thiz-mes-psdab
346 fthpym-eta-mes-dfzdap
347 bhs-edian2-ocho-psdap
348 ibhs-mepipe-emo-bhsdap
349 edothpym-pipa-pro-zdap
350 bzl-am2-sem-npsdap
351 pippy-dimephmep-emo-bphabs
352 mam2py-pipmea-napo-bnsdap
353 me2py-dimephmem-mes-betapy
354 imhs-24thizman2-no2-asppha
355 am4py-n2nme2n-no2-bhsdap
356 mam2py-tetradi-no2-dfzdap
357 imhs-dis-meo-zdabs
358 bimhs-propa2s-oem-asppha
359 chmhs-24thiz-napo-glyzdap
360 me2py-edian2-5amo-aspbzla
361 dmbim-eta-fo-asppha
362 amim-amn2-mes-thizzdap
363 mepip-pazi2n-5pho-betapy
364 bim-mepipe-oem-basdap
365 imhs-eta-5pho-zdab
366 me2py-am3-oem-npsdap
367 pippy-tetradi-imo-glyzdap
368 thpym-m24thizman2-oem-dfzdap
369 piraz-pipmea-cpro-betapy
370 deam-mepipe-cpeo-bnsdap
371 dhim-25oxman2-napo-psdab
372 amim-n2nme2n-5amo-bsdap
373 prhs-24thizman2-mommo-csdap
374 2py-edia2-oem-nbetapy
375 bimhs-din-meo-bhsdab 376 chhs-pyma2-ocho-betapy
377 2py-amn3-5pho-psdab
378 thpym-eta-5pho-bhsdap
379 piraz-pyma2-meo-psdab
380 chhs-thizn-fo-betainyl
381 pippy-m25thiz-chexo-zorn
382 fthpym-pnymea-oem-bnsdap
383 bhs-24thizman2-no2-bphabs
384 pippy-edian2-chexo-psdab
385 imhs-amn2-no2-betapy
386 2py-25thiz-no1-aval
387 impy-pymea-peo-aspbzla
388 pyraz-tridi-cpro-bphabs
389 me2py-din-imo-bhsdab
390 phhs-hexadi-5amo-psdap
391 mepip-m25thiz-ocho-zdabs
392 imhs-amn2-5pho-bhsdap
393 bhs-m25thiz-fo-ppsdap
394 dhim-edian2-imo-bsdap
395 me2py-dimen-aco-zorn
396 2py-eta-oem-zdapee
397 cl3pyme-25oxman2-5amo-bphabs
398 phpip-edian2-fo-psdap
399 am2py-trias-oem-psdapee
400 nmhs-3pazin-imo-dfzdap
401 thpym-dimen-napo-bhsdab
402 amim-24thizman2-meo-psdab
403 bim-dipch-eoco-zdabs
404 ppy-m25thiz-no1-aspbzla
405 ec-eta-meo-aspibua
406 thpym-pipa-oeto-mezphe
407 2py-tetras-no2-csdap
408 2py-25oxman2-cno-psdap
409 chhs-pipmeo-oem-betadcph
410 bzl-eta-fo-mezphe
411 bim-pazin-no1-bnsdap
412 nim-am3-oem-nzdab
413 bim-dimen-eoco-zdabs
414 bhs-amn2-5pho-zdab
415 mepip-pymea-emo-zdap
416 am2py-pipmea-fo-zdab
417 hythDym-diphmem-pheo-zdap
418 piraz-ams2-5pho-zdabs
419 impy-edia2-sem-nbetabnaphth
420 thpym-eta-meo-mezphe
421 prhs-m25thiz-meo-dfzdap
422 bhs-pazin-mes-zdab
423 am2py-thizn-4amo-bphabs
424 am2py-dio-no1-psdap
425 gua-mepipen2-no2-thizzdap
426 am-dimen-5pho-glubzla
427 nim-amn3-paco-zdabs
428 moegua-eta-chexo-bhsdab
429 dhim-pymea-chexo-zdabs
430 amim-edia2-sem-nbetameph
431 piraz-pazin-baeo-aspbzla
432 nmhs-24thizman2-5amo-bhsdap
433 bim-dis-imo-betainyl
434 amim-mepipen2-fo-csdap
435 piraz-pyma2-fo-dfzdap
436 pippy-thizo-no2-betapy
437 2py-pipmea-chexo-osdap
438 impy-dipch-no1-zdabs
439 chmhs-trias-paco-asppha
440 mepip-diphmem-fo-betainyl
441 me2py-dich-eoco-dfzdap
442 bhs-dimen-ocho-aspibua
443 bzl-edian2-aco-betainyl
444 im-eta-aco-bhsdap
445 dmthpym-mepipen2-pro-aspbzla
446 bim-props-no1-asppha
447 impy-24thizman2-5pho-zdabs
448 bz-am2-oem-nbetapy
449 npip-m24thiman2-chexo-bhsdab
450 2py-diphmem-chexo-psdab
451 prhs-25thizman2-no2-betadcph
452 piraz-pymea-napo-psdap
453 amim-edian2-5pho-betapy
454 hythpym-m25thiman2-chexoglubzla
455 ec-amn2-mmen-bsdap
456 impy-pazin-5pho-betapy
457 am2py-amo2-fo-bhsdap
458 dhimn-edian2-aco-dfzdap
459 mam2py-dis-no2-bnsdap
460 2py-eta-ocho-bhsdap
461 imhs-amn3-5pho-psdap
462 emnim-m25thiz-mes-bsdap
463 ibhs-edia2-oem-npsdap
464 bhs-pazin-no1-bhsdap
465 thpym-mepipe-5pho-bsdap
466 2py-pnymea-ocho-aspbzla
467 pyraz-pazin-fo-aspbzla
468 nmor-pymea-men-zdabs
469 gua-amo3-oeto-mezphe
470 bzl-mepazin-hso-aspibua
471 amim-mepazin-baeo-zdab
472 mam2py-24thizman2-cno-glubzla
473 bimhs-amn3-ocho-aspbzla
474 hythpym-dimephmep-no2-csdap
475 pippy-pipa-cno-mezphe
476 dhim-pymea-mecpo-aval
477 piraz-pnymea-oem-glyzdap
478 2py-amn2-ocho-bhsdap
479 ibhs-24thiz-meteto-bsdap
480 cl3pyme-am2-sem-nbeta34dimeoph
481 phhs-edian2-fo-zdap
482 nim-m24thizman2-men-osdap
483 dhim-dimen-imo-csdap
484 bim-din-emo-zdap
485 phpip-dimephmep-pyo-zdabs
486 impy-amn3-meo-zdab
487 imhs-amn2-oem-psdap
488 2py-dimephmep-men-glyzdap
489 phpip-pymea-oeto-mezphe
490 tolhs-eta-eoco-aspibua
491 me2py-mepipe-imo-psdap
492 emnim-mepazin-napo-zdab
493 2pmhs-amn3-oem-psdab
494 edothpym-24thiman-meteto-psdap
495 thpym-dimen-mes-dfzdap
496 thpym-tetradi-chexo-aspibua
497 bhs-thizn-no2-bhsdab
498 mam2py-tridi-fo-betadcph
499 thpym-dimen-mes-csdap
500 am2py-24thizman2-oem-ppsdap
501 am2py-dimen-oem-bsdap
502 bimhs-pymea-pheo-bhsdab
503 imhs-amn2-imo-psdab
504 me2py-mepipe-4amo-betainyl
505 mam2py-m25thiz-imo-psdap
506 mam2py-m24thizman2-oem-bhsdab
507 hythpym-pyma2-fo-psdap
508 impy-trias-fo-bsdap
509 nim-diphmep-cnmo-betainyl 510 mam2py-diphmem-no1-bhsdap
511 phhs-pazin-oem-betaet
512 edothpym-butn-5pho-zdab
513 thpym-eta-mes-zdab
514 impy-tridi-no2-dfzdap
515 piraz-dimephmem-nmo-aspibua
516 dhim-dimephmep-oem-bhsdap
517 bhs-pazin-baeo-zdabs
518 imhs-amn2-ocho-psdab
519 bhs-dimen-no2-betadcph
520 bim-thizn-paco-bhsdab
521 gua-am3-sem-nzdab
522 pippy-pymea-meto-betainyl
523 prhs-thizn-napo-betapy
524 2py-dis-imo-zdap
525 fthpym-3pazin-meto-aspbzla
526 piraz-24thiman-5amo-betainyl
527 pippy-tetradi-men-csdap
528 morhs-dimephmem-oem-betainyl
529 dhim-am3-sem-nbetameph
530 thpym-mepipe-eoco-zdap
531 bim-24thiman-oem-mezphe
532 fthpym-thizn-pheo-betainyl
533 bhs-ams2-ocho-bhsdab
534 bhs-din-emo-aspbzla
535 bimhs-24thiman-eoco-bnsdap
536 chhs-din-men-glupha
537 phpip-24thizman2-mecpo-bhsdab
538 piraz-edian2-5amo-bsdap
539 bim-dimen-mes-betaet
540 thpym-edian2-no2-bnsdap
541 deam-diphmem-chexo-bhsdab
542 bimhs-mepipen2-hso-betapy
543 thpym-am3-sem-nzdap
544 dhim-tetradi-imo-zdabs
545 piraz-ams2-5pho-psdap
546 bhs-amn2-oem-zdap
547 hythpym-tridi-mmen-psdab
548 pyraz-amn2-fo-mezphe
549 2py-am2-oem-nbetameph
550 dmbim-mepipe-chexo-betaet
551 hythpym-eta-fo-bsdap
552 dhim-mepipe2-sem-nbetameph
553 2py-amn2-5pho-zdab
554 hythpym-trias-ocho-osdap
555 bimhs-pyma2-napo-glyzdap
556 dpam-mepipen2-meo-aspbzla
557 am4py-24thizman2-eoco-osdap
558 bim-edian2-eoco-bhsdap
559 thpym-eta-ocho-zdab
560 2py-pnymea-no2-aspibua
561 hythpym-pyma2-emo-betadcph
562 imhs-amn3-cno-aspbzla
563 imhs-mepipe-eoco-bsdap
564 imhs-pyma2-no1-psdap
565 moegua-m24thizman2-ocho-zdab
566 bz-pymea-napo-betadcph
567 npip-pyma2-eoco-zorn
568 me-mepazin-oeto-bphabs
569 am2py-dimephmep-eoco-betainyl
570 nim-props-meto-aspbzla
571 me2py-pipmea-5pho-mezphe
572 piraz-mepipe-5pho-mezphe
573 hythpym-trias-cpro-psdap
574 bhs-dio-imo-mezphe
575 pyr-trias-5pho-aspibua
576 dpam-25thizman2-meo-aval
577 bim-pazin-ocho-bnsdap
578 pippy-eta-fo-asppha
579 dhim-24oxman2-men-aspibua
580 dmam-dis-baeo-zdap
581 n2py-din-mes-bphabs
582 am2py-24thizman2-chexo-zdab
583 bim-eta-meo-zdab
584 phpip-mea2s-meto-bhsdap
585 bzl-m24thizman2-5amo-glubzla
586 ibhs-25thizman2-baeo-betainyl
587 me2py-m24thizman2-eoco-zdab
588 chmhs-pazin-pheo-aspibua
589 impy-diphmem-4pho-bnsdap
590 piraz-m25thiz-peo-bnsdap
591 hythpym-25thiman2-no2-ppsdap
592 im-pnymea-paco-dfzdap
593 impy-eta-mommo-bnsdap
594 bim-edia2-oem-nbetabnaphth
595 thpym-m24thizman2-chexo-mezphe
596 mam2py-thizn-imo-glubzla
597 pippy-dimen-mes-betapy
598 bim-amn2-ocho-bnsdap
599 z-edia2-oem-nbetapy
600 ec-m25thiz-5pho-betainyl
601 thpym-edian2-no2-betapy
602 me-diphmem-5pho-betadcph
603 thpym-trias-imo-dfzdap
604 me2py-n2nme2n-fo-bphabs
605 bimhs-amn2-5pho-mezphe
606 inhs-eta-meo-asppha
607 impy-m24thizman2-meo-bnsdap
608 z-amn3-no1-bphabs
609 am-24thiz-5amo-glyzdap
610 dhim-tridi-oem-zdab
611 dhim-dis-aco-ibsdap
612 npip-pyma2-imo-zorn
613 chhs-pnymea-5amo-zdabs
614 nim-pnymea-4pho-psdab
615 bim-pazi2n-cnmo-betadcph
616 hythpym-pipmea-emo-bhsdab
617 pyr-pipa-paco-betainyl
618 bim-pipa-no1-ppsdap
619 n2py-dimephmem-ocho-zdapee
620 2py-am3-oem-npsdap
621 thpym-edian2-eoco-bphabs
622 ppy-m25thiz-5amo-bhsdab
623 dhim-pipmea-mecpo-bnsdap
624 tolhs-am3diaz-imo-zdabs
625 n2py-pnymea-men-glyzdap
626 imhs-25oxman2-imo-aspbzla
627 me2py-amn2-baeo-aspibua
628 hythpym-mepipe2-sem-nbeta34-dimeoph
629 moegua-m25thiz-cpro-zdap
630 thpym-edian2-meo-psdab
631 impy-pymea-meto-bphabs
632 imhs-edian2-oem-betapy
633 2py-pyma2-5amo-zdabs
634 thpym-tridi-meo-aspibua
635 bhs-pnymea-no2-betainyl
636 dhim-mepipe-chexo-aspibua
637 hythpym-mepipen2-men-betainyl
638 2py-ms-pro-betadcph
639 bhs-m25thiz-daco-zdap
640 mam2py-amo3-fo-aspibua
641 dmam-25oxman2-fo-zdap
642 hythpym-ams2-napo-bhsdab
643 bhs-amn3-hso-psdab 644 me2py-indan2-eoco-bphabs
645 bim-amn2-eoco-psdab
646 thpym-m24thizman2-ocho-psdap
647 me2py-m25thiman2-no1-zlys
648 2py-m24thizman2-no1-bphabs
649 dhim-tridi-chexo-bnsdap
650 amim-pipmeo-5pho-aspibua
651 pippy-24thizman2-nmo-betadcph
652 pippy-propn-5pho-betadcph
653 nmor-m25thiman2-mes-zdabs
654 ppy-propa2s-baeo-psdap
655 bhs-mepipen2-meo-dfzdap
656 bhs-edian2-eoco-zdap
657 2py-amn2-oem-bsdap
658 morhs-amo2-ocho-psdap
659 nmhs-dis-no2-bhsdap
660 am2py-am3-sem-nbetameph
661 hythpym-n2nme2n-men-psdab
662 bim-pyma2-no2-bphabs
663 imhs-eta-mes-bsdap
664 me2py-mepipen2-5amo-mezphe
665 amim-am2-sem-npsdap
666 ibhs-thizn-ocho-psdab
667 phpip-pazin-men-csdap
668 dmam-25oxman2-oem-glyzdap
669 thpym-eta-5pho-zdab
670 2pmhs-pyma2-5amo-betadcph
671 bhs-25thiz-men-glyzdap
672 thpym-ams2-pyo-aspbzla
673 2py-m24thizman2-4pho-psdap
674 thpym-pazin-meo-psdap
675 me2py-amo3-meo-glyzdap
676 me2py-mepazin-4pho-bsdap
677 am2py-dimephmep-men-zdab
678 cl3pyme-mepipe-4amo-bhsdap
679 me2py-pentas-5pho-psdab
680 imhs-eta-imo-mezphe
681 ibhs-m24thiman2-4pho-glubzla
682 amim-pipmea-ocho-glupha
683 emnim-diphmem-peo-psdap
684 pippy-eta-aco-bnsdap
685 imhs-mepipe-5pho-aspibua
686 bim-pipa-oem-bhsdab
687 bhs-amn2-meo-zdap
688 pippy-mepipe2-sem-nbetabnaphth
689 dmbim-dimen-cnmo-betadcph
690 z-m24thizman2-napo-bphabs
691 bim-m24thizman2-baeo-betapy
692 thpym-am2-sem-nbetabnaphth
693 ec-indan2-napo-bhsdab
694 bhs-pymea-meo-dfzdap
695 hythpym-tetradi-no2-zdap
696 piraz-ams2-5pho-glubzla
697 pyrhs-24thiz-eoco-aspibua
698 bim-m24thizman2-5pho-betainyl
699 cl3pyme-pentas-daco-asppha
700 dhim-25oxman2-no2-bphabs
701 thpym-pazin-emo-zdab
702 phpip-24thiz-napo-psdap
703 4pmhs-m25thiman2-4amo-bsdap
704 am2py-props-mes-bhsdab
705 morhs-trias-mecpo-zdap
706 dhim-n24thiman2-cpeo-betainyl
707 z-edia2-sem-nbetabnaphth
708 dhim-dimephmem-eoco-aspibua
709 deam-diphmep-5amo-bphabs
710 mam2py-amn2-imo-ibsdap
711 2py-2pazin-peo-betapy
712 thpym-m24thiz-cpeo-glupha
713 bimhs-mepipe-5pho-zdabs
714 piraz-dimen-imo-asppha
715 bim-dich-meo-bnsdap
716 tolhs-am3-oem-nbetapy
717 bimhs-25oxman2-eoco-thizzdap
718 pyraz-pentadi-no1-zlys
719 bim-3diaz-oem-betainyl
720 piraz-amn2-no2-aval
721 bimhs-amo3-cpro-mezphe
722 pyrhs-amn3-4pho-bhsdab
723 imhs-pazin-oem-zdap
724 dpam-edian2-imo-zdabs
725 bim-25oxman2-chexo-zorn
726 am2py-ams2-chexo-bphabs
727 2py-mepipe-hso-asppha
728 imhs-dis-meteto-bnsdap
729 imhs-pazin-5pho-psdap
730 piraz-dimephmep-no2-zorn
731 thpym-butn-mes-aspibua
732 phpip-tetradi-4pho-psdap
733 me2py-pnymea-napo-mezphe
734 bz-pymea-mes-dfzdap
735 pippy-amn3-napo-betadcph
736 am4py-diphmem-mommo-bsdap
737 hythpym-edian2-no2-betapy
738 imhs-edian2-5pho-psdab
739 mam2py-m24thizman2-fo-betainyl
740 bhs-tridi-5pho-psdap
741 bimhs-n2nme2n-emo-bhsdap
742 bim-dimen-oem-betaet
743 mam2py-amo2-oem-asppha
744 pippy-eta-4pho-aval
745 pyrhs-m25thiman2-oem-glyzdap
746 hythpym-mepipe-chexo-mezphe
747 am4py-pyma2-imo-bnsdap
748 pippy-edian2-eoco-bhsdap
749 piraz-am2-oem-nbeta34dimeoph
750 dpam-am3-oem-nzdap
751 amim-24thiz-no1-bphabs
752 bhs-m25thiz-pheo-zdap
753 bhs-eta-fo-betadcph
754 hythpym-dipch-5amo-aspbzla
755 4pmhs-tetras-no2-ppsdap
756 am2py-hexas-meto-dfzdap
757 amim-24thizman2-pyo-bsdap
758 tolhs-mepipen2-fo-zdapee
759 thpym-m24thizman2-imo-bhsdab
760 npip-m25thiz-hso-betadcph
761 chhs-mepipe-mes-glyzdap
762 gua-edian2-eoco-aspibua
763 z-amn3-no2-aspibua
764 pippy-dimephmep-fo-bsdap betadcph
765 dhim-m25thiman2-meo-tsdap
766 hythpym-trias-eoco-zorn
767 im-25oxman2-emo-oxal
768 imhs-dipch-oem-aspbzla
769 hythpym-tridi-chexo-zdabs
770 bhs-amn2-chexo-zdabs
771 bimhs-mepipe-napo-tsdap
772 imhs-mepipe-meo-psdab
773 bim-mepipe-napo-betadcph
774 piraz-m25thizman2-mes-betapy
775 ibhs-dich-eoco-zdab
776 amim-am3-oem-nbetameph
777 fthpym-pipa-men-zdap 778 edothpym-pyma2-ocho-mezphe
779 imhs-pipmea-imo-psdap
780 amthiaz-pyma2-imo-betapy
781 thpym-mepipe-mes-psdap
782 amthiaz-am2-sem-abeta34dimeoph
783 bhs-diphmem-chexo-mezphe
784 am2py-pipmea-pro-bsdap
785 ibhs-amn3-fo-asppha
786 dmam-amn3-5amo-psdab
787 nmhs-24thiz-oem-aspibua
788 nmor-dis-napo-psdap
789 nmor-mepazin-4pho-glubzla
790 morhs-tetradi-emo-betapy
791 hythpym-dimephmep-mommo-bnsdap
792 me2py-pymea-men-ibsdap
793 thpym-mepipe-no1-bnsdap
794 am2py-pymea-fo-csdap
795 2py-diphmem-imo-aspibua
796 ibhs-trias-men-bhsdap
797 mam2py-dimephmep-pro-aspibua
798 bim-pazin-mes-psdab
799 dpam-tridi-ocho-bsdap
800 dhim-24thiz-5amo-bhsdap
801 2py-edian2-mes-zdap
802 2pmhs-dimephmem-napo-aspbzla
803 piraz-tridi-fo-betainyl
804 bim-24thizman2-5pho-zdab
805 bhs-diaz-oem-betainyl
806 thpym-pyma2-oem-bsdap
807 imhs-eta-mes-zdap
808 2py-mepipe-mes-betapy
809 bim-pymea-chexo-zdap
810 ibhs-dis-oem-betadcph
811 pyrhs-pipa-5amo-aspbzla
812 dhim-dimen-meo-betapy
813 nmor-pipa-chexo-aspibua
814 bhs-m24oxman2-fo-betapy
815 piraz-m24thizman2-5amobetadcph
816 ec-25oxman2-cno-glubzla
817 bhs-diphmep-men-betadcph
818 impy-diphmep-mes-betainyl
819 pippy-pazin-napo-asppha
820 bim-eta-5pho-oxal
821 pippy-amo2-aco-ppsdap
822 bzl-eta-mes-aval
823 am2py-amo2-men-bsdap
824 dhim-25oxman2-napo-zdap
825 dmthpym-hexadi-mes-bsdap
826 nmor-amn3-oem-bhsdap
827 thpym-pazin-meo-bhsdap
828 pippy-24thiz-oem-zorn
829 2py-24thizman2-chexo-mezphe
830 imhs-mepipe-eoco-psdab
831 ec-25oxman2-men-zorn
832 thpym-m24thiz-chexo-bhsdab
833 2py-mepipe-oem-bsdap
834 impy-amn2-no2-psdapee
835 gua-pnymea-fo-mezphe
836 dmam-24thizman2-daco-csdap
837 bhs-amn2-ocho-bsdap
838 thpym-diphmem-5pho-bnsdap
839 me2py-trias-no2-aspibua
840 z-pyma2-mmen-csdap
841 npip-indan2-napo-zdabs
842 am2py-pyma2-daco-betapy
843 chhs-24thizman2-fo-glyzdap
844 pippy-tetradi-no2-bsdap
845 am2py-m24thiman2-nmo-bsdap
846 bzl-m24thizman2-oem-glyzdap
847 hythpym-dimen-meo-csdap
848 dmbim-eta-pyo-thizzdap
849 pyraz-pnymea-imo-psdap
850 2py-tetradi-4pho-bphabs
851 impy-props-meo-psdap
852 edothpym-thizn-cpeo-dfzdap
853 dhim-eta-emo-dfzdap
854 bim-pnymea-5amo-zdab
855 piraz-dimephmep-chexo-betainyl
856 bhs-m24oxman2-imo-aspbzla
857 bzl-m24oxman2-meo-zdap
858 imhs-am3-oem-nbeta34dimeoph
859 me2py-eta-emo-aspbzla
860 cl3pyme-eta-napo-zdap
861 mam2py-thizn-imo-betadcph
862 npip-25oxman2-napo-betapy
863 thpym-mepipe-no1-betapy
864 amim-pazin-napo-bphabs
865 hythpym-eta-mes-glupha
866 bim-mepipe-no2-bhsdap
867 thpym-pazin-meo-zdab
868 me-diphmen-no2-zdap
869 2py-thizo-men-zdab
870 z-25thiman2-napo-betadcph
871 bzl-pazin-eoco-glyzdap
872 pippy-diphmep-oem-mezphe
873 imhs-25oxman2-fo-aval
874 ibhs-m24thizman2-baeo-betaet
875 bz-mepipen2-no2-csdap
876 imhs-diphmep-pyo-bsdap
877 am2py-thizn-meo-asppha
878 impy-butn-ocho-psdap
879 bhs-pazin-no1-betapy
880 bhs-amn3-men-betainyl
881 impy-dimen-imo-zdabs
882 piraz-amn3-mmen-psdap
883 2py-amn2-mommo-betadcph
884 me2py-din-meo-glyzdap
885 2py-mepazin-fo-ibsdap
886 imhs-pentadi-5pho-aspibua
887 dmam-m25thiz-meo-betapy
888 bim-edia2-oem-nbetameph
889 bim-amo2-eoco-aspbzla
890 bhs-m24thizman2-mommo-csdap
891 bim-pipmea-nmo-bhsdap
892 impy-pipa-mes-betainyl
893 impy-24thiz-men-zdap
894 im-dich-imo-aspbzla
895 bhs-eta-ocho-zdab
896 2py-amn3-cpeo-betapy
897 amim-tetradi-peo-asppha
898 imhs-mepipen2-no2-zdab
899 thpym-24thizman2-eoco-betadcph
900 thpym-pazin-mes-betapy
901 tolhs-amo2-eoco-aspbzla
902 2py-mepipe-no2-zdab
903 thpym-trias-men-zdapee
904 bhs-edian2-eoco-betapy
905 bhs-eta-no2-bnsdap
906 impy-amo2-hso-asppha
907 imhs-edian2-oeto-aspibua
908 chmhs-24thizman2-5amo-dfzdap
909 2py-eta-5pho-psdab
910 bhs-mepipen2-eoco-bhsdap
911 bimhs-pnymea-meo-bnsdap 912 bhs-pyma2-napo-aspibua
913 pippy-mepazin-5amo-zlys
914 2py-m25thiz-imo-bphabs
915 piraz-24thiz-fo-dfzdap
916 edothpym-edia2-sem-abetameph
917 impy-diphmem-meo-betapy
918 tolhs-amo2-no2-zdabs
919 me-thizn-fo-asppha
920 dpam-25thizman2-chexo-csdap
921 bhs-edian2-5pho-psdap
922 phpip-m25oxman2-no1-osdap
923 pippy-diphmem-5amo-psdap
924 hythpym-dimephmem-5amo-asppha
925 chmhs-edian2-pro-betainyl
926 bhs-pymea-no2-zdab
927 im-amn2-no2-betainyl
928 edothpym-am2-sem-nbetabnaphth
929 mam2py-pymea-men-zdab
930 dmthpym-mepipe-no2-bphabs
931 phhs-pipa-imo-betadcph
932 me2py-edian2-5amo-ibsdap
933 thpym-dimen-fo-psdap
934 mam2py-pymea-oem-dfzdap
935 amim-tridi-fo-bnsdap
936 ibhs-trias-no1-zlys
937 2py-pyma2-napo-thizzdap
938 pyraz-am2-oem-nzdap
939 me2py-dimen-peo-bhsdap
940 bhs-am2-oem-nbetabnaphth
941 imhs-24thiz-no1-bnsdap
942 2py-pazin-meo-psdab
943 nmor-tetradi-meo-zdap
944 thpym-edian2-chexo-betapy
945 am2py-24thizman2-imo-bphabs
946 4pmhs-m24thizman2-emo-aspbzla
947 imhs-pazin-eoco-betapy
948 bimhs-25oxman2-imo-zdapee
949 me2py-thizo-meo-csdap
950 bimhs-amn2-fo-psdap
951 piraz-pentas-4amo-aspibua
952 piraz-eta-no1-psdap
953 imhs-mepipe-oem-psdap
954 bimhs-edian2-eoco-tsdap
955 im-thizs-men-zdab
956 mam2py-pazin-oem-ibsdap
957 tolhs-diphmep-5amo-psdap
958 thpym-pazin-ocho-bhsdap betadcph
959 2py-pnymea-emo-bhsdap
960 2py-dimephmep-meo-glyzdap
961 2py-butn-ocho-zdabs
962 imhs-amn3-no1-aspbzla
963 bim-eta-meo-betapy
964 2py-mepipen2-fo-mezphe
965 bzl-ams2-5pho-dfzdap
966 4pmhs-pipmea-fo-betapy
967 me2py-pentadi-mes-bhsdab
968 pyrhs-tridi-meo-zdabs
969 amim-3diaz-mes-psdab
970 pippy-tridi-5pho-bsdap
971 amim-pentas-mes-dfzdap
972 am2py-mea-pheo-aval
973 im-dis-imo-dfzdap
974 mepip-thizn-no2-dfzdap
975 deam-3pazin-oem-psdapee
976 bim-thizs-cnmo-bnsdap
977 am2py-dimephmem-fo-bnsdap
978 bhs-pyma2-men-zdabs
979 bhs-dimen-meo-glyzdap
980 am2py-eta-5pho-asppha
981 am2py-diphmem-emo-asppha
982 thpym-edian2-eoco-betapy
983 prhs-tetradi-ocho-bhsdap
984 hythpym-pyma2-5amo-bhsdab
985 2py-eta-oem-zdap
986 bim-24thiz-men-psdab
987 amim-mea2s-hso-psdab
988 piraz-edia2-oem-npsdap
989 dpam-dimephmep-imo-mezphe
990 pippy-ams2-meo-bnsdap
991 amim-dis-napo-asppha
992 amim-mepipe-imo-bphabs
993 bhs-edian2-eoco-zdab
994 me2py-edian2-oem-aspbzla
995 4pmhs-dimephmep-napo-zdap
996 bzl-dimen-no1-betadcph
997 2py-amn3-chexo-csdap
998 gua-pymea-meteto-bhsdap
999 chmhs-tridi-meo-zdab
1000 bimhs-amn2-no1-zlys
1001 me2py-am3-sem-nbetapy
1002 pippy-amo2-men-bhsdap
1003 pippy-trias-meo-mezphe
1004 mam2py-pyma2-imo-aspbzla
1005 bz-eta2s-5amo-betapy
1006 amim-pymea-men-zdab
1007 cl3pyme-amn2-mecpo-bhsdap
1008 imhs-ams2-ocho-bhsdab
1009 hythpym-m24thizman2-emobetadcph
1010 imhs-mepipe-meo-zdab
1011 4pmhs-25oxman2-mes-dfzdap
1012 bhs-mepipen2-pheo-bphabs
1013 tolhs-edian2-5amo-aspibua
1014 npip-thizn-eoco-psdab
1015 bhs-dimephmep-chexo-bphabs
1016 bhs-pazin-ocho-zdap
1017 bim-mepipe-oem-bhsdap
1018 bhs-m25thiz-aco-zdap
1019 amim-mepipen2-ocho-bphabs
1020 dhim-din-nmo-zdabs
1021 bim-dimephmep-chexo-betainyl
1022 2py-eta-meo-zdab
1023 pyrhs-edia2-sem-nbetabnaphth
1024 2py-pipmea-5amo-bphabs
1025 me2py-25oxman2-no1-betainyl
1026 bim-m25thiz-oem-csdap
1027 deam-am2-sem-nbetapy
1028 impy-dio-cno-betapy
1029 pippy-am3-oem-nzdap
1030 bimhs-dis-5amo-thizzdap
1031 am-propa2s-5pho-glyzdap
1032 imhs-edian2-ocho-bsdap
1033 phpip-tetradi-fo-asppha
1034 npip-amo2-napo-betainyl
1035 pippy-thizn-no1-psdap
1036 bimhs-din-aco-bsdap
1037 npip-dipch-cnmo-aspibua
1038 am2py-3diaz-meo-psdapee
1039 ec-dipch-pyo-asppha
1040 n2py-m25oxman2-4amo-glupha
1041 nmor-amn2-5amo-mezphe
1042 hythpym-ams2-ocho-bphabs
1043 emnim-eta-ocho-psdap
1044 bzl-mepazin-pyo-bhsdab
1045 bhs-tridi-oeto-zdab 1046 emnim-tetradi-eoco-bsdap
1047 thpym-amn2-eoco-betapy
1048 amthiaz-pipa-men-oxal
1049 amim-pipmea-5amo-oxal
1050 hythpym-24thiman2-pro-bsdap
1051 imhs-mepipe-5amo-bnsdap
1052 bhs-amn2-meo-psdab
1053 dhim-m24thizman2-no1-dfzdap
1054 thpym-mepipe-no2-zdap
1055 am-dimen-no1-psdap
1056 amthiaz-edian2-4pho-bphabs
1057 4pmhs-24thizman2-ocho-aspibua
1058 phpip-tetradi-emo-aspbzla
1059 mam2py-propn-fo-mezphe
1060 dhim-m25thiz-5amo-psdapee
1061 mam2py-din-5amo-psdap
1062 n2py-pipmea-5pho-aspbzla
1063 gua-tridi-napo-ibsdap
1064 amim-mepipe2-oem-nbeta34-dimeoph
1065 2py-mepipe-eoco-bsdap
1066 mam2py-eta-meteto-csdap
1067 hythpym-mea-paco-bphabs
1068 mam2py-dipch-oem-zdap
1069 thpym-pazin-mes-psdap
1070 dpam-pipa-men-aspbzla
1071 piraz-amn3-cpeo-mezphe
1072 2py-pymea-cno-bhsdap
1073 2py-24thiman-oem-bhsdab
1074 thpym-trias-oem-mezphe
1075 nmor-eta-ocho-glyzdap
1076 thpym-pazin-meo-betapy
1077 pyr-edia2-oem-nzdap
1078 mam2py-tetradi-ocho-aspibua
1079 2py-m25thiman2-napo-mezphe
1080 imhs-diphmem-mes-asppha
1081 thpym-eta-ocho-betapy
1082 bimhs-edian2-men-bphabs
1083 imhs-pazin-oem-bhsdap
1084 impy-edia2-oem-npsdap
1085 me2py-dimen-cpeo-betapy
1086 pyrhs-mepazin-men-bsdap
1087 me2py-dipch-ocho-csdap
1088 pippy-mepipe-pheo-mezphe
1089 bim-tetradi-men-betapy
1090 dhim-m24thiz-5pho-zdab
1091 bim-am3diaz-no2-zdabs
1092 impy-propa2s-men-bnsdap
1093 imhs-amn2-eoco-bsdap
1094 bim-mepazin-ocho-bsdap
1095 piraz-amo2-meo-aspibua
1096 bhs-pazin-meo-zdab
1097 amim-pnymea-men-psdab
1098 pippy-3diaz-fo-psdab
1099 phpip-mea-emo-asppha
1100 4pmhs-25oxman2-5amo-glubzla
1101 bim-pnymea-fo-csdap
1102 bim-edian2-ocho-psdap
1103 2py-edian2-mes-bsdap
1104 bim-dimen-ocho-zdapee
1105 am-m24thizman2-ocho-psdap
1106 dmbim-eta2s-fo-asppha
1107 bim-pazin-no2-zdap
1108 morhs-m25thiz-emo-bnsdap
1109 n2py-amn3-eoco-zdap
1110 2pmhs-pipmea-napo-bhsdab
1111 mam2py-25oxman2-napo-aspibua
1112 nmhs-dimephmem-oem-bhsdap
1113 ppy-mepipe2-oem-npsdap
1114 me2py-mepipe2-oem-nzdap
1115 impy-25thiman2-men-csdap
1116 impy-24thizman2-5amo-bphabs
1117 chmhs-amn2-eoco-psdab
1118 emnim-m25thiz-5pho-betapy
1119 amim-mepazin-pro-zlys
1120 mam2py-pazin-meto-bhsdap
1121 bhs-edian2-ocho-bnsdap
1122 bhs-pazin-meo-bnsdap
1123 imhs-pyma2-ocho-zlys
1124 imhs-diphmem-mes-psdap
1125 thpym-thizn-fo-asppha
1126 npip-24thizman2-mes-psdab
1127 bimhs-m24thiman2-4amo-aspibua
1128 bimhs-mepazin-mmen-glyzdap
1129 dmthpym-pnymea-peo-betapy
1130 dhim-mepipe-men-dfzdap
1131 dhim-25oxman2-nmo-bnsdap
1132 mam2py-amo2-mes-psdap
1133 piraz-pnymea-napo-zdab
1134 pyrhs-pyma2-oem-oxal
1135 npip-pnymea-meo-psdap
1136 pyr-m24thizman2-ocho-betapy
1137 am2py-dimephmep-no2-tsdap
1138 me2py-pentadi-no1-csdap
1139 bimhs-am2-sem-nzdab
1140 bim-pipmea-5pho-psdap
1141 mam2py-dich-eoco-zdap
1142 cl3pyme-propa2s-fo-osdap
1143 imhs-mepipe-ocho-psdap
1144 dhim-am3-oem-nzdab
1145 emnim-edia2-oem-nbetapy
1146 pyr-am2-oem-nbetameph
1147 dhim-amo2-napo-psdap
1148 bim-edian2-meo-psdab
1149 bim-edian2-mes-psdab
1150 bhs-amn2-oem-zdab
1151 imhs-propn-mes-bsdap
1152 z-dimephmem-mes-asppha
1153 dmthpym-thizn-men-aspibua
1154 amim-thizo-men-psdap
1155 dmthpym-amo3-baeo-csdap
1156 imhs-hexadi-nmo-zdabs
1157 4pmhs-pipmea-imo-bphabs
1158 bim-pazin-no1-betapy
1159 thpym-25thiz-imo-ppsdap
1160 piraz-thizn-oem-bphabs betapy
1161 impy-pymea-chexo-mezphe
1162 me2py-diphmem-chexo-dfzdap
1163 pippy-24thizman2-peo-bnsdap
1164 2py-pipmeo-emo-dfzdap
1165 phpip-25oxman2-men-betainyl
1166 bim-amn2-oem-zdap
1167 mepip-pnymea-oem-betadcph
1168 thpym-pazin-ocho-bnsdap
1169 n2py-edian2-daco-bhsdap
1170 hythpym-trias-meteto-betadcph
1171 amim-pnymea-oem-glyzdap
1172 prhs-am3-sem-nzdap
1173 amim-24thiman-5amo-psdap
1174 bim-eta-5pho-psdap
1175 hythpym-amn3-paco-bhsdap
1176 bimhs-m25thiman2-meo-betapy
1177 pyraz-trias-emo-bhsdap
1178 imhs-mepipe-no2-zdap
1179 dhim-mepipen2-5amo-aspibua 1180 imhs-am3diaz-emo-aspibua
1181 am2py-m25thiz-paco-zorn
1182 hythpym-din-ocho-psdap
1183 edothpym-dimephmem-mommo-bphabs
1184 me-mepipen2-no2-bphabs
1185 n2py-thizn-5amo-oxal
1186 bim-pazin-ocho-psdap
1187 me2py-diphmem-mes-csdap
1188 me-pymea-men-zdap
1189 nim-24thiz-5pho-glyzdap
1190 hythpym-m24thiz-daco-ppsdap
1191 2py-mepipe-oem-zdap
1192 2py-tridi-mes-zdabs
1193 thpym-pazin-eoco-betapy
1194 am-tetras-men-aspibua
1195 piraz-din-mes-mezphe
1196 hythpym-diphmem-5pho-psdapee
1197 bim-24oxman2-baeo-aspbzla
1198 moegua-dich-no1-betainyl
1199 bhs-pipa-chexo-betainyl
1200 thpym-pazi2n-chexo-betapy
1201 bhs-eta-eoco-psdab
1202 hythpym-dis-meo-aspaba
1203 am2py-pentas-mes-mezphe
1204 hythpym-tridi-mes-bphabs
1205 amim-tetradi-cpro-zdab
1206 bhs-pazin-eoco-psdap
1207 pippy-amo2-fo-psdab
1208 im-diphmep-mes-zdap
1209 impy-pazin-peo-glupha
1210 hythpym-m24thizman2-5phobetapy
1211 am2py-25oxman2-5amo-zdab
1212 mam2py-pyma2-paco-bnsdap
1213 fthpym-am3diaz-5amo-bnsdap
1214 emnim-tridi-peo-betainyl
1215 am4py-eta-cpro-betadcph
1216 me2py-eta-chexo-ibsdap
1217 bhs-thizo-ocho-glyzdap
1218 me2py-25oxman2-meo-zdabs
1219 chmhs-amo2-no2-glyzdap
1220 bhs-thizn-eoco-betapy
1221 chhs-mea2s-chexo-zdap
1222 hythpym-n2nme2n-oem-zdab
1223 am2py-tetradi-no2-psdap
1224 mepip-ms-daco-betapy
1225 piraz-dimen-emo-aspbzla
1226 am2py-hexas-oem-dfzdap
1227 bhs-edian2-oem-bhsdap
1228 4pmhs-dis-oem-zdabs
1229 dmthpym-am3diaz-5amo-aspibua
1230 thpym-tetradi-eoco-aspibua
1231 impy-am2-oem-nbetabnaphth
1232 impy-hexas-imo-psdab
1233 2py-dimephmem-cpro-betapy
1234 ²py-24thiz-mes-aspbzla
1235 bimhs-dimephmem-no1-betapy
1236 phhs-tetradi-meteto-asppha
1237 piraz-pyma2-fo-betapy
1238 am2py-dimephmem-5pho-csdap
1239 phhs-hexadi-meo-bphabs
1240 moegua-am2-sem-npsdap
1241 amthiaz-m24thiman2-chexo-zorn
1242 piraz-eta-cno-bhsdap
1243 2py-amo2-meo-betapy
1244 mam2py-m25thiz-chexo-zdap
1245 2py-hexas-peo-aspibua
1246 2py-pazin-mes-zdap
1247 menim-25thiz-pheo-psdap
1248 chmhs-diphmem-oem-bnsdap
1249 ec-24thiz-mes-bsdap
1250 2py-eta-mmen-zlys
1251 dmam-trias-chexo-bhsdab
1252 impy-din-meo-aspibua
1253 me2py-propa2s-5pho-aspibua
1254 bhs-pyma2-chexo-bhsdap
1255 ibhs-amn2-emo-bnsdap
1256 imhs-diphmem-napo-bphabs
1257 thpym-pipmea-peo-glyzdap
1258 mam2py-din-emo-zdab
1259 mepip-pentadi-napo-betapy
1260 bimhs-tridi-meto-dfzdap
1261 bhs-mepipe-no1-bnsdap
1262 imhs-eta-meo-zdab
1263 mam2py-n2o2n-chexo-aspibua
1264 nmhs-pnymea-eoco-zdapee
1265 dpam-pipmea-5amo-bhsdap
1266 4pmhs-pazin-mommo-glyzdap
1267 imhs-tetradi-4pho-ibsdap
1268 bhs-25thiman2-fo-glyzdap
1269 imhs-dimephmem-oem-bhsdab
1270 impy-24thiman2-eoco-bhsdab
1271 am2py-pyma2-pyo-ppsdap
1272 bimhs-tridi-aco-tsdap
1273 nmhs-eta-no2-aspibua
1274 bim-pazin-no2-bsdap
1275 mam2py-trias-imo-bnsdap
1276 me2py-m25thiz-4pho-zdabs
1277 imhs-pnymea-mes-aspibua
1278 thpym-amn2-5pho-psdap
1279 morhs-diphmep-5amo-osdap
1280 thpym-edian2-no1-bhsdap
1281 tolhs-pnymea-5amo-zdab
1282 cl3pyme-25oxman2-5pho-bhsdap
1283 me2py-24thiman2-meo-mezphe
1284 pyrhs-25oxman2-ocho-zdab
1285 2py-dimen-mmen-csdap
1286 pyraz-24thiman2-peo-bphabs
1287 npip-dio-fo-csdap
1288 impy-pnymea-men-betapy
1289 piraz-24thiz-no2-bphabs
1290 phhs-25thizman2-men-aspibua
1291 thpym-ams2-no1-zdap
1292 pippy-pipa-eoco-bhsdab
1293 edothpym-mepazin-pheo-zdab
1294 me2py-tetradi-oem-zdap
1295 am-ams2-fo-aval
1296 bim-eta-5pho-betapy
1297 impy-pyma2-men-bnsdap
1298 edothpym-pazin-emo-aspibua
1299 impy-24thiz-cnmo-bnsdap
1300 nim-pazin-emo-bhsdap
1301 me2py-diphmep-5pho-dfzdap
1302 thpym-eta-ocho-psdab
1303 gua-am2-sem-npsdap
1304 me2py-25oxman2-emo-bphabs
1305 imhs-thizo-meto-asppha
1306 thpym-eta-emo-glyzdap
1307 pippy-diphmem-peo-betainyl
1308 2py-edian2-meo-zdap
1309 bim-amn2-eoco-psdap
1310 mam2py-24thizman2-pheo-glyzdap
1311 pippy-trias-4pho-aspbzla
1312 imhs-dimen-no1-aspbzla
1313 phpip-tetradi-eoco-bhsdap 1314 2py-tetradi-fo-zdap
1315 nmor-amn2-5amo-bsdap
1316 pyr-diphmep-aco-psdab
1317 me2py-25thiz-cpro-oxal
1318 imhs-mepipe-meo-psdap
1319 ec-thizn-imo-zdab
1320 bzl-pipa-imo-bhsdab
1321 menim-amo3-mes-zdabs
1322 thpym-24thizman2-men-zdapee
1323 dmam-ams2-men-bnsdap
1324 2py-amn2-ocho-betapy
1325 bhs-diaz-meo-ibsdap
1326 impy-n2o2n-napo-glyzdap
1327 amim-pipa-napo-bnsdap
1328 2py-edian2-mes-bhsdap
1329 bim-amn2-mes-betapy
1330 piraz-diphmem-fo-glyzdap
1331 gua-tetradi-no1-aspibua
1332 bhs-ams2-aco-zdab
1333 deam-amo2-emo-psdab
1334 pyrhs-m25oxman2-no2-zdabs
1335 4pmhs-tridi-mes-zdap
1336 hythpym-eta-mes-csdap
1337 bhs-pazin-ocho-bhsdap
1338 thpym-eta-oem-zdab
1339 pyrhs-amo2-daco-dfzdap
1340 menim-propa2s-chexo-zdab
1341 im-din-mes-betainyl
1342 2py-eta-ocho-psdab
1343 bhs-tetradi-fo-aspbzla
1344 pippy-ams2-napo-betadcph
1345 me2py-25thiz-fo-bphabs
1346 me2py-25oxman2-meo-psdapee
1347 imhs-pazin-mes-zdap
1348 me2py-pipmea-5pho-zdapee
1349 nmor-m25oxman2-no2-mezphe
1350 cl3pyme-dimephmem-mes-bhsdab
1351 imhs-pipmea-emo-csdap
1352 bzl-tridi-5amo-glubzla
1353 pyrhs-dis-mes-zdab
1354 emnim-amn2-chexo-bphabs
1355 chhs-mepipe2-oem-npsdap
1356 imhs-dis-no2-betainyl
1357 dmthpym-pymea-peo-bsdap
1358 bhs-diphmem-emo-bhsdap
1359 imhs-hexadi-5pho-zdab
1360 impy-m24oxman2-fo-betainyl
1361 bimhs-dimen-fo-betainyl
1362 thpym-pazin-ocho-zdap
1363 bim-pazin-eoco-psdap
1364 am2py-dis-meo-csdap
1365 imhs-amn2-eoco-bhsdap
1366 deam-pyma2-eoco-tsdap
1367 me2py-tetradi-no1-aval
1368 n2py-pymea-meo-psdab
1369 bim-amn2-mes-zdab
1370 dhim-amn3-napo-aspbzla
1371 ec-m24thizman2-emo-ppsdap
1372 imhs-m25thiz-oem-ppsdap
1373 impy-dis-meo-zlys
1374 dhim-dimephmem-pyo-bsdap
1375 nim-amo2-mes-bhsdap
1376 tolhs-m24thiman2-ocho-zdab
1377 impy-25oxman2-pyo-zdabs
1378 bim-edian2-ocho-zdab
1379 cl3pyme-dimen-men-psdab
1380 imhs-diphmep-oem-betapy
1381 imhs-tetradi-5amo-bsdap
1382 morhs-pipmea-pyo-betainyl
1383 4pmhs-n24thiman-napo-aspibua
1384 hythpym-pipa-mmen-aspbzla
1385 bimhs-amn3-eoco-mezphe
1386 am4py-amn2-ocho-zdabs
1387 bhs-pazin-no1-bsdap
1388 bzl-mepipen2-peo-dfzdap
1389 2pmhs-dis-imo-zdabs
1390 fthpym-25oxman2-chexo-mezphe
1391 mepip-m25thiman2-mommo-bhsdap
1392 bimhs-edian2-oem-aspbzla
1393 dmthpym-dimen-5pho-bhsdab
1394 bim-pazin-hso-mezphe
1395 2py-pipa-nmo-zdab
1396 pippy-pipmea-5pho-bhsdap
1397 chmhs-tetras-no1-mezphe
1398 fthpym-m25thiman2-eoco-bphabs
1399 amim-m25thiz-napo-csdap
1400 piraz-din-eoco-mezphe
1401 2py-pipmea-mes-aspaba
1402 2py-amn3-napo-zdab
1403 mam2py-24thizman2-meo-dfzdap
1404 piraz-amo2-eoco-dfzdap
1405 moegua-mea2s-no2-psdap
1406 thpym-pazin-5pho-bsdap
1407 bhs-amn2-eoco-bhsdap
1408 am2py-pyma2-napo-zdabs
1409 amim-dich-eoco-tsdap
1410 bhs-edian2-ocho-bsdap
1411 2py-m25thiz-imo-aspbzla
1412 am2py-pazin-5pho-csdap
1413 pippy-am2-sem-nbetameph
1414 thpym-diphmep-no1-aspibua
1415 nmhs-dich-eoco-zdab
1416 bim-pipmea-men-bhsdap
1417 thpym-mepipen2-mes-betaet
1418 edothpym-indan2-eoco-zdabs
1419 hythpym-m24thiz-cnmo-csdap
1420 me2py-25oxman2-emo-glupha
1421 edothpym-dimephmep-4amo-csdap
1422 ec-am3-oem-nbeta34dimeoph
1423 thpym-eta-eoco-bhsdap
1424 dmam-tetradi-no2-psdap
1425 mam2py-pymea-no1-mezphe
1426 dhim-m25thiz-5pho-osdap
1427 amim-thizn-chexo-bnsdap
1428 am2py-amn3-no1-psdap
1429 bhs-m24thizman2-men-betadcph
1430 phpip-dimephmem-chexo-zdabs
1431 chmhs-m24thiman2-oem-bphabs
1432 bim-dimephmem-men-zdap
1433 am2py-pentas-meo-bnsdap
1434 morhs-pipmea-5pho-aspibua
1435 mam2py-mepazin-pheo-mezphe
1436 mam2py-am3-sem-nzdab
1437 impy-pipa-men-zdab
1438 amim-24oxman2-emo-betadcph
1439 imhs-props-imo-bsdap
1440 imhs-mepipe-5pho-psdap
1441 me2py-pazin-napo-bsdap
1442 mam2py-mepipen2-pyo-zdap
1443 2py-eta-mes-bnsdap
1444 amim-tetradi-meto-betapy
1445 am-pymea-5pho-betadcph
1446 amim-pipa-eoco-aspibua
1447 am2py-mepipe2-oem-nbetapy 1448 pippy-am3-sem-nzdap
1449 mam2py-dimephmem-fo-betainyl
1450 2py-dimephmem-oem-zdab
1451 me2py-tetradi-pyo-psdapee
1452 bhs-mepazin-mes-bnsdap
1453 imhs-ms-fo-csdap
1454 imhs-pazi2n-chexo-tsdap
1455 pippy-diphmep-emo-bnsdap
1456 bhs-pnymea-oem-bhsdab
1457 deam-m25thiz-chexo-asppha
1458 hythpym-3pazin-imo-zdab
1459 thpym-diphmem-napo-csdap
1460 pippy-diphmem-chexo-zdab
1461 ppy-thizn-ocho-glyzdap
1462 dhim-pipa-oem-psdap
1463 imhs-ams2-no1-zdab
1464 bim-mepipe-no2-psdap
1465 chmhs-dis-imo-aspbzla
1466 bim-mea2s-meo-oxal
1467 bz-25thizman2-mmen-asppha
1468 dhim-mepipe-5amo-bphabs
1469 bhs-pazin-ocho-psdab
1470 amim-dimephmep-5amo-bhsdap
1471 tolhs-diphmem-no1-zlys
1472 imhs-pipmeo-fo-aspbzla
1473 phhs-dimephmem-baeo-dfzdap
1474 hythpym-3diaz-paco-aval
1475 2py-pentas-ocho-bhsdab
1476 me-n24thiman-fo-dfzdap
1477 pyr-25oxman2-5amo-bnsdap
1478 thpym-trias-5pho-ibsdap
1479 bim-amn3-no2-psdab
1480 dmthpym-dipch-imo-aspibua
1481 chhs-24thiz-fo-aspibua
1482 dhim-diphmem-no2-zdap
1483 me2py-n24thiman-5amo-psdap
1484 am-dimephmep-chexo-asppha
1485 imhs-thizo-emo-glubzla
1486 prhs-tridi-napo-zdabs
1487 2py-edian2-5pho-psdap
1488 n2py-am3-oem-nzdab
1489 cl3pyme-eta-no1-bphabs
1490 ibhs-pymea-oem-zdab
1491 thpym-amn2-mes-bhsdap
1492 thpym-24thiz-no2-tsdap
1493 pyr-24thizman2-eoco-betainyl
1494 bim-edian2-meo-betapy
1495 piraz-propn-chexo-aspbzla
1496 dmthpym-am3-sem-nzdap
1497 pippy-m24oxman2-mes-bhsdab
1498 thpym-mepipe-ocho-bsdap
1499 impy-amn3-5pho-bhsdab
1500 bim-propn-nmo-bhsdab
1501 bhs-mepipe-napo-ibsdap
1502 thpym-mepipe2-oem-nzdap
1503 2py-3pazin-4amo-psdab
1504 imhs-pipa-meo-betapy
1505 chhs-pipa-no2-zdap
1506 hythpym-thizn-meo-psdab
1507 me-pnymea-emo-bnsdap
1508 menim-dimephmem-meto-zdabs
1509 bimhs-mepipen2-cpeo-zorn
1510 bhs-pazin-pyo-asppha
1511 chhs-pazin-oem-betapy
1512 bim-pazin-ocho-bhsdap
1513 imhs-m24thizman2-cnmo-asppha
1514 2py-edian2-oem-psdab
1515 imhs-tetradi-mmen-zdabs
1516 2py-edian2-no2-psdap
1517 dmam-dimephmem-men-bhsdap
1518 am2py-24thiz-mes-bphabs
1519 imhs-amn2-no2-bhsdap
1520 pyr-dis-aco-bhsdap
1521 chmhs-pymea-daco-aspibua
1522 impy-ams2-men-aspbzla
1523 morhs-pyma2-no2-zdabs
1524 im-24thiz-fo-zdabs
1525 hythpym-tetradi-cpro-betadcph
1526 2py-eta-oem-betapy
1527 piraz-thizn-baeo-bphabs
1528 bim-amo3-oem-aval
1529 npip-mea2s-chexo-betapy
1530 bim-diphmep-meo-bphabs
1531 bz-mepipe2-oem-nzdap
1532 2py-pyma2-eoco-asppha
1533 bim-dimephmep-emo-asppha
1534 am2py-amn2-5pho-csdap
1535 mam2py-24thiman-napo-zdap
1536 pippy-diphmem-oem-betadcph
1537 impy-amo2-5pho-betadcph
1538 bimhs-am2-sem-nbetapy
1539 imhs-2pazin-aco-mezphe
1540 dhim-amo2-ocho-aspbzla
1541 bim-m24thizman2-eoco-betapy
1542 ec-eta-imo-psdab
1543 dmbim-am3-oem-nzdab
1544 cl3pyme-amn2-mes-zdab
1545 dpam-amn2-emo-dfzdap
1546 bhs-edian2-napo-bhsdap
1547 pyrhs-ms-oem-zdab
1548 im-mepazin-baeo-ppsdap
1549 pippy-ams2-emo-psdap
1550 imhs-pazin-mes-bsdap
1551 hythpym-m25thiz-emo-bsdap
1552 phpip-pipa-eoco-csdap
1553 mam2py-pazi2n-no1-asppha
1554 bimhs-dich-meo-zdab
1555 z-tridi-eoco-betapy
1556 z-am3-oem-nzdab
1557 2py-pnymea-oem-zdab
1558 thpym-eta-mes-psdab
1559 hythpym-mepipe-oem-betainyl
1560 am2py-propn-mes-bsdap
1561 am2py-ams2-paco-bhsdab
1562 imhs-amn2-meo-bsdap
1563 bhs-edia2-sem-nbetapy
1564 moegua-dis-meo-csdap
1565 pyr-tetradi-mommo-dfzdap
1566 2py-pnymea-no1-glyzdap
1567 n2py-edian2-men-bphabs
1568 me2py-pentadi-meo-zdap
1569 cl3pyme-pipmea-no2-dfzdap
1570 2py-dis-meo-bhsdab
1571 me2py-m24thizman2-oeto-psdab
1572 bir-diphmem-chexo-asppha
1573 pippy-pymea-5pho-glyzdap
1574 pippy-trias-no2-betainyl
1575 edothpym-eta-napo-aspbzla
1576 dmbim-pipmeo-emo-zdab
1577 bim-pazin-ocho-bsdap
1578 2py-n2nme2n-napo-aspibua
1579 impy-mepazin-napo-bhsdap
1580 thpym-diaz-meo-bnsdap
1581 bim-edia2-oem-npsdap 1582 dhim-dimephmem-hso-asppha
1583 npip-mepazin-pro-bphabs
1584 thpym-eta-eoco-aspbzla
1585 imhs-24thizm an2-mommo-aval
1586 am2py-edian2-aco-psdab
1587 bimhs-amn3-mecpo-glyzdap
1588 mam2py-dimephmem-cpro-bphabs
1589 bim-diphmep-ocho-psdap
1590 ppy-diphmem-eoco-bnsdap
1591 2py-mepipen2-daco-bphabs
1592 dmam-amo3-cnmo-bhsdab
1593 imhs-eta-cnmo-betainyl
1594 pyraz-hexadi-eoco-bnsdap
1595 pippy-24thiz-oeto-glyzdap
1596 2pmhs-mepipe-fo-psdab
1597 nim-pipmea-mes-betapy
1598 phhs-n2nnme2n-ocho-zdap
1599 dmthpym-edian2-mes-bphabs
1600 pippy-3diaz-emo-betadcph
1601 pyr-dimephmep-no1-bsdap
1602 amim-butn-4amo-glyzdap
1603 bim-dimen-emo-glubzla
1604 impy-propa2s-ocho-dfzdap
1605 dhim-amn3-men-bphabs
1606 mam2py-dis-emo-glyzdap
1607 impy-dimephmem-ocho-zdabs
1608 am2py-m24thizman2-emo-bhsdap
1609 bhs-pyma2-no2-bnsdap
1610 me2py-diphmep-ocho-mezphe
1611 bimhs-propa2s-mecpo-bhsdap
1612 hythpym-mepipe2-sem-nbeta-34dimeoph
1613 bimhs-pentadi-napo-aspibua
1614 thpym-mepipe-eoco-psdap
1615 gua-tetras-emo-bphabs
1616 thpym-am2-oem-nbetapy
1617 emnim-mepipen2-eoco-zdabs
1618 pippy-m25thiman2-eoco-bphabs
1619 tolhs-dich-imo-oxal
1620 dmbim-edian2-men-bhsdap
1621 bimhs-dimephmem-no1-zdab
1622 bhs-hexadi-fo-glyzdap
1623 hythpym-pymea-napo-bsdap
1624 pippy-mepipe2-oem-nbetapy
1625 apip-edia2-oem-nbetabnaphth
1626 bimhs-edian2-cpeo-bhsdap
1627 dmbim-tetradi-men-bhsdab
1628 pippy-24thiman2-eoco-bhsdap
1629 bzl-m25oxman2-cnmo-dfzdap
1630 pippy-pipmes-cnmo-psdap
1631 im-n2nme2n-no2-bsdap
1632 bim-thizn-no1-bsdap
1633 thpym-2pazin-meo-mezphe
1634 tolhs-pipa-eoco-bnsdap
1635 impy-dich-ocho-betaet
1636 imhs-amn2-meo-betapy
1637 ibhs-mepipe-5pho-betadcph
1638 me-eta2s-no1-aspbzla
1639 2py-mepipe-meo-zdab
1640 am2py-amo2-fo-psdapee
1641 ibhs-edian2-eoco-csdap
1642 me-amo2-eoco-zdap
1643 bhs-mepipe-ocho-zdap
1644 bim-tetras-meteto-tsdap
1645 nmhs-dimephmep-napo-psdap
1646 amim-mepipen2-meo-psdab
1647 bim-amn2-oem-betapy
1648 mepip-dis-napo-zdabs
1649 bim-mepazin-meo-aspibua
1650 npip-pymea-men-bphabs
1651 mam2py-tridi-ocho-betainyl
1652 ec-m25thizman2-meto-glyzdap
1653 am2py-pazin-fo-zlys
1654 hythpym-24thiz-no2-asppha
1655 imhs-eta-eoco-bsdap
1656 dhim-mea2s-men-tsdap
1657 am2py-tetradi-5amo-psdap
1658 bhs-amn3-napo-glyzdap
1659 thpym-din-fo-bhsdap
1660 am2py-mepipe2-oem-nbetameph
1661 hythpym-24thiman2-napoaspbzla
1662 me2py-m25thiz-eoco-bphabs
1663 dpam-m25thiz-oeto-zdap
1664 edothpym-pentas-fo-aspbzla
1665 tolhs-tetradi-no1-bhsdab
1666 mam2py-am3diaz-men-bhsdab
1667 bimhs-pyma2-chexo-zorn
1668 2py-ams2-ocho-csdap
1669 ppy-diphmem-5pho-glupha
1670 2py-dimephmem-ocho-asppha
1671 dhim-pipmes-chexo-asppha
1672 thpym-pentadi-men-tsdap
1673 mam2py-thizn-men-bhsdap
1674 impy-eta2s-chexo-thizzdap
1675 impy-eta-emo-zdabs
1676 bim-hexas-4amo-betaet
1677 pippy-m25thizman2-chexobphabs
1678 nmhs-thizn-chexo-psdab
1679 impy-3pazin-5pho-psdap
1680 2py-tridi-chexo-glubzla
1681 2py-dis-cnmo-betapy
1682 pippy-mepipen2-meo-psdap
1683 mam2py-dimen-emo-aspbzla
1684 mam2py-dis-napo-zdap
1685 2py-pazin-ocho-psdab
1686 me2py-amo2-napo-asppha
1687 impy-m25thiz-emo-ppsdap
1688 me2py-thizs-mmen-mezphe
1689 bim-eta-ocho-bsdap
1690 moegua-mepipen2-oem-glyzdap
1691 dmthpym-m25thiz-eoco-betadcph
1692 prhs-trias-meteto-zdabs
1693 thpym-m24thizman2-fo-mezphe
1694 impy-edian2-no2-psdap
1695 phhs-eta-napo-dfzdap
1696 impy-hexadi-oem-zlys
1697 pyraz-dich-5amo-psdap
1698 npip-pnymea-mes-zdap
1699 chmhs-2pazin-men-aspbzla
1700 edothpym-dis-nmo-mezphe
1701 dhim-diphmem-no1-ibsdap
1702 bim-diphmep-mecpo-bhsdab
1703 amim-tetradi-fo-zorn
1704 thpym-tetradi-eoco-bhsdap
1705 morhs-diphmem-imo-zdab
1706 ppy-m25thiman2-pyo-betadcph
1707 imhs-pazin-fo-csdap
1708 morhs-pipmea-5amo-asppha
1709 am2py-diphmep-cno-zdabs
1710 thpym-m25thiz-4pho-ppsdap
1711 imhs-amn2-no2-zdab
1712 bhs-amn2-ocho-bhsdap
1713 bimhs-propa2s-peo-mezphe
1714 thpym-pipmea-5pho-aspibua
1715 dhim-25thizman2-no1-zdab 1716 amthiaz-24oxman2-imo-bhsdab
1717 2py-pymea-aco-psdab
1718 imhs-mepipe-no2-glyzdap
1719 4pmhs-n2nme2n-imo-glubzla
1720 bimhs-dimephmem-napo-betadcph
1721 z-edia2-oem-nbetapy
1722 thpym-edian2-mes-bhsdap
1723 tolhs-dimephmem-ocho-betapy
1724 pyrhs-trias-men-asppha
1725 mam2py-n2o2n-napo-glyzdap
1726 thpym-thizo-meo-betainyl
1727 chhs-ams2-mes-betainyl
1728 me2py-am3-sem-npsdap
1729 2py-dio-imo-bphabs
1730 mam2py-indan2-oem-betainyl
1731 dhim-dimen-emo-betadcph
1732 pippy-24thiman-men-zdap
1733 impy-dis-emo-aspibua
1734 imhs-amn2-5pho-zdab
1735 impy-m25thiz-ocho-csdap
1736 bz-pentadi-meo-bsdap
1737 thpym-mepipe-no1-zdab
1738 2py-eta-peo-aspibua
1739 mam2py-din-fo-tsdap
1740 thpym-edian2-5pho-psdab
1741 thpym-tetradi-oem-ibsdap
1742 amim-amn3-imo-bsdap
1743 hythpym-eta-fo-aspibua
1744 ppy-24oxman2-imo-zdab
1745 edothpym-dimephmem-5amo-osdap
1746 pyrhs-dimephmem-meo-betapy
1747 bhs-mepipe-ocho-bhsdap
1748 2py-mepipe-no1-bsdap
1749 piraz-dimephmep-emo-aspibua
1750 bhs-eta-meo-zdap
1751 piraz-dimephmep-emo-dfzdap
1752 me2py-dimephmem-imo-bhsdap
1753 npip-amo2-no2-betapy
1754 bhs-dimephmep-4pho-osdap
1755 2py-edian2-oem-zdap
1756 dhim-pipmea-emo-zdab
1757 nim-24thiz-pro-aspibua
1758 dhim-edian2-daco-glyzdap
1759 4pmhs-trias-no1-betadcph bhsdab
1760 edothpym-dis-no1-bphabs
1761 impy-m24thizman2-cpeo-bhsdab
1762 bim-eta-mes-zdab
1763 nmor-eta2s-emo-psdap
1764 dhim-tridi-mes-zdap
1765 impy-mepipe2-oem-nbetameph
1766 bim-m24thiman2-5amo-bsdap
1767 impy-amn3-imo-bhsdap
1768 amim-25thizman2-emo-aspibua
1769 ibhs-n2nme2n-imo-aspbzla
1770 4pmhs-mepipe2-oem-nbetab naphth
1771 thpym-24thizman2-fo-zdabs
1772 chmhs-dimephmem-napo-dfzdap
1773 me2py-pyma2-daco-ibsdap
1774 bim-mepazin-cnmo-zorn
1775 me2py-tetradi-ocho-zdapee
1776 amim-pyma2-no1-csdap
1777 am2py-mepazin-oem-bhsdap
1778 bhs-amn2-5pho-bhsdap
1779 edothpym-pazin-napo-csdap
1780 thpym-amo3-no2-csdap
1781 am4py-dimephmem-mes-dfzdap
1782 amim-edia2-sem-nbetabnaphth
1783 2py-propn-chexo-betapy
1784 bimhs-din-mecpo-psdap
1785 bimhs-mepipe-imo-bhsdap
1786 mepip-eta-nmo-asppha
1787 tolhs-2pazin-napo-bhsdap
1788 me2py-dipch-chexo-zdabs
1789 2py-amn2-no2-zdap
1790 bim-mepazin-oem-betainyl
1791 thpym-eta-meo-betapy
1792 impy-dimephmep-5amo-bnsdap
1793 piraz-2pazin-no2-aspibua
1794 imhs-pnymea-cnmo-zdap
1795 thpym-m25thiman2-fo-zdap
1796 amim-dimen-no2-aspibua
1797 thpym-amn2-eoco-psdab
1798 amim-tetradi-ocho-aspbzla
1799 pippy-dis-fo-betadcph
1800 bhs-m24oxman2-meto-glubzla
1801 im-m24oxman2-eoco-psdap
1802 hythpym-amo2-emo-glubzla
1803 am2py-pipa-mommo-ibsdap
1804 bhs-amn2-ocho-bhsdap
1805 dhim-3pazin-cnmo-bhsdap
1806 z-pipmea-eoco-bphabs
1807 mam2py-am3diaz-5amo-bsdap
1808 imhs-24thiz-imo-asppha
1809 morhs-m24thizman2-chexo-bhsdab
1810 phpip-diphmep-oem-dfzdap
1811 me2py-ams2-napo-mezphe
1812 phpip-24thiz-no1-psdap
1813 bhs-edian2-no2-bsdap
1814 dhim-edian2-cnmo-dfzdap
1815 bimhs-pipmea-meto-ibsdap
1816 piraz-dimephmep-meo-glyzdap
1817 mepip-mepipen2-napo-psdab
1818 imhs-edian2-oem-psdap
1819 mam2py-dimephmem-pheo-mezphe
1820 thpym-mepipen2-cno-zdabs
1821 bim-mepipen2-no2-bnsdap
1822 hythpym-ams2-5pho-psdab
1823 hythpym-pyma2-daco-mezphe
1824 impy-dis-oeto-aspbzla
1825 chmhs-tridi-imo-psdap
1826 imhs-m24thizman2-oem-bhsdap
1827 npip-dimephmem-men-bphabs
1828 pippy-trias-imo-bhsdab
1829 tolhs-pymea-no1-dfzdap
1830 amim-m24thizman2-imo-thizzdap
1831 me2py-eta-emo-psdab
1832 bim-pazin-5pho-betapy
1833 amim-thizn-fo-zdapee
1834 am2py-mepipe-pyo-bhsdap
1835 mam2py-thizn-5pho-dfzdap
1836 dhim-24thizman2-napo-psdab
1837 me2py-25oxman2-napo-dfzdap
1838 amim-am2-oem-nbetapy
1839 bim-24thiz-cno-glyzdap
1840 piraz-2pazin-chexo-betaet
1841 cl3pyme-mepazin-chexo-glyzdap
1842 2py-ams2-eoco-betapy
1843 mam2py-am2-oem-nzdap
1844 imhs-pazin-5pho-betapy
1845 thpym-edian2-eoco-zdab
1846 impy-m24thizman2-ocho-betapy
1847 cl3pyme-diphmem-5pho-bnsdap
1848 4pmhs-ams2-pheo-oxal
1849 2py-pymea-no1-betadcph 1850 pippy-am3-oem-nbetapy
1851 piraz-tridi-pro-betainyl
1852 2py-eta-men-bnsdap
1853 phpip-mepipe-eoco-betainyl
1854 edothpym-amn3-pyo-zdabs
1855 im-pentas-ocho-betadcph
1856 cl3pyme-ams2-mes-betadcph
1857 bim-pyma2-ocho-betadcph
1858 bim-amn2-no1-bsdap
1859 imhs-pazin-no1-bsdap
1860 dhim-dimephmep-oeto-betainyl
1861 bim-thizn-no2-zdab
1862 prhs-pazin-5pho-csdap
1863 chmhs-m24oxman2-mommo-bphabs
1864 2py-mepipen2-men-dfzdap
1865 npip-edia2-sem-rbetameph
1866 bhs-tridi-ocho-bnsdap
1867 bhs-pazin-no2-betadcph
1868 moegua-amo2-chexo-zdap
1869 mepip-amn3-emo-aspibua
1870 dmthpym-am3-sem-nbeta34-dimeoph
1871 emnim-diphmem-oeto-zlys
1872 ibhs-m25thiz-chexo-bphabs
1873 thpym-pyma2-imo-glyzdap
1874 gua-24thiz-oeto-psdap
1875 am2py-thizn-mes-csdap
1876 amthiaz-24thizman2-pheo-csdap
1877 am4py-mepipe2-oem-nbetameph
1878 ec-m25thiman2-meo-aspibua
1879 dhim-amn3-cpro-bhsdab
1880 dmthpym-m24thizman2-5amo-bhsdap
1881 imhs-mepipe-oem-zdap
1882 bim-pazin-oem-betapy
1883 bhs-eta-oem-betapy
1884 dhim-props-imo-zlys
1885 thpym-pipa-eoco-mezphe
1886 2py-ams2-5pho-zdabs
1887 hythpym-amo2-eoco-mezphe
1888 bim-eta-meo-zdap
1889 dhim-pipmes-5pho-zdap
1890 hythpym-thizn-mes-zdabs
1891 gua-pipa-fo-bphabs
1892 nmhs-pipmea-mes-zdabs
1893 dhim-trias-imo-zdab
1894 mam2py-pymea-eoco-csdap
1895 imhs-eta-eoco-betapy
1896 dpam-mepazin-4amo-glyzdap
1897 bimhs-diphmep-no2-thizzdap
1898 am2py-m24thizman2-mes-psdap
1899 nmhs-am2-oem-nbetapy
1900 bhs-mepipen2-napo-bhsdap
1901 dhim-diphmem-mes-zlys
1902 me2py-25thiz-eoco-zdabs betadcph
1903 2py-dis-imo-psdap
1904 bim-mepipe-5pho-bnsdap
1905 edothpym-pazin-mes-betainyl
1906 imhs-am2-sem-nbetameph
1907 dmthpym-pymea-imo-aspibua
1908 bhs-mea-imo-betapy
1909 hythpym-mepipe2-sem-nzdap
1910 menim-24thiman2-napo-bhsdab
1911 amim-pazin-fo-zdap
1912 amim-props-no1-zdab
1913 bim-eta-5pho-psdap
1914 am2py-thizs-eoco-zdap
1915 phpip-dimen-5pho-betainyl
1916 bhs-edian2-eoco-bnsdap
1917 am2py-dimephmem-emo-bsdap
1918 bz-mepipe-meo-glubzla
1919 me2py-m25thiz-no2-aspbzla
1920 ppy-pyma2-men-csdap
1921 me2py-ams2-mes-bphabs
1922 bhs-dimen-emo-bphabs
1923 emnim-24oxman2-fo-betapy
1924 imhs-diphmem-emo-aspibua
1925 hythpym-mepipe-cnmo-betadcph
1926 dhim-n24thiman-cno-csdap
1927 mam2py-pipmea-nmo-csdap
1928 z-ms-meo-zdab
1929 am4py-pyma2-cno-psdap
1930 am4py-mepazin-no2-betainyl
1931 thpym-eta-meo-psdab
1932 chhs-pymea-napo-bhsdap
1933 pyraz-m24thizman2-meo-tsdap
1934 pippy-24thizman2-4amo-mezphe
1935 imhs-edian2-eoco-zdap
1936 amim-thizo-5amo-bnsdap
1937 me2py-24thizman2-cnmo-zdabs
1938 thpym-pazin-ocho-betapy
1939 impy-m24thizman2-5amo-aspbzla
1940 amim-tridi-5amo-asppha
1941 thpym-dimephmep-emo-glyzdap
1942 thpym-am3diaz-napo-csdap
1943 prhs-pentas-eoco-bsdap
1944 phhs-pipmea-5amo-dfzdap
1945 prhs-dich-mes-zdapee
1946 thpym-edian2-5pho-bnsdap
1947 piraz-m24thizman2-napo-bhsdap
1948 dmam-amn3-cnmo-zdabs
1949 phpip-pymea-cno-aspibua
1950 bhs-pipa-mes-ppsdap
1951 am4py-trias-mes-bphabs
1952 am2py-dimephmem-chexo-psdab
1953 dmthpym-dimephmem-mmen-betadcph
1954 pippy-mepipen2-emo-betadcph
1955 bim-mepipe-meo-betapy
1956 moegua-mepipe-5amo-zdabs
1957 dhim-mepipen2-emo-bphabs
1958 z-eta-no2-betadcph
1959 dpam-pnymea-men-bhsdab
1960 bimhs-diphmem-chexo-bphabs
1961 2pmhs-thizn-mes-mezphe
1962 piraz-25oxman2-5pho-zdap
1963 imhs-amn2-5pho-bsdap
1964 phhs-24oxman2-eoco-zdapee
1965 2py-pazin-ocho-aspibua
1966 ibhs-dipch-emo-betapy
1967 bhs-amn2-eoco-psdap
1968 thpym-tridi-4amo-asppha
1969 ec-ams2-meo-aspibua
1970 2py-pazin-meo-psdap
1971 2py-pazin-fo-csdap
1972 thpym-pazin-ocho-bsdap
1973 moegua-diphmep-meo-betadcph
1974 am4py-diphmep-5pho-asppha
1975 2py-edian2-no1-psdab
1976 menim-mepipe-ocho-zdab
1977 chmhs-2pazin-fo-betainyl
1978 amthiaz-25thizman2-eoco-betapy
1979 imhs-amo2-mes-mezphe
1980 amim-ams2-fo-oxal
1981 dhim-pymea-men-bphabs
1982 2pmhs-din-no2-bhsdap
1983 am4py-25thiman2-no1-betadcph 1984 edothpym-ams2-baeo-bnsdap
1985 nim-dis-eoco-aspibua
1986 mepip-edia2-sem-npsdap
1987 hythpym-pymea-mecpo-glubzla
1988 ppy-am3-oem-npsdap
1989 hythpym-edian2-4pho-glyzdap
1990 amim-24thiman-ocho-betadcph
1991 imhs-eta-oem-bnsdap
1992 am2py-mepipe-napo-zorn
1993 morhs-mepazin-oeto-ibsdap
1994 bim-dimephmem-ocho-betainyl
1995 am2py-pipmea-oem-zdap
1996 dhim-pyma2-no2-bhsdab
1997 moegua-ams2-ocho-zdab
1998 bim-eta-ocho-psdab
1999 impy-edian2-eoco-glubzla
2000 bimhs-n24thiman-emo-betadcph
2001 pyr-eta-5amo-bnsdap
2002 pyrhs-thizn-baeo-psdab
2003 2py-ms-meo-psdap
2004 chmhs-ams3-mes-bphabs
2005 cl3pyme-3pazin-emo-psdap
2006 imhs-amo2-chexo-aspbzla
2007 piraz-pentadi-4amo-ppsdap
2008 dmam-amo3-ocho-bhsdap
2009 impy-am3-sem-nzdab
2010 dpam-2pazin-daco-asppha
2011 bhs-m25thiz-chexo-psdap
2012 impy-diaz-peo-aspibua
2013 dhim-pymea-meo-aspibua
2014 bhs-pipmea-no1-betainyl
2015 bimhs-n24thiman-mes-betapy
2016 dhim-pipmes-fo-psdap
2017 phhs-dimen-ocho-zdab
2018 thpym-dipch-no2-bphabs
2019 bhs-mea-meteto-asppha
2020 morhs-tetradi-4pho-psdab
2021 amthiaz-n2nme2n-baeo-bnsdap
2022 pippy-mepipe-eoco-bhsdab
2023 2py-amn2-no1-bnsdap
2024 me2py-25oxman2-imo-psdab
2025 bhs-edian2-no2-bnsdap
2026 bhs-mepipe-emo-glyzdap
2027 cl3pyme-m25thiz-fo-asppha
2028 impy-amo2-napo-ibsdap
2029 ppy-dimephmep-5amo-csdap
2030 chhs-dimen-mes-betapy
2031 hythpym-ams2-ocho-bhsdap
2032 bim-thizn-emo-psdap
2033 2py-eta-ocho-bsdap
2034 bz-am3-oem-nbetapy
2035 ibhs-mepipen2-pro-zdabs
2036 pippy-dimephmep-no1-mezphe
2037 piraz-m25thiz-oem-zdap
2038 cl3pyme-dimephmem-men-aspibua
2039 2py-25thiman2-5pho-betainyl
2040 2py-tridi-napo-dfzdap
2041 dhim-dimephmem-pro-bhsdap
2042 dmthpym-am3-sem-nzdab
2043 morhs-m25thiz-meo-zdab
2044 pippy-dimen-pyo-mezphe
2045 amim-tetradi-no2-aspibua
2046 piraz-m25oxman2-ocho-psdap
2047 me2py-mepipe-mes-bhsdab
2048 pippy-diphmem-men-betadcph
2049 phhs-pazi2n-chexo-glyzdap
2050 piraz-trias-oem-bphabs
2051 2py-am3-oem-nzdab
2052 n2py-pipa-fo-csdap
2053 mam2py-24thiz-paco-bhsdab
2054 phhs-amn2-mes-betadcph
2055 mam2py-pazin-napo-bphabs
2056 bhs-pnymea-mommo-aval
2057 bim-pazin-eoco-bnsdap
2058 bimhs-amn3-eoco-glyzdap
2059 me2py-eta2s-5amo-dfzdap
2060 hythpym-eta-ocho-bhsdab
2061 menim-mepipe-men-zdabs
2062 am2py-pipmea-oem-bnsdap
2063 tolhs-diphmep-fo-glyzdap
2064 bim-24thizman2-men-aspibua
2065 am-pazin-no1-zdabs
2066 moegua-2pazin-meteto-zdabs
2067 impy-24thiz-eoco-betapy
2068 me-edian2-imo-asppha
2069 mam2py-dimen-imo-glyzdap
2070 mam2py-thizn-imo-betadcph
2071 thpym-dimen-4pho-aspibua
2072 bim-ams2-5amo-bsdap
2073 bhs-25oxman2-fo-aspbzla
2074 morhs-props-oem-psdab
2075 phpip-amn2-5amo-bsdap
2076 edothpym-2pazin-pro-asppha
2077 imhs-pnymea-men-betainyl
2078 amim-props-pyo-psdapee
2079 2py-mepipe2-sem-nbeta34-dimeoph
2080 piraz-dio-imo-betainyl
2081 bz-amn2-napo-csdap
2082 thpym-dimen-no2-bnsdap
2083 amim-butn-ocho-zdabs
2084 prhs-pipa-nmo-ibsdap
2085 ec-tridi-napo-bphabs
2086 piraz-pipa-oeto-zdabs
2087 menim-thizn-no1-zdab
2088 thpym-amn2-no1-zdap
2089 me2py-24thiman2-daco-bsdap
2090 thpym-mepipe-mes-betapy
2091 am2py-pyma2-no2-osdap
2092 2py-pazin-mes-dfzdap
2093 dmam-diphmem-chexo-zdabs
2094 pyr-pipa-men-bhsdap
2095 imhs-m25thiz-fo-bnsdap
2096 im-dis-5pho-dfzdap
2097 piraz-24thiman2-imo-betainyl
2098 hythpym-diphmem-paco-betainyl
2099 phhs-25oxman2-5pho-glupha
2100 bim-eta-mes-bsdap
2101 impy-am3-sem-nbetapy
2102 bim-24thizman2-no2-aspaba
2103 me2py-thizn-5pho-glyzdap
2104 amim-dimephmep-5pho-glubzla
2105 bimhs-m25thiz-eoco-betainyl
2106 piraz-24thizman2-meteto-betapy
2107 bhs-edian2-meteto-bsdap
2108 chmhs-3pazin-no2-zdabs
2109 bhs-amn3-emo-dfzdap
2110 dhim-amo2-peo-psdab
2111 2pmhs-tetradi-noi-ppsdap
2112 2-py-dich-5amo-betadcph
2113 hythpym-24thiz-ocho-bsdap
2114 menim-mepipen2-oem-cadap
2115 4-pmhs-pipa-no1-glyzdap
2116 dhim-butn-cpro-zdap
2117 hythpym-am3-sem-nbetameph 2118 bhs-edia2-sem-nzdap
2119 edothpym-dis-no2-bphabs
2120 bimhs-din-meteto-mezphe
2121 thpym-ams2-ocho-betadcph
2122 menim-mepazin-eoco-psdab
2123 dhim-tridi-oem-bsdap
2124 pippy-amn2-5amo-asppha
2125 amim-dis-eoco-bsdap
2126 thpym-edia2-sem-nbetameph
2127 bim-eta-no1-zdab
2128 dhim-24thizman2-4amo-asppha
2129 2py-pazin-eoco-bnsdap
2130 bim-amn3-paco-bphabs
2131 imhs-dimen-no2-psdab
2132 cl3-pyme-25thiz-eoco-zlys
2133 npip-diphmep-chexo-csdap
2134 dhim-mepipen2-aco-zdab
2135 bhs-mepipe-ocho-betapy
2136 mam2py-pnymea-oem-mezphe
2137 dpam-am2-oem-nbetabnaphth
2138 edothpym-trias-chexo-betainyl
2139 imhs-n24thiman-no2-aspaba
2140 nim-pipmes-baeo-bezphe
2141 bhs-amn2-eoco-bnsdap
2142 me-dis-5pho-zdab
2143 bimhs-m25thiz-emo-psdab
2144 impy-dimephmem-oetao-csdap
2145 me2py-din-5pho-zdabs
2146 impy-24thiz-imo-mezphe
2147 am-amo3-no1-glyzdap
2148 dhim-am3-sem-npsdap
2149 dhim-dis-5amo-psdap
2150 2py-mepazin-peo-bhsdap
2151 thpym-dis-5amo-aspbzla
2152 pippy-dimephmem-5pho-glyzdap
2153 mepip-mepipe-chexo-psdap
2154 dhim-amn2-meto-betainyl
2155 bhs-dimephmem-mes-aspbzla
2156 impy-m25thiz-daco-bsdap
2157 bim-thizo-oem-bnsdap
2158 amim-mepipe-no1-betadcph
2159 bim-25oxman2-napo-bhsdap
2160 piraz-dipch-napo-zdap
2161 bhs-tridi-paco-betapy
2162 mam2py-m25thiman2-chexo-betainyl
2163 chmhs-am3-sem-nbetameph
2164 me2py-pipmeo-no1-zdap
2165 pippy-m24thiz-daco-betainyl
2166 piraz-dimephmep-paco-dfzdap
2167 mam2py-25oxman2-5pho-aspibua
2168 bhs-eta-5pho-bhsdap
2169 bim-thizn-eoco-aspbzla
2170 me2py-n2o2n-5amo-bnsdap
2171 bim-edia2-sem-nbetapy
2172 am2py-din-no1-mezphe
2173 2py-tetras-eoco-bphabs
2174 bimhs-am3diaz-fo-dfzdap
2175 dpam-24thizman2-5pho-zdabs
2176 bimhs-mepipen2-ocho-betapy
2177 bim-edian2-no2-bhsdap
2178 edothpym-dimephmep-5amo-bsdap
2179 bzl-ams2-oeto-csdap
2180 tolhs-n2nme2n-chexo-glubzla
2181 impy-pymea-5amo-betadcph
2182 2py-m24thizman2-fo-bhsdap
2183 amim-pipa-meteto-bsdap
2184 bhs-25oxman2-no2-aspbzla
2185 thpym-pentadi-oeto-bsdap
2186 me2py-diphmep-daco-psdap
2187 bim-edian2-hso-bnsdap
2188 dhim-dimephmem-hso-asppha
2189 pippy-thizn-eoco-oxal
2190 impy-ms-mes-betapy
2191 piraz-edia2-sem-npsdap
2192 am2py-m25thiz-eoco-aspibua
2193 chhs-24thiz-meo-bhsdap
2194 phhs-mepipen2-peo-oxal
2195 pyrhs-eta-peo-oxal
2196 piraz-pipa-imo-bnsdap
2197 morhs-din-men-asppha
2198 pippy-pentadi-eoco-zdap
2199 gua-ams3-daco-zdap
2200 bimhs-m25oxman2-emo-zdap
2201 nmhs-m24thiz-pro-bphabs
2202 4pmhs-edia2-sem-nbetameph
2203 phpip-diphmem-fo-bphabs
2204 4pmhs-dimen-no2-bhsdap
2205 bim-eta-oem-zdab
2206 me2py-eta-chexo-thizzdap
2207 deam-pymea-mes-csdap
2208 4pmhs-dimephmem-napo-dfzdap
2209 amim-tridi-napo-aspbzla
2210 thpym-n2nme2n-cpro-zdabs
2211 thpym-pipa-5amo-csdap
2212 n2py-din-napo-zdab
2213 piraz-pyma2-men-csdap
2214 imhs-dis-oeto-psdapee
2215 menim-trias-men-betainyl
2216 ibhs-diphmem-no2-psdap
2217 z-24thiman-no2-betainyl
2218 bhs-eta-emo-asppha
2219 bhs-propn-cpro-dfzdap
2220 bimhs-dimen-chexo-zdabs
2221 bim-din-mes-tsdap
2222 dhim-25thiz-napo-bnsdap
2223 dpam-m24thizman2-chexo-bhsdab
2224 bimhs-ms-oeto-aspbzla
2225 2py-n2o2n-5pho-aspbzla
2226 4pmhs-mepipen2-mommo-zdapee
2227 am2py-dimephmep-oem-psdap
2228 bimhs-24thizman2-imo-mezphe
2229 am2py-edia2-sem-nbetameph
2230 amim-ams2-cpro-aspbzla
2231 chhs-24thiz-5amo-tsdap
2232 ppy-dis-oem-glyzdap
2233 am-dimephmem-napo-tsdap
2234 am2py-diphmem-chexo-psdap
2235 thpym-mepipe-ocho-betapy
2236 npip-butn-ocho-bsdap
2237 me2py-diphmem-cno-tsdap
2238 thpym-mepipe-no2-glyzdap
2239 tolhs-mepipen2-imo-psdapee
2240 amim-diphmep-peo-bsdap
2241 piraz-amn2-5amo-bphabs
2242 dhim-hexadi-ocho-csdap
2243 hythpym-3diaz-4pho-bhsdab
2244 me2py-diphmem-oem-aval
2245 am-mepipen2-eoco-mezphe
2246 am2py-m25thiz-oem-glyzdap
2247 imhs-pipa-emo-bsdap
2248 piraz-trias-aco-bhsdap
2249 bim-trias-chexo-psdab
2250 deam-mepipen2-no2-aspbzla
2251 bim-pnymea-meto-aspbzla 2252 bhs-diaz-aco-zdab
2253 bhs-mepipe-oem-zorn
2254 impy-24thiz-fo-zdabs
2255 imhs-tetradi-imo-zdap
2256 thpym-edian2-meo-bhsdap
2257 mam2py-am2-oem-npsdap
2258 am2py-pymea-no1-aspibua
2259 chhs-pipmea-mes-psdap
2260 mam2py-tridi-4amo-csdap
2261 imhs-24thizman2-emo-betadcph
2262 gua-pyma2-chexo-bhsdab
2263 hythpym-amn3-mecpo-tsdap
2264 bimhs-diphmep-fo-bhsdap
2265 bim-eta-5pho-bhsdap
2666 2py-m24thizman2-oem-betapy
2267 dhim-thizo-imo-bphabs
2268 menim-dimen-5amo-psdap
2269 pippy-diphmem-eoco-bhsdap
2270 morhs-propn-eoco-aspaba
2271 2py-pazin-ocho-zdap
2272 fthpym-thizn-4amo-bsdap
2273 menim-tridi-baeo-bnsdap
2274 hythpym-pymea-oeto-bsdap
2275 piraz-pipa-oem-psdap
2276 deam-dimephmem-napo-psdab
2277 dhim-tetras-cnmo-bnsdap
2278 amim-diaz-chexo-bsdap
2279 inhs-mepipe-ocho-bsdap
2280 ibhs-24thiz-chexo-psdab
2281 chmhs-din-eoco-bhsdab
2282 imhs-eta-oem-zdab
2283 bhs-n2nme2n-no2-tsdap
2284 amim-pipa-meo-oxal
2285 2py-m24thiz-mommo-bhsdab
2286 2py-pazin-meo-bnsdap
2287 me2py-edian2-meo-zdab
2288 bhs-eta-no2-zdab
2289 am2py-pipa-mes-aspaba
2290 amthiaz-edian2-cnmo-bsdap
2291 impy-tridi-emo-bhsdab
2292 impy-dimephmep-chexo-zdap
2293 pippy-propn-mecpo-bnsdap
2294 dhim-mepipe-emo-zorn
2295 hythpym-mepipe-fo-betadcph
2296 2py-24thiz-ocho-betaet
2297 bimhs-edian2-meo-csdap
2298 2py-25oxman2-no1-mezphe
2299 deam-m24thizman2-eoco-glyzdap
2300 imhs-propa2s-no1-aspbzla
2301 pippy-pazin-no1-csdap
2302 bimhs-mepazin-chexo-csdap
2303 bimhs-dimen-eoco-bhsdap
2304 me2py-mepipe-men-dfzdap
2305 am-amo2-fo-bhsdab
2306 impy-24thiz-imo-csdap
2307 piraz-25thiz-oem-csdap
2308 ibhs-indan2-mommo-betapy
2309 morhs-mepipen2-mes-bnsdap
2310 thpym-mepipe-5pho-zdap
2311 bimhs-m24thizman2-oeto-betapy
2312 piraz-dimephmem-imo-bphabs
2313 imhs-pyma2-imo-aspibua
2314 imhs-amo2-oem-bnsdap
2315 am4py-dis-meo-asppha
2316 am2py-tridi-pheo-aspibua
2317 am2py-pymea-eoco-zorn
2318 am2py-pymea-napo-psdap
2319 pippy-mepazin-emo-psdab
2320 bim-diphmem-eoco-betainyl
2321 impy-25oxman2-pyo-betadcph
2322 bim-25oxman2-5pho-psdap
2323 bim-diphmep-mes-ppsdap
2324 bhs-pazin-eoco-psdab
2325 me2py-mepipe-nmo-dfzdap
2326 prhs-pipa-mecpo-zdab
2327 dhim-m25oxman2-ocho-bsdap
2328 hythpym-24thizman2-pro-bnsdap
2329 bhs-24thiz-cpeo-bsdap
2330 imhs-mepipe2-sem-nbetameph
2331 z-25thizman2-ocho-aspibua
2332 imhs-trias-5amo-bsdap
2333 thpym-ams2-ocho-glyzdap
2334 imhs-pazin-eoco-zdap
2335 ibhs-24thizman2-oem-bsdap
2336 bhs-hexadi-men-bphabs
2337 thpym-pipmea-5amo-aspibua
2338 bim-pyma2-men-aspbzla
2339 tolhs-amn2-peo-psdap
2340 chmhs-m24thiz-imo-zdabs
2341 bim-amn2-no2-zdap
2342 dhim-diphmep-eoco-betainyl
2343 piraz-edian2-oem-asppha
2344 bz-pnymea-meto-betapy
2345 dhim-dimen-oem-bhsdab
2346 bimhs-trias-meteto-bhsdap
2347 me2py-ams2-fo-betainyl
2348 imhs-pentas-cnmo-asppha
2349 ec-pazin-eoco-aspibua
2350 amim-24thizman2-napo-betapy
2351 hythpym-dimephmep-no2-zdap
2352 am4py-eta-5amo-aspibua
2353 bhs-eta-no2-bhsdap
2354 imhs-eta-eoco-bhsdap
2355 amim-tetradi-napo-bhsdab
2356 thpym-edian2-meo-zdap
2357 bim-thizs-hso-zdab
2358 thpym-mepipen2-imo-aspbzla
2359 tolhs-pazin-napo-zdap
2360 tolhs-dimephmem-paco-betadcph
2361 amthiaz-pipmea-5amo-aspibua
2362 me2py-24thiz-fo-glyzdap
2363 ppy-din-fo-zdab
2364 mam2py-amn-eoco-csdap
2365 orhs-thizs-men-zdap
2366 impy-n24thiman-meo-bhsdap
2367 amim-trias-pheo-asppha
2368 me2py-indan2-pyo-psdap
2369 bim-mepipe2-sem-npsdap
2370 bhs-mepipe-oem-betapy
2371 nmor-pymea-peo-zdab
2372 mam2py-pipa-no1-zdab
2373 2py-pazin-ocho-zdab
2374 bim-diaz-napo-osdap
2375 ibhs-mepipen2-napo-dfzdap
2376 hythpym-mepipen-eoco-aspibua
2377 thpym-mepipe-no2-psdab
2378 impy-mea-no2-bsdap
2379 amim-dimephmep-no2-psdab
2380 bim-din-pyo-bhsdab
2381 2py-m25oxman2-no1-psdab
2382 bimhs-25oxman2-5amo-zdabs
2383 imhs-24thizman2-ocho-bhsdap
2384 dmbim-mepazin-cno-oxal
2385 impy-25oxman2-emo-ibsdap 2386 bhs-3pazin-5amo-zdab
2387 amim-m24thizman2-no1-aspibua
2388 fthpym-ams2-men-zdabs
2389 n2py-dich-meo-oxal
2390 amim-24thizman2-oeto-zdabs
2391 pippy-mepazin-ocho-zdap
2392 thpym-amn2-oem-zdab
2393 me2py-amo2-pro-bhsdab
2394 2py-edian2-5pho-zdap
2395 hythpym-pentas-chexo-aspibua
2396 2py-amn2-5pho-bsdap
2397 bim-eta-eoco-bnsdap
2398 pippy-thizn-pyo-oxal
2399 bim-edian2-no1-zdab
2400 bz-m24thizman2-oeto-aspbzla
2401 amthiaz-24thizman2-baeo-asppha
2402 chmhs-m25thiman2-imo-aspbzla
2403 mam2py-24thizman2-chexo-psdap
2404 bim-din-emo-bhsdab
2405 thpym-pazin-eoco-zdap
2406 me2py-eta2s-emo-betapy
2407 am2py-pipa-mes-zorn
2408 dhim-thizs-napo-bphabs
2409 bimhs-am2-oem-npsdap
2410 am2py-m25thiz-daco-bnsdap
2411 pyr-eta-ocho-betainyl
2412 pippy-diphmep-5amo-csdap
2413 am4py-mepazin-fo-psdab
2414 4pmhs-diphmem-meto-psdap
2415 pyr-amn3-hso-zdabs
2416 prhs-thizn-no2-bsdap
2417 mam2py-mea-4amo-psdap
2418 bimhs-dich-meo-bhsdap
2419 piraz-dimephmem-cno-bnsdap
2420 imhs-mepipe-5pho-psdab
2421 dmam-amo2-meo-zlys
2422 thpym-m24thizman2-chexo-betapy
2423 edothpym-trias-fo-bhsdap
2424 am2py-pyma2-chexo-dfzdap
2425 edothpym-edia2-sem-nzdap
2426 edothpym-tetradi-men-betapy
2427 amim-dimen-mes-psdab
2428 nim-pyma2-cnmo-bhsdab
2429 mam2py-2pazin-ocho-betadcph
2430 imhs-pyma2-eoco-glyzdap
2431 nmor-thizn-hso-bsdap
2432 me2py-m24oxman2-pheo-zdabs
2433 impy-mepipen2-eoco-psdapee
2434 bim-mepipe-no2-zdab
2435 am2py-tetradi-ocho-psdap
2436 dmthpym-25thiz-meo-betainyl
2437 imhs-25oxman2-imo-bsdap
2438 piraz-edian2-4pho-bphabs
2439 thpym-amn2-meo-zdab
2440 thpym-indan2-no2-dfzdap
2441 am2py-24thiman2-hso-bhsdab
2442 dhim-pymea-meo-betadcph
2443 bz-pipa-cpeo-bhsdab
2444 nim-propn-no2-glyzdap
2445 bimhs-pazin-no1-zdab
2446 impy-thizo-fo-mezphe
2447 fthpym-pazin-no2-mezphe
2448 pyrhs-pazin-oem-betainyl
2449 thpym-2pazin-men-aspbzla
2450 2py-diphmep-oem-bhsdab
2451 impy-ams2-5pho-betainyl
2452 piraz-diphmem-napo-psdab
2453 imhs-edian2-ocho-bhsdap
2454 bimhs-dich-pro-psdab
2455 bim-edian2-ocho-zdap
2456 bim-edia2-sem-nbetameph
2457 mam2py-eta-imo-zdabs
2458 pippy-indan2-chexo-zdabs
2459 piraz-tridi-eoco-glyzdap
2460 pippy-pipa-meo-psdab
2461 bimhs-amo2-emo-aspibua
2462 impy-diphmem-fo-asppha
2463 am-25thiman2-meto-betainyl
2464 pyraz-m24thiman2-baeo-zdabs
2465 imhs-amn2-no1-bhsdap
2466 hythpym-m25thiz-oem-zdabs
2467 deam-amn3-imo-bsdap
2468 mam2py-mepazin-hso-psdab
2469 pippy-tridi-napo-dfzdap
2470 hythpym-amn3-ocho-zdabs
2471 thpym-pipa-imo-zdap
2472 4pmhs-mepipe2-sem-nzdap
2473 2py-mepipe-no2-psdab
2474 amim-pipmea-eoco-betadcph
2475 fthpym-amn2-cpro-glyzdap
2476 nmhs-m24thizman2-men-asppha
2477 hythpym-24thiz-emo-glyzdap
2478 2py-propa2s-napo-betapy
2479 pyr-din-hso-bsdap
2480 imhs-mepipe-no1-bhsdap
2481 hythpym-thizn-chexo-betainyl
2482 deam-mepazin-imo-bnsdap
2483 ibhs-mepipe-4pho-glyzdap
2484 n2py-edian2-no2-tsdap
2485 bhs-m24thizman2-ocho-thizzdap
2486 pippy-pazin-oem-csdap
2487 deam-diphmem-ocho-bhsdap
2488 impy-diaz-fo-mezphe
2489 n2py-mepipe2-sem-npsdap
2490 impy-pipmea-no1-psdap
2491 thpym-pnymea-men-bsdap
2492 ibhs-thizs-chexo-csdap
2493 bim-pazin-4pho-aspbzla
2494 cl3pyme-thizo-5pho-zdap
2495 thpym-m25thizman2-eoco-aval
2496 bimhs-pazin-meo-aspbzla
2497 bhs-pipmea-oem-zdab
2498 bim-tetradi-men-zdab
2499 dpam-24thizman2-peo-csdap
2500 bimhs-pentadi-no1-aval
2501 am2py-pymea-meo-asppha
2502 bhs-edian2-mes-betapy
2503 amim-amo2-mmen-tsdap
2504 moegua-24thiman-napo-bphabs
2505 am2py-3pazin-mes-asppha
2506 mam2py-m24thizman2-no2-zorn
2507 nmor-pipa-no1-betapy
2508 amim-thizn-ocho-asppha
2509 bim-mepipe-mes-aspbzla
2510 2py-amn3-napo-dfzdap
2511 bhs-m25thiman2-no2-csdap
2512 impy-propa2s-baeo-zdap
2513 imhs-amn2-oem-bsdap
2514 nmor-ams2-ocho-betapy
2515 am2py-diphmep-chexo-betainyl
2516 bhs-amn2-oem-betapy
2517 hythpym-dimen-paco-psdab
2518 bimhs-pipa-5pho-psdap
2519 piraz-25thiman2-emo-glyzdap 2520 imhs-amn3-daco-bhsdab
2521 pyr-thizs-mmen-psdapee
2522 bim-eta-meo-aspibua
2523 thpym-diphmep-5pho-zdabs
2524 imhs-amn2-no1-psdap
2525 chmhs-m24thiz-emo-mezphe
2526 2py-pyma2-no1-zdabs
2527 piraz-pipmes-no2-tsdap
2528 hythpym-24thizman2-pheo-aspibua
2529 bimhs-dimephmem-emo-zdabs
2530 phhs-dich-5pho-asppha
2531 imhs-pazin-ocho-zdab
2532 moegua-n2nme2n-oem-zdabs
2533 bimhs-m24thizman2-5amo-mezphe
2534 amthiaz-25oxman2-fo-zdap
2535 thpym-24thiman2-no1-aspbzla
2536 me2py-pipa-aco-thizzdap
2537 bhs-am3diaz-baeo-psdap
2538 bhs-eta-no1-aspibua
2539 impy-amo2-emo-psdap
2540 piraz-diphmep-meo-aspbzla
2541 bz-m24thizman2-5pho-psdap
2542 gua-tetradi-no2-glyzdap
2543 2py-mepipe-no1-betapy
2544 nmhs-m25thizman2-napo-ppsdap
2545 pyraz-25oxman2-fo-betainyl
2546 nmor-pnymea-baeo-csdap
2547 me-pnymea-no1-bnsdap
2548 pippy-amo2-men-zdab
2549 bhs-props-4amo-betaet
2550 am2py-trias-pyo-bphabs
2551 impy-eta-emo-zlys
2552 bim-eta-hso-betapy
2553 me2py-mepipen2-emo-zorn
2554 2py-mepipe-meo-bsdap
2555 imhs-eta-mes-psdab
2556 gua-pazin-fo-psdab
2557 chhs-amn-meo-osdap
2558 2py-mepipe-no2-betapy
2559 thpym-eta-oem-betapy
2560 dhim-thizs-ocho-betainyl
2561 2py-eta-meo-psdap
2562 am2py-pazin-no2-zdap
2563 mam2py-mepipen2-chexo-psdab
2564 4pmhs-m24thizman2-aco-betainyl
2565 hythpym-25oxman2-4pho-ibsdap
2566 moegua-dimephmep-emo-zdap
2567 fthpym-tetradi-paco-bsdap
2568 bimhs-amn2-eoco-aspibua
2569 n2py-amn2-meo-bsdap
2570 imhs-amo3-men-asppha
2571 fthpym-25thiz-mes-dfzdap
2572 chmhs-dimen-paco-bphabs
2573 dhim-24thizman2-emo-bsdap
2574 2py-pipa-pheo-bhsdab
2575 amim-dio-oem-glubzla
2576 pippy-25oxman2-mes-psdab
2577 am-pipmeo-mecpo-psdab
2578 moegua-pipa-fo-psdap
2579 amim-amo2-5amo-zdap
2580 im-m25thiman2-ocho-betapy
2581 piraz-pnymea-ocho-psdap
2582 imhs-eta-ocho-psdap
2583 bimhs-mepipe-oem-bphabs
2584 dmbim-dimen-no1-zdapee
2585 me2py-m24oxman2-no2-bnsdap
2586 mam2py-dimephmem-fo-betainyl
2587 hythpym-25oxman2-emo-zdab
2588 bhs-diphmep-5amo-betapy
2589 ec-tetradi-chexo-zdab
2590 hythpym-dio-cpro-betapy
2591 tolhs-mepipen2-ocho-mezphe
2592 bzl-pentadi-mmen-ppsdap
2593 am2py-25thizman2-pheo-glyzdap
2594 bimhs-m24thizman2-peo-glyzdap
2595 dmbim-dis-no1-aspbzla
2596 amim-m25thiz-fo-betainyl
2597 binhs-eta-no2-glyzdap
2598 2py-edian2-mes-zdab
2599 amim-amn3-chexo-zdabs
2600 hythpym-pyma2-ocho-bnsdap
2601 thpym-m24oxman2-no2-asppha
2602 thpym-pnymea-men-betaet
2603 pippy-trias-imo-zdab
2604 thpym-amn2-no1-bhsdap
2605 dpam-25oxman2-oem-bphabs
2606 ibhs-mepazin-5amo-bhsdab
2607 tolhs-pentadi-5pho-ibsdap
2608 pyrhs-pipa-pro-betainyl
2609 piraz-24thiz-imo-bsdap
2610 impy-pipa-5amo-bnsdap
2611 me2py-props-imo-betadcph
2612 cl3pyme-diphmep-meo-aspbzla
2613 n2py-diphmep-baeo-zdabs
2614 ibhs-24oxman2-meo-dfzdap
2615 amim-mepazin-mes-betadcph
2616 bzl-diphmep-chexo-glyzdap
2617 pippy-pipa-emo-zdap
2618 imhs-pipa-oem-psdap
2619 chhs-amo3-mommo-bhsdab
2620 n2py-din-5amo-betadcph
2621 hythpym-trias-meto-betadcph
2622 me2py-mepipe2-sem-nbeta34-dimeoph
2623 deam-24thiz-4amo-mezphe
2624 bhs-amn2-mes-bnsdap
2625 imhs-edian2-ocho-zdap
2626 pippy-props-mmen-asppha
2627 amim-pazin-no2-glyzdap
2628 chhs-ams2-napo-zdap
2629 amthiaz-mepipe-5pho-bhsdap
2630 imhs-pazi2n-no2-betapy
2631 hythpym-thizn-fo-aspibua
2632 hythpym-mepazin-pro-zdap
2633 thpym-amo2-emo-zlys
2634 z-eta-imo-bsdap
2635 prhs-25thiz-4pho-dfzdap
2636 amim-dimen-no2-aspbzla
2637 2py-dimephmem-fo-csdap
2638 pippy-ams3-5pho-aspbzla
2639 im-dimephmem-napo-psdap
2640 4pmhs-24oxman2-5amo-dfzdap
2641 piraz-mea2s-no1-zdab
2642 am2py-pipa-fo-bhsdap
2643 pyr-mepipen2-ocho-zdab
2644 bhs-24thiman-meo-glyzdap
2645 amim-mepipe2-oem-npsdap
2646 phhs-eta-chexo-betadcph
2647 bimhs-24thiz-imo-bnsdap
2648 dmbim-25oxman2-pheo-betapy
2649 bimhs-amn3-napo-zdab
2650 dhim-24thizman2-chexo-psdab
2651 pyrhs-tridi-eoco-betadcph
2652 am2py-amn3-imo-zdabs
2653 bzl-pazin-emo-zdap 2654 deam-pyma2-meo-tsdap
2655 bz-m25thiz-mes-dfzdap
2656 4pmhs-3diaz-daco-betadcph
2657 nmor-edia2-sem-nbetameph
2658 pippy-propa2s-napo-bhsdap
2659 morhs-pipa-5amo-zdap
2660 pippy-mepipe2-oem-nbetapy
2661 dpam-pentadi-no2-psdab
2662 amim-din-ocho-betadcph
2663 hythpym-m24thizman2-ocho-aspbzla
2664 phpip-dimephmep-fo-ibsdap
2665 imhs-dio-meo-csdap
2666 bhs-pazin-eoco-bsdap
2667 mam2py-dimen-4pho-bphabs
2668 pyrhs-amo2-emo-thizzdap
2669 chmhs-dimephmem-oem-bhsdab
2670 prhs-thizn-meo-bnsdap
2671 prhs-pipa-eoco-betadcph
2672 impy-am2-oem-nbetameph
2673 thpym-24thizman2-no2-betapy
2674 impy-din-peo-betadcph
2675 rnhs-amo2-napo-thizzdap
2676 pyraz-dimephmem-5amo-psdab
2677 bimhs-diphmem-men-bhsdap
2678 nim-tetradi-5pho-mezphe naphth
2679 me2py-m24thizman2-cnmo-betadcph
2680 nim-trias-paco-glubzla
2681 amim-n2nme2n-ocho-betainyl
2682 bhs-pyma2-mes-bnsdap
2683 thpym-amn3-imo-aspbzla
2684 amthiaz-25thizman2-5pho-glyyzdap
2685 thpym-ams2-meteto-aspibua
2686 ibhs-dimen-chexo-osdap
2687 morhs-24oxman2-5amo-psdap
2688 hythpym-dio-aco-zdapee
2689 tolhs-tetradi-mmen-aspbzla
2690 phhs-dimephmem-mommo-bphabs
2691 chhs-pyma2-men-aspbzla
2692 ec-mepipen2-aco-osdap
2693 n2py-m24thiz-no1-glyzdap
2694 z-diphmep-oem-zdabs
2695 bz-dimen-no1-betainyl
2696 thpym-eta-oem-bsdap
2697 impy-diphmep-ocho-zdap
2698 dhim-eta-eoco-zdabs
2699 me2py-amn3-aco-betadcph
2700 bim-ams2-no2-dfzdap
2701 bim-edian2-no1-betainyl
2702 bimhs-24thizman2-meteto-asppha
2703 am2py-am2-sem-nbetabnaphth
2704 ec-ams2-imo-aspibua
2705 im-edia2-oem-nbetameph
2706 impy-hexadi-men-bsdap
2707 impy-m25oxman2-ocho-psdab
2708 bimhs-pymea-chexo-osdap
2709 me2py-pymea-meo-ppsdap
2710 chmhs-25oxman2-mes-betaet
2711 nim-dimephmem-imo-psdab
2712 hythpym-pazin-no1-betadcph
2713 am2py-m24thizman2-mes-betainyl
2714 am2py-pymea-no1-zdap
2715 dpam-dimen-napo-bsdap
2716 imhs-dich-imo-mezphe
2717 ibhs-mepipe-men-bphabs
2718 bimhs-24thizman2-no1-zdabs
2719 phpip-pipa-cpro-aspibua
2720 mam2py-pnymea-paco-glubzla
2721 dmbim-hexadi-mecpo-psdapee
2722 dmbim-dis-pyo-psdap
2723 amim-m24thizman2-meo-csdap
2724 am-eta-pheo-betapy
2725 thpym-mepipe2-oem-nbetab
2726 piraz-pnymea-eoco-bhsdap
2727 impy-pipa-napo-aspibua
2728 bz-diphmep-meo-thizzdap
2729 bim-indan2-meto-psdap
2730 me2py-pipa-mmen-aspibua
2731 impy-pyma2-cnmo-betapy
2732 me2py-dimephmem-oem-aspibua
2733 bhs-edian2-men-zdab
2734 imhs-edian2-5pho-psdap
2735 thpym-edian2-ocho-zdab
2736 piraz-dis-5pho-betapy
2737 gua-diphmem-emo-bphabs
2738 hythpym-pazin-5amo-bhsdap
2739 pyrhs-dimephmem-pyo-psdap
2740 amim-edian2-no2-osdap
2741 me2py-amn-daco-mezphe
2742 bimhs-m25thiz-chexo-bnsdap
2743 nmhs-butn-chexo-csdap
2744 me2py-ams2-5pho-dfzdap
2745 fthpym-dis-meto-bhsdap
2746 pippy-mepipen2-cnmo-psdap
2747 am4py-m24thizman2-5pho-csdap
2748 bim-24thiman-eoco-betaet
2749 thpym-amn2-no1-betapy
2750 2py-25oxman2-imo-betainyl
2751 pippy-din-emo-bhsdab
2752 dmbim-m24thiz-hso-psdab
2753 amim-dimen-emo-osdap
2754 pippy-m25thizman2-meo-bsdap
2755 pippy-25thiman2-paco-zorn
2756 dpam-tetradi-eoco-zdap
2757 bhs-dis-men-psdap
2758 edothpym-propn-imo-mezphe
2759 bim-diphmep-napo-bphabs
2760 imhs-am3-oem-nzdab
2761 imhs-24thizman2-mes-zdap
2762 bhs-24thizman2-chexo-glyzdap
2763 amim-trias-meo-bhsdab
2764 amthiaz-dich-oem-bhsdab
2765 pyraz-thizn-oem-betaet
2766 amim-m24thizman2-4pho-aspbzla
2767 dpam-pazin-eoco-aspibua
2768 impy-24thiz-napo-bphabs
2769 2pmhs-dis-no1-betainyl
2770 dmam-thizn-baeo-bsdap
2771 pippy-am2-sem-nzdab
2772 bimhs-pnymea-baeo-mezphe
2773 morhs-edian2-cnmo-psdap
2774 mam2py-pazin-ocho-betadcph
2775 nmor-hexadi-no2-psdap
2776 chmhs-25oxman2-men-betainyl
2777 dmam-m24thizman2-ocho-glyzdap
2778 pippy-dimen-chexo-bhsdab
2779 thpym-pazin-oem-zdab
2780 bim-24thizman2-paco-zdabs
2781 morhs-pnymea-pro-betadcph
2782 me2py-dis-5amo-betapy
2783 dhim-pipa-men-ppsdap
2784 nim-din-pro-betapy
2785 dmthpym-3pazin-eoco-betapy
2786 2py-pazin-eoco-dfzdap
2787 dhim-mepazin-meo-bhsdab 2788 thpym-din-no2-betainyl
2789 dmthpym-amn3-aco-zdab
2790 deam-m24thizman2-men-dfzdap
2791 bhs-mepipe-4amo-betadcph
2792 impy-props-hso-betainyl
2793 bhs-amn2-imo-bhsdap
2794 pyr-25oxman2-no2-bhsdap
2795 mam2py-dimen-mommo-psdab
2796 npip-eta-aco-bphabs
2797 bhs-m25thiz-mmen-betainyl
2798 chmhs-mepipe2-oem-nbeta34-dimeoph
2799 bim-ms-no2-betapy
2800 bim-pipa-imo-betadcph
2801 2py-amo3-cpro-glyzdap
2802 thpym-edian2-no1-zdap
2803 bz-edia2-oem-nzdab
2804 impy-dimen-men-betadcph
2805 amthiaz-tetradi-ocho-bphabs
2805 amthiaz-tetradi-ocho-bphabs
2806 menim-pipa-oem-psdab
2807 thpym-dimen-chexo-bhsdab
2808 pippy-24oxman2-emo-oxal
2809 hythpym-diphmem-meo-mezphe
2810 thpym-amn2-mmen-bnsdap
2811 piraz-ams3-paco-zorn
2812 pyraz-din-baeo-zdabs
2813 mam2py-dimephmem-oem-zdap
2814 piraz-25thizman2-no1-tsdap
2815 nim-25thizman2-imo-aspbzla
2816 pippy-mepipe-eoco-aspibua
2817 imhs-pyma2-meo-zdap
2818 hythpym-mepazin-imo-psdab
2819 hythpym-24thiz-daco-psdab
2820 2py-m24thiz-5pho-oxal
2821 bimhs-eta-hso-mezphe
2822 2py-eta-5pho-betapy
2823 nmhs-pymea-fo-zdab
2824 mam2py-amn3-oem-mezphe
2825 am-tetradi-baeo-aspbzla
2826 hythpym-pymea-mes-glyzdap
2827 bhs-pazin-no2-aval
2828 impy-dimephmem-no2-bsdap
2829 dhim-mepazin-5pho-zdap
2830 piraz-pyma2-5pho-glyzdap
2831 impy-am2-oem-npsdap
2832 2py-m25thiz-oem-betadcph
2833 pippy-edian2-chexo-betainyl
2834 amim-ams2-mes-asppha
2835 pyraz-dimen-fo-bsdap
2836 fthpym-mepazin-ocho-asppha
2837 menim-m24thiman2-eoco-zdap
2838 piraz-propn-oem-aspaba
2839 imhs-eta-meo-betapy
2840 thpym-edian2-no1-zdab
2841 piraz-am3-oem-nbetameph
2842 hythpym-tetras-pro-bnsdap
2843 am2py-dimen-chexo-glyzdap
2844 2py-propa2s-oem-glyzdap
2845 bhs-mepipe-no2-bsdap
2846 imhs-pazin-oem-zdab
2847 dpam-pnymea-no2-psdap
2848 am2py-mepipe2-sem-nbetapy
2849 dmam-25oxman2-no2-bhsdap
2850 2py-mepipen2-chexo-zdabs
2851 dpam-25thiman2-peo-mezphe
2852 pyraz-24thizman2-emo-bhsdap
2853 bz-24thiz-chexo-zdab
2854 bimhs-24thiz-eoco-tsdap
2855 2pmhs-dis-cpro-thizzdap
2856 hythpym-din-cpeo-zdab
2857 2py-pipmeo-5pho-aspibua
2858 bimhs-m24oxman2-imo-bhsdap
2859 bimhs-pymea-chexo-mezphe
2860 phpip-diphmem-ocho-csdap
2861 me2py-25oxman2-oeto-zdap
2862 pippy-amo2-imo-bhsdab
2863 amim-trias-oem-zdabs
2864 dhim-butn-chexo-bsdap
2865 impy-n24thiman-chexo-asppha
2866 bhs-pipmes-emo-betainyl
2867 imhs-edian2-oem-psdab
2868 emnim-pymea-no1-betapy
2869 thpym-mepipe-mes-bhsdap
2870 me2py-dimephmep-emo-mezphe
2871 amim-25thizman2-chexo-oxal
2872 pippy-24thizman2-5amo-psdab
2873 impy-amn2-4amo-aval
2874 imhs-pipmeo-men-dfzdap
2875 imhs-pymea-ocho-bhsdap
2876 am4py-tetradi-meo-bhsdab
2877 2py-pazin-no2-bnsdap
2878 imhs-dimephmem-oem-zdap
2879 ppy-pymea-fo-bsdap
2880 pippy-25oxman2-mommo-zdap
2881 amim-tetradi-emo-zlys
2882 chhs-tridi-no2-zdabs
2883 hythpym-amn3-emo-psdap
2884 bhs-pazin-oem-betapy
2885 hythpym-pipa-imo-bhsdap
2886 piraz-mepipe-men-glyzdap
2887 piraz-edian2-imo-betapy
2888 imhs-dis-pro-betapy
2889 bzl-edian2-imo-betainyl
2890 chmhs-amn3-cno-bnsdap
2891 thpym-trias-cnmo-zorn
2892 hythpym-ams2-mes-glyzdap
2893 dhim-diphmem-emo-betainyl
2894 imhs-edia2-oem-nbeta34dimeoph
2895 bimhs-m24thiman2-meto-betainyl
2896 2py-eta-no1-psdab
2897 imhs-edian2-eoco-psdap
2898 impy-edia2-oem-nbetapy
2899 piraz-hexas-chexo-bsdap
2900 thpym-dis-5amo-zdabs
2901 impy-din-meto-mezphe
2902 piraz-eta-imo-zdabs
2903 thpym-amn2-meo-bhsdap
2904 dmthpym-amo2-meo-zorn
2905 mam2py-mepazin-chexo-betadcph
2906 hythpym-eta-paco-bnsdap
2907 pippy-diphmep-mes-bhsdap
2908 pippy-24thiz-hso-glubzla
2909 ec-din-mes-csdap
2910 me2py-dich-chexo-betaet
2911 piraz-pipmea-eoco-zdap
2912 2py-eta-eoco-bhsdap
2913 z-diphmep-oem-glyzdap
2914 ec-m24thizman2-imo-betapy
2915 bimhs-amn2-5amo-bnsdap
2916 mam2py-trias-mes-csdap
2917 inhs-edian2-ocho-zdab
2918 bhs-mepipe-ocho-zdab
2919 piraz-din-5pho-zdap
2920 me2py-ams2-men-psdapee 2921 pyrhs-diphmem-imo-bphabs
2922 bim-butn-napo-zdapee
2923 bim-edian2-no2-bsdap
2924 bz-pymea-emo-bnsdap
2925 pippy-24thizman2-oem-aspbzla
2926 4pmhs-pyma2-oem-dfzdap
2927 bim-diphmep-cpro-glupha
2928 pippy-amo3-emo-aspibua
2929 pippy-m25thiz-ocho-zdab
2930 2py-pazin-no2-zdapee
2931 pyraz-pipmeo-cpeo-psdap
2932 bimhs-pyma2-5pho-zdab
2933 dhim-m25thiman2-meo-betapy
2934 gua-m25thiz-imo-aspbzla
2935 me2py-dimephmem-cnmo-bhsdap
2936 me-trias-no2-bsdap
2937 am-dis-ocho-bphabs
2938 bim-tridi-mes-betainyl
2939 mepip-trias-fo-bhsdap
2940 am-ams3-cno-csdap
2941 piraz-am2-sem-nzdap
2942 z-dimephmem-imo-glyzdap
2943 bimhs-diphmem-5amo-betaet
2944 thpym-pipmeo-5amo-glyzdap
2945 gua-m24thizman2-daco-aspbzla
2946 me2py-dimephmep-4amo-glyzdap
2947 imhs-mea2s-meo-bhsdab
2948 imhs-eta-no2-bsdap
2949 mepip-dis-eoco-psdab
2950 amim-mea2s-no2-psdap
2951 chhs-tetradi-ocho-bnsdap
2952 amim-3diaz-emo-glyzdap
2953 hythpym-mepipen2-aco-zdap
2954 gua-thizn-oem-bhsdab
2955 mam2py-tetradi-emo-dfzdap
2956 impy-dimen-meo-dfzdap
2957 impy-n24thiman-oem-psdab
2958 impy-24thiman2-mes-aspaba
2959 dhim-dimen-meo-aspibua
2960 bim-dimephmem-imo-psdab
2961 pippy-pipmeo-oem-bphabs
2962 am2py-tetras-cpro-zorn
2963 am2py-thizn-cno-bhsdab
2964 mam2py-24thizman2-cpro-csdap
2965 bim-mepipe-oem-zdap
2966 pippy-pazin-oem-aspbzla
2967 thpym-pazin-no1-psdab
2968 thpym-eta-chexo-betadcph
2969 bzl-amo2-4amo-asppha
2970 amthiaz-mepipe-no2-csdap
2971 bimhs-m24thizman2-meteto-aspbzla
2972 thpym-diphmem-pyo-mezphe
2973 ppy-24thiz-eoco-dfzdap
2974 hythpym-tridi-chexo-glyzdap
2975 amim-dimen-5pho-zorn
2976 pippy-pyma2-mmen-thizzdap
2977 am4py-pyma2-hso-aspbzla
2978 imhs-pazin-5pho-zdab
2979 hythpym-diphmep-peo-zdap
2980 bim-mepipe-meo-psdap
2981 menim-ams3-baeo-aspibua
2982 thpym-edian2-eoco-bnsdap
2983 menim-mepipe2-oem-nzdap
2984 phhs-mepazin-chexo-mezphe
2985 phhs-25oxman2-meo-betadcph
2986 thpym-pazin-meo-bnsdap
2987 chmhs-m25thiz-eoco-betapy
2988 mam2py-props-no2-betadcph
2989 me-pipmea-meo-aspbzla
2990 bim-ams2-daco-bhsdab
2991 dmbim-pipmea-no2-betadcph
2992 thpym-amn2-ocho-zdap
2993 dmam-butn-5pho-csdap
2994 npip-m24thiman2-oem-dfzdap
2995 mam2py-dimephmep-imo-mezphe
2996 me-ams2-meo-bhsdab
2997 nim-pipa-napo-asppha
2998 binhs-amo3-napo-bsdap
2999 2py-diphmep-4pho-tsdap
3000 2py-pymea-meo-bhsdab
3001 mam2py-m25thizman2-5pho-betapy
3002 bim-tetradi-oem-glubzla
3003 piraz-m24oxman2-ocho-betainyl
3004 bim-pazin-oem-zdap
3005 am2py-25oxman2-oem-ibsdap
3006 dhim-pymea-imo-bphabs
3007 piraz-pyma2-oem-bhsdap
3008 dmam-mepipe-5amo-dfzdap
3009 bim-amn2-meo-zdap
3010 pyr-din-oem-zdab
3011 bim-edian2-no1-bsdap
3012 bzl-pazin-meo-bphabs
3013 tolhs-thizn-peo-zdap
3014 amim-pipmea-mes-bhsdab
3015 dmbim-eta-pheo-oxal
3016 amim-mepipe-imo-asppha
3017 pyrhs-diphmem-ocho-csdap
3018 imhs-eta-no1-psdap
3019 z-diphmem-pyo-betadcph
3020 cl3pyme-hexadi-eoco-asppha
3021 thpym-ms-eoco-betainyl
3022 amim-edia2-oem-nbeta34dimeoph
3023 thpym-amo2-eoco-bsdap
3024 am2py-dipch-chexo-csdap
3025 pippy-m25thiman2-peo-psdap
3026 mam2py-trias-fo-psdab
3027 pippy-3pazin-meo-zdab
3028 gua-din-fo-ibsdap
3029 nmor-dimephmem-oem-dfzdap
3030 piraz-butn-oem-aspbzla
3031 thpym-diphmep-oem-bhsdab
3032 dhim-25thizman2-meto-betadcph
3033 pippy-tetradi-meto-bhsdap
3034 am4py-amn3-ocho-asppha
3035 morhs-pazin-5amo-glyzdap
3036 pippy-24thizman2-mes-zdabs
3037 dhim-3diaz-5amo-bnsdap
3038 mam2py-25oxman2-cpeo-psdapee
3039 bhs-am=2-oem-psdab
3040 hythpym-mepipe-oem-glyzdap
3041 npip-m24thizman2-men-aspbzla
3042 dhim-dimephmem-ocho-aspbzla
3043 piraz-thizs-fo-glyzdap
3044 pyrhs-thizn-men-zdabs
3045 bim-amo2-mes-thizzdap
3046 deam-edia2-sem-nzdab
3047 mam2py-pipmea-emo-csdap
3048 prhs-dimephmem-fo-bhsdab
3049 piraz-m24thizman2-aco-psdab
3050 imhs-pymea-no2-betainyl
3051 pippy-am3-sem-nbetabnaphth
3052 bimhs-pipa-chexo-glubzla
3053 imhs-pazin-oem-betapy
3054 bhs-24thizman2-aco-bhsdap 3055 am2py-m24thizman2-cpro-aval
3056 pyr-25oxman2-napo-glyzdap
3057 imhs-pyma2-oem-mezphe
3058 bhs-24thizman2-emo-bhsdab
3059 amim-24thizman2-emo-betainyl
3060 am2py-pymea-emo-zdab
3061 amthiaz-tetradi-mes-zdab
3062 piraz-dimephmem-5amo-csdap
3063 ppy-n2o2n-fo-asppha
3064 prhs-25oxman2-chexo-aspibua
3065 am2py-amn2-mecpo-psdab
3066 bimhs-tridi-5pho-bhsdap
3067 mam2py-m25thiz-ocho-zdabs
3068 edothpym-pipa-emo-betapy
3069 imhs-mepipe-no2-betapy
3070 pyrhs-edia2-oem-nbetameph
3071 impy-pnymea-no2-betadcph
3072 amim-diphmem-imo-psdab
3073 dmam-am2-sem-nzdab
3074 dmbim-24thiz-fo-aspibua
3075 am2py-amn2-meo-aspibua
3076 thpym-amn2-no2-bhsdap
3077 am4py-pipmea-fo-psdapee
3078 am-din-peo-asppha
3079 dhim-edian2-cpeo-betapy
3080 piraz-eta-fo-bsdap
3081 ibhs-m25thiz-meo-csdap
3082 phhs-edian2-eoco-aspibua
3083 imhs-amn2-fo-bhsdap
3084 impy-25thiman2-fo-bnsdap
3085 bz-diphmem-mes-zdab
3086 bim-dimephmep-hso-mezphe
3087 phhs-m24oxman2-5pho-glyzdap
3088 2py-pazin-5pho-betapy
3089 mam2py-mepazin-oem-zdabs
3090 me2py-din-meo-betapy
3091 gua-pazin-cnmo-bhsdab
3092 imhs-edian2-5pho-bhsdap
3093 prhs-am2-oem-nbetabnaphth
3094 impy-edia2-sem-nbetabnaphth
3095 me2py-pipmea-napo-glupha
3096 bimhs-props-emo-psdab
3097 bim-mea2s-mes-betapy
3098 dhim-pipmes-meteto-dfzdap
3099 me2py-diaz-men-betadcph
3100 dhim-tetradi-emo-zdabs
3101 bhs-mepipen2-mes-thizzdap
3102 4pmhs-m25thiman2-imo-bhsdab
3103 z-m24thizman2-mes-aspibua
3104 mam2py-mea2s-pyo-bhsdap
3105 imhs-pyma2-5pho-betapy
3106 n2py-m25thizman2-no1-betapy
3107 piraz-dimephmem-eoco-betainyl
3108 piraz-diphmem-no1-betapy
3109 prhs-ms-4amo-betadcph
3110 2py-pipmes-no1-ibsdap
3111 bim-dimephmep-5pho-bhsdab
3112 impy-diphmep-5amo-psdab
3113 bimhs-eta2s-emo-dfzdap
3114 me2py-pymea-men-mezphe
3115 deam-eta-mes-aspibua
3116 bz-pazin-nmo-zdabs
3117 bhs-pazin-5pho-bnsdap
3118 tolhs-dis-pyo-aspbzla
3119 bim-pazin-oem-psdab
3120 nmor-pymea-mecpo-bphabs
3121 impy-mepazin-ocho-zdabs
3122 am-pipmes-fo-psdab
3123 fthpym-24thizman2-fo-betapy
3124 dhim-pipmes-pro-mezphe
3125 pippy-mepazin-mmen-betainyl
3126 hythpym-pazin-fo-bhsdap
3127 2py-m24oxman2-no1-betapy
3128 amim-mepipen2-meto-ppsdap
3129 bhs-mepipe-eoco-psdab
3130 am-hexadi-5pho-betainyl
3131 z-propa2s-meo-glyzdap
3132 2py-diphmep-emo-bhsdab
3133 mepip-trias-mes-zdabs
3134 bim-mepazin-fo-osdap
3135 pippy-pipa-fo-dfzdap
3136 rnmhs-diphmem-4pho-mezphe
3137 bhs-amn2-eoco-betapy
3138 am2py-mepipe2-oem-nbetameph
3139 bzl-thizn-5amo-dfzdap
3140 pyrhs-mepipe2-oem-nbetapy
3141 pippy-amo3-no2-psdap
3142 me2py-mepipen2-no1-asppha
3143 am2py-mepipen2-paco-betainyl
3144 me2py-pymea-oem-csdap
3145 tolhs-25oxman2-5amo-zdabs
3146 chhs-dimen-emo-osdap
3147 me2py-diphmem-5amo-dfzdap
3148 pyrhs-mepipe2-oem-nbetapy
3149 mam2py-pnymea-meto-zdapee
3150 z-m25thiz-meo-psdab
3151 me2py-mepazin-oem-psdap
3152 am4py-pymea-mes-glyzdap
3153 bhs-mepipe-oem-zdap
3154 bhs-eta-meo-zdab
3155 dmam-tridi-5pho-glupha
3156 piraz-diphmem-aco-zlys
3157 bim-pymea-mes-mezphe
3158 imhs-mepipe-mes-bhsdap
3159 hythpym-diphmep-meteto-zdap
3160 menim-pipa-daco-psdab
3161 amim-3pazin-eoco-bphabs
3162 thpym-thizs-emo-bhsdap
3163 npip-24thiz-ocho-dfzdap
3164 am2py-25oxman2-meo-aspbzla
3165 4pmhs-amo2-chexo-aspibua
3166 bhs-mepipe-no2-zdab
3167 me2py-mepipen2-meo-bhsdab
3168 imhs-edian2-no2-psdab
3169 edothpym-dimephmep-5pho-zdap
3170 imhs-pazin-imo-bhsdap
3171 bhs-pazin-meo-zdap
3172 bhs-n24thiman-ocho-mezphe
3173 am4py-24thiz-5amo-betainyl
3174 bim-eta-5pho-bnsdap
3175 bim-mepipe-no1-psdap
3176 im-m25thiz-meto-ibsdap
3177 am2py-25oxman2-4pho-psdab
3178 imhs-amn2-5pho-bnsdap
3179 bimhs-25oxman2-meo-bphabs
3180 am-thizn-5pho-bnsdap
3181 thpym-m24thizman2-mes-zdab
3182 nim-pipmea-men-betadcph
3183 bzl-tridi-meo-aspibua
3184 amim-ms-chexo-zorn
3185 nim-eta2s-napo-bhsdab
3186 dhim-amn2-eoco-psdab
3187 phpip-m24thizman2-5amo-bphabs
3188 bhs-propa2s-no2-betadcph 3189 thpym-amn2-no1-zdab
3190 hythpym-ams3-meo-zdabs
3191 inhs-edian2-5pho-zdap
3192 hythpym-diphmep-emo-betainyl
3193 me-pymea-no2-bnsdap
3194 bimhs-am2-sem-nzdap
3195 bim-hexadi-5amo-bhsdap
3196 imhs-mepipe-mes-bnsdap
3197 bimhs-amo3-men-bsdap
3198 hythpym-mepipen2-chexo-betainyl
3199 mam2py-mepazin-imo-asppha
3200 bhs-pyma2-meteto-bhsdab
3201 cl3pyme-am3diaz-no1-betadcph
3202 dmthpym-diphmem-emo-betainyl
3203 imhs-thizn-no1-bhsdap
3204 imhs-eta-5pho-zdap
3205 bimhs-dimen-baeo-bnsdap
3206 piraz-mepipen2-ocho-zdab
3207 thpym-eta-oem-bnsdap
3208 imhs-mepipe-meo-psdab
3209 bimhs-mepazin-cpro-zdabs
3210 dmthpym-mepipe-ocho-zorn
3211 thpym-tridi-oeto-aspbzla
3212 piraz-24thiz-5pho-zdabs
3213 npip-m25thiz-mes-zdap
3214 ec-25thiman2-meo-aspibua
3215 amim-tetras-5pho-mezphe
3216 pippy-diphmem-men-bphabs
3217 nim-pipmea-peo-zdab
3218 nim-amo2-imo-dfzdap
3219 hythpym-amo2-eoco-aspbzla
3220 bim-pazin-ocho-betapy
3221 thpym-pyma2-chexo-zdabs
3222 imhs-mepipe2-oem-nbetapy
3223 imhs-edian2-4pho-zlys
3224 prhs-am3diaz-napo-bsdap
3225 cl3pyme-amo2-pheo-mezphe
3226 hythpym-hexas-pro-bhsdab
3227 thpym-diaz-chexo-dfzdap
3228 edothpym-am2-sem-npsdap
3229 bimhs-m24thizman2-emo-mezphe
3230 bhs-am2-sem-nbetabnaphth
3231 emnim-pymea-ocho-dfzdap
3232 thpym-2pazin-mmen-ibsdap
3233 bzl-diphmem-no2-bsdap
3234 mam2py-diphmem-meo-mezphe
3235 4pmhs-amn2-mes-mezphe
3236 thpym-pazin-oem-bnsdap
3237 me2py-dis-mmen-zlys
3238 imhs-25oxman2-emo-bhsdab
3239 dhim-amo2-emo-mezphe
3240 bhs-24thiman-oem-oxal
3241 mam2py-diphmep-imo-betainyl
3242 dhim-diphmem-oeto-bnsdap
3243 bim-3diaz-daco-bhsdap
3244 me2py-mepipen2-eoco-betapy
3245 ec-24thiz-ocho-ppsdap
3246 am2py-mepazin-cpro-psdab
3247 nmor-mepipe-4pho-zdap
3248 2py-m24thizman2-aco-zdab
3249 bim-25thiman2-no1-psdab
3250 pippy-edia2-sem-nzdab
3251 2py-mepipe-oem-bhsdap
3252 thpym-mepipe-no2-bsdap
3253 imhs-25thiz-chexo-glubzla
3254 amim-pnymea-no1-psdab
3255 pyrhs-eta-mes-zlys
3256 moegua-diphmep-cpeo-betadcph
3257 pyrhs-din-napo-zdap
3258 thpym-amo2-men-tsdap
3259 me2py-m25oxman2-meo-zdapee
3260 hythpym-trias-no1-betainyl
3261 bimhs-dimephmem-emo-betainyl
3262 dhim-tetras-5pho-bhsdap
3263 am-mepazin-emo-aspaba
3264 am2py-amn2-men-betapy
3265 bim-din-meo-aspbzla
3266 pippy-butn-emo-betadcph
3267 im-pyma2-mommo-psdab
3268 thpym-amn3-men-psdab
3269 am2py-am2-sem-nzdab
3270 pippy-trias-5pho-glyzdap
3271 hythpym-mepipe-no1-zdab
3272 am2py-m25thiz-mes-csdap
3273 thpym-pazin-5pho-betapy
3274 ibhs-dio-napo-zdabs
3275 pyrhs-m24oxman2-napo-aspibua
3276 bim-eta-5pho-zdab
3277 bhs-amn2-pro-thizzdap
3278 bim-mepipe2-sem-nbetameph
3279 me2py-diphmep-imo-zdap
3280 nmhs-m24thizman2-no2-betainyl
3281 amim-amn3-aco-glyzdap
3282 impy-pnymea-5pho-aspibua
3283 2py-props-cpeo-ppsdap
3284 pippy-din-no2-glyzdap
3285 dhim-25thiz-oeto-aspbzla
3286 impy-thizo-4pho-dfzdap
3287 mam2py-trias-mecpo-dfzdap
3288 impy-eta2s-nmo-dfzdap
3289 bz-24thizman2-pro-bphabs
3290 dpam-din-imo-psdab
3291 phhs-24thiz-meo-psdap
3292 imhs-25thiz-emo-zdap
3293 hythpym-diphmem-no1-psdab
3294 chhs-mepazin-no1-psdap
3295 prhs-edian2-cno-bphabs
3296 bz-pyma2-5amo-zdap
3297 am2py-dich-emo-bsdap
3298 pyrhs-pymea-4pho-mezphe
3299 impy-trias-imo-thizzdap
3300 dhim-thizn-emo-glyzdap
3301 thpym-m25thiman2-pheo-bhsdab
3302 moegua-amo2-ocho-psdab
3303 chmhs-dimephmem-oem-aspibua
3304 z-n24thiman-men-bnsdap
3305 bim-amn2-5pho-bhsdap
3306 ec-m25oxman2-no2-aspbzla
3307 ec-24thiz-no1-zdabs
3308 bim-edian2-no2-glyzdap
3309 hythpym-dimephmep-men-betapy
3310 n2py-mepipen2-napo-betapy
3311 bhs-mepipe-no1-mezphe
3312 bz-dis-eoco-aspaba
3313 bimhs-edia2-oem-nbetabnaphth
3314 pippy-diphmep-meo-csdap
3315 chmhs-dimen-fo-zdab
3316 piraz-trias-eoco-aspaba
3317 hythpym-24thizman2-imo-bnsdap
3318 amim-pymea-cpeo-bnsdap
3319 piraz-din-fo-psdap
3320 nim-25thiz-no2-psdab
3321 bimhs-m24thizman2-imo-zlys
3322 am2py-mepipe2-oem-nbetab naphth 3323 bzl-mepipen2-imo-bnsdap
3324 me2py-dis-meo-psdap
3325 amim-trias-5pho-psdab
3326 menim-amo2-men-dfzdap
3327 hythpym-tridi-mes-bsdap
3328 2py-25oxman2-no1-asppha
3329 ec-amn2-chexo-aspbzla
3330 prhs-edia2-sem-nbetabnaphth
3331 2pmhs-trias-chexo-csdap
3332 am2py-dis-mommo-bsdap
3333 dmbim-din-5amo-csdap
3334 imhs-mepipe-no2-zdab
3335 4pmhs-edian2-chexo-asppha
3336 hythpym-2pazin-eoco-bhsdap
3337 piraz-24thizman2-meo-dfzdap
3338 bhs-mepipe-no1-psdab
3339 thpym-am3diaz-emo-bnsdap
3340 imhs-dimephmem-mes-psdap
3341 piraz-din-chexo-mezphe
3342 impy-butn-5pho-betainyl
3343 dmthpym-3diaz-pro-mezphe
3344 piraz-pazin-5pho-dfzdap
3345 bim-trias-no1-ppsdap
3346 mam2py-pipmea-no2-psdap
3347 imhs-amn2-mes-bhsdap
3348 dpam-25oxman2-chexo-thizzdap
3349 pyrhs-amn2-emo-zdap
3350 mam2py-dich-no2-bhsdab
3351 mam2py-mepipen2-ocho-zdabs
3352 n2py-trias-ocho-betapy
3353 me2py-diphmem-baeo-aspbzla
3354 bim-m25thiz-men-betainyl
3355 bz-m24thizman2-emo-betainyl
3356 thpym-dimephmem-5pho-psdap
3357 bim-pazin-5pho-bnsdap
3358 thpym-amn2-5amo-aspaba
3359 deam-ams2-emo-bsdap
3360 bhs-24thiz-oem-betaet
3361 2py-eta-oem-bnsdap
3362 bzl-mepipe-imo-ppsdap
3363 am4py-25thizman2-fo-csdap
3364 bzl-24thizman2-cpeo-csdap
3365 mam2py-tetradi-imo-dfzdap
3366 mam2py-25oxman2-ocho-tsdap
3367 hythpym-dio-oem-dfzdap
3368 2py-dipch-aco-bhsdab
3369 cl3pyme-diphmep-mes-bsdap
3370 nim-dimephmep-oem-betadcph
3371 emnim-pyma2-oem-betapy
3372 2py-am2-sem-nzdap
3373 bhs-amn2-mes-zdap
3374 impy-ms-4amo-betadcph
3375 hythpym-24thiz-no2-zdabs
3376 cl3pyme-amn2-ocho-zdab
3377 z-pazin-5amo-glupha
3378 me2py-pyma2-ocho-betadcph
3379 bimhs-dimephmep-cnmo-bhsdab
3380 mam2py-eta-meo-betaet
3381 bimhs-diphmem-fo-bphabs
3382 mam2py-ams3-imo-glyzdap
3383 mam2py-am3-oem-nbetameph
3384 npip-dis-imo-bhsdap
3385 bhs-24thizman2-imo-betainyl
3386 2py-diphmem-mes-betainyl
3387 bim-diphmem-no1-mezphe
3388 thpym-pnymea-no2-bhsdap
3389 dhim-thizs-napo-glubzla
3390 menim-diphmep-meo-tsdap
3391 piraz-pipmes-mes-bhsdab
3392 bim-pazin-meo-bnsdap
3393 pippy-diphmep-fo-zorn
3394 bzl-m25thiman2-napo-glyzdap
3395 bim-amn3-emo-glyzdap
3396 bhs-24thiz-no1-psdab
3397 bim-pazin-no1-betaet
3398 bhs-tetradi-men-aspibua
3399 mam2py-amn3-oem-psdap
3400 chhs-pipmea-no1-betadcph
3401 piraz-din-chexo-bsdap
3402 menim-din-meto-bhsdap
3403 emnim-pipmea-napo-bhsdap
3404 impy-pnymea-meo-bnsdap
3405 imhs-edian2-5pho-zdab
3406 mam2py-am2-sem-nbeta34dimeoph
3407 me2py-hexas-mes-bphabs
3408 am2py-amn3-no1-zlys
3409 bimhs-ams2-paco-zdapee
3410 bimhs-pazin-emo-ibsdap
3411 imhs-amn2-5pho-psdap
3412 chmhs-pyma2-fo-aspaba
3413 dhim-dimephmem-5pho-psdap
3414 deam-24thiz-ocho-zdap
3415 bz-pnymea-chexo-bphabs
3416 impy-mepazin-5amo-zdap
3417 am2py-pipmea-napo-bnsdap
3418 me2py-3diaz-pheo-glubzla
3419 piraz-butn-oem-csdap
3420 2pmhs-props-no1-betainyl
3421 2py-dis-oem-betadcph
3422 chhs-thizo-chexo-zorn
3423 2py-pentas-cpeo-betapy
3424 am-m25thiz-chexo-glupha
3425 piraz-25thiman2-hso-bhsdab
3426 hythpym-pipmea-chexo-tsdap
3427 piraz-dio-emo-csdap
3428 im-pipmeo-4amo-bphabs
3429 bim-m25thiz-emo-mezphe
3430 amim-pymea-ocho-psdab
3431 impy-dimephmep-eoco-csdap
3432 ibhs-dis-5pho-betainyl
3433 dhim-m24thizman2-meo-bhsdab
3434 dmbim-pipmea-imo-glyzdap
3435 cl3pyme-eta-napo-bphabs
3436 bhs-eta-ocho-zdap
3437 bim-pazin-5pho-psdab
3438 bhs-pnymea-imo-bsdap
3439 chmhs-pymea-meo-zdab
3440 piraz-pnymea-oem-zdabs
3441 chhs-mepipen2-meo-psdab
3442 amim-dimen-meto-betainyl
3443 hythpym-thizn-mes-psdap
3444 amim-eta-cno-glyzdap
3445 mam2py-mepipen2-imo-psdap
3446 dhim-pazin-ocho-dfzdap
3447 inhs-pazin-cno-zdab
3448 gua-propn-eoco-bphabs
3449 bhs-mepipe-mes-zdap
3450 2py-diphmep-fo-betadcph
3451 im-props-men-betadcph
3452 impy-ams3-cnmo-zlys
3453 n2py-dimephmep-napo-bnsdap
3454 fthpym-diphmem-pro-psdap
3455 me2py-dio-5amo-betainyl
3456 bim-pipmea-chexo-betadcph 3457 amim-n2o2n-imo-zdab
3458 am2py-thizo-chexo-betainyl
3459 hythpym-pymea-5pho-betaet
3460 bhs-tetradi-eoco-betainyl
3461 bim-am3-sem-npsdap
3462 morhs-tridi-napo-ppsdap
3463 imhs-pentadi-5amo-bhsdap
3464 bz-mepipen2-paco-zdabs
3465 piraz-tridi-5pho-aspbzla
3466 thpym-edian2-ocho-bsdap
3467 mam2py-thizn-no2-betapy
3468 hythpym-tetradi-meo-bsdap
3469 z-mepipe2-sem-nbetabnaphth
3470 thpym-pazin-ocho-psdab
3471 thpym-25oxman2-fo-glubzla
3472 ppy-diphmep-napo-aspibua
3473 imhs-mepazin-eoco-aspbzla
3474 imhs-diaz-eoco-betadcph
3475 4pmhs-pyma2-chexo-aspibua
3476 me-3pazin-emo-asppha
3477 bim-amn2-eoco-bsdap
3478 amim-dimephmem-mes-betainyl
3479 bimhs-tetradi-imo-glyzdap
3480 imhs-pipmea-baeo-zdab
3481 me2py-dimephmem-emo-bsdap
3482 impy-pymea-imo-betadcph
3483 me2py-3pazin-no2-glyzdap
3484 me-dimen-emo-zdapee
3485 hythpym-din-napo-aspbzla
3486 thpym-edian2-ocho-bhsdap
3487 2py-dimephmem-men-bphabs
3488 piraz-pymea-no1-bphabs
3489 bhs-pipmea-pyo-betadcph
3490 dhim-pyma2-emo-bhsdap
3491 nmhs-thizn-eoco-betadcph
3492 2py-din-5amo-betainyl
3493 mam2py-dis-ocho-dfzdap
3494 bhs-trias-meo-bphabs
3495 imhs-dimephmep-cpeo-aspibua
3496 hythpym-mepipen2-imo-mezphe
3497 amim-dimen-no2-zdap
3498 piraz-dimephmem-pro-dfzdap
3499 me2py-trias-ocho-bsdap
3500 piraz-pymea-4amo-betadcph
3501 mam2py-n24thiman-5amo-psdab
3502 bim-24thiz-men-glupha
3503 phpip-dich-imo-bhsdab
3504 mam2py-m25thizman2-fo-zdap
3505 2py-thizn-5pho-zdab
3506 thpym-pipa-mes-mezphe
3507 mam2py-25oxman2-cpeo-bhsdab
3508 z-dimephmem-meo-bphabs
3509 amim-24thiz-cno-aspbzla
3510 nim-thizn-napo-betapy
3511 dmbim-dimen-meo-zdap
3512 pyrhs-pymea-baeo-aval
3513 imhs-edian2-emo-dfzdap
3514 thpym-mepipe-eoco-bsdap
3515 2py-dis-no2-betapy
3516 amim-pipa-nmo-psdapee
3517 bhs-tetras-5amo-betadcph
3518 am-m25oxman2-ocho-glubzla
3519 bim-pazin-eoco-psdab
3520 bhs-amn2-no1-bhsdap
3521 me2py-din-5pho-zdabs
3522 thpym-mepipen2-oem-glyzdap
3523 2py-n2o2n-imo-glyzdap
3524 hythpym-tetradi-emo-bhsdap
3525 dhim-24thizman2-5amo-aspbzla
3526 hythpym-pnymea-mes-aspbzla
3527 binhs-amn3-napo-glubzla
3528 bim-pazin-oem-bnsdap
3529 n2py-m25oxman2-men-bsdap
3530 thpym-mepipe-eoco-zdab
3531 me2py-edia2-sem-nbetabnaphth
3532 mepip-pnymea-mes-psdap
3533 dpam-25oxman2-5amo-psdab
3534 thpym-n2nme2n-no2-bhsdab
3535 nmor-amn3-emo-glyzdap
3536 hythpym-25oxman2-fo-betainyl
3537 hythpym-pyma2-hso-aspibua
3538 hythpym-dimephmem-men-tsdap
3539 4pmhs-mepazin-imo-bhsdap
3540 impy-tetradi-no1-betaet
3541 n2py-diphmep-meo-betaet
3542 piraz-pnymea-napo-glyzdap
3543 imhs-mepipe-eoco-bsdap
3544 bhs-dimen-fo-bsdap
3545 bim-thizo-napo-zlys
3546 tolhs-pyma2-5amo-csdap
3547 am2py-amn2-no2-glubzla
3548 hythpym-mepipe-paco-psdab
3549 me-trias-5pho-zdabs
3550 amim-tridi-oem-betainyl
3551 prhs-24thiz-ocho-psdap
3552 am2py-dimephmep-ocho-bnsdap
3553 chmhs-pazin-mes-betaet
3554 imhs-thizn-5pho-glubzla
3555 bhs-tetras-mes-dfzdap
3556 am2py-mepazin-eoco-mezphe
3557 n2py-dimen-meteto-zlys
3558 dhim-pazin-pro-csdap
3559 am4py-m25oxman2-eoco-dfzdap
3560 am-am2-oem-npsdap
3561 impy-mea2s-meo-zorn
3562 am2py-trias-no1-thizzdap
3563 dmthpym-amn2-napo-betapy
3564 me-dis-pheo-betadcph
3565 pippy-thizs-peo-bhsdap
3566 2py-amn2-no1-zdap
3567 mam2py-pipmes-napo-aspbzla
3568 piraz-24thiz-napo-psdab
3569 bim-mepipe-napo-bnsdap
3570 bhs-edian2-men-psdap
3571 me2py-mepazin-chexo-bhsdab
3572 hythpym-eta-emo-bsdap
3573 imhs-tetradi-eoco-betapy
3574 nim-24thiman-no1-csdap
3575 thpym-eta-meo-psdap
3576 nmor-tridi-men-bsdap
3577 z-25oxman2-chexo-bhsdap
3578 deam-amo2-no1-zorn
3579 me-pyma2-meto-asppha
3580 4pmhs-mepazin-oem-aspbzla
3581 imhs-diphmep-men-mezphe
3582 nmor-diphmep-fo-bhsdab
3583 dhim-dimephmem-men-zdapee
3584 z-ams2-daco-aspibua
3585 mepip-eta2s-oem-bphabs
3586 piraz-edian2-ocho-betaet
3587 hythpym-pipa-4pho-glyzdap
3588 am2py-tetradi-5amo-zdap
3589 pippy-mea2s-imo-glyzdap
3590 am2py-mepipen2-no2-zdapee 3591 2py-eta2s-chexo-zdab
3592 2py-edia2-sem-npsdap
3593 bim-eta-no2-bnsdap
3594 2py-dimen-5pho-bnsdap
3595 am2py-pnymea-pro-bhsdap
3596 bhs-amn2-oem-bsdap
3597 thpym-mepipe-eoco-psdab
3598 impy-24thiman2-no1-betainyl
3599 pyr-din-no2-betapy
3600 2pmhs-edian2-hso-aspibua
3601 impy-trias-men-zdab
3602 bim-din-eoco-mezphe
3603 am2py-dimephmem-no1-psdab
3604 imhs-amn2-ocho-betapy
3605 piraz-m25thiz-paco-asppha
3606 chhs-pipa-nmo-psdab
3607 me2py-pipa-aco-zdab
3608 impy-dipch-meo-zdab
3609 bz-edian2-chexo-zdapee
3610 bzl-diphmep-eoco-psdapee
3611 amim-ams2-napo-betadcph
3612 bimhs-tridi-4amo-mezphe
3613 am4py-amo2-emo-betainyl
3614 dhim-pentas-ocho-psdap
3615 ibhs-m24thiz-oem-aspibua
3616 dhim-m24thiz-imo-betainyl
3617 ppy-eta-mes-betainyl
3618 z-dimephmem-no2-bhsdap
3619 imhs-pazin-no2-bsdap
3620 thpym-eta2s-fo-bhsdap
3621 piraz-pazin-peo-bnsdap
3622 imhs-eta-no1-bhsdap
3623 me2py-ms-meo-dfzdap
3624 thpym-edian2-oem-bnsdap
3625 mepip-diphmep-hso-bhsdap
3626 thpym-dimephmep-mes-psdab
3627 bz-24thiz-chexo-glyzdap
3628 ibhs-pyma2-meteto-zdap
3629 bim-eta-meo-bhsdap
3630 pippy-din-napo-glyzdap
3631 bim-24thizman2-hso-zdap
3632 bim-mepipe-no2-zdap
3633 bimhs-pipa-chexo-zdab
3634 thpym-m25thiz-meo-psdap
3635 am-tridi-ocho-glyzdap
3636 am-dis-men-zdap
3637 bhs-ams3-oem-psdab
3638 hythpym-pipa-men-psdap
3639 amim-25thiz-men-zdapee
3640 imhs-24thiz-ocho-glyzdap
3641 hythpym-ms-meo-bphabs
3642 me-amn2-emo-dfzdap
3643 bim-amo2-eoco-bphabs
3644 bim-mepipe-no1-zdab
3645 dhim-dimephmem-imo-bphabs
3646 amim-mepipe-oem-csdap
3647 dhim-hexas-peo-betapy
3648 chmhs-dimephmem-imo-zorn
3649 dhim-mea-eoco-zlys
3650 me2py-propa2s-eoco-aspibua
3651 mam2py-pipmes-cpeo-dfzdap
3652 thpym-butn-chexo-bhsdap
3653 im-mepipen2-emo-asppha
3654 am4py-24thiz-mmen-zdabs
3655 dmthpym-dich-ocho-zdab
3656 thpym-amn2-mes-bnsdap
3657 thpym-24thizman2-no1-betadcph
3658 2py-pazin-oem-betapy
3659 bim-edian2-no2-psdab
3660 bz-mepazin-no1-betainyl
3661 phpip-pnymea-no2-asppha
3662 2py-diphmep-mes-zdab
3663 amthiaz-dimephmep-paco-bnsdap
3664 pippy-edia2-oem-nbeta34-dimeoph
3665 me-dimephmem-chexo-bphabs
3666 imhs-dimephmep-emo-bphabs
3667 me2py-pipmeo-napo-bnsdap
3668 phpip-tridi-imo-bsdap
3669 bimhs-dich-pro-aspbzla
3670 chhs-eta-oem-zdap
3671 amthiaz-trias-oem-csdap
3672 bimhs-pymea-5pho-glyzdap
3673 dhim-n24thiman-4amo-csdap
3674 bhs-tridi-mmen-dfzdap
3675 inhs-dimephmem-men-psdap
3676 bim-pymea-chexo-bnsdap
3677 pippy-amo2-cnmo-bhsdab
3678 mam2py-pymea-imo-psdab
3679 dhim-pyma2-meo-aspibua
3680 piraz-ams3-meo-psdapee
3681 bz-pyma2-no2-aspbzla
3682 hythpym-amo2-no1-aspaba
3683 am4py-am2-oem-nbetameph
3684 me2py-m25thiz-fo-mezphe
3685 bz-24thiz-4pho-bhsdab
3686 imhs-amo2-no1-psdap
3687 nmhs-diphmep-chexo-betapy
3688 thpym-eta-imo-betainyl
3689 bzl-ms-oem-bhsdap
3690 impy-mepipe-cno-glubzla
3691 thpym-tridi-eoco-zdap
3692 impy-butn-eoco-bnsdap
3693 amim-pnymea-5amo-psdab
3694 bim-m25thiz-napo-asppha
3695 ppy-dimephmem-ocho-dfzdap
3696 me2py-amo2-5amo-thizzdap
3697 pippy-m25thiman2-meteto-betadcph
3698 thpym-amn2-mes-zdap
3699 amim-amn3-cpeo-asppha
3700 imhs-tetradi-no1-bhsdap
3701 bimhs-edia2-oem-npsdap
3702 thpym-props-emo-csdap
3703 piraz-tridi-oem-psdap
3704 z-diaz-emo-betadcph
3705 bhs-eta-no2-bsdap
3706 n2py-m25thizman2-mes-bsdap
3707 bim-eta-imo-bsdap
3708 2py-amn2-oem-bhsdap
3709 me2py-dimephmem-imo-dfzdap
3710 imhs-diphmep-imo-asppha
3711 bimhs-edia2-oem-nzdab
3712 deam-pyma2-imo-mezphe
3713 cl3pyme-thizn-men-bnsdap
3714 imhs-edian2-ocho-betapy
3715 edothpym-amo3-imo-zorn
3716 bim-pipmea-mecpo-glyzdap
3717 imhs-m24thizman2-5amo-bsdap
3718 bim-pazin-oem-zdab
3719 hythpym-tetradi-oeto-betainyl
3720 morhs-amo2-ocho-tsdap
3721 ppy-pyma2-5amo-aspibua
3722 imhs-amn2-eoco-psdab
3723 im-25oxman2-5pho-asppha
3724 pippy-25oxman2-fo-aspibua 3725 piraz-diphmem-no2-aspibua
3726 bz-24thizman2-pyo-betadcph
3727 amim-dimen-mes-csdap
3728 dhim-pipa-chexo-zdap
3729 menim-n2o2n-pyo-csdap
3730 thpym-hexadi-mommo-oxal
3731 am2py-dich-fo-bhsdap
3732 imhs-eta-no1-zdab
3733 bhs-24thiman-mes-betapy
3734 gua-amn3-pyo-aspbzla
3735 me2py-m24thizman2-5pho-bsdap
3736 nmor-am3-oem-nbetameph
3737 2py-am3-oem-nzdap
3738 imhs-din-mmen-zdab
3739 bimhs-edian2-mmen-bsdap
3740 cl3pyme-edian2-napo-asppha
3741 am4py-dis-fo-aspaba
3742 pyraz-tridi-no1-psdap
3743 thpym-m25thiman2-chexo-zdab
3744 am2py-amo2-5amo-asppha
3745 am2py-amn2-nmo-aval
3746 dmthpym-thizs-napo-bphabs
3747 am2py-dimephmep-aco-dfzdap
3748 bim-pazin-no1-bsdap
3749 edothpym-amn3-oem-ppsdap
3750 z-amo2-pro-bphabs
3751 impy-mepipe-nmo-asppha
3752 dmam-mepipe-ocho-bnsdap
3753 2py-mepipe-no1-psdap
3754 dmthpym-ams2-cpeo-psdap
3755 imhs-dimephmem-eoco-psdap
3756 pyrhs-mepazin-oem-csdap
3757 dhim-din-ocho-asppha
3758 me2py-mea-chexo-zdab
3759 bzl-am2-sem-nbetameph
3760 amthiaz-amo2-meo-bsdap
3761 bim-tetradi-eoco-aspbzla
3762 am2py-thizn-cpro-csdap
3763 pippy-diphmep-fo-aspaba
3764 chhs-m25thiz-ocho-bphabs
3765 imhs-m24thizman2-no1-glyzdap
3766 bhs-2pazin-no2-psdap
3767 4pmhs-diphmep-cnmo-betainyl
3768 piraz-mepipe-5pho-betapy
3769 amim-tetras-emo-psdab
3770 am2py-thizn-mes-zdab
3771 thpym-am2-oem-nzdap
3772 thpym-amn2-ocho-bsdap
3773 impy-m24thizman2-men-bphabs
3774 am-propa2s-imo-csdap
3775 hythpym-diphmem-mecpo-zdap
3776 dpam-mepipe-4pho-bhsdap
3777 amim-ams2-nmo-betapy
3778 2pmhs-edian2-5pho-bhsdab
3779 imhs-pazin-no2-bnsdap
3780 am-m25oxman2-mes-glyzdap
3781 amthiaz-diphmem-oem-aspibua
3782 nmhs-diphmep-eoco-psdap
3783 piraz-24thizman2-men-psdap
3784 2py-edian2-mes-bnsdap
3785 nim-24thiz-fo-betapy
3786 bimhs-ams2-pyo-psdap
3787 fthpym-hexas-cnmo-betainyl
3788 pyrhs-amo3-mes-betadcph
3789 bhs-tridi-oem-mezphe
3790 mepip-butn-hso-asppha
3791 impy-ams2-meo-mezphe
3792 im-24thizman2-emo-bnsdap
3793 pyraz-tetras-5pho-csdap
3794 nmor-mepipe-emo-glubzla
3795 pyraz-ms-emo-betainyl
3796 moegua-m24thizman2-eoco-bhsdab
3797 menim-eta-oeto-aspibua
3798 imhs-edian2-eoco-psdab
3799 thpym-propa2s-cpro-zdap
3800 bzl-pymea-men-bnsdap
3801 piraz-din-no2-bhsdap
3802 fthpym-tetradi-eoco-betapy
3803 amim-pnymea-meo-psdapee
3804 thpym-m24thiman2-men-aspaba
3805 imhs-24thiman2-pheo-aspibua
3806 am2py-pymea-no2-dfzdap
3807 amim-eta-meo-asppha
3808 bimhs-pentadi-mes-aspibua
3809 bim-pazin-oem-bhsdap
3810 fthpym-3pazin-imo-zorn
3811 me2py-propa2s-eoco-psdap
3812 bzl-pymea-oeto-zdapee
3813 phhs-mepipe2-oem-nbetabnaphth
3814 am2py-edian2-5pho-bhsdap
3815 bhs-amn2-no1-zdap
3816 hythpym-tridi-5amo-aspibua
3817 ec-pipmea-ocho-glyzdap
3818 bim-edian2-5pho-aspibua
3819 impy-pymea-4amo-betapy
3820 am2py-m25thiman2-meo-tsdap
3821 hythpym-ms-napo-psdap
3822 imhs-pnymea-emo-glyzdap
3823 amim-amn2-chexo-bhsdab
3824 imhs-edian2-mes-bhsdap
3825 2py-hexadi-meo-dfzdap
3826 ibhs-ams3-nmo-asppha
3827 piraz-amn2-chexo-psdapee
3828 am2py-24thizman2-nmo-aspbzla
3829 bim-am3-oem-nbetapy
3830 thpym-mepipe-meo-aspbzla
3831 bhs-eta-ocho-psdab
3832 imhs-amn2-ocho-psdap
3833 bhs-m24thizman2-pro-glyzdap
3834 moegua-pymea-mes-ibsdap
3835 bhs-mepipe2-oem-nbetabnaphth
3836 nmor-ams2-5pho-aspaba
3837 hythpym-mepipe2-oem-nbetameph
3838 bhs-edian2-mes-psdap
3839 pippy-pazin-chexo-asppha
3840 imhs-25thizman2-mes-betadcph
3841 chhs-diphmem-napo-thizzdap
3842 impy-amn3-meo-bphabs
3843 chhs-mepipe-men-glyzdap
3844 am2py-pazin-mes-bphabs
3845 thpym-amn2-mes-psdab
3846 2py-edian2-chexo-bsdap
3847 2py-amo2-5pho-bnsdap
3848 n2py-m24thiz-meto-glyzdap
3849 bim-amn2-ocho-bhsdap
3850 piraz-din-eoco-tsdap
3851 bim-24thiman-cpeo-zorn
3852 am2py-diphmep-cnmo-glyzdap
3853 pyraz-tetradi-mommo-asppha
3854 pippy-ams2-baeo-betapy
3855 chmhs-am2-oem-nbetabnaphth
3856 impy-dimephmep-napo-bnsdap
3857 npip-pentadi-5amo-csdap
3858 2py-eta-eoco-zdab 3859 bhs-mepazin-oem-betadcph
3860 hythpym-pazin-fo-bphabs
3861 thpym-dimephmem-emo-zdap
3862 bim-mepipe-oeto-csdap
3863 am2py-pazi2n-ocho-betapy
3864 bzl-mepipen2-eoco-bphabs
3865 2py-amn2-eoco-mezphe
3866 impy-mepipe-no1-bsdap
3867 bim-edian2-no1-bsdap
3868 hythpym-m24thizman2-ocho-aspibua
3869 2py-dimephmep-chexo-zdabs
3870 2py-amn3-eoco-bhsdab
3871 mam2py-25thiman2-mes-betainyl
3872 bimhs-dimephmep-mecpo-betaet
3873 hythpym-24oxman2-meo-glyzdap
3874 mam2py-tridi-napo-asppha
3875 im-24thiz-meo-zlys
3876 am2py-pipa-no1-mezphe
3877 amim-m25thizman2-imo-bnsdap
3878 am2py-pymea-men-asppha
3879 bhs-amn2-eoco-bsdap
3880 piraz-mepipen2-ocho-bhsdab
3881 bimhs-24thizman2-pyo-betainyl
3882 am4py-tridi-emo-aval
3883 morhs-pazin-napo-aspibua
3884 binhs-Z4thiz-emo-bhsdap
3885 piraz-dimen-napo-psdap
3886 nmor-mepipe-cno-aspaba
3887 edothpym-am3-sem-nbeta34-dimeoph
3888 2py-n2o2n-no2-zdabs
3889 deam-dis-no1-bphabs
3890 bim-mepipe-5pho-zdap
3891 bimhs-din-5amo-bsdap
3892 2py-mepipe-eoco-psdap
3893 2py-pazin-no2-zdab
3894 amim-mepipe-mes-psdap
3895 phpip-pymea-oem-bhsdap
3896 bim-hexadi-5pho-betainyl
3897 dhim-pyma2-ocho-bsdap
3898 thpym-ams2-ocho-psdap
3899 am-pentas-eoco-csdap
3900 bhs-24thiz-meo-glupha
3901 n2py-amn3-meo-osdap
3902 mepip-m24oxman2-men-aspibua
3903 emnim-dimephmem-5pho-psdab
3904 gua-m24thizman2-no1-psdap
3905 imhs-edian2-mes-betapy
3906 hythpym-mepazin-ocho-bhsdab
3907 imhs-pazin-meo-bhsdap
3908 bim-edian2-eoco-glupha
3909 dmthpym-pipa-imo-asppha
3910 pippy-pipmea-no2-aspbzla
3911 am2py-pnymea-napo-bhsdap
3912 dhim-mepipe2-sem-nbetapy
3913 nmor-pazin-chexo-dfzdap
3914 morhs-din-ocho-betainyl
3915 dmbim-propn-5amo-zdapee
3916 imhs-amn3-cno-betadcph
3917 morhs-pnymea-cpeo-bhsdap
3918 nmhs-ams2-men-glyzdap
3919 hythpym-amn3-imo-asppha
3920 tolhs-pymea-5pho-dfzdap
3921 mam2py-diphmep-eoco-glyzdap
3922 impy-indan2-no2-aspbzla
3923 dpam-25thiman2-daco-zlys
3924 2py-pipa-cnmo-betainyl
3925 bhs-eta-no2-zdap
3926 thpym-pnymea-men-zdab
3927 dhim-pyma2-4amo-bsdap
3928 2py-pymea-meo-bsdap
3929 emnim-dimephmem-men-psdab
3930 amim-edia2-oem-nbetabnaphth
3931 me2py-amn2-eoco-thizzdap
3932 thpym-pyma2-cpeo-betadcph
3933 me2py-25oxman2-no2-oxa1
3934 2py-m24thizman2-cnmo-bphabs
3935 imhs-props-fo-betainyl
3936 me-dipch-no1-bphabs
3937 z-dimen-no1-bnsdap
3938 pippy-mepipen2-mmen-asppha
3939 bhs-m24thiz-chexo-zdap
3940 ec-pipmea-men-zdab
3941 chmhs-pipmeo-5pho-bhsdap
3942 thpym-eta-mes-bsdap
3943 bhs-dimen-men-zdap
3944 impy-m24thizman2-meo-zdab
3945 pyr-edia2-oem-npsdap
3946 prhs-mea-emo-zdab
3947 2py-mepipe-ocho-zdap
3948 me2py-eta-aco-betadcph
3949 dmbim-mepazin-mecpo-bhsdap
3950 amim-pymea-no2-zdap
3951 imhs-24thizman2-emo-betainyl
3952 pyr-hexadi-imo-glyzdap
3953 am2py-mepipen2-no2-ibsdap
3954 edothpym-trias-ocho-zdap
3955 chmhs-2pazin-napo-psdab
3956 bim-pazin-ocho-zdab
3957 pippy-m24oxman2-eoco-psdab
3958 thpym-pazin-no2-psdap
3959 dhim-3diaz-fo-zdap
3960 imhs-mepipe-no1-bsdap
3961 piraz-pipmea-chexo-glyzdap
3962 bim-eta-no1-betapy
3963 bhs-amn2-no1-zdab
3964 bim-pipmea-pro-bnsdap
3965 2pmhs-mepipe2-oem-nbetapy
3966 2py-eta-no1-zdab
3967 hythpym-24thizman2-emo-zdabs
3968 bhs-edian2-oem-zdap
3969 dhim-mepipe2-oem-nbetapy
3970 pippy-m25oxman2-men-dfzdap
3971 moegua-pipa-ocho-ibsdap
3972 deam-trias-eoco-csdap
3973 am2py-2pazin-napo-aspbzla
3974 thpym-edian2-eoco-bhsdap
3975 dhim-dimephmem-no2-bhsdab
3976 me2py-25oxman2-emo-ibsdap
3977 dpam-m25thiz-4amo-zdab
3978 dhim-pymea-imo-glyzdap
3979 mam2py-pentas-fo-asppha
3980 2pmhs-25thiz-mes-bhsdap
3981 bhs-mepazin-men-mezphe
3982 dhim-pazin-mes-asppha
3983 tolhs-pipmes-napo-dfzdap
3984 bhs-thizo-mes-psdap
3985 pippy-edian2-eoco-bhsdab
3986 piraz-dis-oem-bphabs
3987 thpym-pazin-mes-bhsdap
3988 imhs-edian2-ocho-psdab
3989 ibhs-mepipe-mes-psdab
3990 hythpym-indan2-chexo-dfzdap
3991 phpip-tetras-eoco-zdabs
3992 piraz-mepipe-meo-betadcph 3993 hythpym-m25thiz-aco-oxal
3994 mam2py-tridi-no2-bphabs
3995 ppy-diphmem-4amo-asppha
3996 am-amo2-emo-psdap
3997 imhs-m24thiz-meo-zdabs
3998 me2py-amo2-no1-csdap
3999 am2py-pnymea-5pho-aspbzla
4000 menim-pnymea-eoco-bnsdap
4001 menim-edian2-napo-mezphe
4002 hythpym-25oxman2-mecpo-csdap
4003 imhs-pymea-napo-betadcph
4004 impy-24thiz-4amo-oxal
4005 dhim-dis-no2-betapy
4006 bim-pazin-mes-bsdap
4007 prhs-pnymea-ocho-psdap
4008 hythpym-trias-eoco-betainyl
4009 bim-mepipe-meo-psdab
4010 me2py-n2o2n-chexo-betainyl
4011 emnim-pipmea-5amo-betainyl
4012 menim-thizn-oem-psdap
4013 dhim-3pazin-ocho-psdap
4014 qua-edian2-mes-osdap
4015 bim-mepipe-5pho-betapy
4016 am2py-dimephmep-fo-bsdap
4017 thpym-pipmes-mes-csdap
4018 pyrhs-24thiz-ocho-glyzdap
4019 thpym-edian2-5pho-zdab
4020 imhs-dimephmem-ccho-betainyl
4021 nim-trias-napo-glyzdap
4022 dhim-am3diaz-5pho-glupha
4023 menim-tridi-5amo-bhsdap
4024 ec-diphmep-no1-bhsdab
4025 moegua-amo2-oem-ibsdap
4026 mam2py-m24thizman2-men-csdap
4027 amthiaz-pazin-ocho-aspaba
4028 dmthpym-mepipe2-oem-nzdab
4029 pyr-tetradi-no2-glubzla
4030 impy-pymea-chexo-csdap
4031 am4py-din-5amo-zdap
4032 amim-amn3-emo-zdab
4033 dhim-pipmea-chexo-asppha
4034 bim-pipmea-meo-zdab
4035 bhs-mea2s-paco-zdabs
4036 me2py-mepipen2-mes-betapy
4037 piraz-amn2-mes-dfzdap
4038 imhs-amn2-ocho-zdab
4039 imhs-pazin-no2-zdap
4040 bim-25oxman2-ocho-aspbzla
4041 impy-tetradi-peo-bhsdab
4042 bhs-24thizman2-imo-betadcph
4043 pyrhs-pnymea-4pho-bhsdap
4044 thpym-m25thiz-oem-aspibua
4045 deam-dis-no2-aspaba
4046 amim-hexadi-peo-bsdap
4047 thpym-m24thiz-ocho-csdap
4048 pyraz-m24thiz-cpro-psdab
4049 bim-amn2-oem-dfzdap
4050 inhs-am3diaz-ocho-betadcpb
4051 2py-mepipen2-mes-ibsdap
4052 bimhs-amo2-eoco-csdap
4053 n2py-diphmem-5pho-bhsdap
4054 bimhs-pazin-baeo-psdap
4055 2py-trias-mecpo-psdap
4056 pyr-dimephmem-fo-asppha
4057 hythpym-dimen-pyo-betadcph
4058 mam2py-pyma2-ocho-zdabs
4059 me2py-dipch-ocho-zdab
4060 bhs-diphmem-5pho-psdapee
4061 dhim-diphmep-mes-zdap
4062 pyraz-m25thiz-pheo-aspibua
4063 imhs-mepipe-meo-betapy
4064 irnhs-edian2-5pho-bsdap
4065 am2py-propn-fo-bsdap
4066 mam2py-24thizman2-chexo-bnsdap
4067 2py-pazin-5pho-bnsdap
4068 bhs-eta-no1-psdap
4069 nmhs-pipmea-meo-asppha
4070 impy-dis-napo-betadcph
4071 imhs-edian2-oem-zdap
4072 dmthpym-tetradi-fo-bhsdab
4073 imhs-mepipen2-chexo-dfzdap
4074 cl3pyme-din-emo-aspibua
4075 2py-pazin-spho-psdab
4076 am4py-m24oxman2-chexo-mezphe
4077 emnim-tetradi-oem-betapy
4078 bim-m25thiz-pyo-glyzdap
4079 imhs-n2nme2n-eoco-thizzdap
4080 cl3pyme-diphmem-emo-bsdap
4081 mam2py-m25thiman2-men-glyzdap
4082 prhs-pipmes-cpeo-bhsdap
4083 bhs-mepipe-mes-bsdap
4084 amim-mepipe-napo-zdap
4085 pippy-ams2-hso-zdap
4086 dmam-edian2-ocho-mezphe
4087 imhs-mepipe-no1-betapy
4088 hythpym-2pazin-men-betapy
4089 imhs-eta-meo-asppha
4090 mam2py-pymea-mes-betadcph
4091 impy-pipmea-no2-mezphe
4092 am2py-dimephmep-chexo-aspbzla
4093 thpym-pazin-fo-zdap
4094 am2py-24thizman2-pyo-zlys
4095 bimhs-tridi-cpro-bnsdap
4096 amim-m24thizman2-ocho-betainyl
4097 amthiaz-tridi-mmen-psdap
4098 phhs-mepipe2-oem-nzdap
4099 npip-pipmeo-meo-zdab
4100 thpym-amn2-meo-betapy
4101 bhs-pazin-eoco-zdap
4102 bimhs-dimephmem-aco-glyzdap
4103 nmor-trias-5pho-psdab
4104 bim-mepipe2-sem-nbeta34-dimeoph
4105 am2py-thizn-5amo-ppsdap
4106 phhs-ams2-chexo-bnsdap
4107 mam2py-24thiman-5pho-psdab
4108 imhs-thizn-mes-aspibua
4109 dmthpym-24thiz-eoco-glyzdap
4110 bzl-indan2-oem-mezphe
4111 ppy-amo2-men-glupha
4112 hythpym-trias-oem-zdapee
4113 n2py-amn2-imo-betapy
4114 bimhs-m24thiman2-men-zdabs
4115 2py-mepipe-ocho-zdab
4116 amim-eta-napo-zdap
4117 pippy-pazin-chexo-asppha
4118 bimhs-amn2-men-zdab
4119 am2py-pentas-emo-aval
4120 impy-tetradi-pyo-aval
4121 pyrhs-dich-emo-psdapee
4122 amim-dipch-ocho-csdap
4123 hythpym-din-fo-bsdap
4124 hythpym-thizn-emo-aspaba
4125 amim-thizn-no1-betapy
4126 amim-mepipe-mes-psdab 4127 dhim-tetradi-5amo-bhsdab
4128 dhim-pipa-emo-betainyl
4129 2pmhs-pipa-fo-psdap
4130 bim-pazin-no1-psdab
4131 mam2py-diphmep-meo-betapy
4132 dmam-amn3-oem-zdabs
4133 me2py-24thizman2-emo-zdab
4134 impy-m24thizman2-aco-betapy
4135 dmam-24thizman2-5pho-zdabs
4136 bhs-mepipe-meo-zdab
4137 piraz-trias-oem-aval
4138 2py-edia2-sem-nbetapy
4139 piraz-m24thizman2-meo-bhsdab
4140 am2py-eta-fo-thizzdap
4141 pippy-24thizman2-5amo-zdabs
4142 pippy-mepazin-imo-betapy
4143 hythpym-edian2-eoco-zdapee
4144 moegua-tridi-5amo-aspbzla
4145 deam-n2o2n-eoco-bsdap
4146 thpym-din-no1-bhsdap
4147 2py-edian2-mes-psdap
4148 hythpym-dipch-5pho-csdap
4149 imhs-mepipe-eoco-zdap
4150 ppy-25thiz-napo-aspaba
4151 me2py-pipmea-emo-glyzdap
4152 hythpym-m25thiz-cnmo-mezphe
4153 bimhs-m24thizman2-emo-psdap
4154 2py-dipch-5pho-csdap naphth
4155 fthpym-dimen-pyo-glyzdap
4156 phpip-dimephmem-pro-mezphe
4157 amim-pnymea-eoco-bphabs
4158 pippy-24thiz-chexo-zdab
4159 mam2py-amn2-napo-bnsdap
4160 piraz-edian2-meo-bhsdab
4161 hythpym-ams2-ocho-zorn
4162 thpym-thizo-meo-psdap
4163 chmhs-dis-5amo-bsdap
4164 bhs-eta-no1-bhsdap
4165 amim-m25thiz-men-zdabs
4166 bhs-amn2-5pho-psdab
4167 dhim-diphmep-napo-asppha
4168 z-amn3-napo-asppha
4169 amim-m25thiman2-napo-dfzdap
4170 deam-3pazin-5amo-asppha
4171 menim-eta2s-meo-asppha
4172 im-eta-emo-psdab
4173 bhs-amn2-meo-betapy
4174 ppy-ams2-cnmo-glubzla
4175 bhs-m25thiz-pheo-zdap
4176 dhim-mepipe-men-bnsdap
4177 deam-2pazin-peo-asppha
4178 am2py-amo2-pyo-aspibua
4179 dmthpym-am3-oem-npsdap
4180 piraz-din-pheo-bhsdap
4181 dmam-diphmep-eoco-glyzdap
4182 amim-din-nmo-betapy
4183 moegua-24thiz-emo-betainyl
4184 impy-diphmem-imo-bphabs
4185 hythpym-pentadi-no2-dfzdap
4186 4pmhs-tridi-imo-betaet
4187 2py-amn3-men-bhsdab
4188 chmhs-pazin-5pho-zorn
4189 piraz-pazin-eoco-glyzdap
4190 emnim-pnymea-no2-bsdap
4191 thpym-eta-oem-zdap
4192 dmam-mepazin-no1-bnsdap
4193 me2py-amn2-ocho-betainyl
4194 imhs-amn2-oem-betadcph
4195 am2py-m25thiz-5pho-zdab
4196 2py-pymea-imo-zdap
4197 bz-din-cno-zdab
4198 bimhs-edian2-oem-zorn
4199 mam2py-25thizman2-eoco-mezphe
4200 me2py-thizn-4pho-glupha
4201 hythpym-pazin-emo-ppsdap
4202 imhs-thizn-meto-betadcph
4203 me2py-mepipe-ocho-psdap
4204 impy-amn2-meo-dfzdap
4205 dmbim-mepipe2-sem-nbetab
4206 bhs-dis-men-betadcph
4207 am2py-pipa-5pho-bnsdap
4208 me2py-n2o2n-4amo-betadcph
4209 bim-pazi2n-eoco-glyzdap
4210 dhim-pyma2-eoco-psdab
4211 imhs-amo2-5pho-zlys
4212 dhim-edian2-oeto-betainyl
4213 2pmhs-mepipe-meto-bnsdap
4214 me2py-pipmea-daco-aspbzla
4215 pyr-am2-oem-nbeta34dimeoph
4216 moegua-mepipe-no1-bphabs
4217 hythpym-pyma2-fo-betainyl
4218 me2py-ams2-5pho-betapy
4219 im-dis-imo-aspibua
4220 2py-24thizman2-men-zdapee
4221 ibhs-24thiz-oem-dfzdap
4222 nmhs-ams3-emo-bhsdap
4223 npip-pipmeo-imo-dfzdap
4224 mam2py-amo2-meteto-betainyl
4225 am2py-pentas-emo-bsdap
4226 bhs-m25thiz-fo-glupha
4227 phpip-pnymea-eoco-betainyl
4228 piraz-amn3-oem-bhsdab
4229 bim-tetradi-daco-psdab
4230 2py-diaz-5pho-psdap
4231 piraz-tridi-meto-zdabs
4233 hythpym-25oxman2-chexo-psdab
4232 thpym-mepipe-ocho-bnsdap
4233 hythpym-25oxman2-chexo-psdab
4234 bim-m25thiz-oem-asppha
4235 emnim-amn2-no2-asppha
4236 pippy-am3-oem-nbetapy
4237 amim-dimephmem-emo-psdap
4238 2py-3diaz-fo-zdap
4239 bimhs-dimen-men-zdapee
4240 impy-m25oxman2-cnmo-betadcph
4241 am2py-ams2-5pho-bsdap
4242 2py-edian2-oem-bnsdap
4243 am2py-tridi-ocho-psdap
4244 pyraz-24thiz-no2-asppha
4245 thpym-trias-imo-bnsdap
4246 mepip-pipmeo-fo-bnsdap
4247 dmbim-amn2-nmo-csdap
4248 gua-pazin-no2-betadcph
4249 2py-amn2-baeo-aspibua
4250 am2py-hexadi-men-csdap
4251 phhs-dipch-imo-bnsdap
4252 imhs-pyma2-pheo-bnsdap
4253 npip-amn3-oem-bnsdap
4254 2py-edian2-oem-betapy
4255 nmor-24thiz-meto-psdap
4256 ec-props-oem-zdab
4257 2pmhs-mepipe-oem-betainyl
4258 phpip-trias-no2-zlys
4259 thpym-thizn-no2-bphabs 4260 pippy-pipmea-emo-betapy
4261 hythpym-dimephmep-emo-betainyl
4262 me2py-dimephmep-napo-betadcph
4263 thpym-pnymea-5pho-ppsdap
4264 deam-25thiman2-napo-bhsdap
4265 imhs-pazin-meo-bsdap
4266 bimhs-amn3-oem-betadcph
4267 mam2py-edian2-meo-psdab
4268 imhs-mepipen2-5pho-psdap
4269 mam2py-amn3-meo-csdap
4270 2py-eta2s-no1-bhsdab
4271 impy-mepazin-imo-mezphe
4272 ibhs-thizo-ocho-betapy
4273 bim-din-no2-zdap
4274 piraz-trias-mes-zdap
4275 imhs-mepazin-eoco-zorn
4276 bim-pipmeo-men-zdap
4277 bim-dimephmem-pyo-betainyl
4278 dmam-eta-men-zdabs
4279 amthiaz-eta-5pho-betainyl
4280 chmhs-dis-fo-dfzdap
4281 mam2py-thizo-5amo-zdab
4282 bim-pipmea-imo-bnsdap
4283 hythpym-n2o2n-no1-aspibua
4284 hythpym-mepazin-men-betainyl
4285 nim-diphmem-eoco-zdap
4286 mam2py-pyma2-4amo-bnsdap
4287 moegua-dis-mmen-bhsdab
4288 me2py-mepipen2-napo-csdap
4289 2py-tetradi-no2-zdap
4290 cl3pyme-n2nme2n-emo-aspbzla
4291 ppy-tridi-mecpo-bhsdap
4292 dhim-tetradi-imo-glyzdap
4293 bim-tridi-no1-bhsdab
4294 chhs-pymea-emo-bhsdab
4295 2py-amn2-oem-psdab
4296 imhs-edian2-eoco-zdab
4297 2py-m24thizman2-fo-zdab
4298 ec-mepipen2-no1-dfzdap
4299 bim-edian2-fo-aspbzla
4300 pyr-trias-ocho-bhsdab
4301 npip-am3diaz-oem-psdab
4302 thpym-mepipe-5pho-bnsdap
4303 bim-am24thizman2-oem-aval
4304 bzl-dich-emo-psdab
4305 mam2py-thizo-chexo-aspibua
4306 2py-thizn-oeto-psdap
4307 thpym-24thizman2-mes-csdap
4308 piraz-eta-oem-mezphe
4309 bhs-mepipe-mes-psdab
4310 bhs-eta-eoco-psdap
4311 thpym-pnymea-5amo-psdap
4312 edothpym-n2nme2n-napo-psdab
4313 me-pymea-chexo-asppha
4314 mam2py-dimephmem-no1-bhsdab
4315 me-diphmep-oem-zdapee
4316 imhs-eta-mes-psdap
4317 am2py-amo2-meo-psdap
4318 fthpym-m24thizman2-napo-osdap
4319 pyrhs-mea2s-fo-psdap
4320 me-25oxman2-5amo-aval
4321 am2py-pyma2-mes-csdap
4322 bim-amn2-5pho-bsdap
4323 thpym-ams3-eoco-zdap
4324 imhs-am2-sem-nbetameph
4325 bhs-25oxman2-men-psdapee
4326 mam2py-25thizman2-eoco-asppha
4327 imhs-pipmea-5pho-aspbzla
4328 dmam-pyma2-no2-glubzla
4329 gua-ams3-no1-zlys
4330 im-pazin-emo-bnsdap
4331 bim-pazin-mes-bnsdap
4332 me2py-pazin-5amo-glyzdap
4333 bimhs-mepipe2-oem-nbetameph
4334 piraz-trias-cpro-betainyl
4335 bim-tetras-5amo-glyzdap
4336 me2py-m25thiman2-chexo-tsdap
4337 imhs-eta-eoco-psdap
4338 prhs-ams2-pheo-zdap
4339 amim-tetradi-fo-zdab
4340 bim-amn2-peo-bnsdap
4341 dhim-dimen-no1-zlys
4342 dhim-thizn-5pho-asppha
4343 dhim-amo2-pheo-dfzdap
4344 me2py-din-no1-aspbzla
4345 bim-pyma2-5amo-aspibua
4346 dhim-pipa-chexo-mezphe
4347 4pmhs-mepipen2-4amo-psdap
4348 mam2py-mepazin-mommo-aspibua
4349 pyr-dis-fo-mezphe
4350 dhim-ams2-oem-dfzdap
4351 mam2py-n24thiman-fo-csdap
4352 piraz-tridi-hso-zdabs
4353 edothpym-eta2s-emo-dfzdap
4354 bim-m24thizman2-mes-bphabs
4355 dpam-dimen-imo-bphabs
4356 pippy-din-pro-betainyl
4357 2pmhs-dis-fo-bhsdab
4358 edothpym-pazin-fo-betadcph
4359 impy-2pazin-mmen-betadcph
4360 am2py-hexas-pro-dfzdap
4361 2py-am3-sem-npsdap
4362 morhs-dio-no2-aspbzla
4363 2py-thizn-5amo-glyzdap
4364 mam2py-pyma2-meto-betapy
4365 ibhs-amo2-meo-bphabs
4366 pyraz-tetradi-imo-bhsdap
4367 thpym-din-oem-zdap
4368 nmhs-din-meto-betadcph
4369 me2py-hexas-peo-oxal
4370 edothpym-amn2-ocho-bphabs
4371 2py-diphmep-oem-psdap
4372 bhs-eta-meo-bnsdap
4373 bimhs-pnymea-meo-bhsdab
4374 impy-pazin-eoco-psdap
4375 pyr-24oxman2-ocho-csdap
4376 2py-diphmep-men-betainyl
4377 bimhs-dimephmep-emo-bhsdab
4378 tolhs-tetradi-meo-zdap
4379 bim-mepipe2-sem-nbetameph
4380 imhs-amn2-no1-zdap
4381 2py-pnymea-men-mezphe
4382 nmhs-24thiman-emo-aspaba
4383 z-pnymea-fo-csdap
4384 thpym-edian2-oem-bsdap
4385 imhs-mepazin-ocho-bhsdab
4386 dhim-mepazin-mommo-glyzdap
4387 thpym-amn2-no1-bsdap
4388 am4py-props-nmo-zdabs
4389 imhs-2pazin-eoco-zdab
4390 phpip-24thizman2-eoco-aspibua
4391 me2py-m24thizman2-aco-ibsdap
4392 2py-edian2-eoco-psdab
4393 impy-pymea-ocho-zdabs 4394 2pmhs-dimen-mes-bphabs
4395 piraz-amn3-eoco-zdabs
4396 pyrhs-m25oxman2-chexo-oxal
4397 pyrhs-pazin-meo-betadcph
4398 mam2py-dipch-ocho-bhsdap
4399 piraz-ams2-men-dfzdap
4400 pyr-diaz-fo-osdap
4401 z-tridi-5pho-bphabs
4402 thpym-edian2-ocho-bnsdap
4403 piraz-pnymea-ocho-glupha
4404 imhs-diphmep-5amo-bhsdap
4405 me2py-dimephmem-chexo-aspibua
4406 hythpym-amn3-men-zdab
4407 thpym-mea2s-no2-bsdap
4408 bhs-am3diaz-eoco-bphabs
4409 bim-mepazin-meo-zdap
4410 npip-pipmea-no2-dfzdap
4411 amim-pazin-cpeo-mezphe
4412 bimhs-amo2-no1-psdap
4413 pyr-am2-sem-nzdap
4414 emnim-amo2-5amo-zdap
4415 imhs-24thizman2-meo-betadcph
4416 bimhs-dimephmep-peo-betadcph
4417 amim-din-5pho-zdab
4418 me-thizn-chexo-bhsdab
4419 bhs-pipa-oem-betadcph
4420 piraz-pipa-pyo-aspaba
4421 bhs-eta-5pho-zdap
4422 2pmhs-t tras-meteto-tsdap
4423 bim-pazin-ocho-zdap
4424 am2py-trias-oem-psdab
4425 bimhs-pipa-men-df zdap
4426 piraz-pazin-mes-aspbzla
4427 pippy-pipmea-5pho-bsdap
4428 bhs-edian2-fo-bsdap
4429 ibhs-am3-oem-nzdap
4430 nim-eta-eoco-mezphe
4431 am2py-pymea-oem-betadcph
4432 impy-trias-imo-betainyl
4433 phpip-m24thizman2-men-asppha
4434 impy-amn2-no1-bhsdab
4435 gua-mepipen2-mes-aspaba
4436 nmor-eta-no2-bhsdap
4437 me2py-tridi-pro-thizzdap
4438 bzl-mepipe2-oem-nbetabnaphth
4439 2pmhs-mepipen2-no1-betapy
4440 amim-diphmem-eoco-zdabs
4441 impy-amn3-mecpo-zdapee
4442 amim-mepipe-men-betapy
4443 dhim-pymea-emo-psdab
4445 bimhs-m25thiman2-no2-mezphe
4446 amim-24thiz-aco-zdap
4447 fthpym-trias-5pho-zdab
4448 dmthpym-mea-oem-dfzdap
4449 2pmhs-pymea-ocho-zdabs
4450 imnhs-amn2-5pho-psdap
4451 thpym-pipmea-no2-bhsdab
4452 bim-eta-oem-mezphe
4453 thpym-dimen-meo-psdap
4454 dhim-m24thizman2-5amo-csdap
4455 am4py-pazin-chexo-zdabs
4456 mam2py-3diaz-oem-aspibua
4457 moegua-mepazin-eoco-bsdap
4458 piraz-24thiz-napo-dfzdap
4459 edothpym-pazi2n-ocho-betainyl
4460 me-diphmep-chexo-bhsdab
4461 me2py-24thizman2-eoco-mezphe
4462 imhs-amn2-no1-bsdap
4463 bimhs-tridi-no2-psdab
4464 mam2py-trias-pyo-bnsdap
4465 chhs-tetras-eoco-aspibua
4466 thpym-pipmea-oeto-dfzdap
4467 impy-25oxman2-mmen-betadcph
4468 imhs-edian2-mes-betapy
4469 npip-tetras-4pho-bhsdap
4470 thpym-thizn-men-df zdap
4471 im-diphmem-imo-betainyl
4472 emnim-pipmea-ocho-asppha
4473 edothpym-ams2-men-zdap
4474 me2py-m25oxman2-meo-bhsdab
4475 hythpym-m25thiz-ocho-betadcph
4476 dmbim-dimephmem-chexo-psdab
4477 mam2py-pyma2-chexo-csdap
4478 prhs-pnymea-chexo-zdap
4479 bim-amn2-5pho-psdab
4480 bimhs-dimen-ocho-betapy
4481 emnim-am3-oem-npsdap
4482 imhs-amn2-ocho-bsdap
4483 imhs-diphmep-meo-psdap
4484 am2py-am3-oem-nzdab
4485 phhs-24thiman-5amo-bphabs
4486 piraz-mepipen2-eoco-bhsdap
4487 impy-24thiz-no2-aspaba
4488 bzl-propa2s-emo-csdap
4489 bim-amn2-meo-zlys
4490 bimhs-trias-baeo-bphabs
4491 piraz-dimephmep-5amo-bsdap
4492 am4py-mepazin-no1-aspibua
4493 thpym-diphmep-emo-betapy
4494 2py-pipa-napo-zdap
4495 am2py-dimephmep-ocho-bphabs
4444 2py-25oxman2-pro-betapy
4496 amim-mepazin-no1-psdap
4497 menim-dimen-meo-appha
4498 me-pnymea-eoco-zdab
4499 mam2py-ams2-chexo-betapy
4500 bim-edian2-oem-zdap
4501 am2py-pazin-nmo-bphabs
4502 me2py-pazi2n-mes-asppha
4503 dmthpym-pipa-5amo-zdap
4504 mam2py-edian2-imo-bhsdab
4505 thpym-mepipe2-sem-nzdap
4506 im-dimephmem-cno-betaet
4507 mam2py-pipmeo-no2-bphabs
4508 thpym-24thizman2-daco-zdap
4509 amim-diphmep-chexo-bhsdab
4510 pippy-m25thiman2-5pho-csdap
4511 impy-pipmea-imo-aspibua
4512 bim-amn2-ocho-psdap
4513 hythpym-eta-mecpo-zdabs
4514 2py-eta-no2-zdab
4515 bimhs-dimephmep-5amo-bphabs
4516 amim-amn3-no1-bphabs
4517 mam2py-pymea-oem-bphabs
4518 me-amo2-pheo-aspbzla
4519 am2py-diphmem-ocho-bhsdap
4520 am2py-ams2-oem-bhsdap
4521 nmor-mepazin-imo-ppsdap
4522 2py-edian2-meo-psdap
4523 thpym-pazin-5pho-zdap
4524 npip-mepipe-paco-aspbzla
4525 pippy-amn3-oeto-oxal
4526 nmhs-m25oxman2-5pho-asppha
4527 am2py-mepazin-fo-betadcph 4528 thpym-tetras-fo-betainyl
4529 piraz-tridi-ocho-betadcph
4530 pippy-trias-fo-bhsdap
4531 chhs-edian2-peo-bphabs
4532 phhs-pyma2-meo-bhsdab
4533 deam-25oxman2-ocho-psdab
4534 amim-ams2-oem-aspbzla
4535 dhim-pyma2-oem-betainyl
4536 imhs-mepipe-meo-zdap
4537 piraz-din-fo-bsdap
4538 2py-eta-oem-psdab
4539 piraz-trias-5amo-psdab
4540 amim-pyma2-meo-betadcph
4541 4pmhs-pentadi-mecpo-psdap
4542 2py-pazin-eoco-betapy
4543 imhs-m24oxman2-imo-dfzdap
4544 amim-25thiman2-oem-aspibua
4545 npip-m24thizman2-imo-dfzdap
4546 hythpym-.mepipe-eoco-bnsdap
4547 pyrhs-pipmeo-ocho-bhsdap
4548 bim-24thiz-5amo-betainyl
4549 me2py-pazin-napo-glyzdap
4550 nmor-dimephmem-no1-asppha
4551 ibhs-am3-oem-nzdab
4552 dmthpym-mepipe-5amo-zdabs
4553 impy-dis-pheo-betapy
4554 me2py-pipmea-mes-bnsdap
4555 pyraz-dimephmem-no1-aspbzla
4556 imhs-mepipe-oem-bhsdap
4557 emnim-dimephmep-pro-mezphe
4558 am-diphmep-eoco-psdab
4559 am2py-pentadi-imo-bsdap
4560 2py-pazin-oem-zdap
4561 imhs-indan2-no1-aspbzla
4562 4pmhs-diphmem-hso-aspbzla
4563 impy-edian2-no1-betainyl
4564 menim-mepipe2-sem-nbetameph
4565 emnim-amo3-no1-glyzdap
4566 hythpym-pipa-napo-bnsdap
4567 phhs-tetras-5amo-glyzdap
4568 bim-mepipen2-ocho-bsdap
4569 phhs-25oxman2-men-ibsdap
4570 dhim-tridi-mes-asppha
4571 am-pymea-baeo-dfzdap
4572 2py-mepipe-eoco-bhsdap
4573 moegua-indan2-napo-bnsdap
4574 impy-n2o2n-emo-osdap
4575 tolhs-dipch-oem-asppha
4576 pyr-m25oxman2-cpro-betapy
4577 bz-n2nme2n-fo-oxal
4578 n2py-mepipe2-sem-nzdap
4579 bz-propa2s-no2-osdap
4580 2py-edian2-no1-psdap
4581 bimhs-thizs-eoco-tsdap
4582 nim-mepazin-meo-dfzdap
4583 amim-m25thiz-emo-betadcph
4584 morhs-tridi-imo-bsdap
4585 bimhs-amo3-men-psdab
4586 mam2py-din-nmo-bphabs
4587 bimhs-24oxman2-no2-bphabs
4588 thpym-pazin-mes-zdab
4589 bhs-eta-mes-bsdap
4590 pippy-amn2-emo-aspbzla
4591 moegua-pnymea-men-betadcph
4592 2py-24thiman-cno-bhsdab
4593 dhim-diaz-meo-bsdap
4594 bhs-pazin-no2-zdap
4595 bim-pnymea-imo-zdab
4596 deam-hexadi-emo-aspibua
4597 npip-24thizman2-men-betapy
4598 dhim-24thiman-no2-betapy
4599 ec-ams2-no2-betadcph
4600 bim-mepipen2-no2-betainyl
4601 bim-dich-emo-zorn
4602 bz-24thizman2-fo-betadcph
4603 imhs-mepipe-oem-bnsdap
4604 amthiaz-pazin-ocho-zdabs
4605 bhs-butn-oem-thizzdap
4606 2py-eta-ocho-zdap
4607 npip-dimephmep-mes-psdap
4608 2py-mepipe-5amo-bphabs
4609 ppy-propa2s-imo-glyzdap
4610 mam2py-indan2-emo-zorn
4611 me2py-m25thiz-ocho-psdab
4612 2py-tridi-chexo-psdab
4613 tolhs-25oxman2-imo-csdap
4614 imhs-din-cpro-psdap
4615 z-dimen-4amo-glyzdap
4616 thpym-pnymea-chexo-dfzdap
4617 am-tridi-5pho-betaet
4618 bim-25thiz-baeo-tsdap
4619 mam2py-dich-emo-bphabs
4620 nmor-edian2-men-bnsdap
4621 tolhs-diphmem-emo-csdap
4622 2py-edian2-no2-zdab
4623 imhs-amn2-oem-bhsdap
4624 mam2py-indan2-meo-psdap
4625 pyr-dimen-men-psdab
4626 imhs-mepipe-eoco-bhsdap
4627 bim-mepipe-mes-psdab
4628 amim-pnymea-4pho-csdap
4629 me2py-amn2-emo-bhsdab
4630 gua-dimephmem-daco-asppha
4631 deam-24thizman2-fo-ibsdap
4632 ppy-25oxman2-ocho-bhsdab
4633 bhs-m25thiz-chexo-psdab
4634 4pmhs-25oxman2-imo-aspibua
4635 bhs-mepipe-oem-psdab
4636 2py-dimephmem-5amo-dfzdap
4637 bim-eta-emo-bhsdab
4638 tolhs-3diaz-cno-zdab
4639 am2py-24thiz-mecpo-zdab
4640 bhs-diphmep-mes-betadcph
4641 am2py-am3-sem-nzdap
4642 n2py-thizo-men-aspibua
4643 mam2py-tridi-fo-psdab
4644 2pmhs-24thiman-napo-thizzdap
4645 mam2py-ams2-no2-aspbzla
4646 bim-tridi-eoco-betapy
4647 morhs-pipmea-imo-mezphe
4648 piraz-m25thizman2-pyo-bphabs
4649 piraz-edia2-sem-nzdap
4650 imhs-pazin-eoco-bnsdap
4651 z-dimephmem-5pho-betadcph
4652 dhim-pnymea-oem-psdap
4653 bhs-amn2-no1-psdap
4654 thpym-mepipe-meo-bhsdap
4655 mam2py-ms-oeto-betadcph
4656 moegua-mepazin-pro-bhsdab
4657 imhs-diphmem-oem-betadcph
4658 2py-pazin-ocho-bsdap
4659 bhs-24thiz-pro-psdapee
4660 am2py-m24thizman2-ocho-ibsdap
4661 thpym-dimephmep-no1-zdap 4662 hythpym-pazin-meo-betainyl
4663 thpym-eta-5pho-betapy
4664 imhs-24thizman2-5pho-csdap
4665 amim-pipmea-cno-bnsdap
4666 am4py-pnymea-5pho-bhsdab
4667 bim-ams2-no1-psdap
4668 mam2py-24thiz-no1-aspibua
4669 pippy-3pazin-chexo-bsdap
4670 amim-dimen-daco-betainyl
4671 bim-thizn-meteto-zdabs
4672 bhs-pymea-meo-oxal
4673 me2py-pentas-5amo-psdap
4674 bim-pazin-emo-bhsdab
4675 bhs-pazin-ocho-bnsdap
4676 thpym-tridi-baeo-zdap
4677 morhs-tridi-eoco-bnsdap
4678 impy-amn3-mecpo-bhsdab
4679 edothpym-mepipen2-eoco-aspaba
4680 am2py-trias-5pho-betaet
4681 pippy-dimephmep-oem-bsdap
4682 me2py-25oxman2-5amo-psdapee
4683 chhs-trias-eoco-betainyl
4684 nim-mepipe-cno-bhsdap
4685 thpym-din-5pho-betaet
4686 2py-tetradi-imo-bphabs
4687 dhim-dis-ocho-aspibua
4688 impy-mepazin-men-dfzdap
4689 2py-dipch-no2-tsdap
4690 bim-pyma2-5amo-betadcph
4691 im-pymea-fo-bhsdap
4692 bhs-24thiz-napo-zdabs
4693 pyr-dimephmem-eoco-asppha
4694 morhs-24thiman-daco-bhsdap
4695 2py-amn2-men-oxal
4696 im-dimephmep-5pho-aspbzla
4697 mam2py-am2-oem-nbeta34dimeoph
4698 cl3pyme-24thizman2-mecpo-betapy
4699 nim-amo3-men-aspbzla
4700 bim-edian2-5pho-bhsdap
4701 mam2py-pipa-4amo-ppsdap
4702 2py-amn2-mes-betapy
4703 2py-ams2-meo-bhsdab
4704 me-diphmep-imo-bhsdap
4705 4pmhs-m25thiman2-5amo-bphabs
4706 2py-edian2-meo-bnsdap
4707 dhim-n2nme2n-baeo-betaet
4708 thpym-amn2-oem-zdap
4709 pippy-thizo-fo-dfzdap
4710 dhim-24thizman2-emo-psdab
4711 tolhs-din-pheo-aspbzla
4712 piraz-amo2-5pho-aspbzla
4713 bhs-diaz-mommo-glyzdap
4714 pyr-m25thiz-pyo-aspbzla
4715 morhs-dimephmem-emo-psdapee
4716 hythpym-pymea-meo-zdabs
4717 pyrhs-pipmea-daco-bphabs
4718 me2py-am3-sem-npsdap
4719 me2py-mepipen2-no1-betapy
4720 2pmhs-ams2-fo-oxal
4721 thpym-24thiz-ocho-osdap
4722 bim-edian2-pheo-mezphe
4723 thpym-pentadi-meo-betapy
4724 bhs-25oxman2-meo-mezphe
4725 me2py-edia2-oem-nbetapy
4726 am-diphmep-no1-psdab
4727 hythpym-thizn-meo-aspibua
4728 amthiaz-dis-meto-csdap
4729 imhs-tridi-no1-betainyl
4730 gua-amn2-5amo-betainyl
4731 bimhs-eta2s-oeto-dfzdap
4732 4pmhs-25thiman2-men-betapy
4733 bimhs-25oxman2-oem-aspaba
4734 mam2py-tetradi-oeto-zdab
4735 bim-tri as-fo-psdap
4736 z-amo3-5amo-zdab
4737 n2py-dimephmep-napo-zdabs
4738 bim-amn2-emo-betadcph
4739 fthpym-mepazin-emo-bnsdap
4740 me2py-dich-no2-psdab
4741 pippy-amo2-meo-asppha
4742 bimhs-pnymea-mommo-glupha
4743 dhim-dimephmep-oem-zdap
4744 piraz-24thiz-imo-betadcph
4745 2py-diphmep-no2-betadcph
4746 dpam-thizo-imo-mezphe
4747 2pmhs-dipch-5amo-glyzdap
4748 imhs-3diaz-fo-aspibua
4749 bhs-24thizman2-4amo-aspbzla
4750 impy-ams2-imo-bhsdab
4751 dhim-diphmem-pro-bsdap
4752 mepip-m24thizman2-oem-psdap
4753 bimhs-24thizman2-mecpo-glyzdap
4754 chhs-dis-mes-betadcph
4755 impy-n2nme2n-daco-zdap
4756 dhim-mepipe2-oem-nzdab
4757 menim-pymea-chexo-glyzdap
4758 cl3pyme-pyma2-no1-betainyl
4759 piraz-amn3-cpro-bnsdap
4760 imhs-mepipen2-no1-glupha
4761 piraz-diphmem-no1-bphabs
4762 deam-pentadi-eoco-aspibua
4763 dmam-dimen-5pho-oxal
4764 gua-24thiz-ocho-psdab
4765 bhs-mepipe-oem-bsdap
4766 nmor-pazin-5amo-bphabs
4767 bzl-ams2-napo-mezphe
4768 me2py-pentadi-mmen-zorn
4769 nmhs-m24oxman2-4pho-bsdap
4770 impy-24thiz-imo-asppha
4771 hythpym-pymea-cno-bhsdap
4772 bhs-25oxman2-mecpo-betadcph
4773 cl3pyme-dimen-oeto-aspbzla
4774 amim-dipch-no2-dfzdap
4775 2py-m25thizman2-cpro-psdab
4776 me2py-diphmep-meo-dfzdap
4777 thpym-amn-ocho-bhsdap
4778 bhs-mepipe-ocho-bsdap
4779 dpam-pnymea-ocho-bhsdab
4780 imhs-m24thizman2-ocho-zorn
4781 thpym-n24thiman-oem-zdabs
4782 thpym-pipmea-pheo-csdap
4783 prhs-m25thizman2-no2-oxal
4784 imhs-24thiz-meo-bnsdap
4785 me2py-pazin-no2-aspibua
4786 me2py-mepipe-no2-zdab
4787 me2py-trias-meo-aspibua
4788 imhs-edian2-meo-zdab
4789 me2py-24thiz-imo-bnsdap
4790 bim-eta-meo-bnsdap
4791 am4py-thizn-meo-aspbzla
4792 2py-edian2-no2-zdap
4793 amthiaz-mepipen2-5pho-zdab
4794 am2py-24thizman2-eoco-psdapee
4795 am2py-tridi-fo-bsdap 4796 imhs-amn2-fo-ppsdap
4797 bimhs-dimen-5pho-bphabs
4798 amim-eta-napo-dfzdap
4799 bim-eta-no2-psdab
4800 thpym-amn2-5pho-bsdap
4801 thpym-dimen-pheo-psdap
4802 amim-m24thiman2-eoco-bnsdap
4803 bhs-am3diaz-men-zdab
4804 thpym-edian2-5pho-bsdap
4805 imhs-tetradi-imo-betainyl
4806 4pmhs-edia2-oem-nbeta34-dimeoph
4807 amthiaz-25oxman2-fo-psdab
4808 imhs-dimen-mes-zdabs
4809 moegua-dimephmep-napo-zdabs
4810 2py-dimephmep-no2-psdap
4811 amim-eta-no2-dfzdap
4812 pyraz-25oxman2-chexo-asppha
4813 bim-mepazin-4pho-psdapee
4814 cl3pyme-pazi2n-napo-csdap
4815 fthpym-indan2-peo-psdapee
4816 am2py-n2o2n-oeto-csdap
4817 mam2py-eta-meto-bhsdap
4818 2pmhs-pazi2n-mmen-dfzdap
4819 cl3pyme-dimephmem-oem-bsdap
4820 prhs-tridi-no1-dfzdap
4821 dmthpym-tridi-5amo-zdab
4822 hythpym-eta-no1-dfzdap
4823 morhs-ams2-mes-bsdap
4824 thpym-mepipe-no2-bnsdap
4825 bz-amn2-napo-zdab
4826 hythpym-pazi2n-meo-psdap
4827 dhim-mepazin-eoco-bphabs
4828 ec-mepipen2-imo-zdabs
4829 z-pipmes-napo-asppha
4830 mam2py-m24thizman2-emo-zdabs
4831 2py-amn2-5pho-zdap
4832 bz-amn2-5amo-csdap
4833 thpym-mepipe-meo-zdab
4834 mam2py-m24thizman2-fo-asppha
4835 bhs-mepipe-mes-psdap
4836 nim-edian2-men-bhsdab
4837 piraz-n24thiman-men-betapy
4838 piraz-mepazin-no2-zdab
4839 hythpym-m24thizman2-emo-zdap
4840 phhs-diphmem-5pho-betapy
4841 mam2py-3pazin-no1-psdap
4842 bim-dis-napo-bphabs
4843 me2py-diphmem-imo-aspbzla
4844 emnim-ams2-napo-bhsdab
4845 deam-pipa-ocho-asppha
4846 morhs-props-emo-aspbzla
4847 pyr-diphmep-paco-psdapee
4848 bim-pentadi-mes-tsdap
4849 bim-mepipe-mes-bnsdap
4850 bimhs-trias-meo-bsdap
4851 bhs-mepipe-no1-betapy
4852 ec-pipa-oem-aspbzla
4853 2py-dimephmep-peo-zdap
4854 bim-mepazin-5pho-aspbzla
4855 hythpym-am3-sem-nbeta34-dimeoph
4856 thpym-pyma2-men-ppsdap
4857 imhs-pazin-5pho-psdab
4858 2py-eta-no2-betapy
4859 dhim-pazin-hso-psdab
4860 piraz-dimen-men-psdab
4861 2pmhs-tetradi-napo-zdab
4862 pippy-pipa-chexo-aspaba
4863 bhs-am3diaz-chexo-aspaba
4864 bhs-dis-baeo-mezphe
4865 pippy-25thiman2-oem-dfzdap
4866 menim-edian2-cnmo-betadcph
4867 2pmhs-m25thiz-no1-psdab
4868 thpym-amn2-5pho-zdab
4869 pippy-m24thizman2-eoco-betadcph
4870 phpip-ams2-oem-psdap
4871 amim-trias-no1-zdab
4872 morhs-tetradi-no2-bphabs
4873 mepip-mepazin-chexo-betapy
4874 emnim-pymea-5pho-dfzdap
4875 me2py-24thiman2-5amo-dfzdap
4876 hythpym-amo2-5amo-zdab
4877 impy-mepipen2-no1-betapy
4878 dhim-pipmea-men-zlys
4879 phhs-m25thiz-no1-zdabs
4880 nim-pipa-no1-aspbzla
4881 impy-pazin-emo-zorn
4882 hythpym-dimephmep-meo-zdabs
4883 pippy-pipa-cpeo-bsdap
4884 nmor-pentas-napo-aspibua
4885 mepip-tridi-mommo-bhsdab
4886 amim-dimephmep-men-glyzdap
4887 phhs-propa2s-meo-zdabs
4888 bim-amn2-meo-zdab
4889 2py-3pazin-daco-tsdap
4890 imhs-pentadi-fo-aspbzla
4891 hythpym-din-mes-tsdap
4892 piraz-diphmep-napo-zdab
4893 ec-amo2-oeto-zdap
4894 imhs-eta-no1-bsdap
4895 imhs-n24thiman-oem-bphabs
4896 mam2py-eta2s-fo-asppha
4897 dhim-diphmem-meo-betainyl
4898 mepip-dimen-men-psdab
4899 amthiaz-tridi-emo-glyzdap
4900 pyrhs-mepazin-5amo-csdap
4901 bimhs-25thiman2-ocho-zdabs
4902 bimhs-trias-pyo-aspibua
4903 hythpym-ams2-mommo-aval
4904 impy-pyma2-5amo-glubzla
4905 npip-25oxman2-no2-bphabs
4906 mam2py-dimephmem-emo-bsdap
4907 2pmhs-din-5amo-betainyl
4908 bimhs-butn-chexo-psdab
4909 impy-indan2-mes-bhsdab
4910 ppy-dimephmem-fo-csdap
4911 bz-pazin-oem-bhsdab
4912 2py-diphmep-napo-zdap
4913 pyr-25thiz-emo-bphabs
4914 bhs-pyma2-mmen-ppsdap
4915 impy-pipmea-men-aval
4916 dhim-m24thizman2-daco-bnsdap
4917 tolhs-trias-4amo-bphabs
4918 pippy-dis-no1-dfzdap
4919 dhim-mepipen2-mes-aspbzla
4920 pyrhs-25oxman2-5amo-zlys
4921 nmhs-diphmem-fo-psdab
4922 prhs-mepazin-4amo-bhsdab
4923 am2py-m24thizman2-no1-dfzdap
4924 bhs-pazin-no2-bsdap
4925 nmhs-24thiz-fo-aspibua
4926 pippy-25oxman2-5pho-ibsdap
4927 dhim-trias-imo-asppha
4928 hythpym-m25thiz-aco-bhsdap
4929 piraz-pipmea-meto-bhsdab 4930 bhs-amo2-chexo-oxal
4931 bhs-edian2-meo-betapy
4932 imhs-trias-napo-zdab
4933 bhs-mepipe-emo-zorn
4934 nmor-eta-no1-psdap
4935 impy-thizo-fo-bhsdab
4936 thpym-pipa-meo-glyzdap
4937 2pmhs-dimen-fo-zdabs
4938 am2py-pipa-5amo-betainyl
4939 imhs-pazin-mes-zdab
4940 amim-25thiz-mmen-asppha
4941 bim-diphmem-cpeo-betadcph
4942 thpym-mepipe-5pho-betapy
4943 chhs-mepipe2-oem-nzdab
4944 nmor-n2o2n-imo-glubzla
4945 bz-amn2-meo-dfzdap
4946 pippy-din-5pho-bnsdap
4947 amthiaz-m25thizman2-peo-bnsdap
4948 dhim-m25thiz-mmen-csdap
4949 2py-thizn-5amo-bphabs
4950 bim-24thizman2-ocho-psdapee
4951 am4py-ams2-cpeo-asppha
4952 prhs-mepazin-eoco-aspbzla
4953 hythpym-tridi-oem-bphabs
4954 am4py-25oxman2-hso-osdap
4955 me2py-propa2s-mes-aspbzla
4956 2py-edian2-no1-asppha
4957 dpam-2pazin-5amo-zdabs
4958 piraz-edia2-sem-npsdap
4959 thpym-ams2-eoco-betadcph
4960 bhs-25thiman2-emo-zdapee
4961 mam2py-n24thiman-pyo-bnsdap
4962 emnim-pipa-ocho-asppha
4963 dhim-amn2-cpro-ppsdap
4964 imhs-pazin-no2-zdab
4965 dhim-m24thiz-napo-aspbzla
4966 pippy-din-cpro-psdab
4967 bim-mepipe-mes-betapy
4968 thpym-pymea-no2-aspbzla
4969 piraz-amo2-5amo-bnsdap
4970 prhs-m25thiz-daco-bnsdap
4971 me2py-amo2-fo-bhsdab
4972 amthiaz-hexas-5pho-aspibua
4973 gua-pnymea-eoco-aspbzla
4974 hythpym-trias-no2-psdap
4975 impy-25oxman2-napo-betadcph
4976 piraz-mepipen2-mes-zorn
4977 dhim-mepipen2-5pho-bhsdap
4978 amim-tetradi-fo-betadcph
4979 am2py-pazin-oem-bphabs
4980 bhs-pipmea-no2-aspibua
4981 thpym-tridi-meo-aspbzla
4982 imhs-amn3-napo-zlys
4983 me2py-dimephmep-no1-aspibua
4984 morhs-am2-oem-nzdap
4985 phhs-trias-5amo-dfzdap
4986 bhs-amo2-imo-bsdap
4987 pippy-pnymea-napo-mezphe
4988 am2py-thizn-5amo-csdap
4989 bim-eta-ocho-betapy
4990 nim-amn2-meteto-betadcph
4991 bhs-eta-ocho-bsdap
4992 me2py-am2-sem-nbetapy
4993 piraz-ams2-no2-asppha
4994 am-25oxman2-eoco-zdab
4995 nmhs-pazi2n-5amo-bsdap
4996 bim-indan2-emo-csdap
4997 imhs-dimen-peo-psdab
4998 4pmhs-25oxman2-paco-glyzdap
4999 dmam-mea-imo-zorn
5000 emnim-m25thiz-pro-ppsdap
5001 hythpym-amn3-oem-glyzdap
5002 dpam-pymea-emo-zdabs
5003 me2py-tetradi-peo-bhsdab
5004 nmhs-am3-oem-nbetabnaphth
5005 thpym-mepipe-no1-psdap
5006 4pmhs-pyma2-oem-aspibua
5007 impy-pnymea-hso-dfzdap
5008 pippy-m25thiz-chexo-psdap
5009 imhs-eta-meo-zdap
5010 pyr-hexadi-men-bsdap
5011 2py-ams2-meo-glyzdap
5012 deam-pymea-daco-bhsdab
5013 mam2py-diphmep-mes-zorn
5014 pippy-mepipe-mommo-bsdap
5015 bim-tridi-5pho-aspbzla
5016 bimhs-25oxman2-oem-bhsdab
5017 me2py-diphmep-no1-csdap
5018 2py-tetradi-mes-betapy
5019 pyraz-eta-5pho-zdap
5020 bim-pymea-mes-zdabs
5021 2py-pazin-no1-betapy
5022 bim-pazin-meo-psdab
5023 2py-amn3-mecpo-zdap
5024 2py-pnymea-ocho-psdap
5025 dhim-24thiman-cpro-betainyl
5026 bim-pipa-5pho-mezphe
5027 pippy-dimephmem-5pho-asppha
5028 bhs-edian2-eoco-bhsdap
5029 ec-edia2-sem-nbetabnaphth
5030 thpym-pazin-mes-psdab
5031 tolhs-dimen-5pho-betainyl
5032 imhs-amn2-meo-zdap
5033 piraz-3diaz-daco-mezphe
5034 bim-25thizman2-napo-bnsdap
5035 ec-ams2-cnmo-glyzdap
5036 bim-mepipe-no1-bsdap
5037 2py-pazin-eoco-psdab
5038 bimhs-mea2s-ocho-betadcph
5039 me2py-m24thizman2-eoco-glyzdap
5040 nim-m25thiz-emo-bhsdap
5041 imhs-thizn-5pho-psdapee
5042 me2py-trias-5amo-asppha
5043 2py-eta-hso-zdab
5044 nim-dis-chexo-zdab
5045 am2py-din-imo-betainyl
5046 me2py-mepipen2-eoco-psdab
5047 imhs-eta-oem-zdap
5048 2py-dimen-eoco-asppha
5049 mam2py-3diaz-emo-aspbzla
5050 thpym-eta-meo-zdab ******
5051 mam2py-amo2-daco-bsdap
5052 bim-thizn-meo-zdap
5053 am2py-hexadi-oem-bsdap
5054 bim-pymea-cno-dfzdap
5055 imhs-dis-no1-zdabs
5056 menim-din-meo-glyzdap
5057 2py-pnymea-men-asppha
5058 bhs-amn2-ocho-psdap
5059 dpam-amo2-eoco-zdap
5060 impy-amn3-pro-asppha
5061 pyr-amn3-5amo-osdap
5062 hythpym-amo2-ocho-bnsdap
5063 imhs-eta-meo-bhsdap 5064 bimhs-mepipe-paco-bhsdap
5065 pippy-pyma2-oeto-betainyl
5066 nmhs-mepipe-5amo-zdab
5067 dmbim-tetradi-pyo-aspbzla
5068 im-pnymea-pyo-csdap
5069 emnim-ams2-emo-betapy
5070 bhs-dimephmem-mes-glupha
5071 hythpym-pipa-chexo-aval
5072 piraz-mepazin-chexo-csdap
5073 hythpym-eta2s-napo-glyzdap
5074 me2py-diphmep-fo-oxal
5075 bim-25thiz-eoco-bphabs
5076 mam2py-dis-men-aspibua
5077 am2py-eta2s-meo-dfzdap
5078 me2py-tridi-no2-aspibua
5079 bim-am3-oem-nzdab
5080 chhs-dimen-pheo-dfzdap
5081 thpym-eta-ocho-psdap
5082 nmhs-m24thiz-napo-psdab
5083 mam2py-am3-oem-nbetapy
5084 impy-pymea-mecpo-thizzdap
5085 n2py-24thizman2-chexo-psdab
5086 bzl-pazin-mommo-oxal
5087 thpym-am3diaz-no2-bsdap
5088 prhs-24thizman2-oeto-bhsdab
5089 bhs-24thiz-pro-zdabs
5090 moegua-24thiman-emo-mezphe
5091 am2py-edia2-sem-nzdab
5092 dpam-ams2-5amo-aspbzla
5093 am2py-dimephmep-baeo-betapy
5094 dhim-trias-meteto-bnsdap
5095 2py-amn2-mes-bhsdap
5096 imhs-diphmem-ocho-thizzdap
5097 bhs-edian2-mes-bnsdap
5098 2py-pazin-no2-zdap
5099 amim-eta-oeto-zdapee
5100 nmor-25oxman2-imo-asppha
5101 imhs-eta-5pho-bnsdap
5102 2py-pnymea-5pho-betadcph
5103 bimhs-trias-peo-bhsdab
5104 bhs-am2-oem-nzdap
5105 amim-ams2-mes-bsdap
5106 am4py-thizn-no1-betainyl
5107 hythpym-pymea-napo-tsdap
5108 deam-propn-meo-csdap
5109 am2py-mepipe-cpeo-bhsdab
5110 2py-mepipe-5pho-bnsdap
5111 bhs-pazin-5pho-psdab
5112 morhs-butn-pro-betapy
5113 mepip-24thiz-oeto-psdab
5114 piraz-edian2-napo-bsdap
5115 mam2py-trias-imo-zdabs
5116 impy-hexas-napo-bnsdap
5117 imhs-dich-mes-glubzla
5118 2py-propa2s-aco-csdap
5119 impy-dimephmem-5amo-bnsdap
5120 bim-am3diaz-men-betapy
5121 4pmhs-tridi-5pho-bsdap
5122 mam2py-pazi2n-cpeo-glyzdap
5123 2py-m24oxman2-baeo-zdapee
5124 dmam-ams2-imo-dfzdap
5125 amim-mepipe-chexo-psdab
5126 dmbim-pipmeo-mes-thizzdap
5127 imhs-eta-imo-zdap
5128 2py-eta-no2-bhsdap
5129 bimhs-pyma2-meo-zdabs
5130 2py-n2o2n-chexo-zdabs
5131 morhs-pymea-hso-aspbzla
5132 2pmhs-indan2-5pho-zdabs
5133 hythpym-25oxman2-cno-psdab
5134 bim-pazin-5pho-bhsdap
5135 dpam-thizn-imo-dfzdap
5136 thpym-mepipe-5pho-psdap
5137 imhs-ams2-mes-betainyl
5138 gua-thizo-5pho-glyzdap
5139 prhs-dipch-men-zdap
5140 amim-m25thiman2-oem-betadcph
5141 me2py-m25thiaman2-no1-betainyl
5142 bhs-pyma2-5amo-tsdap
5143 dhim-25oxman2-no1-betainyl
5144 bimhs-25oxman2-mes-glyzdap
5145 dpam-24thizman2-oem-aspibua
5146 imhs-dipch-5pho-psdap
5147 dmthpym-pipmea-eoco-zdabs
5148 nmor-mea-imo-betaet
5149 z-ams2-oem-zdab
5150 me2py-edian2-no1-zdab
5151 ppy-propn-pyo-zdabs
5152 nmhs-tridi-5pho-aspibua
5153 dmam-edian2-emo-dfzdap
5154 pippy-m25thiz-chexo-bhsdab
5155 impy-diphmep-no1-bphabs
5156 2py-n2nme2n-5amo-betainyl
5157 imhs-mepazin-meo-asppha
5158 pyr-mepipe-imo-glyzdap
5159 hythpym-dimephmep-napo-glubzla
5160 phpip-eta-napo-mezphe
5161 dmam-pazin-men-betainyl
5162 bhs-eta-5amo-zdabs
5163 2py-edian2-oem-bsdap
5164 chhs-amo2-4pho-bnsdap
5165 2py-tridi-mecpo-asppha
5166 n2py-diphmep-no2-betainyl
5167 me2py-eta-paco-asppha
5168 bhs-amo2-aco-psdap
5169 2py-mepipe-ocho-bnsdap
5170 amim-pyma2-fo-ibsdap
5171 gua-mepazin-napo-betainyl
5172 bhs-am2-sem-nbetapy
5173 gua-m24thizman2-5pho-dfzdap
5174 edothpym-m25thizman2-mes-aspbzla
5175 amthiaz-thizn-fo-psdab
5176 mam2py-pazin-emo-ibsdap
5177 pippy-25thiz-oem-zdapee
5178 bimhs-pnymea-meo-zdap
5179 mam2py-props-meo-glubzla
5180 dhim-dimen-mecpo-aspibua
5181 nmor-eta-5amo-glyzdap
5182 impy-pnymea-imo-bnsdap
5183 pyrhs-24thiz-emo-zorn
5184 dmbim-din-chexo-psdab
5185 amim-tetradi-napo-zdabs
5186 am2py-amn3-ocho-mezphe
5187 dhim-pipmea-napo-betainyl
5188 thpym-m24thiz-napo-bhsdap
5189 tolhs-mepazin-5pho-betainyl
5190 mam2py-dimen-pro-ibsdap
5191 mam2py-pazin-mes-dfzdap
5192 ec-amn3-fo-betadcph
5193 2py-diphmem-baeo-csdap
5194 ec-eta-men-mezphe
5195 amim-24thizman2-5amo-bnsdap
5196 2py-edia2-sem-nzdab
5197 pyraz-25thiman2-mes-dfzdap 5198 bhs-eta-eoco-bnsdap
5199 thpym-tridi-no2-aspibua
5200 ec-dich-nmo-bnsdap
5201 pyr-pipmea-4pho-tsdap
5202 dhim-24thiman-imo-psdab
5203 amim-thizn-mes-dfzdap
5204 chhs-edian2-5pho-csdap
5205 thpym-amn2-oem-psdab
5206 fthpym-pipmea-no1-dfzdap
5207 nim-mepipen2-no1-betadcph
5208 piraz-edian2-no2-ibsdap
5209 am2py-amn-men-betainyl
5210 emnim-m25thiz-napo-dfzdap
5211 amim-edia2-oem-azdab
5212 bhs-mepipe-eoco-betapy
5213 dmthpym-pazin-no2-zdabs
5214 piraz-edian2-napo-bsdap
5215 me2py-edia2-sem-nbetameph
5216 am2py-din-eoco-zdab
5217 imhs-amn3-meteto-aspbzla
5218 ec-m24thizman2-oem-bhsdap
5219 bim-dipch-mecpo-betainyl
5220 pippy-dimephmem-fo-aspbzla
5221 fthpym-amo2-chexo-asppha
5222 fthpym-pymea-meo-psdab
5223 pyraz-ams2-emo-psdap
5224 bhs-eta-meo-psdab
5225 bhs-edian2-mes-zdap
5226 nim-diphmem-men-dfzdap
5227 amim-pipmea-daco-thizzdap
5228 2py-25oxman2-meo-csdap
5229 dpam-diphmep-napo-bhsdap
5230 mam2py-dimen-men-aval
5231 bimhs-m24thizman2-4pho-psdab
5232 dhim-am3-sem-nzdap
5233 impy-mepipe-meo-betadcph
5234 bz-mepazin-emo-bhsdap
5235 fthpym-tridi-5amo-bsdap
5236 am2py-pipa-meto-glyzdap
5237 bhs-mepipe-meo-bsdap
5238 me2py-propa2s-fo-bnsdap
5239 cl3pyme-trias-mecpo-glyzdap
5240 phhs-mea-no2-betainyl
5241 hythpym-tetradi-no1-mezphe
5242 bhs-eta-eoco-betapy
5243 phpip-mepazin-ocho-psdap
5244 piraz-trias-eoco-zdap
5245 bim-dimephmep-oem-zdabs
5246 am2py-m24thizman2-men-asppha
5247 bhs-pazin-mes-psdab
5248 2py-trias-chexo-zdabs
5249 bimhs-mepipen2-mes-zdabs
5250 pyrhs-25oxman2-meo-aspaba
5251 gua-edia2-sem-nzdap
5252 2py-mepipen2-cpro-psdap
5253 me2py-mepazin-5amo-zdap
5254 am2py-pazin-5pho-betainyl
5255 amim-dich-imo-psdab
5256 piraz-dipch-cpeo-mezphe
5257 hythpym-24thizman2-no2-zdab
5258 deam-24thiman2-no2-asppha
5259 bhs-25oxman2-ocho-asppha
5260 amim-amo2-5pho-thizzdap
5261 bhs-amo2-imo-betadcph
5262 dmthpym-mea-5amo-mezphe
5263 dhim-m25thizman2-5amo-betainyl
5264 dmthpym-propn-eoco-dfzdap
5265 pyr-24thiz-fo-aspbzla
5266 impy-diphmep-mes-psdap
5267 pyrhs-pazi2n-imo-betadcph
5268 mam2py-trias-meo-bhsdap
5269 piraz-tetradi-ocho-psdab
5270 fthpym-pipmeo-meo-mezphe
5271 tolhs-edia2-oem-npsdap
5272 2py-mepipe-no1-betapy
5273 pyraz-25oxman2-oem-aspbzla
5274 bhs-pipa-hso-csdap
5275 mam2py-pnymea-oem-psdab
5276 im-eta-daco-zorn
5277 cl3pyme-diphmem-ocho-bsdap
5278 fthpym-dimen-5amo-bsdap
5279 impy-pipmeo-daco-zdap
5280 dhim-edian2-5pho-betadcph
5281 bimhs-dimen-fo-bphabs
5282 dhim-pnymea-emo-betainyl
5283 thpym-m25thiz-mommo-csdap
5284 hythpym-25oxman2-imo-zdab
5285 pyr-am2-sem-nzdab
5286 phhs-m25thiz-5amo-bhsdab
5287 thpym-pazin-mes-zdap
5288 dhim-props-napo-betainyl
5289 cl3pyme-edia2-sem-nzdab
5290 2py-ams2-imo-bhsdap
5291 bim-edian2-eoco-zdap
5292 piraz-mea2s-ocho-zdab
5293 piraz-edian2-eoco-glyzdap
5294 bimhs-diphmep-5pho-csdap
5295 ec-thizn-daco-betaet
5296 bim-pnymea-5amo-asppha
5297 z-tetradi-napo-betapy
5298 amim-diphmem-eoco-asppha
5299 pippy-pnymea-fo-glyzdap
5300 dhim-ams2-mes-dfzdap
5301 mam2py-pnymea-napo-osdap
5302 me2py-dis-imo-glupha
5303 dhim-ams2-fo-bhsdap
5304 piraz-ams2-men-bnsdap
5305 chhs-pnymea-chexo-mezphe
5306 n2py-m24thizman2-5amo-aspbzla
5307 bimhs-thizo-emo-betainyl
5308 gua-24thizman2-meo-zdabs
5309 hythpym-24oxman2-oem-psdab
5310 bim-mepipe2-oem-nbeta34-dimeoph
5311 bim-pazin-no2-bhsdap
5312 4pmhs-n24thiman-oem-csdap
5313 dhim-thizs-eoco-bphabs
5314 phhs-pazin-meo-zdabs
5315 mam2py-25oxman2-meo-bhsdap
5316 am2py-mepipe2-sem-npsdap
5317 impy-m24thiz-ocho-asppha
5318 2py-24thiman-oeto-psdap
5319 hythpym-pyma2-5amo-zlys
5320 hythpym-thizn-napo-aspbzla
5321 amim-n2nme2n-ocho-psdapee
5322 mam2py-thizn-mommo-dfzdap
5323 bim-dimephmem-5amo-bhsdap
5324 bim-pipmea-no2-dfzdap
5325 ppy-dimephmep-emo-dfzdap
5326 am2py-amo2-oem-betadcph
5327 dmthpym-24thiz-mes-zdap
5328 2py-amn2-napo-betapy
5329 impy-diphmep-pro-bsdap
5330 ibhs-mepipen2-5pho-bhsdap
5331 2py-m24oxman2-5amo-aspaba 5332 bhs-amn2-meo-bhsdap
5333 moegua-m25thiz-pro-glyzdap
5334 thpym-ams2-meto-betaet
5335 me2py-pipmea-imo-bphabs
5336 amim-pazin-5pho-osdap
5337 pyraz-pymea-pheo-betaet
5338 dmam-pyma2-cnmo-zorn
5339 bhs-edian2-eoco-psdap
5340 phpip-pipa-ocho-asppha
5341 am2py-propa2s-oem-zdap
5342 emnim-am2-oem-nzdap
5343 gua-trias-peo-csdap
5344 imhs-m25thiman2-napo-betainyl
5345 bhs-am3-oem-nbeta34dimeoph
5346 dmbim-25thi2-chexo-zdap
5347 ppy-m24thizman2-5amo-zdap
5348 moegua-m24thiz-5amo-psdap
5349 impy-dimephmem-napo-mezphe
5350 me2py-24thiz-meo-oxal
5351 thpym-amn3-5amo-aspbzla
5352 menim-mepipe-pro-aspibua
5353 2py-tetradi-5amo-bnsdap
5354 edothpym-am3-oem-nbetabnaphth
5355 bimhs-propn-napo-glyzdap
5356 imhs-am2-sem-nbetabnaphth
5357 piraz-mepipe-oem-betadcph
5358 piraz-edian2-chexo-betainyl
5359 bzl-24thiz-eoco-asppha
5360 bim-trias-meteto-oxal
5361 imhs-edian2-no1-betapy
5362 amthiaz-tridi-mes-glyzdap
5363 im-24thiman2-ocho-asppha
5364 piraz-24thiz-5amo-bsdap
5365 amim-pipmea-4pho-csdap
5366 me2py-24oxman2-hso-ibsdap
5367 bhs-pazin-ocho-bhsdap
5368 bhs-amn2-5pho-zdap
5369 2pmhs-tridi-cno-bphabs 5420 bz-3diaz-imo-zdab
5370 bz-25thiman2-oeto-aspibua
5371 ppy-diphmep-cpeo-betainyl
5372 bimhs-pyma2-hso-psdap
5373 thpym-pazin-5pho-bnsdap
5374 me2py-edia2-oem-nbetapy
5375 bimhs-diaz-oem-glyzdap
5376 nmor-pymea-fo-psdap
5377 piraz-m24thiz-eoco-betainyl
5378 moegua-pazin-eoco-dfzdap
5379 imhs-edian2-mes-bnsdap
5380 am2py-din-emo-thizzdap
5381 me2py-pentas-oem-bnsdap
5382 dhim-dimephmem-crmo-zdapee
5383 bhs-pymea-no2-glubzla
5384 bhs-m25thiz-mes-psdab
5385 2py-mepipe-ocho-betapy
5386 bhs-edian2-napo-psdab
5387 thpym-edian2-oem-zdap
5388 bim-edian2-oem-psdap
5389 pippy-24thizman2-5pho-mezphe
5390 am-dimen-mes-psdab
5391 am2py-props-men-psdab
5392 mam2py-pipa-mes-betadcph
5393 am2py-pipmea-napo-glupha
5394 fthpym-mepipe-nmo-bnsdap
5395 me2py-pipmea-pro-dfzdap
5396 mam2py-3diaz-4amo-ibsdap
5397 piraz-3pazin-oem-bsdap
5398 mepip-m24thizman2-fo-mezphe
5399 me2py-mepipe-5amo-glyzdap
5400 bzl-mepipen2-imo-zdabs
5401 bim-eta-mes-bhsdap
5402 me2py-amo3-emo-betainyl
5403 gua-tetradi-pro-zdab
5404 n2py-pipa-chexo-betainyl
5405 edothpym-24thizman2-imo-zdabs
5406 dhim-pipa-no2-tsdap
5407 nmor-ams2-ocho-bhsdab
5408 amthiaz-amn2-no1-zdabs
5409 2py-ams2-emo-zdabs
5410 2pmhs-indan2-eoco-mezphe
5411 pippy-am3diaz-oem-asppha
5412 amim-pazin-men-bhsdab
5413 hythpym-mepipe-ocho-betapy
5414 amim-diphmem-cpro-aspbzla
5415 pyraz-eta2s-ocho-glyzdap
5416 bim-pazin-5pho-aval
5417 amim-mepazin-mes-psdap
5418 dhim-amn3-emo-zdab
5419 amthiaz-m24thizman2-5pho-psdab
5421 bimhs-amo2-emo-asppha
5422 bim-tetradi-fo-betainyl
5423 2py-amn2-no1-betapy
5424 amim-amo2-oem-psdap
5425 2py-n2o2n-peo-betadcph
5426 bhs-pazin-oem-zdap
5427 phhs-m24thizman2-5pho-zdab
5428 nim-m24oxman2-5amo-bhsdap
5429 thpym-eta-ocho-bnsdap
5430 imhs-tetradi-meo-csdap
5431 2py-pazin-oem-bnsdap
5432 hythpym-ams2-napo-betapy
5433 ec-din-imo-aspbzla
5434 thpym-din-nmo-bsdap
5435 n2py-tetradi-emo-tsdap
5436 bimhs-n24thiman-4pho-thizzdap
5437 dhim-diphmep-mes-dfzdap
5438 bhs-mepipe-no1-zdap
5439 bhs-mepipe-no2-psdab
5440 inhs-amn2-no1-bnsdap
5441 impy-pnymea-ocho-psdab
5442 dhim-din-ocho-betainyl
5443 chmhs-m24thizman2-mommo-osdap
5444 bimhs-pazin-mes-betaet
5445 2py-m25oxman2-eoco-betapy
5446 me2py-m24oxman2-oem-bsdap
5447 bhs-dimephmep-chexo-bphabs
5448 emnim-pipa-ocho-csdap
5449 dhim-thizn-no1-bhsdab
5450 dhim-diaz-5pho-dfzdap
5451 bimhs-m24thiman2-emo-bhsdap
5452 2py-amo2-napo-dfzdap
5453 4pmhs-thizo-cno-csdap
5454 dhim-diphmem-oem-zdab
5455 bim-ams2-5amo-psdap
5456 dhim-thizn-no1-aspbzla
5457 dhim-25thiz-fo-bhsdap
5458 imhs-mepipe-5pho-bsdap
5459 amim-trias-imo-dfzdap
5460 dmbim-dimephmep-napo-betapy
5461 2py-24thiman2-imo-betainyl
5462 imhs-pyma2-oem-betapy
5463 am2py-dio-eoco-bnsdap
5464 fthpym-25oxman2-oeto-bnsdap
5465 me-ams2-cno-glyzdap
5466 impy-am3-sem-npsdap 5467 me2py-eta-ocho-dfzdap
5468 bhs-thizn-pheo-mezphe
5469 mam2py-24thiz-imo-betainyl
5470 dhim-amo2-fo-zdap
5471 emnim-m25thiz-napo-zdap
5472 thpym-m24thizman2-mes-zdap
5473 dhim-pyma2-napo-bhsdap
5474 thpym-m24thizman2-napo-tsdap
5475 me2py-25thizman2-eoco-betadcph
5476 thpym-edian2-5pho-ppsdap
5477 2py-dio-mommo-glyzdap
5478 bimhs-butn-meo-zdabs
5479 dhim-24thiz-cnmo-ibsdap
5480 pippy-amo2-pyo-bhsdap
5481 bim-dimen-ocho-betaet
5482 bim-m25oxman2-imo-zdabs
5483 imhs-dimen-paco-zdapee
5484 2py-eta-mes-bsdap
5485 2py-pentas-men-dfzdap
5486 me2py-amn2-meteto-aspbzla
5487 me-mepazin-emo-aspibua
5488 bim-dimephmep-emo-dfzdap
5489 bim-diphmep-emo-zdabs
5490 me2py-n2nme2n-fo-betapy
5491 phhs-pipmeo-men-bhsdab
5492 bimhs-am3diaz-no1-betainyl
5493 bhs-edian2-oem-zdab
5494 thpym-tetradi-no2-csdap
5495 thpym-m25thiz-emo-bnsdap
5496 am2py-amn3-eoco-bhsdap
5497 cl3pyme-amo2-daco-psdap
5498 z-dipch-men-glyzdap
5499 2py-mepipe-no2-bnsdap
5500 moegua-tridi-5amo-psdapee
5501 hythpym-m24thiman2-cpro-csdap
5502 am4py-24thiman2-nmo-csdap
5503 me2py-eta-cnmo-glyzdap
5504 am4py-tetradi-eoco-betadcph
5505 piraz-eta-peo-tsdap
5506 bim-eta2s-men-mezphe
5507 phhs-dimephmep-oem-mezphe
5508 emnim-pipmes-eoco-ibsdap
5509 bim-mepipe-no1-betapy
5510 2pmhs-24thiz-napo-bnsdap
5511 pyrhs-amn3-mes-bhsdab
5512 dhim-edia2-sem-nbetabnaphth
5513 piraz-diphmem-men-zdab
5514 phpip-pyma2-napo-bnsdap
5515 bim-mepipe-eoco-betapy
5516 im-pipa-5pho-aspbzla
5517 me2py-eta-5amo-bsdap
5518 bim-eta-eoco-zdap
5519 ibhs-pipa-cpeo-glyzdap
5520 cl3pyme-eta-mes-zdab
5521 2py-eta-ocho-zdap
5522 dhim-eta-peo-dfzdap
5523 dhim-24thiz-mes-betaet
5524 thpym-pnymea-meo-zdap
5525 fthpym-dis-chexo-zorn
5526 mam2py-dimephmem-cnmo-csdap
5527 bimhs-24thizman2-pro-glubzla
5528 bim-amn2-oem-zdab
5529 morhs-ams2-5amo-csdap
5530 mam2py-amo2-fo-zdab
5531 thpym-mepipe-oem-psdap
5532 impy-ms-chexo-glyzdap
5533 tolhs-pentas-mes-glyzdap
5534 bim-eta-no2-zdab
5535 imhs-mepipe-ocho-psdab
5536 me2py-thizn-mes-aspibua
5537 bhs-m25oxman2-5amo-betadcph
5538 mepip-din-4amo-glyzdap
5539 am2py-mepipe-baeo-bhsdab
5540 moegua-m24thiz-mes-csdap
5541 bhs-mepipe-ocho-psdap
5542 bhs-eta-5pho-bsdap
5543 dpam-m24thizman2-cpeo-zdab
5544 bhs-eta-chexo-bhsdap
5545 2py-propn-imo-bphabs
5546 dhim-amn2-4pho-betapy
5547 me-tetradi-oem-dfzdap
5548 bim-dis-ocho-bhsdap
5549 bim-amn2-ocho-zdab
5550 thpym-edian2-mes-bsdap
5551 mam2py-edian2-fo-zdap
5552 2py-pyma2-no2-bhsdab
5553 gua-diphmem-emo-osdap
5554 piraz-25oxman2-no1-mezphe
5555 thpym-edian2-5pho-bhsdap
5556 bim-edian2-meo-bhsdap
5557 thpym-amn2-5pho-bhsdap
5558 me2py-mepipen2-imo-zdap
5559 imhs-dimephmem-oem-bhsdap
5560 phpip-m25oxman2-no1-bhsdab
5561 impy-edian2-no2-psdab
5562 bimhs-trias-ocho-aval
5563 imhs-edian2-mmen-mezphe
5564 me2py-m24oxman2-5pho-mezphe
5565 amim-dimen-napo-zdap
5566 piraz-pnymea-cpro-aspbzla
5567 am2py-m25thiz-5amo-betainyl
5568 deam-m25thiz-napo-asppha
5569 piraz-diphmem-5pho-ibsdap
5570 impy-dimephmem-daco-thizzdap
5571 impy-m24thizman2-no2-bnsdap
5572 bhs-eta-ocho-bnsdap
5573 pyraz-am2-sem-nbetapy
5574 amim-24thizman2-no1-bsdap
5575 2py-amn3-5pho-bnsdap
5576 dmthpym-butn-pyo-dfzdap
5577 bim-amn2-no2-bnsdap
5578 moegua-indan2-chexo-betapy
5579 pippy-m24oxman2-meo-csdap
5580 bimhs-tridi-no2-betainyl
5581 pippy-edian2-no1-psdap
5582 dpam-n2o2n-eoco-oxal
5583 fthpym-pipa-chexo-glyzdap
5584 am-pazin-5pho-zdabs
5585 hythpym-dis-chexo-psdab
5586 pyrhs-propn-meto-zdap
5587 bhs-24thiz-no1-aspibua
5588 thpym-amn2-ocho-psdap
5589 amim-n2o2n-oem-zdab
5590 amim-mepipe-5pho-oxal
5591 dmam-m24thiz-5pho-aspaba
5592 n2py-3pazin-chexo-bsdap
5593 impy-dio-chexo-betadcph
5594 bim-hexas-meo-bphabs
5595 npip-edian2-no2-glyzdap betadcph
5596 amim-pipmea-ocho-bphabs
5597 ibhs-mepipe-emo-bphabs
5598 mepip-pnymea-meteto-aspibua
5599 piraz-am3-sem-nbeta34dimeoph
5600 me2py-dipch-5amo-csdap 5601 morhs-3pazin-chexo-zlys
5602 imhs-dimen-fo-betapy
5603 ibhs-24thiz-chexo-bhsdab
5604 piraz-pipa-meo-mezphe
5605 mepip-pipmea-chexo-glyzdap
5606 hythpym-m25thiz-paco-bnsdap
5607 piraz-m24thizman2-mes-betaet
5608 bz-edian2-men-aspbzla
5609 bim-edia2-oem-nbetabnaphth
5610 bhs-m25thiz-napo-bhsdap
5611 bimhs-25oxman2-mecpo-mezphe
5612 deam-24thiz-pheo-aspbzla
5613 bimhs-edian2-paco-ppsdap
5614 mam2py-ams2-fo-bnsdap
5615 me2py-pipa-no2-zorn
5616 bim-mepipe2-sem-nbeta34-dimeoph
5617 bhs-amn2-ocho-zdab
5618 4pmhs-trias-napo-zdab
5619 emnim-m25oxman2-men-bhsdap
5620 bim-mepipe-ocho-bhsdap
5621 impy-25oxman2-oem-zdap
5622 thpym-pnymea-no1-zdabs
5623 am2py-mepazin-oem-bphabs
5624 thpym-amn2-eoco-bnsdap
5625 me2py-24thizman2-ocho-zdabs
5626 emnim-m25thiz-ocho-asppha
5627 gua-tetradi-aco-zdab
5628 nim-m25thizman2-peo-zdab
5629 bimhs-24thiz-no2-betapy
5630 phhs-pnymea-4pho-aspbzla
5631 hythpym-ams3-5pho-bphabs
5632 dmam-dis-oem-bsdap
5633 bhs-edian2-meo-psdap
5634 pyr-eta-oeto-betapy
5635 hythpym-mepipe-men-aspibua
5636 dhim-pentadi-ocho-bhsdab
5637 mam2py-m24thizman2-eoco-psdap
5638 am2py-thizn-mes-asppha
5639 ec-pipmes-men-bsdap
5640 amim-ms-mecpo-aspbzla
5641 edothpym-trias-men-asppha
5642 am2py-mepipen2-no2-bphabs
5643 bimhs-tridi-imo-glyzdap
5644 imhs-propn-no1-bhsdap
5645 hythpym-25oxman2-5pho-betadcph
5646 imhs-pazin-ocho-psdab
5647 dhim-dimephmep-pheo-zdab
5648 amim-pyma2-pyo-zdap
5649 imhs-pazin-ocho-zdap
5650 me2py-24thiz-cno-bsdap
5651 bimhs-edian2-mes-csdap
5652 impy-pnymea-ocho-zdap
5653 mam2py-pymea-oem-bsdap
5654 n2py-dipch-aco-aspbzla
5655 mam2py-m24thizman2-eoco-mezphe
5656 npip-butn-oem-betaet
5657 amim-ms-eoco-zdabs
5658 bim-mepipe-ocho-zdap
5659 am2py-mepipe-5pho-zdapee
5660 imhs-eta-ocho-betapy
5661 2py-eta-5pho-zdap
5662 dhim-edia2-oem-nbetameph
5663 pyraz-amo2-eoco-betaet
5664 pyrhs-24thiz-meteto-psdapee
5665 mam2py-am3diaz-fo-bhsdap
5666 dhim-25oxman2-emo-zdab
5667 fthpym-thizs-peo-glubzla
5668 bzl-amo2-imo-bsdap
5669 dmthpym-pipa-chexo-betadcph
5670 bz-mepipe-napo-glyzdap
5671 thpym-amo2-chexo-zdab
5672 2py-pipmea-oem-zdapee
5673 pippy-amn2-chexo-zdab
5674 bim-amn2-5pho-psdap
5675 bzl-mepipen2-5pho-csdap
5676 me-m24thiz-meo-aspbzla
5677 pippy-n2nme2n-daco-aspbzla
5678 menim-24thiz-napo-mezphe
5679 mam2py-mepipe-fo-glupha
5680 bim-24thizman2-cno-mezphe
5681 thpym-am3diaz-imo-csdap
5682 hythpym-tridi-men-mezphe
5683 thpym-mepazin-emo-psdab
5684 am2py-n24thiman-napo-glyzdap
5685 bimhs-edian2-no2-mezphe
5686 amim-dimephmem-no1-betadcph
5687 2py-thizn-ocho-osdap
5688 impy-dis-mes-zdapee
5689 2py-edian2-mes-psdab
5690 piraz-mepipe-meo-asppha
5691 mam2py-edian2-meo-zdap
5692 phhs-dimen-no1-csdap
5693 dhim-mepipen2-chexo-bsdap
5694 dmbim-pipa-no2-tsdap
5695 2py-edian2-meo-betapy
5696 thpym-3diaz-5pho-zorn
5697 emnim-amn2-4pho-mezphe
5698 amim-am3-sem-nbeta34dimeoph
5699 me2py-dio-men-glupha
5700 amim-diphmem-mecpo-csdap
5701 am-pipmea-oem-betapy
5702 me2py-edian2-5amo-zdab
5703 bim-dis-oeto-psdap
5704 nim-pazin-mes-zdap
5705 4pmhs-pipa-napo-betadcph
5706 mam2py-eta-fo-psdap
5707 impy-mepipe-fo-asppha
5708 bimhs-m24thizman2-mes-psdab
5709 bim-pazin-chexo-mezphe
5710 bimhs-pnymea-napo-bhsdap
5711 2py-eta-meo-bsdap
5712 amim-amn3-chexo-aspbzla
5713 phhs-mepipe-mecpo-zlys
5714 amim-mepipe2-sem-nbetabnaphth
5715 bimhs-hexas-napo-zdap
5716 piraz-dimephmep-5pho-bphabs
5717 am4py-dich-paco-aval
5718 piraz-diaz-no1-bnsdap
5719 morhs-pymea-5amo-betapy
5720 ppy-pnymea-imo-psdab
5721 thpym-edian2-men-glupha
5722 nmhs-m25thiz-men-betainyl
5723 edothpym-24thiman-oem-zdab
5724 mam2py-25thiman2-5amo-zdapee
5725 2py-hexas-mmen-tsdap
5726 bimhs-din-mes-betapy
5727 pippy-dio-emo-dfzdap
5728 dhim-thizn-eoco-glyzdap
5729 npip-edian2-hso-bphabs
5730 nmhs-25oxman2-cno-asppha
5731 bimhs-thizn-5pho-psdab
5732 dmbim-edian2-oem-bnsdap
5733 pippy-24thizman2-napo-betaet
5734 me2py-din-men-bsdap 5735 bhs-pazin-ocho-betapy
5736 4pmhs-din-baeo-betainyl
5737 amthiaz-mepazin-no2-bnsdap
5738 npip-pipmes-no2-osdap
5739 2py-pipa-imo-aspibua
5740 phpip-mepazin-no2-mezphe
5741 piraz-pipa-5amo-betapy
5742 imhs-edian2-mes-psdab
5743 bim-pymea-ocho-glyzdap
5744 amim-thizn-ocho-bhsdap
5745 bimhs-dimephmep-chexo-aspibua
5746 dmbim-hexadi-5pho-betadcph
5747 bhs-mepazin-paco-bsdap
5748 imhs-dimephmem-aco-asppha
5749 bim-pazin-eoco-bhsdap
5750 4pmhs-ams2-napo-asppha
5751 dhim-am3diaz-ocho-betadcph
5752 impy-m25thiz-mes-csdap
5753 pyraz-diaz-5amo-bsdap
5754 bim-mepipe-ocho-zdab
5755 imhs-eta-5pho-bsdap
5756 amim-25oxman2-no1-ibsdap
5757 amthiaz-amn3-eoco-zdab
5758 thpym-mepipe-5pho-psdap
5759 hythpym-pazin-imo-aval
5760 hythpym-dimephmem-eoco-betapy
5761 bhs-hexas-ocho-aspibua
5762 dmbim-tetradi-chexo-aspbzla
5763 pyrhs-am2-sem-nzdap
5764 pyraz-mepipe2-sem-nbeta34-dimeoph
5765 mam2py-pipmea-imo-zdap
5766 prhs-amn3-imo-betainyl
5767 2py-24oxman2-paco-oxal
5768 impy-24thiman2-mecpo-psdap
5769 mam2py-pnymea-ocho-aspibua
5770 bzl-mepazin-fo-aspbzla
5771 impy-tridi-eoco-betadcph
5772 im-3diaz-4amo-osdap
5773 npip-diphmem-5amo-oxal
5774 dhim-pipmes-4amo-dfzdap
5775 imhs-25oxman2-men-csdap
5776 bimhs-m24thizman2-ocho-glyzdap
5777 imhs-dis-no2-zdab
5778 am2py-24thizman2-5amo-bsdap
5779 2py-dimephmep-meteto-bphabs
5780 piraz-trias-chexo-dfzdap
5781 imhs-amn-no1-betapy
5782 tolhs-m24oxman2-emo-zdab
5783 hythpym-pyma2-5amo-dfzdap
5784 bim-indan2-men-tsdap
5785 4pmhs-amn3-cno-glyzdap
5786 imhs-dimen-imo-osdap
5787 2py-indan2-aco-mezphe
5788 2py-dimen-ocho-psdap
5789 hythpym-eta2s-chexo-bsdap
5790 edothpym-pazin-pyo-zdabs
5791 bhs-edian2-no1-zdap
5792 pippy-pazin-mes-csdap
5793 am2py-mepazin-mommo-betadcph
5794 bz-mepipe-meo-zdab
5795 bim-amn3-ocho-zorn
5796 phpip-m24thizman2-mes-aspbzla
5797 bim-tridi-no1-tsdap
5798 tolhs-tridi-emo-aspibua
5799 am2py-m25thiz-5pho-zdabs
5800 impy-edian2-no1-glyzdap
5801 hythpym-m25thiz-men-aspbzla
5802 thpym-amn2-mes-psdap
5803 pyrhs-ams2-emo-dfzdap
5804 pyraz-dis-eoco-csdap
5805 am2py-pazin-men-aspbzla
5806 hythpym-edian2-cpeo-bhsdab
5807 am2py-amn3-5pho-zdapee
5808 gua-pyma2-emo-bphabs
5809 imhs-din-men-betadcph
5810 pyrhs-trias-eoco-psdap
5811 am2py-pymea-ocho-bhsdap
5812 2pmhs-dis-nmo-zdabs
5813 tolhs-tetradi-hso-dfzdap
5814 dhim-24thiz-pheo-osdap
5815 am2py-pymea-cno-zdab
5816 bim-dimephmep-no2-bhsdap
5817 pippy-thizn-mes-zdap
5818 bimhs-25thizman2-fo-betapy
5819 amim-am3-sem-nbeta34dimeoph
5820 me2py-propn-eoco-psdab
5821 npip-dimephmem-imo-betapy
5822 im-pnymea-mecpo-betainyl
5823 am2py-n2nme2n-no2-aspbzla
5824 prhs-dimephmem-4pho-ibsdap
5825 am2py-thizs-ocho-bhsdap
5826 impy-mepipe-no1-psdap
5827 bhs-amo3-mes-bsdap
5828 thpym-pymea-chexo-csdap
5829 deam-edia2-oem-nzdap
5830 bzl-m25thiman2-5amo-zdap
5831 2py-amn2-meo-psdap
5832 hythpym-diaz-hso-bsdap
5833 dhim-24thiz-ocho-csdap
5834 nmor-pentadi-mecpo-zorn
5835 imhs-pazin-no2-psdap
5836 fthpym-dimephmep-napo-aspbzla
5837 bim-pazin-5pho-bsdap
5838 mam2py-pymea-napo-bsdap
5839 piraz-pipmea-fo-psdap
5840 imhs-m25thiz-no2-bhsdap
5841 bimhs-m25thiz-ocho-glyzdap
5842 bhs-diphmep-emo-betapy
5843 tolhs-dimephmem-hso-zlys
5844 dhim-m25oxman2-ocho-psdap
5845 pyr-pnymea-no1-asppha
5846 am2py-amn2-mes-bhsdab
5847 chhs-pipmea-fo-zdap
5848 imhs-edian2-no1-psdab
5849 chhs-dimephmem-5amo-zdabs
5850 bzl-dimephmem-4pho-aspbzla
5851 z-24thiz-4amo-bphabs
5852 hythpym-amn2-imo-psdapee
5853 thpym-mepipe-oem-bhsdap
5854 2py-25thizman2-peo-asppha
5855 impy-pnymea-mmen-bhsdap
5856 am2py-thizn-napo-zdap
5857 am2py-amn2-ocho-betapy
5858 bim-din-no2-psdab
5859 dhim-thizn-cpro-bhsdap
5860 mam2py-tetradi-meto-csdap
5861 amim-mepazin-imo-csdap
5862 bhs-24thiz-men-bphabs
5863 mepip-edian2-cpro-betapy
5864 impy-dimephmep-napo-bsdap
5865 dhim-25thizman2-chexo-bsdap
5866 phhs-trias-oem-mezphe
5867 impy-tridi-4amo-aval
5868 piraz-pipa-meo-csdap 5869 bz-m25oxman2-emo-asppha
5870 menim-diphmep-imo-aspbzla
5871 pyraz-mepipen2-imo-betapy
5872 imhs-dimephmem-nmo-bphabs
5873 2py-25oxman2-meo-glyzdap
5874 morhs-eta-no2-betainyl
5875 pyr-mepipen2-5amo-psdab
5876 pyr-ams3-imo-asppha
5877 im-thizs-napo-zdap
5878 bimhs-24thizman2-nmo-zdabs
5879 phhs-din-5amo-betapy
5880 2py-pipa-ocho-zdap
5881 piraz-pipmea-cpeo-thizzdap
5882 dmbim-pyma2-napo-glubzla
5883 amthiaz-24thizman2-emo-zdabs
5884 mepip-tridi-nmo-bhsdap
5885 tolhs-mepipe-napo-betapy
5886 thpym-24thiman2-no1-aspbzla
5887 pyr-3diaz-paco-aspbzla
5888 amim-mepazin-men-psdapee
5889 piraz-25oxman2-no2-csdap
5890 ibhs-amn3-no1-dfzdap
5891 pippy-tridi-mecpo-zdabs
5892 2py-25thiman2-meo-betapy
5893 me2py-m25thiz-fo-asppha
5894 chhs-24thiz-imo-psdab
5895 bhs-mepipe-no1-bhsdap
5896 bz-pentas-mes-asppha
5897 phpip-mepipen2-no2-asppha
5898 thpym-pipa-chexo-thizzdap
5899 am2py-dimephmem-chexo-dfzdap
5900 am2py-amn2-eoco-aspibua
5901 hythpym-diphmem-imo-glyzdap
5902 deam-dimephmep-fo-ibsdap
5903 imhs-amn2-mes-zdap
5904 edothpym-tetradi-meo-zdab
5905 dmthpym-thizn-5amo-aspbzla
5906 bhs-dimephmem-men-bsdap
5907 am2py-pyma2-pro-psdab
5908 imhs-n24thiman-no1-bnsdap
5909 2py-thizn-no1-bhsdab
5910 bim-mepipe-oem-zdab
5911 am2py-2pazin-napo-ppsdap
5912 bzl-pymea-men-bphabs
5913 morhs-tetradi-pyo-csdap
5914 imhs-tridi-chexo-zdap
5915 2py-edian2-eoco-bhsdap
5916 fthpym-pipa-cno-betadcph
5917 bimhs-m24thizman2-emo-aval
5918 dhim-pnymea-5pho-aspibua
5919 imhs-diphmem-men-psdab
5920 mam2py-amn2-meo-bhsdap
5921 inhs-pentadi-mes-psdab
5922 imhs-3diaz-fo-bhsdap
5923 2py-dimephmem-no1-betapy
5924 bim-mepipe-meo-bsdap
5925 mam2py-pipmes-no2-aspbzla
5926 impy-am3-oem-nzdap
5927 phpip-tetras-cnmo-csdap
5928 dhim-amn3-5pho-psdap
5929 bim-eta-ocho-bnsdap
5930 bimhs-amn3-cnmo-bhsdap
5931 dhim-dis-no1-aval
5932 tolhs-trias-men-psdab
5933 bzl-dimephmep-napo-psdapee
5934 am2py-dimen-emo-bnsdap
5935 2py-mepazin-emo-aspbzla
5936 amim-eta2s-ocho-bhsdap
5937 me-mepipen2-napo-bsdap
5938 imhs-amo2-5amo-zdabs
5939 ibhs-mepazin-ocho-betadcph
5940 bimhs-amo2-mommo-csdap
5941 nmor-diphmep-baeo-mezphe
5942 cl3pyme-am3-oem-nbetabnaphth
5943 bimhs-am2-sem-npsdap
5944 amim-mepipe-5amo-betapy
5945 thpym-n2nme2n-ocho-zdap
5946 thpym-pyma2-no2-zdab
5947 imhs-thizn-no2-aspibua
5948 n2py-edian2-aco-aspbzla
5949 amim-25thiman2-oem-bhsdab
5950 amthiaz-thizs-napo-thizzdap
5951 2py-24thiz-meo-bnsdap
5952 thpym-eta-no1-zdab
5953 morhs-pyma2-5amo-bnsdap
5954 am2py-amn3-peo-betadcph
5955 pippy-25thiz-5amo-asppha
5956 bimhs-mepipen2-no1-psdab
5957 bhs-edian2-mes-zdab
5958 mam2py-trias-chexo-aspibua
5959 thpym-amo2-ocho-bsdap
5960 2py-diphmem-no2-bphabs
5961 2py-am3diaz-napo-glyzdap
5962 2py-tetradi-mes-bhsdap
5963 mam2py-tridi-no1-mezphe
5964 hythpym-ams2-oem-zdap
5965 bim-edian2-eoco-bnsdap
5966 nmhs-trias-ocho-ppsdap
5967 imhs-dimen-no1-dfzdap
5968 npip-m24thizman2-emo-psdab
5969 gua-24thizman2-no1-bnsdap
5970 bimhs-25oxman2-cpeo-psdap
5971 bhs-amo2-ocho-aspibua
5972 bzl-ams2-meo-bhsdap
5973 dmthpym-25oxman2-no1-betapy
5974 dhim-dimephmem-chexo-betainyl
5975 me2py-dimephmem-men-aval
5976 deam-pipa-emo-bnsdap
5977 bim-pipmea-chexo-asppha
5978 bim-diphmem-oem-asppha
5979 menim-pyma2-4pho-bphabs
5980 pippy-pymea-no2-aspbzla
5981 bimhs-amn2-mes-betainyl
5982 am2py-trias-men-betapy
5983 mam2py-tetras-4pho-dfzdap
5984 imhs-24thizman2-napo-bsdap
5985 tolhs-pipa-no1-zdabs
5986 cl3pyme-tridi-mes-asppha
5987 cl3pyme-pipmea-men-glyzdap
5988 piraz-mepipe-nmo-bhsdab
5989 imhs-eta-ocho-psdab
5990 bimhs-propn-5pho-betapy
5991 dhim-pnymea-emo-glyzdap
5992 nmhs-pipa-no1-thizzdap
5993 imhs-amn2-oem-zdab
5994 tolhs-edia2-sem-npsdap
5995 amim-mepipe-cno-osdap
5996 pippy-edian2-imo-asppha
5997 me2py-amn3-5pho-zdabs
5998 gua-pipmea-fo-zdap
5999 ec-dimephmem-no1-glyzdap
6000 me2py-edia2-sem-npsdap
6001 bim-amn2-no1-betapy
6002 am2py-trias-chexo-dfzdap 6003 impy-24thizman2-aco-csdap
6004 amim-diphmep-oem-aspbzla
6005 bhs-dimen-men-mezphe
6006 pippy-ams2-mommo-glubzla
6007 morhs-am2-oem-nbetapy
6008 tolhs-tetradi-fo-ibsdap
6009 piraz-3diaz-fo-bhsdap
6010 hythpym-m25thiz-men-bphabs
6011 piraz-amn3-5pho-betapy
6012 dpam-m25thiz-no1-zdap
6013 bhs-dimen-no2-zdabs
6014 piraz-25thiz-aco-psdap
6015 bim-din-oeto-thizzdap
6016 fthpym-mepipe-5pho-psdap
6017 hythpym-mepazin-meto-asppha
6018 thpym-edian2-mes-betapy
6019 2pmhs-dimephmem-ocho-asppha
6020 amthiaz-pyma2-5pho-bsdap
6021 2py-edian2-eoco-betapy
6022 imhs-pazin-oem-psdap
6023 pippy-ams2-meo-aspibua
6024 dmthpym-25oxman2-daco-bphabs
6025 n2py-25oxman2-5amo-aspibua
6026 bim-am3-oem-nbeta34dimeoph
6027 thpym-tetradi-paco-betapy
6028 tolhs-25oxman2-emo-aspbzla
6029 im-thizs-emo-aspbzla
6030 imhs-24thiz-4pho-bhsdab
6031 im-tridi-no2-dfzdap
6032 tolhs-edia2-oem-nbeta34-dimeoph
6033 mepip-indan2-fo-zdap
6034 pippy-pnymea-ocho-betainyl
6035 dhim-diphmep-imo-aspaba
6036 piraz-3pazin-cnmo-psdap
6037 bhs-thizo-cno-zorn
6038 bhs-mepipe-no2-zdap
6039 bhs-tridi-ocho-zdabs
6040 imhs-amn3-aco-bnsdap
6041 thpym-24thiz-ocho-csdap
6042 mam2py-trias-chexo-zdab
6043 amim-pazin-5pho-bhsdap
6044 bim-tetradi-imo-glubzla
6045 2py-eta-no1-bhsdap
6046 dmthpym-pnymea-men-bhsdap
6047 dhim-am2-sem-nbetapy
6048 2py-eta-eoco-bsdap
6049 dmbim-pymea-emo-zorn
6050 thpym-dis-imo-zdab
6051 bim-amn2-meo-bsdap
6052 hythpym-n2nme2n-5amo-psdab
6053 pippy-25oxman2-napo-psdab
6054 2py-amn2-meo-psdab
6055 gua-ams2-ocho-csdap
6056 imhs-tetradi-mes-betainyl
6057 bim-dimephmem-napo-bnsdap
6058 amim-m25thiz-imo-psdap
6059 thpym-dimen-nmo-ibsdap
6060 bim-edian2-mes-psdap
6061 mam2py-eta-napo-bhsdab
6062 gua-pymea-5amo-dfzdap
6063 piraz-amn-mes-glyzdap
6064 imhs-mepipen2-cno-aspbzla
6065 thpym-amn2-no1-bnsdap
6066 bhs-pipa-oeto-zdab
6067 am2py-trias-fo-ibsdap
6068 dhim-mea2s-cpeo-csdap
6069 pippy-thizn-no1-csdap
6070 bhs-mepazin-fo-aval
6071 pippy-am2-sem-nzdab
6072 piraz-am3-sem-nbetameph
6073 bhs-amn2-5pho-bnsdap
6074 nmor-24thiman2-fo-zdapee
6075 am2py-diphmem-imo-bhsdap
6076 bhs-mepipe-5pho-bnsdap
6077 dmthpym-mepipen2-pheo-csdap
6078 bimhs-dis-cno-zdabs
6079 imhs-amo2-mommo-psdab
6080 mam2py-indan2-emo-aspbzla
6081 me-pipa-hso-glyzdap
6082 bhs-eta-mes-bnsdap
6083 piraz-din-cno-ppsdap
6084 pippy-diphmem-fo-bhsdap
6085 nmor-n2o2n-imo-aspbzla
6086 2py-n24thiman-imo-zdab
6087 pippy-pipmeo-4pho-aspibua
6088 amim-dimephmem-emo-bnsdap
6089 im-pipmea-fo-bhsdab
6090 2py-amn2-no1-psdap
6091 bim-amn2-meo-bhsdap
6092 thpym-amn3-fo-zlys
6093 dhim-m24thizman2-5pho-betapy
6094 impy-n24thiman-mes-zdabs
6095 bimhs-tridi-mes-zlys
6096 bzl-pymea-no2-bphabs
6097 emnim-dis-meo-betadcph
6098 hythpym-25oxman2-no2-glubzla
6099 4pmhs-amn3-nmo-zdab
6100 nim-butn-cno-glupha
6101 im-amn2-eoco-mezphe
6102 bim-pazin-eoco-zdab
6103 2py-pazin-mes-bnsdap
6104 bim-dimephmep-eoco-zdap
6105 imhs-m25thiz-napo-betadcph
6106 menim-mepipe-5pho-betapy
6107 nmhs-eta-pro-bnsdap
6108 thpym-thizn-5amo-aspibua
6109 amim-dimen-5amo-bnsdap
6110 bim-edian2-eoco-zdab
6111 fthpym-dimephmep-meteto-asppha
6112 nmhs-amn2-napo-bphabs
6113 nmhs-din-peo-betapy
6114 dhim-pipmea-meo-glupha
6115 deam-ms-oem-bsdap
6116 thpym-mepipen2-no2-betadcph
6117 n2py-trias-eoco-aspbzla
6118 am2py-butn-no2-osdap
6119 npip-ams2-ocho-bhsdap
6120 bimhs-dimephmem-5pho-asppha
6121 phpip-pyma2-5pho-betapy
6122 mam2py-edian2-chexo-zdabs
6123 bzl-25thizman2-mes-bphabs
6124 amim-thizn-cpeo-psdab
6125 dhim-tridi-4pho-bhsdap
6126 chhs-am3-sem-nzdap
6127 moegua-mepipen2-no1-bsdap
6128 imhs-pazin-meo-zdap
6129 gua-dimen-mes-zdabs
6130 amim-ams2-no2-glyzdap
6131 bz-pentas-mes-asppha
6132 2py-pazin-meo-betapy
6133 mepip-pipmea-cnmo-aspbzla
6134 nmhs-pipmeo-chexo-bhsdab
6135 chmhs-pyma2-daco-bhsdab
6136 menim-edia2-sem-nzdab 6137 morhs-mepazin-oem-mezphe
6138 ibhs-pipa-mes-bhsdap
6139 pippy-tetradi-chexo-zdabs
6140 gua-eta2s-mecpo-csdap
6141 bzl-am2-sem-nbetameph
6142 impy-mepipe-meo-betapy
6143 bim-dimephmem-ocho-psdap
6144 thpym-dimen-aco-glyzdap
6145 2py-edian2-no2-bhsdap
6146 hythpym-tetras-no2-bhsdab
6147 2py-ams3-no1-betadcph
6148 2pmhs-edian2-oem-betapy
6149 emnim-ams2-meto-csdap
6150 imhs-eta-meo-basdap
6151 im-25oxman2-imo-dfzdap
6152 nmor-pipa-mes-mezphe
6153 bimhs-diphmem-men-zdap
6154 2py-m25oxman2-meo-osdap
6155 imhs-mepipe-eoco-betapy
6156 z-thizn-fo-zdabs
6157 bimhs-butn-5pho-aspbzla
6158 amim-ams2-meo-oxal
6159 piraz-dimephmem-no1-aspaba
6160 me2py-amn3-men-psdab
6161 mepip-m25thiz-5amo-bhsdap
6162 thpym-24thiz-no2-bhsdab
6163 hythpym-25oxman2-ocho-asppha
6164 hythpym-thizn-5pho-zdab
6165 thpym-hexadi-eoco-bhsdab
6166 impy-pyma2-mecpo-betapy
6167 mam2py-amn3-ocho-aspibua
6168 tolhs-mepipe-no1-aspbzla
6169 2py-amn2-ocho-bsdap
6170 pyr-m24thiman2-eoco-mezphe
6171 2py-24thizman2-5pho-zdabs
6172 dmbim-pipmes-5amo-psdab
6173 im-propa2s-ocho-bhsdab
6174 2pmhs-diphmep-imo-ppsdap
6175 thpym-amn2-5pho-betapy
6176 bimhs-pyma2-eoco-betainyl
6177 bim-pazin-eoco-bsdap
6178 imhs-mepazin-mecpo-glupha
6179 piraz-thizn-5amo-betainyl
6180 bimhs-m24thiman2-cpro-zlys
6181 am2py-24thizman2-daco-zdabs
6182 dhim-mepipe-meo-psdapee
6183 impy-m25thizman2-meo-bnsdap
6184 am2py-pazi2n-napo-psdap
6185 z-24thiz-5amo-zdab
6186 chmhs-tetradi-nmo-zorn
6187 impy-pipmea-meo-csdap
6188 imhs-pazin-5pho-bhsdap
6189 dhim-trias-mes-betapy
6190 cl3pyme-pazin-napo-glupha
6191 phpip-am2-sem-nbetapy
6192 piraz-tetradi-nmo-osdap
6193 dhim-indan2-napo-zdabs
6194 imhs-pipmea-napo-bnsdap
6195 bhs-dimen-5pho-thizzdap
6196 piraz-2pazin-napo-aspbzla
6197 bhs-edian2-oem-glubzla
6198 am2py-dis-eoco-bsdap
6199 pippy-dimen-oem-bphabs
6200 thpym-edian2-eoco-bsdap
6201 edothpym-trias-mes-bnsdap
6202 im-2pazin-oem-dfzdap
6203 dmbim-pymea-chexo-zdab
6204 2py-ams3-oem-oxal
6205 dhim-pymea-hso-betadcph
6206 chhs-3pazin-mecpo-zdabs
6207 phhs-dimen-aco-betainyl
6208 imhs-pnymea-napo-bnsdap
6209 bim-m24thiz-no1-zdap
6210 me2py-pipa-peo-zdap betadcph
6211 mam2py-amo3-ocho-csdap
6212 pyrhs-amn2-chexo-bhsdab
6213 phpip-3pazin-napo-glyzdap
6214 pyrhs-diphmep-5pho-aspbzla
6215 dmam-dimephmep-men-zdab
6216 2py-pazin-5pho-bhsdab
6217 mam2py-m25oxman2-meto-aspibua
6218 bimhs-24thizman2-5pho-mezphe
6219 hythpym-dimen-imo-zdab
6220 dhim-m25thiz-napo-aspibua
6221 impy-pyma2-meo-aspaba
6222 thpym-amn3-5amo-psdap
6223 dmam-amn2-daco-glyzdap
6224 impy-pyma2-napo-zdab
6225 phhs-dimephmep-meo-csdap
6226 4pmhs-diphmep-chexo-glyzdap
6227 dhim-pipmea-mommo-zdab
6228 ibhs-mepipen2-imo-aspibua
6229 me2py-mepipe2-oem-npsdap
6230 2py-tridi-ocho-betaet
6231 bim-edian2-ocho-betadcph
6232 2py-mepipe-mes-zdab
6233 moegua-ams2-emo-mezphe
6234 bzl-n24thiman-imo-bnsdap
6235 amim-mea2s-men-betadcph
6236 nmor-mepazin-cno-bphabs
6237 mam2py-24thizman2-pheo-osdap
6238 prhs-am3-oem-nzdap
6239 amthiaz-dimephmem-oem-psdab
6240 mam2py-thizn-chexo-betapy
6241 piraz-mepazin-oeto-csdap
6242 bimhs-mepipen2-imo-psdapee
6243 dpam-dimen-meo-bsdap
6244 morhs-dio-imo-psdab
6245 am2py-diphmem-no1-psdab
6246 prhs-amn2-eoco-thizzdap
6247 am2py-mepazin-aco-bnsdap
6248 bim-mepipe-meo-zdap
6249 bhs-thizo-no2-bhsdab
6250 bhs-amn2-cno-psdap
6251 bhs-pnymea-chexo-zdap
6252 mam2py-trias-chexo-bnsdap
6253 bhs-diphmep-no2-glyzdap
6254 dhim-am2-oem-nbetabnaphth
6255 2pmhs-pazin-mecpo-dspbzla
6256 hythpym-24thizman2-ocho-bnsdap
6257 chhs-pyma2-oem-bhsdab
6258 bzl-amn3-eoco-mezphe
6259 deam-tridi-no1-bnsdap
6260 edothpym-dimephmep-mes-betadcph
6261 bim-din-cno-bnsdap
6262 pippy-amo2-5pho-zdap
6263 phhs-24thiz-emo-zdap
6264 bim-m24thizman2-cpro-bhsdab
6265 bim-24thizman2-imo-zdab
6266 piraz-m24thizman2-paco-aspibus
6267 impy-amn3-men-asppha
6268 bhs-amn2-eoco-psdab
6269 dmam-thizn-5pho-aspbzla
6270 2py-mea-eoco-aspibua 6271 2py-propa2s-napo-bsdap
6272 am2py-pipa-5pho-glubzla
6273 hythpym-mepipe-5pho-betadcph
6274 npip-pymea-emo-psdap
6275 thpym-din-ocho-aspibua
6276 pyr-25oxman2-emo-aspibua
6277 imhs-dio-cpeo-bsdap
6278 dmthpym-edian2-paco-zdab
6279 gua-edian2-mes-asppha
6280 imhs-mepipen2-5pho-ibsdap
6281 pyr-m24thizman2-ocho-aspaba
6282 mam2py-dis-men-zdab
6283 piraz-25oxman2-peo-oxal
6284 2py-pentas-imo-bhsdap
6285 bimhs-trias-napo-asppha
6286 mam2py-mepipen2-no2-bnsdap
6287 impy-mepazin-ocho-mezphe
6288 impy-pipmea-5amo-asppha
6289 bim-mepipen2-oem-zdab
6290 bim-pazin-eoco-zdap
6291 hythpym-m25thiz-paco-aval
6292 dhim-dimephmem-ocho-zdab
6293 ibhs-amo2-5amo-bsdap
6294 bhs-mepipe-no2-betapy
6295 2py-m25thiz-peo-bphabs
6296 piraz-m24thizman2-mommo-dfzdap
6297 deam-dimephmem-emo-csdap
6298 bim-pazin-no1-psdap
6299 dhim-pentadi-meo-psdap
6300 thpym-din-chexo-bhsdab
6301 bim-edian2-no2-aspibua
6302 mam2py-edian2-no1-bsdap
6303 me2py-24thizman2-fo-aspibua
6304 hythpym-pipa-fo-zdabs
6305 2py-amn2-eoco-bhsdap
6306 phhs-edian2-mes-bnsdap
6307 imhs-amn3-5amo-bhsdab
6308 cl3pyme-25thizman2-oeto-bhsdap
6309 hythpym-diphmem-men-bhsdap
6310 dhim-dich-chexo-aspbzla
6311 fthpym-propa2s-mes-betainyl
6312 mam2py-diphmep-emo-asppha
6313 amim-dich-meo-csdap
6314 z-n2nme2n-men-zdapee
6315 morhs-pipa-no2-betadcph
6316 2py-pazin-ocho-bhsdap
6317 bim-m25oxman2-no1-bphabs
6318 mam2py-props-imo-betainyl
6319 ppy-m24thizman2-peo-betapy
6320 dhim-amn2-meto-mezphe
6321 bim-tetradi-ocho-bnsdap
6322 bhs-am3-oem-npsdap
6323 bim-trias-5amo-asppha
6324 moegua-amn3-imo-csdap
6325 thpym-amn2-meo-bnsdap
6326 bhs-amo2-cpro-zdap
6327 me2py-thizs-no1-bphabs
6328 am4py-diphmem-napo-mezphe
6329 dhim-m24thizman2-5pho-zdab
6330 morhs-eta2s-no2-glyzdap
6331 bim-amn2-ocho-betapy
6332 n2py-dis-5pho-psdab
6333 chmhs-pymea-oem-psdap.
6334 mam2py-pipmea-mes-betapy
6335 chhs-mepazin-mes-betadcph
6336 moegua-trias-ocho-betainyl
6337 amim-tetradi-no2-mezphe
6338 chmhs-24oxman2-eoco-betadcph
6339 bhs-edian2-mes-zdap
6340 hythpym-m24thizman2-meo-dfzdap
6341 menim-dis-aco-aspibua
6342 2py-eta-oem-bsdap
6343 me2py-hexas-5pho-betapy
6344 tolhs-tetradi-5amo-psdap
6345 mam2py-mepipen2-mes-dfzdap
6346 2py-mepazin-meo-betainyl
6347 hythpym-amo2-fo-betainyl
6348 thpym-pazin-oem-betapy
6349 me-pipmea-oem-bhsdab
6350 imhs-pnymea-oem-bphabs
6351 bhs-eta-no1-zdap
6352 bimhs-hexadi-4amo-ppsdap
6353 bimhs-mepipe2-sem-nbetameph
6354 bim-pipa-mecpo-bhsdab
6355 pippy-eta-napo-psdab
6356 n2py-dimen-5pho-aspbzla
6357 am2py-amn2-oem-aspibua
6358 ppy-24thiz-5pho-psdap
6359 bhs-trias-eoco-betadcph
6360 dmthpym-amo3-men-oxal
6361 me2py-eta-ocho-zdabs
6362 dmam-pentas-meo-mezphe
6363 bim-edian2-oem-psdab
6364 am2py-25oxman2-chexo-zdabs
6365 phhs-25oxman2-aco-bhsdab
6366 am4py-pyma2-meo-betainyl
6367 2py-24thizman2-fo-betadcph
6368 thpym-amn2-imo-bhsdap
6369 deam-24thiz-baeo-bphabs
6370 gua-amn3-5pho-aspibua
6371 piraz-dipch-5pho-zdap
6372 2py-pipmes-meo-mezphe
6373 am4py-dimephmem-cno-aspibua
6374 impy-mepipen2-oem-aspbzla
6375 chmhs-hexas-imo-bnsdap
6376 ibhs-dimen-5pho-aspibua
6377 me2py-dimephmem-ocho-mezphe
6378 imhs-tetradi-hso-asppha
6379 amim-ams2-imo-betainyl
6380 2py-n24thiman-oem-aspaba
6381 gua-trias-napo-psdab
6382 mam2py-mepazin-meteto-glyzdap
6383 bimhs-pnymea-baeo-bhsdap
6384 impy-amn3-men-psdab
6385 me2py-ams3-fo-aspibua
6386 hythpym-n2nme2n-napo-betainyl
6387 pyr-amn2-no2-bhsdab
6388 2py-eta-no1-bsdap
6389 piraz-mepipe-fo-zdab
6390 bzl-m25thiman2-meteto-zdap
6391 chmhs-pyma2-napo-betaet
6392 am-24thiman-mes-oxal
6393 thpym-edian2-oem-zdab
6394 am2py-mepipe-napa-bhsdap
6395 chhs-pyma2-emo-betadcph
6396 ec-m25thiz-meo-bhsdap
6397 piraz-diphmem-emo-betainyl
6398 emnim-diaz-5pho-bhsdap
6399 npip-mepazin-5pho-osdap
6400 phpip-amn2-emo-zdap
6401 npip-24thizman2-napo-ibsdap
6402 am2py-3diaz-mes-psdap
6403 ibhs-eta-eoco-zdap
6404 pyraz-amn3-ocho-osdap 6405 thpym-amn2-no1-psdab
6406 cl3pyme-tridi-eoco-bnsdap
6407 am2py-edian2-emo-bphabs
6408 bim-mepipe-mes-zdab
6409 am2py-25oxman2-4amo-psdapee
6410 pippy-eta-5pho-mezphe
6411 mam2py-2pazin-meto-bsdap
6412 2py-amn3-fo-betadcph
6413 imhs-pnymea-napo-aspbzla
6414 n2py-propa2s-ocho-aspbzla
6415 z-25thiz-5amo-zdab
6416 gua-edian2-men-betainyl
6417 ec-din-mmen-ppsdap
6418 dhim-tridi-no2-aspbzla
6419 am2py-trias-men-bphabs
6420 2py-amn2-no2-bsdap
6421 dhim-mepazin-pyo-betapy
6422 2py-amn2-no2-bnsdap
6423 nmhs-thizn-fo-zdabs
6424 bim-pyma2-5pho-psdab
6425 amim-24thizman2-ocho-psdab
6426 hythpym-mepipen2-emo-zdap
6427 mam2py-25oxman2-chexo-asppha
6428 imhs-edian2-meo-bsdab
6429 am-amn3-imo-zdabs
6430 hythpym-diphmem-no2-aspibua
6431 4pmhs-tridi-fo-betadcph
6432 thpym-m25thiman2-nmo-zdabs
6433 mam2py-pyma2-no1-zdabs
6434 mam2py-pipmes-imo-psdab
6435 phpip-m25thiz-mes-glubzla
6436 mam2py-diphmep-mommo-glubzla
6437 bimhs-thizn-pheo-mezphe
6438 dhim-pnymea-5pho-asppha
6439 nmhs-amn2-5pho-glyzdap
6440 2py-eta-5pho-bsdap
6441 hythpym-m25oxman2-chexo-osdap
6442 pippy-pnymea-chexo-betaet
6443 edothpym-25oxman2-ocho-zdabs
6444 me2py-amn2-imo-psdab
6445 me2py-pnymea-eoco-aspbzla
6446 thpym-edian2-meo-zdab
6447 bhs-edian2-ocho-psdab
6448 ppy-tridi-chexo-bnsdap
6449 dmam-24thiz-mea-aspibua
6450 imhs-m25thiz-eoco-thizzdap
6451 am2py-pentas-oeto-bnsdap
6452 piraz-pazin-eoco-bnsdap
6453 imhs-pipmeo-chexo-bnsdap
6454 n2py-dich-5amo-aspibua
6455 imhs-amn2-mes-psdap
6456 amim-amo2-pyo-mezphe
6457 pippy-amn2-cnmo-aspibua
6458 thpym-pazin-eoco-bnsdap
6459 tolhs-thizn-peo-zdabs
6460 thpym-pyma2-mes-bphabs
6461 pippy-mepipen2-men-zdabs
6462 am2py-dis-fo-zdap
6463 impy-pipa-oem-betadcph
6464 phpip-thizn-no1-betadcph
6465 dhim-tridi-mecpo-zdab
6466 im-m25thiman2-no2-zdabs
6467 bimhs-tridi-5amo-zdap
6468 2py-pazin-meo-bhsdap
6469 ppy-thizn-pheo-psdapee
6470 thpym-tetradi-no2-mezphe
6471 bim-m25thiman2-oeto-glyzdap
6472 amim-m24thizman2-eoco-psdap
6473 amim-dimephmep-meo-csdap
6474 impy-trias-imo-zdap
6475 imhs-amn3-nmo-bsdap
6476 pyrhs-pazin-napo-aspibua
6477 dhim-trias-oem-osdap
6478 pippy-diphmep-chexo-psdap
6479 hythpym-mepipen2-hso-csdap
6480 edothpym-eta2s-oem-zorn
6481 mam2py-diphmem-aco-bhsdap
6482 dhim-amn3-oem-psdapee
6483 hythpym-edian2-fo-betainyl
6484 n2py-props-mes-zdab
6485 bhs-din-ocho-asppha
6486 bim-3pazin-5amo-bnsdap
6487 chhs-din-cpeo-aspbzla
6488 2py-pazin-5pho-zdab
6489 mam2py-m24thizman2-mmen-oxal
6490 bhs-mepipe-mes-bhsdap
6491 bim-m25thiz-imo-osdap
6492 pippy-3diaz-mes-csdap
6493 imhs-pnymea-no2-bsdap
6494 hythpym-dimen-napo-ppsdap
6495 2py-pnymea-meo-bhsdab
6496 bhs-2pazin-cpro-zdap
6497 2py-mepipe-oem-zdab
6498 dhim-pyma2-emo-bnsdap
6499 dhim-tetradi-no1-bsdap
6500 mam2py-dis-daco-asppha
6501 bim-eta-mes-psdap
6502 bhs-eta-oem-bhsdap
6503 bhs-mepipe-5pho-psdab
6504 bimhs-diphmep-fo-asppha
6505 piraz-mepipe-emo-dfzdap
6506 amim-diphmep-eoco-csdap
6507 2py-edian2-ocho-betapy
6508 thpym-amn2-eoco-psdap
6509 me2py-pipmea-no1-betainyl
6510 dhim-25oxman2-mecpo-zdabs
6511 imhs-m25thiz-men-betainyl
6512 amim-trias-meto-bnsdap
6513 thpym-amn2-meo-zdap
6514 bim-amn2-no2-bsdap
6515 hythpym-dis-5amo-zdab
6516 pippy-2pazin-imo-osdap
6517 phhs-25oxman2-imo-tsdap
6518 bim-mepipe-eoco-psdap
6519 amim-dimephmep-oem-psdab
6520 piraz-n2o2n-pro-bhsdab
6521 mam2py-butn-baeo-glyzdap
6522 amim-edia2-oem-nzdab
6523 bim-diphmep-eoco-glyzdap
6524 piraz-m24thizman2-emo-csdap
6525 amim-tetras-ocho-aspbzla
6526 thpym-dimephmep-no2-csdap
6527 am2py-diaz-daco-zdap
6528 ec-tetradi-meo-bphabs
6529 pippy-pazi2n-no2-zdap
6530 imhs-mepipen2-ocho-aspaba
6531 dmbim-amn2-meo-zorn
6532 bhs-dis-ocho-csdap
6533 imhs-ams2-no2-aspibua
6534 nmor-m24thizman2-no2-zdab
6535 dhim-thizn-napo-zdab
6536 phpip-24thiz-emo-aspibua
6537 nmor-dimephmep-no2-csdap
6538 am2py-dimephmem-meo-bhsdap 6539 ppy-mepazin-cpeo-csdap
6540 bhs-props-mecpo-bphabs
6541 thpym-pnymea-napo-glyzdap
6542 moegua-pipmea-oem-bphabs
6543 nim-diphmep-chexo-bsdap
6544 bimhs-pipmea-hso-zdap
6545 thpym-diphmep-men-zdabs
6546 am2py-eta-eoco-betainyl
6547 am-m24thizman2-no2-zdabs
6548 dhim-mepazin-eoco-bhsdap
6549 bim-pipmeo-men-betadcph
6550 z-propa2s-no1-csdap
6551 z-m25thiz-no1-betainyl
6552 thpym-m25thiz-men-betadcph
6553 me-m24thizman2-imo-bsdap
6554 dhim-edian2-ocho-csdap
6555 pippy-dio-imo-bsdap
6556 me2py-amn3-emo-bnsdap
6557 hythpym-eta-5amo-bnsdap
6558 am2py-tridi-fo-asppha
6559 fthpym-pipa-5amo-bsdap
6560 pyr-mepipe-meteto-zdapee
6561 bhs-tetradi-fo-psdab
6562 amim-dis-fo-betapy
6563 bhs-dich-men-tsdap
6564 nim-dimephmep-ocho-glyzdap
6565 binhs-dich-meepo-zdabs
6566 hythpym-pyma2-meo-bphabs
6567 phhs-edia2-sem-nbetapy
6568 mepip-diphmep-nmo-csdap
6569 amthiaz-ams2-chexo-osdap
6570 nim-m25thiz-imo-betadcph
6571 dpam-m25oxman2-emo-asppha
6572 imhs-tetradi-4pho-psdap
6573 pippy-pymea-eoco-osdap
6574 pippy-m24thizman2-oeto-zdabs
6575 deam-am3-sem-nzdap
6576 am2py-pymea-hso-bsdap
6577 mam2py-props-5pho-bphabs
6578 pyrhs-diphmep-men-betadscph
6579 bim-amn2-oem-bsdap
6580 impy-n2o2n-emo-bphabs
6581 thpym-dis-cpeo-betadcph
6582 chhs-diphmem-5amo-asppha
6583 moegua-tridi-pro-aspibua
6584 impy-dis-napo-betapy
6585 chhs-pipmea-ocho-zdap
6586 phhs-pipmea-5amo-zdap
6587 bimhs-24thiman-aco-dfzdap
6588 dhim-edian2-chexo-zdap
6589 thpym-amn2-meo-psdab
6590 phpip-24oxman2-meto-zorn
6591 piraz-thizo-5amo-zdapee
6592 thpym-amn3-4pho-betapy
6593 impy-mea2s-chexo-bsdap
6594 amim-dis-eoco-aval
6595 bim-pnymea-emo-mezphe
6596 menim-dimephmep-imo-bhsdab
6597 thpym-dimephmem-mmen-betadcph
6598 bz-tridi-cpro-dfzdap
6599 bim-trias-chexo-dfzdap
6600 bzl-trias-napo-aspibua
6601 am4py-am3-sem-nbetapy
6602 thpym-eta-eoco-betapy
6603 impy-pentadi-ocho-aspbzla
6604 mam2py-dimephmem-aco-dfzdap
6605 z-24thiz-5pho-dfzdap
6606 hythpym-pipa-cno-bhsdab
6607 emnim-25thiman2-daco-psdap
6608 am2py-trias-no1-betapy
6609 thpym-eta-no1-psdab
6610 imhs-tetradi-napo-bhsdap
6611 dpam-3diaz-napo-bnsdap
6612 bimhs-24thiz-no2-bnsdap
6613 thpym-tetradi-no2-aspibua
6614 piraz-pipmea-eoco-bphabs
6615 bhs-am3-sem-npsdap
6616 amthiaz-edian2-ocho-zdab
6617 bim-eta-oeto-psdab
6618 4pmhs-n2o2n-eoco-zorn
6619 imhs-m25thiz-4amo-betapy
6620 hythpym-amn2-emo-aspibua
6621 bz-pnymea-no2-aval
6622 pippy-pentas-fo-zdab
6623 amim-edian2-cno-asppha
6624 emnim-m25thiz-napo-csdap
6625 bim-24thizman2-imo-zdap
6626 piraz-ms-5amo-oxal
6627 npip-mepipen2-ocho-psdap
6628 bhs-edian2-ocho-zdab
6629 phpip-pipa-men-bphabs
6630 thpym-25thiz-men-bhsdap
6631 am2py-pipmea-5pho-mezphe
6632 dhim-ams2-emo-zdab
6633 thpym-mea-fo-aspibua
6634 am2py-diphmem-5pho-psdap
6635 me2py-amn2-nmo-psdab
6636 hythpym-din-meo-aspibua
6637 thpym-pnymea-napo-psdap
6638 am2py-dimen-imo-dfzdap
6639 piraz-mepazin-meo-aspibua
6640 me2py-pazin-napo-bphabs
6641 2py-edian2-meo-zdab
6642 imhs-trias-meteto-glyzdap
6643 bim-dimephmep-no2-zdap
6644 amim-m25thizman2-oem-bhsdab
6645 bimhs-amo2-no2-zdap
6646 nim-thizn-oem-zdabs
6647 bhs-tetradi-cnmo-bhsdap
6648 me2py-mepipen2-cpeo-aspibua
6649 gua-m25thizman2-men-dfzdap
6650 thpym-m25thiz-imo-zdabs
6651 me2py-mepipe2-sem-nzdab
6652 piraz-mepipen2-mes-glyzdap
6653 moegua-pazi2n-emo-bnsdap
6654 z-am2-oem-nbetameph
6655 impy-pipmea-pyo-bhsdap
6656 nmhs-mea-meo-dfzdap
6657 mepip-pentadi-5amo-zdabs
6658 prhs-24thiz-aco-bsdap
6659 piraz-amn3-cno-betapy
6660 piraz-pazi2n-imo-glyzdap
6661 bim-eta-no1-zdap
6662 dmthpym-pazin-imo-psdab
6663 dmthpym-amn3-meo-psdab
6664 deam-mepipen2-mommo-dfzdap
6665 amim-m24oxman2-meo-bhsdab
6666 inhs-m24thizman2-eoco-dfzdap
6667 pyrhs-n24thiman-chexo-betadcph
6668 bhs-tridi-mes-thizzdap
6669 thpym-dich-pro-glyzdap
6670 phpip-ams2-5pho-bsdap
6671 amim-pyma2-imo-zdab
6672 amim-pazin-eoco-psdap
6673 pippy-mepazin-pheo-aspbzla 6674 bimhs-pnymea-mommo-csdap
6675 me2py-pazin-daco-dfzdap
6676 bhs-tridi-meo-glyzdap
6677 bzl-din-no1-aspibua
6678 im-pipa-emo-bhsdap
6679 hythpym-3pazin-ocho-psdab
6680 nim-hexas-fo-aval
6681 ibhs-pyma2-oeto-psdap
6682 dhim-pipa-oeto-zdabs
6683 me2py-pipa-no1-betainyl
6684 impy-24thiz-chexo-aspbzla
6685 cl3pyme-24thiman-no2-bnsdap
6686 pippy-mepazin-chexo-zdap
6687 dpam-tridi-fo-aspbzla
6688 thpym-25oxman2-men-zdab
6689 impy-dis-oeto-bnsdap
6690 2py-diphmem-daco-psdab
6691 deam-dimephmem-oem-bhsdap
6692 bhs-eta-no2-psdab
6693 thpym-mea2s-mes-betapy
6694 am2py-mea-ocho-bhsdap
6695 am4py-thizo-imo-betainyl
6696 mam2py-25thizman2-ocho-glyzdap
6697 piraz-24thizman2-fo-bhsdap
6698 2py-dio-napo-glyzdap
6699 phpip-dimephmem-oem-bnsdap
6700 pyrhs-trias-emo-glyzdap
6701 impy-dimen-men-psdap
6702 dhim-24thizman2-men-bnsdap
6703 2py-pipa-5pho-bhsdap
6704 impy-dimephmem-5amo-psdab
6705 imhs-amn2-eoco-zdab
6706 moegua-props-oem-betadcph
6707 hythpym-dis-5amo-tsdap
6708 thpym-m25thiz-meo-betaet
6709 tolhs-diaz-napo-bsdap
6710 mam2py-mepazin-ocho-ibsdap
6711 hythpym-24thiz-cpro-glyzdap
6712 amim-tridi-fo-psdab
6713 bhs-amo2-eoco-glyzdap
6714 me2py-amn2-nmo-psdap
6715 chhs-pentadi-no2-bphabs
6716 mam2py-24thizman2-pyo-bsdap
6717 hythpym-dimen-5pho-zdapee
6718 edothpym-am2-sem-nzdab
6719 bim-eta-meteto-betadcph
6720 dhim-mepipen2-chexo-betapy
6721 2py-24thiz-no1-betainyl
6722 menim-mepipen2-no1-zdab
6723 am2py-amn3-5amo-zdabs
6724 piraz-edia2-oem-nzdab
6725 hythpym-mepazin-hso-psdap
6726 2py-pazin-meo-bsdap
6727 bimhs-tetradi-hso-aspibua
6728 imhs-amn3-eoco-ppsdap
6729 am2py-24thizman2-men-zdabs
6730 dhim-amo2-cno-betainyl
6731 impy-pyma2-eoco-bnsdap
6732 mam2py-amo2-ocho-zdab
6733 2py-amo3-eoco-bsdap
6734 amim-24thizmari2-mes-oxal
6735 me2py-diphmep-5amo-zdab
6736 dpam-din-mecpo-asppha
6737 imhs-amo2-5pho-betadcph
6738 edothpym-m25thiz-mecpo-asppha
6739 imhs-pazin-no1-zdab
6740 imhs-n24thiman-meo-bnsdap
6741 npip-24thizman2-5pho-aspibua
6742 dhim-am3diaz-daco-bsdap
6743 dmam-amo2-oeto-bhsdap
6744 bimhs-24thizman2-emo-csdap
6745 menim-propn-5pho-zdab
6746 pippy-butn-fo-bsdap
6747 bhs-mepipen2-daco-aspibua
6748 mepip-pipmea-mes-bhsdab
6749 z-pipmea-napo-zdap
6750 bzl-diphmem-no1-betadcph
6751 2py-ams2-fo-asppha
6752 chhs-din-5pho-csdap
6753 pyr-dich-fo-betainyl
6754 menim-pipmea-men-psdab
6755 am-mepipe-eoco-asppha
6756 me2py-pipa-napo-mezphe
6757 phpip-pyma2-ocho-bnsdap
6758 imhs-edian2-no1-zdab
6759 phhs-pazin-pro-aspibua
6760 2py-eta-mes-bhsdap
6761 phpip-tetradi-imo-aspibua
6762 bhs-eta-no2-psdap
6763 tolhs-amo2-no2-psdap
6764 2py-pazin-5pho-psdap
6765 amim-m25thiz-emo-betadcph
6766 z-diphmem-eoco-glubzla
6767 pippy-mepipe2-sem-nbeta34-dimeoph
6768 z-diaz-5pho-aspbzla
6769 imhs-pazin-ocho-bnsdap
6770 am-din-no2-asppha
6771 2py-amn2-eoco-psdap
6772 pyraz-dimephmep-4pho-osdap
6773 dhim-thizn-imo-mezphe
6774 bhs-25oxman2-mes-betapy
6775 amthiaz-pipmea-napo-bhsdab
6776 morhs-pipa-no2-psdap
6777 nim-24thiz-imo-zlys
6778 bz-propn-5amo-zdap
6779 moegua-din-men-aspibua
6780 chmhs-dipch-daco-bsdap
6781 pyr-tridi-mes-csdap
6782 chhs-eta-chexo-bphabs
6783 dhim-3diaz-ocho-betaet
6784 pippy-m24thiman2-napo-bsdap
6785 2py-edian2-no2-bsdap
6786 piraz-2pazin-fo-zdap
6787 hythpym-pentas-imo-mezphe
6788 bhs-amn3-chexo-dfzdap
6789 2py-dimen-meo-tsdap
6790 impy-m24thizman2-daco-tsdap
6791 tolhs-pyma2-eoco-zdabs
6792 imhs-dis-pyo-psdap
6793 dmthpym-trias-no2-oxal
6794 piraz-pipa-men-osdap
6795 amim-24thiz-emo-bphabs
6796 bim-amn3-ocho-aspbzla
6797 bimhs-pazin-emo-betapy
6798 imhs-25oxman2-chexo-psdapee
6799 imhs-amo2-baeo-asppha
6800 thpym-ams3-fo-bnsdap
6801 impy-amn2-chexo-bphabs
6802 amim-pyma2-men-bsdap
6803 2py-eta-5pho-psdap
6804 me2py-mepipe2-sem-npsdap
6805 bhs-mepipe-no1-bsdap
6806 bhs-amn2-ocho-betapy
6807 bim-eta-aco-oxal dimeoph 6808 impy-edia2-oem-nbetameph
6809 impy-diphmep-pro-psdap
6810 chmhs-pymea-emo-asppha
6811 amim-mepipe2-sem-npsdap
6812 pyraz-m25thiz-no2-dfzdap
6813 pippy-tridi-no2-bhsdap
6814 amim-mepipe-no1-psdab
6815 pyr-n2o2n-5pho-zdabs
6816 imhs-24thiz-men-zdap
6817 impy-m24thizman2-mes-oxal
6818 me2py-pnymea-imo-bhsdap
6819 inhs-eta-5pho-bhsdap
6820 bim-24thiman-meteto-aspbzla
6821 ibhs-am2-sem-nzdab
6822 hythpym-amn3-baeo-mezphe
6823 imhs-edian2-eoco-bnsdap
6824 mam2py-tetradi-5pho-zdap
6825 am2py-amn3-eoco-betadcph
6826 hythpym-amn3-meo-aspibua
6827 piraz-2pazin-5pho-bhsdab
6828 fthpym-pnymea-chexo-mezphe
6829 pippy-m25thiz-emo-asppha
6830 hythpym-mea2s-cnmo-betainyl
6831 amim-eta-5amo-bhsdab
6832 me2py-amo2-napo-aspibua
6833 me-dimephmem-no2-aspibua
6834 mepip-3pazin-5pho-psdap
6835 2py-amn2-ocho-zdap
6836 ec-mea-emo-betaet
6837 pippy-amn2-oem-zdabs
6838 dhim-m24oxman2-meo-zdabs
6839 amim-dimephmem-cno-psdap
6840 ppy-ams3-imo-csdap
6841 bim-eta-imo-bsdap
6842 bim-dis-eoco-zorn
6843 pippy-trias-chexo-csdap
6844 4pmhs-tridi-eoco-betainyl
6845 pyrhs-24oxman2-no1-bsdap
6846 2pmhs-m24thiz-ocho-aspbzla
6847 nmhs-pipmea-5pho-bphabs
6848 2py-ams2-emo-psdap
6849 menim-3diaz-hso-aval
6850 imhs-edian2-eoco-bsdap
6851 bimhs-tridi-fo-zdab
6852 me2py-diphmem-napo-glubzla
6853 impy-n24thiman-imo-psdap
6854 me2py-edian2-napo-bsdap
6855 bhs-edian2-chexo-psdap
6856 bhs-hexas-napo-zdap
6857 npip-pnymea-ocho-zorn
6858 2py-mepipe2-oem-nbeta34-dimeoph
6859 pyr-3diaz-5amo-zdabs
6860 bhs-din-5pho-aspibua
6861 bim-dimen-5pho-mezphe
6862 imhs-pentas-men-bhsdap
6863 amim-dis-emo-csdap
6864 am2py-25oxman2-chexo-csdap
6865 bimhs-din-chexo-bsdap
6866 bimhs-m25thiman2-mes-betaet
6867 am2py-dio-no2-psdab
6868 amim-diaz-mommo-aspibua
6869 pyrhs-amn2-pyo-zdabs
6870 hythpym-props-daco-betainyl
6871 ppy-24thiman-meo-csdap
6872 thpym-propa2s-fo-betaet
6873 deam-dimen-fo-zdab
6874 imhs-amn2-oem-zdap
6875 am2py-din-meo-zdap
6876 piraz-pipa-emo-psdap
6877 ppy-amn2-oem-aspibua
6878 ibhs-ams2-men-aspaba
6879 2pmhs-pymea-5pho-psdap
6880 dmbim-tridi-chexo-zdap
6881 2py-mepipe-eoco-zdab
6882 dmthpym-pymea-mes-zdab
6883 hythpym-pymea-eoco-bnsdap
6884 impy-diphmep-napo-zdap
6885 thpym-pazin-no1-bsdap
6886 mam2py-mepipen2-5amo-asppha
6887 pippy-25oxman2-napo-bhsdap
6888 bzl-n2o2n-meo-zdabs
6889 pyrhs-mepipen2-5pho-psdap
6890 mam2py-dio-imo-aspibua
6891 nmor-am3-sem-nbetapy
6892 mam2py-25thiz-fo-psdab
6893 piraz-propa2s-baeo-aspbzla
6894 mam2py-thizo-5amo-tsdap
6895 amim-mepipe-meo-bsdap
6896 impy-hexadi-no1-csdap
6897 dpam-pipmea-meo-psdap
6898 bhs-dimephmem-napo-mezphe
6899 am2py-diphmep-5pho-mezphe
6900 dhim-din-oem-bhsdap
6901 z-pnymea-pro-mezphe
6902 hythpym-n2nme2n-hso-glyzdap
6903 thpym-amn2-5pho-psdap
6904 dhim-dimephmem-peo-bhsdap
6905 fthpym-amo2-imo-aspbzla
6906 mam2py-25oxman2-mecpo-psdap
6907 piraz-pazin-napo-thizzdap
6908 bim-amn2-ocho-bsdap
6909 piraz-m24thizman2-mes-bphabs
6910 thpym-dimephmem-mommo-bsdap
6911 bimhs-pipa-meo-bhsdab
6912 me2py-hexas-5pho-psdap
6913 bim-dis-meo-psdap
6914 hythpym-24thiz-men-glyzdap
6915 hythpym-mepipen2-no1-psdap
6916 4pmhs-edian2-5amo-zdab
6917 phhs-ams2-pro-psdapee
6918 am2py-pipa-chexo-psdab
6919 bim-mepipe-no2-psdab
6920 ec-am3-sem-npsdap
6921 mam2py-propn-imo-bnsdap
6922 impy-dich-pro-ppsdap
6923 bim-mepipe-eoco-psdap
6924 am2py-ams2-cpro-psdapee
6925 imhs-ms-imo-asppha
6926 hythpym-m25oxman2-men-zorn
6927 imhs-25oxman2-baeo-csdap
6928 thpym-pazin-meo-bsdap
6929 dmthpym-tridi-no1-zdabs
6930 amim-thizn-napo-bhsdab
6931 menim-trias-men-zlys
6932 deam-2pazin-pro-mezphe
6933 deam-mepazin-4amo-zorn
6934 pippy-tetradi-chexo-bnsdap
6935 bhs-eta-mes-psdab
6936 chhs-amn2-no2-betainyl
6937 bhs-pipmea-ocho-glubzla
6938 tolhs-ams2-pyo-zdapee
6939 ibhs-eta-no1-betainyl
6940 hythpym-25oxman2-4pho-bhsdap
6941 pippy-pymea-ocho-dfzdap 6942 nim-din-eoco-psdap
6943 impy-edian2-chexo-bhsdab
6944 imhs-diphmem-napo-dfzdap
6945 impy-amo2-imo-zdabs
6946 impy-24thiz-no2-bphabs
6947 amthiaz-24thizman2-no1-psdab
6948 bhs-25oxman2-emo-psdap
6949 am-diphmep-5pho-zdab
6950 me2py-tridi-mes-zdabs
6951 4pmhs-amo2-5amo-asppha
6952 imhs-pymea-5amo-bnsdap
6953 nmor-pnymea-no2-bhsdap
6954 4pmhs-pazin-meo-asppha
6955 me-dimephmep-cpeo-betadcph
6956 2py-mepipen2-emo-betapy
6957 bhs-tetradi-mecpo-aspbzla
6958 imhs-25oxman2-napo-glupha
6959 piraz-24thizman2-mmen-betadcph
6960 piraz-ams2-men-csdap
6961 thpym-pazin-emo-betainyl
6962 bim-mepipe-oem-betapy
6963 2py-mepipe-eoco-psdab
6964 thpym-amn3-5pho-oxal
6965 thpym-edian2-mes-zdap
6966 fthpym-thizn-4amo-psdapee
6967 mam2py-diaz-no1-zdap
6968 imhs-amn2-ocho-zdap
6969 thpym-24thiman2-cpeo-oxal
6970 bimhs-tridi-napo-zdap
6971 imhs-2pazin-emo-glyzdap
6972 dmam-24thiman2-no2-csdap
6973 hythpym-m24thizman2-oem-zlys
6974 bhs-25thiz-oem-aspibua
6975 am2py-edian2-meo-aspbzla
6976 thpym-pipmeo-5amo-bhsdab
6977 impy-amn3-mes-asppha
6978 impy-pyma2-5amo-bsdap
6979 morhs-hexas-ocho-dfzdap
6980 am2py-am3-sem-nbetameph
6981 bhs-propn-eoco-zdabs
6982 fthpym-25oxman2-me6-bnsdap
6983 dhim-pentadi-4amo-glubzla
6984 pippy-pipa-mommo-psdab
6985 dmbim-thizn-meo-bphabs
6986 npip-edian2-5pho-tsdap
6987 nim-tridi-pheo-betainyl
6988 amthiaz-mepipe2-sem-npsdap
6989 emnim-pnymea-imo-bhsdap
6990 pippy-pipmes-mommo-glyzdap
6991 am2py-pnymea-men-bhsdab
6992 piraz-din-imo-bhsdab
6993 ppy-pazin-men-zdap
6994 am2py-tridi-chexo-mezphe
6995 am-eta-no2-bnsdap
6996 am2py-trias-meo-ppsdap
6997 imhs-dimephmep-5pho-bphabs
6998 thpym-pazin-oem-psdab
6999 hythpym-edian2-4pho-psdap
7000 bhs-edian2-no1-bnsdap
7001 2py-eta-5amo-aval
7002 pippy-diphmep-5amo-bhsdab
7003 bhs-pipa-napo-dfzdap
7004 imhs-pazi-mes-psdap
7005 thpym-din-chexo-glyzdap
7006 me2py-pentadi-ocho-bphabs
7007 fthpym-25oxman2-mommo-betapy
7008 bim-hexas-emo-betainyl
7009 z-dimen-men-aspbzla
7010 me-diphmem-5pho-bphabs
7011 piraz-24thiz-eoco-aspibua
7012 am2py-tetradi-5pho-zdabs
7013 thpym-pipmea-ocho-betainyl
7014 bim-diphmep-emo-asppha
7015 ec-tetradi-ocho-asppha
7016 n2py-m24thiz-oem-mezphe
7017 impy-ms-napo-psdab
7018 z-m25thiman2-no1-bnsdap
7019 im-m25oxman2-baeo-asppha
7020 pippy-pyma2-napo-asppha
7021 deam-dimephmep-5pho-dfzdap
7022 deam-dis-paco-bhsdap
7023 piraz-pymea-no1-betadcph
7024 bhs-24thizman2-mes-zdap
7025 bimhs-pazin-no1-mezphe
7026 am2py-pyma2-imo-bsdap
7027 pippy-2pazin-4pho-bsdap
7028 bim-edian2-mes-bsdap
7029 nmor-mepazin-5amo-ppsdap
7030 moegua-mepipe-ocho-zdabs
7031 2py-m24thizman2-cpro-zdap
7032 me2py-pyma2-cpro-aspbzla
7033 bim-pazin-ocho-psdab
7034 pippy-edian2-no2-bsdap
7035 bim-thizs-mommo-bnsdap
7036 am2py-pyma2-napo-glyzdap
7037 nmor-24thizman2-ocho-bphabs
7038 npip-pymea-imo-bsdap
7039 mam2py-trias-napo-bhsdab
7040 impy-m24thizman2-4amo-betapy
7041 mam2py-mepipe-mes-bphabs
7042 imhs-edian2-meo-zdap
7043 2py-pipmea-5amo-betapy
7044 am-tridi-mes-df zdap
7045 piraz-propa2s-oem-ibsdap
7046 bim-2pazin-no2-betapy
7047 mam2py-mea2s-5amo-bsdap
7048 ibhs-edian2-oem-psdab
7049 dpam-diphmem-no1-betapy
7050 hythpym-edia2-sem-nbetapy
7051 n2py-24oxman2-mes-aspaba
7052 thpym-dis-aco-aspibua
7053 hythpym-24thiman2-mes-zdap
7054 dhim-diphmep-5pho-bnsdap
7055 2py-pentas-5amo-betapy
7056 moegua-25oxman2-oem-betadcph
7057 dhim-thizs-mes-aspibua
7058 hythpym-24thiz-mes-csdap
7059 gua-tridi-mes-bhsdap
7060 2pmhs-edian2meo-asppha
7061 am2py-diphmem-napo-zdap
7062 2py-24thiz-imo-psdab
7063 bim-mepipe-no1-bhsdap
7064 bz-mepipen2-fo-betainyl
7065 bim-mepipe-mes-bhsdap
7066 gua-amo2-emo-glyzdap
7067 piraz-24thizman2-cnmo-asppha
7068 mepip-tetradi-5pho-zdab
7069 hythpym-diphmem-emo-bnsdap
7070 bim-pazi2n-aco-psdapee
7071 n2py-din-mommo-zdabs
7072 bimhs-diphmem-mecpo-oxal
7073 piraz-mepipe-no1-bsdap
7074 am2py-mepipen2-no2-bhsdab
7075 dpam-mepipen2-napo-glyzdap 7076 nmhs-pazi2n-men-betadcph
7077 imhs-m25oxman2-men-oxal
7078 thpym-amn2-oem-bhsdap
7079 piraz-amo3-fo-psdab
7080 mam2py-diphmem-oem-zdap
7081 nim-butn-oeto-bphabs
7082 tolhs-2pazin-fo-zdab
7083 2py-mea2s-no1-bsdap
7084 phhs-edia2-sem-nbetabnaphth
7085 me2py-pnymea-baeo-psdab
7086 bhs-edian2-meo-psdab
7087 amim-dimephmem-chexo-mezphe
7088 dmbim-pyma2-pheo-bsdap
7089 bim-mepipen2-fo-aspaba
7090 2py-mepipen2-5pho-aspibus
7091 ec-diphmem-imo-aspbzla
7092 ec-trias-no2-betainyl
7093 piraz-m25oxman2-no1-bhsdab
7094 ibhs-pymea-no2-ppsdap
7095 pippy-2pazin-meo-betainyl
7096 n2py-diphmem-5pho-aspaba
7097 me2py-din-oem-bsdap
7098 dhim-dimephmep-meo-aspibua
7099 fthpym-indan2-imo-psdapee
7100 2py-edian2-eoco-zdab
7101 nmor-dimephmep-no2-bnsdap
7102 bhs-pazin-meo-betapy
7103 ec-din-eoco-betadcph
7104 am2py-hexadi-no2-glyzdap
7105 ec-pyma2-5amo-zdab
7106 bhs-edian2-meo-zdap
7107 bhs-pyma2-emo-aspbzla
7108 bim-3pazin-5pho-aspibua
7109 ec-diphmep-emo-bnsdap
7110 me-pnymea-meo-psdap
7111 chmhs-amn3-mes-bhsdap
7112 amim-mepipe-4pho-zdap
7113 2pmhs-dipch-mes-betainyl
7114 hythpym-pazi2n-ocho-bhsdab
7115 dmam-dis-4amo-zlys
7116 bimhs-tridi-oeto-bhsdab
7117 bim-dimephmep-no2-betaet
7118 bhs-24thiz-pro-psdab
7119 emnim-pipmea-no1-glubzla
7120 fthpym-amo2-eoco-bsdap
7121 bzl-amo2-napo-glyzdap
7122 am2py-m25thiz-men-thizzdap
7123 am2py-ams2-5amo-betadcph
7124 me2py-dimephmem-emo-mezphe
7125 im-am2-sem-nbetabnaphth
7126 me2py-eta2s-emo-psdap
7127 2py-pazin-cnmo-bhsdap 7178 bim-eta-oem-bsdap
7128 dmthpym-amo2-ocho-psdab
7129 piraz-mepipe2-oem-nzdap
7130 hythpym-m25thiz-chexo-thizzdap
7131 2py-n2o2n-chexo-betainyl
7132 imhs-amn2-4amo-aspaba
7133 am-pipmea-hso-betainyl
7134 bimhs-m24thiman2-eoco-zdab
7135 chhs-pazin-oeto-psdap
7136 am2py-dimen-meo-aspbzla
7137 fthpym-dimephmep-cpro-zdap
7138 piraz-dimephmep-fo-zdabs
7139 bhs-ams2-eoco-zdab
7140 am-tridi-eoco-zdapee
7141 am2py-pipa-no1-psdap
7142 bhs-ms-emo-aspaba
7143 chmhs-m25thiman2-5amo-zdap
7144 mam2py-dimen-fo-zdab
7145 thpym-dis-5pho-aval
7146 amim-amn3-ocho-ibsdap
7147 bim-dis-men-bhsdap
7148 nim-hexadi-napo-dfzdap
7149 pyr-tridi-men-zdap
7150 2py-m25thiz-no1-aspbzla
7151 bhs-edia2-sem-nbeta34dimeoph
7152 2py-edia2-oem-nbetameph
7153 amim-24thiz-mes-zdap
7154 dhim-pnymea-chexo-bnsdap
7155 bhs-25oxman2-5pho-betainyl
7156 tolhs-dio-5amo-glyzdap
7157 me-din-meo-betadcph
7158 impy-mepazin-chexo-bphabs
7159 2py-ms-emo-zdap
7160 n2py-diphmep-oeto-betainyl
7161 2py-25oxman2-no2-bsdap
7162 am2py-pazi2n-meto-betapy
7163 npip-pipa-imo-bhsdap
7164 dhim-ams2-pro-zdabs
7165 imhs-eta-ocho-zdap
7166 dmbim-mepipen2-oem-zdap
7167 thpym-eta-no2-psdap
7168 2py-mepipe-no2-csdap
7169 dpam-24oxman2-ocho-dfzdap
7170 imhs-amn2-mes-glupha
7171 dhim-m24thizman2-oem-psdap
7172 bimhs-amn3-eoco-aval
7173 me2py-dimephmem-men-bhsdap
7174 ec-pentadi-fo-bphabs
7175 bimhs-din-pheo-psdap
7176 bzl-thizs-fo-betapy
7177 phpip-24thizman2-no1-bphabs
7179 thpym-edian2-oem-bhsdap
7180 mepip-din-paco-psdab
7181 thpym-eta-ocho-zdap
7182 bimhs-pentadi-daco-asppha
7183 bhs-25oxman2-imo-bsdap
7184 dmbim-mepazin-cnmo-aspbzla
7185 dhim-dis-mes-psdap
7186 imhs-25oxman2-eoco-aval
7187 pippy-dis-oeto-zdap
7188 emnim-mepazin-4amo-betapy
7189 piraz-24thizman2-oem-dfzdap
7190 piraz-mepipe2-sem-nzdap
7191 imhs-pymea-napo-oxal
7192 bim-25oxman2-napo-dfzdap
7193 deam-25oxman2-4pho-glyzdap
7194 mam2py-dimephmem-ocho-betapy
7195 4pmhs-25thizman2-no2-psdap
7196 thpym-24thizman2-5amo-bsdap
7197 amim-ams2-oem-bhsdab
7198 bhs-ams2-meo-betapy
7199 2py-pipmes-5amo-mezphe
7200 imhs-eta-meo-psdap
7201 bim-pazin-meo-zdab
7202 im-m25thizman2-mes-zdap
7203 imhs-pnymea-men-bhsdab
7204 pyraz-m25oxman2-imo-bhsdab
7205 dhim-ams3-mes-aspibua
7206 dhim-thizn-ocho-betainyl
7207 bim-props-meo-aspibua
7208 piraz-24thizman2-mes-bhsdap
7209 thpym-mepipe2-oem-nbetab naphth
7210 im-am3-oem-nzdab 7211 thpym-amn2-eoco-bhsdap
7212 dmbim-dimen-no2-bphabs
7213 dhim-mepipe-napo-bhsdab
7214 impy-m25thiz-5pho-psdap
7215 bim-edian2-5pho-bnsdap
7216 dhim-trias-imo-csdap
7217 amthiaz-n2o2n-emo-asppha
7218 z-dimephmep-no2-zdap
7219 nmor-mepazin-chexo-csdap
7220 bimhs-mepipen2-chexo-aspbzla
7221 hythpym-m24thiman2-mes-dfzdap
7222 bim-tridi-pheo-bhsdab
7223 bim-edia2-oem-npsdap
7224 imhs-tridi-5amo-bphabs
7225 bim-diphmem-cpeo-zdab
7226 emnim-m25thiz-imo-betadcph
7227 2py-din-mes-bnsdap
7228 thpym-mepipe-ocho-psdap
7229 chmhs-mepipe-no1-betadcph
7230 bim-mepipe2-sem-nzdap
7231 ec-dimen-paco-oxal
7232 cl3pyme-mepazin-men-bnsdap
7233 imhs-tetras-meteto-aspibua
7234 piraz-3diaz-eoco-dfzdap
7235 dhim-amn2-no2-csdap
7236 chhs-pyma2-chexo-psdap
7237 am2py-m25thiz-5amo-csdap
7238 bimhs-m25thiz-chexo-zdab
7239 me2py-mepipe-mes-ppsdap
7240 bimhs-mepazin-oem-csdap
7241 me2py-24oxman2-chexo-zdap
7242 dmthpym-3pazin-fo-zdab
7243 thpym-m25thiz-meo-zdap
7244 morhs-3pazin-meo-glyzdap
7245 nim-mepipen2-5pho-mezphe
7246 bhs-tetras-5pho-bhsdab
7247 hythpym-dimen-no1-betainyl
7248 im-m25thiz-chexo-psdab
7249 thpym-pyma2-chexo-zdab
7250 pippy-dio-mes-dfzdap
7251 mam2py-pyma2-no2-aspbzla
7252 am2py-amo2-mommo-ppsdap
7253 2py-tetradi-5pho-osdap
7254 mam2py-mepipen2-meo-psdab
7255 ec-pazi2n-eoco-betaet
7256 imhs-n2nme2n-eoco-betainyl
7257 imhs-mepipe-no2-psdap
7258 menim-amn2-cnmo-ibsdap
7259 me2py-m25thiman2-ocho-glubzla
7260 amim-25oxman2-fo-psdapee
7261 thpym-ms-5amo-bhsdab
7262 bhs-pazin-5amo-zdab
7263 imhs-n2nme2n-peo-bhsdap
7264 me2py-eta-emo-glyzdap
7265 impy-pipa-napo-zdab
7266 am-mepipen2-no1-bnsdap
7267 bimhs-mepazin-imo-betapy
7268 am2py-dimephmep-men-bphabs
7269 imhs-pazin-no1-betapy
7270 pyraz-pyma2-5pho-bnsdap
7271 me2py-pipmes-oem-aspbzla
7272 emnim-mepipe2-sem-npsdap
7273 thpym-butn-ocho-bsdap
7274 n2py-din-eoco-betadcph
7275 dhim-mepipen2-no2-bhsdap
7276 emnim-din-peo-asppha
7277 n2py-dimephmem-no1-bhsdap
7278 impy-pyma2-no2-dfzdap
7279 bimhs-thizo-cpro-zdab
7280 am4py-dimephmem-5pho-zdab
7281 ppy-mepazin-eoco-betapy
7282 mam2py-m24thiman2-pro-zdap
7283 2py-24oxman2-mes-zdab
7284 hythpym-dimephmem-paco-ppsdap
7285 hythpym-n2o2n-chexo-zdab
7286 hythpym-mea2s-mes-bhsdab
7287 bim-m25thiz-chexo-aval
7288 nmhs-pazi2n-chexo-betadcph
7289 dhim-dimephmem-ocho-bsdap
7290 me2py-pazin-eoco-aspibua
7291 bimhs-25oxman2-pheo-psdapee
7292 pippy-25oxman2-cpro-psdap
7293 dhim-pipa-emo-bhsdab
7294 amim-25oxman2-men-bnsdap
7295 dmthpym-dimephmep-5amo-bsdap
7296 ppy-edian2-no2-osdap
7297 am4py-25thiman2-5amo-mezphe
7298 amim-pazin-chexo-csdap
7299 dhim-pazi2n-chexo-betapy
7300 phpip-amo2-5amo-bhsdap
7301 hythpym-24thiz-napo-zdabs
7302 me2py-edia2-oem-nbetabnaphth
7303 mam2py-mepipe-cpro-glubzla
7304 edothpym-pymea-chexo-aspaba
7305 z-pipmea-oem-betapy
7306 bim-amn2-no2-bhsdap
7307 thpym-m25thiz-mecpo-psdab
7308 gua-trias-pro-betapy
7309 2py-pazin-emo-psdab
7310 dhim-pipmeo-no2-bsdap
7311 am-pymea-4amo-zdap
7312 imhs-pazin-eoco-psdap
7313 hythpym-props-fo-psdab
7314 bz-pipa-imo-bphabs
7315 bhs-edian2-eoco-psdap
7316 amim-trias-mommo-glyzdap
7317 chhs-am3-sem-nzdap
7318 gua-25thiz-meo-aspibua
7319 dmthpym-24thizman2-no1-aval
7320 piraz-3diaz-5amo-zdab
7321 2py-amo2-5amo-betadcph
7322 bim-eta-oem-bnsdap
7323 dhim-pnymea-men-betapy
7324 imhs-amn2-5pho-bhsdap
7325 piraz-pnymea-cno-betainyl
7326 bhs-amn2-no2-betapy
7327 pippy-diphmep-cpeo-betapy
7328 deam-thizn-5amo-aspibua
7329 bimhs-m24thiman2-cnmo-mezphe
7330 bhs-diphmem-eoco-betainyl
7331 imhs-eta-ocho-bhsdap
7332 2py-amo2-meo-mezphe
7333 dpam-pnymea-emo-betadcph
7334 impy-24thizman2-mes-bsdap
7335 piraz-pymea-fo-csdap
7336 menim-25oxman2-peo-bnsdap
7337 bhs-m25thiz-no2-zdabs
7338 hythpym-thizn-ocho-bhsdab
7339 edothpym-pymea-fo-zdapee
7340 piraz-diphmep-mes-bsdap
7341 2py-am2-oem-nzdap
7342 2py-trias-chexo-bhsdap
7344 bimhs-n2o2n-no1-glyzdap
7345 deam-eta-no2-zdabs 7346 bimhs-diphmem-fo-aspbzla
7347 dhim-n2nme2n-imo-psdap
7348 2py-eta-meo-zdap
7349 binhs-dimephmep-nmo-osdap
7350 2py-amn2-meto-zorn
7351 thpym-pazin-eoco-zdab
7352 bimhs-pnymea-5pho-aspaba
7353 thpym-diphmem-oem-glyzdap
7354 thpym-diaz-no2-psdap
7355 nmhs-trias-no2-tsdap
7356 bimhs-dimephmem-5amo-aspbzla
7357 mam2py-tetradi-oem-mezphe
7358 bim-edia2-sem-nzdap
7359 imhs-pymea-eoco-oxal
7360 moegua-dimephmem-5pho-glyzdap
7361 bim-amn3-napo-zdab
7362 me2py-mepipe-napo-bsdap
7363 imhs-edian2-eoco-mezphe
7364 hythpym-diphmem-mecpo-bhsdab
7365 4pmhs-trias-mes-bhsdab
7366 imhs-am3-oem-nbeta34dimeoph
7367 2pmhs-trias-mes-mezphe
7368 amim-pipa-ocho-zdapee
7369 me2py-dimen-no1-psdab
7370 nim-pnymea-meto-zdabs
7371 chmhs-amo2-eoco-asppha
7372 bim-25oxman2-napo-bhsdap
7373 pippy-n24thiman-5amo-bnsdap
7374 pyrhs-am2-oem-nbetameph
7375 imhs-trias-5pho-bhsdah
7376 morhs-eta-emo-ppsdap
7377 am2py-m25thizman2-no2-betapy
7378 bhs-pazin-eoco-bsdap
7379 mepip-mepipen2-chexo-zdap
7380 menim-am3-oem-nbeta34dimeoph
7381 piraz-am3-oam-nbeta34dimeoph
7382 2py-eta-no2-psdab
7383 2py-eta-meo-betapy
7384 2py-mepipe-chexo-zdabs
7385 nmhs-pazin-aco-asppha
7386 bim-pazin-meo-bsdap
7387 2py-mepipe-no2-zdap
7388 imhs-pymea-napo-zdab
7389 amthiaz-pipmea-daco-bsdap
7390 amim-3pazin-no1-betaet
7391 imhs-pazin-eoco-bsdap
7392 bim-dis-cno-zdabs
7393 pippy-thizn-chexo-betadcph
7394 2py-mepipen2-eoco-psdab
7343 mam2py-pymea-imo-aspibua
7395 bim-thizn-5amo-psdab
7396 dhim-tetras-imo-bnsdap
7397 im-pnymea-chexo-aspbzla
7398 amim-eta-ocho-bhsdab
7399 me2py-pipa-napo-bnsdap
7400 piraz-amn3-mes-psdap
7401 am2py-pymea-emo-bsdap
7402 edothpym-dimen-nmo-ppsdap
7403 me2py-24thiman-chexo-zdabs
7404 dpam-eta2s-ocho-asppha
7405 an2py-m25thiz-eoco-betainyl
7406 ppy-mepipen2-5amo-betapy
7407 nim-pipa-men-bphabs
7408 thpym-mepipen2-meo-zdabs
7409 am2py-25oxman2-oeto-zdabs
7410 thpym-tetradi-fo-betapy
7411 me2py-amo2-emo-thizzdap
7412 bimhs-pnymea-imo-psdab
7413 am4py-pazin-napo-psdab
7414 am2py-mepazin-napo-bphabs
7415 piraz-pazin-imo-zdab
7416 2py-pymea-no2-aspbzla
7417 impy-pipa-pheo-dfzdap
7418 menim-pnymea-no2-aspaba
7419 prhs-dimephmep-pheo-zdap
7420 pippy-pipmea-men-oxal
7421 phpip-dimephmem-imo-mezphe
7422 bhs-n24thiman-imo-zdap
7423 me2py-25thiz-mmen-zdabs
7424 bim-pipa-5pho-glyzdap
7425 cl3pyme-m24thiman2-pyo-thizzdap
7426 me2py-dimephmem-5amo-aspibua
7427 pippy-diphmep-eoco-bphabs
7428 impy-din-napo-csdap
7429 hythpym-trias-pheo-aspibua
7430 2py-eta-no1-bnsdap
7431 fthpym-eta-napo-psdap
7432 nmhs-tetradi-eoco-aspaba
7433 mam2py-m24thizman2-chexo-betaet
7434 2py-tridi-emo-mezphe
7435 imhs-m24thizman2-no1-dfzdap
7436 menim-amo3-ocho-zdab
7437 mam2py-24oxman2-meo-betaet
7438 dhim-amn2-napo-bnsdap
7439 2py-propa2s-meteto-thizzdap
7440 dmam-mepipen2-no2-bsdap
7441 fthpym-dis-pheo-zdabs
7442 hythpym-m25thizman2-oem-betainyl
7443 dhim-diphmep-emo-psdap
7444 me2py-dimephmem-imo-betapy
7445 piraz-pipmea-oem-betadcph
7446 hythpym-diphmep-no2-bnsdap
7447 dpam-edian2-pro-psdab
7448 mam2py-amo2-men-csdap
7449 edothpym-24thiman-aco-glyzdap
7450 imhs-am3-sem-nbetabnaphth
7451 piraz-eta-meo-psdab
7452 thpym-24thiman-no1-bnsdap
7453 bhs-mepazin-men-zdap
7454 im-amn2-ocho-zdabs
7455 2py-trias-fo-bnsdap
7456 thpym-trias-oem-bphabs
7457 nmor-pymea-men-csdap
7458 phpip-pyma2-ocho-betapy
7459 piraz-n24thiman-no2-betapy
7460 piraz-ams2-no2-aspibua
7461 2py-mepipe-eoco-bnsdap
7462 2pmhs-mepazin-oeto-bsdap
7463 fthpym-pipmea-imo-bhsdab
7464 impy-pazin-meo-psdab
7465 dpam-thizn-meo-mezphe
7466 mam2py-tridi-eoco-glyzdap
7467 pippy-m24thiman2-ocho-glyzdap
7468 bim-amn2-fo-zdab
7469 2py-amo2-oeto-ibsdap
7470 nim-25thizman2-meteto-betadcph
7471 am2py-dimephmem-eoco-aspibua
7472 emnim-indan2-fo-zdapee
7473 bim-mepipe-5pho-psdab
7474 mam2py-pipa-oem-csdap
7475 pippy-pipmea-emo-psdap
7476 tolhs-24thiman2-chexo-glyzdap
7477 nim-mepipe2-sem-nzdab
7478 me2py-dis-chexo-zdab 7479 edothpym-pipmeo-5amo-psdab
7480 thpym-edian2-eoco-bsdap
7481 am2py-pnymea-ocho-csdap
7482 am2py-ams2-imo-betaet
7483 nmhs-dis-cpro-bphabs
7484 dhim-amo2-eoco-bhsdap
7485 pippy-dimephmep-4pho-bhsdab
7486 am2py-din-imo-bphabs
7487 bim-mepipe-oem-bsdap
7488 2py-eta-fo-oxal
7489 chhs-thizn-daco-betainyl
7490 mam2py-ams2-5pho-psdab
7491 dpam-tetradi-mes-dfzdap
7492 nmhs-n2o2n-5amo-bhsdab
7493 imhs-tridi-napo-betapy
7494 2py-edian2-5pho-bnsdap
7495 mam2py-dimen-peo-aspbzla
7496 dpam-edian2-mes-betadcph
7497 piraz-pyma2-daco-mezphe
7498 amthiaz-24thiz-fo-psdab
7499 imhs-dimen-men-bhsdap
7500 phhs-trias-5amo-zdap
7501 thpym-24thiz-pyo-psdab
7502 thpym-eta-no2-betapy
7503 bhs-tridi-mes-bnsdap
7504 hythpym-mepazin-pro-bsdap
7505 dhim-m25thizman2-5pho-psdab
7506 ppy-ms-fo-aspibua
7507 2py-pazin-eoco-bsdap
7508 thpym-eta-5pho-psdap
7509 dmthpym-diphmep-mes-aspibua
7510 bhs-diphmep-men-betapy
7511 nmhs-25oxman2-men-dfzdap
7512 morhs-thizn-ocho-aspbzla
7513 dhim-amn2-eoco-aspbzla
7514 imhs-pyma2-imo-mezphe
7515 pyrhs-dis-eoco-betapy
7516 z-amn2-mmen-betadcph
7517 2py-25oxman2-oem-osdap
7518 thpym-dimen-eoco-zdap
7519 prhs-25oxman2-5pho-csdap
7520 imhs-m24thiz-mecpo-psdap
7521 dpam-edian2-meo-dfzdap
7522 hs-eta-no1-bnsdap
7523 hythpym-diphmem-napo-zdab
7524 pippy-mepipen2-napo-asppha
7525 2py-pipmea-fo-bhsdab
7526 amim-24thizman2-cnmo-zdab
7527 bim-eta-eoco-psdap
7528 dpam-mepipen2-mommo-betainyl
7529 bhs-mepipe-oem-bhsdap
7530 pippy-pyma2-napo-bhsdap
7531 bhs-mepipe-5pho-bhsdap
7532 hythpym-24thizman2-eoco-bnsdap
7533 amim-m25oxman2-mmen-betadcph
7534 edothpym-diphmem-fo-betaet
7535 bim-mepipe-ocho-bsdap
7536 bim-eta-ocho-zdab
7537 imhs-edian2-no2-psdap
7538 bhs-pipmea-napo-dfzdap
7539 bimhs-tridi-cpeo-dfzdap
7540 bim-amn2-eoco-zdap
7541 dmbim-thizn-men-bhsdap
7542 2py-pazin-mes-bhsdap
7543 2py-amn2-5pho-betapy
7544 mepip-trias-ocho-psdab
7545 hythpym-thizs-imo-asppha
7546 prhs-tetradi-5pho-dfzdap
7547 ppy-am3diaz-chexo-asppha
7548 am-pipmeo-hso-asppha
7549 dmbim-dimephmem-mommo-thizzdap
7550 bimhs-pipa-no1-zdabs
7551 bhs-pazin-5pho-bhsdap
7552 impy-3pazin-no2-betadcph
7552 impy-3pazin-no2-betadcph
7553 morhs-am3-oem-nbetapy
7554 bim-mepipe2-sem-nbetapy
7555 bimhs-mepipen2-5amo-bsdap
7556 dmbim-tetradi-meo-aspbzla
7557 2pmhs-dimephmep-5amo-bhsdap
7558 2py-dich-pyo-bhsdap
7559 2py-amn2-eoco-psdab
7560 imhs-eta-ocho-aspbzla
7561 me-am3-oem-nbeta34dimeoph
7562 mam2py-amo2-ocho-ibsdap
7563 dpam-25thiz-chexo-bnsdap
7564 2py-mepipe-5pho-psdap
7565 impy-dich-eoco-bhsdap
7566 piraz-m24thizman2-cno-csdap
7567 am2py-pymea-no2-psdap
7568 prhs-thizn-no2-bsdap
7569 me2py-tetradi-mommo-betadcph
7570 nmor-pazi2n-oem-bhsdap
7571 z-pyma2-5pho-asppha
7572 pyraz-dis-peo-aval
7573 am-m25thiz-meto-bnsdap
7574 gua-pnymea-no1-aspbzla
7575 nmhs-amn3-ocho-betadcph
7576 bimhs-dio-oem-bnsdap
7577 bim-amn2-eoco-bnsdap
7578 me2py-25oxman2-oeto-bhsdap
7579 gua-dipch-imo-bsdap
7580 bimhs-tetradi-cpro-glyzdap
7581 piraz-mepipe-mes-zdab
7582 am2py-mepipen2-no2-betapy
7583 hythpym-hexadi-cpeo-zdabs
7584 piraz-trias-4amo-asppha
7585 bhs-mepazin-no1-bhsdab
7586 pippy-din-imo-betapy
7587 thpym-m24thiman2-5amo-csdap
7588 imhs-dimephmep-cpro-zdab
7589 ibhs-diphmep-no2-glyzdap
7590 impy-pymea-no2-psdab
7591 dhim-ams3-5pho-mezphe
7592 amim-pymea-no1-asppha
7593 bhs-pipa-5pho-glyzdap
7594 dmbim-m24thizman2-oeto-zdab
7595 am2py-24thizman2-aco-aspbzla
7596 dhim-pipmeo-5pho-osdap
7597 me2py-am3-sem-npsdap
7598 impy-diphmem-nmo-glyzdap
7599 dhim-24thizman2-eoco-psdab
7600 bimhs-24thiz-emo-betainyl
7601 me2py-pazin-meo-zdab
7602 impy-trias-men-dfzdap
7603 am2py-dimephmep-meo-osdap
7604 phhs-am3-sem-nbetapy
7605 bz-dimephmep-mecpo-zdab
7606 mam2py-dis-5pho-asppha
7607 impy-tetradi-cno-dfzdap
7608 impy-am3-sem-nzdap
7609 2py-props-no1-tsdap
7610 deam-mepazin-5pho-psdap
7611 bim-edian2-5pho-psdap 7612 bim-diphmem-emo-bnsdap
7613 piraz-hexas-hso-aspaba
7614 z-dimephmem-ocho-zdap
7615 hythpym-am3diaz-meto-glyzdap
7616 mepip-mepipe2-sem-nbeta34-dimeoph
7617 2pmhs-25thizman2-pro-glyzdap
7618 nim-ams2-fo-tsdap
7619 pyrhs-pipa-no2-betapy
7620 pippy-amn2-emo-psdap
7621 piraz-diphmep-imo-betainyl
7622 pyr-m24thiz-napo-betaet
7623 thpym-propn-napo-mezphe
7624 amim-m24oxmaa2-emo-psdapee
7625 pippy-pymea-fo-aspibua
7626 amim-mepipen2-men-zdabs
7627 dhim-mepipe-napo-glyzdap
7628 me2py-din-mecpo-betadcph
7629 bimhs-pnymea-cno-aspbzla
7630 thpym-pipmes-men-bsdap
7631 am2py-mepazin-ocho-dfzdap
7632 impy-am2-sem-nbetabnaphth
7633 nmhs-amn3-5pho-betadcph
7634 pippy-edia2-oem-npsdap
7635 amthiaz-pipmea-no2-betainyl
7636 hythpym-pipmea-meteto-zdabs
7637 hythpym-eta-5amo-psdap
7638 emnim-mepazin-no2-csdap
7639 pippy-tetradi-5amo-bhsdab
7640 chmhs-thizn-mes-psdap
7641 imhs-eta-no1-zdap
7642 z-m25thiz-cpeo-bhsdap
7643 amim-diphmep-no2-glyzdap
7644 4pmhs-dimen-imo-csdap
7645 imhs-eta-5pho-psdap
7646 me2py-pipa-5pho-zdab
7647 npip-amn2-no2-bhsdap
7648 me2py-25oxman2-imo-bsdap
7649 prhs-pazin-mes-glubzla
7650 imhs-mepipe-5pho-bhsdap
7651 hythpym-diphmem-ocho-bsdap
7652 morhs-dimen-men-aval
7653 thpym-pipa-hso-asppha
7654 thpym-pazin-ocho-psdap
7655 impy-pipmea-oem-csdap
7656 dpam-dis-eoco-bsdap
7657 impy-n24thiman-ocho-mezphe
7658 piraz-din-5amo-glyzdap
7659 pippy-dimephmem-fo-oxal
7660 mam2py-dimephmep-no2-zdap
7661 me2py-dimephmep-ocho-bnsdap
7662 piraz-am3diaz-no1-zdab
7663 bimhs-m25oxman2-ocho-glyzdap
7664 thpym-tetras-cno-bphabs
7665 imhs-24thizman2-eoco-zlys
7666 pippy-tetradi-emo-bnsdap
7667 nmhs-m25thiman2-ocho-zdapee
7668 bimhs-24oxman2-no1-bnsdap
7669 amim-ams2-cpeo-bhsdap
7670 me2py-dis-oem-psdap
7671 impy-m25thiz-men-betadcph
7672 bhs-mepipe-oem-zdab
7673 bhs-mepipe-mes-betapy
7674 bzl-amn2-mes-aspibua
7675 pyraz-din-5amo-psdap
7676 bz-m24thiman2-chexo-csdap
7677 hythpym-ams2-men-thizzdap
7678 mam2py-diphmem-no1-zdabs
7679 bim-dich-meo-zdabs
7680 impy-edian2-5pho-aspibua
7681 imhs-edian2-no1-bsdap
7682 ec-25oxman2-nmo-mezphe
7683 ec-din-oem-aspibua
7684 4pmhs-pazin-paco-psdap
7685 piraz-edia2-oem-nbetabnaphth
7686 morhs-edian2-5amo-aspbzla
7687 dhim-ams2-fo-betadcph
7688 deam-m25thiz-emo-bphabs
7689 cl3pyme-24thizman2-4amo-ppsdap
7690 dhim-din-mommo-glyzdap
7691 me-m24thizman2-meo-glyzdap
7692 dmam-25thizman2-4amo-thizzdap
7693 bim-am2-oem-nbetameph
7694 pippy-24thiz-meteto-psdab
7695 2py-am3-oem-nbeta34dimeoph
7696 2py-amn2-eoco-betapy
7697 dmbim-pentadi-no2-bsdap
7698 dhim-24thiz-meo-asppha
7699 impy-thizn-ocho-mezphe
7700 thpym-mepipe-oem-psdab
7701 pippy-n24thiman-5amo-psdap
7702 hythpym-dimephmem-men-betainyl
7703 gua-25thiman2-paco-betainyl
7704 bim-pazin-eoco-betapy
7705 thpym-mepipe-5pho-bphabs
7706 2py-24thiz-napo-zlys
7707 impy-pipmes-mes-aspbzla
7708 bhs-thizn-meo-ibsdap
7709 ppy-tridi-chexo-mezphe
7710 thpym-tridi-imo-betainyl
7711 chhs-24thiz-no1-aval
7712 chmhs-trias-men-mezphe
7713 am2py-diphmep-ocho-dfzdap
7714 pippy-edian2-imo-zdabs
7715 deam-24thiz-no1-dfzdap
7716 nmor-amn3-cpeo-bnsdap
7717 bhs-m25thiz-chexo-zdabs
7718 dhim-dimen-4pho-betapy
7719 gua-24thiman-aco-zdap
7720 mam2py-diphmem-oem-bhsdap
7721 am4py-mea2s-napo-aspbzla
7722 amim-pyma2-daco-thizzdap
7723 amim-dimephmep-5amo-betadcph
7724 bimhs-m25thiz-mes-zdabs
7725 me2py-thizs-fo-asppha
7726 am2py-din-eoco-betapy
7727 bim-edian2-pheo-zdap
7728 bhs-mepipe-mes-bnsdap
7729 moegua-24thiman2-emo-csdap
7730 imhs-eta-eoco-bnsdap
7731 imhs-mepipen2-no2-oxal
7732 thpym-edia2-oem-nbetapy
7733 ec-eta-meo-aspbzla
7734 hythpym-amn2-eoco-aval
7735 n2py-pymea-meo-zdap
7736 amim-24thizman2-no2-bsdap
7737 thpym-pnymea-ocho-betadcph
7738 2py-24oxman2-cnmo-bhsdap
7739 me2py-amo2-no2-aspbzla
7740 menim-dipch-mes-betapy
7741 n2py-thizo-no1-betainyl
7742 bhs-mepipe-eoco-bsdap
7743 moegua-eta-emo-zdabs
7744 me-m25thiz-mes-bphabs
7745 bzl-dio-aco-bnsdap 7746 2py-n2o2n-meto-dfzdap
7747 thpym-dimen-no2-ibsdap
7748 ec-mepipen2-fo-bnsdap
7749 am2py-pyma2-imo-zdap
7750 dmam-thizn-4amo-bhsdab
7751 imhs-edian2-5pho-betapy
7752 bhs-24thiz-5amo-psdab
7753 am2py-dimephmem-no2-bhsdab
7754 bhs-pazin-emo-betapy
7755 im-mepipe2-oem-npsdap
7756 bim-tetras-cpeo-psdap
7757 amim-amo2-oem-betaet
7758 n2py-trias-men-betainyl
7759 me2py-edian2-5amo-betainyl
7760 z-edia2-sem-nzdap
7761 chhs-mepipe-chexo-zdap
7762 dhim-25oxman2-men-csdap
7763 impy-mea2s-5pho-zdap
7764 bimhs-dis-mes-bnsdap
7765 bhs-amn2-meo-betapy
7766 thpym-25oxman2-no2-zdap
7767 bim-edian2-oem-betapy
7768 bim-dimen-hso-betapy
7769 mam2py-pnymea-fo-mezphe
7770 prhs-pymea-ocho-csdap
7771 2py-amn2-no1-zdab
7772 hythpym-mepipe-meteto-psdapee
7773 hythpym-3diaz-cpro-zdap
7774 deam-pnymea-no1-bhsdab
7775 phhs-pyma2-no2-zdabs
7776 mam2py-ams2-paco-psdab
7777 bhs-edian2-mes-bhsdap
7778 pippy-thizs-no1-betaet
7779 nim-pazin-imo-ibsdap
7780 nmor-amn3-men-mezphe
7781 menim-pipmes-meo-bphabs
7782 dhim-dimephmep-imo-dfzdap
7783 z-24thiz-aco-betaet
7784 bhs-amn3-mmen-zdap
7785 edothpym-hexas-mes-csdap
7786 amim-diphmem-ocho-csdap
7787 n2py-24thiz-mommo-bphabs
7788 piraz-pazin-eoco-dfzdap
7789 bhs-mepazin-no2-betainyl
7790 ec-m24thizman2-mecpo-glyzdap
7791 hythpym-amo3-oem-zdap
7792 n2py-pymea-cnmo-zdabs
7793 2py-diphmem-chexo-psdap
7794 bzl-din-no2-glyzdap
7795 bim-amn2-no2-psdap
7796 mam2py-eta2s-no1-zdabs
7797 2py-edian2-no1-zdab
7798 dhim-eta-baeo-ppsdap
7799 bim-dis-mecpo-betapy
7800 me2py-pipa-oem-aspibua
7801 2py-m24thizman2-5pho-asppha
7802 pyr-propn-peo-mezphe
7803 2py-24thiz-napo-ibsdap
7804 thpym-butn-meo-asppha
7805 pippy-mepipen2-emo-zdab
7806 bim-pyma2-no1-mezphe
7807 amim-mepipen2-no1-bhsdab
7808 mam2py-mepipen2-ocho-aspbzla
7809 imhs-pyma2-no1-betadcph
7810 imhs-dimephmep-imo-bhsdab
7811 ibhs-pipmea-4pho-mezphe
7812 mam2py-dimephmem-5pho-psdap
7813 bimhs-24thizman2-chexo-betadcph
7814 2pmhs-dimephmep-5pho-psdap
7815 hythpym-pyma2-oem-csdap
7816 2py-tetras-emo-bhsdap
7817 imhs-mepipe-ocho-bnsdap
7818 dhim-amo2-emo-csdap
7819 bimhs-mepipe-mommo-glyzdap
7820 imhs-pazin-eoco-psdab
7821 dpam-mepazin-chexo-asppha
7822 impy-pyma2-imo-dfzdap
7823 am2py-eta-mes-psdap
7824 hythpym-tridi-5pho-oxal
7825 mam2py-dimephmep-emo-zdap
7826 bhs-dimephmep-men-bphabs
7827 emnim-24thizman2-mmen-bhsdab
7828 hythpym-trias-emo-zdab
7829 ibhs-mepazin-4amo-ibsdap
7830 dmthpym-diphmem-5amo-glyzdap
7831 dhim-mepipe-oem-psdap
7832 imhs-3diaz-fo-aspbzla
7833 me2py-diphmep-no1-betadcph
7834 bim-diphmep-emo-zdap
7835 bimhs-diphmep-peo-zdabs
7836 bhs-tetradi-imo-betapy
7837 me2py-trias-mommo-betadcph
7838 bzl-m25thiz-mmen-dfzdap
7839 pippy-tetradi-mommo-csdap
7840 dhim-edia2-sem-nbetabnaphth
7841 moegua-eta-pro-betainyl
7842 bhs-ams3-no1-psdab
7843 impy-pipa-peo-betaet
7844 edothpym-n2nme2n-mes-bhsdab
7845 n2py-thizn-eoco-psdap
7846 cl3pyme-hexas-men-glyzdap
7847 ppy-n2nme2n-emo-betadcph
7848 ppy-mepipe2-oem-nbetabnaphth
7849 ppy-dimen-napo-betapy
7850 imhs-amn2-ocho-bnsdap
7851 cl3pyme-diphmep-aco-zdapee
7852 imhs-edian2-fo-zdapee
7853 chmhs-eta-fo-bphabs
7854 chmhs-mepazin-meo-zdap betainyl
7855 thpym-din-5amo-psdab
7856 bz-pyma2-5amo-zdapee
7857 bimhs-pipmea-ocho-betainyl
7858 piraz-tridi-pyo-zdap
7859 imhs-eta-ocho-bsdap
7860 bim-dimephmem-imo-betadcph
7861 imhs-tridi-aco-bphabs
7862 mam2py-24thiz-ocho-bhsdap
7863 piraz-amn3-mes-zdab
7864 thpym-24thiz-imo-aspbzla
7865 hythpym-tridi-no1-asppha
7866 amthiaz-mepipe-oem-betainyl
7867 imhs-amo2-imo-zdabs
7868 am2py-m24oxman2-no1-ppsdap
7869 mam2py-ams2-fo-bsdap
7870 fthpym-ams3-pheo-zdap
7871 me2py-pazin-pheo-bsdap
7872 gua-pnymea-cpeo-betadcph
7873 amim-amo2-no1-bhsdab
7874 prhs-edian2-4pho-bhsdab
7875 2py-amn3-mommo-bphabs
7876 nim-edian2-meto-csdap
7877 2py-thizn-pheo-bphabs
7878 nim-mepipe2-sem-nbeta34-dimeoph
7879 pyrhs-ams2-mmen-mezphe 7880 emnim-diphmem-no1-betainyl
7881 dpam-hexadi-aco-betainyl
7882 hythpym-indan2-napo-glyzdap
7883 imhs-mepipe-eoco-bnsdap
7884 am2py-mepazin-no1-mezphe
7885 pippy-pyma2-napo-psdab
7886 bhs-mepipe-emo-dfzdap
7887 ppy-edian2-oeto-bhsdap
7888 2py-diphmem-no2-mezphe
7889 dhim-amn2-eoco-bphabs
7890 pyrhs-mepazin-chexo-bphabs
7891 bim-pazin-oem-psdap
7892 am2py-dimen-imo-betadcph
7893 ppy-ams3-cnmo-betainyl
7894 bzl-mepazin-hso-betadcph
7895 amim-pyma2-emo-zdabs
7896 hythpym-ms-no1-aspaba
7897 bim-mepazin-mes-psdab
7898 me2py-mepipe2-sem-nzdap
7899 amim-pymea-napo-bsdap
7900 pippy-eta-fo-asppha
7901 me-n2nme2n-baeo-bhsdab
7902 pyr-24thiz-fo-zdab
7903 piraz-pnymea-no1-aspibua
7904 amim-24thizman2-chexo-betainyl
7905 2py-eta-no1-psdap
7906 menim-amo2-mes-betadcph
7907 npip-eta-fo-mezphe
7908 piraz-dimen-pro-bhsdap
7909 2py-amn2-oem-bnsdap
7910 dmbim-ams2-mes-bhsdap
7911 bim-din-ocho-csdap
7912 n2py-trias-5amo-glyzdap
7913 me2py-n24thiman-meo-bhsdap
7914 imhs-edian2-no2-betapy
7915 amim-mepipe-napo-psdap
7916 phpip-pazin-emo-aspibua
7917 thpym-amn2-oem-psdap
7918 bimhs-eta-oem-bhsdap
7919 pippy-am3diaz-oem-mezphe
7920 bim-amn2-meo-bnsdap
7921 am2py-tridi-fo-psdap
7922 imhs-din-men-bhsdab
7923 imhs-amn2-eoco-bnsdap
7924 imhs-amo2-chexo-betapy
7925 thpym-pipmeo-cnmo-aval
7926 piraz-mea-5pho-bsdap
7927 pippy-eta-meo-csdap
7928 piraz-mepazin-men-zdap
7929 bz-eta-cnmo-glyzdap
7930 bhs-eta-fo-csdap
7931 imhs-amn3-cpro-dfzdap
7932 pippy-dimephmep-ocho-glyzdap
7933 ppy-tetradi-mes-bnsdap
7934 tolhs-trias-fo-betapy
7935 piraz-trias-cpeo-zdab
7936 am2py-tridi-chexo-zdab
7937 impy-25oxman2-ocho-betapy
7938 bz-pipmea-no2-asppha
7939 dmam-mea-mmen-bhsdab
7940 mam2py-pipmea-no1-psdab
7941 dmthpym-pipmea-oem-zdap
7942 me-24thiz-nmo-csdap
7943 cl3pyme-propn-cnmo-bphabs
7944 mam2py-tetradi-4amo-betainyl
7945 bim-edian2-no1-zdap
7946 dhim-edian2-5amo-zdapee
7947 bim-dimephmep-fo-zdab
7948 bz-dio-mes-oxal
7949 piraz-pipa-no2-bsdap
7950 me2py-diphmep-cnmo-csdap
7951 mam2py-am2-sem-nbetameph
7952 gua-amo2-aco-psdap
7953 dmthpym-dis-emo-thizzdap
7954 4pmhs-mepipe-5pho-bnsdap
7955 mam2py-m24thizman2-fo-bphabs
7956 im-mea2s-no1-betadcph
7957 moegua-dis-meteto-betapy
7958 hythpym-trias-mes-betapy
7959 me2py-24thizman2-pyo-bhsdap
7960 am2py-pymea-napo-mezphe
7961 piraz-hexadi-paco-glyzdap
7962 me2py-tridi-fo-psdab
7963 bim-amn2-eoco-bsdap
7964 bimhs-thizo-meo-psdab
7965 2py-dimen-eoco-bnsdap
7966 mepip-am3-oem-npsdap
7967 pippy-tetradi-5amo-bhsdab
7968 bim-pazin-mes-betapy
7969 hythpym-ams2-meo-bhsdap
7970 npip-dimephmep-ocho-bnsdap
7971 bhs-m25thiz-fo-aval
7972 pippy-trias-cpro-glupha
7973 2py-eta-fo-aspibua
7974 mam2py-2pazin-men-aspibua
7975 thpym-dimen-eoco-aspbzla
7976 bhs-m25oxman2-men-bhsdap
7977 bim-dimephmem-5pho-aspbzla
7978 pippy-25thiz-5amo-aspibua
7979 morhs-propa2s-no2-bnsdap
7980 thpym-mepipe-no1-psdab
7981 amthiaz-din-oem-bphabs
7982 impy-pyma2-men-aspbzla
7983 z-eta-ocho-asppha
7984 bimhs-hexadi-eoco-mezphe
7985 bhs-amn2-pro-zdabs
7986 bim-edian2-5pho-zdab
7987 pyraz-din-men-zdabs
7988 2py-tetras-4amo-zdabs
7989 n2py-thizs-ocho-asppha
7990 bhs-hexadi-oem-bhsdab
7991 mam2py-pipmes-5pho-asppha
7992 am-mea2s-no1-zdap
7993 bim-pipa-ocho-bhsdab
7994 bimhs-tridi-no2-aspbzla
7996 phpip-ms-meteto-aspibua
7997 4pmhs-diphmem-eoco-zdap
7998 bim-eta-no1-bnsdap
7999 mepip-n2o2n-fo-bnsdap
8000 ppy-24thiz-oem-betapy
8001 tolhs-dimephmem-ocho-dfzdap
8002 hythpym-2pazin-imo-bhsdab
8003 thpym-pazin-eoco-psdap
8004 thpym-mepipen2-oem-betadcph
8005 amim-tetras-imo-bphabs
8006 am4py-m24thiz-mes-bhsdab
8007 bim-dimen-imo-osdap
8008 phpip-din-imo-aspaba
8009 thpym-mepipen2-5amo-psdap
8010 me2py-tetradi-5pho-psdap
8011 thpym-pazin-fo-bhsdab
8012 mam2py-25oxman2-imo-betadcph
8013 am2py-m24thizman2-fo-bhsdap
8014 4pmhs-24thiman2-oem-bhsdab 8015 bhs-pazin-mes-betapy
8016 bimhs-pazin-mes-betaet
8017 thpym-pazin-meo-psdab
8018 phhs-24thizman2-5pho-betadcph
8019 thpym-edian2-meo-betapy
8020 mam2py-ams2-5amo-mezphe
8021 bim-edian2-ocho-bnsdap
8022 am2py-amn3-men-osdap
8023 mepip-24oxman2-mes-tsdap
8024 dmbim-amn3-4amo-mezphe
8025 piraz-pentadi-emo-oxal
8026 bhs-edian2-5pho-betapy
8027 bim-thizn-cno-betaet
8028 mam2py-dis-cnmo-bhsdab
8029 me2py-hexas-cno-bphabs
8030 dhim-pazin-no1-bphabs
8031 chhs-thizn-baeo-bhsdab
8032 npip-amn3-peo-bsdap
8033 impy-edian2-imo-aspibua
8034 emnim-pipmeo-no1-tsdap
8035 2py-m25thiman2-ocho-aspibua
8036 2py-24thiz-fo-betadcph
8037 pyr-24thiman2-imo-mezphe
8038 dmthpym-n2o2n-paco-zdap
8039 impy-edia2-oem-nzdap
8040 pippy-m25thiz-hso-zorn
8041 piraz-24thizman2-emo-asppha
8042 amim-24thiz-no2-asppha
8043 impy-thizo-cno-psdap
8044 chhs-mepipen2-mes-zdap
8045 nmhs-pazin-chexo-zdab
8046 me-m25thiz-mommo-mezphe
8047 cl3pyme-pipmes-meo-psdapee
8048 mam2py-propn-no1-mezphe
8049 chhs-din-meo-mezphe
8050 npip-25oxman2-pro-zdabs
8051 me-dis-4pho-bnsdap
8052 imhs-amn3-5amo-betaet
8053 dhim-24thiz-cnmo-aspibua
8054 2py-amn2-no1-psdab
8055 bimhs-mepazin-pyo-betadcph
8056 amthiaz-dimen-nmo-psdap
8057 bhs-pentas-baeo-glyzdap
8058 mam2py-n24thiman-5pho-bhsdab
8059 inhs-edian2-eoco-betapy
8060 2py-eta-eoco-betapy
8061 amim-pyma2-napo-zdab
8062 thpym-pymea-eoco-betadcph
8063 emnim-pyma2-oem-aspibua
8064 bimhs-mepipen2-no2-asppha
8065 mepip-thizn-meo-betadcph
8066 pyr-mepipe-mes-aspibua
8067 am2py-tetradi-no2-thizzdap
8068 me2py-mepazin-men-aspbzla
8069 imhs-ams2-no2-aspbzla
8070 imhs-m24thizman2-eoco-dfzdap
8071 dhim-dimen-no1-aspibua
8072 2py-edian2-hso-csdap
8073 bhs-propa2s-oem-psdap
8074 2py-pentadi-meto-dfzdap
8075 dmthpym-thizn-napo-psdab
8076 dhim-m25thiz-chexo-bphabs
8077 bimhs-eta-eoco-aspbzla
8078 4pmhs-ams3-4pho-betainyl
8079 bimhs-pazin-no1-zdab
8080 me2py-pymea-imo-psdapee
8081 bimhs-edian2-mes-zdab
8082 bimhs-mepipe-baeo-aspbzla
8083 inhs-amn2-no2-psdap
8084 dhim-25oxman2-cem-zdab
8085 mam2py-eta-pro-zdabs
8086 prhs-tetradi-5amo-osdap
8087 ppy-tridi-napo-dfzdap
8088 2py-eta-oem-zdap
8089 hythpym-din-cno-bsdap
8090 amim-pipmea-men-aspbaba
8091 ppy-pipmea-5pho-betapy
8092 hythpym-tridi-5amo-aspbzla
8093 thpym-pymea-oem-asppha
8094 deam-24thizman2-emo-thizzdap
8095 amthiaz-pipmea-chexo-bnsdap
8096 dmthpym-pyma2-chexo-bhsdap
8097 ppy-n2nme2n-oem-dfzdap
8098 thpym-mepipe2-sem-npsdap
8099 am4py-am2-oem-nbetabnaphth
8100 bim-am3-sem-nbetabnaphth
8101 amthiaz-dimephmep-cpeo-aspbzla
8102 bim-eta-eoco-betapy
8103 me2py-dimephmep-ocho-bsdap
8104 imhs-hexas-nmo-aspbzla
8105 deam-m24oxman2-chexo-bphabs
8106 tolhs-eta-chexo-aspibua
8107 am-tetradi-mes-psdab
8108 gua-dimephmem-cpeo-psdab
8109 mam2py-diphmep-no1-zdabs
8110 pyraz-din-emo-betadcph
8111 dmthpym-dis-meo-csdap
8112 amim-thizn-pro-bnsdap
8113 impy-mea2s-men-bphabs
8114 me2py-25oxman2-baeo-bhsdab
8115 ibhs-diphmem-meo-thizzdap
8116 imhs-pazin-5pho-bnsdap
8117 edothpym-pipmea-meo-mezphe
8118 me2py-n24thiman-eoco-csdap
8119 2py-diphmep-emo-tsdap
8120 pippy-diphmep-imo-mezphe
8121 amim-hexadi-emo-aspibua
8122 dmthpym-diphmem-5amo-psdapee
8123 moegua-24thizman2-napo-zdabs
8124 pippy-pazi2n-men-zorn
8125 imhs-ams2-ocho-oxal
8126 bimhs-pipmea-oeto-glupha
8127 2py-edian2-ocho-bnsdap
8128 thpym-m25thiman2-mecpo-zdab
8129 thpym-amn-ocho-bnsdap
8130 dhim-pyma2-no1-osdap
8131 bhs-edian2-meo-bsdap
8132 dmthpym-pazin-no2-psdab
8133 pippy-am3-oem-nzdap
8134 bimhs-24thiz-no2-zdapee
8135 thpym-pazin-no1-zdap
8136 mam2py-amo2-oeto-zdabs
8137 nmor-3diaz-ocho-asppha
8138 hythpym-propn-emo-bhsdab
8139 ibhs-m25thiz-cpro-bhsdab
8140 bimhs-thizn-cpeo-dfzdap
8141 thpym-eta-mes-bnsdap
8142 me2py-tridi-men-bhsdap
8143 bim-pymea-men-bhsdab
8144 bim-24thiz-ocho-aspbzla
8145 dhim-mepazin-fo-psdap
8146 nim-dis-emo-mezphe
8147 impy-dimephmep-5pho-betainyl
8148 me2py-diphmep-5pho-mezphe 8149 nim-pymea-cpro-csdap
8150 amim-dimen-meto-zdab
8151 am2py-pnymea-emo-psdab
8152 pippy-tridi-fo-psdab
8153 am2py-thizs-napo-bphabs
8154 bimn-pazin-meo-psdap
8155 piraz-mepipen2-mmen-thizzdap
8156 imhs-pazin-mes-bhsdab
8157 im-amo2-ocho-psdap
8158 ec-ams3-meo-glubzla
8159 bim-dimephmep-emo-betapy
8160 bhs-24thizman2-ocho-dfzdap
8161 nmhs-24thizman2-oem-bsdap
8162 tolhs-dimen-emo-bhsdab
8163 pippy-24thizman2-meo-aspaba
8164 bhs-edian2-5amo-ppsdap
8165 2py-amo2-meo-bnsdap
8166 2pmhs-m25thiz-ocho-psdab
8167 imhs-trias-eoco-mezphe
8168 nmhs-m25thiz-mommo-aspibua
8169 bhs-mepipe-eoco-psdap
8170 pippy-mea2s-ocho-zdab
8171 menim-m24thiz-mes-aspibua
8172 hythpym-eta-napo-glyzdap
8173 dhim-diphmem-meo-psdap
8174 thpym-amn2-fo-psdab
8175 am2py-amn3-chexo-dfzdap
8176 imhs-edian2-5pho-bnsdap
8177 n2py-24oxman2-no1-bnsdap
8178 im-mepazin-pyo-bhsdap
8179 dhim-tetradi-oem-mezphe
8180 2pmhs-mepipe2-oem-nzdab
8181 piraz-25thizman2-mecpo-csdap
8182 2pmhs-din-5pho-betapy
8183 2py-amn2-no2-bhsdap
8184 impy-propn-meo-zdab
8185 moegua-am2-sem-nzdab
8186 2py-amn2-men-osdap
8187 pippy-trias-eoco-tsdap
8188 dpam-mepipe2-oem-nzdap
8189 thpym-pymea-pro-bnsdap
8190 amim-3diaz-meo-dfzdap
8191 bim-amn2-no1-bhsdap
8192 dhim-dimephmep-napo-betainyl
8193 bimhs-pipa-mecpo-zdap
8194 prhs-mepipe-meo-betapy
8195 pippy-diphmep-no1-mezphe
8196 bim-edian2-eoco-psdap
8197 bhs-dimen-chexo-betapy
8198 amim-pnymea-no2-dfzdap
8199 pippy-3pazin-eoco-mezphe
8200 nmhs-dis-no1-zdap
8201 dmbim-pyma2-pro-ibsdap
8202 thpym-eta-mes-bhsdap
8203 prhs-am2-oem-nzdab
8204 deam-amn3-5amo-aspaba
8205 impy-dimephmep-no1-betadcph
8206 bhs-pymea-no1-zdabs
8207 z-amn3-napo-glyzdap
8208 amim-25oxman2-men-zdab
8209 bim-diphmep-meo-betainyl
8210 piraz-24thizman2-4amo-bnsdap
8211 4pmhs -propn-imo-aspibua
8212 nim-din-chexo-psdab
8213 hythpym-thizn-emo-bsdap
8214 pyrhs-trias-hso-psdab
8215 ibhs-dimen-eoco-betapy
8216 am2py-m24thizman2-meo-mezphe
8217 dhim-dimephmep-no1-bphabs
8218 am2py-24thizman2-no1-aval
8219 mepip-trias-napo-bnsdap
8220 nmhs-dimephmep-chexo-zdap
8221 fthpym-mepipe-hso-aspbzla
8222 imhs-mepipe-mes-glyzdap
8223 bhs-dipch-5amo-betainyl
8224 dhim-pazin-eoco-bphabs
8225 dmbim-dimephmep-no2-asppha
8226 nmor-ams2-pro-betadcph
8227 nim-3diaz-5amo-ppsdap
8228 impy-eta-meo-psdab
8229 pippy-dimen-mmen-zdabs
8230 2py-pnymea-emo-bhsdap
8231 impy-edian2-fo-psdap
8232 bim-diphmep-imo-mezphe
8233 hythpym-thizn-emo-psdap
8234 phhs-din-fo-bhsdab
8235 dmbim-edian2-5pho-glupha
8236 prhs-am2-oem-nbetabnaphth
8237 bhs-mepipe2-oem-nbetameph
8238 nmor-diphmep-oem-aspbzla
8239 2py-edian2-oem-psdap
8240 pyrhs-edian2-baeo-bphabs
8241 2py-dimen-hso-oxal
8242 2py-mepipen2-5amo-psdab
8243 mepip-mepipen2-5amo-thizzdap
8244 thpym-m24thiz-chexo-bnsdap
8245 bhs-indan2-imo-bsdap
8246 tolhs-mepipen2-oeto-aspibua
8247 bimhs-eta-no2-zorn
8248 thpym-mepipe-eoco-bnsdap
8249 bhs-eta-no1-zdab
8250 edothpym-24thizman2-men-betapy
8251 dmbim-pnymea-5amo-aspaba
8252 impy-thizo-fo-betaet
8253 imhs-mepipe-eoco-zdab
8254 mepip-amo2-pyo-psdap
8255 chhs-m25thiz-chexo-bhsdab
8256 hythpym-m25thiz-no2-dfzdap
8257 nim-ams2-5pho-aspibua
8258 am4py-pnymea-oem-zdap
8259 gua-pipa-men-bphabs
8260 bimhs-25oxman2-oem-mezphe
8261 2py-amn2-eoco-bsdap
8262 ibhs-pymea-cpeo-zdapee
8263 z-amn3-pheo-aval
8264 bz-dimephmem-cnmo-zorn
8265 mam2py-thizn-5pho-bsdap
8266 piraz-ms-oeto-bsdap
8267 bimhs-24thizman2-imo-aspibua
8268 fthpym-propa2s-imo-bhsdab
8269 thpym-am3diaz-napo-aspbzla
8270 hythpym-dis-aco-betadcph
8271 bhs-amo2-meo-betadcph
8272 bimhs-am3-oem-nzdab
8273 hythpym-pipmea-napo-zdabs
8274 amim-ms-5pho-psdap
8275 hythpym-pnymea-ocho-bphabs
8276 2py-24thiz-oem-zorn
8277 2py-pipa-chexo-mezphe
8278 ppy-dimephmem-fo-betainyl
8279 mam2py-mepipe-napo-betadcph
8280 hythpym-edian2-fo-betapy
8281 piraz-propa2s-fo-bhsdab
8282 pyrhs-tridi-nmo-betainyl 8283 piraz-diphmep-5amo-csdap
8284 ppy-pipmea-ocho-bphabs
8285 2pmhs-thizn-napo-asppha
8286 impy-25thiman2-chexo-zdap
8287 bhs-mepipe-eoco-zdap
8288 thpym-25oxman2-oem-zdap
8289 2py-pyma2-napo-psdab
8290 thpym-amn2-mes-bsdap
8291 mam2py-25oxman2-5amo-betaet
8292 dmbim-am2-sem-nbeta34dimeoph
8293 pippy-pipmes-meteto-zdabs
8294 hythpym-pentadi-no1-zdabs
8295 mam2py-butn-napo-thizzdap
8296 thpym-pipa-napo-betadcph
8297 pippy-ams2-nmo-betapy
8298 am4py-diphmem-oem-glyzdap
8299 bimhs-mepipe2-oem-nbetab naphth
8300 thpym-2pazin-peo-glyzdap
8301 bhs-eta-eoco-psdap
8302 2pmhs-diphmem-oem-zdap
8303 pippy-pnymea-no1-csdap
8304 bim-edia2-sem-nbetameph
8305 mam2py-25thizman2-fo-mezphe
8306 imhs-trias-pheo-zdabs
8307 pyrhs-m25thizman2-napo-glyzdap
8308 hythpym-24thizman2-no1-bhsdab
8309 imhs-ams2-pyo-psdab
8310 phpip-amo2-oem-ppsdap
8311 bhs-24thizman2-men-betapy
8312 impy-m25thiz-pyo-betapy
8313 impy-m25thiz-nmo-glyzdap
8314 hythpym-din-cpeo-aspibua
8315 thpym-pymea-no1-zdap
8316 nmor-3diaz-pyo-psdap
8317 me-thizn-men-bphabs
8318 bim-eta-no1-psdab
8319 bim-mepipen2-imo-aspbzla
8320 bhs-mepipe-no2-bnsdap
8321 me2py-m25thizman2-napo-ppsdap
8322 pippy-propa2s-mecpo-bhsdab
8323 imhs-25oxman2-imo-mezphe
8324 bimhs-pipm es-5pho-mezphe
8325 bim-25thizman2-napo-betainyl
8326 moegua-trias-imo-betadcph
8327 am2py-pipmea-eoco-dfzdap
8328 mam2py-ams2-fo-glyzdap
8329 prhs-din-meo-bphabs
8330 pippy-pipa-oem-betadcph
8331 am2py-mepazin-ocho-bsdap
8332 amim-mepipen2-eoco-mezphe
8333 thpym-mea-fo-asppha
8334 ec-amn3-chexo-aspaba
8335 mam2py-mea-chexo-zdap
8336 amim-amn2-no1-dfzdap
8337 hythpym-25thizman2-no1-bhsdab
8338 bimhs-dimen-emo-glyzdap
8339 mam2py-m24thizman2-5pho-bsdap
8340 hythpym-dich-no1-betainyl
8341 amim-tetras-oem-zdabs
8342 prhs-diphmep-cno-mezphe
8343 2py-dimephmem-fo-glupha
8344 morhs-mepipe-ocho-bhsdab
8345 pippy-m25thiz-fo-aval
8346 impy-25thiz-fo-aval
8347 impy-indan2-mecpo-betapy
8348 2py-dimen-emo-betaet
8349 thpym-pipa-no1-bsdap
8350 am2py-mepipe-meteto-zdabs
8351 dmam-diphmem-eoco-aspbzla
8352 thpym-tetradi-meo-csdap
8353 2py-eta-mes-betapy
8354 am2py-pipmea-baeo-betaet
8355 bim-m25oxman2-oeto-zdap
8356 pippy-amn2-meo-dfzdap
8357 dmthpym-tridi-fo-dfzdap
8358 gua-mepazin-meto-csdap
8359 ppy-dimephmem-emo-psdapee
8360 mam2py-eta-meo-osdap
8361 pyraz-eta-emo-bhsdab
8362 me2py-ms-5amo-aspibua
8363 mepip-tetradi-cnmo-psdab
8364 z-25thiz-5amo-zlys
8365 amim-am3-oem-nbetapy
8366 nmor-m24thiman2-fo-mezphe
8367 fthpym-mea2s-chexo-betadcph
8368 am2py-24thiz-cnmo-dfzdap
8369 moegua-dimen-5pho-osdap
8370 morhs-dipch-emo-zdap
8371 amim-edian2-peo-betainyl
8372 2py-tetradi-chexo-betapy
8373 imhs-am3diaz-oem-csdap
8374 moegua-mepipen2-mecpo-bsdap
8375 z-diphmep-no2-zdab
8376 me2py-pnymea-pro-bhsdap
8377 n2py-m24thizman2-emo-psdab
8378 impy-tetradi-pyo-betapy
8379 piraz-edian2-napo-betapy
8380 thpym-edian2-no2-zdap
8381 prhs-diphmem-baeo-bsdap
8382 bim-pyma2-5amo-bnsdap
8383 nim-tetradi-chexo-aspbzla
8384 amthiaz-pazin-5amo-zdap
8385 amim-pipmea-meo-mezphe
8386 impy-25oxman2-4amo-betadcph
8387 amim-tetradi-imo-aspibua
8388 2py-amn2-mes-psdab
8389 deam-dio-cnmo-dfzdap
8390 2py-hexadi-5pho-aspbzla
8391 bhs-mepipe-meo-betapy
8392 amim-props-pheo-bsdap
8393 me2py-24thiz-paco-betainyl
8394 impy-tetradi-no1-psdab
8395 edothpym-amn3-cpro-bhsdab
8396 bhs-mepipe-oem-bnsdap
8397 piraz-m24thiman2-no1-bhsdab
8398 ppy-pymea-ocho-csdap
8399 imhs-m25thiz-meto-ppsdap
8400 phpip-amn2-fo-glyzdap
8401 am2py-25oxman2-no1-bhsdab
8402 me2py-dimephmem-eoco-asppha
8403 n2py-edian2-meo-betainyl
8404 me-trias-no2-mezphe
8405 npip-2pazin-emo-bsdap
8406 piraz-mepipen2-emo-psdapee
8407 cl3pyme-pipmea-eoco-bphabs
8408 am4py-trias-no2-ibsdap
8409 impy-m25thiz-meo-zlys
8410 piraz-dimen-emo-zdab
8411 2pmhs-tetradi-5amo-glyzdap
8412 am2py-dimephmem-ocho-bhsdap
8413 phhs-tridi-5amo-betadcph
8414 2py-24thizman2-men-bnsdap
8415 am2py-pentas-pheo-tsdap
8416 impy-pipmeo-mes-zdabs 8417 me-m25oxman2-5pho-dfzdap
8418 piraz-diphmep-pro-bsdap
8419 dhim-dis-chexo-betadcph
8420 imhs-3pazin-no1-aspibua
8421 dmbim-pazin-imo-aval
8422 2py-pnymea-mmen-asppha
8423 bhs-mepipe-meo-bnsdap
8424 hythpym-dimephmem-no2-betainyl
8425 ppy-24thiz-men-betainyl
8426 bhs-amn3-ocho-bsdap
8427 menim-25oxman2-daco-zdab
8428 me2py-dis-aco-bhsdab
8429 imhs-dis-emo-psdap
8430 4pmhs-edia2-sem-nbeta34 dimeoph
8431 bim-edian2-no2-psdap
8432 thpym-pipmea-no2-aspibua
8433 bhs-am2-oem-nbetameph
8434 amim-mepipe2-sem-nbetameph
8435 me2py-thizs-paco-bhsdap
8436 ec-am2-sem-nbeta34dimeoph
8437 mam2py-din-no1-glyzdap
8438 am2py-dipch-mes-zdap
8439 piraz-dimephmep-no1-aspibua
8440 hythpym-dio-mes-osdap
8441 imhs-thizo-pro-glyzdap
8442 bimhs-pipa-hso-aspbzla
8443 amim-pipa-5pho-zdabs
8444 me2py-mepazin-men-zdabs
8445 imhs-amn2-mes-betainyl
8446 im-eta-mecpo-zdap
8447 imhs-25thiman2-no2-aspbzla
8448 bz-25thiz-cpro-aspaba
8449 bhs-diphmem-no2-psdap
8450 bhs-m25thiz-5amo-bsdap
8451 piraz-tetradi-5amo-bphabs
8452 thpym-edian2-oem-psdap
8453 moegua-ams2-nmo-psdab
8454 moegua-mea2s-chexo-bhsdab
8455 hythpym-eta-men-betainyl
8456 nim-25thiz-4amo-betapy
8457 mam2py-25thiman2-eoco-aspibua
8458 chmhs-thizn-eoco-betainyl
8459 z-m24thiz-5pho-csdap
8460 pippy-pnymea-imo-bnsdap
8461 bhs-edian2-no1-zdab
8462 z-ams2-ocho-zdabs
8463 nmor-amo3-5amo-mezphe
8464 ppy-thizn-no2-csdap
8465 hythpym-dipch-chexo-csdap
8466 pyraz-pipmea-oem-bhsdab
8467 bhs-pazin-mes-bsdap
8468 me-amn3-pro-dfzdap
8469 piraz-24thizman2-ocho-glyzdap
8470 ppy-amn3-eoco-betapy
8471 amim-diphmep-nmo-betapy
8472 me2py-m25thiz-4pho-zdap
8473 me2py-pymea-napo-aspaba
8474 emnim-edia2-sem-nbetabnaphth
8475 pyraz-mepipen2-napo-zdabs
8476 chhs-edian2-no1-dfzdap
8477 deam-din-no2-ibsdap
8478 gua-thizn-fo-tsdap
8479 mam2py-m24thizman2-5pho-zdab
8480 piraz-m24thiman2-no2-zdabs
8481 dhim-edian2-chexo-bhsdab
8482 thpym-mea2s-no2-bhsdap
8483 dhim-diphmep-pheo-csdap
8484 me2py-mepipen2-no2-asppha
8485 amim-am3-sem-nbetabnaphth
8486 piraz-tridi-imo-zdabs
8487 fthpym-amo2-5pho-glyzdap
8488 pippy-amn2-napo-zdap
8489 piraz-amn3-no1-betadcph
8490 z-tridi-nmo-mezphe
8491 bimhs-pipmea-5amo-bphabs
8492 am4py-edia2-oem-nzdab
8493 emnim-m25thiz-meto-bhsdab
8494 bimhs-pyma2-cno-mezphe
8495 pippy-dimephmep-men-bsdap
8496 hythpym-am3-sem-nbetabnaphth
8497 piraz-n2nme2n-oem-zdap
8498 mam2py-dis-5amo-betapy
8499 hythpym-dimephmem-chexo-dfzdap
8500 mam2py-ams2-daco-osdap
8501 pyraz-edian2-ocho-psdab
8502 am2py-m24thizman2-meto-aval
8503 hythpym-thizn-emo-bhsdap
8504 moegua-ams2-no2-zdab
8505 moegua-ams2-imo-aspbzla
8506 bim-dimephmem-meo-betadcph
8507 am2py-m24thizman2-aco-bnsdap
8508 mepip-tridi-men-bnsdap
8509 bhs-pipa-no1-aspibua
8510 ibhs-dimephmep-men-bnsdap
8511 piraz-dis-chexo-bsdap
8512 edothpym-amn2-emo-zdapee
8513 mepip-24oxman2-fo-aval
8514 impy-tetradi-5amo-glyzdap
8515 2py-mepipen2-eoco-zdap
8516 am-diphmep-no2-betadcph
8517 bim-pnymea-hso-mezphe
8518 piraz-24thiz-cno-glyzdap
8519 amim-2pazin-napo-tsdap
8520 bimhs-n24thiman-mommo-bnsdap
8521 am-amn3-5pho-aspibua
8522 bim-eta-chexo-betapy
8523 dmam-pazin-5amo-zdap
8524 imhs-m24thizman2-napo-bnsdap
8525 thpym-ams2-eoco-psdap
8526 chhs-24thizman2-imo-betadcph
8527 pippy-diphmep-meo-glyzdap
8528 am4py-am2-sem-nzdap
8529 bhs-amn2-5pho-psdap
8530 pippy-dimephmep-5amo-bnsdap
8531 menim-indan2-no1-tsdap
8532 me2py-tridi-meo-bphabs
8533 cl3pyme-ams2-4pho-psdap
8534 imhs-amn2-5pho-betapy
8535 pippy-diaz-fo-psdapee
8536 bhs-mepipe2-oem-nbetabnaphth
8537 hythpym-mepipen2-no1-betapy
8538 2py-edian2-no2-betapy
8539 2py-diphmep-imo-glubzla
8540 me-mepipe2-oem-nbeta34dimeoph
8541 edothpym-eta-oeto-bsdap
8542 pyr-diphmep-fo-bnsdap
8543 pippy-dimen-cnmo-aspbzla
8544 hythpym-pazi2n-ocho-betainyl
8545 thpym-dis-napo-psdab
8546 chmhs-2pazin-men-dfzdap
8547 bim-edian2-ocho-bhsdap
8548 pippy-pipa-5amo-betadcph
8549 bzl-n2nme2n-men-psdab
8550 2py-amn2-napo-psdab 8551 bimhs-mepipen2-mes-mezphe
8552 me2py-diphmep-mes-dfzdap
8553 morhs-ams2-nmo-glubzla
8554 edothpym-hexadi-fo-zdabs
8555 thpym-pazin-no2-zdap
8556 bimhs-pentas-5amo-glyzdap
8557 am2py-tridi-cpro-csdap
8558 bimhs-m25thiz-mes-aspaba
8559 impy-24thizman2-no2-betainyl
8560 4pmhs-m25thiman2-imo-zlys
8561 dmbim-eta2s-meteto-aspibua
8562 me2py-m24thizman2-meteto-zorn
8563 bz-thizn-cno-psdab
8564 edothpym-diaz-emo-bnsdap
8565 amim-amn3-fo-csdap
8566 thpym-amn2-5pho-psdap
8567 me2py-dimephmep-imo-ppsdap
8568 me2py-m25thiz-daco-asppha
8569 amim-dimen-imo-aspibua
8570 morhs-dimephmem-fo-mezphe
8571 thpym-pazin-5pho-zdab
8572 2py-mepipen2-5pho-thizzdap
8573 bimhs-amo2-5amo-asppha
8574 nmor-am3-sem-nbeta34dimeoph
8575 bim-dimephmep-meto-aspbzla
8576 bhs-diphmem-oem-aspbzla
8577 me2py-pazin-nmo-psdab
8578 me2py-am3-sem-nbetapy
8579 hythpym-24thizman2-napo-aval
8580 2py-eta-eoco-zdap
8581 dhim-pipmea-5amo-ppsdap
8582 impy-amo2-cnmo-zdabs
8583 pyr-amo3-ocho-aspaba
8584 bimhs-edian2-napo-bphabs
8585 pippy-mepipen2-no2-glubzla
8586 pippy-dich-mommo-aspibua
8587 thpym-din-no2-aspibua
8588 bhs-pazin-meo-psdap
8589 npip-amn3-mommo-csdap
8590 n2py-dimephmem-meo-bhsdap
8591 bim-dis-oem-betainyl
8592 2py-pipa-4amo-psdap
8593 n2py-thizs-ocho-bphabs
8594 imhs-eta-napo-psdab
8595 im-pnymea-emo-betainyl
8596 hythpym-dimen-no1-asppha
8597 4pmhs-25thiz-oem-betadcph
8598 2py-din-pro-oxal
8599 bim-edian2-no2-zdap
8600 gua-mea2s-fo-zdap
8601 thpym-pipmea-chexo-csdap
8602 bhs-n2o2n-mommo-bsdap
8603 phhs-diphmep-5amo-psdab
8604 ppy-thizn-imo-csdap
8605 4pmhs-diaz-imo-psdap
8606 nmhs-am2-oem-npsdap
8607 tolhs-mea-fio-csdap
8608 impy-pipmeo-no1-ppsdap
8609 4pmhs-trias-imo-betadcph
8610 thpym-pazin-5pho-bhsdap
8611 mam2py-din-meo-mezphe
8612 bim-eta-no2-bhsdap
8613 bhs-25thiz-fo-bphabs
8614 2py-amo2-mecpo-asppha
8615 hythpym-dis-no1-bphabs
8616 bim-pipa-meto-ppsdap
8617 me2py-2pazin-5pho-betapy
8618 nmhs-25oxman2-men-bnsdap
8619 tolhs-diphmep-daco-betadcph
8620 pippy-pentas-fo-mezphe
8621 pyrhs-tetradi-cno-mezphe
8622 z-mepipe2-oem-nbeta34dimeoph
8623 mepip-ams3-mes-glupha
8624 4pmhs-tridi-5pho-bhsdab
8625 bhs-mepipe-eoco-bnsdap
8626 am-edian2-fo-bphabs
8627 phhs-pyma2-napo-bnsdap
8628 mepip-dis-nmo-aspbzla
8629 2py-mepipe-ocho-bhsdap
8630 impy-edia2-sem-nbeta34dimeoph
8631 ec-amn3-men-dfzdap
8632 im-thizn-baeo-psdab
8633 bhs-mepipe-5pho-zdap
8634 2py-25oxman2-meo-psdap
8635 chmhs-din-chexo-asppha
8636 bim-amn2-mes-zdap
8637 bhs-tetradi-men-csdap
8638 bim-24thizman2-oem-betapy
8639 amim-mepipen2-eoco-aspibua
8640 imhs-m2thiz-no2-aspibua
8641 chmhs-m25thiz-chexo-zdabs
8642 pyr-am2-oem-nbeta34dimeoph
8643 impy-24thiman2-napo-betadcph
8644 cl3pyme-dich-meo-psdap
8645 ibhs-diphmem-no2-betainyl
8646 mepip-24thizman2-mes-ibsdap
8647 z-24thizman2-mes-bsdap
8648 tolhs-tetras-mommo-psdab
8649 amim-mea-pyo-bhsdap
8650 bhs-amo3-5amo-glupha
8651 bim-dimen-meteto-zdapee
8652 me2py-mepipe-daco-bhsdap
8653 bimhs-dimephmem-5pho-bhsdab
8654 bim-25thizman2-nmo-psdab
8655 bimhs-mea-occho-bsdap
8656 am2py-tridi-imo-asppha
8657 pippy-mepipe2-sem-nbetapy
8658 emnim-diphmep-imo-bsdap
8659 piraz-m25thiz-oem-bphabs
8660 amim-am2-sem-nzdab
8661 piraz-diphmem-eoco-zorn
8662 bim-edian2-no2-bnsdap
8663 bim-24thizman2-imo-betapy
8664 am2py-amn3-no2-bhsdap
8665 amim-dich-eoco-bsdap
8666 bzl-am2-sem-npsdap
8667 impy-m2sthiz-daco-csdap
8668 z-24thiman-mes-mezphe
8669 imhs-dimephmem-pheo-zorn
8670 amim-amn2-pheo-bhsdap
8671 bhs-diphmep-emo-bhsdab
8672 nmor-pipmea-chexo-betainyl
8673 bhs-pazin-meo-bhsdap
8674 phpip-pipmea-imo-aspbzla
8675 dhim-din-chexo-aspibua
8676 pippy-amn3-oem-zdabs
8677 bim-tridi-chexo-aspibua
8678 thpym-pazin-5amo-aspbzla
8679 me2py-24oxman2-fo-mezphe
8680 me2py-diaz-5pho-zdap
8681 bimhs-dimen-chexo-mezphe
8682 phpip-pymea-men-bhsdap
8683 bhs-ms-4amo-mezphe
8684 dhim-pipa-napo-betadcph 8685 bimhs-thizn-mmen-asppha
8686 bhs-mepipen2-no2-betainyl
8687 2pmhs-thizn-5amo-zlys
8688 piraz-ams2-mmen-psdab
8689 impy-dio-no1-betainyl
8690 imhs-eta-meo-bsdap
8691 imhs-amn2-no2-bsdap
8692 pippy-pyma2-5amo-dfzdap
8693 bz-thizn-no1-zdabs
8694 2pmhs-thizn-no1-ibsdap
8695 thpym-tridi-imo-zdap
8696 am4py-m25thiz-cnmo-csdap
8697 imhs-m25thizman2-ocho-csdap
8698 bzl-24oxman2-meo-zdap
8699 mam2py-edian2-pro-bphabs
8700 2py-mepipe-no1-bhsdap
8701 amim-amn3-paco-glyzdap
8702 morhs-24thiz-5pho-psdap
8703 dpam-dis-emo-betainyl
8704 imhs-pazin-eoco-zdab
8705 ibhs-n24thiman-imo-dfzdap
8706 pippy-pipa-chexo-aspibua
8707 am2py-diphmem-mommo-bhsdab
8708 imhs-pnymea-pheo-aspbzla
8709 bim-pazin-oem-bsdap
8710 morhs-pymea-mes-betainyl
8711 thpym-pentas-ocho-betadcph
8712 thpym-trias-men-bhsdap
8713 2py-edian2-oem-bhsdap
8714 chhs-dimen-nmo-betapy
8715 imhs-ams2-oem-betainyl
8716 bhs-m25thiz-baeo-dfzdap
8717 am-amn3-mecpo-betapy
8718 menim-dio-men-bphabs
8719 bhs-m24thiman2-baeo-zdab
8720 imhs-m24thiman2-pyo-betapy
8721 pyraz-pyma2-imo-dfzdap
8722 nmhs-mea-meto-psdab
8723 am4py-25oxman2-no1-aspibua
8724 imhs-amn3-ocho-zdap
8725 ibhs-diphmep-meo-glyzdap
8726 piraz-ams2-no1-aspibua
8727 gua-edian2-cpro-aspibua
8728 am-trias-5amo-ibsdap
8729 hythpym-mepazin-imo-bsdap
8730 am4py-edia2-oem-npsdap
8731 bhs-tetras-men-bhsdab
8732 dhim-mepipen2-cpro-glubzla
8733 bim-pnymea-chexo-betapy
8734 pyraz-pnymea-5pho-dfzdap
8735 phpip-pazin-pyo-csdap
8736 moegua-amo2-emo-bsdap
8737 imhs-edian2-no1-zdap
8738 chmhs-tetras-no1-zdap
8739 thpym-amn2-ocho-betapy
8740 npip-eta-eoco-csdap
8741 amthiaz-mepipe-5pho-psdab
8742 pyrhs-amn3-eoco-betadcph
8743 mepip-diphmep-5amo-zdab
8744 amim-dimephmep-mes-zlys
8745 bim-thizn-emo-bnsdap
8746 imhs-ams2-meo-bnsdap
8747 am-din-no2-bhsdap
8748 imhs-eta-mes-bhsdap
8749 impy-am2-oem-nzdab
8750 thpym-ams2-mecpo-psdapee
8751 2py-24thiz-napo-glyzdap
8752 bzl-25oxman2-mes-bnsdap
8753 edothpym-mepazin-aco-aspbzla
8754 thpym-eta-no1-zdap
8755 bz-tetras-pheo-bhsdap
8756 me2py-thizn-eoco-bsdap
8757 bim-mepazin-emo-aspibua
8758 gua-pipa-meto-csdap
8759 ppy-am3diaz-emo-psdab
8760 am2py-din-eoco-aval
8761 am4py-pyma2-fo-csdap
8762 dmthpym-24thiman-emo-betainyl
8763 dmam-mepipen2-no2-zdabs
8764 bimhs-m24thizman2-no1-bhsdab
8765 me2py-24thiz-emo-zdab
8766 imhs-mepipe-5pho-zdab
8767 moegua-mea-ocho-zdab
8768 piraz-diphmem-emo-zlys
8769 prhs-diphmem-no2-aspibua
8770 imhs-pipmea-mes-bhsdap
8771 piraz-pazin-napo-psdab
8772 am2py-pipa-4amo-ibsdap
8773 edothpym-dio-imo-bhsdap
8774 thpym-pymea-emo-mezphe
8775 thpym-eta-mes-zdap
8776 thpym-2pazin-imo-zdabs
8777 piraz-dimephmep-meto-csdap
8778 am2py-24thizman2-5pho-psdap
8779 chmhs-pipa-no2-ppsdap
8780 amthiaz-din-emo-csdap
8781 bim-dis-mes-zdap
8782 pyrhs-pipmea-mes-ppsdap
8783 dhim-diphmep-oem-bnsdap
8784 nmhs-mepipe-nmo-asppha
8785 mam2py-eta-5amo-bphabs
8786 edothpym-m25thiz-oem-psdap
8787 pippy-dimephmem-imo-psdapee
8788 piraz-dimephmep-5pho-zdabs
8789 emnim-pazin-daco-tsdap
8790 impy-am3-sem-nbeta34dimeoph
8791 moegua-edia2-sem-nbetameph
8792 am2py-tetradi-eoco-oxal
8793 pyrhs-amn2-mes-bphabs
8794 bim-hexadi-no1-zdab
8795 pyraz-ams2-no2-bphabs
8796 bim-m25thizman2-emo-csdap
8797 am2py-dimephmem-meo-aspibua
8798 bimhs-dimephmep-men-bphabs
8799 bhs-amn3-emo-dfzdap
8800 thpym-diphmem-meteto-mezphe
8801 2py-edian2-men-glupha
8802 dpam-m24thizman2-oem-glyzdap
8803 impy-thiz-eoco-betadcph
8804 pippy-pipa-5amo-bhsdab
8805 dhim-mepazin-oem-csdap
8806 2py-amn2-5pho-bhsdap
8807 bz-diphmem-mommo-betainyl
8808 impy-mepipe-oem-betainyl
8809 chmhs-24thiz-meo-aspibua
8810 bhs-25thiz-cno-dfzdap
8811 nmor-diphmem-napo-psdapee
8812 me2py-24thiz-men-betainyl
8813 me2py-amn2-5pho-tsdap
8814 am2py-diphmem-daco-zdab
8815 dhim-mepipe2-oem-nbeta34-dimeoph
8816 imhs-tridi-men-dfzdap
8817 4pmhs-pipa-napo-dfzdap
8818 bhs-din-pyo-mezphe 8819 imhs-pazi2n-ocho-glyzdap
8820 bhs-25oxman2-chexo-aval
8821 piraz-pymea-emo-dfzdap
8822 phpip-m25thiz-napo-zdap
8823 dhim-dimen-ocho-bhsdab
8824 am2py-trias-emo-zdap
8825 bimhs-diphmem-emo-betapy
8826 dmbim-mepipe-oem-betainyl
8827 mepip-dimephmep-cpeo-bhsdab
8828 amim-m25oxman2-5pho-betapy
8829 moegua-propa2s-5amo-aspibua
8830 bhs-24thizman2-napo-oxal
8831 2py-mepipe-5pho-betapy
8832 z-amn3-emo-asppha
8833 thpym-tetras-mes-dfzdap
8834 imhs-diphmem-5amo-zdabs
8835 pippy-amn2-napo-zdap
8836 bhs-indan2-no2-psdap
8837 thpym-m24thiman2-cpro-dfzdap
8838 2py-pazin-5pho-bhsdap
8839 pippy-amo2-fo-asppha
8840 n2py-pipmea-napo-zdab
8841 me2py-am2-oem-nzdab
8842 amim-tridi-mes-psdapee
8843 dhim-pazin-eoco-dfzdap
8844 thpym-eta-no2-bsdap
8845 amim-24thizman2-ocho-dfzdap
8846 2py-amn2-5pho-psdab
8847 pippy-din-5amo-betadcph
8848 am2py-m25thiz-mes-bsdap
8849 am2py-25oxman2-emo-zdabs
8850 bhs-mea-cpro-bsdap
8851 imhs-eta-no2-bhsdap
8852 menim-mepipe-daco-zdabs
8853 moegua-pipmeo-mommo-bnsdap
8854 am4py-diphmep-oem-bsdap
8855 2py-pazin-oem-bhsdap
8856 hythpym-pazin-5pho-zdabs
8857 me-pipmea-no2-zdabs
8858 dpam-mepazin-no1-betadcph
8859 nmor-dis-fo-bphabs
8860 hythpym-edia2-oem-nbetab naphth
8861 phpip-pyma2-mes-mezphe
8862 inLhs-n2o2n-eoco-zdap
8863 imhs-eta-no1-zdabs
8864 dmbim-m24thiz-napo-betapy
8865 mam2py-diphmep-emo-psdap
8866 pyraz-trias-meo-mezphe
8867 emnim-24thiz-oem-psdapee
8868 dhim-pnymea-cpeo-zdap
8869 bim-mepipen2-imo-betadcph
8870 pippy-24thizman2-no2-zdab
8871 nmor-pipmea-men-zdabs
8872 imhs-mepipe2-oem-npsdap
8873 bz-amn2-5amo-aval
8874 me-ams2-cno-betainyl
8875 bim-pnymea-napo-betadcph
8876 bhs-dimephmem-emo-mezphe
8877 chhs-dimephmep-chexo-aval
8878 bim-mepipe-mes-zdap
8879 gua-am3-sem-nzdap
8880 cl3pyme-ms-mes-aspbzla
8881 imhs-mepipe-fo-psdap
8882 dmthpym-amn3-eoco-betapy
8883 bhs-pazin-oem-zdap
8884 bim-din-4amo-psdap
8885 hythpym-diphmep-ocho-betainyl
8886 dhim-tetradi-mommo-bhsdab
8887 nmhs-thizn-5amo-zdab
8888 imhs-diphmep-napo-zdab
8889 dhim-thizo-fo-glyzdap
8890 bz-dis-no1-aval
8891 bhs-eta-oem-psdab
8892 am-dimephmem-5amo-glyzdap
8893 piraz-thizn-no2-zdabs
8894 z-dis-cno-bhsdap
8895 tolhs-24thiz-imo-bsdap
8896 bim-24thiz-imo-glubzla
8897 imhs-din-napo-mezphe
8898 bhs-dimen-emo-bhsdab
8899 impy-m24thizman2-oem-zdap
8900 imhs-amn2-no1-zdab
8901 ibhs-din-5amo-zdap
8902 z-pipmea-emo-betadcph
8903 thpym-ams2-chexo-bsdap
8904 thpym-mepipe-no2-bhsdap
8905 bim-amn2-ocho-zdap
8906 bhs-dis-5pho-zdab
8907 dhim-amo2-meo-bphabs
8908 tolhs-dis-paco-zdab
8909 npip-din-5pho-zlys
8910 impy-eta-ocho-zdabs
8911 pippy-eta-ocho-glyzdap
8912 pippy-amo2-no2-glyzdap
8913 amim-edian2-no2-dfzdap
8914 bimhs-m25thiz-meo-zdabs
8915 thpym-24thiman2-daco-psdap
8916 npip-dimephmep-emo-psdap
8917 am-mepazin-meo-asppha
8918 me2py-dimephmem-ocho-zdapee
8919 amim-diaz-emo-ibsdap
8920 bim-dimephmem-no2-bsdap
8921 impy-pnymea-fo-betaet
8922 pyr-ams2-napo-dfzdap
8923 2py-pipmea-eoco-bphabs
8924 me2py-mepazin-eoco-osdap
8925 thpym-mepipen2-emo-zdap
8926 am2py-dimephmep-pheo-bsdap
8927 pyrhs-pipmea-men-bsdap
8928 bim-pipmea-emo-mezphe
8929 deam-pipmea-meo-csdap
8930 2py-pipmes-fo-psdap
8931 dmam-pyma2-men-aspibua
8932 bim-trias-napo-bhsdab
8933 gua-pipmea-4amo-mezphe
8934 dhim-pyma2-emo-dfzdap
8935 bim-diaz-napo-glyzdap
8936 edothpym-dimen-5amo-mezphe
8937 amim-mn3-emo-bhsdap
8938 dmam-thizn-no2-zlys
8939 am2py-m24thizman2-emo-psdap
8940 pippy-am3diaz-hso-dfzdap
8941 bhs-eta-eoco-zdap
8942 dpam-propn-fo-betadcph
8943 me-am2-sem-npsdap
8944 im-am2-oem-nbeta34dimeoph
8945 me-n-2o2n-eoco-aspaba
8946 imhs-tetradi-5pho-bhsdab
8947 fthpym-n24thiman-napo-psdap
8948 amim-n2nme2n-mes-bhsdab
8949 dmthpym-thizn-eoco-zdab
8950 amim-pyma2-cnmo-asppha
8951 bimhs-n2nme2n-no2-bnsdap
8952 cl3pyme-24oxman2-ocho-ibsdap 8953 amim-ams2-momno-asppha
8954 2pmhs-25oxman2-ocho-bsdap
8955 hythpym-tridi-no2-bphabs
8956 bimhs-mepazin-5amo-thizzdap
8957 pyrhs-amn3-oeto-asppha
8958 imhs-amn2-mes-psdab
8959 2pmhs-indan2-chexo-psdab
8960 pippy-amn3-eoco-psdap
8961 dmthpym-mepazin-chexo-bhsdab
8962 mam2py-24thizman2-no2-mezphe
8963 pippy-diphmem-cnmo-zdabs
8964 mam2py-amn3-ocho-zdab
8965 me2py-mepipen2-aco-mezphe
8966 bhs-mepipe-paco-zlys
8967 dhim-trias-no1-bsdap
8968 piraz-pnymea-chexo-bhsdap
8969 dhim-dimephmep-5amo-csdap
8970 n2py-edian2-imo-betadcph
8971 thpym-butn-5amo-asppha
8972 bim-mepazin-emo-dfzdap
8973 me2py-pymea-napo-bnsdap
8974 2pmhs-25oxman2-baeo-zdabs
8975 bzl-m25thiz-no2-aspbzla
8976 bimhs-25oxman2-emo-betapy
8977 fthpym-diaz-ocho-betapy
8978 thpym-eta-no2-zdap
8979 phpip-m25thiman2-fo-bhsdap
8980 me2py-ams2-emo-betadcph
8981 pippy-pipmea-no1-bhsdap
8982 piraz-eta-5amo-mezphe
8983 hythpym-m24thizman2-men-asppha
8984 aim-pnymea-chexo-psdab
8985 dhim-tetradi-5pho-betainyl
8986 amim-amo2-eoco-bhsdap
8987 2py-amn2-meo-zdap
8988 thpym-mepipe-mes-zdap
8989 impy-mepipe-5amo-zdab
8990 bhs-am2-sem-npsdap
8991 menim-m24thiz-eoco-aspbzla
8992 2pmhs-amo2-hso-bphabs
8993 me2py-mepipe2-sem-nbetapy
8994 mam2py-pipmea-men-betadcph
8995 dmam-ams2-no2-aspibua
8996 dhim-pipmea-emo-aspibua
8997 2py-ams3-men-aspaba
8998 amim-pymea-eoco-aspibua
8999 2py-mepipe-meo-psdap
9000 bimhs-thizn-eoco-bhsdap
9001 impy-pipmea-daco-dfzdap
9002 mam2py-24thizman2-oem-psdap
9003 menim-ams2-oem-oxal
9004 bim-edian2-mes-betapy
9005 thpym-amn2-5pho-bnsdap
9006 2py-eta-no1-zdap
9007 ec-24thiz-chexo-asppha
9008 2py-pazin-eoco-zdap
9009 moegua-amo2-5pho-zdab
9010 pyrhs-mepazin-oem-csdap
9011 bimhs-am2-sem-npsdap
9012 me2py-edia2-sem-nbeta34-dimeoph
9013 4pmhs-amn3-napo-glyzdap
9014 me2py-2pazin-5pho-dfzdap
9015 bimhs-m24thizman2-napo-csdap
9016 bim-mepipe-ocho-zdabs
9017 npip-pyma2-fo-betainyl
9018 deam-eta-eoco-csdap
9019 4pmhs-pnymea-mes-zdabs
9020 2py-m25thiman2-5amo-zdap
9021 2py-25thiz-no2-csdap
9022 bhs-pipa-4amo-thizzdap
9023 amim-pipmeo-paco-aspbzla
9024 menim-trias-meo-glyzdap
9025 pyrhs-24thiman-men-dfzdap
9026 2py-24thiman2-5pho-bnsdap
9027 thpym-edian2-mes-psdap
9028 mam2py-mepipen2-meo-aspibua
9029 bimhs-pentadi-5amo-betapy
9030 imhs-amn2-imo-zdab
9031 nmhs-tridi-chexo-glyzdap
9032 thpym-24thiz-no2-ppsdap
9033 hythpym-amn2-5amo-bphabs
9034 am2py-dimephmem-fo-zdabs
9035 pyr-thizn-fo-betapy
9036 pippy-ams2-no1-aspbzla
9037 bz-mepipen2-mes-bnsdap
9038 piraz-mepazin-mecpo-betapy
9039 hythpym-amn2-oeto-zdap
9040 piraz-tridi-eoco-psdap
9041 bimhs-pipmea-ocho-betapy
9042 dhim-propa2s-peo-tsdap
9043 hythpym-dimephmep-napo-csdap
9044 2py-24thiman2-ocho-bhsdab
9045 2pmhs-propn-5pho-betainyl
9046 pippy-eta-mes-betainyl
9047 morhs-eta-chexo-zdap
9048 dmam-n2nme2n-5pho-dfzdap
9049 4pmhs-m25thiman2-no2-asppha
9050 am2py-diphmep-oeto-psdab
9051 amthiaz-tetradi-oem-betainyl
9052 prhs-pipmes-5pho-dfzdap
9053 hythpym-ams2-napo-glyzdap
9054 bhs-eta-no2-betapy
9055 am2py-pipmea-5amo-bhsdab
9056 phhs-diphmep-cno-bphabs
9057 imhs-dimephmem-ocho-bhsdab
9058 bzl-24thiz-meo-mezphe
9059 piraz-tridi-no2-bphabs
9060 impy-pipmea-aco-betapy
9061 me2py-mepazin-emo-bsdap
9062 amim-thizn-5amo-zdab
9063 bim-diphmep-eoco-zdap
9064 bim-pymea-no2-betaet
9065 am4py-indan2-5pho-bhsdab
9066 edothpym-m25thiz-meteto-psdab
9067 ec-edia2-oem-nbeta34dimeoph
9068 pippy-mepazin-peo-bnsdap
9069 impy-25oxman2-meo-mezphe
9070 dmam-pnymea-mes-zdab
9071 hythpym-m25thiz-pheo-bsdap
9072 hythpym-dimephmem-mes-glupha
9073 imhs-edian2-mes-zdab
9074 amim-tridi-ocho-bhsdap
9075 amim-pyma2-daco-betapy
9076 dhim-pipa-no1-bsdap
9077 thpym-mepazin-imo-zdabs
9078 imhs-eta-oem-bsdap
9079 n2py-24thizman2-no2-bnsdap
9080 mam2py-dimen-napo-glupha
9081 bzl-trias-meo-mezphe
9082 bhs-pazin-mes-bnsdap
9083 bhs-24thiz-hso-zdap
9084 pyrhs-eta-eoco-betainyl
9085 mepip-25oxman2-no2-zdabs
9086 imhs-amn2-ocho-bhsdap 9087 me2py-pipmea-oem-zdab
9088 hythpym-ams2-no2-glyzdap
9089 thpym-edian2-5pho-betapy
9090 im-hexadi-no1-bphabs
9091 pippy-tridi-emo-zdabs
9092 hythpym-m25thiz-men-bnsdap
9093 thpym-dimephmem-imo-mezphe
9094 impy-indan2-pyo-bhsdap
9095 dpam-tridi-mommo-mezphe
9096 thpym-diphmem-no2-bphabs
9097 ec-24thiz-5pho-zdap
9098 bim-m25thiman2-chexo-zdabs
9099 dpam-pipmea-daco-psdap
9100 pippy-m24oxman2-meo-ibsdap
9101 edothpym-25thiz-chexo-asppha
9102 mam2py-dimephmep-5pho-ppsdap
9103 bhs-edian2-5pho-zdab
9104 pyr-3pazin-napo-betainyl
9105 imhs-dimephmem-men-bphabs
9106 bhs-pnymea-napo-bhsdab
9107 am2py-m24thizman2-baeo-aspibua
9108 ec-m24thizman2-chexo-zorn
9109 am-mepipe-oem-aspbzla
9110 npip-amo2-5amo-bphabs
9111 dmam-pyma2-5pho-asppha
9112 cl3pyme-pyma2-imo-asppha
9113 bimhs-eta2s-no2-aspbzla
9114 pippy-25thiz-napo-psdab
9115 pippy-ms-5pho-zdap
9116 pippy-pentas-no1-dfzdap
9117 bim-amn3-eoco-zdapee
9118 moegua-pipmea-napo-psdap
9119 bhs-mepipe-meo-psdap
9120 dhim-trias-5amo-bhsdab
9121 hythpym-n24thiman-eoco-bphabs
9122 phhs-diphmem-emo-aspaba
9123 npip-tetradi-oem-bnsdap
9124 imhs-tridi-chexo-bhsdab
9125 piraz-pnymea-napo-psdab
9126 piraz-edia2-oem-nbetapy
9127 bim-amn2-5pho-bnsdap
9128 impy-pipmeo-pro-asppha
9129 piraz-m24thizman2-cpro-tsdap
9130 am2py-diphmem-emo-ppsdap
9131 am4py-pnymea-oem-aspbzla
9132 bhs-mepipen2-pro-betadcph
9133 2py-pymea-ocho-aspibua
9134 me2py-pipmea-fo-zdab
9135 cl3pyme-pymea-fo-zdabs
9136 me2py-m24thizman2-no1-zdab
9137 pippy-25oxman2-no2-mezphe
9138 bhs-pyma2-men-csdap
9139 inhs-m25thizman2-no2-betapy
9140 2py-ams2-hso-psdab
9141 dhim-25thizman2-imo-bhsdab
9142 bimhs-dimen-mes-zdap
9143 am-pyma2-fo-betainyl
9144 am-dimen-eoco-zdap
9145 menim-am3-sem-nbetameph
9146 pippy-amo2-eoco-psdab
9147 bhs-m24thiz-oem-zdabs
9148 imhs-pazin-oem-bnsdap
9149 morhs-pnymea-meteto-psdab
9150 amim-edia2-oem-nzdap
9151 dhim-m24thiz-cpeo-bsdap
9152 mam2py-m25thizman2-mes-betapy
9153 chhs-diphmep-5amo-tsdap
9154 z-diphmem-no2-bnsdap
9155 bimhs-edia2-oem-nbetabnaphth
9156 amim-pnymea-napo-bsdap
9157 piraz-pazin-emo-bnsdap
9158 am2py-din-eoco-bnsdap
9159 menim-tridi-no2-bhsdap
9160 mepip-pymea-pheo-betapy
9161 imhs-amn2-meo-zdab
9162 amim-pipa-fo-zdapee
9163 me2py-diphmem-no1-zlys
9164 thpym-eta-oem-bhsdap
9165 phhs-amn3-eoco-osdap
9166 imhs-thizn-oem-aspibua
9167 pippy-diphmem-cno-betapy
9168 phhs-tetradi-men-psdap
9169 pyraz-dimen-cpeo-psdapee
9170 bz-pnymea-eoco-zdap
9171 imhs-dis-ocho-psdap
9172 bim-thizn-baeo-mezphe
9173 imhs-pipmea-mes-psdap
9174 piraz-pipmea-no1-csdap
9175 bimhs-mea2s-cpro-bnsdap
9176 bim-edian2-no2-zdab
9177 mam2py-dimephmep-emo-betadcph
9178 am2py-mepazin-oeto-csdap
9179 2py-amn2-ocho-psdab
9180 me2py-dimephmep-imo-aspaba
9181 ec-24thizman2-ocho-bphabs
9182 bz-thizn-fo-zdab
9183 impy-m24thiz-oem-betadcph
9184 pyraz-dimephmem-4amo-psdab
9185 hythpym-pipa-5amo-betapy
9186 4pmhs-hexas-mes-bhsdap
9187 me2py-25thizman2-5amo-csdap
9188 tolhs-amn3-men-bnsdap
9189 mam2py-thizn-ocho-csdap
9190 thpym-ams2-mes-aspbzla
9191 2py-edian2-oem-zdab
9192 nmhs-amo2-napo-bhsdab
9193 bhs-mepazin-daco-zdabs
9194 dhim-eta2s-meo-zdabs
9195 mepip-dimen-mes-bnsdap
9196 pippy-thizn-fo-bhsdap
9197 mam2py-edia2-oem-npsdap
9198 thpym-thizo-no2-zdap
9199 npip-mea-emo-dfzdap
9200 bhs-amn2-mes-psdap
9201 ec-thizn-emo-aspbzla
9202 amim-n24thiman-daco-bhsdab
9203 dpam-amn2-imo-asppha
9204 imhs-24thizman2-cpro-asppha
9205 imhs-edian2-meo-bsdap
9206 2py-amn2-men-betadcph
9207 thpym-am2-sem-nbetapy
9208 bhs-m25thiz-5amo-aspibua
9209 im-n2o2n-5pho-zdab
9210 piraz-25oxman2-pro-bhsdap
9211 mam2py-mepipe-daco-csdap
9212 fthpym-m24thiman2-napo-betapy
9213 imhs-eta-mes-betapy
9214 bimhs-m24thizman2-men-zdabs
9215 hythpym-diphmep-oeto-aspibua
9216 dpam-m25thiz-no2-mezphe
9217 pyr-24oxman2-napo-bphabs
9218 piraz-mepipe-no1-bnsdap
9219 hythpym-mepipe-oem-psdab
9220 hythpym-25thiman-4pho-mezphe 9221 cl3pyme-thizs-cnmo-csdap
9222 me2py-edian2-5amo-glupha
9223 amim-trias-imo-asppha
9224 hythpym-m25thiz-emo-zdap
9225 piraz-pyma2-meo-zdap
9226 dhim-m25thiman2-aco-psdab
9227 thpym-mepipe-meo-psdab
9228 bimhs-din-no2-zdab
9229 amim-am2-oem-nzdap
9230 impy-pyma2-daco-glyzdap
9231 bimhs-eta-ocho-bhsdab
9232 prhs-mea2s-no1-asppha
9233 mam2py-25oxman2-napo-dfzdap
9234 gua-thizn-eoco-bphabs
9235 phpip-eta-men-bhsdap
9236 mam2py-dimephmem-5amo-glyzdap
9237 pippy-dis-ocho-psdap
9238 bimhs-m24thizman2-no2-dfzdap
9239 amim-m25thiz-pyo-csdap
9240 me2py-pymea-eoco-bsdap
9241 piraz-dimephmem-chexo-bhsdab
9242 2py-ms-mes-psdab
9243 pyr-dimephmem-mes-glyzdap
9244 impy-pymea-oem-bnsdap
9245 2pmhs-diphmem-5amo-bsdap
9246 bimhs-pipmea-fo-bsdap
9247 dmam-thizn-no1-zdabs
9248 mepip-dis-cpeo-betadcph
9249 2py-din-meo-osdap
9250 menim-pnymea-oeto-bphabs
9251 am2py-hexas-napo-bphabs
9252 impy-ams2-mes-mezphe
9253 thpym-pazin-pheo-dfzdap
9254 thpym-mepazin-ocho-betadcph
9255 pyraz-mepipen2-napo-aspibua
9256 bz-amn3-men-zdabs
9257 amim-pymea-pyo-mezphe
9258 4pmhs-mepipe-no2-zdabs
9259 bhs-amo2-baeo-dfzdap
9260 phpip-amn2-no1-dfzdap
9261 me2py-edia2-sem-nzdap
9262 amthiaz-24thizman2-imo-aspbzla
9263 ibhs-tetradi-oem-betadcph
9264 2py-mepipen2-eoco-bhsdab
9265 dmam-dimen-no2-betainyl
9266 dmthpym-dimephmep-5pho-mezphe
9267 ec-ams2-mes-psdab
9268 2py-eta-mes-zdap naphth
9269 nmhs-diphmem-daco-psdab
9270 mepip-mepipe-chexo-asppha
9271 2py-24thiz-emo-bhsdap
9272 imhs-amn2-oem-bnsdap
9273 impy-thizn-meo-bhsdab
9274 mam2py-tetradi-imo-zdab
9275 dhim-eta-oem-ppsdap
9276 bim-amo2-ocho-dfzdap
9277 imhs-pazin-mes-bnsdap
9278 bz-dimephmem-ocho-betapy
9279 pippy-25oxman2-pheo-bphabs
9280 thpym-mepipe-oem-betainyl
9281 bim-3diaz-5pho-glyzdap
9282 piraz-m24thizman2-hso-oxal
9283 menim-m25thiz-eoco-aspbzla
9284 z-din-no2-aspibua
9285 nmor-tetradi-4pho-csdap
9286 dhim-pymea-men-betapy
9287 me-pnymea-fo-asppha
9288 tolhs-amo2-no1-psdab
9289 imhs-eta-ocho-bnsdap
9290 2pmhs-m24thizman2-ocho-psdab
9291 am-edian2-5amo-zdab
9292 thpym-eta-no2-bnsdap
9293 pyr-24thizman2-chexo-bhsdap
9294 pyrhs-dimephmem-peo-dfzdap
9295 morhs-pazin-meteto-mezphe
9296 mam2py-24thizman2-meteto-bnsdap
9297 impy-edian2-4pho-zdabs
9298 amim-ams2-5pho-dfzdap
9299 thpym-edian2-eoco-psdab
9300 amthiaz-pazin-oem-bhsdap
9301 2py-pentas-cnmo-betainyl
9302 imhs-dimen-ocho-glupha
9303 pippy-24thiz-oem-zdap
9304 impy-amo2-mes-bnsdap
9305 mepip-mepazin-fo-betapy
9306 pippy-tridi-oem-bsdap
9307 prhs-mepazin-emo-asppha
9308 mam2py-din-cnmo-bhsdap
9309 binhs-amo2-mecpo-psdap
9310 bim-eta-mes-zdab
9311 hythpym-pipmea-no1-glyzdap
9312 impy-amn3-chexo-oxal
9313 npip-eta-no1-bsdap
9314 me2py-dimephmem-mes-bhsdap
9315 impy-diphmem-mommo-csdap
9316 pippy-m24thiz-mes-betadcph
9317 dhim-pipa-fo-thizzdap
9318 cl3pyme-edia2-sem-nbetab
9319 hythpym-24thizman2-oem-osdap
9320 binhs-mea-chexo-betadcph
9321 imhs-mepipe-no2-bhsdap
9322 me2py-dimephmem-mes-dfzdap
9323 bim-mepipen2-oem-zdabs
9324 me2py-amo2-meo-aspibua
9325 4pmhs-24thiz-napo-zdab
9326 chmhs-24thizman2-ocho-glubzla
9327 thpym-edian2-mes-psdab
9328 bhs-eta-5pho-psdap
9329 4pmhs-am3-sem-nzdap
9330 amim-pipa-imo-ibsdap
9331 bimhs-pipmea-5pho-betapy
9332 hythpym-dimephmem-mes-bphabs
9333 amthiaz-tetradi-5amo-psdap
9334 am2py-pazin-hso-mezphe
9335 am2py-din-ocho-mezphe
9336 imhs-mepipe-oem-betapy
9337 amthiaz-tetradi-no1-mezphe
9338 dhim-am2-sem-nbetabnaphth
9339 piraz-edian2-daco-zdab
9340 impy-amo2-eoco-bnsdap
9341 am2py-amo2-eoco-csdap
9342 dhim-amn2-eoco-zdap
9343 phpip-3diaz-5pho-bsdap
9344 2py-pazin-noi-zdap
9345 dmbim-24thiz-imo-bnsdap
9346 moegua-24thizman2-no1-betapy
9347 deam-pipmea-fo-zdab
9348 piraz-dimephmem-napo-aspbzla
9349 thpym-dis-nmo-betapy
9350 dhim-n24thiman-chexo-mezphe
9351 bz-mepazin-ocho-aval
9352 phhs-m24thiman2-baeo-psdapee
9353 cl3pyme-din-imo-dfzdap
9354 hythpym-pymea-eoco-bhsdap 9355 bhs-amn2-meto-dfzdap
9356 bim-amn2-oem-bhsdap
9357 am-dimephmem-fo-betainyl
9358 dpam-pipmes-napo-zdabs
9359 chmhs-diphmem-chexo-glubzla
9360 imhs-thizs-5amo-mezphe
9361 bim-amo2-hso-asppha
9362 bhs-ams2-no1-bhsdap
9363 am2py-trias-mmen-psdap
9364 amim-amn2-meteto-zdabs
9365 pippy-eta-pheo-betapy
9366 2py-indan2-imo-aspibua
9367 bim-diphmep-fo-zorn
9368 bhs-edian2-ocho-zdap
9369 thpym-edian2-oem-psdab
9370 bimhs-24thizman2-chexo-ibsdap
9371 n2py-25oxman2-chexo-mezphe
9372 amim-pentas-no2-bnsdap
9373 2py-m25thiz-oem-glyzdap
9374 npip-mepipe2-sem-nbetapy
9375 am2py-m25thiz-men-bhsdab
9376 imhs-eta-no1-bnsdap
9377 bhs-edian2-no1-betapy
9378 pippy-m25thiz-cno-betapy
9379 hythpym-24oxman2-oem-bphabs
9380 bimhs-thizo-5pho-glyzdap
9381 mam2py-mepazin-men-betapy
9382 bimhs-ams3-chexo-betapy
9383 edothpym-edia2-oem-npsdap
9384 pyrhs-amo2-imo-tsdap
9385 dhim-mepipe2-sem-nbetabnaphth
9386 bim-mepipe-meo-bnsdap
9387 bim-amo2-meo-bsdap
9388 am2py-edia2-oem-nbeta34-dimeoph
9389 pyr-24thiz-no1-bphabs
9390 am2py-2pazin-napo-zorn
9391 imhs-24thizman2-pro-glyzdap
9392 thpym-mepipen2-5pho-ibsdap
9393 moegua-mepazin-no1-bnsdap
9394 me2py-amn2-cnmo-zdabs
9395 impy-dis-imo-bhsdap
9396 pippy-dimen-no2-aspbzla
9397 pippy-n24thiman-5pho-betainyl
9398 imhs-pipmea-imo-mezphe
9399 dpam-dich-no2-psdap
9400 thpym-din-5amo-psdap
9401 imhs-24thiman-eoco-zdab
9402 pippy-mepazin-5amo-zdab
9403 mam2py-ams2-paco-bsdap
9404 2py-25oxman2-meto-aspibua
9405 bim-din-meteto-zdabs
9406 dmthpym-thizn-imo-glyzdap
9407 bim-din-fo-bhsdab
9408 mam2py-ams3-mes-thizzdap
9409 piraz-din-napo-betapy
9410 chhs-dimephmem-ocho-betapy
9411 me2py-din-mes-ibsdap
9412 am-24thizman2-baeo-asppha
9413 thpym-edian2-no1-bsdap
9414 bhs-pymea-4amo-betainyl
9415 dhim-butn-fo-betainyl
9416 mam2py-25oxman2-5amo-betadcph
9417 bim-amn2-no1-psdap
9418 thpym-24thiz-fo-zdabs
9419 dhim-n2nme2n-pheo-oxal
9420 amim-n2o2n-cpeo-bnsdap
9421 pippy-trias-napo-glupha
9422 me2py-amn2-no2-bphabs
9423 gua-dis-5amo-dfzdap
9424 am2py-m25thiz-eoco-zdabs
9425 me2py-trias-imo-asppha
9426 amim-pymea-imo-csdap
9427 imhs-pazin-oem-psdab
9428 fthpym-pentas-hso-dfzdap
9429 2py-pazin-no2-bhsdap
9430 pippy-pipmes-cno-psdapee
9431 me2py-dimephmem-oem-ppsdap
9432 chmhs-am3diaz-eoco-betadcph
9433 emnim-amn2-mes-oxal
9434 chhs-m25thiz-oem-betainyl
9435 am-thizn-mmen-aspbzla
9436 bim-mepipe-meo-bhsdap
9437 2py-thizn-daco-glyzdap
9438 pippy-mepipe-oeto-glyzdap
9439 impy-tridi-ocho-betadcph
9440 mam2py-25oxman2-4amo-psdap
9441 bhs-pipmeo-napo-bnsdap
9442 mam2py-mepipe2-sem-nzdap
9443 bhs-mepipen2-mes-asppha
9444 bhs-mea-no2-ibsdap
9445 thpym-edian2-5pho-bnsdap
9446 2pmhs-24thiman2-eoco-glyzdap
9447 am2py-25oxman2-ocho-betapy
9448 me2py-am3diaz-ocho-bhsdab
9449 dpam-amo3-men-zdab
9450 me2py-pipa-fo-csdap
9451 thpym-props-chexo-betainyl
9452 am2py-24thiman2-men-dfzdap
9453 thpym-edian2-no2-psdap
9454 npip-2pazin-mmen-csdap
9455 bim-edian2-no1-bhsdap
9456 im-pnymea-cpeo-mezphe
9457 hythpym-amn3-chexo-zorn
9458 2py-din-no1-betainyl
9459 imhs-pazin-oem-bsdap
9460 dhim-mepazin-nmo-bsdap
9461 nmor-25oxman2-cpro-bsdap
9462 hythpym-amo2-emo-zdap
9463 hythpym-amn2-no1-glupha
9464 2py-pnymea-chexo-betainyl
9465 dmbim-24thiz-imo-betainyl
9466 hythpym-diphmem-emo-zdap
9467 menim-mepazin-meo-psdab
9468 me2py-25oxman2-ocho-bnsdap
9469 bim-edian2-no2-psdap
9470 am2py-mepipen2-meteto-glyzdap
9471 imhs-ams3-5pho-betapy
9472 amim-m24thiz-5pho-glyzdap
9473 pippy-dimen-no1-psdap
9474 me2py-tridi-imo-zlys
9475 bhs-mepipe-no1-zdab
9476 impy-dimephmem-napo-bsdap
9477 edothpym-thizs-no1-bnsdap
9478 pyr-pyma2-napo-psdapee
9479 2py-pazin-no1-bnsdap
9480 bzl-diaz-imo-csdap
9481 piraz-tridi-imo-asppha
9482 hythpym-ams2-paco-aspbzla
9483 mam2py-mepipe-mes-psdab
9484 imhs-pyma2-no1-bphabs
9485 impy-ms-oem-bhsdap
9486 dhim-dimen-men-aspibua
9487 piraz-dimephmem-emo-asppha
9488 bhs-pazin-mes-bhsdap 9489 bim-tridi-meteto-zdab
9490 2py-amn3-men-betainyl
9491 pippy-amn3-aco-psdap
9492 dhim-tetradi-mmen-betapy
9493 ibhs-dimen-imo-psdapee
9494 thpym-din-eoco-zdap
9495 bhs-edian2-5pho-bhsdap
9496 am2py-diphmep-meo-bhsdab
9497 am2py-am2-oem-nzdap
9498 2py-pazin-mes-osdap
9499 dhim-ams2-paco-mezphe
9500 bz-ams2-pyo-bhsdab
9501 2py-trias-no1-aspbzla
9502 me2py-m25thiz-no2-zdab
9503 am2py-pipmea-4pho-betainyl
9504 piraz-24thizman2-mes-zdapee
9505 amim-dipch-5pho-bnsdap
9506 am2py-diphmep-ocho-bsdap
9507 2py-amn2-no1-bhsdap
9508 pippy-pazin-no2-betapy
9509 edothpym-pazin-no1-asppha
9510 bimhs-pazin-men-dfzdap
9511 dhim-mepipen2-fo-glyzdap
9512 am-butn-5amo-psdab
9513 dhim-pipmea-pyo-betapy
9514 pippy-m24thizman2-ocho-zdabs
9515 thpym-amn2-emo-aspbzla
9516 bhs-mepipe2-sem-nzdab
9517 edothpym-25thiz-emo-aspbzla
9518 gua-24thiz-5amo-asppha
9519 imhs-pazin-imo-asppha
9520 phhs-diphmem-cpeo-psdab
9521 am4py-tridi-oem-zdab
9522 2pmhs-m24thizman2-chexo-betadcph
9523 mepip-m24oxman2-men-betainyl
9524 hythpym-amo2-no2-betapy
9525 2pmhs-mepipe-ocho-mezphe
9526 z-ams2-ocho-mezphe
9527 4pmhs-n24thiman-oem-zdapee
9528 fthpym-mepipen2-meteto-zdab
9529 dhim-edian2-eoco-csdap
9530 hythpym-pipa-hso-bhsdap
9531 ppy-n2nme2n-5pho-dfzdap
9532 imhs-mepazin-cno-zdabs
9533 bimhs-24thizman2-nmo-betaet
9534 ppy-eta-eoco-psdap
9535 fthpym-hexas-no1-csdap
9536 me-tetras-eoco-bhsdab
9537 2py-ams2-peo-bhsdab
9538 amthiaz-diaz-emo-bnsdap
9539 hythpym-tetradi-cnmo-zdabs
9540 bz-amo2-emo-bsdap
9541 bhs-eta-pheo-mezphe
9542 chmhs-3pazin-no2-glyzdap
9543 2py-dimen-cno-csdap
9544 emnim-thizn-meteto-bsdap
9545 imhs-pazin-no2-betapy
9546 2py-m24thizman2-eoco-zdabs
9547 chmhs-pymea-cpro-betainyl
9548 pyraz-n2nme2n-napo-aspbzla
9549 impy-diphmep-imo-aspibua
9550 impy-pazi2n-chexo-zdabs
9551 thpym-eta-no1-betapy
9552 edothpym-pnymea-men-dfzdap
9553 mam2py-ams2-cpeo-psdap
9554 nmhs-edian2-eoco-aspibua
9555 mam2py-dipch-no2-zdabs
9556 bhs-pazin-ocho-bsdap
9557 thpym-edian2-no1-psdap
9558 bimhs-dimephmep-no2-psdab
9559 ec-24thiman-imo-glyzdap
9560 mam2py-tetradi-meteto-betadcph
9561 mam2py-dimephmep-no1-betaet
9562 nmhs-amn2-men-asppha
9563 pippy-dis-cnmo-bsdap
9564 mam2py-amn3-oem-psdap
9565 am2py-din-no2-dfzdap
9566 ibhs-m25oxman2-eoco-csdap
9567 me2py-m24thiz-5amo-zdab
9568 pippy-tetradi-paco-bnsdap
9569 impy-25oxman2-5amo-aval
9570 emnim-tetradi-no1-aspbzla
9571 pippy-dimephmem-fo-aspaba
9572 tolhs-dimephmem-5pho-psdap
9573 bimhs-eta-men-tsdap
9574 ec-dis-oem-glyzdap
9575 bim-tetradi-mes-aval
9576 dmthpym-mepipen2-5amo-zdapee
9577 z-mepipe2-sem-nzdab
9578 bimhs-pazin-mmen-psdap
9579 edothpym-dimen-mes-ppsdap
9580 am2py-m24oxman2-pheo-zdap
9581 thpym-mepazin-meo-zdab
9582 thpym-tridi-ocho-aspibua
9583 am4py-ams2-napo-betapy
9584 impy-dipch-chexo-bsdap
9585 mam2py-pipmea-meo-psdap
9586 me2py-din-no2-csdap
9587 dhim-pyma2-no1-bhsdap
9588 impy-amo2-fo-aspbzla
9589 bimhs-amn2-meteto-zdapee
9590 bim-tridi-mmen-mezphe
9591 imhs-mepipe-5pho-betapy
9592 cl3pyme-edia2-sem-nbetapy
9593 pippy-mepipe2-sem-nzdap
9594 ibhs-m25thiz-meo-zdab
9595 2pmhs-trias-ocho-bsdap
9596 thpym-dimephmem-no1-betadcph
9597 pyraz-dimen-men-glubzla
9598 bim-eta-no1-bnsdap
9599 2py-mepipen2-men-bsdap
9600 tolhs-pipa-no2-betaet
9601 mam2py-eta-mmen-bsdap
9602 morhs-m24oxman2-fo-csdap
9603 pyr-m25thiz-imo-asppha
9604 bhs-mea2s-fo-mezphe
9605 amim-dis-eoco-mezphe
9606 bim-hexadi-peo-bsdap
9607 dhim-din-5pho-bsdap
9608 amim-amn2-no2-betainyl
9609 hythpym-mepipe-daco-aspibua
9610 piraz-25oxman2-fo-zdabs
9611 pyr-3diaz-oem-psdab
9612 phhs-m25oxman2-no2-zdab
9613 2py-mepipe-4amo-betapy
9614 thpym-m24oxman2-5amo-bhsdap
9615 dhim-mepazin-aco-psdap
9616 mam2py-3diaz-cno-betapy
9617 piraz-pymea-fo-zdabs
9618 am2py-dimephmem-ocho-bhsdap
9619 emnim-m24oxman2-fo-zdabs
9620 bim-amn2-mes-bsdap
9621 2py-pazin-no1-bhsdap
9622 dhim-amn2-ocho-ibsdap 9623 piraz-eta-napo-oxal
9624 ppy-pymea-no2-psdap
9625 mam2py-25thiman2-5pho-bphabs
9626 pyraz-edian2-meo-aspibua
9627 thpym-mepipe-no1-bhsdap
9628 2py-props-napo-bhsdap
9629 phpip-din-emo-betapy
9630 bhs-diphmep-mecpo-zdab
9631 deam-tetradi-mes-psdab
9632 dhim-thizn-eoco-bphabs
9633 amthiaz-thizo-oem-bhsdap
9634 bhs-pnymea-5amo-mezphe
9635 thpym-mepipe-ocho-zdap
9636 thpym-dimephmem-mes-csdap
9637 nmhs-amn3-eoco-bphabs
9638 bhs-eta-mes-bhsdap
9639 am2py-amn3-meo-bphabs
9640 bim-dimephmep-fo-aspbzla
9641 dpam-pipa-fo-bphabs
9642 amim-pnymea-men-aspibua
9643 thpym-diphmep-chexo-betainyl
9645 dhim-eta-no2-csdap
9644 bim-amn2-ocho-psdab
9646 morhs-amo3-meo-aval
9647 piraz-ams2-nmo-bhsdab
9648 n2py-dis-imo-psdap
9649 bhs-thizn-napo-bnsdap
9650 2py-pymea-5pho-zdabs
9651 dmthpym-din-napo-ibsdap
9652 dpam-m24oxman2-meo-zdab
9653 thpym-mepipe-oem-zdap
9654 2py-mepipe-mes-zdap
9655 moegua-m24thizman2-chexo-aspbzla
9656 deam-dis-pro-glyzdap
9657 bhs-pazin-no2-bnsdap
9658 mam2py-m25thiz-no1-aspibua
9659 dhim-amn2-imo-zdabs
9660 phpip-amo2-meo-bnsdap
9661 prhs-tetradi-meo-glyzdap
9662 bimhs-thizn-imo-zdabs
9663 2py-eta-ocho-zdab
9664 me2py-tetradi-meo-betainyl
9665 dhim-m25thiz-meto-aspibua
9666 n2py-pymea-pro-mezphe
9667 chhs-pymea-4pho-bhsdab
9668 amim-pipa-cpeo-betainyl
9669 thpym-amn2-no2-psdab
9670 thpym-dimen-mes-zdabs
9671 cl3pyme-trias-chexo-psdap
9672 chmhs-thizn-5amo-aspbzla
9673 imhs-pipmea-ocho-betainyl
9674 amim-ams3-ocho-bphabs
9675 ibhs-m24thizman2-meto-bsdap
9676 piraz-24thiz-napo-csdap
9677 nmhs-edian2-no2-asppha
9678 deam-m25thiz-fo-csdap
9679 bz-thizn-ocho-bnsdap
9680 2py-amo3-chexo-bnsdap
9681 amim-mepipe-mmen-thizzdap
9682 fthpym-diaz-mes-betapy
9683 me2py-mepazin-5pho-psdab
9684 am-25oxman2-no1-bhsdap
9685 thpym-mepipe-ocho-bhsdap
9686 bimhs-pyma2-5amo-ppsdap
9687 thpym-am3diaz-imo-mezphe
9688 dmam-mepipe2-oem-nzdap
9689 dpam-trias-no1-csdap
9690 dmam-tetradi-napo-betadcph
9691 imhs-edian2-no2-zdab
9692 pyr-pipmea-4amo-psdapee
9693 morhs-m25thiz-chexo-zdabs
9694 dhim-mepipe-oem-bnsdap
9695 hythpym-tetradi-mes-bhsdab
9696 bim-thizo-men-psdab
9697 bz-pnymea-no1-glyzdap
9698 dhim-pyma2-eoco-asppha
9699 ibhs-amo2-mecpo-csdap betapy
9700 bhs-dimen-men-bsdap
9701 4pmhs-amn3-meo-bphabs
9702 hythpym-24thiman-cno-bhsdap
9703 bimhs-mepazin-4pho-zdap
9704 bimhs-propn-pheo-bnsdap
9705 pippy-tetradi-meo-glyzdap
9706 thpym-eta-eoco-zdap
9707 imhs-pazin-ocho-betapy
9708 thpym-pipmes-no1-ibsdap
9709 edothpym-indan2-cno-psdap
9710 me2py-diphmep-meteto-aspbzla
9711 thpym-pazin-mes-bnsdap
9712 me-pnymea-men-psdab
9713 amim-n2o2n-oem-bsdap
9714 tolhs-amn2-5amo-thizzdap
9715 bhs-edian2-napo-aspbzla
9716 n2py-24thiz-eoco-zdabs
9717 hythpym-eta-5pho-oxal
9718 dhim-eta-4pho-asppha
9719 bim-am2-sem-nbetabnaphth
9720 mam2py-eta-eoco-zorn
9721 dhim-mepazin-no1-bphabs
9722 prhs-din-meto-glupha
9723 hythpym-pipmeo-napo-betapy
9724 amthiaz-dimephmep-no2-betainyl
9725 fthpym-m24thizman2-5amo-dfzdap
9726 impy-pnymea-men-zdap
9727 mepip-diaz-daco-bhsdap
9728 dpam-pipmea-no2-zdabs
9729 bimhs-m24thiz-oeto-bphabs
9730 amim-mepazin-eoco-dfzdap
9731 im-amo2-fo-glyzdap
9732 moegua-eta-fo-aspbzla
9733 bhs-edian2-no2-betapy
9734 nmor-amn3-men-oxal
9735 dmthpym-dimen-eoco-psdab
9736 am2py-m25thiman2-ocho-aval
9737 bz-amo2-no1-psdap
9738 nmhs-edian2-mmen-zdapee
9739 piraz-m24thizman2-ocho-psdab
9740 dmbim-24thiman-pyo-aspbzla
9741 bim-tridi-no2-bphabs
9742 phpip-din-imo-betadcph
9743 me2py-diphmep-4pho-aspbzla
9744 imhs-edian2-mes-psdap
9745 2py-pazin-no1-bsdap
9746 prhs-trias-imo-csdap
9747 bhs-edian2-oem-psdap
9748 pippy-m24thizman2-chexo-betapy
9749 2py-tridi-napo-asppha
9750 fthpym-amn-pyo-bhsdap
9751 amim-dis-no2-aspibua
9752 piraz-pipa-no1-betainyl
9753 mam2py-tridi-napo-psdap
9754 bimhs-25oxman2-nmo-bhsdap
9755 2py-mepipe-no1-bnsdap
9756 am2py-pipmea-meo-zdab 9757 pyr-pyma2-men-dfzdap
9758 bzl-24thiz-no2-aspibua
9759 bhs-eta-no2-bphabs
9760 tolhs-amn2-fo-aspibua
9761 am2py-mepazin-mes-dfzdap
9762 pippy-din-meto-betapy
9763 piraz-butn-cpeo-zdap
9764 imhs-eta-oem-betapy
9765 amim-am2-oem-nzdab
9766 hythpym-tetradi-mes-bhsdab
9767 impy-eta-napo-bhsdap
9768 thpym-pyma2-meo-bphabs
9769 bhs-mepipen2-mes-bhsdap
9770 am4py-amn2-men-dfzdap naphth
9771 n2py-25oxman2-mes-aspbzla
9772 nim-tridi-5amo-bsdap
9773 me2py-din-fo-psdab
9774 bim-mepipe-no2-bsdap
9775 amim-24thiz-fo-psdab
9776 me2py-pipa-meo-bhsdap
9777 dmthpym-m25thiz-no2-bphabs
9778 amim-din-men-csdap
9779 pippy-diaz-no2-bhsdab naphth
9780 am2py-pipmeo-ocho-zdabs
9781 bimhs-dimephmem-napo-glubzla
9782 imhs-dimephmep-meo-asppha
9783 pippy-m24thizman2-5pho-bnsdap
9784 n2py-tridi-oem-csdap
9785 me2py-24thizman2-cpro-asppha
9786 bim-eta-no2-bsdap
9787 bim-am2-oem-nzdab
9788 dhim-24thizman2-men-mezphe
9789 pyrhs-n2o2n-5amo-betadcph
9790 me-ams2-eoco-bhsdab
9791 dhim-dimephmem-meo-csdap
9792 am2py-mepipe-paco-csdap
9793 pyraz-mepipen2-meo-betapy
9794 npip-eta-pro-bsdap
9795 amim-edian2-4pho-aspibua
9796 phhs-pipmea-men-aspbzla
9797 piraz-dis-men-bphabs
9798 2py-m25thiz-5pho-bsdap
9799 hythpym-pymea-oem-aspbzla
9800 impy-thizn-men-dfzdap
9801 mam2py-24thiz-oem-betapy
9802 2py-amn2-no2-zdabs
9803 amthiaz-pazin-no1-zdap
9804 bhs-25oxman2-ocho-bnsdap
9805 thpym-pazin-meo-zdap
9806 hythpym-trias-fo-betapy
9807 pyr-dimephmem-cpro-bhsdab
9808 prhs-eta-fo-betadcph
9809 bim-eta-no1-bsdap
9810 hythpym-pipmea-fo-aspbzla
9811 z-eta-pro-zlys
9812 imhs-dis-chexo-dfzdap
9813 am2py-25oxman2-napo-dfzdap
9814 piraz-dimephmem-no1-aspibua
9815 mam2py-dimen-imo-csdap
9816 thpym-din-fo-glubzla
9817 imhs-amn2-oem-psdap
9818 prhs-pipa-no2-bnsdap
9819 thpym-eta-oem-psdab
9820 me2py-pnymea-eoco-zdab
9821 edothpym-edia2-oem-nbetab
9822 fthpym-butn-ocho-zorn
9823 n2py-edian2-emo-mezphe
9824 thpym-eta-no2-bhsdap
9825 dhim-amn3-mes-aspbzla
9826 pyr-edia2-oem-nzdab
9827 bhs-mepipen2-chexo-bphabs
9828 bhs-24thiman-baeo-zdab
9829 morhs-mepipe2-sem-nbetab
9830 me2py-trias-5amo-betainyl
9831 ppy-thizn-nmo-ibsdap
9832 thpym-eta-no1-asppha
9833 2py-amn2-5pho-psdap
9834 piraz-pazin-napo-bphabs
9835 am2py-thizn-eoco-asppha
9836 bim-pipmea-napo-zdap
9837 dhim-dimephmem-emo-psdab
9838 dpam-diphmem-emo-psdab
9839 bz-n2o2n-daco-bnsdap
9840 bhs-amn3-meteto-betainyl
9841 imhs-edian2-oem-glyzdap
9842 dhim-pipmea-fo-aspaba
9843 bimhs-diphmem-fo-bhsdap
9844 am2py-pipa-mmen-betapy
9845 ppy-m25thiz-fo-bhsdab
9846 me2py-edian2-napo-aspbzla
9847 z-dimephmem-men-thizzdap
9848 bzl-amn3-meo-aspibua
9849 imhs-edian2-oem-bhsdap
9850 bim-edian2-mes-zdab
9851 dhim-diphmem-fo-zdap
9852 prhs-ams2-mes-mezphe
9853 mam2py-dimephmem-meo-betadcph
9854 moegua-3diaz-no2-psdap
9855 piraz-dis-5pho-betainyl
9856 imhs-pipa-eoco-aspibua
9857 chhs-pazin-cpro-bnsdap
9858 emnim-24thiz-no1-mezphe
9859 me-am3-oem-nbetameph
9860 amim-tetradi-emo-glubzla
9861 thpym-pazin-5pho-zdab
9862 piraz-n2nme2n-mes-csdap
9863 dhim-mea2s-napo-csdap
9864 edothpym-thizo-pro-betainyl
9865 amthiaz-amo2-men-betapy
9866 me2py-amn2-baeo-asppha
9867 imhs-mepipe-5pho-bnsdap
9868 mam2py-mepazin-napo-zdap
9869 dhim-dich-mes-psdab
9870 thpym-tridi-mes-betapy
9871 thpym-trias-5amo-bphabs
9872 chmhs-dis-4pho-bsdap
9873 bhs-eta-eoco-bhsdap
9874 pippy-am2-oem-nbetapy
9875 ibhs-mepazin-4pho-betapy
9876 imhs-dimephmep-pyo-zdap
9877 imhs-mepipe-meo-bsdap
9878 thpym-pnymea-ocho-zdapee
9879 bhs-pazin-mes-zdap
9880 inhs-mepipe-5pho-zdap
9881 bzl-thizo-eoco-betainyl
9882 hythpym-m25thiman2-fo-glyzdap
9883 chhs-tetras-meto-betaet
9884 2py-m24thizman2-oem-aspibua
9885 pippy-din-5pho-psdab
9886 pyr-mepipen2-no2-betadcph
9887 pippy-m25thiz-napo-betadcph
9888 npip-eta2s-no1-aspibua
9889 bim-dis-no1-psdab
9890 thpym-m25thiz-ocho-bhsdap 9891 bim-amo2-no2-thizzdap
9892 dhim-n2o2n-meo-betapy
9893 am4py-eta-cpro-bsdap
9894 amim-pazi2n-peo-bphabs
9895 hythpym-m25thiz-hso-csdap
9896 impy-n2o2n-mommo-dfzdap
9897 chhs-amn3-no2-mezphe
9898 imhs-pyma2-ocho-csdap
9899 moegua-mea-napo-glupha
9900 amim-pipmea-chexo-zdabs
9901 thpym-amo2-chexo-zdapee
9902 impy-3diaz-no1-oxal
9903 me2py-dis-baeo-bsdap
9904 thpym-pazin-no2-betapy
9905 mam2py-mepipe2-oem-nbetameph
9906 binhs-pipmea-oem-glyzdap
9907 amthiaz-mea2s-napo-mezphe
9908 deam-25thiz-emo-aspibua
9909 hythpym-hexas-5amo-psdapee
9910 prhs-trias-meo-mezphe
9911 thpym-amn2-oem-betapy
9912 amim-24thizman2-4pho-bhsdap
9913 impy-m25thiz-chexo-aspbzla
9914 2py-amn2-meo-asppha
9915 am2py-am3-sem-nzdab
9916 am2py-ams2-imo-psdab
9917 dhim-dimephmep-chexo-mezphe
9918 ec-edian2-5pho-bnsdap
9919 chmhs-am3-oem-nzdap
9920 2py-eta-oem-psdap
9921 bhs-mepipe-ocho-psdab
9922 cl3pyme-pyma2-men-betapy
9923 bimhs-diphmem-mes-tsdap
9924 thpym-pyma2-fo-oxal
9925 bimhs-mepazin-eoco-aspbzla
9926 tolhs-eta-chexo-aspbzla
9927 am4py-24oxman2-4pho-csdap
9928 me2py-trias-men-bsdap
9929 bhs-ams3-ocho-psdap
9930 pippy-24thiz-fo-df zdap
9931 piraz-24thizman2-hso-bsdap
9932 imhs-m24thizman2-peo-asppha
9933 2py-eta-no2-zdap
9934 bzl-dimen-paco-bnsdap
9935 deam-25oxman2-fo-betapy
9936 2py-tetradi-chexo-betapy
9937 bimhs-dis-hso-asppha
9938 amim-tetras-emo-psdap
9939 hythpym-thizs-napo-bphabs
9940 bhs-am2-oem-nbetapy
9941 thpym-eta-ocho-bhsdap
9942 bimhs-pipmea-imo-aspaba
9943 piraz-mepipe2-oem-nzdab
9944 2py-edian2-mes-betapy
9945 menim-24oxman2-5pho-betapy
9946 bz-25oxman2-mes-betainyl
9947 imhs-ams2-eoco-betapy
9948 mam2py-m25thiz-emo-mezphe
9949 2py-edian2-eoco-psdap
9950 hythpym-dimephmep-emo-aspbzla
9951 me2py-pazin-no2-psdapee
9952 bim-edia2-sem-nzdap
9953 bhs-eta-mes-betapy
9954 dpam-m25thiz-pro-glubzla
9955 amthiaz-m24oxman2-mommo-tsdap
9956 thpym-amn2-no2-bnsdap
9957 thpym-diphmem-peo-asppha
9958 bhs-amn2-chexo-bhsdap
9959 4pmhs-am3-oem-nbetapy
9960 pippy-ams2-emo-asppha
9961 thpym-edian2-5pho-zdap
9962 me2py-mepipen2-5pho-aspibua
9963 bim-pazin-no2-bnsdap
9964 amim-pipa-no2-bnsdap
9965 amim-m25thiz-meo-bnsdap
9966 cl3pyme-24thizman2-oem-aspi-bua
9967 bhs-m25thiman2-acho-aspbzla
9968 edothpym-edian2-5amo-bhsdab
9969 ibhs-pyma2-emo-mezphe
9970 mam2py-pipmea-mecpo-bhsdab
9971 bimhs-pipmea-no1-psdab
9972 bimhs-24thiz-pyo-dfzdap
9973 hythpym-trias-no1-mezphe
9974 dhim-am2-oem-nbetameph
9975 impy-din-oem-betainyl
9976 npip-hexas-4pho-aspibua
9977 amim-25thizman2-ocho-betaet
9978 2py-pazin-mes-psdap
9979 amim-amo2-fo-bphabs
9980 bhs-pazin-no2-betapy
9981 imhs-mepipe-mes-psdap
9982 piraz-mepipe-emo-betapy
9983 dmbim-pipmea-5pho-bsdap
9984 imhs-thizn-no2-zdabs
9985 edothpym-diphmem-men-aspibua
9986 dhim-din-fo-bhsdap
9987 me-24thizman2-pro-glyzdap
9988 pippy-pazin-meo-bnsdap
9989 menim-tridi-no1-bsdap
9990 bimhs-thizn-chexo-dfzdap
9991 piraz-diphmem-men-glubzla
9992 deam-amn3-chexo-zdab
9993 bhs-mepipe-oem-psdap
9994 2py-pipmea-no1-zdap
9995 dmam-thizs-nmo-aspbzla
9996 dpam-thizn-mes-betapy
9997 bim-amn2-meo-betapy
9998 me-dio-pro-psdap
9999 2py-amn2-napo-betainyl
10000 2py-eta-no2-psdap
10001 bhs-eta-meo-psdap
10002 imhs-pyma2-fo-zdab
10003 thpym-pazin-no2-bsdap
10004 piraz-amn-chexo-bnsdap
10005 impy-propn-oem-psdab
10006 me2py-edia2-sem-nzdap
10007 bz-pipa-no2-csdap
10008 nim-pyma2-men-psdap
10009 hythpym-edian2-5pho-aspibua
10010 bim-amn2-oem-psdap
10011 impy-indan2-chexo-bnsdap
10012 am4py-trias-emo-bhsdap
10013 dhim-ams2-meto-psdab
10014 edothpym-propa2s-chexo-bhsdap
10015 npip-m25thizman2-no1-aspibua
10016 imhs-25oxman2-5pho-bnsdap
10017 bhs-eta-men-zorn
10018 nim-24thizman2-ocho-mezphe
10019 me2py-amn3-chexo-zdab
10020 emnim-thizs-imo-betapy
10021 2py-pazin-meo-zdab
10022 2py-eta-ocho-betapy
10023 me2py-dimephmep-pyo-psdapee
10024 pyraz-amn2-mes-bsdap 10025 phpip-mepazin-5pho-psdab
10026 thpym-pentadi-emo-glyzdap
10027 me2py-pazin-cpro-betapy
10028 bhs-mepipe-eoco-zdab
10029 cl3pyme-pnymea-mes-ibsdap
10030 am2py-diphmem-nmo-bsdap
10031 bhs-m25thiz-nmo-zdab
10032 thpym-amn2-meto-bnsdap
10033 thpym-am2-oem-nzdap
10034 mam2py-tetradi-fo-psdap
10035 am-mepazin-eoco-zdabs
10036 mepip-pazin-emo-zdap
10037 amim-amo2-mes-tsdap
10038 menim-dis-peo-bphabs
10039 pippy-trias-men-dfzdap
10040 2py-edian2-ocho-mezphe
10041 me2py-3diaz-5pho-psdab
10042 ec-tridi-no1-psdab
10043 hythpym-propa2s-mes-betapy
10044 2py-amo2-emo-dfzdap
10045 imhs-amn2-5pho-zdap
10046 hythpym-mepazin-mes-ppsdap
10047 bhs-mepipe-meo-bhsdap
10048 dmbim-amn2-napo-psdap
10049 bhs-pazin-mes-psdap
10050 bim-tetradi-men-betadcph
10051 bhs-edian2-5pho-bnsdap
10052 pippy-dimen-oem-psdap
10053 amim-dis-oem-zdapee
10054 dmam-mepazin-no1-psdapee
10055 hythpym-amn3-meo-zdabs
10056 tolhs-ams2-5pho-bphabs
10057 prhs-dimen-5pho-bnsdap
10058 bimhs-pnymea-5pho-betapy
10059 hythpym-dimephmep-no2-bnsdap
10060 piraz-diphmem-imo-aspbzla
10061 bhs-eta-eoco-bsdap
10062 dmthpym-pentadi-pheo-bphabs
10063 bzl-tetradi-ocho-glupha
10064 phpip-dich-imo-psdab
10065 hythpym-trias-pyo-betapy
10066 bimhs-mepipe-napo-osdap
10067 mam2py-diphmem-emo-glyzdap
10068 amim-pyma2-ocho-csdap
10069 thpym-ams2-imo-mezphe
10070 thpym-diphmep-nmo-oxal
10071 hythpym-hexadi-daco-bsdap
10072 piraz-m24thizman2-5pho-zorn
10073 thpym-dimephmem-no1-csdap
10074 mam2py-amo3-eoco-mezphe
10075 impy-eta-5pho-zdab
10076 pippy-diphmep-fo-zdabs
10077 piraz-dipch-cnmo-bphabs
10078 dhim-pazin-pro-bsdap
10079 2py-mepipe-5pho-psdab
10080 edothpym-mepipe-napo-dfzdap
10081 chmhs-amn2-cpeo-dfzdap
10082 bhs-hexadi-daco-zdabs
10083 amim-25thizman2-ocho-zdap
10084 2py-amn2-napo-betadcph
10085 emnim-mepipe2-sem-npsdap
10086 npip-24thiman2-cno-glyzdap
10087 imhs-dimephmep-emo-asppha
10088 impy-amn2-paco-zdabs
10089 deam-pyma2-5amo-bhsdap
10090 piraz-tridi-chexo-aspaba
10091 me2py-m25oxman2-meo-mezphe
10092 am2py-edian2-imo-bhsdab
10093 dmam-pnymea-no2-asppha
10094 imhs-edian2-fo-bsdap
10095 am2py-amo2-no1-zdab
10096 mepip-mepazin-napo-csdap
10097 me-edian2-aco-psdap
10098 2py-edian2-no1-bhsdap
10099 amim-pazin-oeto-glubzla
10100 pyraz-am2-sem-nbetabnaphth
10101 mam2py-pnymea-men-aspbzla
10102 dhim-pyma2-no2-aspaba
10103 bim-diphmem-chexo-psdab
10104 impy-dipch-imo-psdab
10105 hythpym-pyma2-men-bhsdab
10106 pippy-mepipen2-men-betainyl
10107 bhs-amn2-mes-psdab
10108 nmor-thizs-fo-zdap
10109 tolhs-dimen-chexo-dfzdap
10110 dmam-amn3-napo-bhsdap
10111 2pmhs-amn2-imo-zdap
10112 dmbim-pyma2-5pho-aspibua
10113 impy-tetradi-mes-glyzdap
10114 bimhs-pentadi-meo-zdab
10115 imhs-eta-no1-psdab
10116 dhim-dimephmep-nmo-psdab
10117 fthpym-24thizman2-5pho-thizzdap
10118 bim-dimephmep-eoco-ppsdap
10119 bhs-mepipe-5pho-bsdap
10120 imhs-pazin-meo-bnsdap
10121 thpym-mepipe-no1-zdap
10122 $^2$pmhs-mepipe2-sem-nzdab
10123 impy-amn2-meteto-betaet
10124 thpym-pyma2-meteto-betainyl
10125 am4py-24thizman2-men-bnsdap
10126 nim-25thiman2-ocho-aspbzla
10127 n2py-mepipe-mes-aspibua
10128 pippy-m25oxman2-5pho-zdabs
10129 dpam-edia2-sem-nzdap
10130 bimhs-din-napo-asppha
10131 me2py-mepipe-5pho-bphabs
10132 amthiaz-trias-hso-betainyl
10133 me2py-25thiman2-chexo-dfzdap
10134 pippy-dimen-hso-betapy
10135 piraz-amn2-5pho-csdap
10136 me2py-amo2-napo-bnsdap
10137 pippy-am2-sem-nzdap
10138 imhs-n24thiman-fo-psdap
10139 n2py-pipmeo-no1-betadcph
10140 dmam-24thizman2-nmo-betaet
10141 2py-thizn-5pho-dfzdap
10142 pippy-hexadi-fo-bhsdab
10143 amthiaz-ams2-oem-asppha
10144 emnim-amo2-cpeo-aspibua
10145 2py-pazin-no1-zdab
10146 thpym-pazin-oem-bsdap
10147 thpym-eta-meo-bnsdap
10148 pippy-dimephmep-mes-bhsdab
10149 piraz-amo3-no2-zdabs
10150 amim-amn3-fo-zdabs
10151 mam2py-diphmem-chexo-bhsdab
10152 thpym-amn2-mes-betapy
10153 bim-tetradi-eoco-zdab
10154 2py-dimephmem-meo-psdap
10155 hythpym-dimephmem-imo-bsdap
10156 menim-thizo-ocho-asppha
10157 dmam-ams3-4pho-bsdap
10158 thpym-mepipe-oem-bsdap 10159 dhim-m24thizman2-5amo-betaet
10160 dmthpym-m25thiz-men-bhsdab
10161 bhs-amn2-oem-bhsdap
10162 2py-pazin-no2-bsdap
10163 hythpym-pipmes-meo-betapy
10164 prhs-m24oxman2-no2-ppsdap
10165 piraz-diphmem-no2-betainyl
10166 bhs-24thiz-men-glupha
10167 bim-eta2s-men-psdap
10168 2pmhs-diphmep-meto-zdab
10169 amim-mepipe-emo-betadcph
10170 piraz-mepazin-emo-psdap
10171 bim-pazin-meo-zdap
10172 2py-24thiz-cpro-zdap
10173 2py-diaz-men-bphabs
10174 bim-eta-mes-bnsdap
10175 pippy-pyma2-imo-psdap
10176 bhs-3diaz-imo-glyzdap
10178 bhs-dimen-5pho-glubzla
10179 bhs-amn3-5pho-betadcph
10180 dhim-25oxman2-no2-bhsdab
10181 2py-pazin-oem-bsdap
10182 imhs-am2-oem-nbetapy
10183 bim-mepipen2-fo-bphabs
10184 dpam-24thiz-imo-psdap
10185 impy-edian2-4pho-bhsdap
10186 4pmhs-dimephmem-chexo-bhsdap
10187 dmthpym-dimephmem-cno-zdab
10188 bhs-eta-meo-betapy
10189 2py-dis-fo-glubzla
10190 edothpym-pnymea-mecpo-glyzdap
10191 phpip-pymea-eoco-zdab
10192 phpip-edian2-fo-bhsdap
10193 ppy-mepipe2-sem-nbetabnaphth
10194 hythpym-n2o2n-emo-bhsdab
10195 amthiaz-pazin-eoco-zdab
10196 impy-diphmem-pyo-zdapee
10197 bhs-m25thizman2-pyo-asppha
10198 n2py-pazin-imo-mezphe
10199 dhim-m24thizman2-oem-bhsdap
10200 2py-tetradi-meo-bhsdab
10201 bhs-mepipe-ocho-asppha
10202 dmbim-mepazin-emo-aval
10203 piraz-amo2-fo-aspibua
10204 imhs-pazin-mes-bhsdap
10205 am2py-dimen-no2-bphabs
10206 thpym-ams2-napo-psdab
10207 emnim-amo3-5pho-csdap
10208 mam2py-am2-oem-nbetapy
10209 bim-dimephmep-ocho-psdap
10210 bim-pipa-pyo-zdab
10211 bhs-edian2-oem-betapy
10212 bz-propn-no1-psdap
10213 dmbim-hexas-oeto-aspibua
10214 dpam-dis-nmo-csdap
10215 tolhs-dimephmem-emo-dfzdap
10216 2py-edian2-no1-bsdap
10217 imhs-thizs-chexo-bphabs
10218 ibhs-edia2-sem-nbetameph
10219 nim-pipmea-eoco-dfzdap
10220 ppy-24thiz-chexo-aspibua
10221 amim-24thiz-chexo-bhsdap
10222 bimhs-thizn-imo-aspibua
10223 menim-24thizman2-meo-bhsdab
10224 mam2py-diphmem-imo-glubzla
10225 bhs-pazin-no1-bnsdap
10226 phpip-3pazin-oem-bsdap
10228 pippy-eta-meo-zdab
10229 2py-pazin-5amo-aspbzla
10230 dhim-24thizman2-oeto-bphabs
10231 nmhs-thizs-meto-mezphe
10232 amim-pentas-nmo-oxal
10233 amim-mepipe2-sem-nzdab
10234 bhs-pyma2-4amo-ppsdap
10235 npip-dimephmep-pheo-betainyl
10236 pippy-diphmem-oem-bsdap
10237 pippy-eta-peo-csdap
10238 dhim-tetradi-mes-bnsdap
10239 piraz-dimephmem-ocho-bhsdab
10240 2pmhs-m24thizman2-4amo-psdab
10241 impy-dimephmep-ocho-dfzdap
10242 hythpym-mepipe-men-psdab
10243 pippy-pymea-chexo-aspbzla
10244 fthpym-m24thizman2-nmo-betapy
10245 bhs-amn2-no1-psdab
10246 bim-dis-pheo-zdab
10247 piraz-tetradi-mecpo-aspibua
10248 moegua-mepazin-mmen-aspbzla
10249 gua-diphmem-5amo-mezphe
10250 bim-24thizman2-ocho-psdab
10251 emnim-diphmem-fo-psdap
10252 bim-m25thiz-aco-zdab
10253 2py-mepipe-oem-psdap
10254 thpym-24thizman2-meo-psdap
10255 dmthpym-amo2-men-bhsdap
10256 gua-dimephmep-mes-betapy
10257 dmbim-dimephmep-oeto-psdap
10258 pippy-pazin-nmo-aspibua
10259 gua-dio-cnmo-zlys
10260 amthiaz-amn3-cno-mezphe
10261 bz-pazin-mmen-zdab
10262 piraz-dis-mes-zdap
10263 bimhs-pazi2n-pheo-aspibua
10264 imhs-pazin-meo-betapy
10265 dhim-amo2-5pho-zdapee
10266 bim-mepipe-cpro-tsdap
10267 bhs-diphmep-eoco-glyzdap
10268 2py-m24thiz-men-bhsdab
10269 fthpym-m24thizman2-chexo-csdap
10270 cl3pyme-dimephmep-4amo-betadcph
10271 nim-24thizman2-meto-aspbzla
10272 2py-edian2-eoco-zdap
10273 dhim-24thiz-emo-glyzdap
10274 piraz-pipmeo-mommo-zlys
10275 ibhs-eta-men-aspbzla
10276 binhs-diaz-no2-zdabs
10277 thpym-eta2s-4pho-aspbzla
10278 deam-diphmem-mes-bnsdap
10279 emnim-diphmem-cpro-psdap
10280 bimhs-25oxman2-cpro-zdap
10281 bzl-24thiz-chexo-betapy
10282 pyr-diphmep-cnmo-aspibua
10283 piraz-mepazin-no2-aspbzla
10284 pippy-trias-mmen-csdap
10285 pippy-edian2-5amo-psdap
10286 piraz-m25thiz-5pho-psdab
10287 dmbim-pipmea-ocho-dfzdap
10288 amthiaz-am2-sem-nbetapy
10289 dmbim-hexadi-ocho-betadcph
10290 n2py-dipch-mes-aspibua
10291 imhs-diphmep-cnmo-aspbzla
10292 pippy-indan2-chexo-psdab
10293 hythpym-thizn-pro-betadcph
10294 impy-mea2s-men-bnsdap 10295 impy-diphmem-4pho-bhsdab
10296 impy-m25oxman2-ocho-psdap
10297 chhs-pipa-emo-aspbzla
10298 cl3pyme-diphmep-cno-zdab
10299 nmor-pnymea-5pho-asspha
10300 impy-am3-sem-npsdap
10301 cl3pyme-dimephmep-meteto-aspaba
10302 dhim-m24thizman2-ocho-zdabs
10303 amim-pyma2-napo-betadcph
10304 pippy-eta-nmo-aspibua
10305 gua-am2-oem-npsdap
10306 bimhs-24thiz-napo-dfzdap
10307 prhs-24thizman2-oem-zorn
10308 pippy-mepazin-4amo-glupha
10309 2pmhs-din-fo-aspibua
10310 2py-amn2-no2-zdab
10311 bhs-pnymea-chexo-bhsdap
10312 pippy-24thiz-mes-zlys
10313 dmthpym-pymea-napo-bhsdab
10314 2py-din-5amo-zdab
10315 bimhs-am3-sem-nbetameph
10316 bim-mepazin-chexo-psdap
10317 bhs-thizs-oem-glyzdap
10318 bzl-pazin-mes-bsdap
10319 hythpym-dimen-5pho-thizzdap
10320 amthiaz-pipa-nmo-bhsdap
10321 nmor-eta-imo-bsdap
10322 am2py-thizo-oem-osdap
10323 phpip-amn-no2-dfzdap
10324 thpym-edian2-no2-psdab
10325 impy-pipmes-pro-betainyl
10326 moegua-ams2-5amo-bhsdap
10327 amim-ann2-men-asppha
10328 ibhs-pymea-no1-bhsdab
10329 imhs-pyma2-men-bhsdab
10330 amim-24thiz-mes-bhsdap
10331 hythpym-amn2-no2-betadcph
10332 me-tridi-men-asppha
10333 bzl-thizn-5pho-dfzdap
10334 dhim-mepazin-emo-bnsdap
10335 bhs-eta-ocho-psdap
10336 im-amo2-eoco-csdap
10337 dmthpym-m24thizman2-5pho-zdap
10338 thpym-24thizman2-no2-psdab
10339 thpym-n24thiman-aco-psdab
10340 2py-indan2-5pho-bnsdap
10341 piraz-pipmes-chexo-betainyl
10342 bimhs-eta-meo-bsdap
10343 bhs-trias-emo-bphabs
10344 bim-pazin-meo-betapy
10345 pippy-pazin-mes-betadcph
10346 mam2py-dis-fo-bhsdap
10347 piraz-thizs-emo-tsdap
10348 fthpym-24thizman2-eoco-psdap
10349 me-m25thizman2-pyo-psdab
10350 pippy-edian2-cno-csdap
10351 me2py-din-4amo-zdabs
10352 mam2py-pentas-5pho-dfzdap
10353 bim-mepipe-eoco-zdab
10354 2py-tridi-5pho-zdapee
10355 mam2py-ams2-no1-betapy
10356 moegua-n2nme2n-baeo-glyzdap
10357 npip-pipmea-no1-psdab
10358 amim-diphmep-imo-glyzdap
10359 mam2py-dimephmep-emo-psdap
10360 piraz-mepipe2-sem-nbetameph
10361 bim-pyma2-cnmo-aspbzla
10362 am2py-pipmea-4amo-aspbzla
10363 bhs-24thizman2-oem-csdap
10364 bimhs-thizn-men-zdabs
10365 bim-pymea-5amo-betaet
10366 amim-mea2s-mes-psdab
10367 edothpym-edian2-baeo-betadcph
10368 bim-m25thiman2-ocho-oxal
10369 bim-mepipe-no1-zdap
10370 bz-amo2-no2-zdap
10371 amim-thizs-ocho-asppha
10372 4pmhs-dis-no2-asppha
10373 am2py-pentas-oem-bhsdab
10374 hythpym-diphmep-mmen-mezphe
10375 2py-trias-fo-betapy
10376 impy-diphmem-emo-osdap
10377 dmbim-mepipen2-ocho-asppha
10378 2py-amn2-no2-psdab
10379 imhs-amn2-5pho-asppha
10380 me2py-dimephmem-ocho-glyzdap
10381 impy-hexas-fo-zdabs
10382 thpym-pipa-emo-aspibua
10383 imhs-diphmem-imo-psdab
10384 inhs-tridi-ocho-asppha
10385 mam2py-25oxan2-mes-psdap
10386 namhs-ams2-5pho-aspbzla
10387 bz-m24thiman2-5pho-betadcph
10388 bimhs-mepipen2-cpro-zdabs
10389 im-amo2-emo-zdab
10390 am2py-dis-eoco-asppha
10391 2py-amn2-mes-zdab
10392 deam-dis-imo-mezphe
10393 bim-edian2-meo-bsdap
10394 impy-tridi-5amo-bsdap
10395 dhim-m24thiman2-oem-betapy
10396 im-tridi-emo-zdapee
10397 bhs-pazin-5pho-bsdap
10398 thpym-amn2-ocho-psdab
10399 phhs-m24thiz-napo-zdabs
10400 pippy-hexadi-men-bnsdap
10401 am2py-tridi-chexo-bsdap
10402 imhs-dimephmem-eoco-zdap
10403 bhs-edian2-oem-bsdap
10404 hythpym-propa2s-cnmo-zdabs
10405 amim-trias-chexo-asppha
10406 ibhs-pnymea-napo-asppha
10407 imhs-eta-no2-csdap
10408 imhs-pipa-pheo-bhsdab
10409 me2py-m25thiz-men-mezphe
10410 menim-diphmep-5amo-psdap
10411 chmhs-n2nme2n-meteto-aspbzla
10412 impy-m24oxman2-napo-aval
10413 dhim-dis-eoco-glyzdap
10414 mam2py-pazin-5pho-bhsdap
10415 pyr-ams2-pyo-betaet
10416 bimhs-m25thiz-fo-dfzdap
10417 moegua-24thiz-ocho-asppha
10418 chmhs-24thiman2-mes-bhsdab
10419 impy-diphmem-men-osdap
10420 impy-24thiz-emo-glyzdap
10421 inhs-mepipen2-ocho-dfzdap
10422 am2py-amn3-5pho-asppha
10423 menim-amn3-napo-mezphe
10424 bim-mepipe-eoco-bnsdap
10425 amim-din-fo-aspibua
10426 2py-mea2s-imo-aspbzla
10427 bim-pazin-no2-psdab
10428 bim-eta-mes-psdab 10429 am2py-thizn-emo-bhsdap
10430 2py-mepazin-5pho-psdap
10431 imhs-dimephmep-oem-zdab
10432 bhs-ams2-men-betapy
10433 n2py-am2-oem-npsdap
10434 z-24thiz-5pho-csdap
10435 nmhs-dimen-daco-zlys
10436 menim-diphmep-mes-bphabs
10437 dhim-amn2-imo-dfzdap
10438 am2py-pipa-mes-betapy
10439 ppy-trias-no2-aspibua
10440 pyr-am3diaz-fo-bphabs
10441 deam-dimen-mes-dfzdap
10442 n2py-pyma2-no2-bhsdab
10443 dhim-dimephmem-meo-aspibua
10444 bim-eta-eoco-bsdap
10445 phpip-25oxman2-men-asppha
10446 pippy-eta-meteto-zdab
10447 imhs-m24thizman2-no2-bhsdab
10448 2py-edia2-oem-nbetabnaphth
10449 bhs-mepazin-fo-dfzdap
10450 bhs-tetradi-5pho-zdabs
10451 impy-m24thizman2-5amo-bphabs
10452 nim-pnymea-5pho-aspbzla
10453 bim-eta-no2-zdap
10454 dhim-mepipe-oeto-aspibua
10455 n2py-tridi-no2-zdap
10456 imhs-pymea-mes-bhsdap
10457 mam2py-dimen-chexo-betapy
10458 prhs-pazin-oem-asppha
10459 bhs-pazin-no1-psdap
10460 amthiaz-ams2-men-bsdap
10461 2py-thizn-5amo-mezphe
10462 pippy-mepipe-men-bnsdap
10463 bhs-thizn-oem-psdap
10464 bhs-m24oxman2-men-betadcph
10465 am2py-pipmea-mecpo-bhsdab
10466 bimhs-propa2s-mes-zdapee
10467 bz-trias-men-psdab
10468 deam-24thizman2-napo-glupha
10469 bhs-dimephmep-mes-aspbzla
10470 pippy-pazin-5pho-csdap
10471 prhs-dimen-no1-mezphe
10472 dhim-mepipe-5pho-betainyl
10473 pippy-dis-ocho-zdab
10474 bimhs-pipa-mes-csdap
10475 impy-tridi-ocho-bhsdap
10476 hythpym-thizo-cno-zdabs
10477 dhim-3pazin-nmo-betapy
10478 piraz-dimen-fo-glyzdap
10479 nim-mepipe2-sem-npsdap
10480 hythpym-24thizman2-cnmo-zdapee
10481 dmam-amn2-fo-dfzdap
10482 piraz-thizn-eoco-betadcph
10483 mam2py-hexas-eoco-zdabs
10484 dhim-tridi-eoco-bhsdab
10485 hythpym-pnymea-emo-csdap
10486 mam2py-m25thiz-napo-betapy
10487 moegua-edia2-sem-nbetapy
10488 dhim-pymea-nmo-bphabs
10489 im-amn2-imo-glubzla
10490 gua-ams2-fo-dfzdap
10491 pippy-amn2-meo-betadcph
10492 bhs-dio-cnmo-bhsdab
10493 2py-eta-meo-bhsdap
10494 phhs-mea-fo-aval
10495 2py-dimen-oem-betapy
10496 nmhs-mepazin-fo-psdap
10497 edothpym-3pazin-no2-csdap
10498 me2py-tetras-no2-asppha
10499 thpym-pyma2-hso-glyzdap
10500 mam2py-eta-meto-psdab
10501 ec-ams3-5amo-bhsdap
10502 2py-pazin-mes-psdab
10503 thpym-edian2-meo-bnsdap
10504 me-mepipen2-ocho-osdap
10506 amim-tetras-no1-dfzdap
10505 bim-diaz-cno-zdabs
10507 emnim-dimephmem-ocho-psdab
10508 deam-dimen-cpro-psdapee
10509 bhs-mepazin-mecpo-zorn
10510 am2py-pentas-5pho-glupha
10511 ppy-din-fo-betaet
10512 impy-mepipe-no1-glyzdap
10513 pippy-m24thizman2-4amo-aspbzla
10514 bimhs-dis-oem-aspbzla
10515 2py-edian2-5pho-zdab
10516 cl3pyme-tridi-meto-betainyl
10517 piraz-25oxman2-eoco-betaet
10518 me2py-am2-oem-nbetapy
10519 dhim-pymea-5pho-zlys
10520 thpym-trias-meteto-zdabs
10521 thpym-mepipe-5pho-bhsdap
10522 me2py-diphmep-4pho-psdap
10523 amim-butn-chexo-ibsdap
10524 nmor-dimephmep-meo-osdap
10525 2py-edian2-ocho-zdab
10526 2py-diphmep-ocho-mezphe
10527 chmhs-ams2-napo-aspbzla
10528 im-tetradi-mmen-dfzdap
10529 fthpym-pyma2-ocho-bphabs
10530 imhs-amn2-no1-zdab
10531 bimhs-25oxman2-oem-dfzdap
10532 me2py-mepipe2-oem-nzdap
10533 am2py-thizn-no1-aspbzla
10534 ppy-eta2s-cpro-bhsdap
10535 me2py-24thizman2-oem-zdabs
10536 impy-mepipe-meteto-psdab
10537 am2py-m24thiz-mes-bnsdap
10538 pippy-dis-mes-mezphe
10539 2py-pazin-eoco-psdap
10540 thpym-eta-fo-zdap
10541 mam2py-mea2s-nmo-bnsdap
10542 2py-pazin-emo-csdap
10543 im-pyma2-meto-dfzdap
10544 imhs-dimephmep-ocho-bhsdab
10545 bim-mepipe-no2-bhsdab
10546 bim-amn2-eoco-betapy
10547 cl3pyme-dimen-no1-psdapee
10548 ppy-dich-no2-csdap
10549 bz-ms-imo-bhsdap
10550 ppy-dis-pyo-psdap
10551 piraz-diaz-cno-glyzdap
10552 pippy-trias-mmea-zdap
10553 dpam-edia2-sem-nzdab
10554 nmor-24thiman-meo-bnsdap
10555 bimhs-trias-mes-zdabs
10556 npip-ams2-meo-glyzdap
10557 me2py-tetradi-mes-bnsdap
10558 cl3pyme-edian2-eoco-psdap
10559 binhs-pnymea-chexo-tsdap
10560 nmhs-dimephmem-napo-mezphe
10561 bim-ams2-oem-psdap
10562 bim-amn2-ocho-bnsdap 10563 thpym-dis-mes-bphabs
10564 hythpym-ms-mmen-aval
10565 edothpym-diphmep-4pho-psdab
10566 am2py-thizn-men-dfzdap
10567 dmthpym-pazi2n-imo-asppha
10568 hythpym-dimen-men-ppsdap
10569 nmor-m24thizman2-ocho-bhsdab
10570 me-mea-aco-zdap
10571 dmbim-propa2s-no1-zdabs
10572 me2py-mepazin-fo-bphabs
10573 thpym-eta2s-mes-aspibua
10574 cl3pyme-amo-chexo-betadcph
10575 amim-pyma2-eoco-zdabs
10576 impy-dis-oeto-bsdap
10577 hythpym-amo2-ocho-ppsdap
10578 deam-pipa-eoco-zdapee
10579 z-amn2-5pho-psdap
10580 bimhs-24thiz-no1-bphabs
10581 2py-dimen-no2-glubzla
10582 amim-m25thiz-5pho-betapy
10583 piraz-dimephmem-hso-zdap
10584 bhs-24thiz-baeo-zdap
10585 impy-24oxman2-emo-betainyl
10586 dmthpym-pymea-meto-aspibua
10587 piraz-m24oxman2-imo-dfzdap
10588 amthiaz-eta-5pho-glupha
10589 ibhs-pazi2n-fo-aspbzla
10590 imhs-diphmem-chexo-zdab
10591 pyraz-hexadi-oem-betaet
10592 thpym-tetradi-mes-betainyl
10593 mam2py-24thiz-mes-betadcph
10594 impy-pipa-eoco-betadcph
10595 imhs-propn-5pho-asppha
10596 deam-eta-chexo-asppha
10597 bimhs-mepazin-oem-bhsdap
10598 imhs-24thizman2-no2-zdap
10599 edothpym-pyma2-cpeo-zdap
10600 bimhs-eta-oeto-bphabs
10601 2py-diaz-oem-asppha
10602 pippy-25oxman2-cno-tsdap
10603 cl3pyme-25oxman2-oeto-glyzdap
10604 bim-tetradi-cpeo-zdabs
10605 pyr-am2-sem-nbetapy
10606 menim-24thiman-mes-glyzdap
10607 impy-2pazin-5pho-csdap
10608 bim-m24oxman2-napo-asppha
10609 dhim-tetradi-no1-zorn
10610 prhs-ams3-meo-bnsdap
10611 mam2py-dimephmep-ocho-bhsdap
10612 impy-25oxman2-meo-zdab
10613 am2py-dimephmem-pyo-betainyl
10614 pippy-pipmea-napo-zdap
10615 me2py-eta-fo-osdap
10616 mam2py-24oxman2-meo-bhsdab
10617 impy-din-baeo-zdap
10618 npip-mepipe-aco-bnsdap
10619 pyrhs-pnymea-men-osdap
10620 amthiaz-tridi-fo-mezphe
10621 amim-pymea-no1-oxal
10622 impy-tetradi-no1-ppsdap
10623 n2py-24thizman2-5pho-betainyl
10624 2py-din-chexo-bnsdap
10625 nmhs-pipa-emo-glupha
10626 mam2py-dimephmep-no2-bphabs
10627 nmor-m24thizman2-ocho-mezphe
10628 thpym-pazin-oem-bhsdap
10629 bim-pazin-meo-bhsdap
10630 deam-tetradi-paco-psdab
10631 bim-pnymea-emo-betainyl
10632 thpym-dimephmep-pro-thizzdap
10633 imhs-pyma2-no1-aspibua
10634 amthiaz-amo2-pheo-glyzdap
10635 thpym-dimephmem-mecpo-csdap
10636 mam2py-pyma2-cnmo-bsdap
10637 am$^2$py-24oxman2-5amo-bphabs
10638 amim-tetras-5amo-mezphe
10639 mam2py-pymea-imo-betadcph
10640 pyrhs-24thiz-5pho-psdap
10641 ppy-m24thizman2-fo-csdap
10642 bhs-edian2-ocho-betapy
10643 mam2py-dis-napo-zdabs
10644 pyrhs-ams3-napo-betadcph
10645 bhs-pazin-oem-psdab
10646 amim-pyma2-5pho-aspibua
10647 impy-pymea-peo-zorn
10648 nmor-ams2-chexo-bhsdab
10649 hythpym-tridi-5pho-zdab
10650 pippy-diphmem-pheo-betainyl
10651 am2py-dis-hso-dfzdap
10652 am2py-pipmea-emo-bnsdap
10653 ibhs-eta-fo-glubzla
10654 pyraz-amo2-mes-zdap
10655 nim-m24thiman2-meteto-psdap
10656 imhs-amn2-meo-psdab
10657 imhs-amn3-men-betainyl
10658 me2py-am3-oem-nbetameph
10659 bhs-edian2-5pho-zdap
10660 bim-24thiman2-mommo-glupha
10661 edothpym-pnymea-no1-aspibua
10662 menim-edian2-meo-bhsdab
10663 bhs-amo3-cno-zdab
10664 impy-edian2-ocho-psdap
10665 bim-pymea-5pho-betapy
10666 2pmhs-pazin-pheo-asppha
10667 dhim-dis-mes-zdap
10668 bhs-m24thizman2-5amo-bsdap
10669 impy-edia2-oem-nbeta34-dimeoph
10670 bhs-m25thiz-eoco-tsdap
10671 hythpym-ams2-no1-zdabs
10672 me2py-dis-imo-mezphe
10673 me2py-n2nme2n-no2-bsdap
10674 bhs-dimephmep-pyo-bnsdap
10675 pippy-pazin-mommo-asppha
10676 bim-amn2-eoco-zdab
10677 chhs-ams2-baeo-bnsdap
10678 imhs-edian2-no1-psdap
10679 thpym-eta-5pho-psdap
10680 chhs-pazin-5amo-mezphe
10681 dmam-amo2-men-bnsdap
10682 im-diaz-fo-zdab
10683 imhs-eta-no2-zdap
10684 thpym-eta-eoco-zdab
10685 ec-24thizman2-eoco-zdab
10686 dhim-mea-oem-zdab
10687 am2py-diphmem-mes-dfzdap
10688 bhs-dimephmep-chexo-dfzdap
10689 im-24thizman2-men-bphabs
10690 thpym-mepipe-ocho-psdab
10691 thpym-amn2-paco-bphabs
10692 thpym-pazin-no2-bnsdap
10693 nmhs-pipmea-pheo-aspbzla
10694 hythpym-diphmep-fo-bnsdap
10695 ibhs-diphmep-5amo-aspbzla
10696 am2py-edia2-oem-nbetapy 10697 bhs-m24thiz-imo-betainyl
10698 amthiaz-edian2-5amo-psdap
10699 me-pnymea-oem-bhsdab
10700 prhs-tridi-cpro-bhsdab
10701 bim-mepipe-hso-aspibua
10702 imhs-edian2-meo-psdap
10703 imhs-mepipe-mes-bsdap
10704 mam2py-24thiz-ocho-zdab
10705 2py-edian2-no1-bnsdap
10706 amthiaz-amo2-chexo-dfzdap
10707 tolhs-mepipen2-mecpo-asppha
10708 hythpym-din-ocho-bnsdap
10709 bhs-n2o2n-ocho-psdap
10710 bim-am3-sem-nzdap
10711 2py-amo2-mes-zdab
10712 thpym-mepipen2-4amo-psdab
10713 bhs-24thizman2-no1-aspbzla
10714 me2py-dipch-mmen-ibsdap
10715 dhim-pnymea-cpro-psdap
10716 menim-24thizman2-5amo-aspibua
10717 bim-pazin-no2-psdab
10718 mam2py-dimephmem-napo-zdabs
10719 dmbim-ams2-imo-psdap
10720 am2py-diphmem-5pho-zdapee
10721 pippy-tetradi-chexo-mezphe
10722 thpym-edian2-no1-betapy
10723 pyrhs-pazin-chexo-asppha
10724 piraz-mepazin-napo-bsdap
10725 amim-pazin-no1-zdabs
10726 hythpym-24thiz-imo-dfzdap
10727 nim-ams3-5amo-betapy
10728 thpym-mepipe-mes-bnsdap
10729 me-24thiz-mmen-mezphe
10730 me2py-pyma2-5pho-aspbzla
10731 am2py-dimen-oem-zdap
10732 2py-mepipe-oem-betapy
10733 imhs-mepipe-ocho-bhsdap
10734 deam-amo2-5pho-zdap
10735 thpym-tridi-men-csdap
10736 mam2py-pnymea-oem-psdab
10737 imhs-diphmep-mes-zdab
10738 gua-24thiman-chexo-aspbzla
10739 2py-n2nme2n-eoco-zdabs
10740 bhs-eta2s-eoco-glyzdap
10741 ibhs-24thizman2-meo-psdapee
10742 morhs-amo2-men-bhsdab
10743 impy-thizn-men-csdap
10744 hythpym-pyma2-hso-aspaba
10745 2pmhs-pazi2n-no1-betaet
10746 dhim-25oxman2-meo-betadcph
10747 2pmhs-pazi2n-4pho-zdabs
10748 imhs-24thizman2-5amo-bphabs
10749 ibhs-amo2-4pho-zlys
10750 fthpym-pipa-oem-bhsdab
10751 mam2py-mepipen2-emo-aspbzla
10752 pyr-dimephmep-fo-aspbzla
10753 me2py-diphmep-5amo-thizzdap
10754 tolhs-mepazin-meto-aspibua
10755 thpym-pyma2-emo-aspibua
10756 pyraz-m24oxman2-oem-mezphe
10757 moequa-mepipen2-no2-bhsdap
10758 bimhs-ams2-men-zdap
10759 im-pnymea-emo-zdab
10760 bhs-am2-oem-nbetabnaphth
10761 deam-eta-5pho-aspibua
10762 bim-m24thiz-men-mezphe
10763 dmthpym-n2o2n-ocho-bhsdap
10764 impy-pyma2-pheo-glubzla
10765 pyraz-ms-fo-zdabs
10766 am2py-dimephmem-nmo-zdabs
10767 pyr-tetradi-eoco-bphabs
10768 impy-din-cpro-bhsdab
10769 pyr-dimephmep-chexo-glupha
10770 mam2py-mepipe-ocho-betadcph
10771 phpip-m25oxman2-men-betadcph
10772 mepip-indan2-5amo-asppha
10773 thpym-pipmea-meo-asppha
10774 pippy-dimen-eoco-asppha
10775 chmhs-amo2-no1-osdap
10776 2py-eta-mes-zdab
10777 bim-amn2-mes-bhsdap
10778 morhs-amn2-pyo-bhsdap
10779 bhs-m24oxman2-oem-zdap
10780 dmam-mea-chexo-psdap
10781 dhim-mea-meteto-ppsdap
10782 imhs-pymea-imo-betadcph
10783 mam2py-mepipe2-sem-nzdap
10784 piraz-diphmep-eoco-glyzdap
10785 am-dimephmem-5pho-aspbzla
10786 dpam-24thizman2-ocho-bnsdap
10787 2py-tetras-cpro-bphabs
10788 imhs-pazin-no1-zdap
10789 mam2py-dimephmem-chexo-zlys
10790 me2py-pazin-emo-aspibua
10791 thpym-indan2-aco-zdabs
10792 me2py-trias-no2-mezphe
10793 morhs-mepazin-ocho-dfzdap
10794 dhim-dio-no2-aspibua
10795 bim-amo2-ocho-zdabs
10796 imhs-m24oxman2-meo-osdap
10797 piraz-ams2-eoco-ibsdap
10798 thpym-diphmep-cpeo-betadcph
10799 piraz-dimephmep-meteto-glyzdap
10800 pippy-pentadi-emo-bnsdap
10801 bhs-eta-4amo-bnsdap
10802 bimhs-tridi-meo-bsdap
10803 thpym-25oxman2-meteto-psdab
10804 bim-ams2-no2-aspbzla
10805 bhs-pazin-oem-bnsdap
10806 bhs-amn2-mes-betapy
10807 imhs-amn2-eoco-betapy
10808 am2py-edian2-pro-psdap
10809 menim-tetradi-cpro-aspibua
10810 impy-m25thiz-4amo-aspaba
10811 bimhs-24thiz-ocho-bnsdap
10812 edothpym-amn2-pyo-bsdap
10813 me2py-pazin-mommo-zdap
10814 hythpym-25oxman2-chexo-mezphe
10815 n2py-25oxman2-men-zdabs
10816 pyr-m24thizman2-imo-betadcph
10817 dhim-am3-oem-nbetameph
10818 tolhs-dimen-mes-aval
10820 am2py-mepipe2-oem-npsdap
10821 amim-edian2-5amo-glyzdap
10822 dhim-dimephmem-men-psdab
10823 dhim-edian2-5amo-bsdap
10824 pippy-am2-sem-nzdap
10825 am2py-diphmep-fo-mezphe
10826 thpym-mepipe-mmen-betapy
10827 phpip-mepazin-no1-bphabs
10828 2py-eta-oem-zdab
10829 mam2py-tetras-meo-betapy
10830 pippy-diphmep-oem-bphabs
10831 am2py-mepipen2-5amo-bsdap 10832 npip-ams2-eoco-zdap
10833 pyraz-m25thiz-5amo-bsdap
10834 2py-pazin-oem-psdab
10835 cl3pyme-diphmep-napo-tsdap
10836 im-pazin-pheo-betadcph
10837 thpym-pazin-hso-mezphe
10838 imhs-dimephmem-pyo-dfzdap
10839 hythpym-m25thiz-imo-glyzdap
10840 morhs-am3diaz-meo-asppha
10841 amthiaz-dio-meto-csdap
10842 amim-diphmep-imo-psdapee
10843 imhs-mea-chexo-psdap
10844 dhim-mepazin-5pho-aspibua
10845 tolhs-24thiz-no1-betadcph
10846 amim-edian2-fo-bphabs
10847 mam2py-mepipe2-sem-nzdab
10848 pippy-m25thiz-mommo-psdap
10849 mam2py-pentas-5amo-psdap
10850 piraz-propn-5pho-dfzdap
10851 imhs-diphmep-oem-zdabs
10852 mam2py-dimen-oem-zdab
10853 bzl-tridi-fo-bhsdab
10854 dmthpym-pymea-men-betainyl
10855 2py-am3-oem-nbetameph
10856 bimhs-pymea-mes-aspibua
10857 amim-m24thiz-oem-psdap
10858 hythpym-propn-meo-bhsdap
10859 2py-edian2-5pho-psdab
10860 thpym-eta-ocho-bsdap
10861 imhs-diphmep-napo-psdab
10862 me2py-thizn-chexo-zdabs
10863 thpym-dio-men-glubzla
10864 imhs-amn2-no2-zdap
10865 morhs-pipmea-4amo-aval
10866 mam2py-edia2-oem-nbeta34-dimeoph
10867 ec-mepipen2-napo-bnsdap
10868 deam-edian2-5amo-bhsdab
10869 2py-mepipe-meo-bnsdap
10870 2py-tridi-5pho-glubzla
10871 mam2py-amn3-5amo-aspibua
10872 bim-pyma2-napo-zdab
10873 am2py-pazin-mes-bnsdap
10874 dpam-indan2-cnmo-aspibua
10875 nim-24thizman2-chexo-bphabs
10876 amim-pymea-aco-bhsdap
10877 hythpym-dis-no1-betapy
10878 impy-pyma2-emo-bphabs
10879 2py-edian2-5pho-bsdap
10880 amthiaz-mea2s-5pho-mezphe
10881 impy-25oxman2-chexo-zdabs
10882 bimhs-mepipe2-sem-nzdap
10883 imhs-pnymea-no1-betapy
10884 2py-pipa-mes-betapy
10885 pyraz-25oxman2-mecpo-mezphe
10886 tolhs-am2-oem-nbetabnaphth
10887 bhs-diphmep-meto-bsdap
10888 hythpym-amn3-chexo-bnsdap
10889 bim-edian2-5pho-psdab
10890 bim-25oxman2-fo-psdab
10891 imhs-pipa-cpeo-psdap
10892 thpym-mepipe-oem-betapy
10893 me2py-24thizman2-paco-bsdap
10894 edothpym-pentadi-baeo-psdap
10895 gua-pipmeo-mommo-zdabs
10896 chmhs-props-5amo-bphabs
10897 bhs-tridi-oeto-thizzdap
10898 im-tridi-men-psdab
10899 2py-mepipe-ocho-psdab
10900 pyraz-tridi-eoco-zdab
10901 hythpym-diphmep-emo-psdap
10902 nmor-pazin-cpeo-aspaba
10903 bzl-eta-meteto-asppha
10904 tolhs-pipmeo-mes-zdab
10905 bimhs-dimen-oem-asppha
10906 thpym-pnymea-no1-zdabs
10907 bimhs-mepipen2-baeo-tsdap
10908 me2py-mepipen2-ocho-betadcph
10909 2py-eta-eoco-zdab
10910 pippy-dimen-men-psdapee
10911 imhs-25oxman2-napo-zdabs
10912 hythpym-m24thizman2-4amo-asppha
10913 imhs-eta-no2-zdab
10914 am4py-mepipen2-ocho-zdabs
10915 thpym-3diaz-5amo-bsdap
10916 piraz-amn2-oem-betadeph
10917 n2py-dimephmep-no1-betainyl
10918 menim-n2o2n-baeo-betadcph
10919 n2py-tridi-no2-ppsdap
10920 me2py-trias-5pho-betadcph
10921 2py-m25oxman2-no1-bhsdap
10922 dhim-ams2-eoco-asppha
10923 pippy-edian2-oem-bsdap
10924 imhs-amn3-pheo-bphabs
10925 gua-dimephmep-mommo-bphabs
10926 piraz-edian2-daco-tsdap
10927 emnim-amn2-no2-glyzdap
10928 mepip-24thiz-4amo-bsdap
10929 2py-amn3-5pho-bsdap
10930 bimhs-pipa-cpro-aspibua
10931 chmhs-dimephmep-meo-bnsdap
10932 hythpym-n2o2n-imo-betainyl
10933 bimhs-am2-sem-nzdap
10934 pippy-ams3-no2-asppha
10935 hythpym-ams2-5amo-csdap
10936 im-amn3-cpeo-bhsdab
10937 impy-am3-sem-nzdap
10938 bhs-amo3-pro-psdap
10939 ec-pentas-chexo-aspibua
10940 2py-mepipe-mes-bhsdap
10941 me2py-thizn-imo-bhsdap
10942 4pmhs-edian2-ocho-bnsdap
10943 dmbim-am3diaz-no1-bphabs
10944 mam2py-3diaz-no2-bphabs
10945 emnim-24thizman2-fo-zdap
10946 bim-mepipe-eoco-bsdap
10947 bimhs-mepipe-emo-thizzdap
10948 piraz-trias-peo-asppha
10949 dhim-3pazin-imo-mezphe
10950 me2py-amn3-baeo-bhsdap
10951 am4py-pazin-emo-zdap
10952 bhs-amn2-no1-bsdap
10953 imhs-mepipe-mes-betapy
10954 am4py-din-mes-betaet
10955 bhs-eta-oem-betainyl
10956 dhim-dis-4amo-zdabs
10957 phpip-dimephmem-cnmo-psdab
10958 2py-tetradi-5amo-tsdap
10959 bim-props-men-zdab
10960 me2py-pentas-emo-bsdap
10961 mepip-am3diaz-meteto-bhsdap
10962 dmam-dipch-mmen-bphabs
10963 hythpym-eta-oem-psdap
10964 pyrhs-mepipe2-sem-nbeta34-dimeoph
10965 bz-mepipe2-sem-nbetameph 10966 fthpym-m24thizman2-eoco-betapy
10967 nmor-din-no2-betainyl
10968 nmhs-diphmep-5pho-zdab
10969 pippy-dimen-napo-aval
10970 pyrhs-am3-sem-nbetameph
10971 bz-din-5amo-bnsdap
10972 pippy-3pazin-emo-bsdap
10973 bimhs-pazin-5pho-mezphe
10974 dmbim-amn2-napo-mezphe
10975 bim-trias-emo-aspbzla
10976 piraz-amo2-emo-betadcph
10977 npip-diphmep-no2-zdabs
10978 bim-thizs-napo-dfzdap
10979 me2py-trias-imo-glyzdap
10980 pyraz-25oxman2-napo-bnsdap
10981 chhs-dis-eoco-betadcph
10982 imhs-amn2-meo-zdab
10983 imhs-ams2-5amo-bsdap
10984 mam2py-amn2-napo-betadcph
10985 mam2py-n24thiman-no2-aspibua
10986 am4py-pymea-aco-zdap
10987 mam2py-eta-chexo-bhsdap
10988 2py-din-meo-thizzdap
10989 thpym-pazin-fo-bhsdab
10990 morhs-pnymea-emo-betadcph
10991 fthpym-eta-hso-betadcph
10992 dpam-pipa-oem-tsdap
10993 2pmhs-pipmes-men-zlys
10994 pippy-tridi-napo-mezphe
10995 z-edian2-eoco-betadcph
10996 imhs-m25oxman2-5pho-betapy
10997 pippy-amo2-pro-csdap
10998 bimhs-amn2-napo-betapy
10999 am4py-m24thiman2-5amo-zlys
11000 morhs-24thizman2-meo-asppha
11001 4pmhs-am3-sem-nbetapy
11002 mepip-m25thiz-ocho-bhsdap
11003 impy-propn-mmen-zdab
11004 imhs-eta-men-bhsdap
11005 ec-edian2-nmo-dfzdap
11006 pippy-dimephmem-ocho-bnsdap
11007 prhs-mepipen2-fo-dfzdap
11008 thpym-pipa-aco-bsdap
11009 pippy-trias-5pho-aspbzla
11010 dhim-mepipe-eoco-aval
11011 pippy-dimen-eoco-bnsdap
11012 mam2py-tridi-eoco-dfzdap
11013 pyraz-pyma2-imo-psdab
11014 bimhs-am3-sem-nbetapy
11015 ec-trias-ocho-bphabs
11016 bimhs-24thiz-fo-aspbzla
11017 menim-dis-oem-aspbzla
11018 tolhs-thizs-ocho-bhsdab
11019 imhs-pymea-no2-aspaba
11020 dhim-pazin-men-bhsdab
11021 dhim-amn3-eoco-asppha
11022 am2py-edian2-meo-psdab
11023 pippy-pipmea-no1-psdab
11024 bimhs-mepipen2-emo-zdap
11025 me2py-ams3-cnmo-aspaba
11026 thpym-eta-5pho-bnsdap
11027 nmor-pipa-oem-mezphe
11028 fthpym-amn2-cpeo-bphabs
11029 bimhs-mepiphmem-meto-betadcph
11030 bz-eta-fo-mezphe
11031 thpym-mepazin-chexo-betapy
11032 thpym-edian2-mes-bnsdap
11033 bhs-am3diaz-oem-bnsdap
11034 amim-mea-mes-csdap
11035 morhs-tetradi-no2-glubzla
11036 mam2py-m25thiz-cno-psdap
11037 gua-am3-oem-nzdab
11038 mam2py-mepipen2-napo-psdap
11039 bhs-eta-5pho-zdab
11040 me-tetradi-5pho-zdab
11041 ec-24thiz-napo-bsdap
11042 imhs-ams2-no2-glyzdap
11043 edothpym-25oxman2-napo-bhsdap
11044 imhs-eta-eoco-psdab
11045 imhs-dimephmep-mes-zdabs
11046 bim-pymea-mes-glyzdap
11047 bhs-amo2-men-ppsdap
11048 bim-mepipen2-fo-glupha
11049 menim-amo3-napo-betadcph
11050 bhs-edian2-no1-bhsdap
11051 amim-diphmep-no1-bhsdab
11052 bhs-edian2-napo-zdap
11053 am2py-pentas-men-psdap
11054 thpym-eta-oem-psdap
11055 fthpym-pazin-emo-csdap
11056 imhs-pipa-chexo-betapy
11057 pyraz-pnymea-mes-aspbzla
11058 mam2py-pazin-meto-mezphe
11059 ec-24thiman2-emo-bphabs
11060 bhs-amn2-no2-psdap
11061 ibhs-m24thizman2-meo-bhsdap
11062 imhs-eta-eoco-zdab
11063 bhs-mepipe-5pho-betapy
11064 impy-am3-oem-nbeta34dimeoph
11065 am2py-diphmep-cpro-zdap
11066 me2py-n2o2n-fo-psdab
11067 piraz-25oxman2-meo-bnsdap
11068 morhs-25thizman2-nmo-asppha
11069 pyraz-24thiz-5pho-zdap
11070 pyrhs-am2-sem-nbetameph
11071 prhs-edian2-emo-glyzdap
11072 dmthpym-pipmeo-mes-betapy
11073 piraz-24thiz-5pho-bnsdap
11074 pippy-tetradi-oem-mezphe
11075 deam-am2-sem-nzdab
11076 bhs-mepipe-mecpo-bnsdap
11077 amim-2pazin-baeo-bhsdap
11078 n2py-eta-emo-betainyl
11079 chmhs-tetradi-aco-tsdap
11080 chhs-24thiz-mecpo-zdabs
11081 phpip-props-mecpo-betadcph
11082 me2py-pnymea-eoco-mezphe
11083 dmbim-m24thizman2-peo-betadcph
11084 im-25oxman2-fo-betapy
11085 pippy-pyma2-emo-bhsdap
11086 binhs-ms-hso-asppha
11087 imhs-trias-cno-glyzdap
11088 dhim-am3diaz-emo-bhsdab
11089 2py-trias-men-betaet
11090 amim-pipa-5pho-bhsdab
11091 pippy-amn2-no2-zdab
11092 npip-pipmea-meteto-zlys
11093 dhim-pymea-mes-csdap
11094 emnim-pymea-men-thizzdap
11095 nmhs-m25oxman2-emo-psdap
11096 thpym-diphmem-no1-bsdap
11097 mam2py-eta-imo-asppha
11098 bim-amo2-mes-bnsdap
11099 amim-propa2s-mes-betadcph 11100 mam2py-din-hso-glubzla
11101 2py-25oxman2-no1-zdap
11102 bimhs-amn2-men-psdab
11103 bimhs-dimen-ocho-oxal
11104 imhs-edian2-no2-bsdap
11105 me2py-m25thizman2-no1-csdap
11106 impy-din-no1-zdabs
11107 moegua-dimephmep-men-bhsdap
11108 amim-mepipe2-oem-nzdab
11109 imhs-diphmem-emo-mezphe
11110 thpym-pnymea-fo-glyzdap
11111 thpym-din-5amo-betapy
11112 emnim-pymea-men-glyzdap
11113 bhs-amn2-5pho-bsdap
11114 me2py-am3-sem-nzdab
11115 dhim-pnymea-men-psdab
11116 bim-m24thizman2-men-mezphe
11117 amim-amo2-no1-psdab
11118 piraz-dimephmep-ocho-betainyl
11119 me2py-edian2-meo-bsdap
11120 menim-pipmea-5pho-bsdap
11121 me2py-m25thiz-peo-aspibua
11122 thpym-eta-men-asppha
11123 bhs-pnymea-fo-bhsdap
11124 nmor-mepipe-no1-bnsdap
11125 phpip-dimen-chexo-betaet
11126 bim-dis-chexo-dfzdap
11127 2py-mepipe-eoco-betapy
11128 2py-dimephmep-4amo-bhsdap
11129 amim-24thiz-aco-dfzdap
11130 2py-amn2-eoco-zdap
11131 chhs-m25thiz-meo-psdapee
11132 pyrhs-mepipen2-cno-bsdap
11133 menim-25thiman2-5amo-aspibua
11134 2py-dimen-aco-bsdap
11135 hythpym-thizn-emo-csdap
11136 bim-pazin-no1-bhsdap
11137 hythpym-pnymea-imo-bnsdap
11138 bim-amn2-no1-bnsdap
11139 ec-pipmea-meo-bphabs
11140 2py-thizn-5pho-betainyl
11141 imhs-mepipe-mes-zdap
11142 thpym-24thiman-eoco-bnsdap
11143 am2py-mepipe-men-aspbzla
11144 bhs-dimephmem-men-glyzdap
11145 2py-mepipe-no1-psdab
11146 dhim-pipmeo-ocho-asppha
11147 bimhs-mepipe2-oem-nbetab naphth
11148 bim-dimen-no2-bsdap
11149 bim-tetradi-mes-betadcph
11150 dpam-24thizman2-ocho-bhsdab
11151 impy-dimephmep-chexo-aspbzla
11152 menim-mepipen2-meo-betadcph
11153 pippy-trias-oeto-zdap
11154 2py-eta-no1-zdabs
11155 bim-m25thizman2-pheo-zdap
11156 2py-25oxman2-no2-psdab
11157 bimhs-diphmem-no2-zorn
11158 bhs-mepipen2-daco-zdabs
11159 pyraz-diphmep-5amo-psdap
11160 mepip-mepipe2-oem-nbeta34-dimeoph
11161 am2py-25oxman2-mes-psdab
11162 dhim-dimephmem-5pho-csdap
11163 bhs-diphmem-men-bhsdap
11164 bhs-dimephmep-no1-basdap
11165 bhs-m24oxman2-ocho-zdabs
11166 prhs-dis-chexo-bnsdap
11167 mam2py-eta-meo-aspbzla
11168 am2py-amn2-men-glyzdap
11169 hythpym-pazin-napo-csdap
11170 2py-edian2-meo-bhsdap
11171 2py-mea-napo-aspaba
11172 mam2py-tetradi-imo-csdap
11173 im-pnymea-5amo-betapy
11174 emnim-diphmem-no1-betaet
11175 me2py-props-nmo-tsdap
11176 piraz-pnymea-oem-betadcph
11177 emnim-pnymea-mmen-betapy
11178 mepip-amn2-oem-betainyl
11179 dhim-amn3-aco-bnsdap
11180 hythpym-25thiman2-oem-aspibua
11181 dhim-pazin-cnmo-mezphe
11182 2py-thizs-imo-zdapee
11183 imhs-mepipe-no1-bnsdap
11184 impy-tridi-mommo-oxal
11185 amim-diphmep-men-zdab
11186 thpym-amn2-ocho-zdab
11187 nmor-propa2s-mes-aspibua
11188 emnim-m25thiz-aco-zdapee
11189 am2py-dimephmep-mes-betadcph
11190 moegua-mepipe-daco-dfzdap
11191 2py-edian2-nmo-zdab
11192 thpym-butn-mommo-psdapee
11193 thpym-eta-oem-asppha
11194 ibhs-pymea-meo-csdap
11195 thpym-mepipe-mes-zdab
11196 mepip-diphmep-mes-ibsdap
11197 dhim-m25thiz-napo-zlys
11198 pippy-mepipen2-eoco-zdap
11199 pyrhs-am2-sem-nbetabnaphth
11200 nmor-tridi-napo-zdap
11201 imhs-edian2-mmen-psdapee
11202 chhs-mepipe-oem-thizzdap
11203 impy-pazin-no1-betapy
11204 pippy-amn3-peo-psdab
11205 pippy-dimephmem-oem-zdap
11206 emnim-amn2-5amo-betapy
11207 piraz-3diaz-paco-csdap
11208 dmbim-amn2-mes-aspaba
11209 bim-pnymea-fo-betainyl
11210 cl3pyme-25oxman2-eoco-aspbzla
11211 moegua-tetras-ocho-mezphe
11212 mepip-pipmeo-4amo-bhsdap
11213 bim-dis-men-aspaba
11214 ppy-pipmea-eoco-bnsdap
11215 pyraz-edian2-napo-psdab
11216 hythpym-24thiman2-meto-zdap
11217 pippy-amn2-meo-bhsdab
11218 dpam-mea2s-aco-glyzdap
11219 2py-thizo-cnmo-bnsdap
11220 bim-tetradi-meo-asppha
11221 pippy-pazin-chexo-bhsdab
11222 emnim-diphmep-chexo-zdabs
11223 imhs-m24thiman2-meo-csdap
11224 bimhs-mepipen2-napo-tsdap
11225 imhs-25thiman2-no1-bnsdap
11226 thpym-m25thizman2-chexo-bnsdap
11227 ppy-ams2-oeto-csdap
11228 dhim-tetradi-meto-glyzdap
11229 binhs-mea-imo-bphabs
11230 bhs-25oxman2-napo-betainyl
11231 pyr-dimephmem-napo-psdap
11232 dmthpym-pentadi-5amo-mezphe
11233 dmam-indan2-cpro-psdab 11234 im-eta2s-eoco-bhsdab
11235 dhim-butn-mes-osdap
11236 impy-pentas-oem-aspbzla
11237 imhs-mepipe-oem-zdab
11238 piraz-m25thiman2-chexo-zdap
11239 ec-pymea-no1-aval
11240 dmbim-ams2-men-glupha
11241 2py-pnymea-napo-zdap
11242 impy-amo2-chexo-glupha
11243 2py-thizs-no2-bphabs
11244 cl3pyme-24thizman2-5amo-glyzdap
11245 piraz-pazin-emo-glupha
11246 bimhs-trias-eoco-bphabs
11247 2py-butn-fo-aspbzla
11248 me2py-py ma2-men-betapy
11249 bim-mepazin-5amo-zdap
11250 bim-edian2-meo-zdap
11251 imhs-amo2-cno-glyzdap
11252 thpym-m24thiz-emo-betainyl
11253 hythpym-pipa-cnmo-zdab
11254 pippy-eta-imo-thizzdap
11255 bhs-24thiz-fo-glyzdap
11256 bhs-amn2-ocho-psdab
11257 chmhs-mepazin-meo-aspbzla
1125B nmhs-thizn-chexo-glyzdap
11259 imhs-amn2-meto-mezphe
11260 thpym-eta-no1-bsdap
11261 2py-eta-5pho-bnsdap
11262 me2py-eta-oeto-mezphe
11263 fthpym-dimen-no1-psdap
11264 me-24thiman-chexo-glyzdap
11265 pippy-dis-ocho-asppha
11266 chhs-m24thizman2-men-aspibua
11267 am-tetradi-baeo-glubzla
11268 thpym-edia2-sem-nbeta34-dimeoph
11269 thpym-eta-meo-zdab
11270 nmhs-24thizman2-no1-mezphe
11271 bim-3diaz-oem-bhsdap
11272 prhs-edian2-pyo-csdap
11273 pippy-25oxman2-no1-dfzdap
11274 gua-dimen-meo-psdapee
11275 thpym-dis-mes-zdab
11276 am2py-pyma2-men-betainyl
11277 impy-dimephmep-cpro-bnsdap
11278 bhs-mepipe2-sem-nbeta3-4dimeoph
11279 amim-pipa-oeto-csdap
11280 chhs-propn-emo-bhsdap
11281 me2py-pymea-chexo-psdap
11282 bhs-mepipe-ocho-zdabs
11283 2pmhs-m25oxman2-5amo-bphabs
11284 moegua-pazin-mes-zdap
11285 bhs-24thiman2-no1-osdap
11286 me-m25thiz-5pho-psdap
11287 me2py-diphmem-imo-bsdap
11288 chmhs-tridi-5amo-aval
11289 2py-mepipe-meo-bhsdap
11290 impy-amo2-napo-zdabs
11291 pyrhs-diphmep-imo-zdap
11292 am-din-no1-csdap
11293 thpym-amn3-no1-csdap
11294 2py-eta-ocho-bnsdap
11295 thpym-pymea-ocho-asppha
11296 chhs-propn-no2-aspbzla
11297 thpym-amn2-oem-bsdap
11298 hythpym-tridi-cno-aspbzla
11299 menim-m24thiman2-emo-zdap
11300 hythpym-tridi-fo-glyzdap
11301 2py-amn3-emo-psdab
11302 bimhs-amo2-no2-aspbzla
11303 me2py-amn2-men-zdap
11304 mam2py-indan2-5amo-zorn
11305 piraz-tetras-no2-aspbzla
11306 dhim-ams2-imo-aspbzla
11307 moegua-propn-men-dfzdap
11308 bhs-mea-no2-bphabs
11309 piraz-dio-emo-mezphe
11310 bim-edia2-sem-npsdap
11311 thpym-edian2-napo-aspbzla
11312 thpym-amn3-meteto-zdabs
11313 bz-25oxman2-meo-tsdap
11314 am2py-pymea-oem-csdap
11315 thpym-eta-no2-psdap
11316 bim-amn2-cnmo-psdab
11317 thpym-eta-meo-zdap
11318 2pmhs-diphmem-emo-mezphe
11319 imhs-25oxman2-imo-bsdap
11320 bimhs-propa2s-fo-csdap
11321 phpip-thizn-pyo-aval
11322 pippy-amo2-meo-bphabs
11323 bhs-eta-no1-psdab
11324 pippy-am3-sem-nbetabnaphth
11325 mam2py-pyma2-napo-betainyl
11326 pippy-dich-eoco-bhsdap
11327 impy-24thizman2-cpro-psdap
11328 bim-amo2-paco-bnsdap
11329 amim-2pazin-aco-mezphe
11330 n2py-24thiz-cno-bnsdap
11331 thpym-ams2-imo-csdap
11332 bhs-amn3-imo-zdabs
11333 pippy-edian2-5pho-bphabs
11334 pippy-thizs-5amo-asppha
11335 amim-thizs-meteto-glupha
11336 2py-24thiman-no2-bsdap
11337 bim-mepipe-5pho-psdap
11338 prhs-indan2-ocho-aspibua
11339 impy-pyma2-oem-ibsdap
11340 am2py-mepipe-4pho-osdap
11341 pippy-diphmem-men-betapy
11342 dhim-indan2-fo-mezphe
11343 imhs-mepipe-no1-zdap
11344 ec-tetradi-5amo-mezphe
11345 mam2py-m24thizman2-mes-zdap
11346 bzl-amn2-paco-psdab
11347 bhs-tetras-daco-betapy
11348 pyrhs-24thiman-imo-betapy
11349 me-diphmem-eoco-aspaba
11350 bim-pyma2-eoco-aspbzla
11351 bim-edian2-oem-zdab
11352 chhs-eta-meto-betainyl
11353 bimhs-propn-peo-csdap
11354 n2py-m24thizman2-5pho-betapy
11355 dmbim-24oxman2-men-ppsdap
11356 bhs-amn2-ocho-zdap
11357 bimhs-mepipe2-oem-npsdap
11358 dhim-trias-meo-bnsdap
11359 bim-amn3-oem-betapy
11360 2py-tridi-mes-aspbzla
11361 dhim-amn3-5pho-betadcph
11362 dhim-pazin-chexo-ppsdap
11363 prhs-tridi-mes-bphabs
11364 dmam-propn-oem-thizzdap
11365 bimhs-diphmem-nmo-betainyl
11366 imhs-props-chexo-oxal
11367 imhs-thizn-napo-bsdap 11368 bhs-eta-meo-bsdap
11369 amim-mepipen2-emo-betapy
11370 thpym-ms-men-bnsdap
11371 2py-pipa-imo-glyzdap
11372 imhs-diphmep-5amo-betapy
11373 dmbim-25thizman2-emo-bhsdap
11374 emnim-mepazin-eoco-zdabs
11375 imhs-tetradi-meo-bphabs
11376 2py-eta-eoco-psdab
11377 moega-tetradi-meto-bphabs
11378 z-dimephmem-5amo-betadcph
11379 thpym-eta-5pho-zdap
11380 bim-amn2-meo-psdap
11381 dhim-diphmem-imo-betainyl
11382 bimhs-m25oxman2-emo-bsdap
11383 chhs-tetradi-peo-psdap
11384 piraz-propa2s-fo-bnsdap
11385 mepip-mepazin-fo-bhsdap
11386 pippy-dimen-baeo-bhsdab
11387 amim-pipa-emo-psdap
11388 dpam-mepipe-men-bsdap
11389 bhs-butn-mmen-bhsdap
11390 morhs-diphmep-cno-bnsdap
11391 thpym-pazin-oem-psdap
11392 imhs-pazin-5pho-bsdap
11393 moegua-ams2-napo-zdabs
11394 bhs-24thiz-fo-thizzdap
11395 bhs-din-emo-mezphe
11396 am2py-dimen-ocho-csdap
11397 nmhs-mepipe-5pho-aspbzla
11398 pyr-eta-paco-bnsdap
11399 imhs-dimephmep-oem-csdap
11400 me2py-mepipen2-ocho-betadcph
11401 bim-amn2-no2-psdab
11402 bim-mepipe-no1-psdab
11403 pippy-pnymea-5amo-bhsdab
11404 am2py-24thizman2-oem-bnsdap
11405 amim-pipa-4amo-aspibua
11406 dpam-25oxman2-men-mezphe
11407 piraz-dimephmep-no1-betapy
11408 impy-24thiz-chexo-glyzdap
11409 hythpym-pnymea-paco-zorn
11410 mam2py-pipa-eoco-csdap
11411 piraz-mepipe-emo-bphabs
11412 deam-ams2-napo-betapy
11413 n2py-pnymea-chexo-betainyl
11414 me2py-propn-emo-asppha
11415 am2py-m24thizman2-pheo-aspbzla
11416 bim-dimephmep-ocho-zdapee
11417 bzl-thizn-no1-thizzdap
11418 dpam-pipmes-no1-betainyl
11419 pyr-tridi-chexo-psdab
11420 dhim-pymea-5pho-aspibua
11421 bimhs-24thizman2-fo-aspibua
11422 impy-eta-ocho-bhsdap
11423 prhs-n24thiman-aco-aspibua
11424 am2py-pipmea-imo-betapy
11425 nim-pentas-emo-psdap
11426 amim-pipmea-emo-zdab
11427 me2py-pipa-chexo-dfzdap
11428 am4py-thizn-men-bsdap
11429 pippy-indan2-oeto-zdabs
11430 amim-amo2-baeo-bsdap
11431 impy-amn2-5amo-psdab
11432 amim-mepipen2-peo-zdap
11433 bzl-hexas-emo-bsdap
11434 amim-pnymea-chexo-bsdap
11435 dmam-25thiman2-meo-betapy
11436 pippy-diphmep-meo-bsdap
11437 cl3pyme-diphmep-no2-zdab
11438 2py-amn2-mes-bnsdap
11439 dmbim-m24thiz-meo-mezphe
11440 ppy-dimephmep-5amo-dfzdap
11441 mam2py-am2-oem-nbeta34-dimeoph
11442 im-pazin-fo-bhsdap
11443 am2py-amn2-meo-bhsdab
11444 mam2py-amn3-mes-betaet
11445 impy-n2o2n-cno-bsdap
11446 imhs-trias-no1-bhsdap
11447 mam2py-pymea-ocho-bhsdap
11448 amim-24thizman2-peo-bhsdab
11449 2py-amn2-5amo-glubzla
11450 bzl-mepazin-meo-aspbzla
11451 amthiaz-pazin-men-betapy
11452 dhim-amn3-5pho-betadcph
11453 gua-dimen-napo-betapy
11454 pippy-amo2-meto-betadcph
11455 amim-dimen-men-csdap
11456 bimhs-m25thizmaa2-eoco-dfzdap
11457 me2py-pnymea-paco-dfzdap
11458 amim-pyma2-5amo-dfzdap
11459 dhim-ams2-meo-bsdap
11460 bimhs-m24thizman2-mes-oxal
11461 bim-am2-sem-nbetabnaphth
11462 bhs-pazin-eoco-bhsdap
11463 dmam-thizn-nmo-bhsdab
11464 impy-ams2-chexo-asppha
11465 bzl-ams3-meo-psdap
11466 2py-24thizman2-mmen-csdap
11467 nmor-diphmem-oem-mezphe
11468 ec-tetradi-eoco-betapy
11469 bzl-eta2s-meo-bnsdap
11470 pyrhs-pazi2n-no1-zdab
11471 me2py-pentas-mes-mezphe
11472 nim-pymea-oeto-tsdap
11473 imhs-mepipe-oem-zorn
11474 thpym-eta-eoco-psdap
11475 2py-pazin-oem-zdab
11476 imhs-24thiz-meo-aspbzla
11477 ibhs-mepipe-mes-bhsdab
11478 fthpym-dimen-oem-mezphe
11479 dpam-ams2-meo-aspaba
11480 phhs-edian2-eoco-psdap
11481 dpam-mea-mes-bsdap
11482 bhs-tetradi-5amo-glyzdap
11483 me2py-tridi-ocho-bhsdap
11484 thpym-diphmem-5pho-aspaba
11485 menim-amo2-pyo-dfzdap
11486 dhim-m25thiz-imo-psdab
11487 imhs-diphmem-oem-betadcph
11488 nim-m24thizman2-eoco-aspibua
11489 imhs-amo2-pyo-aspbzla
11490 dhim-24thiman2-chexo-psdap
11491 bhs-pazin-no2-psdab
11492 bhs-edian2-5pho-bsdap
11493 edothpym-dio-no2-psdab
11494 piraz-m24thizman2-meo-zorn
11495 dmam-am3-oem-nbetameph
11496 2py-m24thizman2-peo-betadcph
11497 imhs-tetradi-napo-zdab
11498 am2py-amn3-meo-glyzdap
11499 bimhs-tetradi-mes-oxal
11500 me2py-indan2-chexo-zdap
11501 impy-ams2-mommo-bphabs

| | |
|---|---|
| 11502 | thpym-25oxman2-baeo-aspibua |
| 11503 | bimhs-trias-hso-mezphe |
| 11504 | bhs-pnymea-no2-zdab |
| 11505 | thpym-amn3-ocho-bhsdap |
| 11506 | bimhs-thizn-men-csdap |
| 11507 | dmthpym-amn3-napo-bphabs |
| 11508 | pyrhs-pazi2n-baeo-dfzdap |
| 11509 | amthiaz-pipa-cnmo-bphabs |
| 11510 | imhs-amo2-pro-psdab |
| 11511 | dmbim-ams2-5amo-glupha |
| 11512 | pyrhs-24oxman2-5pho-psdab |
| 11513 | bim-amo2-5amo-bhsdap |
| 11514 | me2py-edian2-mommo-zdabs |
| 11515 | 2pmhs-24thiz-no1-glyzdap |
| 11516 | me2py-eta-mes-dfzdap |
| 11517 | moegua-eta-cnmo-aspbzla |
| 11518 | am2py-dis-eoco-csdap |
| 11519 | chhs-trias-5pho-mezphe |
| 11520 | hythpym-m24thizman2-oem-asppha |
| 11521 | prhs-pymea-oeto-mezphe |
| 11522 | chmhs-pipa-mes-psdab |
| 11523 | emnim-pazin-mommo-psdap |
| 11524 | me2py-eta-oem-dfzdap |
| 11525 | pippy-pazin-no1-zdab |
| 11526 | impy-25oxman2-meo-asppha |
| 11527 | hythpym-ams2-no1-asppha |
| 11528 | pippy-ms-eoco-dfzdap |
| 11529 | 2py-tridi-5pho-csdap |
| 11530 | piraz-n24thiman-meo-bphabs |
| 11531 | bhs-24thiz-meteto-betapy |
| 11532 | nmhs-mepazin-mes-bphabs |
| 11533 | prhs-dimen-emo-betadcph |
| 11534 | ec-dio-no1-bhsdab |
| 11535 | chhs-ms-imo-bhsdap |
| 11536 | npip-pipmea-mommo-glyzdap |
| 11537 | piraz-edian2-fo-ibsdap |
| 11538 | mam2py-amn2-fo-betainyl |
| 11539 | piraz-amn2-meo-psdap |
| 11540 | mam2py-24thizman2-baeo-betainyl |
| 11541 | thpym-mepipe-no2-betapy |
| 11542 | impy-3diaz-eoco-zlys |
| 11543 | bim-mea2s-paco-psdab |
| 11544 | amim-hexas-5pho-dfzdap |
| 11545 | morhs-dimephmep-ocho-csdap |
| 11546 | 2py-m25thiz-5pho-betapy |
| 11547 | thpym-diphmep-oem-bnsdap |
| 11548 | me2py-pipmeo-no2-asppha |
| 11549 | 4pmhs-edian2-cnmo-csdap |
| 11550 | hythpym-24thizman2-meo-aspbzla |
| 11551 | piraz-pipa-mes-bnsdap |
| 11552 | piraz-pipmes-chexo-psdab |
| 11553 | bim-edian2-no1-bnsdap |
| 11554 | bim-mepipe-5pho-bsdap |
| 11555 | am4py-pnymea-no1-dfzdap |
| 11556 | bimhs-dis-ocho-zdap |
| 11557 | thpym-thizn-oeto-asppha |
| 11558 | menim-mea-emo-zdabs |
| 11559 | fthpym-pnymea-peo-aspibua |
| 11560 | bim-tetras-eoco-bhsdap |
| 11561 | ec-am2-oem-nbetameph |
| 11562 | impy-trias-no1-betapy |
| 11563 | thpym-amn2-no2-zdap |
| 11564 | pippy-eta-no2-betainyl |
| 11565 | am2py-trias-no1-betadcph |
| 11566 | 2py-25oxman2-imo-betainyl |
| 11567 | impy-thizn-meo-betadcph |
| 11568 | pippy-mepipe-mecpo-psdap |
| 11569 | cl3pyme-25thizman2-mecpo-bnsdap |
| 11570 | me2py-tridi-5pho-betadcph |
| 11571 | impy-25thiman2-no1-psdab |
| 11572 | ec-am3-oem-nbeta34dimeoph |
| 11573 | impy-eta2s-napo-mezphe |
| 11574 | bhs-pazi2n-no1-bhsdap |
| 11575 | thpym-edian2-no1-bnsdap |
| 11576 | bhs-24thizman2-chexo-zdabs |
| 11577 | bim-amo2-aco-zdapee |
| 11578 | phhs-3pazin-mes-psdap |
| 11579 | amim-diaz-emo-betadcph |
| 11580 | bz-amn2-5pho-zdabs |
| 11581 | dmbim-mepipe-no2-aspbzla |
| 11582 | impy-24thiz-meto-csdap |
| 11583 | fthpym-24thiz-oem-csdap |
| 11584 | amim-24thiz-fo-bphabs |
| 11585 | 2py-mea2s-napo-betaet |
| 11586 | pyrhs-pyma2-cpro-glyzdap |
| 11587 | pyraz-am3-oem-nbetapy |
| 11588 | cl3pyme-ams3-5pho-bphabs |
| 11589 | bhs-trias-imo-bphabs |
| 11590 | bimhs-dimen-mes-zdab |
| 11591 | hythpym-edian2-ocho-betapy |
| 11592 | pippy-amn3-baeo-zlys |
| 11593 | hythpym-25oxman2-paco-glupha |
| 11594 | dhim-mepazin-men-dfzdap |
| 11595 | bim-trias-fo-mezphe |
| 11596 | bhs-eta-eoco-zdab |
| 11597 | im-dich-imo-betadcph |
| 11598 | am4py-m24thizman2-no2-dfzdap |
| 11599 | imhs-mepipe-no2-bnsdap |
| 11600 | hythpym-ms-daco-asppha |
| 11601 | nmhs-edian2-eoco-betadcph |
| 11602 | pippy-pyma2-men-betadcph |
| 11603 | 2py-mepipe-meo-zdap |
| 11604 | chhs-am2-oem-nbetabnaphth |
| 11605 | phhs-dimephmep-pyo-zdapee |
| 11606 | am-mepipe-pyo-betadcph |
| 11607 | bhs-eta-mes-zdap |
| 11608 | pippy-pentadi-meto-aval |
| 11609 | 4pmhs-ams2-5amo-dfzdap |
| 11610 | imhs-eta-meo-psdab |
| 11611 | nmor-24thiman-napo-betapy |
| 11612 | pyraz-din-5amo-mezphe |
| 11613 | prhs-mepipen2-mes-ibsdap |
| 11614 | ppy-pipmeo-men-psdap |
| 11615 | 2py-mepipe-no1-zdap |
| 11616 | am-mea-chexo-aspbzla |
| 11617 | bim-eta-oem-betapy |
| 11618 | bim-25oxman2-fo-betapy |
| 11619 | thpym-25thiz-oem-glubzla |
| 11620 | me2py-25thizman2-meo-aspbzla |
| 11621 | dhim-pymea-meo-bhsdap |
| 11622 | moegua-mepipe2-sem-nbeta34-dimeoph |
| 11623 | 2py-eta-paco-zdab |
| 11624 | hythpym-diphmem-5amo-bhsdab |
| 11625 | bim-mepazin-emo-csdap |
| 11626 | piraz-dimephmem-emo-psdab |
| 11627 | bimhs-3diaz-fo-psdab |
| 11628 | thpym-dipch-emo-betainyl |
| 11629 | am2py-indan2-5amo-psdab |
| 11630 | pyrhs-pipmea-napo-psdapee |
| 11631 | imhs-hexadi-imo-dfzdap |
| 11632 | ppy-tridi-paco-psdapee |
| 11633 | amim-amo2-cpeo-dfzdap |
| 11634 | bimhs-pazin-daco-csdap |
| 11635 | cl3pyme-am3diaz-eoco-zdap |

11636 hythpym-mepipe-cpeo-psdap
11637 me2py-props-mes-psdap
11638 thpym-eta2s-napo-mezphe
11639 bim-trias-emo-zdap
11640 dmthpym-24thiz-5pho-zdabs
11641 pyr-pazin-imo-betapy
11642 impy-m25thiz-fo-bsdap
11643 dmbim-eta2s-chexo-bnsdap
11644 piraz-mepipe2-sem-nbeta34-dimeoph
11645 impy-dis-5amo-zdab
11646 impy-dimephmep-ocho-bnsdap
11647 am2py-din-ocho-psdab
11648 mam2py-eta2s-imo-glyzdap
11649 dpam-dimephmem-no2-betadcph
11650 amim-pipmea-imo-thizzdap
11651 bhs-dis-no1-betadcph
11652 imhs-ams2-fo-ibsdap
11653 dhim-mepipen2-no1-glupha
11654 imhs-dimen-men-psdab
11655 2py-ams2-cpeo-aspbzla
11656 thpym-edian2-eoco-zdap
11657 thpym-ams3-emo-zdabs
11658 me-24thiz-emo-mezphe
11659 2pmhs-diphmem-pyo-zdabs
11660 menim-diphmep-peo-asspha
11661 dhim-mepipe2-sem-nbeta34-dimeoph
11662 imhs-mepipe-mes-psdab
11663 dmthpym-trias-mes-bhsdab
11664 nmor-pipmes-men-glupha
11665 me2py-dimephmem-fo-bhsdap
11666 piraz-pnymea-napo-bphabs
11667 mepip-dimephmem-5pho-betadcph
11668 imhs-amn2-eoco-zdap
11669 dhim-amn3-ocho-dfzdap
11670 dpam-pymea-cno-csdap
11671 me2py-pyma2-emo-zdap
11672 bhs-pipmes-napo-aspibua
11673 bim-amo2-no2-aval
11674 am4py-trias-imo-psdap
11675 impy-din-nmo-bhsdab
11676 bhs-hexas-meteto-zdap
11677 thpym-mepipe-meo-bsdap
11678 piraz-pipa-5pho-glubzla
11679 piraz-tridi-no2-aspibua
11680 thpym-mea-mes-dfzdap
11681 bim-mepipe-ocho-psdab
11682 prhs-pyma2-fo-psdap
11683 inhs-ams2-eoco-mezphe
11684 mam2py-dich-mommo-csdap
11685 bim-edian2-eoco-bsdap
11686 mam2py-pyma2-eoco-psdapee
11687 phhs-diphmem-imo-zdap
11688 mam2py-mea-cpeo-dfzdap
11689 bim-amn2-no2-betapy
11690 bhs-edian2-meo-zdab
11691 im-ams2-emo-thizzdap
11692 hythpym-24thiz-oem-osdap
11693 n2py-din-meo-bhsdap
11694 imhs-dimen-emo-betadcph
11695 piraz-25oxman2-men-aspbzla
11696 pippy-thizn-mecpo-bphabs
11697 pyrhs-pymea-imo-bnsdap
11698 pippy-edian2-chexo-asppha
11699 chhs-pnymea-cpeo-bhsdab
11700 pippy-amo2-oem-betainyl
11701 me2py-indan2-men-mezphe
11702 bimhs-tetradi-mecpo-asppha
11703 imhs-eta-mes-zdab
11704 dpam-m24oxman2-baeo-betapy
11705 imhs-pazin-ocho-bhsdap
11706 ppy-thizn-cpro-mezphe
11707 imhs-24thizman2-meo-bhsdab
11708 ibhs-mepipen2-ocho-csdap
11709 mam2py-mepipe-hso-zdap
11710 bhs-dio-eoco-dfzdap
11711 pyraz-indanZ-mes-csdap
11712 bim-m25thiz-eoco-bsdap
11713 thpym-tridi-no1-zdab
11714 piraz-amn3-pyo-bsdap
11715 bim-amn2-no1-zdab
11716 bhs-edian2-no1-psdab
11717 moegua-amn2-imo-zdab
11718 dmam-edian2-meo-aspaba
11719 impy-25thiman2-nmo-psdap
11720 bhs-mepipe-no1-psdap
11721 imhs-diphmem-imo-psdap
11722 mam2py-pnymea-chexo-glyzdap
11723 2py-m24oxman2-ocho-csdap
11724 tolhs-eta-paco-glyzdap
11725 chmhs-pipmea-oeto-betadcph
11726 im-diphmem-baeo-betapy
11727 am4py-tridi-fo-betapy
11728 dhim-m24thizman2-mmen-psdab
11729 hythpym-25thiman2-5pho-csdap
11729 hythpym-25thiman2-5pho-csdap
11730 mam2py-amn2-napo-asppha
11731 bimhs-pazi2n-eoco-zdabs
11732 amthiaz-amn3-fo-zdabs
11733 impy-eta2s-fo-bhsdap
11734 bhs-25oxman2-fo-bhsdab
11735 am-eta-paco-aspibua
11736 2py-pazin-meo-bhsdap
11737 dmbim-pipmea-baeo-bnsdap
11738 impy-amn2-cno-aspibua
11739 2py-pymea-no1-bsdap
11740 cl3pyme-ams2-eoco-psdab
11741 pippy-propa2s-5pho-bsdap
11742 thpymm25thiz-5amo-ibsdap
11743 bim-edian2-ocho-psdab
11744 imhs-pazin-cnmo-bnsdap
11745 dhim-25oxman2-chexo-dfzdap
11746 amim-mepipen2-5pho-betapy
11747 impy-pyma2-no1-zdab
11748 emnim-trias-napo-bsdap
11749 me2py-amn2-meteto-aspbzla
11750 impy-diphmem-5pho-osdap
11751 thpym-mepipe-imo-zdab
11752 thpym-pentas-emo-betapy
11753 amim-m25thizman2-emo-bsdap
11754 impy-diphmep-emo-mezphe
11755 2py-amn2-meo-bhsdap
11756 me2py-eta-cnmo-betadcph
11757 pippy-mepipen2-cno-csdap
11758 prhs-tetradi-no2-aspbzla
11759 thpym-eta-mes-psdap
11760 thpym-ams2-ocho-betadcph
11761 imhs-mepipe-5amo-betapy
11762 thpym-mepipe-mes-psdab
11763 bim-dio-no2-bsdap
11764 pippy-m24thizman2-fo-aval
11765 dpam-thizn-baeo-psdapee
11766 hythpym-m24thiman2-fo-zdabs
11767 thpym-amn2-no2-bsdap
11768 2py-pipmea-napo-betapy 11769 2py-dis-5amo-zdab
11770 bim-din-imo-glyzdap
11771 bim-pazin-chexo-oxal
11772 impy-eta-mes-bsdap
11773 nim-eta-imo-zdabs
11774 amim-pymea-imo-psdap
11775 tolhs-dimen-cpro-bnsdap
11776 dpam-mepazin-men-mezphe
11777 2py-mepipe-5pho-bsdap
11778 dpam-pipa-no1-mezphe
11779 bimhs-m25thizman2-5amo-psdap
11780 im-pymea-fo-bsdap
11781 thpym-amn2-no1-psdap
11782 phhs-dimephmep-no2-bsdap
11783 am2py-thizn-ocho-glyzdap
11784 npip-trias-hso-dfzdap
11785 piraz-mepipen2-napo-bhsdab
11786 thpym-pymea-napo-asppha
11787 4pmhs-pipa-no2-betadcph
11788 4pmhs-mepipe2-oem-nbetameph
11789 tolhs-eta-men-bhsdab
11790 bhs-amn2-no2-bhsdap
11791 impy-ams2-rnmo-betadcph
11792 bimhs-hexas-chexo-aval
11793 pyrhs-dis-no2-bhsdap
11794 me2py-3pazin-imo-bsdap
11795 npip-edian2-5amo-aspibua
11796 imhs-propn-5amo-bphabs
11797 im-24thiz-mes-betainyl
11798 cl3pyme-pentadi-eoco-mezphe
11799 me2py-amn2-fo-zdab
11800 bhs-n2nme2n-5amo-psdab
11801 cl3pyme-m24thiman2-ocho-oxal
11802 amim-pipmes-meo-psdab
11803 dmthpym-dimen-mes-aspibua
11804 amim-amn2-5pho-bhsdab
11805 binhs-mepipe-eoco-asppha
11806 bhs-pipmes-no1-bsdap
11807 2py-dimephmep-mes-zdap
11808 chmhs-dimephmem-meo-bsdap
11809 imhs-edian2-no2-bhsdap
11810 amim-24thizman2-4pho-asppha
11811 piraz-dimephmem-emo-oxal
11812 bimhs-diaz-oem-psdab
11813 hythpym-pazin-mommo-bnsdap
11814 pippy-tetradi-meteto-asppha
11815 pippy-eta2s-mecpo-mezphe
11816 bhs-pnymea-5pho-zdabs
11817 z-dimephmep-ocho-psdap
11818 fthpym-mea-chexo-psdab
11819 bim-amo2-mes-psdab
11820 bim-amn2-no2-zdab
11821 dmthpym-pipmea-5pho-betainyl
11822 gua-edia2-oem-nbeta34dimeoph
11823 mam2py-amo3-mes-zdapee betainyl
11824 2py-edian2-meo-bphabs
11825 hythpym-tridi-ocho-glyzdap
11826 imhs-pazin-5pho-zdap
11827 bhs-diphmem-oem-bnsdap
11828 bhs-propa2s-5amo-bhsdap
11829 2py-mepipe-mes-psdab
11830 imhs-mepazin-4amo-glyzdap
11831 pippy-dimephmep-cpro-csdap
11832 2py-24thizman2-4amo-psdab
11833 pippy-m25oxman2-pheo-zdabs
11834 piraz-mepipen2-meo-zdap
11835 piraz-pipa-eoco-bphabs
11836 imhs-mepipe-no1-psdab
11837 phhs-diphmem-men-zlys
11838 thpym-pazin-no1-psdap
11839 bzl-amn2-ocho-bphabs
11840 dhim-am3-sem-nzdab
11841 im-m25thiz-5amo-psdapee
11842 hythpym-amn2-mommo-betainyl
11843 2py-edian2-meo-bsdap
11844 dmthpym-am2-oem-nbetameph
11845 amthiaz-m24thizman2-emo-bhsdap
11846 bz-ams2-5pho-psdab
11847 tolhs-edian2-no1-bhsdab
11848 am4py-hexas-imo-bphabs
11849 mam2py-eta2s-emo-zdap
11850 bhs-eta-oem-bsdap
11851 am-amn3-chexo-betadcph
11852 bhs-eta2s-5pho-bphabs
11853 bz-m24thizman2-no1-asppha
11854 bhs-24thizman2-men-glyzdap
11855 impy-dimephmep-cpeo-osdap
11856 4pmhs-dimen-imo-bhsdab
11857 imhs-am3-oem-nbetameph
11858 bimhs-m24oxman2-5pho-bhsdap
11859 thpym-amn2-no2-asppha
11860 amim-butn-eoco-osdap
11861 2py-dipch-napo-csdap
11862 mepip-mea2s-5pho-bhsdap
11863 mam2py-dipch-imo-bphabs
11864 2py-pymea-no2-zdapee
11865 me-edian2-emo-csdap
11866 impy-dimephmep-fo-betadcph
11867 ibhs-tetradi-no1-psdap
11868 pyrhs-diaz-paco-dfzdap
11869 bhs-amn2-oem-bnsdap
11870 pyrhs-24thiz-mes-bphabs
11871 thpym-thizs-fo-psdab
11872 me2py-din-napo-psdab
11873 hythpym-diphmem-4amo-betainyl
11874 amim-edian2-paco-bhsdab
11875 2pmhs-amo3-meto-bhsdab
11876 mepip-edia2-oem-npsdap
11877 2py-amn2-meo-betapy
11878 impy-m24thizman2-paco-asppha
11879 bhs-eta-ocho-bhsdap
11880 npip-eta2s-pro-betainyl
11881 mam2py-tetradi-ocho-asppha
11882 am4py-24oxman2-napo-betapy
11883 cl3pyme-pyma2-4amo-bsdap
11884 bhs-eta-5amo-betapy
11885 bhs-edian2-eoco-bsdap
11886 2py-pazin-no2-betapy
11887 thpym-pymea-oem-bhsdap
11888 bz-mepazin-no1-bhsdab
11889 thpym-2pazin-mes-bhsdap
11890 bim-props-peo-zdap
11891 thpym-eta-no1-bhsdap
11892 am2py-m24thizman2-oeto-zdabs
11893 nrhs-mepipen2-5amo-zdabs
11894 nrmhs-dimen-no1-aspaba
11895 impy-eta-napo-bsdap
11896 2py-25thizman2-eoco-asppha
11897 impy-25oxman2-meo-psdap
11898 imhs-thizn-ocho-betadcph
11899 impy-edian2-mommo-bnsdap
11900 phpip-eta-napo-glupha
11901 imhs-pipmes-oeto-bhsdab
11902 thpym-m24thizman2-meo-asppha 11903 pyraz-amn2-fo-aspibua
11904 pippy-mepazin-mmen-asppha
11905 deam-dis-oem-betainyl
11906 imhs-25oxman2-oem-betapy
11907 bim-pazin-5pho-zdap
11908 amim-mepazin-ocho-asppha
11909 dhim-25oxman2-cpro-glyzdap
11910 thpym-amn3-meo-betapy
11911 2py-24thizman2-fo-zdab
11912 bim-tetradi-ocho-tsdap
11913 imhs-amn3-no1-bhsdap
11914 chmhs-dimephmem-imo-aspaba
11915 amthiaz-24thizman2-no2-bsdap
11916 bimhs-trias-no1-aval
11917 me2py-dio-imo-bsdap
11918 pyrhs-pazin-meteto-dfzdap
11919 thpym-pipmea-eoco-bnsdap
11920 hythpym-amo2-4amo-psdap
11921 dmam-thizn-5amo-glyzdap
11922 bhs-eta-mes-betapy
11923 impy-pipa-imo-psdab
11924 pyrhs-amn2-no1-bnsdap
11925 bim-mea2s-fo-mezphe
11926 me2py-pazin-hso-glyzdap
11927 tolhs-pipmea-cpro-bphabs
11928 hythpym-diphmep-meto-dfzdap
11929 hythpym-2pazin-daco-aspibua
11930 amthiaz-trias-napo-psdapee
11931 pyrhs-tridi-5pho-bhsdab
11932 pippy-amo2-chexo-csdap
11933 pyrhs-dimephmem-ocho-psdap
11934 chhs-dimephmem-meo-zdabs
11935 thpym-pazin-eoco-bhsdap
11936 am-thizn-fo-dfzdap
11937 dpam-thizn-5pho-psdap
11938 bhs-ms-mommo-zdap
11939 bhs-eta-5pho-betapy
11940 pippy-24thizman2-5pho-psdap
11941 ppy-diphmem-emo-betainyl
11942 thpym-mepipen2-emo-bsdap
11943 bim-m24thiman2-ocho-glupha
11944 ibhs-diphmem-mes-zdap
11945 2py-24thiman2-5amo-psdap
11946 chmhs-25oxman2-meo-psdab
11947 bim-diphmem-fo-aval
11948 mam2py-mepazin-ocho-asppha
11949 emnim-pyma2-mecpo-zdabs
11950 am2py-trias-no1-dfzdap
11951 bim-pazin-5pho-zdab
11952 ec-dimen-emo-zdab
11953 hythpym-din-men-bsdap
11954 amthiaz-amn2-5pho-aspaba
11955 morhs-tridi-eoco-asppha
11956 hythpym-25oxman2-emo-osdap
11957 me2py-edia2-sem-nbetameph
11958 2pmhs-pipa-pheo-betapy
11959 imhs-mepipe-eoco-psdap
11960 amim-dis-cpeo-betaet
11961 bimhs-mepazin-mecpo-mezphe
11962 npip-dimephmep-pro-bsdap
11963 dhim-tetras-meteto-aspibua
11964 bimhs-m24thiz-men-aspibua
11965 imhs-pazin-no1-psdab
11966 imhs-eta-no2-bhsdap
11967 bhs-trias-cpeo-bnsdap
11968 hythpym-24thizman2-meo-asppha
11969 mam2py-tridi-meo-bphabs
11970 2py-pipmea-cno-zdap
11971 am-m25thiz-mes-betapy
11972 bimhs-3diaz-chexo-betapy
11973 2pmhs-diaz-eoco-psdapee
11974 pyrhs-pymea-emo-dfzdap
11975 2py-dimen-hso-bhsdab
11976 bim-edian2-no1-betapy
11977 bimhs-din-no2-tsdap
11978 bzl-pipmeo-imo-bsdap
11979 ppy-dich-ocho-betadcph
11980 mam2py-pymea-mes-zorn
11981 thpym-eta-no1-bphabs
11982 me2py-pyma2-no2-betapy
11983 am2py-mepipe2-oem-npsdap
11984 thpym-m25thiz-mes-zdabs
11985 pyraz-dimephmep-no1-psdab
11986 chhs-pazi2n-emo-betadcph
11987 me2py-3pazin-eoco-dfzdap
11988 imhs-eta-5pho-bhsdap
11989 2py-mepipe-mes-psdap
11990 pyraz-thizn-eoco-asppha
11991 amim-m24thizman2-mes-bnsdap
11992 bhs-tetradi-meo-dfzdap
11993 nim-am2-oem-nzdab
11994 nmhs-25oxman2-5pho-psdap
11995 mam2py-pentadi-eoco-aspbzla
11996 mam2py-ams2-chexo-csdap
11997 bimhs-mepazin-chexo-oxal
11998 hythpym-mepazin-pro-betapy
11999 pippy-pipmea-meo-bsdap
12000 bhs-pazin-no1-psdab
12001 hythpym-mea-meo-thizzdap
12002 bzl-edia2-sem-nbeta34dimeoph
12003 bimhs-dis-chexo-csdap
12004 nmhs-25thiman2-5pho-bphabs
12005 2py-dipch-fo-bsdap
12006 prhs-mepipen2-eoco-zdab
12007 imhs-mepipen2-napo-aspbzla
12008 bim-tridi-ocho-asppha
12009 phhs-m25thiz-oeto-aspbzla
12010 mam2py-25oxman2-emo-betapy
12011 thpym-eta2s-meo-csdap
12012 thpym-mepipe2-sem-npsdap
12013 amim-mepazin-pheo-zdabs
12014 impy-amo2-no2-zdab
12015 pippy-3diaz-mes-betadcph
12016 hythpym-mepipe2-sem-nbeta34dimeoph
12017 bim-mepipe-emo-psdapee
12018 imhs-m24thizman2-4amo-thizzdap
12019 mam2py-24thiz-4pho-betadcph
12020 me-pnymea-mecpo-zdap
12021 ibhs-pnymea-mecpo-psdap
12022 dhim-dis-eoco-zlys
12023 am2py-pipa-no2-betapy
12024 tolhs-thizn-mes-aspbzla
12025 bhs-m25thiz-pro-zdabs
12026 am2py-am2-oem-npsdap
12027 pippy-dimen-pro-glyzdap
12028 bim-edian2-oem-bnsdap
12029 dmthpym-m25thiz-chexo-asppha
12030 am2py-mepazin-no2-bnsdap
12031 bhs-amn2-ocho-bnsdap
12032 amim-24thiman-aco-zdab
12033 thpym-m24thizman2-cno-dfzdap
12034 pippy-24thizman2-mes-psdab
12035 hythpym-edian2-fo-thizzdap
12036 2py-pnymea-napo-bsdap 12037 amim-25oxman2-emo-zdapee
12038 2py-m25thiz-men-psdapee
12039 bim-pazin-peo-aspibua
12040 me2py-mepipe-ocho-ibsdap
12041 2py-eta-men-betainyl
12042 piraz-dimephmem-chexo-dfzdap
12043 amin-diphmep-5pho-glyzdap
12044 bhs-edian2-5pho-psdab
12045 amim-dimephmep-paco-betapy
12046 am2py-pipmea-mes-bsdap
12047 amim-mepipe-napo-zdabs
12048 bim-edian2-5pho-zdap
12049 ec-3pazin-mes-betapy
12050 pippy-eta-fo-aspibua
12051 piraz-eta-4amo-bphabs
12052 pippy-pipa-no2-bsdap
12053 am2py-dimen-chexo-glubzla
12054 am2py-pipmea-pyo-betadcph
12055 piraz-dipch-napo-aspibua
12056 gua-pipa-men-psdab
12057 chmhs-dis-oem-osdap
12058 fthpym-pymea-5pho-zlys
12059 piraz-m25oxman2-fo-zdabs
12060 imhs-mepipe-ocho-zdap
12061 thpym-eta-imo-aspbzla
12062 bhs-amo3-eoco-dfzdap
12063 npip-din-cpeo-betainyl
12064 me2py-edian2-men-bnsdap
12065 binhs-m24thizman2-mecpo-betadcph
12066 piraz-mepipen2-meo-zlys
12067 edothpym-amn3-daco-zdap
12068 gua-hexas-mes-csdap
12069 piraz-dimephmem-mmen-csdap
12070 am2py-am3-sem-nzdab
12071 mam2py-pymea-no1-aval
12072 z-pnymea-5amo-psdap
12073 piraz-amo2-oem-betainyl
12074 am2py-tetras-men-bnsdap
12075 fthpym-3pazin-chexo-bhsdab
12076 piraz-tetradi-men-aspbzla
12077 dhim-pnymea-oem-bhsdab
12078 moegua-din-oem-bhsdab
12079 morhs-mepipe2-oem-npsdap
12080 bz-diaz-oem-bnsdap
12081 pyraz-mepipe-men-bphabs
12082 inhs-mepipe-meo-bhsdap
12083 impy-25oxman2-oem-aspbzla
12084 amim-diphmem-fo-betapy
12085 dmthpym-thizn-4pho-oxal
12086 thpym-n2o2n-no1-zdab
12087 bhs-edian2-meo-bnsdap
12088 hythpym-pipa-4pho-psdap
12089 pippy-diaz-fo-tsdap
12090 dhim-dimephmem-paco-zdab
12091 bhs-pazin-meo-psdap
12092 phhs-24thizman2-imo-bhsdap
12093 thpym-dimephmep-men-glyzdap
12094 pippy-edia2-sem-nbeta34-dimeoph
12095 menim-pazi2n-chexo-mezphe
12096 imhs-mepipe-meo-bnsdap
12097 nmhs-amo2-imo-thizzdap
12098 phpip-edia2-sem-nbetameph
12099 npip-eta2s-ocho-csdap
12100 fthpym-edian2-4amo-aval
12101 am2py-ms-pheo-asppha
12102 2py-trias-5pho-aspbzla
12103 bhs-pazin-eoco-zdab
12104 impy-mepipe2-sem-nzdap
12105 2py-edian2-no2-bnsdap
12106 bim-eta-oem-zdap
12107 am2py-m24thizman2-meo-betainyl
12108 dhim-trias-5pho-betainyl
12109 bim-amn2-oem-bnsdap
12110 pippy-pipa-imo-dfzdap
12111 chhs-dimen-fo-betapy
12112 2py-mepipe-no2-bhsdap
12113 ppy-m24thizman2-chexo-glyzdap
12114 piraz-n24thiman-5amo-dfzdap
12115 morhs-din-men-zdap
12116 mam2py-amn3-peo-psdab
12117 bim-tetradi-5amo-bhsdap
12118 mam2py-pymea-fo-zorn
12119 2py-pyma2-eoco-betapy
12120 amim-ams2-chexo-psdab
12121 4pmhs-amn2-no1-betainyl
12122 amthiaz-diphmep-mommo-psdap
12123 bim-eta-mes-zdap
12124 deam-m25thiz-fo-betainyl
12125 bhs-din-eoco-bphabs
12126 4pmhs-amn3-ocho-bphabs
12127 dhim-pipa-napo-zdab
12128 dhim-dimephmep-chexo-betainyl
12129 pyraz-mepipe-mmen-betapy
12130 me-edian2-oem-aspibua
12131 am2py-m25thiz-cpro-ppsdap
12132 bz-pentadi-oem-glyzdap
12133 bim-mepipen2-paco-ibsdap
12134 imhs-tridi-mmen-betainyl
12135 prhs-25oxman2-imo-bhsdab
12136 pippy-mepazin-oem-oxal
12137 thpym-m25thizman2-aco-zdabs
12138 pippy-mepazin-cnmo-asppha
12139 mam2py-ams3-ocho-dfzdap
12140 imhs-amo2-oem-bphabs
12141 piraz-eta2s-oeto-betapy
12142 piraz-dimen-imo-bsdap
12143 bimhs-amo2-pyo-zdabs
12144 deam-dimen-no1-thizzdap
12145 am-m24thizman2-imo-aspbzla
12146 pippy-mepipe-5amo-mezphe
12147 piraz-3diaz-cnmo-zdap
12148 dpam-dimephmem-napo-zdap
12149 pippy-pazin-men-bphabs
12150 thpym-tridi-men-betadcph
12151 imhs-mepipen2-5pho-aspibua
12152 am2py-am3-oem-nbetapy
12153 dhim-din-mes-psdab
12154 thpym-dis-chexo-psdab
12155 piraz-dimephmep-mes-dfzdap
12156 piraz-ams2-imo-betapy
12157 2py-edian2-ocho-psdab
12158 piraz-diaz-cpro-asppha
12159 mam2py-dis-fo-bsdap
12160 4pmhs-m24thizman2-aco-psdab
12161 hythpym-ams3-emo-bsdap
12162 morhs-24thizman2-emo-bsdap
12163 im-pyma2-ocho-bnsdap
12164 mepip-tetradi-emo-dfzdap
12165 piraz-tetradi-napo-aspibua
12166 dmthpym-mepipen2-meo-glyzdap
12167 am2py-dimephmep-cnmo-zdap
12168 bim-dimephmep-eoco-mezphe
12169 prhs-din-mmen-psdab
12170 thpym-dimephmep-5amo-bhsdab 12171 dhim-dis-no1-bphabs
12172 pyr-24thiz-oem-bphabs
12173 bim-din-pro-bphabs
12174 imhs-hexadi-meteto-asppha
12175 deam-amn3-eoco-aspibua
12176 mam2py-tetradi-napo-bhsdap
12177 hythpym-ams2-meo-tsdap
12178 2py-pazin-hso-betainyl
12179 amim-25oxman2-meto-bphabs
12180 phhs-am2-sem-nzdap
12181 piraz-dimephmep-4pho-oxal
12182 bim-eta-meo-psdab
12183 bhs-24thizman2-napo-bphabs
12184 thpym-pazin-no1-bnsdap
12185 nim-pipa-cpro-aspibua
12186 amim-dimen-eoco-betainyl
12187 2py-amn3-meo-zdap
12188 me-trias-meo-zdab
12189 am2py-dimen-no2-dfzdap
12190 piraz-dimephmem-ocho-tsdap
12191 thpym-mepipe-no2-psdap
12192 me2py-pipa-no1-bsdap
12193 thpym-ams3-baeo-psdap
12194 emnim-edia2-oem-nzdab
12195 bimhs-trias-meo-zdabs
12196 piraz-din-chexo-betainyl
12197 bimhs-thizn-no2-ppsdap
12198 menim-pnymea-mes-zdabs
12199 imhs-pipmea-meo-asppha
12200 bhs-eta-oem-zdab
12201 fthpym-mepipe-5pho-zdab
12202 bimhs-24thiman2-fo-aspibua
12203 bim-amn3-5amo-glyzdap
12204 chhs-pipa-meo-psdap
12205 impy-24thizman2-men-psdap
12206 npip-trias-mes-zdab
12207 edothpym-m24thizman2-chexo-betadcph
12208 me2py-dimephmep-meo-zorn
12209 im-mepipe2-oem-npsdap
12210 dhim-am2-oem-nzdab
12211 fthpym-pipmes-no1-betadcph
12212 bimhs-24thiz-peo-mezphe
12213 pippy-hexadi-mes-betainyl
12214 thpym-m24thizman2-pyo-asppha
12215 2py-amn2-5pho-bnsdap
12216 thpym-pnymea-meo-glyzdap
12217 n2py-24thizman2-5amo-ppsdap
12218 piraz-diphmep-mes-psdap
12219 dpam-pazin-5amo-bhsdab
12220 piraz-diphmep-meo-zdap
12221 pippy-25thiz-oem-tsdap
12222 amim-mepipe-oem-csdap
12223 nmhs-pipa-no1-bhsdap
12224 pippy-m25thiz-daco-zdabs
12225 am2py-ams3-cpeo-glubzla
12226 hythpym-dis-chexo-zdap
12227 bhs-edian2-no1-bsdap
12228 ec-mepazin-fo-bhsdab
12229 amim-dimephmep-fo-psdap
12230 dpam-amo2-meo-zdab
12231 am2py-pnymea-napo-glyzdap
12232 mam2py-din-5amo-bphabs
12233 z-tridi-mommo-dfzdap
12234 imhs-m24oxman2-cpro-ppsdap
12235 hythpym-24thizman2-4pho-asppha
12236 2py-trias-daco-aspbzla
12237 im-24thiman-emo-zdabs
12238 imhs-dimephmep-eoco-aval
12239 2py-props-emo-dfzdap
12240 bhs-pentas-fo-psdap
12241 bim-diphmep-cpeo-dfzdap
12242 thpym-pyma2-imo-glyzdap
12243 me2py-pnymea-fo-zdab
12244 piraz-din-no2-bnsdap
12245 bimhs-diaz-oem-zdab
12246 am2py-diphmem-aco-dfzdap
12247 dhim-dis-mes-betainyl
12248 bimhs-diphmem-men-bhsdap
12249 ec-mea2s-5pho-bhsdap
12250 bim-24thizman2-5pho-psdap
12251 2py-mepipe-oem-bnsdap
12252 morhs-diphmem-napo-bhsdap
12253 pippy-diaz-cnmo-bsdap
12254 dpam-amo2-napo-betadcph
12255 thpym-dipch-eoco-dfzdap
12256 impy-amn2-ocho-bsdap
12257 bim-pnymea-5pho-ppsdap
12258 hythpym-amo2-5amo-aval
12259 z-pymea-5pho-asppha
12260 imhs-mepipen2-5amo-bphabs
12261 hythpym-mepipe-meteto-tsdap
12262 z-m24thizman2-no2-aspbzla
12263 am2py-dimephmep-imo-zdab
12264 imhs-am3-sem-nbetameph
12265 am2py-mepazin-meo-aspbzla
12266 2py-amn2-oem-betapy
12267 thpym-mepipe-eoco-betapy
12268 bim-trias-no1-zdabs
12269 impy-mepipe-fo-betadcph
12270 bhs-pazin-no1-zdap
12271 impy-25oxman2-napo-bhsdab
12272 bim-din-hso-psdab
12273 mam2py-mepipe2-oem-nbeta34-dimeoph
12274 imhs-mepipe-no1-psdap
12275 me2py-amn3-mes-zdapee
12276 bim-pazin-eoco-bsdap
12277 bimhs-thizn-men-aspibua
12278 bhs-diphmem-eoco-betainyl
12279 pyr-pipmes-fo-aspibua
12280 nmor-thizn-emo-zdap
12281 me-diphmep-eoco-zdab
12282 bz-trias-napo-aspibua
12283 npip-thizn-meteto-asppha
12284 bhs-thizn-fo-glyzdap
12285 pyraz-pymea-oem-betapy
12286 dhim-dis-napo-dfzdap
12287 impy-pipa-chexo-psdap
12288 imhs-mepipe-oem-bsdap
12289 n2py-ams2-meteto-thizzdap
12290 me2py-mepipen2-peo-betadcph
12291 thpym-mepipe-5pho-zdab
12292 amim-m25thiz-emo-betainyl
12293 am2py-diphmep-chexo-zdabs
12294 am-mea-mes-betadcph
12295 2py-mepipe-no2-bsdap
12296 amim-pazin-chexo-zdabs
12297 cl3pyme-diphmep-eoco-zdab
12298 dmam-dimen-men-bphabs
12299 dhim-dimen-4amo-bhsdab
12300 dmthpym-mepipen2-men-bsdap
12301 am2py-mepipen2-napo-aspibua
12302 gua-propa2s-cnmo-zdapee
12303 pippy-edia2-sem-nbetameph
12304 nim-amo2-oem-zdabs 12305 hythpym-24thiman-oem-mezphe
12306 impy-ams2-aco-mezphe
12307 2py-dimen-napo-bsdap
12308 amim-pymea-5pho-dfzdap
12309 hythpym-edia2-sem-npsdap
12310 2py-edia2-sem-nbetabnaphth
12311 bim-edian2-mes-zdap
12312 am2py-amn3-napo-aval
12313 amim-hexas-oem-bsdap
12314 me2py-pazin-eoco-psdab
12315 am2py-diphmep-no2-mezphe
12316 3pyme-pnymea-imo-zdab
12317 2py-amn2-eoco-bnsdap
12318 am2py-m24thizman2-mes-csdap
12319 pippy-dimephmem-ocho-zdab
12320 2py-eta-no1-betapy
12321 pippy-trias-pheo-dfzdap
12322 mam2py-diphmep-mmen-bphabs
12323 amthiaz-m25thiz-men-betapy
12324 amim-amn3-oem-bhsdap
12325 amthiaz-mepipe-fo-bnsdap
12326 imhs-edian2-oem-bsdap
12327 bim-pipmeo-napo-bnsdap
12328 chmhs-ms-aco-mezphe
12329 thpym-mepipe-fo-zdap
12330 bim-25oxman2-cnmo-aspbzla
12331 impy-diphmem-no2-asppha
12332 dhim-edian2-men-csdap
12333 impy-eta-fo-aspibua
12334 am-dimen-cpeo-dfzdap
12335 prhs-pnymea-men-bhsdap
12336 bim-mepipe-oem-psdap
12337 dmam-m25thiz-imo-csdap
12338 pyrhs-mea-peo-mezphe
12339 hythpym-amo2-napo-zdabs
12340 imhs-amn2-mes-bnsdap
12341 bhs-thizn-chexo-betainyl
12342 imhs-pipmea-5amo-bnsdap
12343 mam2py-trias-aco-bsdap
12344 hythpym-dimen-chexo-betainyl
12345 dhim-edia2-oem-nbeta34-dimeoph
12346 am2py-pipmea-hso-aspbzla
12347 dhim-24thiman2-peo-psdapee
12348 hythpym-eta-chexo-betadcph
12349 imhs-dimen-fo-bsdap
12350 z-tetradi-cpeo-bhsdab
12351 bhs-eta-mes-zdab
12352 imhs-mepipe2-oem-nzdab
12353 nmhs-diphmep-men-bhsdab
12354 mam2py-pazin-pyo-bphabs
12355 pippy-pentas-emo-dfzdap
12356 hythpym-dimen-hso-zdab
12357 imhs-eta-5pho-betapy
12358 ibhs-thizn-no1-mezphe
12359 pippy-25thiz-5pho-psdap
12360 piraz-thizs-hso-psdapee
12361 2py-pazin-oem-psdap
12362 impy-trias-oem-bphabs
12363 pippy-dis-5amo-bphabs
12364 pyraz-am3-oem-npsdap
12365 ppy-diphmem-5pho-psdap
12366 am2py-24thiz-pyo-zorn
12367 am2py-pymea-napo-betaet
12368 imhs-eta-no2-bnsdap
12369 hythpym-amn2-baeo-betadcph
12370 dmthpym-mepipen2-eoco-bsdap
12371 phhs-m24thizman2-pheo-zdap
12372 edothpym-trias-napo-zdabs
12373 moegua-n2o2n-oem-psdap
12374 imhs-dis-pheo-psdab
12375 ibhs-thizn-fo-mezphe
12376 me2py-trias-no1-csdap
12377 bim-mepipe-mes-asppha
13237 bim-pipmeo-napo-bnsdap
12378 am-mepipe-ocho-thizzdap
12379 nmhs-dimephmem-pyo-csdap
12380 dmbim-amn3-cnmo-betainyl
12381 bim-m25thiz-5pho-osdap
12382 gua-thizn-meteto-bhsdap
12383 impy-n2o2n-napo-bhsdab
12384 fthpym-24thizman2-mommo-dfzdap
12385 2py-thizn-baeo-betadcph
12386 imhs-pazin-no2-psdab
12387 bim-mepipe-no2-bnsdap
12388 dmam-din-napo-zdap
12389 2py-mepazin-meo-csdap
12390 am2py-edian2-emo-asppha
12391 impy-trias-fo-ppsdap
12392 ec-mepazin-meo-aval
12393 bhs-pipa-no1-zorn
12394 dhim-diphmep-4pho-aspbzla
12395 amthiaz-dimephmep-meteto-psdap
12396 mam2py-pipmea-fo-zdap
12397 morhs-m25thiz-chexo-aspbzla
12398 dhim-diphmem-ocho-csdap
12399 amim-pyma2-no1-mezphe
12400 2py-pazin-ocho-bnsdap
12401 am-hexadi-cpro-bhsdap
12402 bhs-amn2-meo-bnsdap
12403 thpym-amo2-fo-csdap
12404 imhs-pipmeo-meo-betainyl
12405 am2py-eta-5pho-zdap
12406 impy-amn2-5pho-psdap
12407 dmbim-m25thiz-oem-bhsdab
12408 npip-tridi-ocho-psdap
12409 dhim-dimephmem-napo-aspibua
12410 piraz-m25thiz-mommo-zdap
12411 me2py-pymea-no1-bphabs
12412 pippy-dimen-napo-glupha
12413 bim-m25thiz-baeo-betainyl
12414 emnim-mepipe2-oem-nzdap
12415 gua-dimephmep-paco-osdap
12416 dhim-am2-sem-nbetabnaphth
12417 me2py-am2-oem-nbetameph
12418 me2py-24thiz-men-glyzdap
12419 prhs-din-ocho-aspibua
12420 impy-am3diaz-pheo-bphabs
12421 pippy-mea2s-no2-bsdap
12422 imhs-trias-oem-betapy
12423 dhim-din-oem-asppha
12424 bimhs-thizn-eoco-betadcph
12425 dmbim-amn3-pro-psdap
12426 nim-mepipe2-sem-nbetameph
12427 amim-dich-cno-betadcph
12428 ibhs-dio-eoco-bhsdap
12429 impy-dimephmep-oem-aspaba
12430 bim-edian2-mes-bhsdap
12431 bhs-amn2-no2-psdab
12432 thpym-24thiz-chexo-mezphe
12433 mam2py-25thizman2-napo-zdabs
12434 thpym-amn2-5pho-zdap
12435 thpym-pazin-fo-dfzdap
12436 piraz-pymea-pheo-betaet
12437 imhs-diaz-imo-csdap 12438 chmhs-24thiz-emo-asppha
12439 thpym-ms-oem-dfzdap
12440 bzl-am2-oem-nbetabnaphth
12441 prhs-tetradi-paco-dfzdap
12442 ppy-dimen-chexo-zdabs
12443 im-amn3-chexo-bhsdap
12444 dmam-pazin-ocho-mezphe
12445 z-trias-men-psdap
12446 dhim-dimephmep-cnmo-bhsdap
12447 bimhs-25oxman2-5amo-betapy
12448 thpym-tridi-meo-psdap
12449 piraz-thizn-no1-betapy
12450 bhs-amn3-napo-zdabs
12451 me2py-m25thiz-no1-glyzdap
12452 mepip-dimephmep-4pho-glyzdap
12453 bhs-thizs-no1-mezphe
12454 ec-trias-5amo-psdab
12455 2py-dis-pheo-csdap
12456 amim-amo2-fo-bhsdab
12457 bimhs-hexas-emo-betainyl
12458 imhs-dimephmep-fo-bsdap
12459 bzl-edian2-ocho-zlys
12460 mam2py-n24thiman-fo-betapy
12461 dmam-amn2-baeo-bhsdab
12462 ibhs-mepipe-no1-bnsdap
12463 ec-ams2-meteto-zdapee
12464 amim-mepazin-ocho-ppsdap
12465 im-3pazin-no1-betainyl
12466 imhs-m24thizman2-oem-thizzdap
12467 thpym-tetradi-oem-bhsdab
12468 mam2py-pymea-no2-ibsdap
12469 mepip-ams2-ocho-glupha
12470 dhim-24thiz-no1-zdap
12471 pippy-amn3-emo-betapy
12472 2py-amn3-cno-aspibua
12473 chhs-25oxman2-napo-zdab
12474 hythpym-pnymea-ocho-zdab
12475 me2py-25thiz-fo-betapy
12476 impy-amn2-men-zdab
12477 pippy-m24oxman2-no1-csdap
12478 2py-props-ocho-bhsdap
12479 me2py-thizn-chexo-osdap
12480 4pmhs-dimephmem-men-psdapee
12481 bhs-amn2-mes-zdab
12482 imhs-pazin-no1-bnsdap
12483 pippy-mepipe-5amo-aspbzla
12484 imhs-pazin-eoco-bhsdap
12485 mam2py-m25thiz-5amo-zdap
12486 bhs-thizs-no1-bhsdap
12487 im-props-fo-psdap
12488 pyr-dis-imo-bhsdab
12489 me2py-pyma2-no1-aspbzla
12490 pippy-propn-oem-betapy
12491 2py-edian2-ocho-psdap
12492 2py-pazin-ocho-betapy
12493 mepip-pyma2-no1-mezphe
12494 piraz-dimephmep-imo-csdap
12495 amim-pazin-no1-asppha
12496 morhs-25thizman2-men-zdab
12497 tolhs-tetradi-napo-zdabs
12498 thpym-pymea-aco-bsdap
12499 imhs-m25thiz-no1-bsdap
12500 chmhs-amo2-meo-bsdap
12501 nmor-pymea-mes-betapy
12502 dmbim-m25thiz-ocho-aspbzla
12503 imhs-mea-mes-zdabs
12504 am2py-mepipe-mommo-aspibua
12505 bim-mea-no2-asppha
12506 thpym-diphmep-mecpo-betapy
12507 bhs-eta-ocho-betapy
12508 bim-mepipe-eoco-zdap
12509 bimhs-pazin-daco-mezphe
12510 thpym-pazin-chexo-betapy
12511 nim-ams2-imo-betainyl
12512 prhs-25oxman2-no2-betainyl
12513 hythpym-n24thiman-emo-psdab
12514 2py-diphmep-emo-bsdap
12515 morhs-amn2-emo-zdabs
12516 bim-diphmep-mecpo-betapy
12517 bim-eta-ocho-zdap
12518 piraz-mepazin-eoco-betainyl
12519 pyraz-eta-eoco-dfzdap
12520 dhim-pymea-oem-dfzdap
12521 pippy-m24thizman2-mommo-asppha
12522 bhs-mepipe-ocho-bnsdap
12523 bhs-eta-no1-zdabs
12524 bimhs-mepipe2-oem-nbetameph
12525 im-pipmea-cpro-aspbzla
12526 bhs-eta-napo-bhsdap
12527 2pmhs-amo2-mes-bphabs
12528 am4py-pyma2-cpro-bnsdap
12529 hythpym-din-napo-zdabs
12530 dhim-am3-oem-nbetameph
12531 me2py-3diaz-fo-betadcph
12532 2pmhs-tetras-imo-thizzdap
12533 bim-m24thizman2-emo-glupha
12534 pippy-props-no1-mezphe
12535 bhs-pipa-eoco-oxal
12536 mam2py-dimen-no2-glubzla
12537 hythpym-pipa-no2-bsdap
12538 impy-pymea-napo-betadcph
12539 4pmhs-mepipe2-oem-nzdap
12540 2py-mepipen2-mes-bphabs
12541 bhs-dimephmem-oem-zdapee
12542 bhs-edian2-no2-zdap
12543 2py-amo2-men-bnsdap
12544 nmhs-butn-no1-ibsdap
12545 pippy-n24thiman-emo-glupha
12546 bim-3diaz-imo-betapy
12547 n2py-mepipen2-no2-bphabs
12548 impy-amn2-meo-psdab
12549 morhs-pnymea-pheo-bhsdab
12550 imhs-edian2-no1-bhsdap
12551 phpip-m24thizman2-eoco-glupha
12552 piraz-n2nme2n-5pho-zdabs
12553 z-hexas-5amo-zdabs
12554 ibhs-din-mes-aspbzla
12555 amim-tetradi-fo-zdap
12556 2py-edian2-5pho-betapy
12557 ppy-ams2-oeto-glyzdap
12558 hythpym-24thiz-pro-bhsdab
12559 impy-edian2-5amo-csdap
12560 imhs-pazin-mes-psdap
12561 edothpym-m24thizman2-ocho-glupha
12562 phpip-pipmea-5pho-betadcph
12563 amim-ams2-cpro-zdap
12564 imhs-hexadi-oem-asppha
12565 am4py-trias-paco-betainyl
12566 amim-dimephmem-oem-zdap
12567 impy-thizn-meo-bsdap
12568 npip-m25thiz-emo-betadcph
12569 hythpym-tridi-cpro-csdap
12570 fthpym-mepazin-mes-glyzdap
12571 prhs-25oxman2-mes-bhsdap 12572 me2py-pymea-5amo-betadcph
12573 mam2py-din-imo-bsdap
12574 dhim-24thiz-emo-bphabs
12575 thpym-eta-eoco-dfzdap
12576 am2py-25thiman2-fo-aspibua
12577 impy-pipmea-no2-bhsdap
12578 am4py-m25thizman2-meto-bphabs
12579 bim-mepipe2-oem-nzdab
12580 piraz-dimen-oem-betaet
12581 morhs-mea2s-imo-glubzla
12582 thpym-thizn-chexo-zdab
12583 2py-am3diaz-napo-zdab
12584 z-amn2-meo-bnsdap
12585 pyrhs-trias-5amo-betadcph
12586 cl3pyme-24thiz-meo-mezphe
12587 thpym-am3-sem-nbetapy
12588 pyr-mepazin-no1-glyzdap
12589 z-dis-hso-bsdap
12590 thpym-dimephmep-mes-bhsdab
12591 bimhs-amo2-chexo-bhsdap
12592 impy-25oxman2-ocho-asppha
12593 dhim-pazin-fo-osdap
12594 thpym-mepipe-oem-bnsdap
12595 dmbim-pipmea-hso-zdap
12596 mam2py-mea-5pho-betainyl
12597 impy-mepipe-eoco-betapy
12598 am4py-mepipe-eoco-oxal
12599 2py-pazin-ocho-psdap
12600 hythpym-amo3-imo-asppha
12601 2py-pipmea-ocho-aspibua
12602 amim-dio-meo-dfzdap
12603 prhs-mepipen2-no1-betapy
12604 2py-trias-imo-glyzdap
12605 bim-3pazin-meo-bhsdab
12606 2py-props-meo-psdap
12607 pippy-dimephmep-eoco-dfzdap
12608 am2py-pymea-oem-glyzdap
12609 fthpym-25oxman2-no1-csdap
12610 mam2py-m25thiz-fo-zdap
12611 im-pentas-no1-zdabs
12612 mam2py-diphmep-5pho-ppsdap
12613 phpip-n2o2n-imo-dfzdap
12614 am-mepipe-imo-bsdap
12615 imhs-tridi-napo-aspbzla
12616 dhim-am3-sem-nbetabnaphth
12617 pyraz-am3-oem-npsdap
12618 hythpym-ams2-chexo-bnsdap
12619 thpym-amn2-5pho-aspbzla
12620 imhs-dimephmep-no1-betainyl
12621 morhs-props-4pho-glyzdap
12622 impy-m25oxman2-5amo-bhsdab
12623 me2py-dimephmep-men-zdab
12624 bz-mepipe2-oem-nzdab
12625 dmbim-dimen-oem-psdapee
12626 gua-m24thiz-mmen-bnsdap
12627 mam2py-hexas-ocho-bhsdab
12628 imhs-edian2-meo-betapy
12629 hythpym-din-ocho-betainyl
12630 mam2py-propn-men-bhsdap
12631 thpym-25thiz-4pho-tsdap
12632 chmhs-ams3-napo-bphabs
12633 pippy-m25thiz-imo-betadcph
12634 tolhs-pipmea-fo-psdap
12635 bimhs-diphmep-5amo-betadcph
12636 z-amn3-eoco-dfzdap
12637 bhs-pymea-daco-aspibua
12638 dhim-dimephmem-mommo-zlys
12639 mam2py-24thiman2-emo-bphabs
12640 thpym-pazin-oem-zdap
12641 2py-pnymea-eoco-bhsdap
12642 imhs-mepazin-mes-dfzdap
12643 bim-amn3-5pho-betainyl
12644 ppy-amn3-5pho-zdab
12645 dhim-am2-oem-npsdap
12646 thpym-edia2-oem-nzdap
12647 pippy-am2-oem-npsdap
12648 2pmhs-din-aco-psdapee
12649 dmbim-m24thiman2-mommo-bhsdap
12650 2pmhs-thizn-napo-zdab
12651 bhs-24thizman2-men-psdapee
12652 am2py-dimephmem-emo-zdabs
12653 deam-diphmep-napo-zdap
12654 nim-24thizman2-mmen-aspbzla
12655 nmor-dimephmem-oem-aspbzla
12656 mam2py-24thiz-paco-psdap
12657 bim-25thiman2-ocho-bhsdap
12658 cl3pyme-mea2s-ocho-psdab
12659 gua-2sthiman2-imo-zdap
12660 bimhs-butn-daco-dfzdap
12661 impy-pymea-imo-aspbzla
12662 piraz-tetradi-imo-glyzdap
12663 thpym-din-meteto-bsdap
12664 inhs-pnymea-imo-glubzla
12665 bim-mepipe-mes-bsdap
12666 mepip-mepazin-mes-asppha
12667 me-indan2-meo-zdabs
12668 me2py-dimephmem-meo-mezphe
12669 prhs-24thiman2-mes-psdab
12670 bhs-dimephmem-pro-betapy
12671 bzl-m24thizman2-5amo-aspbzla
12672 2py-amo2-5pho-betadcph
12673 dmam-diphmem-no1-asppha
12674 me2py-m25thiz-cno-asppha
12675 impy-dimen-imo-bphabs
12676 hythpym-24thiman-mes-zdap
12677 mam2py-m24thizman2-meo-bsdap
12678 am4py-amo2-meo-aspaba
12679 thpym-m25thiz-meo-betapy
12680 impy-din-fo-psdab
12681 pippy-am2-oem-nbetapy
12682 chmhs-props-fo-psdab
12683 me2py-pyma2-ocho-ppsdap
12684 bhs-tetradi-napo-thizzdap
12685 dhim-tridi-eoco-psdab
12686 hythpym-ams2-mes-betainyl
12687 thpym-24thizman2-peo-dfzdap
12688 am-amn2-imo-betapy
12689 pippy-din-no2-aspaba
12690 am2py-diphmem-5amo-zlys
12691 2py-2pazin-pyo-betainyl
12692 ppy-edian2-oem-glyzdap
12693 mam2py-m24thizman2-oem-glyzdap
12694 amim-25thizman2-aco-zlys
12695 impy-tetradi-meo-asppha
12696 menim-pentas-fo-zorn
12697 impy-edian2-meto-zdabs
12698 2py-m24thizman2-chexo-aspbzla
12699 n2py-pipmes-eoco-csdap
12700 piraz-dimephmem-ocho-bsdap
12701 piraz-pipmea-pro-betadcph
12702 am2py-mepipe2-oem-npsdap
12703 am2py-edian2-chexo-psdap
12704 me2py-pipmes-oem-betapy
12705 mam2py-am3-oem-nbeta34-dimeoph 12706 imhs-pipmea-eoco-glyzdap
12707 me2py-m25thiz-eoco-aspaba
12708 2py-mepipe-5pho-zdap
12709 mam2py-24thiz-cno-osdap
12710 2pmhs-pymea-eoco-asppha
12711 am2py-edian2-5amo-psdap
12712 imhs-mepipen2-5pho-csdap
12713 z-pipmea-meteto-zdap
12714 dhim-eta2s-men-bphabs
12715 mam2py-mepipen2-oeto-bphabs
12716 piraz-tridi-5amo-glubzla
12717 imhs-24thizman2-chexo-csdap
12718 ec-25thiman2-no2-zdab
12719 ppy-pyma2-oem-bphabs
12720 dhim-pymea-nmo-dfzdap
12721 dhim-diphmem-no2-csdap
12722 ec-tridi-oem-betadcph
12723 bim-mea2s-mes-glupha
12724 bim-pazin-no1-zdab
12725 2py-amn2-oem-zdab
12726 nmor-m24thiz-chexo-psdab
12727 pyrhs-amo2-emo-zdap
12728 phhs-24thizman2-emo-psdap
12729 hythpym-m25thizman2-meo-csdap
12730 me2py-am2-oem-nzdab
12731 bimhs-pyma2-cno-aspibua
12732 gua-dimephmem-napo-psdab
12733 deam-mepipen2-5pho-bhsdab
12734 imhs-eta-no2-psdap
12735 me-ams2-no2-dfzdap
12736 2py-edian2-meo-bsdap
12737 am2py-dis-men-psdapee
12738 am2py-dis-chexo-zdapee
12739 pippy-mepazin-ocho-bhsdap
12740 pyrhs-din-ocho-bsdap
12741 thpym-24thizman2-no1-betainyl
12742 nim-pazin-5amo-aspibua
12743 am-mepipe2-sem-nbetabnaphth
12744 am2py-pipa-men-asppha
12745 am2py-dimephmep-imo-zdap
12746 tolhs-mepipen2-chexo-glyzdap
12747 pyraz-diphmem-chexo-zdabs
12748 bim-amn2-meo-psdab
12749 menim-dimephmep-5pho-osdap
12750 edothpym-pipmea-meo-zdabs
12751 ppy-mepipen2-oem-bhsdab
12752 amim-m25thizman2-ocho-zdab
12753 ec-diphmem-napo-zdabs
12754 hythpym-tridi-oem-zdap
12755 bhs-mepipe-eoco-bhsdap
12756 n2py-eta-emo-glupha
12757 nmor-diphmem-mommo-betapy
12758 imhs-pazi2n-oem-zdabs
12759 thpym-dimephmep-ocho-psdab
12760 morhs-24oxman2-cpro-betainyl
12761 dhim-dimen-fo-bsdap
12762 impy-m24thizman2-napo-zorn
12763 thpym-m24thiman2-ocho-mezphe
12764 2py-dis-oeto-zdabs
12765 2py-am3diaz-mes-betaet
12766 nmor-mepazin-4pho-asppha
12767 fthpym-am3diaz-oem-betadcph
12768 impy-din-chexo-zdab
12769 bhs-din-5amo-dfzdap
12770 pippy-pipa-cpro-bsdap
12771 am-pymea-nmo-psdap
12772 2py-pazin-mes-zdab
12773 impy-pipmea-5amo-glyzdap
12774 pippy-m25thiz-eoco-aspibua
12775 piraz-amo2-meto-psdap
12776 piraz-hexadi-5amo-dfzdap
12777 tolhs-pymea-napo-csdap
12778 mam2py-pipa-oem-mezphe
12779 am4py-tetradi-5pho-glyzdap
12780 prhs-trias-oeto-bsdap
12781 bim-am2-sem-nbeta34dimeoph
12782 pippy-mepipe-cpro-aspbzla
12783 am2py-trias-daco-psdab
12784 hythpym-hexas-5pho-zdabs
12785 hythpym-pymea-baeo-ppsdap
12786 morhs-thizn-no2-glyzdap
12787 bimhs-dipch-aco-tsdap
12788 bim-diphmep-no2-bhsdab
12789 imhs-eta-eoco-zdap
12790 hythpym-m25thizman2-5pho-betainyl
12791 pippy-mepipen2-fo-psdab
12792 bim-amo2-eoco-dfzdap
12793 am2py-pipa-mmen-aspibua
12794 2py-m25thiz-eoco-mezphe
12795 thpym-dimephmep-no1-betainyl
12796 imhs-pipa-ocho-psdab
12797 am2py-amo3-chexo-zdab
12798 mepip-m24thizman2-pro-csdap
12799 amim-m25thizman2-mmen-zlys
12800 dhim-edian2-mommo-bhsdab
12801 bim-24thiz-oem-bnsdap
12802 impy-m24thizman2-napo-thizzdap
12803 mam2py-m24thizman2-men-ppsdap
12804 pippy-din-fo-psdap
12805 am4py-m25thizman2-chexo-mezphe
12806 phpip-pnymea-men-asppha
12807 me-dimephmep-imo-psdab
12808 nmhs-m24thiman2-fo-zdabs
12809 emnim-dimephmep-eoco-aspibua
12810 bim-eta-ocho-bhsdap
12811 menim-diphmep-baeo-zdab
12812 impy-m25thiz-mes-csdap
12813 pippy-dimephmep-napo-bhsdap
12814 edothpym-m25thiz-cno-bsdap
12815 mam2py-edian2-cnmo-betainyl
12816 4pmhs-pipmeo-no1-aspbzla
12817 am2py-24thizman2-eoco-csdap
12818 impy-thizn-chexo-psdap
12819 ec-tetradi-nmo-bhsdab
12820 morhs-amn3-mmen-bhsdab
12821 hythpym-amo2-imo-psdab
12822 me2py-m25thiz-5pho-zorn
12823 mepip-amo2-oem-bphabs
12824 mam2py-propa2s-fo-glupha
12825 tolhs-24thizman2-hso-bhsdab
12826 mam2py-amn2-eoco-dfzdap
12827 imhs-pymea-oem-csdap
12828 thpym-eta-no1-bnsdap
12829 pyr-thizn-chexo-aspibua
12830 imhs-mepipe-ocho-betapy
12831 bhs-dimen-5amo-bnsdap
12832 chmhs-amn3-eoco-aspbzla
12833 piraz-m25thiz-mes-dfzdap
12834 amim-m24thizman2-oem-aspibua
12835 2py-tetradi-napo-ppsdap
12836 dhim-m24oxman2-men-bnsdap
12837 2py-pazin-mes-bsdap
12838 chmhs-dimen-mes-dfzdap
12839 npip-amo2-oeto-zdabs 12840 hythpym-mepazin-napo-dfzdap
12841 bhs-m25thiz-pheo-aspibua
12842 me2py-24thizman2-5pho-dfzdap
12843 hythpym-dimen-5amo-bnsdap
12844 phpip-dimephmep-mes-osdap
12845 bim-eta-no1-psdap
12846 bimhs-mepipen2-5pho-ppsdap
12847 mam2py-dimephmem-men-zdap
12848 bimhs-ams2-paco-betainyl
12849 bim-mepipe-oem-psdab
12850 imhs-amn3-eoco-zdap
12851 piraz-mepipe-napo-bhsdab
12852 hythpym-pipmes-imo-zdabs
12853 me2py-m24thizman2-emo-asppha
12854 dhim-m24thiman2-meo-betadcph
12855 bim-edian2-napo-betapy
12856 bhs-edian2-4pho-bphabs
12857 dmbim-amo2-no2-betapy
12858 bimhs-24thizman2-imo-glyzdap
12859 piraz-pipa-eoco-bhsdap
12860 thpym-mepazin-men-bnsdap
12861 edothpym-pipa-mecpo-dfzdap
12862 2pmhs-pentadi-eoco-bphabs
12863 dhim-din-no1-psdab
12864 bimhs-edian2-oeto-bhsdab
12865 pyrhs-pnymea-mes-dfzdap
12866 bhs-mepipe-meo-zdap
12867 2py-2pazin-baeo-glyzdap
12868 bhs-diphmep-imo-zdab
12869 mam2py-props-men-betainyl
12870 hythpym-eta-eoco-thizzdap
12871 pyrhs-mepipe-baeo-zdab
12872 bhs-eta-meo-bhsdap
12873 hythpym-ams2-paco-glyzdap
12874 imhs-mepipe-ocho-zdab
12875 am2py-butn-5amo-bsdap
12876 nmor-mepipe2-oem-npsdap
12877 2py-pazin-eoco-zdab
12878 am2py-edian2-oem-mezphe
12879 mam2py-25thiz-5pho-mezphe
12880 impy-indan2-no1-psdap
12881 thpym-pazin-no1-zdab
12882 bimhs-amo2-napo-bnsdap
12883 impy-am3-oem-nbetapy
12884 me2py-24oxman2-oem-mezphe
12885 amthiaz-dimephmem-fo-betapy
12886 bim-mepipe-5pho-bhsdap
12887 2pmhs-24thiz-men-bhsdap
12888 am4py-dipch-imo-ibsdap
12889 me2py-din-oem-bnsdap
12890 2py-25thiman2-cno-bhsdab
12891 inhs-eta-5pho-bhsdap
12892 dhim-am3diaz-mes-zlys
12893 mam2py-amn2-men-zdap
12894 z-m25oxman2-imo-bnsdap
12895 dhim-mepipen2-chexo-bphabs
12896 dpam-pymea-paco-betainyl
12897 2py-mepipe-no2-psdap
12898 phhs-m25thiz-no2-zdabs
12899 am4py-pipmea-men-ibsdap
12900 tolhs-pnymea-oem-asppha
12901 bim-pazin-meteto-csdap
12902 4pmhs-mepazin-5pho-aspibua
12903 tolhs-mepipe-meo-betadcph
12904 dpam-pymea-paco-betainyl
12905 amim-n2nme2n-4amo-psdap
12906 bim-eta-meto-aspibua
12907 bhs-pazin-5pho-psdap
12908 amthiaz-edia2-oem-nzdab
12909 thpym-eta-cnmo-bsdap
12910 bhs-amn3-paco-psdab
12911 me2py-m24thiz-oeto-glyzdap
12912 hythpym-m24thizman2-mes-bnsdap
12913 hythpym-pazin-oeto-betainyl
12914 thpym-amn2-no2-zdab
12915 thpym-eta-eoco-bnsdap
12916 imhs-pipmea-men-csdap
12917 hythpym-diphmep-men-aspibua
12918 bim-edian2-5pho-bsdap betadcph
12919 moegua-thizn-meo-zdap
12920 pippy-amo2-5pho-bhsdap
12921 pippy-24thizman2-oem-bphabs
12922 hythpym-pymea-imo-mezphe
12923 hythpym-mepazin-no1-betapy
12924 am2py-props-cnmo-betapy
12925 me2py-m24thiman2-fo-ibsdap
12926 piraz-am3diaz-napo-aspbzla
12927 mam2py-mepipen2-oem-psdab
12928 me-tridi-no2-zdab
12929 dmbim-diphmem-eoco-zdabs
12930 piraz-ams2-men-mezphe
12931 amim-dis-mes-betadcph
12932 piraz-pnymea-mmen-bhsdap
12933 bim-25oxman2-cpeo-bphabs
12934 z-24thizman2-no2-betapy
12935 bimhs-am3diaz-5amo-zdabs
12936 imhs-amn2-eoco-psdap
12937 me2py-hexadi-emo-basdap
12938 mam2py-amn3-5amo-bnsdap
12939 emnim-mepazin-mes-betadcph
12940 bimhs-diphmep-napo-bphabs
12941 am-n2nme2n-mecpo-bsdap
12942 pippy-am3-oem-nbetapy
12943 mam2py-amn2-mes-zdab
12944 bim-am3-sem-nbetameph
12945 piraz-diphmep-5pho-psdapee
12946 impy-edian2-oeto-psdap
12947 me-pnymea-5amo-bhsdap
12948 bim-edian2-no2-betapy
12949 bhs-trias-oem-zdap
12950 bhs-amn2-mes-bhsdap
12951 bimhs-trias-no2-asppha
12952 2py-tridi-hso-glupha
12953 n2py-24thiz-pheo-oxal
12954 gua-dimen-mommo-asppha
12955 impy-pnymea-pheo-csdap
12956 mepip-eta-chexo-zdab
12957 4pmhs-pyma2-5pho-betadcph
12958 piraz-diphmem-oem-asppha
12959 dhim-am3diaz-meo-zdab
12960 bimhs-pyma2-cnmo-bsdap
12961 imhs-mepipen2-ocho-betapy
12962 bzl-pazin-5amo-tsdap
12963 2py-amn2-oem-psdap
12964 dhim-am2-sem-npsdap
12965 bhs-dimephmem-imo-csdap
12966 pippy-pyma2-men-aspbzla
12967 nim-mepipe-5pho-zdab
12968 amthiaz-thizn-emo-thizzdap
12969 impy-m24thizman2-aco-betadcph
12970 mam2py-m25thiz-eoco-csdap
12971 me2py-thizn-chexo-betainyl
12972 imhs-pyma2-cpeo-glyzdap
12973 dmam-tridi-chexo-psdab 12974 nmor-ams2-napo-zdap
12975 hythpym-din-no2-psdap
12976 piraz-tridi-fo-bhsdab
12977 am2py-25thiman2-imo-oxal
12978 chhs-eta-cpro-mezphe
12979 mam2py-ams2-no2-betainyl
12980 pippy-24thiz-chexo-zlys
12981 n2py-24thiz-men-bhsdap
12982 npip-m25thiz-oem-betadcph
12983 dhim-edian2-no2-bhsdab
12984 edothpym-m25thiz-oem-aspbzla
12985 me2py-mea2s-imo-bsdap
12986 ppy-mepipen2-no1-betainyl
12987 bim-amn2-oem-psdab
12988 mepip-ams3-no1-betainyl
12989 imhs-eta-oem-psdap
12990 bim-eta-oem-psdap
12991 piraz-dimephmem-meo-asppha
12992 piraz-eta-5pho-zdabs
12993 bhs-eta-5pho-bnsdap
12994 me-edian2-5amo-glubzla
12995 hythpym-trias-cno-aspbzla
12996 am2py-mepipen2-no2-betaet
12997 pyr-24thiz-imo-glyzdap
12998 imhs-amn2-mes-betapy
12999 dhim-pentadi-fo-csdap
13000 me-edian2-chexo-betadcph
13001 bhs-n24thiman-mes-zdabs
13002 bimhs-dis-emo-dfzdap
13003 mepip-m25thizman2-no2-mezphe
13004 hythpym-tridi-no2-betainyl
13005 piraz-thizn-no1-bsdap
13006 npip-dimephmem-ocho-zdap
13007 bim-din-eoco-bsdap
13008 amim-m25thiz-hso-betadcph
13009 dpam-pyma2-men-psdap
13010 mam2py-25thizman2-men-zorn
13011 bim-pipa-chexo-betadcph
13012 bim-eta-5pho-bsdap
13013 2py-m24thiman2-imo-bhsdab
13014 imhs-mepazin-pheo-zdab
13015 imhs-pazin-no1-bhsdap
13016 binhs-amo2-imo-aspaba
13017 hythpym-dio-emo-csdap
13018 amim-dimen-chexo-csdap
13019 bim-m25thiz-emo-dfzdap
13020 pippy-am2-oem-nzdab
13021 dhim-pipmea-5pho-glyzdap
13022 ppy-eta2s-5pho-bhsdab
13023 dhim-24thizman2-nmo-bhsdab
13024 dmam-dimen-fo-glubzla
13025 amthiaz-amo2-ocho-bphabs
13026 tolhs-tetradi-meto-thizzdap
13027 dhim-edian2-men-zdab
13028 dhim-amo3-oem-glyzdap
13029 pyr-butn-oem-zdab
13030 amim-mepipen2-pheo-bnsdap
13031 thpym-pipmea-no2-mezphe
13032 2py-trias-emo-csdap
13033 chmhs-pazin-no2-psdap
13034 amim-25thizman2-cpeo-glyzdap
13035 n2py-tetradi-no1-bnsdap
13036 hythpym-ms-5pho-glupha
13037 imhs-amn2-no2-bhsdap
13038 imhs-diphmem-mmen-glyzdap
13039 amim-m24thizman2-ocho-bhsdap
13040 dhim-mepipe-5amo-aspaba
13041 menim-ams2-cpeo-aval
13042 pippy-butn-daco-bsdap
13043 am2py-dis-imo-aspbzla
13044 dhim-25thizman2-5amo-glyzdap
13045 mam2py-eta-imo-zdap
13046 impy-amn3-emo-zdabs
13047 bhs-dis-mmen-betadcph
13048 bhs-pipmes-napo-glyzdap
13049 dmthpym-tetradi-pheo-csdap
13050 me2py-m24thiz-emo-bhsdab
13051 bhs-amn2-no1-bnsdap
13052 imhs-m25thizman2-chexo-bphabs
13053 bimhs-amn2-fo-bhsdap
13054 imhs-dimen-emo-glyzdap
13055 bimhs-eta-oem-bhsdap
13056 chhs-25thiman2-fo-mezphe
13057 bimhs-3diaz-napo-zdap
13058 amim-ams2-men-dfzdap
13059 tolhs-pnymea-no1-aspibua
13060 dmthpym-pymea-emo-zdapee
13061 bim-edian2-eoco-betapy
13062 hythpym-amn2-mmen-zdap
13063 bim-24thiz-cpeo-psdab
13064 menim-amn2-men-mezphe
13065 bim-mepazin-5amo-ppsdap
13066 me-pipa-4amo-psdap
13067 bimhs-edian2-no1-aspibua
13068 pippy-tetradi-oem-aspbzla
13069 bhs-propa2s-5amo-zdabs
13070 bim-pnymea-napo-zlys
13071 pippy-pipa-napo-zdap
13072 dhim-edian2-meteto-ppsdap
13073 bhs-pazin-no2-zdab
13074 am2py-thizo-emo-zdabs
13075 bim-edian2-oem-bhsdap
13076 ibhs-24oxman2-imo-bnsdap
13077 hythpym-thizo-pro-asppha
13078 pippy-pipa-meto-bhsdab
13079 bhs-indan2-5amo-glubzla
13080 pippy-pymea-5pho-dfzdap
13081 cl3pyme-pnymea-men-zdap
13082 impy-dis-mes-bnsdap
13083 thpym-eta-napo-glyzdap
13084 bim-butn-fo-psdap
13085 bimhs-ams2-no2-mezphe
13086 am2py-mepipe-ocho-zdabs
13087 me2py-tetradi-5amo-zdab
13088 am4py-eta-5amo-dfzdap
13089 hythpym-25oxman2-hso-zlys
13090 gua-pnymea-hso-aspbzla
13091 dhim-eta-paco-psdab
13092 emnim-pymea-napo-bphabs
13093 2pmhs-mepipen2-eoco-glupha
13094 cl3pyme-pazi2n-chexo-zdap
13095 amthiaz-am3-oem-nzdap
13096 thpym-amn2-eoco-zdap
13097 bhs-n2nme2n-5amo-zdapee
13098 2py-mepipen2-napo-aspibua
13099 mam2py-pipa-cnmo-aspbzla
13100 imhs-tetradi-chexo-mezphe
13101 hythpym-amo2-no2-zdabs
13102 bhs-amn2-5pho-betapy
13103 am2py-trias-aco-psdapee
13104 dhim-3pazin-nmo-bnsdap
13105 bim-edian2-no1-psdab
13106 am2py-pazi2n-ocho-glyzdap
13107 dhim-pipmea-oem-zorn 13108 gua-din-meto-aspibua
13109 bimhs-pentadi-5amo-bnsdap
13110 mepip-pymea-imo-asppha
13111 dpam-m25thiz-napo-bsdap
13112 imhs-diphmem-napo-thizzdap
13113 imhs-m24thizman2-mes-psdab
13114 thpym-25oxman2-fo-bsdap
13115 bimhs-thizn-meteto-glyzdap
13116 z-tetradi-chexo-csdap
13117 mam2py-24oxman2-no2-bphabs
13118 am2py-pymea-mes-dfzdap
13119 2py-amn3-napo-zdap glyzdap
13120 bhs-amn2-meo-psdap
13121 am2py-tetras-meo-psdap
13123 bhs-n2nme2n-no1-aspbzla
13124 im-diphmem-meo-betaet
13125 imhs-tridi-oem-ppsdap
13126 imhs-pazin-daco-bsdap
13127 bhs-eta-no1-bsdap
13128 pyraz-pazin-emo-betainyl
13129 thpym-din-mommo-mezphe
13130 ibhs-thizn-chexo-bsdap
13131 menim-dis-oem-zdap
13132 bhs-amn2-no2-bnsdap
13133 bim-amn2-mecpo-dfzdap
13134 phpip-dis-5amo-zdap
13135 hythpym-dimephmem-oem-aspibua
13136 imhs-pazin-cno-csdap
13137 hythpym-diphmem-oem-bphabs
13138 amim-trias-peo-psdab
13139 z-hexas-cpeo-zdap
13140 dhim-amn2-no2-zdab
13141 am2py-25oxman2-4pho-psdapee
13142 am2py-amo2-pheo-bsdap
13143 bhs-thizn-meteto-psdap
13144 bim-pymea-ocho-zdabs
13145 bimhs-diphmep-men-glubzla
13146 me2py-amo2-chexo-zdapee
13147 mam2py-mepazin-chexo-bphabs
13148 pippy-amn2-no2-zdabs
13149 bhs-edian2-no2-psdap
13150 dmthpym-3diaz-men-betadcph
13151 2pmhs-amo3-paco-mezphe
13152 me2py-amn3-napo-betadcph
13153 dmbim-pipmea-meo-psdapee
13154 moegua-diaz-oem-osdap
13155 phhs-ms-4amo-zdab
13156 mam2py-dipch-meteto-dfzdap
13157 ppy-am3-sem-nzdap
13158 bhs-mepazin-men-aspbzla
13159 bhs-pazin-no1-betapy
13160 bhs-amn3-no1-bhsdap
13161 bimhs-indan2-meo-zdap
13162 thpym-eta-5pho-bsdap
13163 bimhs-mepipen2-5amo-aspbzla
13164 z-m25thiz-cnmo-thizzdap
13165 2py-24thiz-meo-asppha
13166 thpym-edia2-sem-nbetameph
13167 bim-mepipe-eoco-psdap
13168 amim-butn-no1-aspibua
13169 mam2py-m24thizman2-mecpo-glyzdap
13170 bim-dis-nmo-bhsdap
13171 mam2py-amo3-chexo-csdap
13172 hythpym-amn3-chexo-glupha
13173 fthpym-25thiman2-men-betadcph
13174 bim-diphmep-no2-zdap
13175 pippy-am2-4amo-glyzdap
13176 hythpym-pazi2n-no2-betapy
13177 dhim-trias-imo-dfzdap
13178 bimhs-thizn-5pho-betapy
13179 me2py-pazin-mecpo-bhsdab
13180 npip-pnymea-mes-asppha
13181 dhim-pnymea-fo-dfzdap
13182 amim-pipmea-4pho-bhsdap
13183 bzl-24thizman2-imo-bnsdap
13184 im-m25thiz-imo-bhsdap
13185 amim-25thizman2-emo-osdap
13186 pippy-pazi2n-fo-psdapee
13187 ppy-mepipe-mommo-psdab
13188 bhs-m24thizman2-no2-mezphe
13189 2py-dich-5pho-glyzdap
13190 mam2py-pipa-meo-betainyl
13191 im-am3-oem-nbetapy
13192 menim-pymea-meo-betadcph
13193 impy-24thiz-cnmo-psdab
13194 bhs-25oxman2-cno-glyzdap
13195 me2py-pymea-daco-zlys
13196 bhs-pazin-oem-zdab
13197 nim-mepazin-men-glyzdap
13198 thpym-ams2-chexo-betainyl
13199 amthiaz-propn-men-zdab
13200 impy-amo3-mes-bphabs
13201 2py-m25oxman2-mmen-zdapee
13202 thpym-dimephmep-imo-zdap
13203 mam2py-am3diaz-chexo-zdap
13204 bz-butn-no1-zdap
13205 bim-mepipe-no2-betapy
13206 npip-edia2-oem-nbeta34-dimeoph
13207 thpym-edian2-oem-betapy
13208 npip-mepipe-meo-asppha
13209 imhs-pazi2n-men-zdap
13210 me2py-din-mes-zdab
13211 hythpym-edian2-no2-betapy
13212 nmhs-pazin-eoco-psdab
13213 bhs-dimen-eoco-psdab
13214 me2py-24thiz-ocho-asppha
13215 imhs-din-mecpo-betadcph
13216 amim-dimephmem-napo-psdab
13217 impy-m25oxman2-fo-csdap
13218 bimhs-dimephmem-5amo-bhsdap
13219 hythpym-m25thiman2-no1-dfzdap
13220 bim-24thizman2-5amo-psdab
13222 dpam-dimephmem-5pho-bhsdab
13223 imhs-pazin-mes-betapy
13224 2py-pazin-5amo-csdap
13225 im-dimephmep-5amo-ppsdap
13226 impy-thizn-5pho-aspbzla
13227 imhs-din-oem-oxal
13228 pippy-diphmem-chexo-zdap
13229 bim-am3diaz-5amo-bnsdap
13230 2py-3diaz-ocho-mezphe
13231 dhim-dipch-cno-mezphe
13233 amim-diphmep-5pho-bhsdab
13234 dhim-dimen-daco-bhsdab
13235 ppy-diphmem-meo-bphabs
13236 dhim-thizo-fo-bnsdap
13237 bimhs-dimephmep-oeto-zdap
13238 bim-mepipe-baeo-psdap
13239 mam2py-amn3-fo-glyzdap
13240 2py-25thiman2-eoco-dfzdap
13241 bimhs-hythn-fo-zdab
13242 mam2py-pyma2-fo-psdab
13243 amim-25oxman2-cno-zdap
13244 impy-pazin-eoco-aspbzla 13245 me2py-mepazin-oem-asppha
13246 nmhs-mepipe-peo-aspbzla
13247 hythpym-mepazin-cpeo-aspaba
13248 thpym-24thiman-5pho-bhsdap
13249 am-25oxman2-ocho-asppha
13250 nmhs-ams3-cpeo-psdab
13251 hythpym-dimephmem-hso-bphabs
13252 nmor-m25oxman2-cpro-bphabs
13253 bhs-pyma2-ocho-oxal
13254 piraz-mepipen2-men-mezphe
13255 2py-dimephmep-4pho-aspbzla
13256 phhs-amn2-men-aspbzla
13257 bhs-tridi-mes-bnsdap
13258 ec-tridi-mes-glubzla
13259 am2py-dipch-paco-betadcph
13260 cl3pyme-m25thiz-pheo-bsdap
13261 am4py-m25thizman2-imo-bhsdap
13262 am2py-pipa-oeto-betainyl
13263 pyraz-amn3-nmo-zdabs
13264 bim-edian2-5pho-betapy
13265 2py-pazin-no2-psdab
13266 2py-pazin-5pho-zdap
13267 deam-24thizman2-nmo-betainyl
13268 phhs-dimephmem-cpro-bhsdab
13269 fthpym-din-meto-betadcph
13270 bimbs-pnymea-5amo-aspaba
13271 imhs-eta-cpro-mezphe
13272 thpym-tridi-mes-aspbzla
13273 2pmhs-mepipe-5pho-betaet
13274 bhs-amn2-mes-bsdap
13275 thpym-25thiman2-no2-dfzdap
13276 pippy-pymea-no2-zdapee
13277 me2py-thizn-emo-bhsdap
13278 cl3pyme-dimephmep-emo-psdab
13279 piraz-thizn-5pho-betadcph
13280 mam2py-amo2-paco-psdapee
13281 dhim-amn2-imo-tsdap
13282 me2py-25oxman2-hso-bsdap
13283 emnim-thizn-meo-zdapee
13284 am2py-dio-cnmo-bhsdab
13285 thpym-pazin-no1-bhsdap
13286 thpym-trias-eoco-betapy
13287 pippy-pnymea-cnmo-betapy
13288 2py-dis-emo-zdapee
13289 phhs-n2o2n-meo-aspbzla
13290 4pmhs-m25thiz-chexo-zorn
13291 pyrhs-eta-no1-zdab
13292 deam-dis-chexo-bhsdab
13293 me-edian2-no2-bnsdap
13294 pippy-pipmea-fo-aspibua
13295 bhs-pipmea-fo-aspaba
13296 fthpym-pipmeo-eoco-psdap
13297 chmhs-diphmem-chexo-csdap
13298 imhs-eta-oem-psdab
13299 am4py-pazin-men-zdab
13300 piraz-m24thizman2-5amo-psdap
13301 2pmhs-dimen-oeto-betapy
13302 menim-dimen-chexo-psdapee
13303 thpym-mepazin-5pho-psdab
13304 menim-edian2-peo-ppsdap
13305 impy-edia2-oem-nzdab
13306 chmhs-diphmep-no2-mezphe
13307 me-m25thiz-5pho-betadcph
13308 bhs-am2-sem-nbeta34dimeoph
13309 bzl-mepipe2-oem-nzdap
13310 nim-m25thizman2-men-osdap
13311 dhim-mepipe-oem-zdabs
13312 mam2py-amo2-men-psdap
13313 impy-pnymea-mommo-aspbzla
13314 amim-24oxman2-no2-betapy
13315 npip-dis-oem-zdap
13316 pippy-diphmep-napo-bsdap
13317 moegua-m25thiz-ocho-betadcph
13318 pyrhs-propaZs-mes-csdap
13319 bhs-m25thiz-chexo-aspibua
13320 thpym-25oxman2-meteto-zdap
13321 bhs-edian2-meo-bhsdap
13322 bim-3pazin-mecpo-oxal
13323 mam2py-amn2-emo-zdab
13324 bhs-eta-no1-betapy
13325 mam2py-diphmem-chexo-zdab
13326 pippy-25thiman2-eoco-asppha
13327 imhs-eta-no1-betapy
13328 thpym-ams2-4pho-zdap
13329 dhim-eta-fo-psdab
13330 dhim-tridi-mes-betapy
13331 amim-dimephmep-emo-dfzdap
13332 edothpym-pazin-mes-betaet
13333 am-25thiman2-fo-glyzdap
13334 hythpym-trias-5amo-glyzdap
13335 thpym-eta-mes-betapy
13336 deam-pazin-fo-betapy
13337 piraz-mepipen2-4amo-dfzdap
13338 hythpym-pazi2n-pro-bhsdap
13339 impy-butn-nmo-bphabs
13340 am2py-mepipe-imo-zorn
13341 thpym-eta-meo-bhsdap
13342 imhs-pazin-meo-psdap
13343 bim-m24thizman2-mecpo-bnsdap
13344 dhim-pazin-men-ibsdap
13345 am2py-24thiman-chexo-zdab
13346 me2py-din-no1-zdap
13347 piraz-tetradi-fo-tsdap
13348 impy-dis-5pho-aspbzla
13349 bim-amo2-mes-csdap
13350 hythpym-pymea-chexo-asppha
13351 emnim-tetras-emo-aspibua
13352 mam2py-pyma2-5pho-betainyl
13353 ppy-amn2-5amo-aspibua
13354 deam-2pazin-baeo-zdab
13355 thpym-mepipe2-sem-nbetab naphth
13356 thpym-pyma2-meo-asppha
13357 mam2py-ams3-imo-psdab
13358 am2py-diphmep-no1-aspbzla
13359 amim-pazin-mes-thizzdap
13360 fthpym-pipa-ocho-asppha
13361 tolhs-mepipe-no1-oxal
13362 emnim-ams2-chexo-psdab
13363 2py-amn3-no2-bhsdap
13364 bhs-amn3-5pho-zdap
13365 dhim-eta-men-bsdap
13366 pippy-dimephmem-baeo-zdap
13367 imhs-dimen-emo-glyzdap
13368 amim-ams3-fo-glupha
13369 edothpym-pnymea-mes-betainyl
13370 mam2py-n24thiman-no2-betaet
13371 hythpym-pipa-mmen-bnsdap
13372 bim-din-imo-zdap
13373 bhs-thizn-no2-bhsdab
13374 bimhs-amn3-imo-zdap
13375 dhim-pipa-fo-zlys
13376 am2py-pyma2-4pho-betainyl
13377 phpip-pipa-meo-dfzdap
13378 edothpym-tetradi-fo-asppha 13379 bimhs-mepazin-fo-thizzdap
13380 2py-edia2-oem-nbetameph
13381 me2py-dimephmem-imo-psdap
13382 2py-diphmep-pyo-bhsdap
13383 amim-24thiman2-emo-psdab
13384 2pmhs-tridi-eoco-aspibua
13385 me2py-pyma2-eoco-csdap
13386 bim-edian2-meo-bnsdap
13387 2pmhs-tridi-imo-aspbzla
13388 npip-thizn-meto-bhsdap
13389 moegua-ams2-no1-psdab
13390 imhs-dimephmep-oem-aspaba
13391 2py-dio-5pho-bphabs
13392 amthiaz-tridi-chexo-psdap
13393 Zpy-pnymea-meo-zdap
13394 thpym-pazin-5pho-psdap
13395 2py-mepipen2-imo-csdap
13396 dhim-diphmem-baeo-glupha
13397 nmhs-din-men-bsdap
13398 amim-dimen-no1-bhsdap
13399 am2py-pnymea-mes-zdabs
13400 edothpym-24thiz-cpeo-bsdap
13401 dmbim-trias-meo-betapy
13402 bhs-dimephmep-ocho-betainyl
13403 pyraz-amo2-chexo-ppsdap
13404 hythpym-dimephmep-men-zdabs
13405 am2py-mepipen2-emo-bsdap
13406 am4py-dis-no2-dfzdap
13407 impy-24thiz-no1-aspibua
13408 cl3pyme-pyma2-cpeo-ibsdap
13409 hythpym-butn-cnmo-zdab
13410 amim-24thizman2-chexo-aspbzla
13411 imhs-tetradi-meo-psdap
13412 pippy-dinephmep-pyo-bhsdap
13413 bimhs-pipmes-men-betadcph
13414 mam2py-amn-no2-glyzdap
13415 2py-mepipen2-imo-betadcph
13416 fthpym-25thizman2-men-bhsdab
13417 2py-eta-mes-psdap
13418 ibhs-din-men-zdap
13419 bim-mepazin-baeo-bhsdab glyzdap
13420 imhs-m25oxman2-men-bnsdap
13421 mam2py-25oxman2-pro-zdab
13422 bimhs-ams2-aco-aspbzla
13423 2pmhs-mepipe-eoco-psdap
13424 me-trias-5pho-zdab
13425 me2py-24thizman2-no2-dfzdap
13426 impy-tetradi-hso-bhsdap
13427 me2py-thizn-nmo-zdap
13428 me2py-pyma2-5amo-zdab
13429 imhs-thizn-imo-psdab
13430 bim-pazi2n-oem-bhsdab
13431 dhim-24thiz-meo-psdab
13432 am2py-thizo-oem-zdab
13433 imhs-25oxman2-emo-psdab
13434 mepip-m24thizman2-meteto-bphabs
13435 ec-diphmep-5pho-bhsdap
13436 2py-trias-oem-mezphe
13437 mepip-n24thiman-5pho-zdabs
13438 thpym-edian2-mes-zdab
13439 bhs-edian2-5pho-psdab
13440 impy-indan2-oem-bhsdab
13441 bhs-mepipe-5pho-zdab
13442 pyrhs-m24oxman2-no1-aspibua
13443 2py-diphmem-5amo-psdap
13444 mam2py-diphmem-mecpo-glyzdap
13445 piraz-mepazin-men-betaet
13446 me2py-thizn-fo-thizzdap
13447 amim-pyma2-imo-aspbzla
13448 me-amn3-napo-ppsdap
13449 nim-ms-mes-assppha
13450 me2py-mepipe2-sem-nbetab naphth
13451 mam2py-thizs-aco-betainyl
13452 am2py-pyma2-chexo-dfzdap
13453 nmor-pipmea-cnmo-bnsdap
13454 imhs-24thizman2-fo-zdap
13455 pyraz-mepipe-cno-asppha
13456 ibhs-eta2s-imo-aspbzla
13457 imhs-amn2-fo-aval
13458 piraz-dimen-5pho-bsdap
13459 bim-edia2-oem-nzdap
13460 mam2py-pipa-no2-betainyl
13461 bz-pipmea-ocho-betadcph
13462 bhs-pazin-oem-bsdap
13463 amim-m25thizman2-men-asppha
13464 bhs-eta-imo-mezphe
13465 bim-mepipe-ocho-bnsdap
13466 bhs-m25oxman2-mes-psdab
13467 pippy-hexadi-fo-osdap
13468 dmthpym-dimephmep-nmo-glyzdap
13469 bimhs-tetradi-chexo-betadcph
13470 hythpym-dimephmem-meto-psdab
13471 pippy-dis-chexo-bhsdab
13472 piraz-m24thizman2-mecpo-asppha
13473 2py-pnymea-cpeo-bnsdap
13474 imhs-mepazin-meo-zdab
13475 prhs-pnymea-mes-zdap
13476 bhs-pazin-eoco-bnsdap
13477 thpym-propa2s-oem-aspibua
13478 cl3pyme-diphmem-5pho-zdap
13479 amim-pipa-imo-bnsdap
13480 bzl-pnymea-chexo-aspbzla
13481 ibhs-amo2-5amo-bnsdap
13482 thpym-indan2-emo-zdabs
13483 me2py-m25thiz-daco-bhsdab
13484 pyr-dimephmep-aco-betapy
13485 4pmhs-tetradi-mes-psdab
13486 dmbim-tridi-eoco-dfzdap
13487 bhs-25thiz-aco-aspbzla
13488 impy-pnymea-eoco-zdab
13489 bim-eta-eoco-bhsdap
13490 dhim-24thiz-5pho-bhsdab
13491 nim-am2-oem-nbetapy
13492 dmbim-25thiman2-fo-dfzdap
13493 pyrhs-pymea-cno-aspibua
13494 me2py-25thiman2-fo-betapy
13495 piraz-pipmes-5pho-aspbzla
13496 me2py-pazin-oem-zdab
13497 deam-trias-5amo-ibsdap
13498 hythpym-24thiz-5amo-mezphe
13499 dhim-amo2-men-csdap
13500 pippy-pipa-5pho-aspbzla
13501 mam2py-pazin-ocho-aspbzla
13502 chmhs-amo3-paco-basdap
13503 bhs-eta-5pho-psdab
13504 dhim-trias-meo-csdap
13505 pippy-mepipe-chexo-asppha
13506 ppy-diphmem-5amo-mezphe
13507 nmhs-diphmem-mes-betainyl
13508 imhs-m25thiz-cno-betainyl
13509 pyraz-m25oxman2-fo-zdab
13510 am2py-pazin-pyo-psdap
13511 2py-mepazin-nrmo-betainyl
13512 me2py-24thizman2-imo-bnsdap 13514 dhim-ms-mecpo-tsdap
13515 hythpym-diphmem-pyo-betapy
13516 phhs-dis-4pho-betapy
13517 ppy-diphmep-meto-bhsdap
13518 am4py-m24thizman2-peo-betapy
13519 amim-eta-5amo-bsdap
13520 menim-pymea-fo-betadcph
13521 bhs-dipch-men-bnsdap
13522 thpym-pnymea-no1-mezphe
13523 dpam-am3-oem-nbetapy
13524 bhs-amn2-ocho-bnsdap
13525 imhs-edian2-no2-zdap
13526 bzl-24thiman2-meto-asppha
13527 hythpym-dis-5amo-bsdap
13528 thpym-24thizman2-no1-bhsdap
13529 ibhs-m24oxman2-cpeo-mezphe
13530 deam-amo2-aco-betainyl
13531 2py-amn2-no1-bsdap
13532 me-indan2-men-betadcph
13533 mam2py-pazin-mes-psdapee
13534 2pmhs-diphmep-5pho-zdabs
13535 bhs-pipmeo-no1-zdabs
13536 bim-propn-no2-bnsdap
13537 dhim-hexas-meteto-psdab
13538 imhs-amn2-meo-bhsdap
13539 pippy-eta2s-5amo-betainyl
13540 impy-trias-fo-bhsdap
13541 npip-diphmem-chexo-glyzdap
13542 am2py-am2-oem-nzdab
13543 pyr-trias-5amo-aspibua
13544 bhs-diphmep-meteto-mezphe
13545 imhs-mepipe-oem-psdab
13546 phpip-dimephmep-mmen-betadcph
13547 phpip-amo2-no2-betadcph
13548 morhs-dis-no1-betainyl
13549 chmhs-m24thizman2-men-mezphe
13550 moegua-m24thizman2-oeto-asppha
13551 dhim-ams2-imo-glyzdap
13552 bhs-hexadi-imo-bhsdab
13553 n2py-amn2-meteto-zdap
13554 amthiaz-tetras-fo-zdab
13555 piraz-diphmem-emo-psdab
13556 bhs-pentas-meo-zdabs
13557 amim-pazin-fo-aspbzla
13558 nmhs-pnymea-mecpo-psdap
13559 piraz-pipmea-mommo-osdap
13560 dhim-n2nme2n-meto-psdap
13561 menim-dimen-eoco-aspaba betadcph
13562 pyrhs-edian2-cno-dfzdap
13563 edothpym-trias-mecpo-betapy
13564 hythpym-amo2-no1-psdab
13565 bim-mepipe-eoco-bhsdap
13566 phpip-din-no1-zdabs
13567 am2py-din-ocho-aspaba
13569 mam2py-mea-imo-bhsdap
13570 2py-mepipe2-sem-nzdab
13571 2py-edian2-ocho-zdap
13572 pyr-amo3-mes-mezphe
13573 impy-pazin-4pho-tsdap
13574 am4py-thizn-mommo-aspaba
13575 mepip-amn3-cnmo-glyzdap
13576 thpym-edian2-meo-psdap
13577 bim-eta-eoco-zdabs
13578 impy-diphmem-oem-betadcph
13579 hythpym-mepazin-mommo-dfzdap
13580 gua-diphmem-eoco-mezphe
13581 hythpym-25thiman2-no2-aspaba
13582 morhs-m25thiz-ocho-bphabs
13583 bimhs-dimephmem-napo-zdabs
13584 mam2py-3pazin-oeto-betapy
13585 nmor-pipa-fo-zdab
13586 me2py-am2-sem-nzdab
13587 dhim-ams2-fo-glyzdap
13588 chmhs-trias-oem-bhsdap
13589 emnim-pnymea-no2-bnsdap
13590 dmbim-dimephmep-meo-csdap
13591 bzl-24thiz-oem-zdab
13592 imhs-pazin-pro-glyzdap
13593 bimhs-mepazin-meteto-bnsdap
13594 impy-mepipen2-cao-zdap
13595 piraz-pazin-oem-bhsdap
13596 thpym-m24oxman2-no1-betainyl
13597 dpam-thizn-cpro-glupha
13598 mam2py-eta-no1-bphabs
13599 fthpym-dimephmep-5pho-betaet
13600 me2py-n24thiman-oem-psdap
13601 impy-m25thiz-fo-psdab
13602 amim-amo3-cpeo-betainyl
13603 bim-mepipe2-oem-nzdab
13604 amim-3pazin-mmen-asppha
13605 amim-m25thiman2-no1-zdap
13606 am4py-pipa-chexo-psdap
13607 me-trias-oem-bhsdap
13608 pippy-24thizman2-ocho-bhsdab
13609 imhs-mea-5amo-aspbzla
13610 amim-edian2-men-bhsdap
13611 dhim-pipa-emo-aspibua
13612 mepip-24thizman2-oem-betadcph
13613 bim-diphmem-mes-aspbzla
13614 dmthpym-mepipe-men-bnsdap
13615 dhim-ams2-oeto-zdabs
13616 bhs-din-men-bsdap
13617 bim-dimephmep-imo-zdabs
13618 piraz-24oxman2-oem-aspbzla
13619 2py-pyma2-imo-zdab
13620 deam-3pazin-5pho-zdapee
13621 mam2py-din-cpro-dfzdap
13622 imhs-edian2-eoco-bhsdap
13623 2py-edian2-ocho-bhsdap
13624 2py-edian2-meo-psdab
13625 emnim-mepipe-baeo-aspbzla
13626 npip-trias-5pho-betadcph
13627 mam2py-din-emo-zdab
13628 phhs-25oxman2-ocho-bhsdap
13629 me2py-dimen-cno-dfzdap
13630 npip-pyma2-ocho-bhsdab
13631 me2py-pyma2-fo-csdap
13632 amim-pyma2-fo-psdab
13633 am2py-dimen-fo-bhsdap
13634 chhs-pymea-no2-glubzla
13635 imhs-n2o2n-men-aspbzla
13636 thpym-pazin-eoco-psdab
13637 deam-diphmep-mmen-bhsdap
13638 amim-eta2s-mes-bphabs
13639 impy-trias-chexo-osdap
13640 pippy-edian2-no1-bnsdap
13641 thpym-mepipe-no1-bsdap
13642 amim-hexadi-oem-betapy
13643 dmbim-24thiman-chexo-aspbzla
13644 imhs-am3diaz-5pho-bhsdab
13645 imhs-edian2-meo-bphabs
13646 morhs-diphmep-imo-mezphe
13647 dhim-n2nme2n-chexo-aspibua
13648 cl3pyme-eta-baeo-betapy 13649 dmam-tetradi-fo-bnsdap
13650 bimhs-pipmes-5amo-zlys
13651 me2py-tetradi-meo-tsdap
13652 mam2py-24oxman2-oem-glupha
13653 bimhs-thizn-imo-glyzdap
13654 pippy-dis-hso-bnsdap
13655 2py-amn2-ocho-psdap
13656 pyraz-dis-fo-bnsdap
13657 nmor-amn2-fo-bhsdab
13658 bim-tridi-no1-asppha
13659 piraz-thizo-fo-csdap
13660 prhs-amo2-hso-glyzdap
13661 bim-dimen-napo-psdab
13662 thpym-amn2-no2-betapy
13663 mam2py-m25thiz-mmen-zdapee
13664 piraz-amo2-ocho-bhsdab betadcph
13665 bimhs-dimephmep-imo-zdabs
13666 am2py-ms-5amo-bphabs
13667 gua-din-5amo-betadcph
13668 ppy-mepipen2-fo-zlys
13669 thpym-trias-fo-zdap
13670 bhs-25oxman2-no1-csdap
13671 bim-edian2-ocho-bsdap
13672 thpym-propa2s-eoco-bnsdap
13673 bimhs-mepazin-ocho-bhsdab
13674 pyrhs-mepipen2-no1-psdab
13675 impy-trias-oem-betadcph
13676 thpym-pyma2-fo-betainyl
13677 me2py-pipmea-eoco-aspbzla
13678 impy-pyma2-no1-bphabs
13679 2py-amn2-no2-betapy
13680 bhs-am3-sem-nzdap
13681 bim-eta-eoco-zdab
13682 cl3pyme-diphmem-paco-glupha
13683 2py-diphmem-imo-bsdap
13684 bz-dis-napo-mezphe
13685 nim-pentadi-4amo-zdap
13686 morhs-m25thiz-no1-asppha
13687 am-m25thizman2-oem-bsdap
13688 ppy-pnymea-mommo-mezphe
13689 moegua-trias-5amo-bhsdab
13690 bhs-pazin-no2-psdap
13691 phpip-m25thiz-eoco-psdap
13692 bim-25oxman2-napo-csdap
13693 dhim-24thiman-napo-bsdap
13694 piraz-pyma2-meo-betadcph
13695 bim-hexadi-fo-asppha
13696 pippy-amo2-imo-aspibua
13697 phhs-edia2-sem-abeta34-dimeoph
13698 2py-3pazin-meo-mezphe
13699 binhs-edian2-5amo-psdab
13700 thpym-amn2-men-asppha
13701 prhs-dimephmep-emo-bhsdap
13702 me2py-2nme2n-baeo-mezphe
13703 imhs-tridi-fo-betapy
13704 thpym-edian2-no2-zdab
13705 me2py-eta-eoco-glupha
13706 bhs-tridi-meteto-zdap
13707 bim-eta-no1-betainyl
13708 bim-edian2-meo-psdap
13709 impy-edia2-sem-nbeta34-dimeoph
13710 prhs-trias-5pho-bhsdap
13711 imhs-edian2-no1-bnsdap
13712 bhs-eta-4amo-zdap
13713 piraz-m24thizman2-cnmo-betadcph
13714 pippy-mepipe2-oem-nbetab naphth
13715 impy-din-napo-bsdap
13716 bhs-trias-napo-betapy
13717 bim-thizo-men-betadcph
13718 nmor-amn2-chexo-psdap
13719 npip-3pazin-men-mezphe
13720 bhs-diphmem-mommo-zdabs
13721 bimhs-ams2-chexo-betainyl
13722 dhim-mepipe2-oem-nbetapy
13723 gua-trias-mes-mezphe
13724 ppy-eta-ocho-ibsdap
13725 pippy-propn-meo-betadcph
13726 prhs-edian2-ocho-dfzdap
13727 bim-thizo-eoco-bphabs
13728 am2py-pipmea-oem-psdab
13729 imhs-edian2-eoco-zdab
13730 amim-dipch-eoco-dfzdap
13731 thpym-mepipe-peo-bsdap
13732 imhs-edian2-oem-zdab
13733 2py-diphmep-pro-asppha
13734 bzl-amn3-emo-betainyl
13735 pippy-dio-emo-psdap
13736 mam2py-thizn-oem-asppha
13737 thpym-25thizman2-meteto-dfzdap
13738 am2py-2pazin-5amo-csdap
13739 imhs-24thiman2-5amo-glyzdap
13740 bimhs-tetradi-5amo-bphabs
13741 hythpym-diphmep-fo-aspaba
13742 chhs-hexas-5amo-mezphe
13743 imhs-pazin-meo-zdab
13744 amim-amn2-mes-betadcph
13745 ibhs-tridi-meteto-bhsdab
13746 thpym-m25thiz-ocho-betadcph
13747 am4py-m25thiz-emo-aspaba
13748 npip-pipmeo-men-bhsdab
13749 bhs-edian2-imo-csdap
13750 imhs-mepipe-no2-bsdap
13751 thpym-n2nme2n-oem-glyzdap
13752 imhs-dipch-cno-ibsdap
13753 thpym-amo2-oem-zdap
13754 prhs-pymea-napo-betainyl
13755 ibhs-trias-napo-csdap
13756 phpip-pymea-chexo-bnsdap
13757 am2py-diphmep-5pho-betainyl
13758 piraz-m25thiz-no2-mezphe
13759 mam2py-hexas-fo-aspibua
13760 2py-eta-no2-bsdap
13761 deam-mea-peo-aspaba
13762 thpym-mepipe-oem-zdab
13763 bimhs-amn2-no1-oxal
13764 imhs-ams2-cnmo-glyzdap
13765 am2py-pyma2-ocho-zdap
13766 gua-m24oxman2-oem-aval
13767 dhim-mepipen2-pyo-betapy
13768 hythpym-2pazin-mes-csdap
13769 tolhs-dimephmep-chexo-betapy
13770 impy-am2-sem-nbetabnaphth
13771 pippy-dimephmem-5pho-aspbzla
13772 thpym-mea-oem-bsdap
13773 amim-amo2-ocho-betadcph
13774 prhs-am2-sem-nzdab
13775 imhs-tetradi-emo-osdap
13776 prhs-24thizman2-mmen-betainyl
13777 2py-eta-5pho-zdab
13778 bimhs-pipa-oeto-aspbzla
13779 hythpym-pipmea-meteto-aspaba
13780 dhim-mepipe-5amo-bsdap
13781 pyraz-eta-fo-aspibua
13782 dmam-m25oxman2-meto-betainyl 13783 thpym-props-fo-bsdap
13784 impy-din-men-bhsdap
13785 mepip-diphmem-ocho-zdabs
13786 2py-edian2-mes-ibsdap
13787 piraz-pipmea-men-zdabs
13788 me-m25thiz-imo-betadcph
13789 dmthpym-m24thizman2-mes-bnsdap
13790 mam2py-dio-oem-psdab
13791 2pmhs-n24thiman-no2-zdap
13792 thpym-eta-eoco-psdab
13793 am-dimephmem-chexo-zdap
13794 hythpym-edian2-ocho-mezphe
13795 me2py-24oxman2-5pho-bnsdap
13796 2py-pazin-mes-betapy
13797 bimhs-ams3-napo-zlys
13798 me2py-edia2-sem-nbetameph
13799 amim-pazi2n-men-osdap
13800 nmor-25thizman2-men-bhsdap
13801 tolhs-m24thizman2-pro-bsdap
13802 menim-dis-imo-mezphe
13803 phhs-25oxman2-napo-zdap
13804 2py-diphmep-daco-mezphe
13805 bhs-dio-oem-betadcph
13806 amim-props-no1-aval
13807 nim-24thizman2-men-aspibua
13808 bzl-m25thizman2-ocho-betainyl
13809 2py-pyma2-napo-psdap
13810 4pmhs-pazin-fo-zlys
13811 am2py-amo2-men-dfzdap
13812 thpym-pipmes-no1-aspibua
13813 bzl-am2-oem-nzdap
13814 me-edian2-no2-zdabs
13815 piraz-dimephmem-no1-aspbzla
13816 hythpym-pnymea-5pho-zdap
13817 bz-24oxman2-eoco-glyzdap
13818 am2py-mepipen2-no2-bphabs
13819 dhim-mea2s-men-psdab
13820 dmbim-mepipe-napo-psdab
13821 nmhs-dimephmep-emo-zdab
13822 hythpym-diphmem-no1-asppha
13823 tolhs-din-men-asppha
13824 bimhs-edia2-sem-nbetameph
13825 mepip-amo2-ocho-csdap
13826 imhs-mepipe-eoco-zdapee
13827 morhs-25oxman2-no2-csdap
13828 thpym-mepipe-eoco-betadcph
13829 am2py-tetras-chexo-bnsdap
13830 phpip-pipmes-ocho-zdap
13831 am2py-25oxman2-ocho-psdap
13832 mam2py-trias-napo-betapy
13833 hythpym-dimephmem-meto-aspbzla
13834 bimhs-thizn-mes-ibsdap
13835 am2py-thizs-5pho-thizzdap
13836 z-thizo-fo-psdap
13837 me2py-mepazin-napo-asppha
13838 2py-ams2-meteto-oxal
13839 pippy-amn3-emo-csdap
13840 bhs-mepipe-no2-aspbzla
13841 n2py-din-no1-oxal
13842 thpym-mepazin-5amo-zdabs
13843 hythpym-tetradi-ocho-osdap
13844 am2py-mepipen2-emo-glubzla
13845 impy-din-eoco-betaet
13846 amim-dis-mes-bhsdap
13847 amim-mepipen2-oeto-dfzdap
13848 mam2py-diphmep-imo-zdap
13849 piraz-amn3-5amo-bhsdab
13850 bhs-m25thizman2-oem-bphabs
13851 bim-m24thizman2-meo-zdab
13852 z-dimephmem-5amo-bphabs
13853 pippy-dich-chexo-bnsdap
13854 pippy-diphmep-5amo-bsdap
13855 bhs-hexadi-5pho-aspibua
13856 hythpym-am3-oem-nzdab
13857 bhs-24oxman2-fo-zdabs
13858 bim-propa2s-cem-betaet
13859 ec-24thizman2-4amo-betadcph
13860 ppy-pnymea-no2-psdab
13861 thpym-dis-5amo-zdab
13862 thpym-eta-meo-bsdap
13863 bhs-amn3-nmo-glyzdap
13864 piraz-dio-mmen-aspibua
13865 amthiaz-tetras-emo-glyzdap
13866 amthiaz-dis-pheo-mezphe
13867 chmhs-dimen-imo-betainyl
13868 me2py-ams2-chexo-aspibua
13869 imhs-amn2-oem-betapy
13870 piraz-m25thizman2-eoco-zdabs
13871 impy-pnymea-napo-bhsdab
13872 hythpym-mepazin-fo-betaet
13873 thpym-edian2-meo-bsdap
13874 moegua-m24thizman2-fo-aspibua
13875 hythpym-dis-men-bhsdab
13876 phhs-trias-chexo-aspibua
13877 piraz-mepipe-meo-betapy
13878 me2py-pipa-mes-zlys
13879 hythpym-m25thiz-napo-dfzdap
13880 am2py-pyma2-no1-bhsdab
13881 bhs-24oxman2-oem-zdab
13882 mam2py-pipa-no2-zdabs
13883 bim-mepipe-meo-zdab
13884 imhs-am3-sem-nbetapy
13885 dmam-din-4pho-betapy
13886 2py-am3-oem-nbetabnaphth
13887 amthiaz-trias-cno-aspbzla
13888 bimhs-edian2-5pho-aspbzla
13889 imhs-pazin-meo-psdab
13890 piraz-mepazin-meo-zdap
13891 bim-pazin-eoco-aspbzla
13892 thpym-dis-no2-psdab
13893 amim-m25thizman2-oem-zdabs
13894 bimhs-tridi-daco-bhsdab
13895 4pmhs-pnymea-oem-psdab
13896 me2py-diphmep-peo-bphabs
13897 imhs-amn2-mes-bsdap
13898 amim-pnymea-imo-betainyl
13899 deam-diaz-mmen-glyzdap
13900 imhs-propn-meo-zdabs
13901 impy-dis-oem-bsdap
13902 imhs-edian2-no2-bnsdap
13903 2py-thizn-napo-aspibua
13904 emnim-m24thiz-eoco-bsdap
13905 dhim-3diaz-aco-aspibua
13906 bhs-eta-oem-bnsdap
13907 bhs-pazin-no2-psdap
13908 amim-eta-meo-betadcph
13909 piraz-mepipe-meo-psdab
13910 bimhs-eta-hso-aspibua
13911 piraz-am3-sem-nbetameph
13912 emnim-amo2-no1-bphabs
13913 deam-pyma2-chexo-zdabs
13914 imhs-amn2-meo-psdab
13915 mam2py-dimen-emo-bsdap
13916 am2py-din-fo-psdap 13917 am4py-diphmem-meo-aspaba
13918 imhs-edian2-oem-bnsdap
13919 bim-dimephmep-napo-aval
13920 tolhs-ams2-emo-aspibua
13921 imhs-trias-men-betaet
13922 bim-pazin-daco-bsdap
13923 mam2py-m24thizman2-no1-zdabs
13924 dmam-ams3-no1-dfzdap
13925 tolhs-trias-chexo-betainyl
13926 phhs-thizo-cnmo-bnsdap
13927 edothpym-m24thizman2-oeta-bphabs
13928 imhs-pnymea-fo-glyzdap
13929 amim-trias-imo-bnsdap
13930 moegua-am3-oem-nbetapy
13931 imhs-pymea-men-bsdap
13932 piraz-eta-meteto-bphabs
13933 bim-eta-ocho-psdap
13934 emnim-amo2-daco-zdabs
13935 me2py-diphmem-ocho-aspbzla
13936 hythpym-butn-napo-glyzdap
13937 bim-pipmea-meo-osdap
13938 pyrhs-dis-men-betapy
13939 am2py-dimen-imo-csdap
13940 bim-edian2-no1-psdap
13941 2py-ann2-no2-psdap
13942 gua-trias-ocho-bnsdap
13943 gua-25oxman2-4amo-bhsdab
13944 me2py-dimephmep-emo-glyzdap
13945 bimhs-amn3-mommo-bnsdap
13946 phpip-m25thiz-4pho-betainyl
13947 piraz-mepipen2-fo-betadcph
13948 bhs-thizn-5pho-bnsdap
13949 imhs-pymea-cpeo-bsdap
13950 menim-dimephmep-eoco-aspbzla
13951 bim-eta-eoco-psdab
13952 me2py-dimen-pheo-betainyl
13953 mam2py-thizn-napo-zdabs
13954 hythpym-eta2s-eoco-zdabs
13955 bim-pazin-mes-psdap
13956 bimhs-m25thiman2-imo-oxal
13957 bhs-mepazin-5amo-bnsdap
13958 am2py-tridi-5pho-asppha
13959 bimhs-tetras-napo-zdab
13960 pyr-2pazin-eoco-zdabs
13961 prhs-amn2-mommo-betadcph
13962 thpym-amn2-eoco-zdab
13963 amim-pnymea-meo-betainyl
13964 bim-24thizman2-mes-betainyl
13965 bhs-mepipe-no2-bhsdap
13966 impy-25oxman2-5amo-glyzdap
13967 dhim-diphmem-5pho-ppsdap
13968 2py-pazin-5amo-aspbzla
13969 amim-trias-mmen-psdap
13970 bim-dis-meo-betainyl
13971 im-mea-meo-betadcph
13972 2py-mepipe-ocho-psdap
13973 nmor-25thizman2-napo-aspibua
13974 mam2py-pyma2-mommo-aspibua
13975 am2py-24thiz-imo-zdab
13976 bhs-din-oem-betainyl
13977 bimhs-thizn-no1-aspaba
13978 impy-24thizman2-5amo-bhsdab
13979 bhs-pazin-no2-bhsdap
13980 2py-am2-sem-npsdap
13981 phpip-dio-mes-csdap
13982 dhim-m25thiz-cpeo-zdap
13983 2py-ams2-napo-bphabs
13984 amim-mepazin-no1-zlys
13985 am-dio-emo-betapy
13986 bim-indan2-meo-asppha
13987 2py-dis-no2-osdap
13988 amim-mepipen2-no2-zdab
13989 am2py-amn2-napo-betadcph
13990 imhs-edian2-meo-bhsdap
13991 prhs-mepazin-oem-betaet
13992 bimhs-edia2-oem-nzdap
13993 mam2py-edia2-oem-nbeta34-dimeoph
13994 dmam-pentadi-cpro-aspibua
13995 bhs-amn2-eoco-zdab
13996 bim-edian2-no1-glupha
13997 pippy-pazin-ocho-ppsdap
13998 me-pipa-imo-betadcph
13999 mam2py-diphmem-no2-betaet
14000 chhs-thizn-oem-bhsdap
14001 4pmhs-mepipen2-ocho-asppha
14002 pyrhs-mepazin-meo-betainyl
14003 4pmhs-diphmep-4pho-psdap
14004 moegua-dimen-nmo-mezphe
14005 dpam-24thizman2-no2-glupha
14006 impy-m24thizman2-5pho-aspaba
14007 cl3pyme-amn2-mes-betaet
14008 bimhs-25oxman2-fo-psdab
14009 imhs-propn-emo-aspibua
14010 menim-edia2-sem-nbetameph
14011 impy-25oxman2-eoco-zdab
14012 hythpym-edian2-nmo-dfzdap
14013 bimhs-edian2-cno-bsdap
14014 bhs-eta-oem-psdap
14015 morhs-pnymea-nmo-bhsdab
14016 bhs-amn2-eoco-zdap
14017 dhim-mea-men-bphabs
14018 amthiaz-25thiman2-emo-betainyl
14019 phhs-mepazin-baeo-bphabs
14020 4pmhs-24thiz-emo-bhsdap
14021 phpip-amn3-mes-aspbzla
14022 fthpym-eta-eoco-dfzdap
14023 bim-pipa-imo-bnsdap
14024 me2py-thizn-imo-oxal
14025 amim-tridi-cnmo-psdapee
14026 2py-pazin-eoco-bhsdap
14027 4pmhs-pnymea-no1-bhsdab
14028 thpym-mepazin-mommo-bsdap
14029 bim-n2nme2n-oem-asppha
14030 bim-pazin-no2-betapy
14031 piraz-amn2-napo-zdapee
14032 am2py-pentadi-emo-aval
14033 gua-amn3-oem-dfzdap
14034 tolhs-m25thiz-emo-asppha
14035 chhs-mepazin-napo-mezphe
14036 pyrhs-24thiman2-pyo-zorn
14037 piraz-mepipen2-cpro-psdab
14038 dmthpym-pipmes-mommo-bnsdap
14039 thpym-edian2-5pho-psdap
14040 amim-dimephmep-ocho-zdap
14041 bimhs-m25thiz-5pho-betadcph
14042 amim-trias-pro-zdabs
14043 piraz-amn2-mes-dfzdap
14044 bhs-mepipe-no2-zorn
14045 bim-pazin-no2-zdab
14046 impy-thizn-peo-ppsdap
14047 amim-pazin-chexo-betadcph
14048 cl3pyme-tetradi-fo-betainyl
14049 bim-dis-chexo-betainyl
14050 pyrhs-mepazin-cno-betaet 14051 chhs-n24thiman-no2-csdap
14052 z-diphmep-5amo-aspbzla
14053 bim-amn2-5pho-zdap
14054 mam2py-dis-spho-betadcph
14055 bhs-indan2-no1-bphabs
14056 fthpym-pipmea-napo-csdap
14057 imhs-amn2-mommo-zdabs
14058 pippy-din-pro-zdab
14059 ec-edian2-men-glupha
14060 piraz-pyma2-4amo-zdap
14061 thpym-trias-mecpo-zdab
14062 pyraz-mepipe-ocho-tsdap
14063 bim-pazin-mes-zdap
14064 impy-dio-ocho-zorn
14065 thpym-pazin-no2-psdab
14066 imhs-edia2-oem-nzdap
14067 prhs-24thiz-5pho-glyzdap
14068 impy-trias-4pho-dfzdap
14069 z-diphmem-no1-mezphe
14070 pyrhs-amn3-5amo-betadcph
14071 cl3pyme-props-no2-betapy
14072 bhs-mepipe-5pho-psdap
14073 piraz-tridi-mes-glyzdap
14074 am2py-amn2-meo-aspbzla
14075 am2py-dimen-peo-aspibua
14076 chmhs-eta-paco-psdap
14077 dmam-24thiz-5amo-thizzdap
14078 hythpym-propa2s-4amo-glyzdap
14079 2pmhs-ams3-no1-bsdap
14080 bhs-pipmeo-ocho-oxal
14081 bim-din-eoco-betainyl
14082 2py-edian2-oem-bhsdap
14083 piraz-diphmep-eoco-dfzdap
14084 bimhs-pipmea-4pho-psdap
14085 pippy-amn2-men-tsdap
14086 bhs-24thiz-no2-mezphe
14087 thpym-amn2-meo-psdap
14088 mam2py-dimephmep-daco-glyzdap
14089 bimhs-dimephmep-pro-bsdap
14090 nmor-edian2-men-csdap
14091 bhs-amn2-meo-zdab
14092 morhs-mepipe-napo-zdap
14093 2py-pnymea-chexo-zdabs
14094 dhim-diphmem-ocho-asppha
14095 npip-n2o2n-ocho-bphabs
14096 impy-mepipe-emo-bsdap
14097 impy-eta-no2-bphabs
14098 cl3pyme-dis-pheo-bhsdab
14099 amthiaz-eta-paco-glyzdap
14100 2py-edian2-no1-betapy
14101 imhs-ams2-no2-bnsdap
14102 impy-pipa-fo-aspibua
14103 mam2py-pnymea-meo-asppha
14104 dpam-25oxman2-chexo-betainyl
14105 prhs-edian2-men-glupha
14106 am-din-imo-asppha
14107 mam2py-pipmea-paco-asppha
14108 morhs-mepazin-ocho-mezphe
14109 piraz-thizs-men-bhsdap
14110 imhs-m24thizman2-peo-bhsdap
14111 hythpym-edian2-fo-betainyl
14112 pippy-m24oxman2-no1-zdap
14113 tolhs-3pazin-aco-zdabs
14114 mam2py-mepipen2-ocho-df zdap
14115 thpym-m25thiman2-no1-aspibua
14116 mepip-25thizman2-oem-aspbzla
14117 dmthpym-amo2-hso-betapy
14118 me2py-am3diaz-men-zdabs
14119 impy-thizn-fo-thizzdap
14120 menim-eta2s-5amo-glupha
14121 bim-pazin-imo-betapy
14122 2py-2pazin-meo-betadcph
14123 amim-amo2-5amo-zlys
14124 dmbim-m24thizman2-peo-csdap
14125 z-pnymea-no1-zdap
14126 dhim-amn3-meo-aspibua
14127 mam2py-24thizman2-emo-dfzdap
14128 2py-n2nme2n-mes-zdap
14129 nmhs-24thiz-no2-zdap
14130 me2py-pentas-mes-aspibua
14131 pyr-ams2-eoco-psdap
14132 hythpym-25thiman2-chexo-aval
14133 mam2py-mepipe-4pho-psdap
14134 bhs-eta-no1-dfzdap
14135 mam2py-props-daco-zdab
14136 dhim-dis-men-psdab
14137 bim-eta-fo-aspbzla
14138 dmam-pyma2-fo-betapy
14139 piraz-m24thizman2-men-aspbzla
14140 am2py-dimen-men-bphabs
14141 2py-eta-oem-bhsdap
14142 phhs-am3-sem-nbetabnaphth
14143 thpym-edian2-ocho-zdap
14144 piraz-trias-men-zdabs
14145 amim-diphmem-eoco-psdapee
14146 2py-pymea-nmo-betapy
14147 me2py-dimen-cpro-betapy
14148 bhs-amn2-meo-bsdap
14149 am-n2o2n-pro-aspaba
14150 dhim-diphmep-hso-aspbzla
14151 menim-dimephmem-peo-bsdap
14152 thpym-25thizman2-mes-glyzdap
14153 thpym-3diaz-5amo-betadcph
14154 bimhs-ams2-meo-zdapee
14155 cl3pyme-pnymea-baeo-zdab
14156 2pmhs-dipch-mecpo-mezphe
14157 imhs-amn2-4amo-osdap
14158 bz-25thiman2-pyo-asppha
14159 bim-mepipe-ocho-psdap
14160 am2py-amn3-cpeo-aspbzla
14161 dmam-thizs-no1-zorn
14162 prhs-diphmem-cno-bhsdab
14163 bhs-amn2-no2-zdab
14164 mam2py-amn3-5pho-betainyl
14165 n2py-diphmem-cnmo-psdap
14166 bzl-mepipe2-oem-nbetabnaphth
14167 mam2py-pazi2n-fo-zdab
14168 bzl-25oxman2-no2-psdab
14169 n2py-ams2-mes-aspibua
14170 dmam-amn2-oeto-asppha
14171 amim-mepipe-mmen-tsdap
14172 am2py-pnymea-pro-df
14173 bimhs-pipa-emo-glubzla
14174 chmhs-dimephmep-men-dfzdap
14175 impy-thizo-pyo-aspbzla
14176 dhim-mepazin-chexo-oxal
14177 bimhs-m24thizman2-no2-betainyl
14178 amim-dis-mes-zdap
14179 imhs-pipa-5amo-bnsdap
14180 emnim-diphmep-napo-zdab
14181 thpym-edian2-no2-bhsdap
14182 mam2py-amo2-meo-bsdap
14183 imhs-edian2-mes-zdap
14184 thpym-24thizman2-fo-betapy 14185 pippy-mepazin-no1-bnsdap
14186 am-3diaz-emo-betapy
14187 piraz-mepazin-fo-bnsdap
14188 mam2py-thizn-no1-zdabs
14189 pyr-thizo-emo-bhsdap
14190 2py-pazin-no1-psdab
14191 moegua-mepazin-meo-ppsdap
14192 mepip-tridi-peo-mezphe
14193 bhs-eta-mes-psdap
14194 chmhs-pazin-mes-aspaba
14195 pyraz-mepipen2-fo-zdabs
14196 imhs-edian2-ocho-bnsdap
14197 pyrhs-mepipe2-sem-nbetameph
14198 edothpym-dimephmep-no2-dfzdap
14199 deam-amo2-no2-csdap
14200 mam2py-m25thiz-5pho-bhsdab
14201 bim-trias-fo-mezphe
14202 chhs-diaz-mes-psdap
14203 deam-dimen-men-psdab
14204 imhs-edian2-meo-bnsdap
14205 bimhs-tridi-hso-bhsdap
14206 hythpym-propn-eoco-aspbzla
14207 tolhs-am2-oem-nbetabnaphth
14208 amim-m24thizman2-no2-betainyl
14209 amthiaz-dis-oem-asppha
14210 hythpym-pipa-4amo-bnsdap
14211 bhs-amn3-no1-betadcph
14212 moegua-diphmep-emo-zdap
14213 thpym-mepipe2-oem-nbetameph
14214 npip-edia2-oem-npsdap
14215 tolhs-pyma2-5pho-zdap
14216 impy-ms-mes-aspbzla
14217 piraz-tridi-oem-bphabs
14218 thpym-tetradi-napo-dfzdap
14219 bhs-trias-oeto-aval
14220 bimhs-edian2-no1-zdab
14221 thpym-hexadi-ocho-zdabs
14222 bim-amn2-5pho-zdab
14223 bimhs-mepipe-eoco-glubzla
14224 nim-dis-emo-dfzdap
14225 dmbim-24oxman2-emo-zdap
14226 pyr-pyma2-4amo-mezphe
14227 2py-eta-mes-psdab
14228 morhs-amo2-eoco-zdap
14229 bimhs-din-ocho-dfzdap
14230 bim-edian2-eoco-psdab
14231 edothpym-mepipen2-meo-bhsdap
14232 bhs-m25thizman2-aco-psdap
14233 imhs-ams3-baeo-csdap
14234 piraz-amo2-men-csdap
14235 tolhs-mepipen2-men-psdab
14236 impy-m24thizman2-meo-betainyl
14237 edothpym-edian2-hso-mezphe
14238 am2py-n24thiman-5pho-bhsdap
14239 me2py-dimen-mes-bhsdab
14240 dhim-24thiman-no1-aspbzla
14241 bhs-25oxman2-pheo-glupha
14242 imhs-dimephmem-emo-betadcph
14243 piraz-24thiz-5pho-bnsdap
14244 2py-mepipe-emo-aspbzla
14245 piraz-24thiz-nmo-bhsdab
14246 tolhs-tridi-no1-glyzdap
14247 chhs-amn3-men-betainyl
14248 chhs-n2o2n-eoco-bhsdap
14249 bimhs-24thiz-imo-bphabs
14250 2py-dimephmep-ocho-psda
14251 pyrhs-pipmeo-men-bhsdab
14252 pippy-pazin-no1-betaet
14253 piraz-amn2-imo-bphabs
14254 prhs-hexadi-cpeo-betapy
14255 pippy-dis-5amo-thizzdap
14256 mam2py-mepipe2-sem-nzdab
14257 pyraz-dimephmep-fo-zdap
14258 me-25thizman2-emo-asppha
14259 dhim-dis-no2-aspbzla
14260 bimhs-butn-chexo-zdap
14261 me2py-dimephmep-no2-glyzdap
14262 thpym-din-monmmo-betadcph
14263 bhs-dimen-men-csdap
14264 thpym-mepipe-5amo-bnsdap
14265 gua-eta2s-fo-aspibua
14266 2py-pipmea-oem-zdabs
14267 amim-amn3-oeto-aspibua
14268 mam2py-25oxman2-no2-glyzdap
14269 bimhs-thizs-aco-psdap
14270 deam-props-ocho-zdab
14271 impy-diphmep-eoco-bsdap
14272 n2py-dimephmem-ocho-zdab
14273 am2py-eta-meteto-zdabs
14274 bim-edian2-oem-bsdap
14275 amim-m24thizman2-baeo-aspbzla
14276 pippy-tridi-cnmo-bnsdap
14277 npip-dimen-paco-glyzdap
14278 thpym-pnymea-emo-psdapee
14279 n2py-dis-no2-asppha
14280 bhs-25oxman2-emo-mezphe
14281 am2py-ams2-cpro-glyzdap
14282 dmam-diphmem-emo-csdap
14283 piraz-pymea-fo-zdap
14284 dhim-dimen-ocho-betaet
14285 dhim-amn2-chexo-zdap
14286 pippy-25thiman2-pyo-glyzdap
14287 bhs-dimephmep-imo-tsdap
14288 moegua-m25oxman2-baeo-dfzdap
14289 nmhs-dis-mes-zdabs
14290 me2py-thizn-men-betainyl
14291 bhs-amn2-no2-bsdap
14292 ppy-tridi-no1-csdap
14293 bim-pipa-oem-psdap
14294 im-dio-5amo-mezphe
14295 amim-props-men-mezphe
14296 am2py-din-no1-asppha
14297 dhim-pazin-no2-psdapee
14298 fthpym-pipa-no2-betaet
14299 bhs-edian2-no1-psdap
14300 edothpym-pentadi-meo-betadcph
14301 cl3pyme-propn-meo-glyzdap
14302 n2py-pipmea-no1-zdabs
14303 bhs-propa2s-chexo-betapy
14304 bim-amn2-meo-bsdap
14305 hythpym-din-men-bhsdap
14306 gua-thizn-oem-betapy
14307 pippy-pymea-no2-psdap
14308 2py-din-5amo-zdap
14309 am2py-ams2-no1-psdab
14310 imhs-pymea-napo-bnsdap
14311 impy-edian2-cpro-asppha
14312 am2py-m25thiz-no2-dfzdap
14313 piraz-24thiz-mecpo-psdap
14314 bim-diphmem-paco-bsdap
14315 piraz-edian2-no1-csdap
14316 pippy-diphmem-no2-psdab
14317 me-mepipe-men-zdab
14318 mam2py-amo2-mes-psdab 14319 imhs-trias-napo-aspibua
14320 thpym-amn2-no2-psdap
14321 nmhs-24thiz-daco-bnsdap
14322 impy-dimephmem-mommo-bsdap
14323 imhs-amo2-no1-bphabs
14324 me-tridi-peo-asppha
14325 dmam-mepipe-meteto-glyzdap
14326 nmor-am3diaz-no2-betapy
14327 am2py-dimephmep-oem-mezphe
14328 thpym-din-mes-betapy
14329 piraz-24thiz-nmo-psdab
14330 bhs-thizs-emo-csdap
14331 pippy-pnymea-baeo-csdap
14332 impy-pipmea-chexo-psdap
14333 amim-amn2-eoco-zdap
14334 thpym-mepipe-meo-psdap
14335 pyraz-amn3-no1-psdab
14336 bhs-mepipe-mes-zdab
14337 impy-ms-meo-dfzdap
14338 4pmhs-diphmem-mmen-aspbzla
14339 thpym-edia2-sem-nbeta34-dimeoph
14340 bim-mepipe-meto-mezphe
14341 bim-eta-5pho-zdap
14342 amim-mepipen2-meo-csdap
14343 ec-dimephmem-men-zdapee
14344 prhs-amo2-oem-bhsdap
14345 deam-thizs-ocho-bsdap
14346 piraz-pentas-fo-csdap
14347 me2py-ms-mmen-zdabs
14348 piraz-diphmep-no1-glubzla
14349 bhs-amn3-5pho-bhsdap
14350 amim-mepipen2-no2-glyzdap
14351 thpym-mepipe-meo-betapy
14352 ibhs-tridi-mes-betainyl
14353 mepip-mepipen2-5pho-asppha
14354 mam2py-pipa-imo-betapy
14355 2py-amn2-oem-zdap
14356 dhim-pazi2n-eoco-zdabs
14357 hythpym-amn3-fo-aspibua
14358 pippy-pymea-men-mezphe
14359 gua-mepazin-mecpo-zdabs
14360 imhs-dimephmem-no2-aspbzla
14361 hythpym-25oxman2-imo-aspbzla
14362 impy-thizo-oem-bnsdap
14363 me2py-trias-fo-asppha
14364 hythpym-mepipe-imo-bphabs
14365 dhim-diphmem-oem-bnsdap
14366 impy-diphmep-daco-aspbzla
14367 2py-amn2-mes-bsdap
14368 imhs-mepipe2-oem-nzdap
14369 morhs-25oxman2-napo-bsdap
14370 thpym-edian2-no2-bsdap
14371 piraz-mepipen2-fo-ppsdap
14372 imhs-pazin-no2-bhsdap
14374 2py-amn2-mes-psdap
14375 2pmhs-25thiz-eoco-csdap
14376 me-edian2-emo-bsdap
14377 thpym-din-pheo-bphabs
14378 bimhs-trias-meo-zdabs
14379 dpam-amo2-fo-zdap
14380 pippy-am3diaz-5pho-mezphe
14381 bimhs-diphmep-mes-betapy
14382 n2py-m25thiz-napo-mezphe
14383 hythpym-hexas-mes-asppha
14384 pippy-amn2-nmo-zdap
14385 amim-diphmem-cnmo-csdap
14386 bhs-pipa-5amo-betainyl
14387 chmhs-dimen-4amo-thizzdap
14388 dhim-amo2-5amo-bhsdab
14389 dmthpym-amo2-chexo-bphabs
14390 phhs-props-oem-csdap
14391 bhs-pazin-eoco-betapy
14392 bim-pazin-mes-zdab
14393 bim-eta-no1-bhsdap
14394 hythpym-mepipen2-men-aspbzla
14395 imhs-dimen-imo-asppha
14396 moegua-m25thiz-oem-psdab
14397 me2py-pyma2-pyo-csdap
14398 bim-pnymea-pheo-osdap
14399 impy-m25thiz-imo-psdap
14400 chhs-m25thiz-mecpo-bphabs
14401 am2py-pipmea-chexo-glyzdap
14402 bhs-dis-chexo-glyzdap
14403 am4py-dis-aco-betadcph
14404 mam2py-eta-emo-betadcph
14405 am2py-indan2-hso-betainyl
14406 pippy-pymea-eoco-zdabs
14407 imhs-eta-eoco-bsdap
14408 cl3pyme-thizs-napo-psdap
14409 impy-pipa-fo-bhsdab
14410 pippy-24thiman2-emo-dfzdap
14411 am2py-pazin-5amo-asppha
14412 imhs-edia2-sem-nbetameph
14413 nmhs-m24thizman2-men-bsdap
14414 amim-mea-cno-betapy
14415 dmbim-am2-oem-nzdap
14416 mam2py-dimen-chexo-bsdap
14417 thpym-edian2-ocho-betapy
14418 impy-diphmem-nmo-dfzdap
14419 moegua-thizs-chexo-zdab
14420 impy-m25thiz-chexo-zorn
14421 me2py-diphmep-no1-bhsdap
14422 am-tetradi-chexo-zdabs
14423 impy-mepazin-men-asppha
14424 bim-25thiz-oem-bohabs
14373 bimhs-dio-fo-betadcph
14425 ec-dimephmem-imo-aspibua
14426 bim-pentadi-5amo-glupha
14427 dmam-pipmea-mes-mezphe
14428 edothpym-dio-5pho-aspbzla
14429 pippy-pyma2-napo-psdap
14430 am2py-din-pro-aspibua
14431 piraz-tridi-ocho-bphabs
14432 ibhs-diaz-eoco-bnsdap
14433 dhim-pymea-emo-zdab
14434 thpym-amn2-meo-bsdap
14435 impy-props-chexo-glubzla
14436 pyr-diphmep-napo-mezphe
14437 phhs-m25thizman2-men-mezphe
14438 2py-pazin-meo-zdap
14439 4pmhs-ms-mes-zdap
14440 2py-amn2-ocho-zdab
14441 thpym-mepipe-mes-bsdap
14442 dhim-pentadi-paco-zdab
14443 am2py-mepazin-paco-csdap
14444 2py-eta-5pho-bhsdap
14445 me2py-24thiz-oem-aval
14446 amim-diphmem-5amo-aspibua
14447 pyr-pazin-men-psdap
14448 me2py-m24thizman2-pheo-bhsdap
14449 2py-n24thiman-mes-psdap
14450 emnim-2pazin-no1-psdap
14451 am2py-pentas-chexo-zorn
14452 imhs-din-meto-bhsdap 14453 impy-thizs-men-zdabs
14454 me2py-tetradi-5pho-mezphe
14455 prhs-props-aco-bphabs
14456 bhs-edian2-mes-psdab
14457 mam2py-amn3-no2-glyzdap
14458 cl3pyme-din-men-psdapee
14459 thpym-am3-oem-nbeta34dimeoph
14460 thpym-m24thizman2-5amo-bsdap
14461 pippy-24thiman2-mecpo-psdab
14462 bhs-thizn-nmo-betainyl
14463 bimhs-diphmep-meo-glyzdap
14464 bhs-eta-ocho-zdap
14465 phpip-25thiz-chexo-psdab
14466 tolhs-amn3-napo-ppsdap
14467 bimhs-thizn-meo-glyzdap
14468 hythpym-mea2s-imo-zlys
14469 pippy-pipmea-meo-betainyl
14470 bim-amn2-mommo-psdap
14471 am2py-pipmea-5amo-glupha
14472 bim-mepipe-no1-bnsdap
14473 amim-pentas-men-glupha
14474 dhim-am3-oem-nbeta34dimeoph
14475 am4py-mepazin-no1-zdabs
14476 imhs-eta-ocho-zdab
14477 bhs-diphmem-5amo-glyzdap
14478 dmthpym-amn2-no2-zdab
14479 pippy-25thiz-imo-bnsdap
14480 dhim-din-napo-betapy
14481 piraz-amn3-no2-csdap
14482 prhs-edian2-men-thizzdap
14483 amthiaz-eta-paco-dfzdap
14484 ppy-25oxman2-5amo-aspibua
14485 bhs-pazin-5pho-zdap
14486 impy-m25thizman2-ocho-zdabs
14487 impy-pnymea-fo-aval
14488 nmhs-pentas-oem-glyzdap
14489 4pmhs-mepipen2-chexo-aspibua
14490 thpym-25thiz-chexo-psdap
14491 dmthpym-din-cno-psdap
14492 bhs-pazin-5pho-betapy
14493 4pmhs-dimen-5amo-bhsdap
14494 me2py-tetradi-no2-mezphe
14495 chhs-dimephmep-5amo-aspbzla
14496 z-am2-sem-nzdap
14497 thpym-amn2-oem-bnsdap
14498 amim-m24oxman2-fo-zdab
14499 morhs-3pazin-oem-zdabs
14500 mam2py-24oxman2-daco-bhsdab
14501 menim-pipmea-fo-zdap
14502 impy-pnymea-fo-zlys
14503 bim-diphmem-imo-mezphe
14504 2py-m25thiman2-chexo-psdab
14505 piraz-dis-oem-asppha
14506 moegua-dio-5amo-zdapee
14507 pippy-pyma2-mecpo-bphabs
14508 am-24thiz-emo-csdap
14509 am2py-din-peo-csdap
14510 imhs-eta-mes-bnsdap
14511 am-indan2-no1-bphabs
14512 mam2py-amo2-mecpo-betadcph
14513 moegua-edian2-emo-betapy
14514 2py-mepipe-mes-bnsdap
14515 im-dimephmep-nmo-dfzdap
14516 bimhs-24thizman2-napo-csdap
14517 amim-diphmep-men-zdab
14518 bim-n24thiman-paco-asppha
14519 am2py-pazin-5pho-bnsdap
14520 am2py-din-meo-csdap
14521 moegua-pyma2-no1-mezphe
14522 bhs-mepazin-mes-psdap
14523 bim-ams2-chexo-betainyl
14524 z-m24thizman2-fo-bsdap
14525 am2py-pipmea-napo-zdabs
14526 2py-24thiman2-emo-aspbzla
14527 bim-am3-sem-nzdap
14528 thpym-pazin-ocho-zdab
14529 bhs-24thizman2-meo-zdab
14530 impy-mepipe-5amo-bnsdap
14531 menim-din-chexo-bnsdap
14532 me2py-diaz-oem-zdab
14533 mam2py-propa2s-eoco-aspbzla
14534 mam2py-dimephmep-baeo-aspibua
14535 pippy-amo2-emo-bphabs
14536 impy-24thiman2-ocho-aspaba
14537 thpym-mepazin-emo-zdapee
14538 2py-trias-paco-bhsdap
14539 bim-pyma2-meo-betapy
14540 am2py-amn3-fo-bhsdap
14541 bim-hexas-oem-zdap
14542 phpip-trias-no1-betainyl
14543 edothpym-amn3-men-zdapee
14544 me2py-tetradi-cpro-aval
14545 piraz-tridi-eoco-betapy
14546 bim-tetradi-paco-psdab
14547 mepip-24thizman2-mmen-bhsdap
14548 phpip-dimephmem-cpeo-osdap
14549 dhim-dimen-fo-asppha
14550 hythpym-diphmem-fo-aspibua
14551 mam2py-trias-pyo-glupha
14552 dmam-pyma2-5amo-bhsdab
14553 impy-mea2s-no2-bnsdap
14554 hythpym-dis-mes-csdap
14555 ibhs-pazin-no2-zdab
14556 am2py-trias-emo-betainyl
14557 am2py-trias-no2-bsdap
14558 amim-tetradi-oeto-betapy
14559 am2py-25oxman2-men-mezphe
14560 impy-pazi2n-5pho-bnsdap
14561 hythpym-ams2-no1-bsdap
14562 pyr-tetradi-4amo-csdap
14563 bhs-pazin-ocho-psdap
14564 mam2py-din-chexo-glyzdap
14565 mepip-amn2-no2-zdabs
14566 fthpym-dimen-pheo-dfzdap
14567 mam2py-edian2-eoco-asppha
14568 bhs-25oxman2-ocho-glyzdap
14569 4pmhs-3diaz-5amo-csdap
14570 bim-pazin-mes-bhsdap
14571 phhs-din-no1-betadcph
14572 impy-24thizman2-oem-bhsdab
14573 npip-edian2-ocho-zdap
14574 thpym-pazin-5pho-psdab
14575 pippy-tetradi-imo-glupha
14576 imhs-pnymea-no1-glyzdap
14577 impy-pymea-5pho-psdab
14578 pippy-trias-no2-betapy
14579 phhs-edian2-oem-aspbzla
14580 bim-amo3-meo-zdab
14581 2py-pnymea-5amo-bsdap
14582 bim-mepazin-imo-zdab
14583 imhs-amn2-no2-bnsdap
14584 bimhs-mepazin-no2-betadcph
14585 thpym-amn2-eoco-bsdap
14586 amthiaz-m25thiz-nmo-csdap 14587 impy-tetradi-mes-bphabs
14588 dhim-am3-sem-nbetameph
14589 bim-mepipe-mes-psdap
14590 thpym-eta-5amo-betainyl
14591 2py-amn2-meo-zdab
14592 menim-diphmep-no2-zdab
14593 thpym-dis-oem-betainyl
14594 imhs-m24thiman2-fo-asppha
14595 phpip-25thizman2-no2-bsdap
14596 thpym-dimen-no1-bnsdap
14597 cl3pyme-amn3-men-bphabs
14598 bimhs-tridi-ocho-betapy
14599 hythpym-thizo-napo-psdab
14600 hythpym-mepazin-aco-oxal
14601 chhs-mepazin-napo-zdap
14602 2py-amn2-eoco-zdab
14603 impy-dis-napo-aspbzla
14604 bim-m25thiz-napo-betainyl
14605 npip-25oxman2-imo-zdap
14606 2py-amn2-mes-zdap
14607 bhs-mea-no2-psdab
14608 dhim-amn3-pyo-zdap
14609 4pmhs-dimen-peo-bphabs
14610 amim-pyma2-ocho-osdap
14611 ec-tridi-ocho-bphabs
14612 4pmhs-mepipen2-eoco-csdap
14613 thpym-din-mommo-zdab
14614 bz-24thiz-oem-aspbzla
14615 bhs-tetras-men-betadcph
14616 bim-pipmea-imo-aspibua
14617 bim-amn2-mes-bnsdap
14618 impy-amn2-meo-bphabs
14619 im-24thiz-mes-zdab
14620 2py-eta-eoco-bnsdap
14621 mam2py-tridi-chexo-mezphe
14622 imhs-mepipe-no1-zdab
14623 piraz-pyma2-fo-csdap
14624 bim-tridi-no1-zdabs
14625 2py-edian2-no1-zdap
14626 impy-25thizman2-pro-dfzdap
14627 dmam-thizn-ocho-betainyl
14628 bhs-dimephmem-chexo-asppha
14629 impy-thizo-oeto-dfzdap
14630 mam2py-thizo-no2-glyzdap
14631 bim-diphmem-mommo-bsdap
14632 dhim-dis-eoco-aspbzla
14633 impy-pyma2-5amo-dfzdap
14634 imhs-24thizman2-fo-bhsdap
14635 piraz-3diaz-no2-aspbzla
14636 imhs-mepipe-mes-zdab
14637 piraz-am2-sem-nzdab
14638 am2py-dimen-chexo-betainyl
14639 dhim-mepipe-eoco-bhsdab
14640 impy-dimephmep-no1-osdap
14641 bim-m25thiz-fo-zdapee bnsdap
14642 bhs-dis-emo-glyzdap
14643 imhs-mepipe-no2-psdab
14644 am4py-ams2-no2-aspibua
14645 bim-pentadi-fo-bphabs
14646 dhim-mepazin-men-bnsdap
14647 piraz-mepipe2-sem-nbetab naphth
14648 mam2py-mepipe-no1-betainyl
14649 amthiaz-m24thiman2-mes-zdabs
14650 mam2py-dimephmep-cno-aval
14651 4pmhs-dimephmep-mecpo-bhsdab
14652 gua-m24thiz-fo-zdab
14653 amim-amn2-ocho-glyzdap
14654 bhs-pazin-meo-bsdap
14655 am4py-dimen-meteto-betainyl
14656 bhs-edian2-ocho-bhsdap
14657 am2py-25oxman2-4pho-bhsdap
14658 bhs-25oxman2-baeo-zlys
14659 binhs-thizn-men-bsdap
14660 pyrhs-dimen-5pho-zdap
14661 nmor-am3diaz-emo-psdab
14662 am2py-diphmem-emo-zlys
14663 impy-pnymea-imo-oxal
14664 dhim-amo2-5pho-csdap
14665 dmbim-pnymea-5pho-bhsdab
14666 imhs-ams2-chexo-csdap
14667 dmthpym-ams2-fo-bhsdap
14668 bzl-25oxman2-oem-zdap
14669 impy-pymea-chexo-glupha
14670 bzl-amo2-mes-aspbzla
14671 ec-eta-cpeo-mezphe bhsdap
14672 moegua-dimephmem-fo-zlys
14673 bimhs-diphmep-meo-dfzdap
14674 ppy-24thiz-baeo-dfzdap
14675 imhs-pymea-4amo-aspbzla
14676 thpym-tetradi-meo-psdab
14677 deam-pnymea-cnmo-zdab
14678 dmbim-amo2-men-bsdap
14679 2py-m25thiz-mes-aspbzla
14680 am2py-din-ocho-psdap
14681 pippy-thizn-napo-betapy
14683 imhs-dich-ocho-bphabs
14684 imhs-dimen-5pho-aspibua
14685 bim-edian2-ocho-betapy
14686 thpym-amn2-oem-zdapee
14687 bhs-hexas-eoco-psdap
14688 pippy-trias-chexo-aval
14689 mam2py-pazi2n-ocho-aspbzla
14690 bimhs-amn2-cno-betadcph
14691 dmbim-m24thizman2-eoco-bnsdap
14692 imhs-amn2-mes-bnsdap
14693 2py-thizo-mommo-bhsdab
14694 bhs-pazin-no1-zdab
14695 am-m24thizman2-ocho-osdap
14696 4pmhs-edian2-mmen-psdab
14697 dpam-thizs-5pho-aval
14698 thpym-pipa-nmo-asppha
14699 n2py-pentas-eoco-psdab
14700 npip-mepipe-meo-mezphe
14701 imhs-dimephmep-cno-csdap
14702 chmhs-pyma2-cno-bnsdap
14703 cl3pyme-pnymea-eoco-bphabs
14704 thpym-edian2-no2-bhsdap
14705 thpym-mepipe-no2-zdab
14706 2py-amn2-ocho-bnsdap
14707 nim-pymea-emo-bnsdap
14708 mam2py-pymea-emo-aspbzla
14709 tolhs-propn-no1-psdab
14710 phhs-tridi-eoco-glyzdap
14711 thpym-edian2-ocho-psdap
14712 nim-pipa-chexo-glyzdap
14713 mam2py-mepipe-mommo-psdab
14714 mam2py-edian2-emo-zdabs
14715 thpym-edian2-eoco-psdap
14716 fthpym-butn-peo-bphabs
14717 bimhs-edian2-5pho-aspbzla
14718 ibhs-edian2-meo-mezphe
14719 imhs-dimephmem-fo-glupha
14720 dmbim-butn-chexo-bhsdab
14721 amthiaz-m25thizman2-5amo-bhsdap 14722 ec-din-mecpo-bhsdab
14723 me-hexas-4pho-bphabs
14724 2py-ams3-meo-psdapee
14725 dhim-tetradi-5pho-betadcph
14726 impy-eta-5amo-bsdap
14727 thpym-edian2-mes-zdap
14728 bhs-mepipen2-no2-aspbzla
14729 2py-eta-eoco-psdap
14730 am2py-amo2-napo-bhsdab
14731 thpym-m25thiman2-chexo-bsdap
14732 bim-menazin-ocho-bhsdab
14733 amim-pipa-no2-osdap
14734 me2py-dipch-hso-bhsdap
14735 fthpym-amn2-no2-bhsdap
14736 amim-tetras-5amo-dfzdap
14737 bz-amo3-meo-mezphe
14738 bimhs-dis-meo-bhsdap
14739 4pmhs-dimephmep-chexo-betapy
14740 thpym-tetradi-cno-aspbzla
14741 thpym-edia2-oem-nzdab
14742 bz-24thiz-mes-betapy
14743 me2py-edia2-oem-nbetameph
14744 emnim-pyma2-no2-oxal
14745 me2py-thizs-4amo-aspbzla
14746 dhim-pipmes-eoco-zdap
14747 me2py-am3-sem-nbetapy csdap
14748 amim-24oxman2-no2-aspbzla
14749 am2py-am2-oem-nzdab
14750 bhs-pipa-no2-csdap
14751 pippy-ams2-emo-aspbzla
14752 pippy-pymea-chexo-zdap
14753 me-pyma2-cpeo-betainyl
14754 mam2py-amo2-mes-mezphe
14755 bimhs-mepipen2-meo-csdap
14756 bim-eta-meo-bsdap
14757 prhs-25oxman2-no1-bhsdab
14758 mam2py-25thiz-mmen-glyzdap
14759 hythpym-dimephmep-oem-bsdap
14760 2pmhs-pazin-meo-bhsdab
14761 mam2py-24thiz-no1-betadcph
14762 thpym-eta-no2-zdab
14763 2py-pipa-meteto-aspibua
14764 imhs-diphmep-men-betapy
14765 impy-pazin-cpro-bhsdap
14766 thpym-eta-no1-psdap
14767 dpam-amn3-pro-mezphe
14768 am2py-eta-ocho-psdab
14769 pippy-trias-meo-aspbzla
14770 imhs-pipmea-oem-bsdap
14771 hythpym-pazin-pheo-oxal
14772 dmthpym-m25oxman2-5pho-psdap
14773 bhs-amn2-no1-betapy
14774 imhs-tetradi-men-csdap
14775 bz-edian2-mes-zdab
14776 pippy-pipmea-mecpo-zdabs
14777 n2py-dimephmep-fo-betapy
14778 dmbim-25oxman2-5pho-betaet
14779 4pmhs-thizn-meo-betaet
14780 thpym-24thiz-no2-mezphe
14781 bhs-tridi-fo-zdap
14782 emnim-tetradi-chexo-aspibua
14783 thpym-24thizman2-meteto-csdap
14784 bim-eta-oem-psdab
14785 amim-m25thiz-5pho-aspbzla
14786 2py-edian2-no2-psdab
14787 bhs-dimephmem-napo-bhsdab
14788 nmhs-25thiman2-5pho-bnsdap
14789 2py-amn2-meo-bnsdap
14790 imhs-amn2-no2-psdab
14791 thpym-mepipe-eoco-bhsdap
14792 dhim-mepazin-cno-bnsdap
14793 z-diphmep-cpeo-glyzdap
14794 amim-pazin-mes-bhsdap
14795 thpym-diphmem-baeo-zdab
14796 pippy-hexas-eoco-asppha
14797 impy-m24thizman2-meteto-csdap
14798 am2py-m24thizman2-fo-csdap
14799 mepip-dis-no1-aspbzla
14800 moegua-pymea-imo-zdab
14801 2py-mepipe-5pho-bhsdap
14802 dhim-tridi-mes-csdap
14803 pippy-amn2-emo-csdap
14804 2py-mepipe-no1-zdab
14805 am2py-25oxman2-aco-bphabs
14806 imhs-pazin-ocho-psdap
14807 amim-24thizman2-fo-bnsdap
14808 dhim-dimephmep-fo-aspbzla
14809 piraz-ams2-5pho-psdapee
14810 dhim-dimephmem-imo-asppha
14811 pippy-dimephmem-oem-bphabs
14812 edothpym-mepipe-fo-zlys
14813 amim-mepazin-emo-oxal
14814 2pmhs-ams2-chexo-aspibua
14815 z-m24thizman2-napo-psdap
14816 bhs-amn2-chexo-psdab
14817 bimhs-24thiz-5amo-betainyl
14818 menim-din-ocho-bhsdap
14819 bimhs-am2-sem-nbetapy
14820 bimhs-24thiz-oem-mezphe
14821 bim-eta-no2-betapy
14822 pyraz-pentas-men-bnsdap
14823 dhim-thizn-imo-dfzdap
14824 amthiaz-pymea-mes-bphabs
14825 amim-tetradi-fo-aspbzla
14826 imhs-am2-sem-nbetameph
14827 thpym-2pazin-meteto-asppha
14828 pippy-24thizman2-napo-bhsdap
14829 pyrhs-ams2-5amo-zdapee
14830 mam2py-am3-sem-nzdap
14831 z-mepazin-napo-aspbzla
14832 amim-amo3-fo-ppsdap
14833 2py-pazin-no1-psdap
14834 2py-dimen-5amo-psdap
14835 mam2py-thizn-meo-bnsdap
14836 2py-mepipen2-eoco-aval
14837 dhim-mepipe-mes-asppha
14838 emnim-tridi-imo-mezphe
14839 mepip-diphmep-mes-mezphe
14840 am2py-thizn-mes-glubzla
14841 4pmhs-dio-mes-psdap
14842 dhim-24thiz-meto-betainyl
14843 hythpym-pazin-4pho-betapy
14844 thpym-m24thizman2-eoco-oxal
14845 pyraz-dimephmep-oem-bphabs
14846 me2py-dimen-no1-betainyl
14847 hythpym-m25thizman2-napo-betainyl
14848 mam2py-pymea-cno-mezphe
14849 piraz-tridi-fo-csdap
14850 bim-pipmea-men-aspibua
14851 bim-amn2-mes-psdab
14852 bim-eta-meo-psdap
14853 hythpym-25thiman2-4pho-mezphe
14854 2py-eta-meo-psdab
14855 am4py-thizo-no2-zorn 14856 thpym-mepipe-meo-betainyl
14857 amim-pipa-5pho-bsdap
14858 bim-mepipe-5pho-zdab
14859 bim-pyma2-men-mezphe
14860 mepip-24thizman2-aco-dfzdap
14861 thpym-ams3-no1-dfzdap
14862 2pmhs-25oxman2-napo-bhsdab
14863 hythpym-dimephmem-imo-zdab
14864 piraz-24thizman2-meto-betapy
14865 pippy-diphmep-eoco-glyzdap
14866 pyraz-tridi-mecpo-mezphe
14867 amim-dis-5amo-thizzdap
14868 emnim-tetradi-pyo-bhsdab
14869 piraz-mepipe-fo-zdabs
14870 amim-pipa-cno-csdap
14871 me2py-ams2-cno-betapy
14872 ec-tetradi-5amo-zdap
14873 gua-amo3-no1-bnsdap
14874 bimhs-mea-emo-glyzdap
14875 pippy-hexadi-imo-betainyl
14876 mam2py-tetradi-eoco-dfzdap
14877 emnim-hexas-4pho-bhsdab
14878 fthpym-din-4amo-bhsdap
14879 2pmhs-dimephmep-meteto-aspbzla
14880 mam2py-pipmea-daco-betainyl
14881 me2py-amo2-ocho-glyzdap
14882 bim-amn2-mes-psdap betadcph
14883 mam2py-amo2-napo-betadcph
14884 thpym-mepipe-meo-bnsdap
14885 bhs-amo2-men-psdab
14886 npip-eta-napo-betainyl
14887 thpym-tridi-napo-ibsdap
14888 nmhs-trias-chexo-bhsdab
14889 phhs-24thizman2-napo-zdab
14890 me2py-dimen-chexo-bphabs
14891 phpip-24thiz-mecpo-asppha
14892 menim-edia2-sem-npsdap
14893 dhim-amo2-men-aspibua
14894 2py-mepipe-ocho-bsdap
14895 mam2py-pymea-meo-bhsdab
14896 thpym-eta-eoco-bsdap
14897 mam2py-tridi-emo-bhsdap
14898 bhs-amn2-no2-zdap
14899 bimhs-pyma2-cpro-psdab
14900 mam2py-dis-meteto-asppha
14901 prhs-mepazin-napo-psdap
14902 nim-thizn-chexo-bphabs
14903 me-hexas-chexo-bsdap
14904 thpym-dimephmep-no1-thizzdap
14905 bhs-din-imo-dfzdap
14906 piraz-amn2-eoco-betaet
14907 bim-m24oxman2-cpro-zdap
14908 2py-eta-meo-bnsdap
14909 me2py-tridi-chexo-asppha
14910 me2py-25thizman2-imo-zdabs
14911 npip-m24thiman2-men-psdap
14912 hythpym-amn3-peo-dfzdap
14913 mepip-m24thizman2-napo-asppha
14914 imhs-ams2-ocho-csdap
14915 gua-ams2-eoco-aspbzla
14916 phpip-pipmea-cpeo-bphabs
14917 bimhs-diphmep-cpeo-bsdap
14918 imhs-eta-oem-bhsdap
14919 prhs-amn2-no2-bnsdap
14920 gua-24thiz-meo-tsdap
14921 amthiaz-diphmep-5amo-aspbzla
14922 bhs-amn2-emo-zdap
14923 amim-trias-5pho-thizzdap
14924 menim-mepazin-emo-betainyl
14925 dmam-mepipe-men-csdap
14926 2py-eta-ocho-psdap
14927 pyr-butn-emo-zdapee
14928 bim-thizn-meteto-bphabs
14929 bimhs-dimephmep-pheo-bsdap
14930 bim-trias-men-bsdap
14931 am2py-edia2-oem-npsdap
14932 am2py-dimephmep-napo-betadcph
14933 impy-thizn-oeto-betadcph
14934 thpym-mepipe-no2-glupha
14935 hythpym-24thizman2-fo-bhsdap
14936 gua-n2o2n-emo-csdap
14937 2py-mepipe-meo-betapy
14938 gua-pazin-men-aspbzla
14939 impy-25oxman2-imo-betadcph
14940 tolhs-diphmep-imo-bhsdab
14941 deam-edia2-oem-nbeta34-dimeoph
14942 imhs-dis-no2-zdap
14943 imhs-pipmea-men-ppsdap
14944 dhim-dimen-5amo-betainyl
14945 piraz-n2nme2n-ocho-zdab
14946 deam-dimen-fo-bphabs
14947 impy-amn2-pyo-glupha
14948 chhs-mea2s-napo-zdap
14949 bhs-indan2-5pho-zdabs
14950 2py-dimephmem-meo-glyzdap
14951 bim-eta-oem-bhsdap
14952 morhs-dimephmep-pyo-bsdap
14953 bimhs-edia2-sem-nbetapy
14954 npip-m25thiz-imo-glubzla
14955 2py-pazin-no2-psdap
14956 moegua-pipmea-imo-zdabs
14957 nmhs-pipa-5amo-asppha
14958 deam-pymea-eoco-betaet
14959 bimhs-amo2-fo-bsdap
14960 impy-tridi-ocho-bsdap
14961 thpym-edian2-5pho-psdap
14962 thpym-mepipen2-5amo-psdab
14963 bimhs-pyma2-aco-zdabs
14964 me2py-propn-no1-csdap
14965 imhs-pymea-eoco-dfzdap
14966 nim-pazin-oem-mezphe
14967 n2py-mepipe-pheo-zdap betainyl
14968 2py-m25thiz-meo-bhsdap
14969 me2py-pnymea-imo-tsdap
14970 bim-tetradi-5pho-bsdap
14971 thpym-pymea-chexo-psdab
14972 imhs-amn3-eoco-mezphe
14973 2py-mepipe2-sem-npsdap
14974 cl3pyme-pazi2n-fo-zorn
14975 imhs-dis-hso-glyzdap
14976 phhs-mepazin-men-psdab
14977 bim-amn3-imo-dfzdap
14978 am-pazi2n-mommo-zdabs
14979 hythpym-dimen-no1-psdapee
14980 impy-mepipe-cnmo-bphabs
14981 am2py-dimephmep-hso-glyzdap
14982 inhs-mepipe-chexo-betainyl
14983 impy-propa2s-baeo-bhsdap
14984 hythpym-amo2-ocho-betapy
14985 dpam-mepazin-chexo-zdab
14986 mam2py-diphmep-meteto-aspbzla
14987 piraz-thizn-no1-asppha
14988 phpip-pipmeo-napo-bhsdap
14989 2py-eta-no2-bnsdap 14990 phhs-dimephmep-men-dfzdap
14991 pippy-pyma2-chexo-psdapee
14992 2pmhs-thizn-5amo-glyzdap
14993 am2py-pazin-4pho-bsdap
14994 hythpym-eta-eoco-osdap
14995 edothpym-din-eoco-bnsdap
14996 imhs-eta-5pho-psdab
14997 2py-pnymea-pyo-betainyl
14998 ec-dis-no1-bhsdap
14999 ppy-amo2-paco-bhsdap
15000 deam-mepipe-emo-asppha
15001 2py-trias-mmen-psdab
15002 dmam-m25thiz-chexo-zdap
15003 impy-ams2-aco-psdap
15004 pyr-pymea-meo-psdab
15005 binhs-mepipen2-mes-zdab
15006 phhs-dimephmem-eoco-bphabs
15007 pippy-m24thizman2-meo-bhsdab
15008 pippy-n24thiman-mommo-mezphe
15009 pippy-amn3-oem-psdap
15010 piraz-amo3-pheo-zdap
15011 bim-diphmep-oem-psdab
15012 bzl-ms-emo-psdapee
15013 bim-pazin-no1-bsdap
15014 piraz-thizn-5amo-zdap
15015 bhs-pazin-5pho-betapy
15016 mam2py-dis-5amo-betadcph
15017 imhs-m24thizman2-cnmo-betainyl
15018 mam2py-pipmea-no2-aspbzla
15019 phpip-pnymea-mes-csdap
15020 am-thizn-no1-betainyl
15021 imhs-propa2s-mmen-bnsdap
15022 gua-pipa-no2-aval
15023 am4py-pnymea-mes-psdab
15024 imhs-am3-oem-nbetapy
15025 impy-ams2-oeto-zdab
15026 imhs-din-meo-glubzla
15027 bzl-tetradi-daco-betapy
15028 hythpym-n2o2n-fo-dfzdap
15029 nmhs-m24thizman2-eoco-glyzdap
15030 pippy-trias-emo-betainyl
15031 am4py-dimephmem-chexo-psdap
15032 thpym-pazin-mes-bsdap
15033 bim-tridi-ocho-glubzla
15034 bim-24thiz-men-zdap
15035 2pmhs-amn3-imo-mezphe
15036 am2py-tetradi-oem-psdap
15037 ec-dimephmep-pyo-dfzdap
15038 menim-edian2-meo-psdap
15039 bimhs-24thiman2-mommo-betapy
15040 z-eta2s-eoco-zdab
15041 bhs-eta-oem-aspibua
15042 2py-dimephmep-chexo-betapy
15043 am2py-mepipen2-meo-ppsdap
15044 bhs-eta-oem-zdap
15045 2py-mepipe-oem-psdab
15046 binhs-amn2-oem-zlys
15047 pyr-pipa-daco-psdap
15048 im-diphmem-men-psdapee
15049 impy-pnymea-men-psdab
15050 bz-amo3-4amo-bphabs
15051 dmam-mepipen2-4amo-zdap
15052 bhs-eta-pyo-bhsdap
15053 2py-edian2-5pho-bhsdap
15054 dhim-m24thizman2-oeto-bhsdab
15055 2py-m25thiz-oeto-glyzdap
15056 bimhs-m25thizman2-meo-zlys
15057 bhs-m24thizman2-cpeo-aval
15058 inhs-trias-chexo-dfzdap
15059 phpip-amn2-meo-psdab
15060 gua-hexadi-mommo-betapy
15061 2py-amn2-meo-bsdap
15062 2py-tetradi-cpeo-zdab
15063 mepip-butn-5pho-zdab
15064 pippy-amn2-no1-zdabs
15065 bimhs-mea-ocho-mezphe
15066 dmbim-diphmem-oem-bphabs
15067 thpym-mepipe2-oem-nbetapy
15068 gua-tetradi-nmo-psdap
15069 pippy-dis-chexo-bhsdap
15070 hythpym-pyma2-fo-zdab
15071 piraz-amn3-fo-mezphe
15072 bhs-mepipen2-meteto-psdab
15073 pyr-25oxman2-fo-thizzdap
15074 am2py-25oxman2-baeo-zdap
15075 ibhs-am3diaz-no1-bhsdab
15076 dhim-pentas-meto-aspbzla
15077 dhim-din-eoco-aspibua
15078 bhs-pyma2-eoco-glyzdap
15079 me-ams2-fo-betainyl
15080 mam2py-amn2-ocho-bsdap
15081 bim-amn2-eoco-bhsdap
15082 3pyme-am3-sem-nbetapy
15083 piraz-pymea-imo-zdap
15084 imhs-mepazin-5amo-bhsdap
15085 bhs-dimephmep-emo-glyzdap
15086 am4py-edian2-meo-bhsdap
15087 pippy-24oxman2-oem-mezphe
15088 phpip-24thiz-eoco-dfzdap
15089 bim-pazin-meo-zdab
15090 morhs-pipa-5pho-zdab
15091 am2py-tridi-nmo-aspbzla
15092 ibhs-m24thizman2-fo-dfzdap
15093 pyr-dis-chexo-asppha
15094 thpym-pymea-no2-zlys
15095 am2py-m25thiz-5amo-zdab
15096 piraz-thizn-emo-betapy
15097 z-pyma2-cno-psdab
15098 am4py-m24thiz-mes-betainyl
15099 bim-edian2-eoco-zdap
15100 piraz-eta2s-hso-mezphe
15101 impy-eta-paco-glyzdap
15102 mam2py-dis-chexo-zdab
15103 pyraz-pyma2-eoco-psdab
15104 dpam-edian2-men-bhsdap
15105 bimhs-dipch-oem-asppha
15106 am2py-3pazin-oeto-psdapee
15107 bhs-edian2-mes-bsdap
15108 bimhs-am3diaz-pyo-bphabs
15109 me2py-am3diaz-mecpo-zdap
15110 bim-pazin-5pho-psdap
15111 dmam-mepipe-chexo-betadcph
15112 am4py-mea2s-napo-csdap
15113 pippy-dipch-meto-bnsdap
15114 am2py-trias-oem-dfzdap
15115 hythpym-pentadi-no2-dfzdap
15116 prhs-amn2-chexo-asppha
15117 prhs-dis-napo-psdab
15118 bimhs-din-pro-aspibua
15119 nmor-pymea-peo-csdap
15120 dhim-amn3-5pho-zlys
15121 me2py-dimephmem-imo-glyzdap
15122 piraz-edian2-paco-dfzdap
15123 pippy-mepipen2-napo-zdabs 15124 bhs-amn3-peo-asppha
15125 dmthpym-amo2-napo-psdab
15126 chhs-25oxman2-oem-betainyl
15127 menim-thizn-5amo-bphabs
15128 npip-mepipen2-mes-zdabs
15129 imhs-dimen-mes-thizzdap
15130 2py-pyma2-men-aspibua
15131 amim-am2-sem-nbetapy
15132 am2py-m24thiz-eoco-aspbzla
15133 dhim-mepipe-no2-bsdap
15134 bz-mepipe2-sem-nbeta34-dimeoph
15135 thpym-m24thizman2-eoco-zdab
15136 dhim-eta2s-hso-asppha
15137 emnim-din-chexo-zdabs
15138 impy-pentadi-meo-betapy
15139 2py-mea-fo-mezphe
15140 imhs-eta-no2-betapy
15141 pyrhs-eta-aco-psdap
15142 dhim-m24thizman2-napo-aval
15143 impy-pazin-mes-mezphe
15144 imhs-pentadi-eoco-betainyl
15145 thpym-n24thiman-imo-bnsdap
15146 dhim-dis-no2-glyzdap
15147 ec-pyma2-oem-aspbzla
15148 npip-diphmem-men-aspibua
15149 piraz-mepipen2-eoco-osdap
15150 gua-pipa-fo-aspaba
15151 im-amn3-no2-bnsdap
15152 bhs-ams2-meo-zdabs
15153 hythpym-edian2-men-bphabs
15154 bim-pyma2-mes-bhsdap
15155 dmthpym-n2o2n-mes-psdab
15156 bim-amn2-no1-psdap
15157 thpym-indan2-no1-betapy
15158 mam2py-24thiz-hso-aspibua
15159 bimhs-pipmes-no2-mezphe
15160 piraz-tridi-pheo-psdab
15161 mam2py-amn2-5pho-zdab
15162 imhs-amn2-no1-psdab
15163 dhim-pyma2-5amo-betainyl
15164 me2py-dipch-chexo-zdap
15165 ec-thizn-cpeo-mezphe
15166 mam2py-am2-oem-nbetapy
15167 tolhs-dimephmem-pro-bphabs
15168 z-mepipen2-peo-zdab
15169 pippy-edian2-5pho-bhsdap
15170 amim-edian2-5pho-mezphe The following abbreviations for the building blocks A, E, G and L are used in the above list.

| A = | Abbreviation | A = | Abbreviation |
|---|---|---|---|
|  | 2py |  | thpym |
|  | dhim |  | nmhs |
|  | bim |  | 4pmhs |
|  | imhs |  | ibhs |
|  | bhs |  | ppy |
|  | moegua |  | dmthpym |

-continued

| A = | Abbreviation | A = | Abbreviation |
|---|---|---|---|
| (structure) | edothpym | (structure) | fthpym |
| (structure) | gua | (structure) | im |
| (structure) | 2pmhs | (structure) | am2py |
| (structure) | impy | (structure) | mam2py |
| (structure) | pippy | (structure) | am4py |
| (structure) | amim | (structure) | piraz |
| (structure) | tolhs | (structure) | phhs |
| (structure) | me2py | (structure) | bimhs |
| (structure) | pyraz | (structure) | hythpym |
| (structure) | pyr | (structure) | prhs |
| (structure) | chhs | (structure) | chmhs |

-continued
| A = | Abbreviation | A = | Abbreviation |
|---|---|---|---|
| 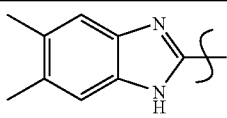 | dmbim | 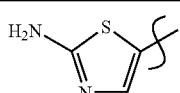 | amthiaz |
|  | am |  | dmam |
| 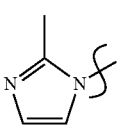 | menim | 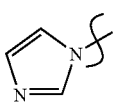 | nim |
| 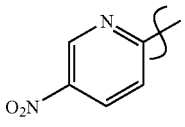 | n2py | 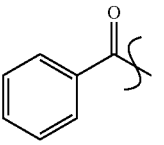 | bz |
| 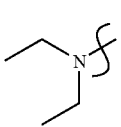 | deam | 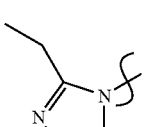 | emnim |
| 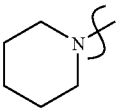 | npip | 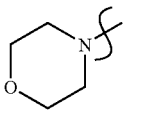 | nmor |
| 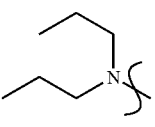 | dpam | 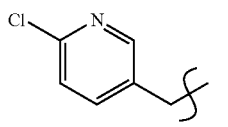 | cl3pyme |
| 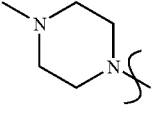 | mepip | 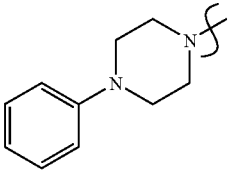 | phpip |
| 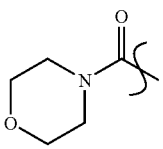 | morhs | 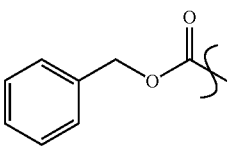 | z |
| 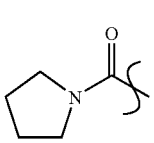 | pyrhs | 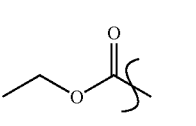 | ec |
| 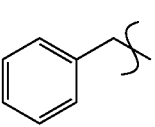 | bzl |  | me |

| E = | Abbreviation | E = | Abbreviation |
|---|---|---|---|
| (piperazine) | pazin | (-NH-CO-CH₂-NH-) | amn2 |
| (-NH-CH₂CH₂-NH-CO-CH₂-NH-) | edian2 | (-NH-CO-CH₂-S-) | ams2 |
| (-NH-CH₂CH₂-NH-CO-CH₂-) | edia2 | (-NH-CO-CH₂-O-) | amo2 |
| (mepipe2 structure) | mepipe2 | (mepipen2 structure) | mepipen2 |
| (pyridine-CH₂-NH-CO-CH₂-NH-) | pyma2 | (-NH-CO-CH₂-) | am2 |
| (-NH-CO-CH₂CH₂-) | am3 | (-NH-CO-CH₂CH₂-NH-) | amn3 |
| (-NH-CO-CH₂CH₂-O-) | amo3 | (-NH-CO-CH₂CH₂-S-) | ams3 |
| (methylpiperazine) | mepazin | (mepipe structure) | mepipe |
| (homopiperazine-propyl) | 3diaz | (homopiperazine-NH-propyl) | am3diaz |
| (thiazole-CH₂-NH-) | thizn | (thiazole-CH₂-S-) | thizs |
| (thiazole-CH₂-O-) | thizo | (-NH-CH₂CH₂-NH-) | din |

-continued

| E = | Abbreviation | E = | Abbreviation |
|---|---|---|---|
| [structure] | dis | [structure] | dio |
| [structure] | dich | [structure] | 24thiman |
| [structure] | pazi2n | [structure] | indan2 |
| [structure] | 25thiman2 | [structure] | 24thiman2 |
| [structure] | m24thiman2 | [structure] | m25thiman2 |
| [structure] | diaz | [structure] | n24thiman |
| [structure] | hexadi | [structure] | mea |
| [structure] | dimen | [structure] | tridi |
| [structure] | tetradi | [structure] | pentadi |
| [structure] | hexas | [structure] | ms |
| [structure] | propn | [structure] | trias |
| [structure] | tetras | [structure] | pentas |

-continued
| E = | Abbreviation | E = | Abbreviation |
|---|---|---|---|
| 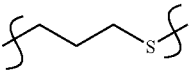 | props | 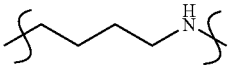 | butn |
| 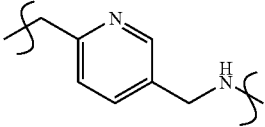 | pymea | 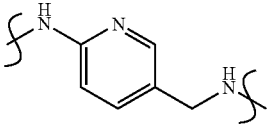 | pnymea |
| 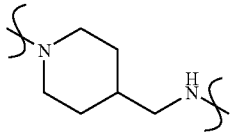 | pipmea | 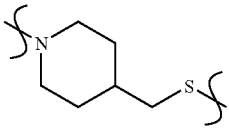 | pipmes |
| 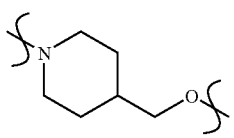 | pipmeo | 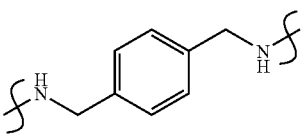 | dimephmep |
| 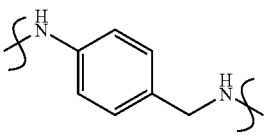 | diphmep | 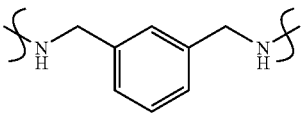 | dimephmem |
| 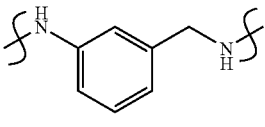 | diphmem | 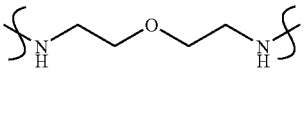 | n2o2n |
| 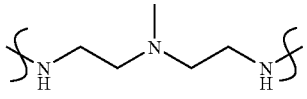 | n2nme2n | 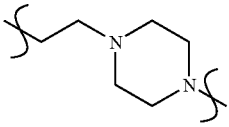 | 2pazin |
| 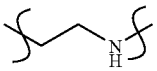 | eta | 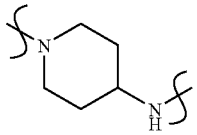 | pipa |
| 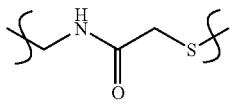 | mea2s | 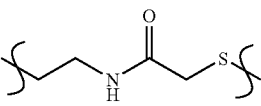 | eta2s |
| 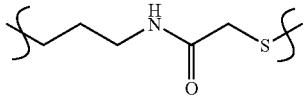 | propa2s | 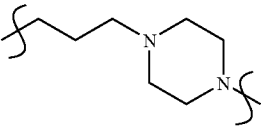 | 3pazin |
| 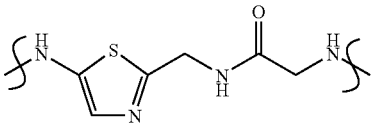 | 25thizman2 | 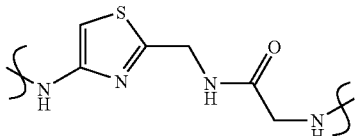 | 24thizman2 |

-continued
| E = | Abbreviation | E = | Abbreviation |
|---|---|---|---|
| 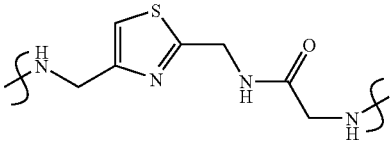 | m24thizman2 | 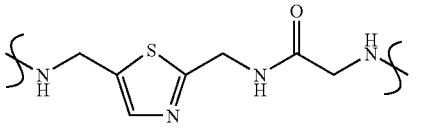 | m25thizman2 |
| 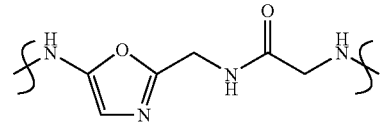 | 25oxman2 | 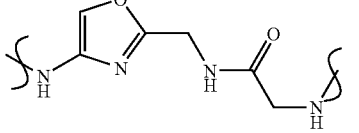 | 24oxman2 |
| 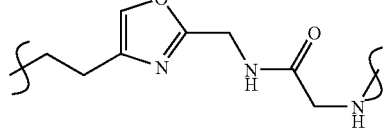 | m24oxman2 | 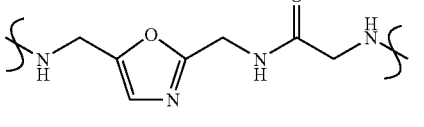 | m25oxman2 |
| 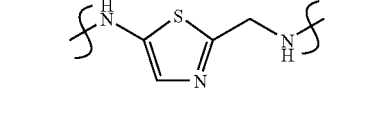 | 25thiz | 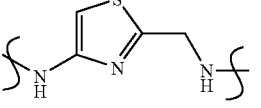 | 24thiz |
| 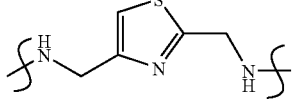 | m24thiz | 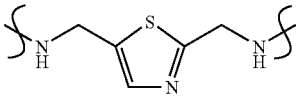 | m25thiz |
| 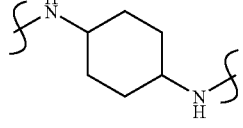 | dipch | | |
| G = | Abbreviation | G = | Abbreviation |
|---|---|---|---|
| 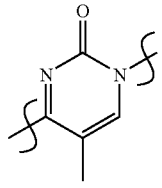 | meo | 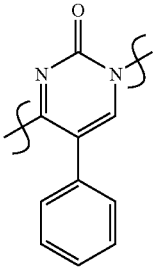 | 5pho |
| 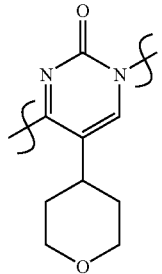 | ocho | 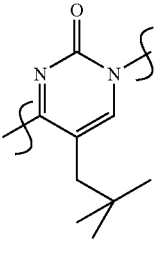 | peo |

-continued

| G = | Abbreviation | G = | Abbreviation |
|---|---|---|---|
| (structure) | pro | (structure) | oem |
| (structure) | mes | (structure) | sem |
| (structure) | men | (structure) | cpro |
| (structure) | cno | (structure) | emo |
| (structure) | no1 | (structure) | no2 |
| (structure) | pheo | (structure) | meto |

-continued
| G = | Abbreviation | G = | Abbreviation |
|---|---|---|---|
| 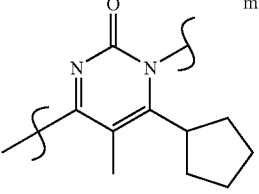 | mecpo | 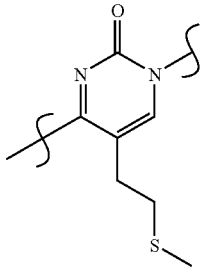 | meteto |
| 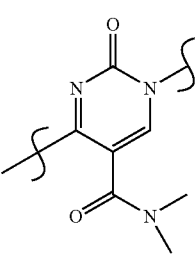 | daco | 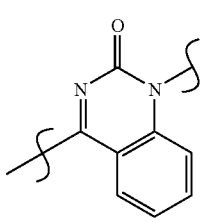 | napo |
| 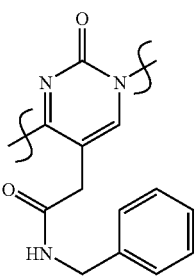 | baeo | 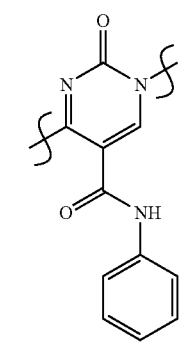 | paco |
| 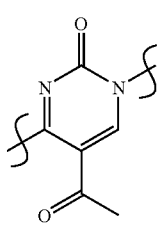 | aco | 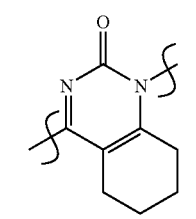 | chexo |
| 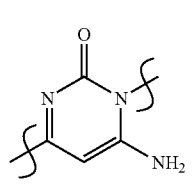 | 4amo | 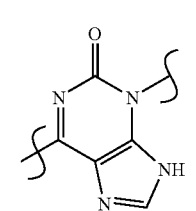 | imo |
| 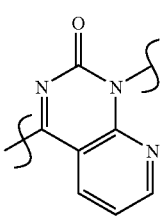 | pyo | 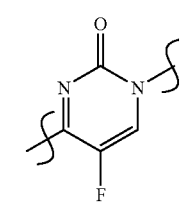 | fo |

-continued
| G = | Abbreviation | G = | Abbreviation |
|---|---|---|---|
| 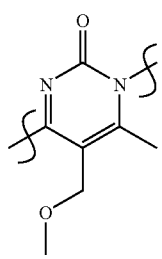 | mommo | 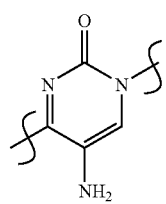 | 5amo |
| 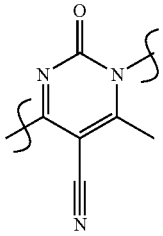 | cnmo | 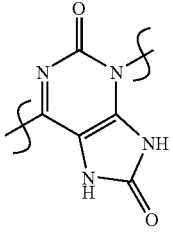 | hso |
| 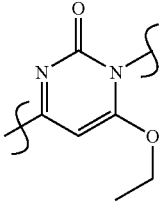 | oeto | 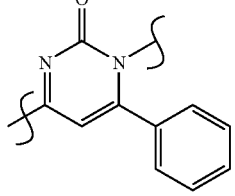 | 4pho |
| 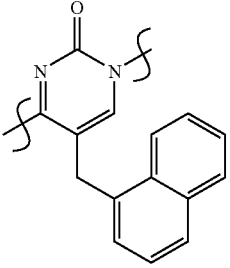 | nmo | 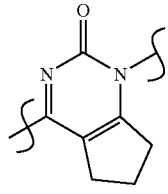 | cpeo |
| 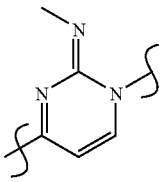 | mmen | 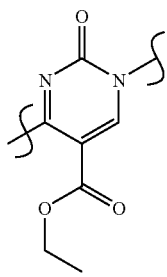 | eoco |

| L = | Abbreviation | L = | Abbreviation |
|---|---|---|---|
| 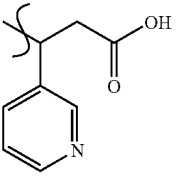 | betapy | 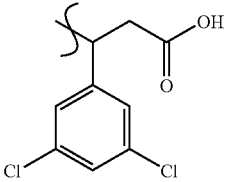 | betadcph |
| 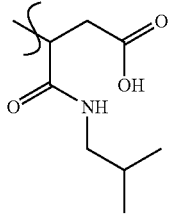 | aspibua | 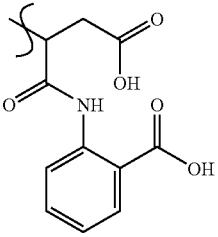 | aspaba |
| 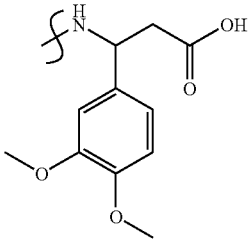 | nbeta34dimeoph | 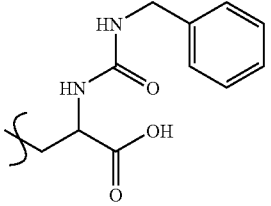 | bhsdap |
| 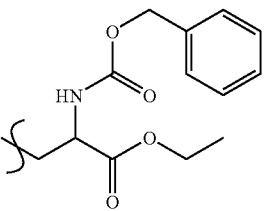 | zdapee | 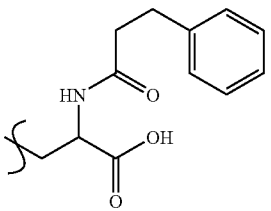 | ppsdap |
| 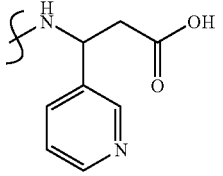 | nbetapy | 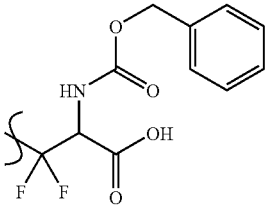 | dfzdap |
| 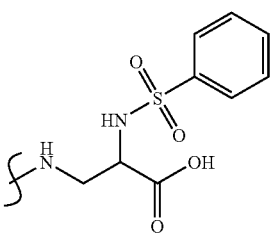 | npsdap | 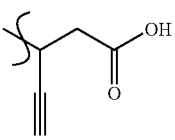 | betainyl |

| L = | Abbreviation | L = | Abbreviation |
|---|---|---|---|
| (structure) | zdab | (structure) | psdab |
| (structure) | betaet | (structure) | bnsdap |
| (structure) | glubzla | (structure) | zdap |
| (structure) | aspbzla | (structure) | psdap |
| (structure) | bsdap | (structure) | csdap |

-continued
| L = | Abbreviation | L = | Abbreviation |
|---|---|---|---|
| 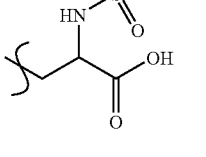 | tsdap | 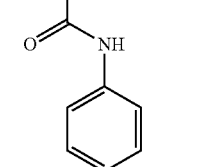 | glupha |
| 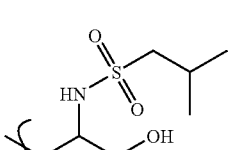 | ibsdap | 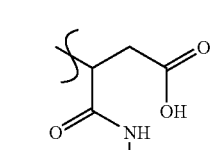 | asppha |
| 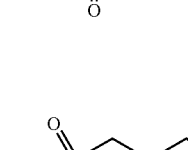 | osdap | 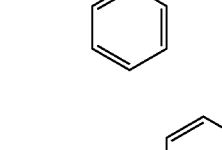 | psdapee |
| 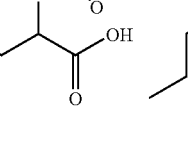 | bhsdab | 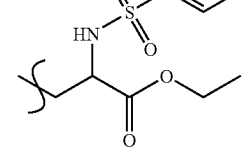 | aval |
| 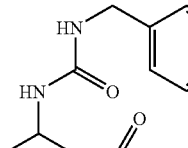 | zorn | 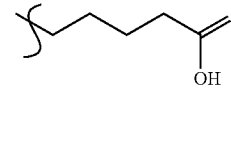 | zlys |
| 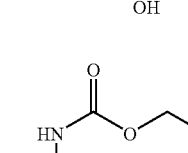 | nzdab | 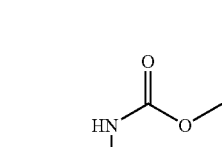 | nbetabnaphth |

-continued

| L = | Abbreviation | L = | Abbreviation |
|---|---|---|---|
|  | bphabs |  | mezphe |
|  | thizzdap |  | nzdap |
|  | nbetameph |  | zdabs |
|  | glyzdap |  | oxal |

The compounds of the formula I and the starting materials used to prepare them can be prepared generally by methods of organic chemistry known to the skilled worker, as described in standard works such as, for example, Houben-Weyl, "Methoden der Organischen Chemie", Thieme-Verlag, Stuttgart, or March "Advanced Organic Chemistry", $4^{th}$ Edition, Wiley & Sons. Further preparation methods are also described in R. Larock, "Comprehensive Organic Transformations", Weinheim 1989, in particular the preparation of alkenes, alkynes, halides, amines, ethers, alcohols, phenols, aldehydes, ketones, nitriles, carboxylic acids, esters, amides and acid chlorides. The selection of suitable protective groups for functional groups, and the introduction or elimination of the protective groups are described, for example, in Greene and Wuts in "Protective Groups in Organic Synthesis", $2^{nd}$ Edition, Wiley & Sons, 1991.

Synthesis of compounds of the formula I can be carried out either in solution or on a polymeric support, the reaction conditions used in each case being those known and suitable for the particular reactions. It is moreover possible to make use of variants which are known per se but which are not mentioned here.

The general synthesis of compounds of type I where, as described above, A-E- may be the structural element B- and -U-T may be the structural element -L is described in Schemes 1 to 7. Unless indicated otherwise, all the starting materials and reagents can be purchased or can be prepared by conventional methods from precursors which can be purchased.

Compounds of the general formula I are synthesized, for example, starting from appropriately substituted 4-thioxo-3,4-dihydropyrimidin-2(1H)-ones of the general formula II as intermediate. 4-Thioxo-3,4-dihydropyrimidin-2(1H)-ones of type II are known and can be prepared by known methods as described, for example, in Katritzky and Rees, "Comprehensive Heterocyclic Chemistry", Pergamon Press, volume 3; pp. 135–139 and the literature quoted therein.

A preferred method for synthesizing 4-thioxo-3,4-dihydro-pyrimidin-2(1H)-ones comprises, for example, addition of enamines onto isothiocyantes with subsequent cyclization as described by Goerdeler et al. in Chem. Ber. 1963, pp. 526–533, and Chem. Ber. 1965, pp. 1531–1542. 4-Thioxo-3,4-dihydropyrimidin-2(1H)-ones can particularly preferably be prepared by the method described by Lamon in J. Heterocycl. Chem. 1968, 5, 837–844, which is based on the reaction of an enamine with alkoxy- or aryloxycarbonyl isothiocyanate. Compounds of the formula I can be synthesized by reacting appropriate enamine derivatives of the general formula III in which X is preferably a morpholine, pyrrolidine or piperidine residue with primary amines to form the subs. 4-thioxo-3,4-dihydropyrimidin-2(1H)-ones II (Scheme 1).

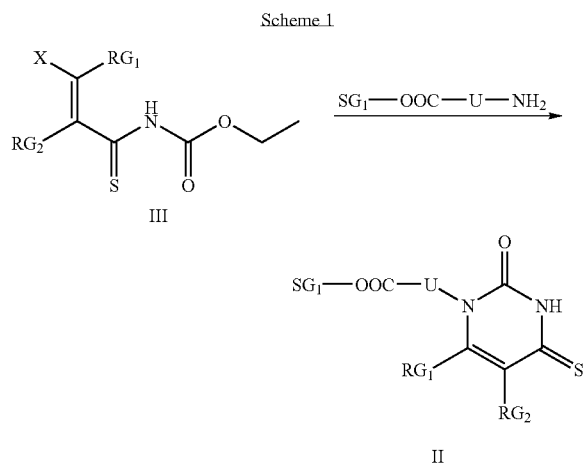

$SG_1$ is a protective group for the carboxyl function, or the $SG_1$—OOC— radical is T, as described above.

It is particularly efficient to carry out the synthesis on solid phase for example, by using the carboxyl function as anchor group for attachment to a solid support ($SG_1$=solid support). Methods for solid-phase synthesis are described in detail, for example, by Bunin in "The Combinatorial Index" (Academic Press, 1998). In the case where U contains another functional group or the side chain of an amino acid which contains a so-called side-chain functionality, this is advantageously protected by suitable protective groups.

For further reaction, the 4-thioxo group in compounds of the general formula II is alkylated by standard methods with addition of a base. It is possible to use as base an alkali metal or alkaline earth metal hydride such as sodium hydride, potassium hydride or calcium hydride, a carbonate such as alkali metal carbonate, for example sodium or potassium carbonate, an alkali metal or alkaline earth metal hydroxide such as sodium or potassium hydroxide, an alcoholate such as, for example, sodium methanolate, potassium tert-butanolate, an organometallic compound such as butyllithium or alkali metal amides such as lithium diisopropylamide, lithium, sodium or potassium bis(trimethylsilyl)amide, tertiary amines such as triethylamine, 1,8-diazabicyclo[5.4.0]undec-7-ene or ethyl diisopropylamine. The use of alkali metal carbonates such as $Cs_2CO_3$ or tertiary amines such as ethyl diisopropylamine is particularly preferred.

In the case where the $U_E$ radical in compounds of the general formula I is oxygen or $NR_E^2$, or in the case where h=0, $U_E$ is absent and thus there is a direct linkage between the fragments A-E and G via an N group present in the fragment, the 4-thioxo group is preferably converted into the corresponding thiocyanate by alkylation with cyanogen bromide, as described, for example, in Tetrahedron Letters 1991, 32 (22), 2505–2508 (Scheme 2). The thiocyanate of the formula IVa can then be reacted with suitable amines or alcohols of the general formula A-E-$(U_E)_h$-H (V) by methods known to the skilled worker, possibly with addition of a base, to give the compounds of the general formula VI (Scheme 2). In this scheme, for illustration, —E'— represents the spacer structural element E without the linker $(U_E)_h$.

In the case where the $U_E$ radical in compounds of the formula I is sulfur, it is possible to use as alkylating agent directly a compound of the general formula A-E-Y (VII), in which case the group Y is a conventional leaving group such as, for example, halogen such as chlorine, bromine, iodine or aryl- or alkylsulfonyl, which is optionally substituted by halogen, alkyl or haloalkyl, such as, for example, toluenesulfonyl, trifluoromethanesulfonyl and methylsulfonyl or another equivalent leaving group (Scheme 2).

Another preferred method for preparing compounds of the general formula I with $U_E$=sulfur is the conversion of compounds of the general formula II into the corresponding sulfanylacetonitriles (IVb), which can then be reacted with thiols of the structure A-E-SH (Vb) to give compounds VI.

Elimination of the protective group $SG_1$ under standard conditions (see below) leads to compounds of the general formula I. In the case where $SG_1$ is $C_1$–$C_4$-alkyl or benzyl or the case where $SG_1$—OOC— is T, the compounds of the general formula VI correspond directly to the compounds of type I.

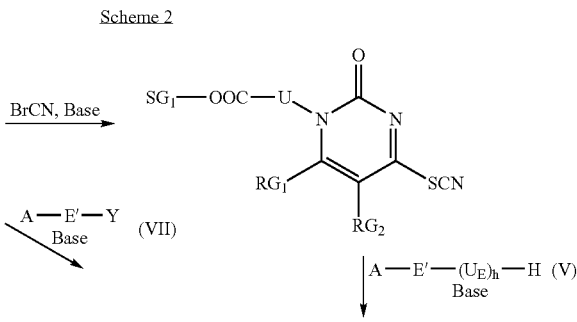

-continued

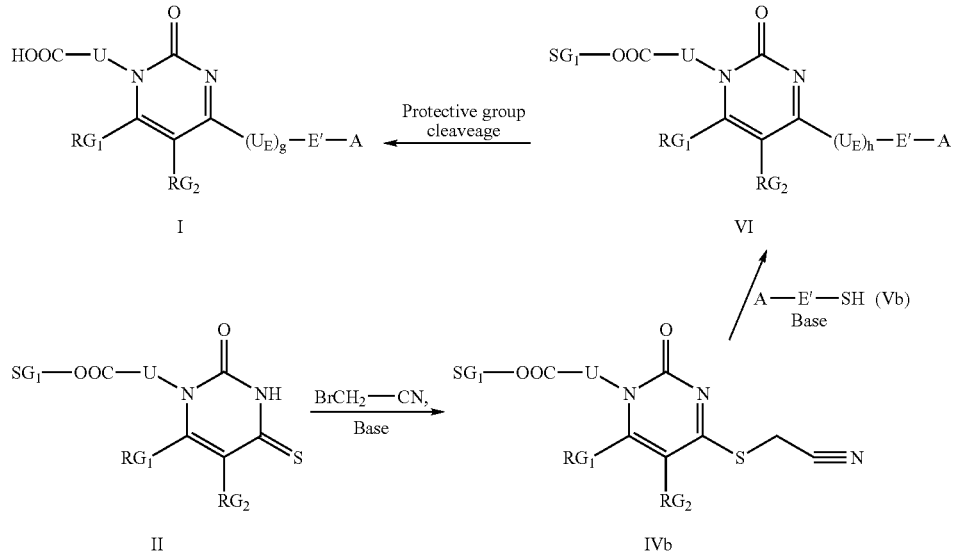

It is possible to use as protective groups SG all protective groups which are in use and are known to the skilled worker from peptide synthesis, and are also described in the standard works such as, for example, Bodanszky "*The Practice of Peptide Synthesis*", 2$^{nd}$ Edition, Springer-Verlag 1994, and Bodanszky "*Principles of Peptide Synthesis*", Springer-Verlag 1984. Elimination of the protective groups in the compounds of the formula VI, and the protective groups used for preparing the compounds V and VII, likewise takes place under conditions known to the skilled worker and described, for example, by Greene and Wuts in "*Protective Groups in Organic Synthesis*", 2$^{nd}$ Edition, Wiley & Sons, 1991.

The amino protective groups preferably used are Boc, Fmoc, benzyloxycarbonyl (Z), acetyl, trityl or Mtr. The acid protective groups used, such as, for example, $SG_1$, are preferably $C_1$–$C_4$-alkyl such as, for example, methyl, ethyl, tert-butyl or else benzyl or trityl, or else polymer-bound protective groups in the form of the commercially available polystyrene resins such as, for example, 2-chlorotrityl chloride-resin or Wang resin (supplied by Bachem or Novabiochem).

Elimination of acid-labile protective groups (for example Boc, tert-butyl, Mtr, trityl) can be effected, depending on the protective group used, with organic acids such as, for example, trifluoroacetic acid (TFA), trichloroacetic acid, perchloric acid, trifluoroethanol, sulfonic acids such as, for example, benzene- or p-toluenesulfonic acid or else inorganic acids such as, for example, hydrochloric acid or sulfuric acid, the acids generally being employed in excess.

In the case of trityl, the addition of thiols such as, for example, thioanisole or thiophenolmay be advantageous. The presence of an additional inert solvent is possible but not always necessary. Suitable and preferred inert solvents are organic solvents, for example carboxylic acids such as acetic acid, ethers such as THF or dioxane, amides such as DMF or dimethylacetamide, halogenated hydrocarbons such as dichloromethane, alcohols such as methanol, isopropanol or water. Mixtures of said solvents are also suitable. The reaction temperature for these reactions is between 10° C. and 50° C., preferably in a range between 0° C. and 30° C.

Base-labile protective groups such as Fmoc are cleaved by treatment with organic amines such as, for example, dimethylamine, diethylamine, morpholine, piperidine, as 5–50% solutions in $CH_2Cl_2$ or DMF. The reaction temperature for these reactions is between 10° C. and 50° C., preferably in a range between 0° C. and 30° C.

Acid protective groups such as methyl or ethyl are preferably cleaved by abisc hydrolysis in an inert solvent. The bases preferably used are alkali metal or alkaline earth metal hydroxides, preferably NaOH, KOH or LiOH. The solvents used are all conventional inert solvents such as, for example, hydrocarbons such as hexane, heptane, petroleum ether, toluene, benzene or xylene, chlorinated hydrocarbons such as trichloroethylene, 1,2-dichloroethane, tetrachloromethane, chloroform, dichloromethane, alcohols such as methanol, ethanol, isopropanol, n-propanol, n-butanol or tert-butanol, ethers such as diethyl ether, methyl tert-butyl ether, diisopropyl ether, tetrahydrofuran, dioxane, glycol ethers such as ethylene glycol monomethyl ether or monoethyl ether, ethylene glycol dimethyl ether, ketones such as acetone, butanone, amides such as dimethylformamide (DMF), dimethylacetamide or acetamide, nitriles such as acetontrile, sulfoxides such as dimethyl sulfoxide, sulfolane, N-methylpyrrolidione, 1,3-dimethyltetrahydro-2(1H)-pyrimidonone (DMPU), 1,3-dimethyl-2-imidazolidinone, nitro compounds such as nitromethane or nitrobenzene, water or mixtures of said solvents. The addition of a phase-transfer catalyst may be advantageous, depending on the solvent or mixture of solvents used. The reaction temperature for these reactions is generally between –10° C. and 100° C.

Protective groups which can be eliminated by hydrogenolysis, such as benzyloxycarbonyl (Z) or benzyl, can be eliminated, for example, by hydrogenolysis in the presence of a catalyst (for example a noble metal catalyst on activated carbon as support). Suitable solvents are those indicated above, and in particular alcohols such as methanol or ethanol, amides such as DMF or dimethylacetamide, esters such as, for example, ethyl acetate. The hydrogenolysis is ordinarily carried out under a pressure of from 1 to 200 bar and at temperatures between 0° C. and 100° C.; the addition of an acid such as, for example, acetic acid or hydrochloric acid may be advantageous. 5–10% Pd on activated carbon is preferably used as catalyst.

Building blocks of type E are generally assembled by methods known to the skilled worker. The building blocks used can be either purchased or obtained by methods known from the literature. The synthesis of some of these building blocks is described by way of example in the examples section.

In the case where the fragments $Q_E$ present in compounds of type V and VII are a hetaryl radical, the building blocks used can either be purchased or obtained by methods known to the skilled worker. A large number of preparation methods are described in detail in Houben-Weyl's "Methoden der organischen Chemie" (volume E6: furans, thiophenes, pyrroles, indoles, benzothiophenes, -furans, -pyrroles; volume E7: quinolines, pyridines, volume E8: isoxazoles, oxazoles, thiazoles, pyrazoles, imidazoles and their benzo-fused representatives, and oxidiazoles, thiadiazoles and triazoles; volume E9: pyridazines, pyrimidines, triazines, azepines and their beno-fused representatives, and purines).

Conversion of compounds of the general formula:

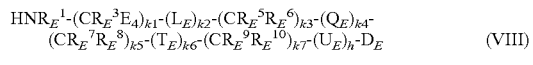

$$HNR_E^1-(CR_E^3E_4)_{k1}-(L_E)_{k2}-(CR_E^5R_E^6)_{k3}-(Q_E)_{k4}-(CR_E^7R_E^8)_{k5}-(T_E)_{k6}-(CR_E^9R_E^{10})_{k7}-(U_E)_h-D_E \quad (VIII)$$

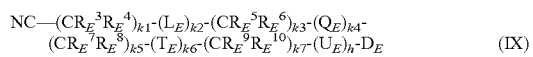

$$NC-(CR_E^3R_E^4)_{k1}-(L_E)_{k2}-(CR_E^5R_E^6)_{k3}-(Q_E)_{k4}-(CR_E^7R_E^8)_{k5}-(T_E)_{k6}-(CR_E^9R_E^{10})_{k7}-(U_E)_h-D_E \quad (IX)$$

into compounds of the general formula:

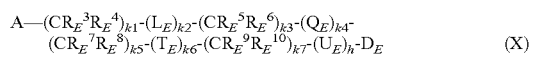

$$A-(CR_E^3R_E^4)_{k1}-(L_E)_{k2}-(CR_E^5R_E^6)_{k3}-(Q_E)_{k4}-(CR_E^7R_E^8)_{k5}-(T_E)_{k6}-(CR_E^9R_E^{10})_{k7}-(U_E)_h-D_E \quad (X)$$

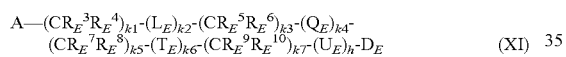

$$A-(CR_E^3R_E^4)_{k1}-(L_E)_{k2}-(CR_E^5R_E^6)_{k3}-(Q_E)_{k4}-(CR_E^7R_E^8)_{k5}-(T_E)_{k6}-(CR_E^9R_E^{10})_{k7}-(U_E)_h-D_E \quad (XI)$$

can take place by methods known to the skilled worker, as described, for example, in WO 97/08145. The group $D_E$ in the formulae VIII to XI is a radical having the meaning H or $NSG_2$. These building blocks can then be reacted either directly or after elimination of the apropriate protective group $SG_2$ to give compounds of the general formula I (Scheme 2).

Schemes 3–7 describe a number of methods for introducing A by way of example, the reaction conditions used in each case being those known and suitable for the particular reactions. It is morevoer possible to make use of variants which are known per se but not mentioned here.

Ureas and thioureas (AE-1 to AE-3) can be prepared by conventional methods of organic chemistry, for example by reacting an isocyanate or isothiocyanate with an amine, where appropriate in an inert solvent with heating (Houben-Weyl, volume VIII, 157 et seq.) (Scheme 3)

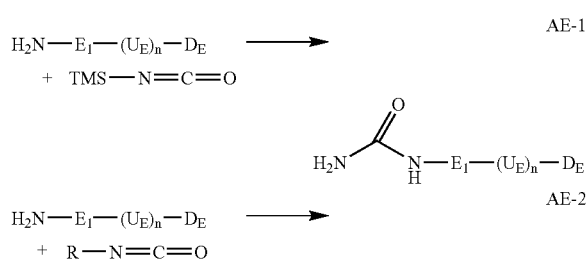

Scheme 3

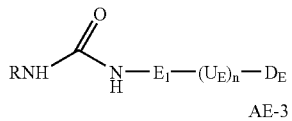

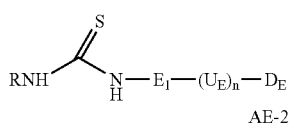

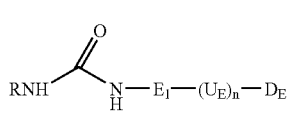

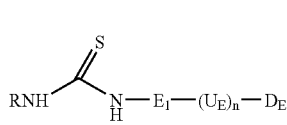

Scheme 4 shows by way of example the preparative of compounds of type AE-4 as described, for example, by Blakemoore et al. in *Eur. J. Med. Chem.* 1987 (22) 2, 91–100, or by Misra et al. in *Bioorg. Med. Chem. Lett.* 1994 4 (18), 2165–2170.

Scheme 4

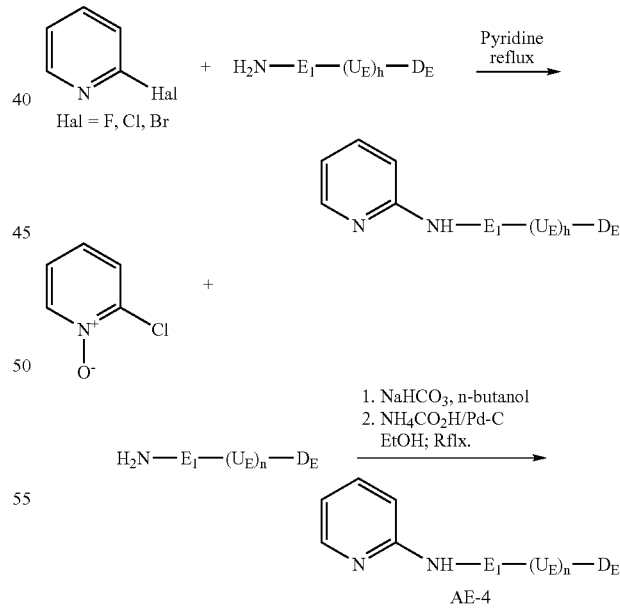

Unsubstituted or cycl. guanidine derivatives of the general formula AE-5 and AE-6 can be prepared using reagents which can be purchased or obtained simply, as described, for example, in *Synlett* 1990, 745, *J. Org. Chem.* 1992, 57, 2497, *Bioorg. Med. Chem.* 1996, 6, 1185–1208; *Bioorg. Med. Chem.* 1998, 1185, or *Synth. Comm.* 1998, 28, 741–746.

Preparation of compounds of the general formula AE-7 can take place in analogy to U.S. Pat. No. 3,202,660, and of compounds of the formula AE-9, AE-10, AE-11 and AE-12 in analogy to WO 97/08145. Compounds of the formula AE-8 can be prepared as shown in Scheme 5, for example by the method described by Perkins et al., *Tetrahedron Lett.* 1999, 40, 1103–1106. Scheme 5 summarizes the synthesis of said compounds.

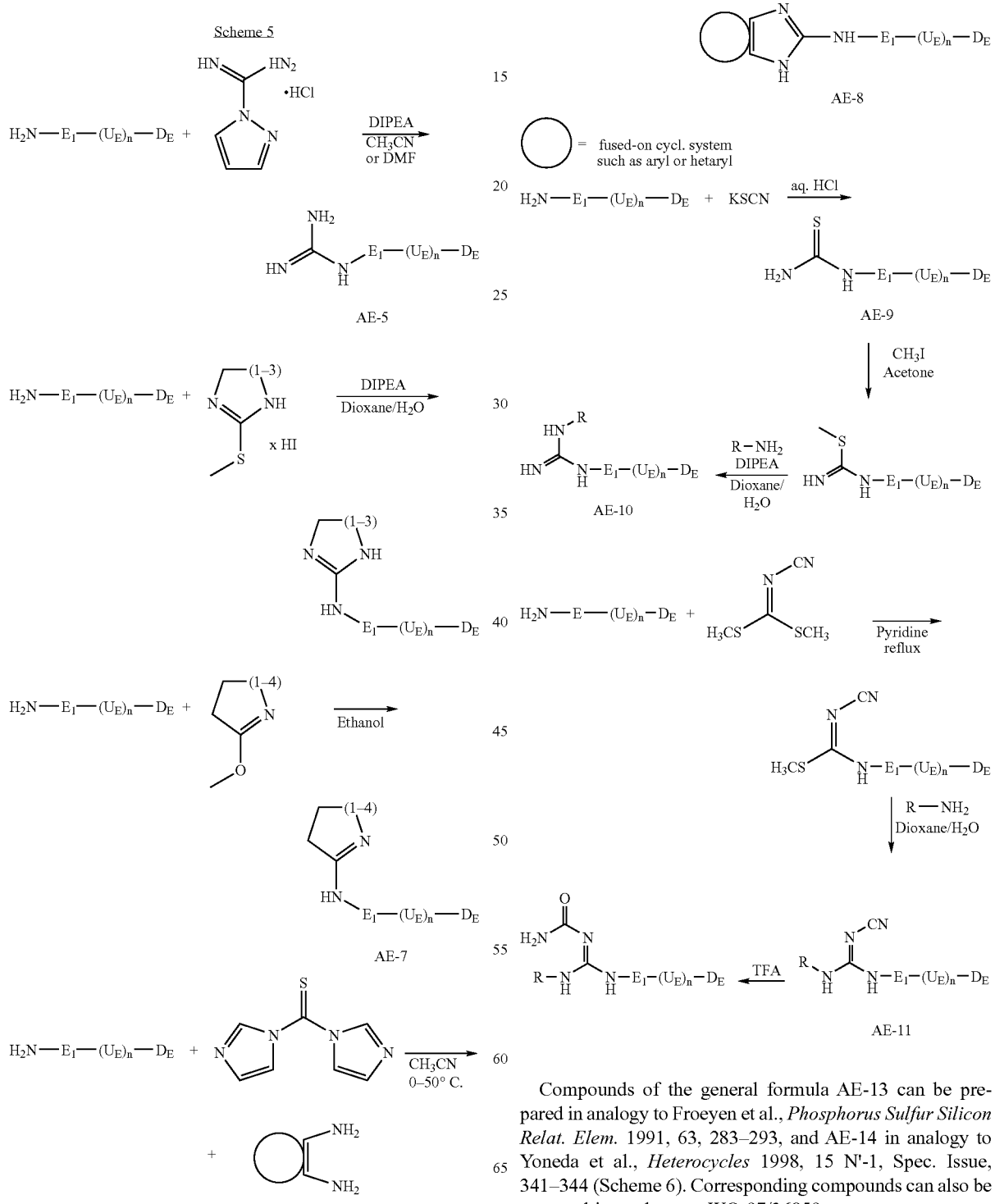

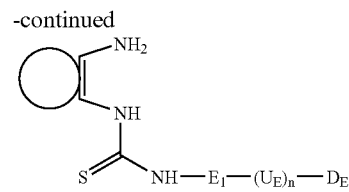

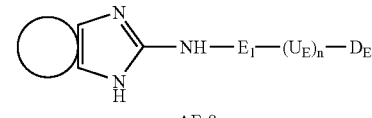

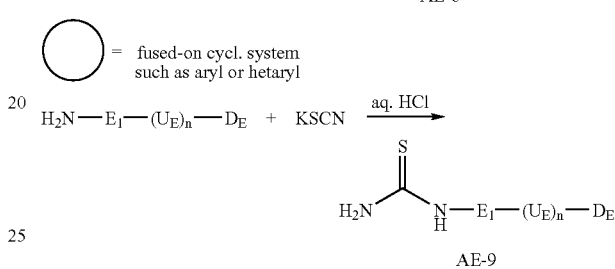

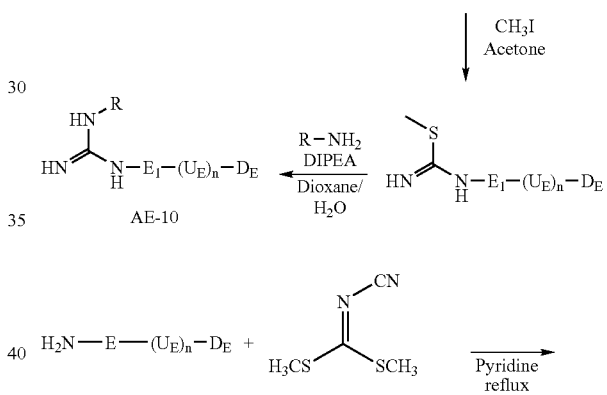

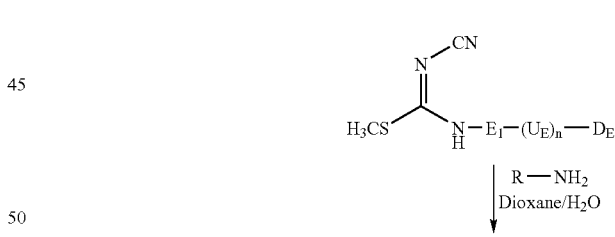

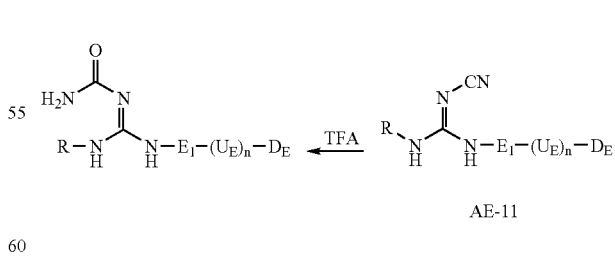

Compounds of the general formula AE-13 can be prepared in analogy to Froeyen et al., *Phosphorus Sulfur Silicon Relat. Elem.* 1991, 63, 283–293, and AE-14 in analogy to Yoneda et al., *Heterocycles* 1998, 15 N'-1, Spec. Issue, 341–344 (Scheme 6). Corresponding compounds can also be prepared in analogy to WO 97/36859:

Scheme 6

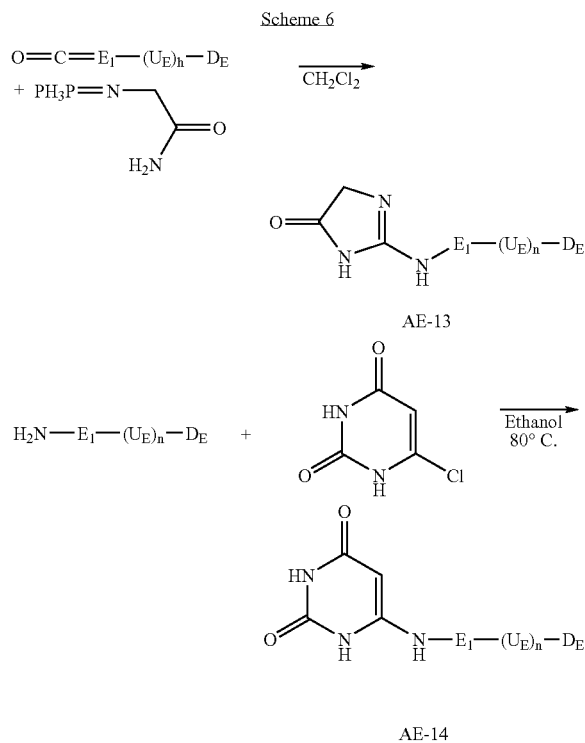

AE-13

AE-14

Compounds of the general formula AE-15 can be prepared as in Synthesis 1981, 963–965 or Synth. Commm. 1997, 27 (15), 2701–2707, and AE-16 in analogy to J. Org. Chem. 1991, 56 (6), 2260–2262 (Scheme 7).

The invention further relates to the use of the structural element of the formula $I_{GL}$ $$—G—L \qquad I_{GL}$$

for preparing compounds which bind to integrin receptors.

The invention further relates to drugs containing the structural element of the formula $I_{GL}$.

The invention further relates to pharmaceutical preparations containing at least one compound of the formula I in addition to conventional pharmaceutical excipients.

The compounds according to the invention can be administered orally or parenterally (subcutaneously, intravenously, intramuscularly, intraperitoneally) in a conventional way. Administration can also take place with vapors or sprays through the nasopharyngeal space. The compounds according to the invention can also be introduced by direct contact with the affected tissue.

The dosage depends on the age, condition and weight of the patient and on the mode of administration. The daily dose of active ingredient is usually between about 0.5 and 50 mg/kg of body weight on oral administration and between about 0.1 and 10 mg/kg of body weight on parenteral administration.

The novel compounds can be used in conventional solid or liquid pharmaceutical forms, for example as uncoated or (film-) coated tablets, capsules, powders, grandules, suppositories, solutions, ointments, creams or sprays. These are produced in a conventional way. The active ingredients can for this purpose be processed with conventional pharmacuetical excipients such as tablet binders, bulking agents, preservatives, tablet disintegrants, flow regulators, plasticizers, wetting agents, dispersants, emulsifiers, solvents, release-slowing agents, antioxidants and/or propellant gases (cf. H. Sucker et al.: Pharmazeutische Technologie, Thieme-Verlag, Stuttgart, 1991). The administration forms obtained

Scheme 7

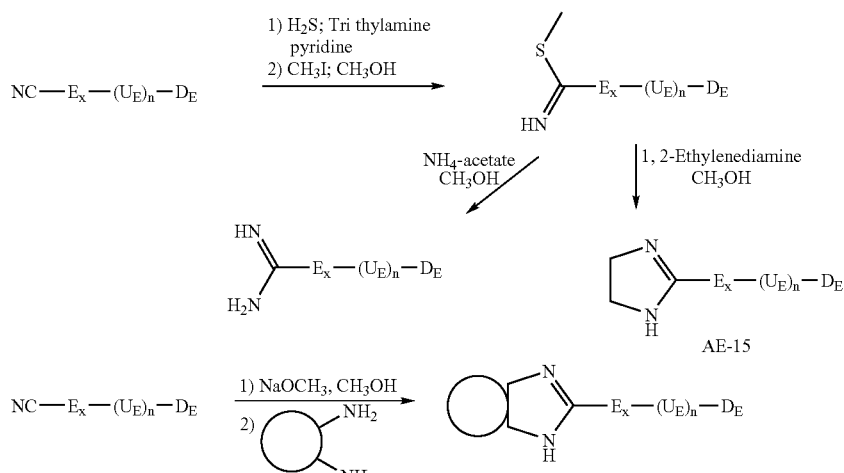

 = fused-on cycl. system such as aryl, hetaryl, cycloalkyl $E_x = —(CR_E^3R_E^4)_{k1}—(L_E)_{k2}—(CR_E^5R_E^6)_{k3}—(Q_E)_{k4}—(CR_E^7R_E^8)_{k5}—(T_E)_{k6}—(CR_E^9R_E^{10})_{k7}—$ in this way normally contain the active ingredient in an amount of from 0.1 to 90% by weight.

The invention further relates to the use of compounds of the formula I for producing drugs for treating diseases. The compounds of the formula I can be used for treating human and animal diseases. The compounds of the formula I bind to integrin receptors. They are therefore suitable preferably as integrin receptor ligands and for producing drugs for treating diseases in which an integrin receptor is involved, in particular for treating diseases associated with dysregulation, that is to say an increase or decrease, of the interaction between integrins and their natural ligands.

Integrin receptor ligands mean agonists and antagonists.

An increased or decreased interaction means both an increased or decreased expression of the natural ligand and/or of the integrin receptor and thus an increased or decreased amount of natural ligand and/or integrin receptor or an increased or decreased affinity of the natural ligand for the integrin receptor.

There is dysregulation of the interaction between integrins and their natural ligands compared with the normal state, that is to say an increase or decrease, when this dysregulation does not correspond to the physiological state. An increased or decreased interaction may lead to pathophysiological situations.

The level of dysregulation leading to a pathophysiological situation depends on the individual organism and on the site and nature of the disorder.

Preferred integrin receptors for which the compounds of the formula I according to the invention can be used are the $\alpha_5\beta_1$, $\alpha_4\beta_1$, $\alpha_v\beta_5$ and $\alpha_v\beta_3$ integrin receptors.

It is particularly preferred for the compounds of formula I to bind to the $\alpha_v\beta_3$ integrin receptor and they can thus be used particularly preferably as ligands of the $\alpha_v\beta_3$ integrin receptor and for treating diseases in which the interaction between $\alpha_v\beta_3$ integrin receptor and its natural ligand is increased or decreased.

The compounds of the formula I are preferably used for treating the following diseases:
cardiovascular disorders such as atherosclerosis, restenosis after vessel injury or stent implantation, and angioplasty (neointima formation, smooth muscle cell migration and proliferation),
acute kidney failure,
angiogenesis-associated microangiopathies such as, for example, diabetic angiopathies or retinopathy or rheumatoid arthritis,
vascular occlusion mediated by blood platelets, arterial thrombosis,
stroke, reperfusion damage after myocardial infarct or stroke,
cancers such as, for example, in tumor metastasis or tumor growth (tumor-induced angiogensis),
osteoporosis (bone resorption after chemotaxis and adhesion of osteoclasts to bone matrix),
high blood pressure, psoriasis, hyperparathyroidism, Paget's disease, malignant hypercalcemia, metastatic osteolytic lesions, inflammation, wound healing, heart failure, congestive heart failure CHF, and for
antiviral, antimycotic, antiparasitic or antibacterial therapy and prophylaxis (adhesion and internalization).

The compounds of the formula I can advantageously be administered in combination with at least one other compound in order to achieve an improved curative effect in a number of indications. These other compounds may have the same or a different mechanism of action as the compounds of the formula I.

The pharmaceutical preparations may therefore contain, besides the compounds of the formula I and the conventional pharmaceutical excipients, at least one other compound, depending on the indication in each case selected from one of the following 10 groups.

Group 1:
inhibitors of blood platelet adhesion, activation or aggregation, such as, for example, acetylsalicylic acid, lysine acetylsalicylate, piracetam, dipyridamole, abciximab, thromboxane antagonists, fibrinogen antagonists such as, for example, tirofiban, or inhibitors of ADP-induced aggregation such as, for example, ticlopidine or clopidogrel, anticoagulants which impede thrombin activity or formation, such as, for example, inhibitors of IIa, Xa, XIa, IXa or VIIa, antagonists of blood platelet-activating compounds and selectin antagonists
for the treatment of vascular occlusion mediated by the blood platelets, or thrombosis, or Group 2:
inhibitors of blood platelet activation or aggregation such as, for example, GPIIb/IIIa antagonists, thrombin inhibitors or factor Xa inhibitors or ADP receptor antagonists, serine protease inhibitors, fibrinogen-reducing compounds, selectin antagonists, antagonists of ICAM-1 or VCAM-1 inhibitors of leukocyte adhesion inhibitors of vessel wall transmigration, fibrinolysis-modulating compounds such as, for example, streptokinase, tPA, plasminogen activation stimulants, TAFI inhibitors, XIa inhibitors or PAI-1 antagonists, inhibitors of complement factors, endothelin receptor antagonists, tyrosine kinase inhibitors, antioxidants and interluekin 8 antagonists
for the treatment of myocardial infarct or stroke, or Group 3:
endothelin antagonists, ACE inhibitors, angiotensin receptor antagonists, endopeptidase inhibitors, beta blockers, calcium channel blockers, phosphodiesterase inhibitors and caspase inhibitors
for the treatment of congestive heart failure, or Group 4:
thrombin inhibitors, inhibitors of factor Xa, inhibitors of the coagulation pathway leading to thrombin formation, such as, for example, heparin or low molecular weight heparins, inhibitors of blood platelet adhesion, activation or aggregation, such as, for example, GPIIb-IIIa antagonists or antagonists of blood platelet adhesion and activation mediated by vWF or GPIb, endothelin receptor antagonists, nitric oxide synthase inhibitors, CD44 antagonists, selectin antagonists, MCP-1 antagonists, inhibitors of signal transduction in proliferating cells, antagonists of the cellular response mediated by EGF, PDGF, VEGF or bFGF and antioxidants
for the treatment of restenosis after vessel injury or stent implantation, or Group 5:
antagonists of the cellular response mediated by EGF, PDGF, VEGF or bFGF, heparin or low molecular weight heparins or other GAGs, inhibitors or MMPs, selectin antagonists, endothelin antagonists, ACE inhibitors, angiotensin receptor antagonists and glycosylation inhibitors or AGE formation inhibitors or AGE breakers and antagonists of their receptors such as, for example, RAGE, for the treatment of diabetic angiopathies or Group 6:
lipid-lowering compounds, selectin antagonists, antagonists of ICAM-1 or VCAM-1 heparin or low molecular weight heparins or other GAGs, inhibitors or MMPs, endothelin antagonists, apolipoprotein Al antagonists, cholesterol antagonists, HMG-CoA reductase inhibitors, ACAT inhibitors, ACE inhibitors, angiotensin receptor antagonists, tyrosine kinase inhibitors, protein kinase C inhibitors, calcium channel blockers, LDL receptor function stimulants, antioxidants LCAT mimetics and free radical scavengers for the treatment of atherosclerosis or Group 7:
cytostatic or antineoplastic compounds, compounds which inhibit proliferation, such as, for example, kinase inhibitors and heparin or low molecular weight heparins or other GAGs for the treatment of cancer, preferably for inhibiting tumor growth or metastasis, or Group 8:
compounds for antiresorptive therapy, compounds for hormone replacement therapy such as, for example, estrogen or progesterone antagonists, recombinant human growth hormone, bisphosphonates such as, for example, alendronate compounds for calcination therapy, calcitonin simulants, calcium channel blockers, bone formation stimulant such as, for example, growth factor agonsits, interleukin-6 antagonists and Src tyrosine kinase inhibitors for the treatment of osteoporosis or Group 9:
TNF antagonists, antagonists of VLA-4 or VCAM-1, antagonists of LFA-1, Mac-1 or ICAMs, complement inhibitors, immunosuppressants, interleukin-1, -5 or -8 antagonists and dihydrofolate reductanse inhibitors for the treatment of rheumatoid arthritis or Group 10:
collagenase, PDGF antagonists and MMPs for improved wound healing.

A pharmaceutical preparation containing at least one compound of the formula I, where appropriate pharmaceutical excipients and at least one other compound, depending on the indication in each case selected from one of the above groups, means a combined administration of at least one of the compounds of the formula I with at least one other compound in each case selected from one of the groups described above and, where appropriate, pharmaceutical excipients.

Combined administration can be effected by a mixture of substances containing at least one compound of the formula I, where appropriate pharmaceutical excipients and at least one other compound, depending on the indication in each case chosen from one of the above groups, but also spatially and/or temporally separate.

For spatially and/or temporally separate administration, the components of the pharmaceutical preparation, the compounds of the formula I and the compounds selected from one of the aforementioned groups, are administered spatially and/or temporally separately.

For the treatment of restenosis after vessel injury or stenting, the administrations of the compounds of the formula I alone or in combination with at least one compound selected from Group 4 can take place locally at the affected sites. It may also be advantageous to coat the stents with these compounds.

For the treatment of osteoporosis, it may be advantageous to carry out administration of compounds of the formula I in combination with an antiresorptive or hormone replacement therapy.

The invention accordingly relates to the use of the aforementioned pharmaceutical preparations for producing drugs for the treatment of diseases.

In a preferred embodiment, the invention relates to the use of the aforementioned combined pharmaceutical preparations for producing drugs for the treatment of vascular occlusion mediated by blood platelets, or thrombosis on use of compounds of group 1, myocardial infarct or stroke on use of compounds of group 2, congestive heart failure on use of compounds of group 3, restenosis after vessel injury or stent implantation on use of compounds of group 4, diabetic angiopathies on use of compounds of group 5, atherosclerosis on use of compounds of group 6, Cancer on use of compounds of group 7, osteoporosis on use of compounds of group 8, rheumatoid arthritis on use of compounds of group 9, wound healing on use of compounds of group 10, The following examples illustrate the invention, the selection of these examples being non-limiting.

I. SYNTHESIS EXAMPLES

I.A. Precursors

Example 1

(1-Pyridin-2-ylpiperidin-4-yl)methanamine (1)

a.) tert-Butyloxycarbonyl-4-(aminomethyl)-1-piperidine (14 g; 65.33 mmol; preparation by method of Prugh et al., Synthetic Communications 22 (16), 2361–2365 (1992)) was dissolved in 50 ml of THF and, at 5° C. 6.6 g of N-methylmorpholine and 12.6 g of benzyl cloroformate were added, and the mixture was stirred for about 2 h. The mixture was concentrated, and the residue was taken up in $CH_2Cl_2$, washed with saturated NaCl solution, dried and filtered. 23.5 g of a yellow oil remained after concentration and were crystallized from methyl tert-butyl ether. 18 g; ESI-MS $[M+H^+]=293.15$ b.) 25 ml of TFA were added to tert-butyloxycarbonyl-4-({[(benzyloxy)carbonyl]amino}methyl)-1-piperidine 1a (15 g; 43.05 mmol) in 125 ml of $CH_2Cl_2$ at 0° C., and the mixture was stirred at 10° C. for 20 min and then at RT. Concentration of the mixture and crystallization of the resulting residue from diethyl ether afforded 14.5 g of the free amine as TFA salt (ESI-MS $[M+H^+]=249.25$; m.p.: 109–110° C.). 5 g of the TFA salt and 2.79 g of ethyldiisopropylamine (DIPEA) were heated to reflux in 15 ml of 2-fluoropyridine. After the reaction was complete, the mixture was concentrated, and the residue was taken up in ethyl acetate and washed 4× with $H_2O$ and saturated NaCl solution. Drying, filtration and concentration afforded 4.49 g of a pale brown oil, which was crystallized from n-pentane. 4.02 g; ESI-MS $[M+H^+]=362.15$ c.) 3.9 g of 1b in 150 ml of $CH_3OH$ were hydrogenated with 0.2 g of Pd (10% on carbon) under saturated conditions.

Filtration of the reaction mixture through Celite and concentration afforded 2.3 g; ESI-MS [M+H$^+$]=192.15.

$^1$H-NMR (270 MHz; DMSO-d$_6$) δ (ppm) 8.1 (m, 1H), 7.5 (m, 1H), 6.8 (m, 1H), 6.55 (m, 1H), 4.3 (m, 2H), 2.7 (m, 2H), 2.45 (m 2H), 1.75 (m 2H), 1.5 (m 1H), 1.05 (m, 2H).

Example 2

N-(Piperidin-4-ylmethyl)pyridin-2-amine (trifluoroacetate) (2)

a.) tert-Butyloxycarbonyl-4-(aminomethyl)-1-piperidine (3 g; 14 mmol) and 10 ml of 2-fluoropyridine were refluxed for 4 h. Concentration and trituration of the crude product in n-pentane afforded 3 g of a white solid, m.p.: 126–130° C.; ESI-MS [M+H$^+$]=292.15.

b.) 1 g of the Boc-protected amine was dissolved in 5 ml of CH$_2$Cl$_2$ and, after addition of 10 ml of TFA at 0° C., stirred at room temperature for 2 h. Evaporation of the reaction mixture afforded 1.9 g of a yellowish oil, which was reacted directly without further purification; ESI-MS [M+H$^+$]=192.15.

Example 3

N-[4-(Aminomethyl)benzyl]pyridin-2-amine (hydrochloride) (3)

a.) 2-Aminopyridine (20 g, 212 mmol) was dissolved in 100 ml of CH$_3$OH, the pH was adjusted to 6 with isopropanolic HCl, 36.2 g (276 mmol) of p-cyanobenzaldehyde were added, and then 9.3 g (148 mmol) of sodium cyanoborohydride were added in portions in 1 h. The yellow suspension was stirred overnight and then concentrated. The residue was taken up in 100 ml of water and adjusted to pH>10 with KOH. The aqueous phase was saturated with NaCl and extracted 3× with diethyl ether. The ether phase was filtered, and the filtrate was washed 3× with FeSO$_4$ solution, dried and concentrated. Chromatography of the residue afforded 40.55 g; ESI-MS [M+H$^+$]=210.15.

b.) 10 g of the nitrile 3a were introduced into 280 ml of methanolic ammonia solution and, after addition of 10 g of methanol-washed Raney nickel, hydrogenated at RT for 28 h. The residue obtained after filtration and concentration was purified by chromaotgraphy on silica gel. The main fraction obtained in this way was dissolved in diethyl ether, mixed with isopropanolic HCl and crystallized overnight. The precipitate which formed was filtered off with suction, washed and boiled with 500 ml of isopropanol. The product was filtered off hot with suction and dried. 11.2 g; ESI-MS [M+H$^+$]=214.05.

Example 4

[4-(1H-Benzimidazol-2-yl)-1,3-thiazol-2-yl]methanamine (trifluoroacetate) (4)

The tert-butyl (4-cyano-1,3-thiazol-2-yl)methylcarbamate used as precursor was prepared by standard methods from 2-(aminomethyl)-1,3-thiazole-4-carbonitrile (WO 98/06741).

a.) 1.89 g of a 30% NaOCH$_3$ solution were added to tert-butyl (4-cyano-1,3-thiazol-2-yl)methylcarbamate (2.5 g; 10.45 mmol) in 25 ml of CH$_3$OH, and the mixture was stirred at room temperature for 2 h. Addition of 1.9 g of 1,2-phenylene-diamine bishydrochloride was followed by stirring overnight, and then the reaction mixture was added to 100 ml of H$_2$O and filtered, and the solid obtained in this way was dried in vacuo. 3.0 g; ESI-MS: [M+H$^+$]=331.15

$^1$H-NMR (400 MHz; DMSO-d$_6$) δ (ppm) 8.25 (s, 1H), 7.95 (m, 1H), 7.65 (m, 1H), 7.55 (m, 1H), (m, 1H), 7.2 (m, 2H), 4.55 (m, 2H), 1.45 (s, 9H).

b.) 1.0 g of the Boc compound 4a was dissolved in 10 ml of CH$_2$Cl$_2$ and, after addition of 10 ml of TFA at 0° C., stirred at room temperature for 2 h. Evaporation of the reaction mixture and trituration with n-pentane afforded 1.5 g of the amine as trifluoroacetate. Mp.: 229–230° C.; ESI-MS: [M+H$^+$]=231.05

Example 5

[4-(1H-Benzimidazol-2-yl)-thien-2-yl]methanamine (trifluoroacetate) (5)

The tert-butyl (4-cyanothien-2-yl)methylcarbamate used as precursor was prepared by standard methods from 5-(aminomethyl)-3-thiophenecarbonitrile (WO 98/06741).

a.) 3.6 g of a 30% NaOCH$_3$ solution were added to tert-butyl (4-cyanothien-2-yl)methylcarbamate (5 g; 20.98 mmol) in 70 ml of CH$_3$OH, and the mixture was stirred at room temperature for 2 h. Addition of 3.6 of 1,2-phenylene-diamine bishydrochloride was followed by stirring overnight, and then the reaction mixture was added to 50 ml of H$_2$O and reacted with CH$_2$Cl$_2$. Drying and concentrating the org. phase afforded 4.3 g of a yellow solid, which was purified by chromatography on silica gel (CH$_2$Cl$_2$/CH$_3$OH 1%→10%). 1.6 g; ESI-MS [M+H$^+$]=333.15 b.) 1.5 g of the Boc compound 5a were dissolved in 10 ml of CH$_2$Cl$_2$ and, after addition of 15 ml of TFA at 0° C., stirred at room tmeperature for 2 h. Evaporation of the reaction mixture and trituration with n-pentane afforded 1.5 g of the amine as trifluoroacetate.

Example 6

[4-(1H-Benzimidazol-2-yl)phenyl]methanamine (trifluoroacetate) (6)

a.) Di(tert-butyl) 4-cyanobenzylimidodicarbonate (10 g; 30.08 mmol; preparation by method of Lila et al., *Synth. Comm.* 28, 23, 1998, 4419 et seq.) in 200 ml of pyridine were mixed with 45 ml of triethylamine and saturated with H$_2$S at 0° C. for 1.5 h. The reaction mixture was left to stand at RT overnight and then evaporated. The residue obtained in this way was then triturated with diethyl ether, filtered off with suction and dried (8.5 g).

b.) 6 g of the thioamide 6a (16.37 mmol) in 40 ml of dry CH$_2$Cl$_2$ were alkylated with 23.2 g of CH$_3$I at RT overnight, and the mixture was then evaporated. The residue obtained in this way was taken up in 40 ml of CH$_3$OH and, after addition of 1.95 g of 1,2-phenylenediamine, again stirred overnight. Evaporation of the reaction mixture and trituration of the solid with n-pentane afforded 6.9 g of the required benzimidazole. Mp.: >170° C. (decomposition); ESI-MS: [M+H$^+$]=424.25 c.) 3 g of the bis-Boc compound 6b were dissolved in 7 ml of CH$_2$Cl$_2$ and, after addition of 20 ml of TFA at 0° C., stirred at room temperature for 3 h. Evaporation of the reaction mixture and trituration with n-pentane afforded 3.2 g of the amine (trifluoroacetate); ESI-MS; [M+H$^+$]=224.05.

Example 7

[3-(1H-Benzimidazol-2-yl)phenyl]methanamine (trifluoroacetate) (7)

a.) 3-(Chloromethyl)benzonitrile (30 g; 197.9 mmol) and di-tert-butyl iminodicarboxylate were reacted in analogy to Lila et al., Synth. Comm. 28, 23, 1998, 4419, to give di(tert-butyl) 3-cyanobenzylimidodicarbonate. 65 g of a reddish oil were obtained and were employed without further purification.

b.) Conversion into the thioamide took place in analogy to 6b with 16.5 g; trituration of the crude product with n-pentane afforded 18.1 g of thioamide as yellow solid.

c.) Alkylation and reaction with 1,2-phenylenediamine were carried out in analogy to the conditions described in 6c; starting from 7.4 g of the thioamide, trituration of the crude product with n-pentane resulted in 8.5 g of the appropriate benzimidazole. ESI-MS: [M+H$^+$]=424.25 d.) 7.2 g of the bis-Boc compound 7c were dissolved in 20 ml of CH$_2$Cl$_2$ and, after addition of 50 ml of TFA at 0° C., stirred at room temperature for 3 h. Evaporation of the reaction mixture and trituration with methyl tert-butyl ether afforded 3.2 g of the amine (trifluoroacetate); ESI-MS: [M+H$^+$]=224.15.

Example 8

N-[4-(Aminomethyl)phenyl]-N'-benzylurea (trifluoroacetate) (8)

a.) Triethylamine (6.8 g, 67.12 mmol) and then, at 0° C., di-tert-butyldicarbonate (18.6 g, 85.00 mmol) were added to 4-aminobenzylamine (10.0 g, 81.85 mmol) in 150 ml of CH$_2$Cl$_2$. The mixture was stirred at 0° C. for 1 h and then at RT for 2 h. For workuyp, 150 ml of a 1% aqueous citric acid solution were added, the phases were separated, and the aqueous phase was back-extracted twice with CH$_2$Cl$_2$ (150 ml). Renewed washing with H$_2$O, drying of the combined organic phases with Na$_2$SO$_4$ and evaporation afforded a solid, which was stirred with a little diisopropyl ether, filtered off with suction and dried. 13.0 g; ESI-MS [M+H$^+$]=167.05.

$^1$H-NMR (360 MHz, CDCl$_3$) δ (ppm): 7.04 (2H, d), 6.61 (2H, d), 4.78 (1H, s br.), 4.17 (2H, d), 3.67 (2H, s br.), 1.46 (9H, s).

b.) Benzyl isocyanate (2.40 g, 18.00 mmol) was added to a solution, cooled in ice, of the protected amine 8a (4.0 g, 17.99 mmol) and triethylamine (1.82 g, 18.00 mmol) in 220 ml of toluene/DMF 10:1. The reaction mixture was stirred at RT overnight. It was possible for part of the urea formed to be filtered off directly as precipitate and dried. The filtrate was washed twice with H$_2$O, dilute tartaric acid to pH 3 and again twice with H$_2$O to pH 5, and the organic phase was then dried and evaporated. A total of 6.0 g was obtained in this way; ESI-MS [M+H$^+$–$^t$Bu]=300.15.

c.) The urea 8b obtained in this way was introduced into 90 ml of CH$_2$Cl$_2$ and, at 0° C., TFA (2.24 g, 196.25 mmol)—dissolved in 90 ml of CH$_2$Cl—was added dropwise. After 3 h, a further 1 ml of TFA was added, and then the mixture was stirred at RT overnight. After renewed addition of 1 ml of TFA, the mixture was stirred for 5 h and then poured into ice-water and extracted with ethyl acetate (2×50 ml). The aqueous phase was made basic with 2 N NaOH solution and extracted with CH$_2$Cl$_2$ (2×50 ml). The insoluble portion between the phases was removed by filtration and dried. 4 g; ESI-MS [2M+H$^+$]=511.35

$^1$H-NMR (200 MHz, DMSO) δ (ppm): 8.52 (1H, s), 7.39–7.07 (9H, m), 6.62 (1H, t), 4.27 (2H, d), 3.61 (2H, s).

Example 9

N-{[5-(Aminomethyl)thien-3-yl]methyl}pyridin-2-amine (trifluoroacetate) (9)

a.) A solution of tert-butyl (4-cyanothien-2-yl)methylcarbamate (7 g; 29.4 mmol) in 120 ml of ethanol was saturated with NH$_3$ and then hydrogenated in the presence of Raney nickel (9 g of aqueous suspension; decanted with ethanol) under standard conditions. Filtration of the reaction mixture, evaporation and chromatography of the resulting residue on silica gel (CH$_2$Cl$_2$/CH$_3$OH plus aqueous NH$_3$) afforded 4.4 g of the amine as yellowish oil.

b.) 1.2 g of the amine 9a (4.3 mmol), 0.6 g of ethyldiisopropylamine and 15 g of 2-fluoropyridine were refluxed for 20 h. The residue obtained after evaporation of the mixture was taken up in CH$_2$Cl$_2$, washed with 0.1 N HCl and saturated NaCl solution, dried and then evaporated again. 1 g; ESI-MS [M+H$^+$]=320.15 c.) 0.9 g of the Boc-protected amine 9b was dissolved in 10 ml of CH$_2$Cl$_2$ and, after addition of 5 ml of TFA at 0° C., stirred at room temperature for 1 h. Evaporation of the reaction mixture afforded 1.65 g of a brownish oil, which was reacted directly without further purification (ESI-MS [M+H$^+$]=220.05).

Example 10

2-[4-(1H-Benzimidazol-2-yl)phenyl]ethanamine (trifluoroacetate) (10)

a.) 7 g of 4-(2-aminoethyl)benzonitrile was converted into the corresponding Boc derivative under standard conditions. Trituration of the resulting crude product afforded 7.3 g of a white solid; ESI-MS [M+H$^+$]=247.15 b.) 4 g of the Boc derivatives 10a were converted into the thioamide in analogy to 6b. Trituration of the crude product with n-pentane afforded 4.2 g of a yellowish solid which was then alkylated and reacted with 1,2-phenylenediamine to give the benzimidazole in analogy to 6b. The crude product obtained in this was purified by chromatography on silica gel (CH$_2$Cl$_2$/CH$_3$OH 4%→50%). 4.8 g; ESI-MS [M+H$^+$]=338.15 c.) 4.8 g of the Boc-protected amine 10b were dissolved in 15 ml of CH$_2$Cl$_2$ and, after addition of 30 ml of TFA at 0° C., stirred at room temperature for 3 h. Evaporation of the reaction mixture and trituration with n-pentane afforded 7.3 g of solid. ESI-MS [M+H$^+$]=238.05

$^1$H-NMR (400 MHz, DMSO) δ (ppm): 8.30 (m, 2H, 8.0 (s br, 3H), 7.85, 7.7 and 7.55 (each m, 2H), 3.18 (m, 2H), 3.05 (m, 2H).

Example 11

N$^1$-Pyridin-2-ylethane-1,2-diamine (11)

Preparation took place in analogy to Nicolaou et al.; Bioorg. Med. Chem. 6 (1998), 1185–1208; starting from 100 g of 2-bromopyridine, distillation of the crude product resulted in 48.4 g.

Example 12

N$^1$-Pyridin-2-ylpropane-1,3-diamine (12)

2-Bromopyridine (100 g; 0.633 mol) and 1,3-diaminopropane (234.5 g; 3.16 mol) was refluxed for 7 h. After the reaction was complete, the mixture was evaporated. Distillation of the remaining residue under oil pump vacuum afforded 43 g of the required product.

$^1$H-NMR (360 MHz, CDCl$_3$) δ (ppm); 8.05 (d, 1H), 7.36 (t, 1H), 6.51 (t, 1H), 6.36 (d, 1H), 4.98 (s, 1H), 3.35 (s, 2H), 2.82 (t, 2H), 1.73 (m, 1H), 1.32 (m, 2H).

Example 13

N$^1$-methyl-N$^2$-pyridin-2-ylethane-1,2-diamine (acetate) (13)

a.) tert-Butyl 2-aminoethyl(methyl)carbamate (2.8 g; 16.1 mmol) and 19 ml of 2-fluoropyridine were refluxed for about 23 h. Evaporation of the reaction mixture afforded 4 g of a brown oil (ESI-MS [M+$^+$]=252.15) which was directly reacted further.

b.) 2 g of the crude product 13a were stirred in 30 ml of TFA at RT overnight. The mixture was evaporated and purified by MPLC on RP silica gel (CH$_2$CN/H$_2$O plus 0.1% acetic acid). 2.2 g; ESI-MS [M+H$^+$]=152.1

Example 14

4-(Aminomethyl)-N-benzylpiperidine-1-carboxamide (14)

a.) Benzyl piperidin-4-yl-ylmethylcarbamate (trifluoroacetate) (4 g; 11.04 mmol; preparation as described for 2) was suspended in 60 ml of toluene and refluxed with 1.43 g of ethyldiisopropylamine and benzyl isocyanate (1.62 g, 12.14 mmol) for 4 h. The residue after evaporation of the reaction mixture was taken up in CH$_2$Cl$_2$ and extracted 2× each with 1 N HCl and saturated NaCl solutions, and the org. phase was dried and concentrated. 4.2 g; ESI-MS [M+H$^+$]=382.25 b.) 4 g of benzylurea 14a were dissolved in a mixture of ethyl acetate/CH$_3$OH 3:1 with heating and, after addition of 0.2 g of 10% Pd on activated carbon, hydrogenated under standard conditions at 35 to 40° C. After the reaction was complete, the mixture was filtered through Celite and evaporated. 2.8 g; ESI-MS [M+H$^+$]=248.15

$^1$H-NMR (400 MHz, DMSO) δ ppm: 7.4–7.15 (m, 11H), 7.05 (t, 1H), 5.08 (s, 2H), 4.25 (d, 2H), 3.95 (d, 2H), 2.8 and 2.65 (each m, 2H), 1.6 (m, 3H), 0.95 (m, 2H).

Example 15 tert-Butyl (5,6-dimethyl-1H-benzimidazol-2-yl)methylcarbamate (15)

1.3 g of a 30% NaOCH$_3$ solution were added to tert-butyl cyanomethylcarbamate (0.4 g; 25.6 mmol) in 10 ml of CH$_3$OH, and the mixture was stirred at room temperature for 1 h. After addition of 5.15 g of 4,5-diamino-ortho-xylene bishydrochloride, the reaction mixture was stirred overnight and then added to 100 ml of H$_2$O, and the solid obtained by filtration was dried at 30° C. in vacuo. 0.5 g; ESI-MS [M+H$^+$]=276

The amine required for the subsequent reaction was obtained by eliminating the Boc group with TFA (under standard conditions); the isolated TFA salts were then employed directly in the appropriate couplings.

Example 16

[6-(1H-Benzimidazol-2-yl)pyridin-3-yl]methanamine (16)

a.) Preparation took place in analogy to 1 starting from tert-butyl (6-cyanopyridin-3-yl)methylcarbamate (6.0 g, 25.72 mmol); crystalline of the crude product from ethanol afforded 5.15 g; ESI-MS [M+H$^+$]=325 b.) 0.55 g of the Boc-protected amine 16a in 10 ml of CH$_2$Cl$_2$ were mixed with 5 ml of TFA and stirred at RT for 2 h. Evaporation of the reaction mixture afforded 0.95 g of a white solid; ESI-MS [M+H$^+$]=225.25

Example 17

3-Amino-N-(1H-imidazol-2-yl)propanamide (17)

a.) Z-β-alanine (10 g; 44.8 mmol) was dissolved in 200 ml of DMF, and 15.86 g (3.5 eq) of N-methylmorpholine and 5.9 g (0.5 eq) of 2-aminoimidazole sulfate were added. At −10° C., 7.87 g (1.3 eq) of HOBt and 11.16 g (1.3 eq) of EDC were added, and the mixture was stirred while warming to RT for 1 h and then for 18 h. 150 ml of ether were added, whereupon a white solid precipitated and was filtered off with suction. The residue was washed with cold ether and suspended in ethyl acetate, and 1 N HCl was added until the reaciton was acidic. The aqueous solution was extracted 1× with ethyl acetate, and then the aqueous phase was adjusted to a basic pH with 10% NaOH at 4° C. The resulting precipitate was filtered off with suction and washed with water. 5.4 g; ESI-MS [M+H$^+$]=289.05 b.) 5.3 g of the Z compound 17a were suspended in 250 ml of ethanol, and 530 mg of 10% Pd on activated carbon were added. Hydrogenation was carried out with H$_2$ at RT for 18 h and then, after dilution with CH$_3$OH, the suspension was boiled, wehreupon the product precipitate dissolved. Filtration and concentration of the solution afforded 1.5 g. ESI-MS [M+H$^+$]=155.05

Example 18 tert-Butyl 4-(aminomethyl)benzylcarbamate (18)

24 g (111 mmol) of di-t-butyldicarbonate were added dropwise to 4-(aminomethyl)benzylamine (50.7 g, 372 mmol) in 1000 ml of CH$_2$Cl$_2$ at 0° C. The mixture was stirred at RT for 21 h, then diluted with CH$_2$Cl$_2$ and washed with 5% Na$_2$CO$_3$ solution, and the CH$_2$Cl$_2$ phase was dried and concentrated. The residue was dissolved in 1 N HCl and extracted 2× with diethyl ether. The aqueous phase was adjusted to pH 10 with 50% NaOH and extracted with ethyl acetate. The org. phases were combined, dried and concentrated. 1.48 g; ESI-MS [2M+H$^+$]=473.25

Example 19

N$^1$-Pyridin-2-ylcyclohexane-1,2-diamine (19)

2-Bromopyridine (20 g; 127.6 mmol) and 72.3 g (633 mmol) of 1,2-diaminocyclohexane (cis/trans) were mixed with 15 ml of pyridine and stirred at 120° C. for a total of 5×8 h and at RT for 2 weeks. The residue which became solid in the cold was stirred with n-heptane, and the solid was filtered off with suction and discarded. The mother liquor was concentrated, the residue was taken up in water, and the pH was adjusted to 8 to 9 with HCl. The solution was extracted with CH$_2$Cl$_2$, and the organic phase was washed with water and concentrated. The remaining oil slowly crystallized and was then stirred with pentane, filtered off with suction and triturated anew with methyl t-butyl ether and filtered off with suction. The resulting product (4.9 g) consists of 85% of the trans compound and 15% of the cis compound.

$^{13}$C-NMR (400 MHz, CDCl$_3$), δ (ppm)=159.09 (Py-C-2/trans), 158.46 (Py-C-2/cis), 58.19, 56.16, 35.03, 32.74, 25.28, 25.03, (cyclohexane ring/trans), 52.28, 49.78, 32.29, 27.75 (cyclohexane ring/cis).

Example 20

N-[4-(Aminomethyl)-1,3-thiazol-2-yl]-N'-benzylurea (hydrochloride) (20)

a.) A solution of 123 g of pyridinium bromide perbromide in 600 ml of THF was slowly added dropwise to 2-(2-oxopropyl)-1H-isoindole-1,3-(2H)-dione (70 g; 0.345 mol) in 600 ml of THF, and the mixture was then stirred for about 3 h. For workup, the precipitated solid was filtered off, the mother liquor was concentrated, the residue was taken up in ethyl acetate, and the solution was thoroughly washed with aqueous bisulfate solution. Drying and concentrating afforded 150 g of a yellow oil, which was triturated with methyl tert-butyl ether. 63.4 g; m.p.: 142–143° C.; ESI-MS [M+H$^+$]=283.95 b.) 2-(3-Bromo-2-oxopropyl)-1H-isoindole-1,3(2H)-dione 20a (6 g; 21.27 mmol) and thiourea (2 g; 26.27 mmol) were stirred in 70 ml of THF at RT for about 2 h. The resulting precipitate was filtered off with suction and dried. 5 g; ESI-MS [M+H$^+$]=260.05 c) 2-[(2-Amino-1,3-thiazol-4-yl)methyl]-1H-isoindole-1,3(2H)-dione hydrobomide 20b (4.5 g; 13.23 mmol), benzyl isocyanate (1.8 g, 13.52 mmol) and 1.7 g of ethyldiisopropylamine were refluxed in 50 ml of toluene. After the reaction was complete, the mixture was concentrated, the reside was taken up in CH$_2$Cl$_2$, and the solution was washed with 1 N HCl, saturated NaHCO$_3$ and NaCl solutions. Drying and concentrating afforded 4.7 g of orange solid, which was recrystallized from CH$_3$OH. 3.0 g; ESI-MS [M+H$^+$]=393.05

$^1$H-NMR (360 MHz, DMSO) δ ppm: 10.65 (s, 1H), 7.9 (m, 4H), 7.25 (m, 5H), 6.85 (s, 1H), 4.7 (s, 2H), 4.35 (d, 2H), d) N-Benzyl-N'-{4-[(1,3-dioxo-1,3-dihydro-2H-isoindol-2-yl)methyl]-1,3-thiazol-2-yl}urea 20c (3 g; 7.64 mmol) was suspended in 50 ml of CH$_3$OH and then, after addition of 2 g of hydrazine hydrate, stirred at RT for 2 h. The resulting solid was filtered off, and the resulting mother liquor was evaporated and triturated with 0.5 N HCl. Renewed filtration and concentration of the mother liquor led to enrichment of the required product, and this purification step was therefore repeated 3×. 0.78 g; ESI-MS [M+H$^+$]=263.05

Example 21

N-(Piperidin-4-ylmethyl)-1H-benzimidazole-2-amine (trifluoroacetate) (21)

a.) A soltuion of tert-butoxycarbonyl-4-(aminomethyl)-1-piperidine (5.39 g; 25 mmol) in 25 ml of CH$_3$CN was added dropwise to 6.75 g of thiocarbonyldiimidazole and 0.5 g of imidazole in 100 ml of CH$_3$CN at 0° C., and the mixture was stirred at RT for 3 h. Then 1,2-phenylenediamine (5.5 g; 50.86 mmol) was added and the mixture was heated at 60° C. for about 1 h. The solid obtained on cooling was filtered off with suction and dried. 6.79 g; ESI-MS [M+H$^+$−$^t$Bu] =309.15 b.) tert-Butyl 4-({[(2-aminoanilino)carbothioyl]amino}methyl)piperidine-1-carboxylate 21a (5 g; 13.72 mmol), 5.94 g of HgO (yellow) and 0.6 g of sulfur in 150 ml of ethanol was refluxed for 1 h. The mixture was filtered 2× through Celite and evaporated, and the resulting crude product was purified by chromatography on silica gel (CH$_2$Cl$_2$/CH$_3$OH 5%→25%). 2.65 g; ESI-MS [M+H$^+$]=331.25

$^1$H-NMR (360 MHz, DMSO) δ ppm: 7.15 und 6.9 (each m, 2H), 3.95 (d, 2H), 3.2 (m 2H), 2.7 (br m; 2H), 1.8 (m, 1H), 1.7 (m, 2H), 1.35 (s, 9H), 1.05 (m, 2H).

c.) tert-Butyl 4-[(1H-benzimidazol-2-ylamino)methyl]piperidine-1-carboxylate 21b (2.65 g; 8.02 mmol) was treated with 10 ml of TFA under standard conditions. Concentration and trituration of the crude prodcut with n-pentane afforded 2.3 g; ESI-MS [M+H$^+$]=231.15.

$^1$H-NMR (360 MHz, DMSO) δ ppm; 13.25 (s, 1H), 9.35 (m, 1H), 8.8 and 8.5 (each br s, 1H), 7.4 and 7.20 (each m, 2H), 3.3 (m, 4H), 2.85 (m, 2H), 1.9 (m, 3H), 1.35 (m, 2H).

Example 22 a) 2-(N-Carbethoxythiocarbamoyl)-1-(N-piperidino)-1-propene (22a)

40 ml of piperidine were added dropwise to 11.85 g (0.2 mol) of propionaldehyde and 10 g of K$_2$CO$_3$ at 0° C. The mixture was subsequently stirred at this temperature for 2 h, and then the insoluble portions were filtered off and the filtrate was fractionated in vacuo. N-Ethoxycarbonyl isothiocyanate (63.7 g; 0.48 mol) was added dropwise to a solution of freshly distilled 1-(N-piperidino)propene (9.58 g; 0.077 mol) in 40 ml of dry diethyl ether with cooling; during the addition, an orange-red precipitate formed. The reaction mixture was stirred further at 0 to 5° C. for about 4 h, and the precipitate was filtered off, washed and dried. The residue remaining after evaporation of the mother liquor was again treated with diethyl ether and filtered. Yield: 6.81 g $^1$H-NMR (400 MHz, CDCl$_3$): δ (ppm) 7.85 (s, 1H; C<u>H</u>=C), 7.70 (br, 1H, NH), 4.15 (q, 2H, CH$_2$), 3.6 (m, 4H, piperidine), 2.2 (s, 3H, CH$_3$), 1.7 (m, 6H, piperidine), 1.3 (t, 3H, CH$_3$).

b) 2-(N-Carbethoxythiocarbamoyl)-1-(N-piperidino)-2-phenylethene (22b)

15.8 ml (0.1 mmol) of a 50% strength solution of phenylacetaldehyde in diethyl phthalate and 5 g of K$_2$CO$_3$ were mixed at 0° C. and, at this temperature, 17.04 g=19.8 ml (0.2 mol) of piperidine were slowly added. The mixture was stirred at 0° C. to 5° C. for 1.5 h. The insoluble portions were then filtered off with suction, and the mother liquor was distilled at a bath temperature of up to 80° C. under oil pump vacuum. The yellow oil obtained as residue (27.15 g, contains about 50% diethyl phthalate) was introduced into 40 ml of abs. diethyl ether at 0° C. under nitrogen. 8.1 ml=9.02 g (80 mmol) of N-ethoxycarbonyl isothiocyanate were slowly injected at 0° C. The mixture was then stirred at 0° C. to 5° C. for 4 h, an orange solid precipitating after about 30 min. The solid was filetered off with suciton under N$_2$, washing with diethyl ehter, and was dried under a stream of N$_2$. Yield: 21.5 g of yellow solid $^1$H-NMR (400 MHz, CDCl$_3$): δ (ppm) 8.45 (s, 1H; C<u>H</u>=C), 7.65 (br, 1H, NH), 7.35 (m, 5H, phenyl), 4.1 (q, 2H, CH$_2$), 3.1 (m, 4H, piperidine), 1.5 (m, 6H, piperidine), 1.15 (t, 3H, CH$_3$).

The following were prepared in analogy to 22a:

c) 4,4-Dimethyl-2-(N-carbethoxythiocarbamoyl)-1-(N-piperidino)-1-pentene (22c)

The enamine obtained from 24.03 g (0.2 mol) of 4,4-dimethylvaleraldehyde, 10 g of $K_2CO_3$ and 39.6 ml of piperidine was reacted with 7.68 ml (65.1 mmol) of N-ethoxycarbonyl isothiocyanate. Yield: 8.86 g of yellow solid.

$^1$H-NMR (270 MHz, CDCl$_3$): δ (ppm) 7.95 (br, 1H, NH), 7.52 (s, 1H; C$\underline{H}$=C), 4.17 (q, 2H, CH$_2$), 3.46 (m, 4H, piperidine), 2.83 (s, 2H, CH$_2$), 1.66 (m, 6H, piperidine), 1.28 (t, 3H, CH$_3$), 0.95 (s, 9H, 3*CH$_3$).

d) 2-(N-Carbethoxythiocarbamoyl)-1-(N-piperidino)-1-pentene (22d)

The enamine obtained from 17.23 g (0.2 mol) of valeraldehyde, 10 g of $K_2CO_3$ and 39.6 ml of piperidine was reacted with 8.84 ml (74.9 mmol) of N-ethoxycarbonyl isothiocyanate. Yield: 15.15 g of dark yellow solid.

$^1$H-NMR (270 MHz, CDCl$_3$): δ (ppm) 7.77 (br, 1H, NH), 7.52 (s, 1H; C$\underline{H}$=C), 4.15 (q, 2H, CH$_2$), 3.5 (m, 4H, piperidine), 2.7 (t, 2H, CH$_2$), 1.7 (m, 6H, piperidine), 1.55 (m, 2H, CH$_2$), 1.3 (t, 3H, CH$_3$), 0.95 (t, 3H, CH$_3$).

e) 2-(N-Carbethoxythiocarbamoyl)-2-(tetrahydro-2H-pyran-4-yl)-1-(N-piperidino)ethene (22e)

The enamine obtained from 25.84 g (0.2 mol) of 4-formylmethyltetrahydropyran, 10 g of $K_2CO_3$ and 39.6 ml of piperidine was reacted with 10.1 ml (85.6 mmol) of N-ethoxycarbonyl isothiocyanate. Yield: 27 g of yellow solid.

$^1$H-NMR (270 MHz, CDCl$_3$): δ (ppm) 8.2 (br, 1H, NH), 6.84 (s, 1H; C$\underline{H}$=C), 4.15 (q, 2H, CH$_2$), 3.95 and 3.5 (each m, 2H, THP-OCH$_2$), 3.2 (m, 4H, piperidine-NCH$_2$), 2.65 (m, 1H, THP-CH), 1.65–1.95 (m, 10H, piperidine-CH$_2$ and THP-CH$_2$), 1.3 (t, 3H, CH$_3$).

Example 23

2-(Piperidin-4-ylamino)pyridine (23)

a) Ethyl 4-amino-1-piperidine carboxylate (6 g; 34.8 mmol) and 25 g of 2-fluoropyridine were refluxed for 48 h. The solid formed after cooling was filtered off with suction, triturated with n-pentane and dried; 6.26 g of yellow powder; ESI-MS [M+H$^+$]=250.15.

b) 6 g of ethyl 4-(pyridin-2-ylamino)piperidine-1-carboxylate (23a) were refluxed in 30 ml of 47% HBr for 6 h. Evaporation of the mixture, trituration of the resulting crude product with ethyl acetate/CH$_3$OH (9:1) and renewed drying afforded 7.1 g of white solid; ESI-MS [M+H$^+$]=178.15.

Example 24

N-[4-(Aminomethyl)phenyl]-1H-benzimidazol-2-amine (trifluoroacetate) (24)

a) tert-Butyl 4-aminobenzylcarbamate (5 g; 22.5 mmol) was reacted in analogy to 21a with 6 g of thiocarbonyldiimidazole, 0.3 g of imidazole and 4.86 g of 1,2-phenylenediamine. The crude product obtained in this way was purified by chromatography on silica gel (CH$_2$Cl$_2$/CH$_3$OH 2→10%). 8.2 g of oil; ESI-MS [M+H$^+$]=373.15

$^1$H-NMR (360 MHz, DMSO) δ ppm: 9.5 and 9.05 (each s, 1H), 7.45 (d, 2H), 7.35 (m, 1H), 7.20 (d, 1H), 7.15, 6.95, 6.75, 6.60 (each m, 1H), 4.85 (s, 2H), 4.10 (d, 2H), 1.35 (s, 9H).

b) tert-Butyl 4-{[(2-aminoanilino)carbothioyl]amino}benzylcarbamate (4.3 g; 11.54 mmol) was refluxed in analogy to 21c with 5 g of HgO (yellow) and 0.05 g of sulfur in 150 ml of ethanol. Filtration of the reaction mixture through Celite and concentration afforded 2.1 g of a dark solid (ESI-MS [M+H$^+$]=339.15). The tert-butyl 4-(1H-benzimidazol-2-ylamino)benzylcarbamate obtained in this way was treated without further purification with 15 ml of TFA at RT for 2 h, and concentration afforded 4.7 g of a dark oil which was reacted further without further purification (ESI-MS [M+H$^+$]=239.05).

$^1$H-NMR (360 MHz, DMSO) δ ppm: 11.25 (s, 1H), 8.25 (s broad, 2–3H), 7.60 (m, 4H), 7.40 (m, 2H), 7.30 (m 2H), 4.15 (m, 2H).

Example 25

[5-(1H-Benzimidazol-2-yl)thien-2-yl]methanamide (25)

a) 5-(Aminomethyl)thiophene-2-carbonitrile (25 g; 146 mmol) (preparation as described in WO 95/23609) was dissolved in 750 ml of CH$_2$Cl$_2$, and 50 ml of ethyldiisopropylamine were added. Di-tert-butyl dicarbonate (35.05 g; 160 mmol) was added to this solution while cooling in ice. After 16 h, the mixture was washed 4× with 10% citric acid, 2× with saturated NaHCO$_3$ solution and 1× with saturated NaCl solution. The organ. phase was dried and concentrated (38.2 g)

b) tert-Butyl (5-cyanothien-2-yl)methylcarbamate (25 g) was dissolved in methanol, and 19.3 ml of a 30% strength sodium methanolate solution in methanol were added. After 16 h, a further 1.9 ml of the sodium methanolate solution were added and the mixture was heated to 40–50° C. After 2 h, the mixture was cooled to room temperature and 1,2-phenylenediamine hydrochloride was added. After 3 days, the suspension was cooled and mixed with 250 ml of water, and the precipitate was filtered off with suction. The solid was washed with water and dried (19.6 g). 9.5 g of this precipitate were suspended in 400 ml of CH$_2$Cl$_2$ and, at RT, 22 ml of TFA were added. After 16 h, the mixture was concentrated, the residue was dissolved in water and extracted 2× with diethyl ether, and the aqueous phase was adjusted to pH 10–11 and then extracted 2× with ethyl acetate. The aqueous phase was saturated with NaCl and again extracted with ethyl acetate. The combined organic phases were dried and concentrated. 6.3 g; ESI-MS [M+H$^+$]=230.1

Example 26

3-[(5,6-Dimethyl-1H-benzimidazol-2-yl)amino]-3-oxopropan-1-amine (hydrochloride) (26)

Boc-β-alanine (1.89 g; 10 mmol) was dissolved in 15 ml of DMF and, after addition of 2.02 g of N-methylmorpholine, 0.122 g of dimethylaminopyridine and 1.92 g of EDC*HCl, stirred for 1 h. 1.93 g (12 mmol) of 2-amino-5,6-dimethylbenzimidazole were added to the clear solution, and the mixture was stirred at RT for 16 h and then at 60° C. for 1 h. After the reaction was complete, NaCl solution was added, followed by extraction 2× with ethyl acetate, and the organic phase was washed with 10% citric acid and 2× with water, dried and concentrated. The residue (1.3 g) was dissolved in 10 ml of CH$_2$Cl$_2$, and 10 ml TFA were added. After 2 h, the mixture was evaporated, the residue was taken up in diethyl ether, ethereal HCl was added. After 1 h, the crystals were filtered off with suction, washed until neutral and dried at 40° C. 0.90 g; ESI-MS [M+H$^+$]=233.2

$^1$H-NMR (270 MHz, DMSO-d6) δ ppm=8.3 (bs, 3H), 7.45 (s, 2H), 3.25–3.0 (m, 4H), 2.35 (s, 6H).

Example 27

3-[(1H-Benzimidazol-2-yl)amino]-3-oxopropan-1-amine (hydrochloride) (27)

Synthesis took place in analogy to the preparation of 26 starting from (1.60 g; 12 mmol) of 2-aminobenzimidazole. 1.20 g; ESI-MS [M+H$^+$]=205.2

$^1$H-NMR (270 MHz; DMSO-d6) δ ppm: 8.3 (bs, 3H), 7.7 (m, 2H), 7.4 (m, 2H), 3.15 (m, 2H), 3.10 (m, 2H).

Example 28

2-[(Piperidinium-4-ylcarbonyl)amino]-1H-benzimidazole (bistrifluoroacetate) (28)

Boc-Isonipecotinic acid (3.0 g; 13.08 mmol) in 10 ml of CH$_2$Cl$_2$ were mixed with 13.4 ml of ethyldiisopropylamine and 1.74 g (13.08 mmol) of 2-aminopyridine. After cooling to 4° C., 15.4 ml of a 50% solution of propanephosphonic anhydride were added dropwise, and the mixture was stirred for 1.5 h. The mixture was subsequently stirred at RT for 4 h and then concentrated and taken up in ethyl acetate. The solution was extracted and dilute NaOH, water, 10% strength citric acid and 3× with saturated NaCl solution. The organ. phase was dried and concentrated, and the residue was recrystallized from diethyl ether (1.30 g). 1.25 g of the precipitate were dissolved in 15 ml of CH$_2$Cl$_2$, and 15 ml of TFA were added. After 3 h, the mixture was concentrated and the residue was recrystallized from diethyl ether. After cooling to 0° C., the residue was filtered off with suction and dried. 1.20 g; ESI-MS [M+H$^+$]=245.2.

Example 29

N-Pyridin-2-ylpiperidine-4-carboxamide (bistrifluoroacetate) (29)

Preparation took place in analogy to 28 starting from 1.23 g (13.08 mmol) of 2-aminopyridine. The resulting product is hygroscopic and was dried by codistillation with toluene. 0.72 g; ESI-MS [M+H$^+$]=206.2.

Example 30

N-[4-(Aminomethyl)-1,3-thiazol-2-yl]pyridin-2-amine (hydrochloride) (30)

a) 2-Aminopyridine (11 g; 116.9 mmol) and benzylisothiocyanate (21 g; 128.7 mmol) were refluxed in 250 ml of acetone for 3 h. The mixture was then evaporated and the resulting residue was triturated first with acetone/n-pentane and then only with n-pentene. 21.4 g; ESI-MS [M+H$^+$]=258.05.

b) N-Benzoyl-N'-pyridin-2-ylthiourea (30a) (5 g; 19.43 mmol) was introduced into 100 ml of an acetone/CH$_3$OH mixture and, after addition of 1.34 g of K$_2$CO$_3$ in 5 ml of H$_2$O, refluxed for 2 h. For workup, the precipitate which had formed was filtered off, the mother liquor was evaporated, and the resulting residue was added to H$_2$O. Extraction with CH$_2$Cl$_2$, drying and evaporation of the org. phases afforded 5.4 g; ESI-MS [M+H$^+$]=154.05.

$^1$H-NMR (270 MHz, DMSO-d6) δ ppm: 10.65 (s, 1H), 10.55 (s, 1H), 8.9 (s, 1H), 8.25, 7.75, 7.20, 7.10 (each m, 1H).

c) N-Pyridin-2-ylthiourea (30b) (5 g; 35.9 mmol) and 2-(3-bromo-2-oxopropyl)-1H-isoindol-1,3(2H)-dione (9.1 g; 32.26 mmol) were stirred in 500 ml of THF at RT for 2 h. The precipitate which had formed was filtered off and dried. 12.3 g of white solid; ESI-MS [M+H$^+$]=337.05.

d) Elimination of the phthaloyl group was carried out in analogy to 20d starting from 2-{[2-(pyridin-2-ylamino)-1,3-thiazol-4-yl]-methyl}-1H-imidazol-1,3(2H)-dione (30c) (10 g; 23.96 mmol) with 7 g of hydrazine hydrate in 250 ml of CH$_3$OH. Subsequent workup afforded 4.15 g of yellow solid; ESI-MS [M+H$^+$]=207.05.

Example 31

4-[(1,4,5,6-Tetrahydropyrimidin-2-ylammonio)methyl]piperidine (trifluoroacetate) (31)

tert-Butyloxycarbonyl-4-(aminomethyl)-1-piperidine (2 g; 9.33 mmol), 2-(methylsulfanyl)-1,4,5,6-tetrahydropyrimidin-1-ium iodide (2.41 g; 9.33 mmol) and 1.2 g of ethyldiisopropylamine were stirred in 10 ml of DMF at RT for 24 h. The mixture was evaporated, toluene/acetone were added, the resulting solids were filtered off, and the filtrate was again evaporated. 2.37 g of a brown oil were obtained as crude product (ESI-MS [M+H$^+$]=297.25), which was treated directly, without further purification, with 10 ml of TFA. Evaporation of the reaction mixture afforded a dark brown oil, which was purified by MPLC (silica gel: Bischoff Prontoprep 60-2540-C18E, 32 mm; eluent: CH$_3$CN/H$_2$O+ 0.1% acetic acid) (1.36 g of oil).

Example 22

[4-(Pyridin-2-ylamino)phenyl]methanamine (hydrochloride) (32)

tert-Butyl 4-aminobenzylcarbamate (4 g; 17.99 mmol) and 17.5 g of 2-fluoropyridine were refluxed for 32 h. After the reaction was complete, the mixture was evaporated and the residue was triturated with n-pentane. The crude product obtained in this way (5.3 g) was dissolved in 100 ml of CH$_2$Cl$_2$ and, at 0° C., 6.9 ml of TFA were added. After 3.5 h, the mixture was evaporated, the residue was taken up in diethyl ether, and ethereal HCl was added. Filtration with suction and drying of the precipitate afforded 3.3 g of the appropriate hydrochloride. M.p.: 208° C. (decomposition); ESI-MS [M+H$^+$]=200.15.

I.B. Compounds of the general formula I

Example I-1

4-({[1-((2S)-2-{[(Benzyloxy)carbonyl]amino}-2-carboxyethyl)-5-methyl-2-oxo-1,2-dihydropyrimidin-4-yl]amino}methyl)-1-pyridin-2-ylpiperidinium acetate (I-1)

a) 1.5 g of Z-Dap(Fmoc)-2-Cl-trityl-resin (0.6 mmol; substitution 0.4 mmol/g of resin) were treated with piperidine in DMF (50%) for 20 min. After washing with DMF (5*1 min) the resin was suspended in 6 ml of DMF and, after addition of 430 mg of 2-(N-carbethoxythiocarbamoyl)-1-(N-piperidino)-3-propene 22a, incubated at RT overnight. It was then washed with DMF, MeOH and CH$_2$Cl$_2$ and NMP. The suspension of the resin in 4.5 ml of NMP was mixed with 1.83 g of Cs$_2$CO$_3$ in 0.89 ml of H$_2$O and 0.56 ml of a 5 M BrCN solution in CH$_3$CN. Incubation at room temperature for 6 h was followed by filtration with suction and washing with NMP and CH$_2$Cl$_2$.

b) 0.037 mmol of the resin obtained in this way was suspended in 3.5 ml of NMP and, after addition of 27 μl of DIPEA, mixed with 14.2 mg of (1-pyridin-2-ylpiperidin-4-yl)methanamine. Incubation overnight was followed by filtration with suction and washing with DMF, H$_2$O, DMF, CH$_2$Cl$_2$, MeOH and CH$_2$Cl$_2$. Cleavage of the product from the resin was carried out with 1.5 ml of trifluoroethanol/ glacial acetic acid/CH$_2$Cl$_2$ (1 h, RT). Filtration was followed by evaporation, taking up in 2 ml of glacial acetic acid and lyophilization. Yield: 22 mg ESI-MS [M+H]$^+$: 521 (calculated: 521).

Example I-2

2-{4-[1-(2-{[(Benzyloxy)carbonyl]amino}-2-carboxyethyl)-2-oxo-5-tetrahydro-2H-pyran-4-yl-1,2-dihydropyrimidin-4-yl]piperazin-1-yl}pyridinium acetate (I-2)

55 mg of Z-Dap-2-Cl-trityl-resin (0.04 mmol) were suspended in 2 ml of DMF, and 3 eq of 22e were added. Incubation overnight was followed by washing with DMF, MeOH, CH$_2$Cl$_2$ and NMP. The resin was then suspended in NMP, and 131 mg of Cs$_2$CO$_3$ in 63 µl of H$_2$O and 40 µl of a 5 M BrCN solution in CH$_3$CN were added. Incubation at room temperature for 6 h was followed by filtration with suction and washing with NMP and CH$_2$Cl$_2$. The resulting resin was suspended in 3.5 ml of NMP and, after addition of 28 µl of DIPEA, mixed with 13.1 mg of 1-(2-pyridyl) piperazine. Incubation overnight was followed by filtration with suction and washing with DMF, H$_2$O, DMF, CH$_2$Cl$_2$, MeOH and CH$_2$Cl$_2$. Cleavage of the product from the resin was carried out with 1.5 ml of trifluoroethanol/glacial acetic acid/CH$_2$Cl$_2$ (1 h, RT). Filtration was followed by evaporation, taking up in 2 ml of glacial acetic acid and lyophilization. Yield: 24 mg ESI-MS [M+H]$^+$: 563 (calculated: 563).

Example I-3

3-(4-[4-(Anilinocarbonyl)piperazin-1-yl]-5-methyl-2-oxopyrimidin-1(2H)-yl)-N-[(benzyloxy)carbonyl]alanine (I-3)

a) 0.28 mmol of the resin obtained in Example I-1a) was added to a solution of 192.6 µl (1.12 mmol) of DIPEA and 2.4 g of piperazine (piperazine does not dissolve completely, insoluble portions were filtered off) in 15 ml of NMP. Incubation overnight was followed by filtration with suction and washing with DMF, H$_2$O, DMF, CH$_2$Cl$_2$, MeOH and CH$_2$Cl$_2$.

b) 0.04 mmol of the resin obtained in this way was suspended in CH$_2$Cl$_2$ and, after addition of 0.08 mmol of phenyl isocyanate, incubated at room temperature overnight. Cleavage of the product from the resin was carried out with 1.5 ml of trifluoroethanol/glacial acetic acid/CH$_2$Cl$_2$ (1 h, RT). Filtration was followed by evaporation, taking up in 2 ml of glacial acetic acid and lyophilization. Yield: 11 mg ESI-MS [M+H]$^+$: 535 (calculated: 535).

Example I-4

2-{[(1-{1-[2-Carboxy-1-(4-methylphenyl)ethyl]-5-methyl-2-oxo-1,2-dihydropyrimidin-4-yl}piperidin-4-yl)methyl] amino}pyridinium trifluoroacetate (I-4)

0.037 mmol of D,L-3-amino-3-(4-methylphenyl)propionic acid-2-Cl-trityl-resin was reacted in analogy to Example I-1a) and then suspended in 3.5 ml of NMP. Addition of 68 µl of DIPEA and 21.7 mg of N-(piperidin-4-ylmethyl)pyridin-2-amine (trifluoroacetate) was followed by incubation at room temperature overnight. This was followed by filtration with suction and washing with DMF, H$_2$O, DMF, CH$_2$Cl$_2$, MeOH and CH$_2$Cl$_2$. Cleavage of the product from the resin was carried out with 1.5 ml of trifluoroethanol/glacial acetic acid/CH$_3$Cl$_2$ (1 h, RT). Filtration was followed by evaporation, taking up in 2 ml of glacial acetic acid and lyophilization. The crude product was purified by RP-HPLC. Yield: 5 mg ESI-MS [M+H]$^+$: 462 (calculated: 462).

Example I-5

2-[(2-{[1-(4-Carboxybutyl)-5-methyl-2-oxo-1,2-dihydropyrimidin-4-yl]amino}ethyl)amino]pyridinium acetate (I-5)

0.04 mmol of 5-aminopentanoic acid-2-Cl-trityl-resin was reacted in analogy to Example I-1a). 28 µl of DIPEA and 11 mg of N$^1$-pyridin-2-ylethane-1,2-diamine were added to a suspension of the resulting resin in 3.5 ml of NMP. Incubation overnight was followed by filtration with suction and washing with DMF, H$_2$O, DMF, CH$_2$Cl$_2$, MeOH and CH$_2$Cl$_2$. Cleavage of the product from the resin was carried out with 1.5 ml of trifluoroethanol/glacial acetic acid/CH$_2$Cl$_2$ (1 h, RT). Filtration was followed by evaporation, taking up in 2 ml of glacial acetic acid and lyophilization. Yield: 16 mg ESI-MS [M+H]$^+$: 346 (calculated: 346).

The following were prepared analogously:

Example

I-6  2-{4-[1-((2S)-2-{[(Benzyloxy)carbonyl]amino}-2-carboxyethyl)-5-methyl-2-oxo-1,2-dihydropyrimidin-4-yl]piperazin-1-yl)-6-methylpyridinium acetate ESI-MS [M+H]$^+$: 507 (calculated: 507)

I-7  2-{4-[1-((2S)-2-{[(Benzyloxy)carbonyl]amino}-2-carboxyethyl)-5-methyl-2-oxo-1,2-dihydropyrimidin-4-yl]piperazin-1-yl}pyridinium acetate ESI-MS [M+H]$^+$: 493 (calculated: 493)

I-8  2-{4-[1-((2S)-2-{[(Benzyloxy)carbonyl]amino}-2-carboxyethyl)-5-methyl-2-oxo-1,2-dihydropyrimidin-4-yl]piperazin-1-yl}pyridinium acetate ESI-MS [M+H]$^+$: 493 (calculated: 493)

I-9 1-[1-((2S)-2-{[(Benzyloxy)carbonyl]amino}-2-carboxyethyl)-5-methyl-2-oxo-1,2-dihydropyrimidin-4-yl]-4-pyrazin-4-ium-2-yl-piperazin-4-ium diacetate ESI-MS [M+H]$^+$: 494 (calculated: 494)

I-10  1-[1-((2S)-2-{[(Benzyloxy)carbonyl]amino}-2-carboxyethyl)-5-methyl-2-oxo-1,2-dihydropyrimidin-4-yl]-4-(pyridinium-4-ylmethyl)piperazin-4-ium diacetate ESI-MS [M+H]$^+$: 507 (calculated: 507)

I-11  4-[1-((2S)-2-{[(Benzyloxy)carbonyl]amino}-2-carboxyethyl)-5-methyl-2-oxo-1,2-dihydropyrimidin-4-yl]-1-(3-pyrrolidinium-1-ylpropyl)-1,4-diazepan-1-ium diacetate ESI-MS [M+H]$^+$: 541 (calculated: 541)

I-12  3-(4-{4-[(Benzylamino)carbonyl]piperazin-1-yl}-5-methyl-2-oxopyrimidin-1(2H)-yl)-N-[(benzyloxy)carbonyl]alanine ESI-MS [M+H]$^+$: 549 (calculated: 549)

I-13  2-[(2-{[1-((2S)-2-{[(Benzyloxy)carbonyl]amino}-2-carboxyethyl)-5-methyl-2-oxo-1,2-dihydropyrimidin-4-yl]amino}ethyl)amino]pyridinium acetate ESI-MS [M+H]$^+$: 467 (calculated: 467)

I-14  2-[(2-{[1-(4-{[(Benzyloxy)carbonyl]amino}-4-carboxybutyl)-5-methyl-2-oxo-1,2-dihydropyrimidin-4-yl]amino}ethyl)amino]pyridinium acetate ESI-MS [M+H]$^+$: 495 (calculated: 495)

I-15  2-[(2-{[1-(5-{[(Benzyloxy)carbonyl]amino}-5-carboxypentyl)-5-methyl-2-oxo-1,2-dihydropyrimidin-4-yl]amino}ethyl)amino]pyridinium acetate ESI-MS [M+H]$^+$: 509 (calculated: 509)

I-16 2-{4-[1-((2S)-2-{[(Benzyloxy)carbonyl]amino}-2-carboxyethyl)-2-oxo-5-methyl-1,2-dihydropyrimidin-4-yl]piperazin-1-yl}pyridinium acetate ESI-MS [M+H]$^+$: 555 (calculated: 555)

I-17 2-{4-[1-((2S)-2-{[(Benzyloxy)carbonyl]amino}-2-carboxyethyl)-5-neopentyl-2-oxo-1,2-dihydropyrimidin-4-yl]piperazin-1-yl}pyridinium acetate ESI-MS [M+H]$^+$: 549 (calculated: 549)

I-18 2-{4-[1-((2S)-2-{[(Benzyloxy)carbonyl]amino}-2-carboxyethyl)-2-oxo-5-propyl-1,2-dihydropyrimidin-4-yl]piperazin-1-yl}pyridinium acetate ESI-MS [M+H]$^+$: 521 (calculated: 521)

I-19 3-(4-[4-(Anilinocarbonyl)-1,4-diazepan-1-yl]-5-methyl-2-oxopyrimidin-1(2H)-yl)-N-[(benzyloxy)carbonyl]alanine ESI-MS [M+H]$^+$: 549 (calculated: 549)

I-20 2-{4-[1-(2-{[(Benzyloxy)carbonyl]amino}-3-carboxypropyl)-5-methyl-2-oxo-1,2-dihydropyrimidin-4-yl]piperazin-1-yl}pyridinium acetate ESI-MS [M+H]$^+$: 507 (calculated: 507)

I-21 2-{4-[1-(2-{[(Benzyloxy)carbonyl]amino}-3-carboxypropyl)-2-oxo-5-phenyl-1,2-dihydropyrimidin-4-yl]piperazin-1-yl}pyridinium acetate ESI-MS [M+H]$^+$: 569 (calclated: 569)

I-22 2-{4-[1-(2-{[(Benzyloxy)carbonyl]amino}-3-carboxypropyl)-2-oxo-5-tetrahydro-2H-pyran-4-yl-1,2-dihydropyrimidin-4-yl]piperazin-1-yl}pyridinium acetate ESI-MS [M+H]$^+$: 577 (calculated: 577)

I-23 2-{4-[1-(2-{[(Benzyloxy)carbonyl]amino}-3-carboxypropyl)-2-oxo-5-propyl-1,2-dihydropyrimidin-4-yl]piperazin-1-yl}pyridinium acetate ESI-MS [M+H]$^+$: 535 (calculated: 535)

I-24 2-[(2-{[1-(2-{[(Benzyloxy)carbonyl]amino}-3-carboxypropyl)-5-methyl-2-oxo-1,2-dihydropyrimidin-4-yl]amino}ethyl)amino]pyridinium acetate ESI-MS [M+H]$^+$: 481 (calculated: 481)

I-25 2-[(2-{[1-(2-{[(Benzyloxy)carbonyl]amino}-3-carboxypropyl)-2-oxo-5-phenyl-1,2-dihydropyrimidin-4-yl]amino}ethyl)amino]pyridinium acetate ESI-MS [M+H]$^+$: 543 (calculated: 543)

I-26 2-[(2-{[1-(2-{[(Benzyloxy)carbonyl]amino}-3-carboxypropyl)-2-oxo-5-tetrahydro-2H-pyran-4-yl-1,2-dihydropyrimidin-4-yl]amino}ethyl)amino]pyridinium acetate ESI-MS [M+H]$^+$: 551 (calculated: 551)

I-27 2-[(2-{[1-(2-{[(Benzyloxy)carbonyl]amino}-3-carboxypropyl)-2-oxo-5-propyl-1,2-dihydropyrimidin-4-yl]amino}ethyl)amino]pyridinium acetate ESI-MS [M+H]$^+$: 509 (calculated: 509)

I-28 3-(4-[(6-{[(Benzylamino)carbonyl]amino}hexyl)amino]-5-methyl-2-oxopyrimidin-1(2H)-yl)-N-[(benzyloxy)carbonyl]alanine ESI-MS [M+H]$^+$: 579 (calculated: 579)

I-29 2-({[1-(2-{[(Benzyloxy)carbonyl]amino}-3-carboxypropyl)-5-methyl-2-oxo-1,2-dihydropyrimidin-4-yl]amino}methyl)-5,6-dimethyl-1H-benzimidazol-1-ium acetate ESI-MS [M+H]$^+$: 519 (calculated: 519)

I-30 2-[5-({[1-(2-{[(Benzyloxy)carbonyl]amino}-3-carboxypropyl)-5-methyl-2-oxo-1,2-dihydropyrimidin-4-yl]amino}methyl)pyridinium-2-yl]-3H-benzimidazol-1-ium diacetate ESI-MS [M+H]$^+$: 568 (calculated: 568)

I-31 4-({[1-(2-{[(Benzyloxy)carbonyl]amino}-3-carboxypropyl)-5-methyl-2-oxo-1,2-dihydropyrimidin-4-yl]amino}methyl)-1-pyridin-2-ylpiperidinium trifluoroacetate ESI-MS [M+H]$^+$: 535 (calculated: 535)

I-32 [4-({[1-(2-{[(Benzyloxy)carbonyl]amino}-3-carboxypropyl)-5-methyl-2-oxo-1,2-dihydropyrimidin-4-yl]amino}methyl)phenyl]methanaminium acetate ESI-MS [M+H]$^+$: 480 (calculated: 480)

I-33 (2S)-3-(4-[({1-[(Benzylamino)carbonyl]piperidin-4-yl}methyl)amino]-5-methyl-2-oxopyrimidin-1(2H)-yl)-2-{[(benzyloxy)carbonyl]amino}propanoic acid ESI-MS [M+H]$^+$: 577 (calculated: 577)

I-34 2-[2-({[1-(2-{[(Benzyloxy)carbonyl]amino}-3-carboxypropyl)-5-methyl-2-oxo-1,2-dihydropyrimidin-4-yl]amino}methyl)-1,3-thiazol-4-yl]-1H-benzimidazol-1-ium trifluoroacetate ESI-MS [M+H]$^+$: 574 (calculated: 574)

I-35 N-(2-{[1-(2-{[(Benzyloxy)carbonyl]amino}-3-carboxypropyl)-5-methyl-2-oxo-1,2-dihydropyrimidin-4-yl]amino}cyclohexyl)pyridin-2-aminium trifluoroacetate ESI-MS [M+H]$^+$: 535 (calculated: 535)

I-36 2-[({1-[1-(2-{[(Benzyloxy)carbonyl]amino}-3-carboxypropyl)-5-methyl-2-oxo-1,2-dihydropyrimidin-4-yl]piperidin-4-yl}methyl)ammonio]pyridinium bistrifluoroacetate ESI-MS [M+H]+: 535 (calculated: 535)

I-37 2-[2-({[1-((2S)-{[(Benzyloxy)carbonyl]amino}-2-carboxyethyl)-5-methyl-2-oxo-1,2-dihydropyrimidin-4-yl]amino}methyl)-1,3-thiazol-4-yl]-1H-benzimidazol-1-ium trifluoroacetate ESI-MS [M+H]$^+$: 560 (calculated: 560)

I-38 N-(2-{[1-((2S)-2-{[(Benzyloxy)carbonyl]amino}-2-carboxyethyl)-5-methyl-2-oxo-1,2-dihydropyrimidin-4-yl]amino}cyclohexyl)pyridin-2-aminium trifluoroacetate ESI-MS [M+H]$^+$: 521 (calculated: 521)

I-39 2-[5-({[1-((2S)-2-{[(Benzyloxy)carbonyl]amino}-2-carboxyethyl)-5-methyl-2-oxo-1,2-dihydropyrimidin-4-yl]amino}methyl)thien-3-yl]-1H-benzimidazol-1-ium trifluoroacetate ESI-MS [M+H]$^+$: 559 (calculated: 559)

I-40 2-[({1-[1-((2S)-2-{[(Benzyloxy)carbonyl]amino}-2-carboxyethyl)-5-methyl-2-oxo-1,2-dihydropyrimidin-4-yl]piperidin-4-yl}methyl)amino]pyridinium trifluoroacetate ESI-MS [M+H]$^+$: 521 (calculated: 521)

I-41 2-({2-[[1-(2-{[(Benzyloxy)carbonyl]amino}-3-carboxypropyl)-5-methyl-2-oxo-1,2-dihydropyrimidin-4-yl](methyl)amino]ethyl}amino)pyridinium trifluoroacetate ESI-MS [M+H]$^+$: 495 (calculated: 495)

I-42 2-({2-[[1-((2S)-2-{[(Benzyloxy)carbonyl]amino}-2-carboxyethyl)-5-methyl-2-oxo-1,2-dihydropyrimidin-4-yl](methyl)amino]ethyl}amino)pyridinium trifluoroacetate ESI-MS [M+H]$^+$: 481 (calculated: 481)

I-43 2-[(3-{[1-((2S)-2-{[(Benzyloxy)carbonyl]amino}-2-carboxyethyl)-5-methyl-2-oxo-1,2-dihydropyrimidin-4-yl]amino}propanoyl)amino]-1H-imidazol-1-ium acetate ESI-MS [M+H]$^+$: 483 (calculated: 483)

I-44 2-{[3-({1-[2-Carboxy-1-(4-methylphenyl)ethyl]-5-methyl-2-oxo-1,2-dihydropyrimidin-4-yl}amino)propanoyl]amino}-4H-imidazol-3-ium acetate ESI-MS [M+H]$^+$: 425 (calculated: 425)

I-45 2-[(3-{[1-(2-{[(Benzyloxy)carbonyl]amino}-3-carboxypropyl)-5-methyl-2-oxo-1,2-dihydropyrimidin-4-yl]amino}propanoyl)amino]-1H-imidazol-1-ium acetate ESI-MS [M+H]$^+$: 498 (calculated: 498)

I-46 2-{[4-({[1-((2S)-2-{[(Benzyloxy)carbonyl]amino}-2-carboxyethyl)-5-methyl-2-oxo-1,2-dihydropyrimidin-4-yl]amino}methyl)benzyl]amino}pyridinium acetate ESI-MS [M+H]$^+$: 543 (calculated: 543)

I-47 (3S)-4-(4-[(4-{[(Benzylamino)carbonyl]amino}benzyl)amino]-5-methyl-2-oxopyrimidin-1(2H)-yl)-3-{[(benzyloxy)carbonyl]amino}butanoic acid ESI-MS [M+H]$^+$: 599 (calculated: 599)

I-48 4-(4-{[4-(1H-Benzimidazol-2-yl)benzyl]amino}-5-methyl-2-oxopyrimidin-1(2H)-yl)-3-{[(benzyloxy)carbonyl]amino}butanoic acid ESI-MS [M+H]$^+$: 567 (calculated: 567)

I-49 (2S)-3-(4-{[(2-{[(Benzylamino)carbonyl]amino}-1,3-thiazol-4-yl)methyl]amino}-5-methyl-2-oxopyrimidin-1

(2H)-yl)-2-{[(benzyloxy)carbonyl]amino}propionic acid ESI-MS [M+H]+: 592 (calculated: 592)

I-50 4-(4-{[2-{[(Benzylamino)carbonyl]amino}-1,3-thiazol-4-yl)methyl]amino}-5-methyl-2-oxopyrimidin-1(2H)-yl)-3-{[(benzyloxy)carbonyl]amino}butanoic acid ESI-MS [M+H]+: 606 (calculated: 606)

I-51 (2S)-3-(4-{[3-(1H-Benzimidazol-2-yl)benzyl]amino}-5-methyl-2-oxopyrimidin-1(2H)-yl)-2-{[(benzyloxy)carbonyl]amino}propionic acid ESI-MS [M+H]+: 553 (calculated: 553)

I-52 (2S)-3-(4-{[4-(1H-Benzimidazol-2-yl)benzyl]amino}-5-methyl-2-oxopyrimidin-1(2H)-yl)-2-{[(benzyloxy)carbonyl]amino}propanoic acid ESI-MS [M+H]+: 553 (calculated: 553)

I-53 (2S)-3-(4-[(4-{[(Benzylamino)carbonyl]amino}benzyl)amino]-5-methyl-2-oxopyrimidin-1(2H)-yl)-2{[(benzyloxy)carbonyl]amino}propionic acid ESI-MS [M+H]+: 585 (calculated: 585)

I-54 2-{[4-({[1-(2-{[Benzyloxy)carbonyl]amino}-3-carboxy-propyl)-5-methyl-2-oxo-1,2-dihydropyrimidin-4-yl]amino}methyl)benzyl]amino}pyridinium trifluoroacetate ESI-MS [M+H]+: 557 (calculated: 557)

I-55 2-{4-[({1-[2-Carboxy-1-(4-methylphenyl)ethyl]-5-methyl-2-oxo-1,2-dihydropyrimidin-4-yl}amino)methyl]phenyl}-1H-benzimidazol-1-ium trifluoroacetate ESI-MS [M+H]+: 494 (calculated: 494)

I-56 3-(4-[(4-{[(Benzylamino)carbonyl]amino}benzyl)amino]-5-methyl-2-oxopyrimidin-1(2H)-yl)-3-(4-methylphenyl)propanoic acid ESI-MS [M+H]+: 526 (calculated: 526)

I-57 3-(4-{[(2-{[Benzylamino)carbonyl]amino}-1,3-thiazol-4-yl)methyl]amino}-5-methyl-2-oxopyrimidin-1(2H)-yl)-3-(4-methylphenyl)propanoic acid ESI-MS [M+H]+: 533 (calculated: 533)

I-58 2-[(3-{[1-((2S)-2-{[(Benzyloxy)carbonyl]amino}-2-carboxy-ethyl)-2-oxo-5-tetrahydro-2H-pyran-4-yl-1,2-dihydropyrimidin-4-yl]amino}propanoyl)amino]-1H-imidazol-1-ium trifluoroacetate ESI-MS [M+H]+: 554 (calculated: 554)

I-59 2-[(3-{[1-((2S)-2-{[(Benzyloxy)carbonyl]amino}-2-carboxy-ethyl)-2-oxo-5-propyl-1,2-dihydropyrimidin-4-yl]amino}propanoyl)amino]-1H-imidazol-1-ium trifluoroacetate ESI-MS [M+H]+: 512 (calculated: 512)

I-60 2-[(3-{[1-((2S)-2-{[(Benzyloxy)carbonyl]amino}-2-carboxy-ethyl)-2-oxo-5-phenyl-1,2-dihydropyrimidin-4-yl]amino}-propanoyl)amino]-1H-imidazol-1-ium trifluoroacetate ESI-MS [M+H]+: 546 (calculated 546)

I-61 2-[(3-{[1-(2-{[(Benzyloxy)carbonyl]amino}-3-carboxy-propyl)-2-oxo-5-tetrahydro-2H-pyran-4-yl-1,2-dihydropyrimidin-4-yl]amino}propanoyl)amino]-1H-imidazol-1-ium trifluoroacetate ESI-MS [M+H]+: 568 (calculated: 568)

I-62 2-[(3-{[1-(2-{[(Benzyloxy)carbonyl]amino}-3-carboxy-propyl)-2-oxo-5-propyl-1,2-dihydropyrimidin-4-yl]amino}-propanoyl)amino]-1H-imidazol-1-ium trifluoroacetate ESI-MS [M+H]+: 526 (calculated: 526)

I-63 2-[(3-{[1-(2-{[(Benzyloxy)carbonyl]amino}-3-carboxy-propyl)-2-oxo-5-phenyl-1,2-dihydropyrimidin-4-yl]amino}-propanoyl)amino]-1H-imidazol-1-ium trifluoroacetate ESI-MS [M+H]+: 560 (calculated: 560)

I-64 2-[({1-[1-((2S)-{[(Benzyloxy)carbonyl]amino}-2-carboxy-ethyl)-2-oxo-5-propyl-1,2-dihydropyrimidin-4-yl]-piperidin-4-yl}methyl)amino]pyridinium trifluoroacetate ESI-MS [M+H]+: 549 (calculated: 549)

I-65 2-[({1-[1-(2-{[(Benzyloxy)carbonyl]amino}-3-carboxy-propyl)-2-oxo-5-tetrahydro-2H-pyran-4-yl-1,2-dihydropyrimidin-4-yl piperidin-4-yl}methyl)amino]pyridinium trifluoroacetate ESI-MS [M+H]+: 605 (calculated: 605)

I-66 2-[({1-[1-(2-{[(Benzyloxy)carbonyl]amino}-3-carboxypropyl)-2-oxo-5-propyl-1,2-dihydropyrimidin-4-yl]-piperidin-4-yl}methyl)amino]pyrimidin trifluoroacetate ESI-MS [M+H]+: 563 (calculated: 563)

I-67 2-[({1-[1-(2-{[(Benzyloxy)carbonyl]amino}-3-carboxypropyl)-2-oxo-5-phenyl-1,2-dihydropyrimidin-4-yl]piperidin-4-yl}methyl)amino]pyridinium trifluoroacetate ESI-MS [M+H]+: 597 (calculated: 597)

I-68 2-{[4-({[1-((2S)-2-{[(Benzyloxy)carbonyl]amino}-2-carboxyethyl)-2-oxo-5-tetrahydro-2H-pyran-4-yl-1,2-dihydropyrimidin-4-yl]amino}methyl)benzyl)amino}pyridinium acetate ESI-MS [M+H]+: 613 (calculated: 613)

I-69 (2S)-3-(4-[(4-{[(Benzylamino)carbonyl]amino}benzyl)amino]-2-oxo-5-tetrahydro-2H-pyran-4-ylpyrimidin-1(2H)-yl)-2-{[(benzyloxy)carbonyl]amino}propanoic acid ESI-MS [M+H]+: 655 (calculated: 655)

I-70 2-{[4-({[1-((2S)-2-{[(Benzyloxy)carbonyl]amino}-2-carboxyethyl)-2-oxo-5-propyl-1,2-dihydropyrimidin-4-yl]amino}methyl)benzyl]amino}pyridinium acetate ESI-MS [M+H]+: 571 (calculated: 571)

I-71 3-(4-[(4-{[(Benzylamino)carbonyl]amino}benzyl)amino]-2-oxo-5-propylpyrimidin-1(2H)-yl)-N-[(benzyloxy)carbonyl]alanine ESI-MS [M+H]+: 613 (calculated: 613)

I-72 2-[({1-[1-((2S)-{[(Benzyloxy)carbonyl]amino}-2-carboxyethyl)-5-methyl-2-oxo-1,2-dihydropyrimidin-4-yl]piperidin-4-yl}methyl)amino]-1H-benzimidazol-1-ium acetate ESI-MS [M+H]+: 560 (calculated: 560)

I-73 2-[3-({[1-(2-{[(Benzyloxy)carbonyl]amino}-3-carboxypropyl)-5-methyl-2-oxo-1,2-dihydropyrimidin-4-yl]amino}methyl)phenyl]-1H-benzimidazol-1-ium trifluoroacetate ESI-MS [M+H]+: 567 (calculated: 567)

I-74 2-({[4-({[1-(2-{[(Benzyloxy)carbonyl]amino}-3-carboxypropyl)-5-methyl-2-oxo-1,2-dihydropyrimidin-4-yl]amino}methyl)thien-3-yl]methyl}amino)pyridinium trifluoroacetate ESI-MS [M+H]+: 563 (calcualted: 563)

I-75 2-{4-[2-({1-[2-Carboxy-1-(4-methylphenyl)ethyl]-5-methyl-2-oxo-1,2-dihydropyrimidin-4-yl}amino)ethyl]phenyl}-1H-benzimidazol-1-ium trifluoroacetate ESI-MS [M+H]+: 508 (calculated: 508)

I-76 2-[({4-[({1-[2-Carboxy-1-(4-methylphenyl)ethyl]-5-methyl-2-oxo-1,2-dihydropyrimidin-4-yl}amino)methyl]thien-3-yl}-methyl)amino]pyridinium trifluoroacetate ESI-MS [M+H]+: 490 (calculated: 490)

I-77 2-[3-({[1-((2S)-{[(Benzyloxy)carbonyl]amino}-2-carboxyethyl)-5-methyl-2-oxo-1,2-dihydropyrimidin-4-yl]amino}methyl)phenyl]-1H-benzimidazol-1-ium trifluoroacetate ESI-MS [M+H]+: 553 (calculated: 553)

I-78 2-[4-(2-{[1-((2S)-2-{[(Benzyloxy)carbonyl]amino}-2-carboxyethyl)-5-methyl-2-oxo-1,2-dihydropyrimidin-4-yl]amino}ethyl)phenyl]-1H-benzimidazol-1-ium trifluoroacetate ESI-MS [M+H]+: 567 (calculated: 567)

I-79 2-({[4-({[1-((2S)-2-{[(Benzyloxy)carbonyl]amino}-2-carboxyethyl)-5-methyl-2-oxo-1,2-dihydropyrimidin-4-yl]amino}methyl)thien-3-yl]methyl}amino)pyridinium trifluoroacetate ESI-MS [M+H]+: 549 (calculated: 549)

I-80 2-({4-[({1-[2-Carboxy-1-(4-methylphenyl)ethyl]-5-methyl-2-oxo-1,2-dihydropyrimidin-4-yl}amino)methyl]benzyl}amino)pyridinium trifluoroacetate ESI-MS [M+H]+: 484 (calculated: 484)

I-81 2-[({1-[1-(2-{[(Benzyloxy)carbonyl]amino}3-carboxypropyl)-5-methyl-2-oxo-1,2-dihydropyrimidin-4-yl]piperidin-4-yl}methyl)amino]-1H-benzimidazol-1-ium trifluoroacetate ESI-MS [M+H]+: 574 (calculated: 574)

I-82 2-{[(1-{1-[2-Carboxy-1-(4-methylphenyl)ethyl]-5-methyl-2-oxo-1,2-dihydropyrimidin-4-yl}piperidin-4-yl)methyl]amino}-1H-benzimidazol-1-ium trifluoroacetate ESI-MS [M+H]+: 501 (calculated: 501)

I-83 2-{[4-({[1-((2S)-2-{[(Benzyloxy)carbonyl]amino}-2-carboxyethyl)-2-oxo-5-phenyl-1,2-dihydropyrimidin-4-yl]amino}methyl)benzyl amino}pyridinium ESI-MS [M+H]+: 605 (calculated: 605)

I-84 (2S)-3-(4-[(4-{[(Benzylamino)carbonyl] amino}benzyl)amino]-2-oxo-5-phenylpyrimidin-1(2H)-yl)-2-{[(benzyloxy)carbonyl]amino}propanoic acid ESI-MS [M+H]+: 647 (calculated: 647)

I-85 4-(4-{[(2-{[(Benzylamino)carbonyl]amino}-1,3-thiazol-4-yl)methyl]amino}-2-oxo-5-tetrahydro-2H-pyran-4-yl-pyrimidin-1(2H)-yl)-3-{[(benzyloxy)carbonyl] amino}butanoic acid ESI-MS [M+H]+: 676 (calculated: 676)

I-86 4-(4-{[(2-{[(Benzylamino)carbonyl]amino}-1,3-thiazol-4-yl)methyl]amino}-2-oxo-5-propylpyrimidin-1(2H)-yl)-3-{[(benzyloxy)carbonyl]amino}butanoic acid ESI-MS [M+H]+: 634 (calculated: 634)

I-87 4-(4-{[(2-{[(Benzylamino)carbonyl]amino}-1,3-thiazol-4-yl)methyl]amino}-2-oxo-5-phenylpyrimidin-1(2H)-yl)-3-{[(benzyloxy)carbonyl]amino}butanoic acid ESI-MS [M+H]+: 668 (calculated: 668)

I-88 2-[(3-{[1-((2S)-2-{[(Benzyloxy)carbonyl]amino}-2-carboxyethyl)-5-methyl-2-oxo-1,2-dihydropyrimidin-4-yl]amino}propyl)amino]pyridinium trifluoroacetate ESI-MS [M+H]+: 481 (calculated: 481)

I-89 2-[(3-{[1-(2-{[(Benzyloxy)carbonyl]amino}-3-carboxypropyl]-5-methyl-2-oxo-1,2-dihydropyrimidin-4-yl]amino}propyl)amino]pyridinium trifluoroacetate ESI-MS [M+H]+: 495 (calculated: 495)

I-90 2-{[3-({1-[2-Carboxy-1-(4-methylphenyl)ethyl]-5-methyl-2-oxo-1,2-dihydropyrimidin-4-yl}amino)propyl] amino}pyridinium trifluoroacetate ESI-MS [M+H]+: 422 (calculated: 422)

I-91 2-[4-({[1-(2-{[(Benzyloxy)carbonyl]amino}-3-carboxypropyl)-5-methyl-2-oxo-1,2-dihydropyrimidin-4-yl]amino}methyl)phenyl]-3H-benzimidazol-1-ium trifluoroacetate ESI-MS [M+H+]: 567 (calculated: 567)

I-92 2-[({1-[1-(2-Carboxyethyl)-5-methyl-2-oxo-1,2-dihydropyrimidin-4-yl]piperidin-4-yl}methyl)amino]pyridinium acetate ESI-MS [M+H]+: 372 (calculated: 372)

I-93 2-[({1-[1-(3-Carboxypropyl)-5-methyl-2-oxo-1,2-dihydropyrimidin-4-yl]piperidin-4-yl}methyl)amino]pyridinium acetate ESI-MS [M+H]+: 386 (calculated: 386)

I-94 2-[({1-[1-(2-Carboxyethyl)-5-methyl-2-oxo-1,2-dihydropyrimidin-4-yl]piperidin-4-yl}methyl)amino]-1H-benzimidazol-1-ium acetate ESI-MS [M+H]+: 411 (calculated: 411)

I-95 2-[({1-[1-(3-Carboxypropyl)-5-methyl-2-oxo-1,2-dihydropyrimidin-4-yl]piperidin-4-yl}methyl)amino]-1H-benzimidazol-1-ium acetate ESI-MS [M+H]+: 425 (calculated: 425)

I-96 2-[(3-{[1-(2-Carboxyethyl)-5-methyl-2-oxo-1,2-dihydropyrimidin-4-yl]amino}propanoyl)amino]-1H-imidazol-1-ium acetate ESI-MS [M+H]+: 335 (calculated: 335)

I-97 2-[(3-{[1-(3-Carboxypropyl)-5-methyl-2-oxo-1,2-dihydropyrimidin-4-yl]amino}propanoyl)amino]-1H-imidazol-1-ium acetate ESI-MS [M+H]+: 349 (calculated: 349)

I-98 2-[5-({[1-((2S)-{[(Benzyloxy)carbonyl]amino}-2-carboxyethyl)-5-methyl-2-oxo-1,2-dihydropyrimidin-4-yl]amino}methyl)thien-2-yl]-3H-benzimidazol-1-ium acetate ESI-MS [M+H]+: 559 (calculated: 559)

I-99 2-[5-({[1-(2-{[(Benzyloxy)carbonyl]amino}-3-carboxypropyl)-5-methyl-2-oxo-1,2-dihydropyrimidin-4-yl]amino}methyl)thien-2-yl]-3H-benzimidazol-1-ium acetate ESI-MS [M+H]+: 573 (calculated: 573)

I-100 2-[4-({[1-((2S)-2-{[(Benzyloxy)carbonyl]amino}-2-carboxyethyl)-5-methyl-2-oxo-1,2-dihydropyrimidin-4-yl]amino}methyl)anilino]-1H-benzimidazol-1-ium trifluoroacetate ESI-MS [M+H]+: 568 (calculated: 568)

I-101 2-[4-({[1-(2-{[(Benzyloxy)carbonyl]amino}-3-carboxypropyl)-5-methyl-2-oxo-1,2-dihydropyrimidin-4-yl]amino}methyl)anilino]-1H-benzimidazol-1-ium trifluoroacetate ESI-MS [M+H]+: 582 (calculated: 582)

I-102 2-[({1-[1-(2-{[(Benzyloxy)carbonyl]amino}-3-carboxypropyl)-5-methyl-2-oxo-1,2-dihydropyrimidin-4-yl]piperidin-4-yl}methy)amino]-1,4,5,6-tetrahydropyrimidin-1-ium trifluoroacetate ESI-MS [M+H]+: 540 (calculated: 540)

I-103 N-{1-[1-((2S)-2-{[(Benzyloxy)carbonyl]amino}-2-carboxyethyl)-5-methyl-2-oxo-1,2-diuhydropyrimidin-4-yl]piperidin-4-yl}pyridin-2-aminium trifluoroacetate ESI-MS [M+H]+: 507 (calculated: 507)

I-104 2-[(3-{[1-((2S)-2-{[(Benzyloxy)carbonyl]amino}-2-carboxyethyl)-5-methyl-2-oxo-1,2-dihydropyrimidin-4-yl]amino}propanoyl]amino]-1H-benzimidazol-1-ium acetate ESI-MS [M+H]+: 534 (calculated: 534)

I-105 2-[(3-{[1-((2S)-2-{[(Benzyloxy)carbonyl]amino}-2-carboxyethyl)-5-methyl-2-oxo-1,2-dihydropyrimidin-4-yl]amino}propanoyl)amino]-5,6-dimethyl-1H-benzimidazol-1-ium acetate ESI-MS [M+H]+: 562 (calculated: 562)

I-106 2-[(3-{[1-(2-{[(Benzyloxy)carbonyl]amino}-3-carboxypropyl)-5-methyl-2-oxo-1,2-dihydropyrimidin-4-yl]amino}propanoyl]amino]-1H-benzimidazol-1-ium trifluoroacetate ESI-MS [M+H]+: 548 (calculated: 548)

I-107 2-[(3-{[1-(2-{[(Benzyloxy)carbonyl]amino}-3-carboxypropyl)-5-methyl-2-oxo-1,2-dihydropyrimidin-4-yl]amino}propanoyl)amino]-5,6-dimethyl-1H-benzimidazol-1-ium trifluoroacetate ESI-MS [M+H]+: 576 (calculated: 576)

I-108 2-[(3-{[1-((2S)-2-{[(Benzyloxy)carbonyl]amino}-2-carboxyethyl)-5-methyl-2-oxo-1,2-dihydropyrimidin-4-yl]amino}propanoyl)amino]pyridinium trifluoroacetate ESI-MS [M+H]+: 481 (calculated: 481)

I-109 2-[4-(2-{[1-((2S)-2-{[(Benzyloxy)carbonyl]amino}-2-carboxyethyl)-5-methyl-2-oxo-1,2-dihydropyrimidin-4-yl]amino}ethyl)phenyl]-1H-benzimidazol-1-ium acetate ESI-MS [M+H]+: 567 (calculated:567)

I-110 2-[({1-[1-((2S)-2-{[(Benzyloxy)carbonyl]amino}-2-carboxyethyl)-5-methyl-2-oxo-1,2-dihydropyrimidin-4-yl]piperidin-4-yl}carbonyl)amino]pyridinium acetate ESI-MS [M+H]+: 535 (calculated: 535)

I-111 2-[({1-[1-((2S)-2-{[(Benzyloxy)carbonyl]amino}-2-carboxyethyl)-5-methyl-2-oxo-1,2-dihydropyrimidin-4-yl]piperidin-4-yl}carbonyl)amino]-3H-benzimidazol-1-ium acetate ESI-MS [M+H]+: 574 (calculated: 574)

I-112 2-[({1-[1-(2-{[(Benzyloxy)carbonyl]amino}-3-carboxypropyl)-5-methyl-2-oxo-1,2-dihydropyrimidin-4-yl]piperidin-4-yl}carbonyl)amino]pyridinium trifluoroacetate ESI-MS [M+H]+: 549 (calculated: 549)

I-113 2-[({1-[1-(2-{[(Benzyloxy)carbonyl]amino}-3-carboxypropyl)-5-methyl-2-oxo-1,2-dihydropyrimidin-4-yl]piperidin-4-yl}carbonyl)amino]pyridinium trifluoroacetate ESI-MS [M+H]+: 588 (calculated: 588)

II. Biological Examples

Example 1

Integrin $\alpha_v\beta_3$ assay

Integrin $\alpha_v\beta_3$ antagonists were identified and assessed using a test system based on competition between the natural integrin $\alpha_v\beta_3$ ligand vitronectin and the test substance for binding to integrin $\alpha_v\beta_3$ bound to a solid phase.

Procedure:
coat microtiter plates with 250 ng/ml integrin-$\alpha_v\beta_3$ in 0.05 M NaHCO$_3$ pH 9.2; 0.1 ml/well;
saturate with 1% milk powder/assay buffer; 0.3 ml/well; 0.5 h/Rt
wash 3× with 0.05% Tween 20/assay buffer
Test substance in 0.1% milk powder/assay buffer, 50 µl/well+0 µg/ml or 2 µg/ml human vitronectin (Boehringer Ingelheim T007) in 0.1% milk powder/assay buffer, 50 µl/well; 1 h/RT
wash 3× with 0.05% Tween 20/assay buffer
1 µg/ml anti human vitronectin antibody coupled to peroxidase (Kordia SAVN-APHRP) in 0.1% milk powder/assay buffer; 0.1 ml/well; 1 h/RT
wash 3× with 0.05 Tween 20/assay buffer
0.1 ml/well peroxidase substrate
stop reaction with 0.1 ml/well 2 M H$_2$SO$_4$
measure the absorption at 450 nm Integrin $\alpha_v\beta_3$: human placenta is solubilized with Nonidet, and integrin $\alpha_v\beta_3$ is affinity-purified on a GRGDSPK matrix (elution with EDTA). Contamination by integrin $\alpha_{IIb}\beta_3$ and human serum albumin, as well as the detergent and EDTA, are removed by anion exchange chromatography.

Assay buffer: 50 mM tris pH 7.5; 100 mM NaCl; 1 mM CaCl$_2$; 1 mM MgCl$_2$; 10 µM MnCl$_2$ Peroxidase substrate: mix 0.1 ml of TMB solution (42 mM TMB in DMSO) and 10 ml of substrate buffer (0.1 M Na acetate pH 4.9) and then add 14.7 µl of 3% H$_2$O$_2$.

Various dilutions of the test substances are employed in the assay, and the IC$_{50}$ values are determined (concentration of the ligand at which 50% of the ligand is displaced). Compounds I-40, I-45, I-54, I-61, I-63, I-64, I-72 and I-49 from the examples showed the best result in this.

Example 2

Integrin $\alpha_{IIb}\beta_3$ assay

The assay is based on competition between the natural integrin $\alpha_{IIb}\beta_3$ ligand fibrinogen and the test substance for binding to integrin $\alpha_{IIb}\beta_3$.

Procedure:
coat microtiter plates with 10 µg/ml fibrinogen (Calbiochem 341578) in 0.05 M NaHCO$_3$ pH 9.2; 0.1 ml/well;
saturate with 1% BSA/PBS; 0.3 ml/well; 30 min/RT
wash 3× with 0.05% Tween 20/PBS
Test substance in 0.1% BSA/PBS; 50 µl/well+200 µg/ml integrin $\alpha_{IIb}\beta_3$ (Kordia) in 0.1% BSA/PBS; 50 µl/well; 2 to 4 h/RT
wash 3× as above
biotinylated anti-integrin $\alpha_{IIb}\beta_3$ antibody (Dianova CBL 130 B); 1:1000 in 0.1% BSA/PBS; 0.1 ml/well; 2 to 4 h/RT
wash 3× as above
streptavidin-peroxidase complex (B.M. 1089153) 1:10, 000 in 0.1% BSA/PBS; 0.1 ml/well; 30 min/RT
wash 3× as above
0.1 ml/well peroxidase substrate
stop reaction with 0.1 ml/well 2 M H$_2$SO$_4$
measure the absorption at 450 nm
Peroxidase substrate: mix 0.1 ml of TMB solution (42 mM TMB in DMSO) and 10 ml of substrate buffer (0.1 M Na acetate pH 4.9), then add 14.7 µl of 3% H$_2$O$_2$ Various dilutions of the test substances are employed in the assay, and the IC$_{50}$ values are determined (concentration of the antagonist at which 50% of the ligand is displaced). The selectivity of the substances can be determined by comparing the IC$_{50}$ values in the integrin $\alpha_{IIb}\beta_3$ and integrin $\alpha_v\beta_3$ assays.

Example 3

CAM assay

The CAM (chorioallantoic membrane) assay is a generally accepted model for assessing the in vitro activity of integrin $\alpha_v\beta_3$ antagonists. It is based on the inhibition of angiogenesis and neovascularization of tumor tissue (Am. J. Pathol. 1975, 79, 597–618; Cancer Res. 1980, 40, 2300–2309; Nature 1987, 329, 630). The procedure is analogous to the prior art. The growth of the chicken embryonic blood vessels and of the transplanted tumor tissue can readily be followed and assessed.

Example 4

Rabbit eye assay

The inhibition of angiogenesis and neovascularization in the presence of integrin $\alpha_v\beta_3$ antagonists can be followed and assessed in this in vivo model in analogy to Example 3. The model is generally accepted and is based on the growth of blood vessels starting from the edge into the cornea of the rabbit eye (Proc. Natl. Acad. Sci. USA. 1994, 91, 4082–4085; Science 1976, 193, 70–72). The procedure is analogous to the prior art.

We claim:

1. A compound of the formula I $$B—G—L \qquad \qquad I$$

where B, G and L have the following meanings:
L is a structural element of the formula I$_L$ $$—U—T \qquad \qquad I_L$$

where
T is a COOH group or COR$^1$
where R$^1$ is a branched or unbranched C$_1$–C$_8$ alkoxy group, and
—U— is —(CR$_L^1$R$_L^2$)$_a$(CR$_L^3$R$_L^4$)$_c$(CR$_L^5$R$_L^6$)$_e$(CR$_L^7$R$_L^8$)$_g$—
where
a, c, e, and g are, independently of one another, 0, 1, 2 or 3, and
R$_L^1$, R$_L^2$, R$_L^3$, R$_L^4$, R$_L^5$, R$_L^6$, R$_L^7$, and R$_L^8$ are, independently of one another, hydrogen, halogen, a hydroxyl group, a branched or unbranched, optionally substituted C$_1$–C$_6$-alkyl, C$_2$–C$_5$-alkenyl, C$_2$–C$_6$-alkynyl or C$_1$–C$_6$-alkylene-C$_3$–C$_7$-cycloalkyl radical, a radical —(CH$_2$)$_w$-(Y$_L$)$_y$-R$_L^9$, an optionally substituted C$_3$–C$_7$-cycloalkyl, aryl, arylalkyl, hetaryl or hetarylalkyl radical or, in each case independently of one another, two radicals are R$_L^1$ and R$_L^2$ or R$_L^3$ and R$_L^4$ or R$_L^5$ and R$_L^6$ or R$_L^7$ and R$_L^8$ together are a 3- to 7-membered, optionally substituted, saturated or unsaturated carbocyclic or heterocyclic system which may contain up to three heteroatoms from the group of O, N or S, w is 0, 1, 2, 3 or 4, y is 0 or 1

$Y_L$ is —CO—, —CO—N($R_y^1$)—, —N($R_y^1$)—CO—, —N($R_y^1$)—CO—N($R_y^{1*}$)—, —N($R_y^1$)—CO—O—, —O—, —S—, —SO$_2$—, —SO$_2$—N($R_y^1$)—, —SO$_2$—O—, —CO—O—, —O—CO—, —O—CO—N($R_y^1$)—, —N($R_y^1$)— or —N($R_y^1$)—SO$_2$—, $R_y^1$ and $R_y^{1*}$ are, independently of one another, hydrogen, a branched or unbranched, optionally substituted $C_1$–$C_6$-alkyl, $C_1$–$C_6$-alkoxyalkyl, $C_2$–$C_6$-alkenyl, $C_3$–$C_{12}$-alkynyl, CO—$C_1$–$C_6$-alkyl, CO—O—$C_1$–$C_6$-alkyl or SO$_2$—$C_1$–$C_6$-alkyl radical or an optionally substituted $C_3$–$C_7$-cycloalkyl, aryl, arylalkyl, CO—O-alkylene-aryl, CO-alkylene-aryl, CO-aryl, SO$_2$-aryl, hetaryl, CO-hetaryl or SO$_2$-alkylene-aryl radical, $R_L^9$ is hydrogen, or a hydroxyl group, CN, halogen, a branched or unbranched, optionally substituted $C_1$–$C_6$-alkyl radical, an optionally substituted $C_3$–$C_7$-cycloalkyl, aryl, heteroaryl or arylalkyl radical, an optionally $C_1$–$C_4$-alkyl- or aryl-substituted $C_2$–$C_6$-alkynyl or $C_2$–$C_6$-alkenyl radical, an optionally substituted $C_6$–$C_{12}$-bicycloalkyl, $C_1$–$C_6$-alkylene-$C_6$–$C_{12}$-bicycloalkyl, $C_7$–$C_{20}$-tricycloalkyl or $C_1$–$C_6$-alkylene-$C_7$–$C_{20}$-tricycloalkyl radical, or a 3- to 8-membered, saturated or unsaturated heterocyclic system which is substituted by up to three identical or different radicals and which may contain up to three different or identical heteroatoms O, N or S, it being possible for two radicals together to be a fused, saturated, unsaturated or aromatic carbocyclic or heteocyclic system which may contain up to three different or identical heteroatoms O, N or S, and it being possible for the cyclic system to be optionally substituted, or for another, optionally substituted, saturated, unsaturated or aromatic cyclic system to be fused to this cyclic system, or the radical $R_L^9$ forms together with $R_y^1$ or $R_y^{1*}$ a saturated or unsaturated $C_3$–$C_7$-heterocycle which may optionally contain up to two further heteroatoms selected from the group of O, S or N, G is a structural element of the formula $I_G$

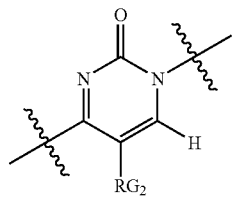

$I_G$ where the structural element L is attached to the nitrogen atom G, and $R_G^2$ is hydrogen, CN, NO$_2$, halogen, a branched or unbranched, optionally substituted $C_1$–$C_6$-alkyl, $C_2$–$C_6$-alkenyl or $C_2$–$C_6$-alkynyl radical, a branched or unbranched, optionally substituted $C_1$–$C_4$-alkylene-O$R_G^4$, $C_1$–$C_4$-alkylene-CO—O$R_G^4$, $C^1$–$C_4$-alklene-N$R_G^5 R_G^6$ or $C_1$–$C_4$-alkylene-S$R_G^4$ radical, an optionally substituted $C_3$–$C_7$-cycloalkyl, $C_1$–$C_4$-alkylene-$C_3$–$C_7$-cycloalkyl, $C_1$–$C_4$-alkylene-$C_3$–$C_7$-heterocycloalkyl or $C_1$–$C_4$-alkylene-$C_3$–$C_7$-heterocycloalkenyl radical, optionally substituted aryl, arylalkyl, hetaryl or hetarylalkyl radical, or an —S—$R_G^4$, —O—$R_G^4$, or —SO—$R_G^4$ radical, $R_G^4$ is hydrogen, a branched or unbranched, optionally substituted $C_1$–$C_8$-alkyl, $C_2$–$C_6$-alkenyl, $C_2$–$C_6$-alkynyl, bisalkylaminoalkylene or acylaminoalkylene radical or an optionally substituted aryl, heterocycloalkyl, heterocycloalkenyl, hetaryl, $C_3$–$C_7$-cycloalkyl, $C_1$–$C_4$-alkylene-$C_3$–$C_7$-cycloalkyl, arylalkyl, $C_1$–$C_4$-alkylene-$C_3$–$C_7$-cycloalkyl, arylalkyl, $C_1$–$C_4$-alkylene-heterocycloalkyl, $C_1$–$C_4$-alkylene-heterocycloalkenyl or hetarylalkyl radical, $R_G^5$ and $R_G^6$ are, independently of one another, hydrogen, a branched or unbranched optionally substituted $C_1$–$C_8$-alkyl, $C_2$–$C_5$-alkenyl, $C_2$–$C_6$-alkynyl, $C_1$–$C_5$-alkylene-$C_1$–$C_4$-alkoxy, mono- and bisalkylaminoalkylene or acylaminoalkylene radical or an optionally substituted aryl, heterocycloalkyl, heterocycloalkenyl, hetaryl, $C_3$–$C_7$-cycloalkyl, $C_1$–$C_4$-alkylene-$C_3$–$C_7$-cycloalkyl, arylalkyl, $C_1$–$C_4$-alkylene-heterocycloalkyl, $C_1$–$C_4$-alkylene-heterocycloalkenyl or hetarylalkyl radical, or an —SO$_2$—$R_G^4$, —CO—O$R_G^4$, —CO—N$R_G^4 R_G^{4*}$ or —CO—$R_G^4$ radical, and $R_G^{4*}$ is an $R_G^4$ radical independent of $R_G^4$, B is a structural element of the formula $I_B$

A—E— $I_B$ where A and E have the following meanings:

A is a structural element selected from the group of structural elements of the formula $I_A^1$ to $I_A^{19}$,

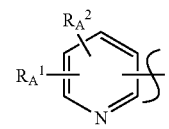

$I_A^1$

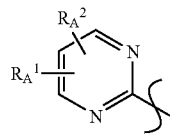

$I_A^2$

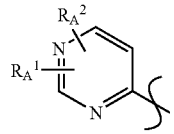

$I_A^3$

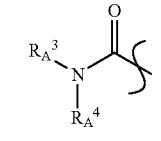

$I_A^4$

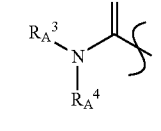

$I_A^5$

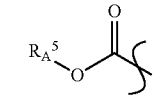

$I_A^6$

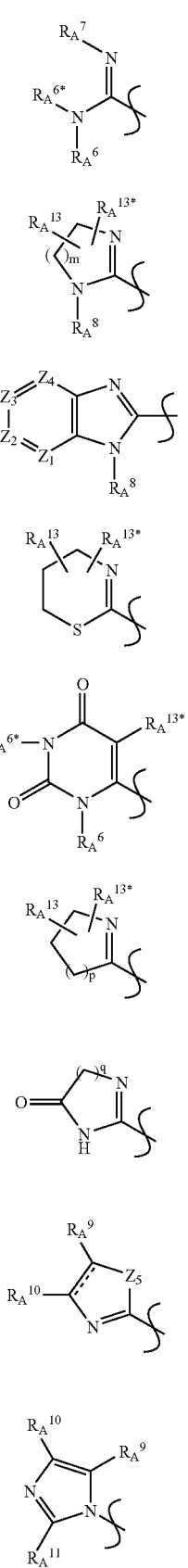

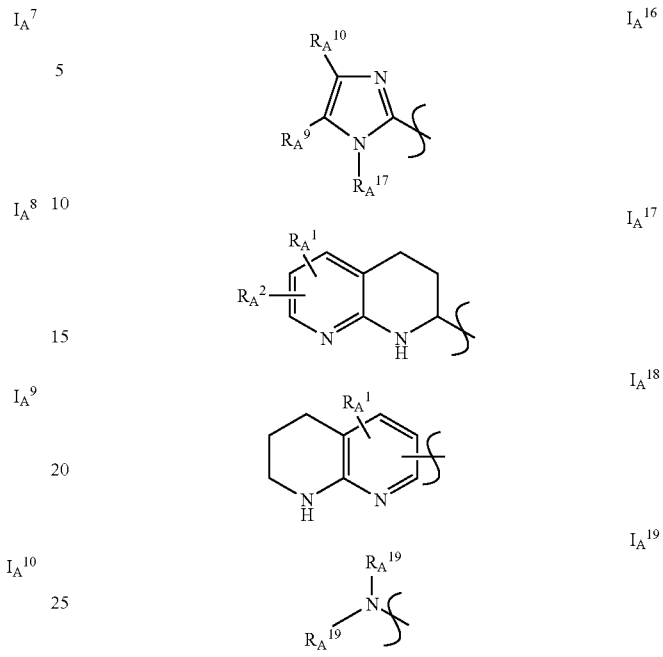

where
m, p, q are, independently, of one another, 1, 2 or 3,
$R_A^1$ and $R_A^2$ are, independently of one another, hydrogen, CN, halogen, a branched or unbranched, optionally substituted $C_1$–$C_6$-alkyl or CO—$C_1$–$C_6$-alkyl radical or an optionally substituted aryl, arylalkyl, hetaryl, hetarylalkyl or $C_3$–$C_7$-cycloalkyl radical or a CO—O—$R_A^{14}$, O—$R_A^{14}$, S—$R_A^{14}$, $NR_A^{15}R_A^{16}$, CO—$NR_A^{15}R_A^{16}$ or $SO_2NR_A^{15}R_A^{16}$ radical or the two radicals $R_A^1$ and $R_A^2$ together are a fused, optionally substituted, 5- or 6-membered, unsaturated or aromatic carbocyclic or heterocyclic system which may contain up to three heteroatoms selected from the group of O, N or S,
$R_A^{13}$ and $R_A^{13*}$ are, independently of one another, hydrogen, CN, halogen, a branched or unbranched, optionally substituted $C_1$–$C_6$-alkyl radical or an optionally substituted aryl, arylalkyl, hetaryl, $C_3$–$C_7$-cycloalkyl radical or a CO—O—$R_A^{14}$, O—$R_A^{14}$, S—$R_A^{14}$, $NR_A^{15}R_A^{16}$, $SO_2$—$NR_A^{15}R_A^{16}$ or CO—$NR_A^{15}R_A^{16}$ radical, where
$R_A^{14}$ is hydrogen, a branched or unbranched, optionally substituted $C_1$–$C_6$-alkyl, alkylene-$C_1$–$C_4$-alkoxy, $C_2$–$C_6$-alkenyl, $C_2$–$C_6$-alkynyl or $C_1$–$C_6$-alkylene-$C_3$–$C_7$-cycloalkyl radical or an optionally substituted $C_3$–$C_7$-cycloalkyl, aryl, arylalkyl, hetaryl or hetarylalkyl radical,
$R_A^{15}$ and $R_A^{16}$ are, independently of one another, hydrogen, a branched or unbranched, optionally substituted $C_1$–$C_6$-alkyl, CO—$C_1$–$C_6$-alkyl, $SO_2$—$C_1$–$C_6$-alkyl, COO—$C_1$–$C_6$-alkyl, CO—NH—$C_1$–$C_6$-alkyl, arylalkyl, COO-alkylene-aryl, $SO_2$-alkylene-aryl, CO—NH-alkylene-aryl, CO—NH-alkylene-hetaryl or hetarylalkyl radical or an optionally substituted $C_3$–$C_7$-cycloalkyl, aryl, CO-aryl, CO—NH-aryl, $SO_2$-aryl, hetaryl, CO—NH-hetaryl, or CO-hetaryl radical,
$R_A^3$, $R_A^4$ are, indpendently of one another, hydrogen, —$(CH_2)_n$—$(X_A)_j$—$R_A^{12}$, or the two radicals together are a 3- to 8-membered, saturated, unsaturated or aroamtic N heterocyclic system which may additionally contain two other, identical or different heteroatoms O, N or S, it being possible for the cyclic system optionally to be substituted, or for another, optionally substituted, saturated, unsaturated or aromatic cyclic system to be fused to this cyclic system, where n is 0, 1, 2 or 3, j is 0 or 1, $X_A$ is —CO—, —CO—N($R_x^1$)—, —N($R_x^1$)—CO—, —N($R_x^1$)—CO—N($R_x^{1*}$)—, —N($R_x^1$)—CO—, —O—, —S—, —SO$_2$—, —SO$_2$—N($R_x^1$)—, —SO$_2$—O—, —CO—O—, —O—CO—, —O—CO—N($R_x^1$)—, —N($R_x^1$)— or —N($R_x^1$)—SO$_2$—, $R_A^{12}$ is hydrogen, a branched or unbranched, optionally substituted $C_1$–$C_6$-alkyl radical, an optionally substituted $C_1$–$C_4$-alkyl- or aryl-substituted $C_2$–$C_6$-alkynyl or $C_2$–$C_6$-alkenyl radical or a 3- to 6-membered, saturated or unsaturated heterocyclic system which is substituted by up to three identical or different radicals and which may contain up to three different or identical heteroatoms O, N or S, or $C_3$–$C_7$-cycloalkyl, aryl or heteroaryl radical, it being possible for two radicals together to be a fused, saturated, unsaturated or aromatic carbocyclic or heterocyclic system which may contain up to three different or identical heteroatoms O, N, or S, and it being possible for the cyclic system optionally to be substituted or for another, optionally substituted, saturated, unsaturated or aromatic cyclic system to be fused to this cyclic system, or the $R_A^{12}$ radical forms together with $R_x^1$ or $R_x^{1*}$ a saturated or unsaturated $C_3$–$C_7$-heterocycle which may optionally contain up to two other heteroatoms selected from the group of O, S or N, $R_x^1$, $R_x^{1*}$ are, independently of one another, hydrogen, a branched or unbranched, optionally substituted $C_1$–$C_6$-alkyl, $C_1$–$C_6$-alkoxyalkyl, $C_2$–$C_6$-alkenyl, $C_2$–$C_{12}$-alkynyl, CO—$C_1$–$C_6$-alkyl, CO—O—$C_1$–$C_6$-alkyl or SO$_2$—$C_1$–$C_6$-alkyl radical or an optionally substituted $C_3$–$C_7$-cycloalkyl, aryl, arylalkyl, CO—O-alkylene-aryl, CO-alkylene-aryl, CO-aryl, SO$_2$-aryl, hetaryl, CO-hetaryl or SO$_2$-alkylene-aryl radical, $R_A^5$ is a branched or unbranched, optionally substituted $C_1$–$C_6$-alkyl, arylalkyl, $C_3$–$C_7$-cycloalkyl or $C_1$–$C_4$-alkylene-$C_3$–$C_7$-cycloalkyl radical or an optionally substituted aryl, hetaryl, heterocycloalkyl or heterocycloalkenyl radical, $R_A^6$ and $R_A^{6*}$ are hydrogen, a branched or unbranched, optionally substituted $C_1$–$C_4$-alkyl, —CO—O—$C_1$–$C_4$-alkyl, arylalkyl, —CO—O-alkylene-aryl, —CO—O-allyl, —CO—$C_1$–$C_4$-alkyl, —CO-alkylene-aryl, $C_3$–$C_7$-cycloalkyl or —CO-allyl radical or the two radicals $R_A^6$ and $R_A^{6*}$ in the structural element $I_A^7$ together are an optionally substituted, saturated, unsaturated or aromatic heterocyclic system which, in addition to the ring nitrogen, may contain up to two other different or identical heteroatoms O, N or S, $R_A^7$ is hydrogen, —OH, —CN, —CONH$_2$, a branched or unbranched, optionally substituted $C_1$–$C_4$-alkyl, $C_1$–$C_4$-akoxy, $C_3$–$C_7$-cycloalkyl or —O—CO—$C_1$–$C_4$-alkyl radical or an optionally substituted arylalkyl, —O-alkylene-aryl, —O—CO-aryl, —O—CO-alkylene-aryl or —O—CO-allyl radical, or the two radicals $R_A^6$ and $R_A^7$ together are an optionally substituted, unsaturated or aromatic heterocyclic system which, in addition to the ring nitrogen, may contain up to two other different or identical heteroatoms O, N or S, $R_A^8$ is hydrogen, a branched or unbranched, optionally substituted $C_1$–$C_4$-alkyl, CO—$C_1$–$C_4$-alkyl, SO$_2$—$C_1$–$C_4$-alkyl or CO—O—$C_1$–$C_4$-alkyl radical or an optionally substituted aryl, CO-aryl, SO$_2$-aryl, CO—O-aryl, CO-alkylene-aryl, SO$_2$-alkylene-aryl, CO—O-alkylene-aryl or alkylene-aryl radical, $R_A^9$ and $R_A^{10}$ are, independently of one another, hydrogen, —CN, halogen, a branched or unbranched, optionally substituted $C_1$–$C_6$-alkyl radical or an optionally substituted aryl, arylalkyl, hetaryl, $C_3$–$C_7$-cycloalkyl radical or a CO—O—$R_A^{14}$, O—$R_A^{14}$, S—$R_A^{14}$, NR$_A^{15}$R$_A^{16}$, SO$_2$—NR$_A^{15}$R$_A^{16}$ or CO—NR$_A^{15}$R$_A^{16}$ radical, or the two radicals $R_A^9$ and $R_A^{10}$ in the structural element $I_A^{14}$ together are a 5- to 7-membered saturated, unsaturated or aromatic carbocyclic or heterocyclic system which may contain up to three different or identical heteroatoms O, N, S and is optionally substituted by up to three identical or different radicals, $R_A^{11}$ is hydrogen, —CN, halogen, a branched or unbranched, optionally substituted $C_1$–$C_6$-alkyl radical or an optionally substituted aryl, arylalkyl, hetaryl, $C_3$–$C_7$-cycloalkyl radical or a CO—O—$R_A^{14}$, O—$R_A^{14}$, S—$R_A^{14}$, NR$_A^{15}$R$_A^{16}$, SO$_2$—NR$_A^{15}$R$_A^{16}$ or CO—NR$^{415}$R$_A^{16}$ radical, $R_A^{17}$ is hydrogen or the two radicals $R_A^9$ and $R_A^{17}$ in the structural element $I_A^{16}$ together are a 5- to 7-membered saturated, unsaturated or aromatic heterocycle which, in addition to the ring nitrogen, may contain up to three different or identical heteroatoms O, N, S and is optionally substituted by up to three identical or different radicals, $R_A^{18}$ and $R_A^{19}$ are, independently of one another, hydrogen, a branched or unbranched, optionally substituted $C_1$–$C_8$-alkyl, $C_2$–$C_6$-alkenyl, $C_2$–$C_6$-alkynyl-, $C_1$–$C_6$-alkylene-$C_1$–$C_4$-alkoxy, mono- and bisalkylaminoalkylene or acylaminoalkylene radical or an optionally substituted aryl, heterocycloalkyl, heterocycloalkenyl, hetaryl, $C_3$–$C_7$-cycloalkyl, $C_1$–$C_4$-alkylene-$C_3$–$C_7$-cycloalkyl, arylalkyl, $C_1$–$C_4$-alkylene-heterocycloalkyl, $C_1$–$C_4$-alkylene-heterocycloalkenyl or hetarylalkyl radical, or an —SO$_2$—R$_G^4$, —CO—OR$_G^4$, —CO—NR$_G^4$R$_G^{4*}$ or —CO—R$_G^4$ radical, $Z^1$, $Z^2$, $Z^3$ and $Z^4$ are, independently of one another, nitrogen, C—H, C-halogen or a branched or unbranched, optionally substituted C—$C_1$–C4-alkyl or C—$C_1$—$C_4$-alkoxy radical, $Z^5$ is NR$_A^8$, oxygen or sulfur, and E is a structural element of the formula $I_E$ $$—(NR_E^1)_i—E^1—(U_E)_h— \qquad I_E$$

where $U_E$ is oxygen, sulfur or NR$_E^2$ h is 0 or 1, i is 0 or 1, $R_E^1$, $R_E^2$ are, independently of one another, hydrogen, a branched or unbranched, optionally substituted $C_1$–$C_6$-alkyl, $C_1$–$C_6$-alkoxyalkyl, $C_2$–$C_6$-alkenyl, $C_2$–$C_{12}$-alkynyl, CO—$C_1$–$C_6$-alkyl, CO—O—$C_1$–$C_6$-alkyl, CO—NH—$C_1$–$C_6$-alkoxyalkyl, CO—NH—$C_1$–$C_6$-alkyl or SO$_2$—$C_1$–$C_6$-alkyl radical or an optionally substituted hetaryl, arylalkyl, $C_3$–$C_7$-cycloalkyl, CO—O-alkylene-aryl, CO—NH-alkylene-aryl, CO-alkylene-aryl, CO-aryl, CO—NH-aryl, $SO_2$-aryl, CO-hetaryl, $SO_2$-alkylene-aryl, $SO_2$-hetaryl or $SO_2$-alkylene-hetaryl radical, $E^1$ is a structural element of the formula $I_E^1$

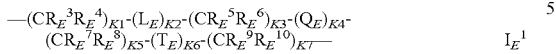

$\qquad I_E^1$ where k2, k4, k6 are 0 or 1 k1, k3, k5, k7 are 0, 1 or 2, $R_E^3$, $R_E^4$, $R_E^5$, $R_E^6$, $R_E^7$, $R_E^8$, $R_E^9$, $R_E^{10}$ are, independently of one another, hydrogen, halogen, a hydroxyl group, a branched or unbranched, optionally substituted $C_1$–$C_8$-alkyl, $C_2$–$C_6$-alkenyl, $C_2$–$C_6$-alkynyl or alkylene-cycloalkyl radical, a —$(CH_2)_x$-$(Y_E)_z R_E^{11}$ radical, an optionally substituted $C_3$–$C_7$-cycloalkyl, aryl, arylalkyl, hetaryl or hetarylalkyl radical or independently of one another, in each case two radicals $R_E^3$ and $R_E^4$ or $R_E^5$ and $R_E^6$ or $R_E^7$ and $R_E^8$ or $R_E^9$, and $R_E^{10}$ together are a 3- to 7-membered, optionally substituted, saturated or unsaturated carbo- or heterocyclic system which may contain up to three heteroatoms from the group of O, N or S, x is 0, 1, 3, 3 or 4, 5 z is 0 or 1 y is —CO—, —CO—H($R_Y^2$)—, N($R_Y^2$)—CO—, —H($R_Y^2$)—CO—N($R_Y^{2*}$)—, —NCR$_Y^2$—CO—O—, —O—, —S—, —SO—, —$SO_2$—N($R_Y^2$)—, —$SO_2$—O—, —CO—O—, —O—CO—, —O—CO—N($R_Y^2$)—, —N($R_Y^2$)— or —N($R_Y^2$)—$SO_2$—, $R_Y^2$, $R_Y^{2*}$ are, independently of one another, hydrogen, a branched or unbranched, optionally substituted $C_1$–$C_6$-alkyl, $C_2$–$C_6$-alkenyl, $C_2$–$C_6$-alkynyl, CO—$C_1$–$C_6$-alkyl, CO—O—$C_1$–$C_6$-alkyl or $SO_2$—$C_1$–$C_6$-alkyl radical or an optionally substituted hetaryl, hetarylalkyl, arylalkyl, $C_3$–$C_7$-cycloalkyl, CO—O-alkylene-aryl, CO-alkylene-aryl, CO-aryl, $SO_2$-aryl, CO-hetaryl or $SO_2$-alkylene-aryl radical $R_E^{11}$ is hydrogen, a hydroxyl group, CN, halogen, a branched or unbranched, optionally substituted $C_1$–$C_6$-alkyl radical, an optionally substituted $C_3$–$C_7$-cycloalkyl, aryl, hetaryl or arylalkyl radical, an optionally $C_1$–$C_4$-alkyl-or aryl-substituted $C_2$–$C_6$-alkynyl or $C_2$–$C_6$-alkenyl radical, an optionally substituted $C_6$–$C_{12}$-bicycloalkyl, $C_1$–$C_6$-alkylene-$C_6$–$C_{12}$-bicycloalkyl, $C_7$–$C_{20}$-tricycloalkyl or $C_1$–$C_6$-alkylene-$C_7$–$C_{20}$-tricycloalkyl radical, or a 3- to 8-membered, saturated or unsaturated heterocyclic system which is substituted by up to three identical or different radicals and which may contain up to three different or identical or different radicals and which may contain up to three different or identical heteroatoms O, N, S, it being possible for two radicals together to be a fused, or N saturated, unsaturated or aromatic carbocyclic or heterocyclic system which may contain up to three different or identical heteroatoms O, N, S, and it being possible for the cyclic system optionally to be substituted or for another, optionally substituted, saturated, unsaturated or aromatic cyclic system to be fused to this cyclic system, or the $R_E^{11}$ radical forms together with $R_Y^2$ and $R_Y^{2*}$ a saturated or unsaturated $C_3$–$C_7$-heterocyclic system which may optionally contain up to two other heteroatoms selected from the group of O, S or N $L_E$, $T_E$ Are, independently of one another, CO, CO—$NR_E^{12}$, $HR_E^{12}$—CO, sulfur, SO, $SO_2$, $SO_2$—$NR_E^{12}$, $NR_E^{12}$—$SO_2$, CS, CS—$NR_E^{12}$, $NR_E^{12}$CS, CS—O, O—CS, CO—O, O—CO, oxygen, ethynylene, $CR_E^{13}$—O—$CR_E^{14}$, C(=$CR_E^{13}R_E^{14}$)—$CR_E^{13}CR_E^{14}$, —$CR_E^{13}(OR_E^{15})$—$CHR_E^{14}$—, —$CHR_E^{13}$—$R_E^{14}$—($OR_E^{15}$)—, $R_E^{12}$ is hydrogen, a branched or unbranched, optionally substituted $C^1$–$C^6$-alkyl, $C^2$–$C^6$-alkenyl, $C^2$–$C^6$-alkynyl, an optionally substituted $C^3$–$C^7$-cycloalkyl, hetaryl, arylalkyl or hetarylalkyl radical or a CO—$R_E^{16}$, COO$R_E^{16}$ or $SO_2$—$R_E^{16}$ radical, $R_E^{13}$, $R_E^{14}$ are, independently of one another, hydrogen, a hydroxyl group, a branched or unbranched, optionally substituted $C_1$–$C_6$-alkyl, $C_1$–$C_4$-alkoxy, $C_2$–$C_6$-alkenyl, $C_2$–$C_6$-alkynyl or alkylene-cycloalkyl radical or an optionally substituted $C_3$–$C_7$-cycloalkyl, aryl, arylalkyl, hetaryl or hetarylalkyl radical, $R_E^{15}$ is hydrogen, a branched or unbranched, optionally substituted $C_1$–$C_6$-alkyl, $C_2$–$C_6$-alkenyl, $C_2$–$C_6$-alkynyl or alkylene-cycloalkyl radical or an optionally substituted $C_3$–$C_7$-cycloalkyl, aryl, arylalkyl, hetaryl or hetarylalkyl radical, $R_E^{16}$ is hydrogen, a hydroxyl group, a branched or unbranched, optionally substituted $C_1$–$C_6$-alkyl, $C_2$–$C_6$-alkenyl, $C_2$–$C_6$-alkynyl or $C_1$–$C_5$-alkylene-$C_1$–$C_4$-alkoxy radical, or an optionally substituted aryl, heterocycloalkyl, heterocycloalkenyl, hetaryl, $C_3$–$C_7$-cycloalkyl-, $C_1$–$C_4$-alkylene-$C_3$–$C_7$-cycloalkyl, arylalkyl, $C_1$–$C_4$-alkylene-$C_3$–$C_7$-heterocycloalkenyl, $C_1$–$C_4$-alkylene-$C_3$–$C_7$-heterocycloalkenyl or hetarylalkyl radical and $Q_E$ is an optionally substituted 4- to 11-membered mono- or polycyclic aliphatic or aromatic hydrocarbon which may contain up to 6 double bonds and up to 6 identical or different heteroatoms selected from the group N, O or S, it being possible for the ring carbons or ring nitrogens optionally to be substituted, and wherein the optional substituents are selected from the group consisting of $NO_2$, $NH_2$, OH, CN, COOH, —$OCH_2$—COOH, halogen, a branched or unbranched $C_1$–$C_4$ alkyl radical, a branched or unbranched —CO—O—$C_1$–$C_4$-alkyl, $C_3$–$C_7$-cyccloalkyl, $C_1$–$C_4$-alkoxy, $C_1$–$C_4$-thioalkyl, —NH—CO—O—$C_1$–$C_4$-alkyl, —O—$CH_2$—COOO—$C_1$–$C_4$-alkyl, —NH—CO—$C_1$–$C_4$-alkyl, —CO—NH—$C_1$–$C_4$-alkyl, —NH—$SO_2$—$C_1$–$C_4$-alkyl, —$SO_2$—NH—$C_1$–$C_4$-alkyl, —N($C_1$–$C_4$-alkyl)$_2$, —NH—$C_1$–$C_4$-alkyl, or —$SO_2$—$C_1$–$C_4$-alkyl, —NH—CO—O-aryl, —NH—CO—O-alkylene-aryl, —NH—$SO_2$-aryl, —$SO_2$—NH-aryl, —CO—NH-benzyl, —NH—$SO_2$-bezyl or —$SO_2$—NH-benzyl, —$SO_2$—$NR^4R^5$, or —CO—$NR^4R^5$, it being possible for $R^4$ and $R^5$ radicals independently of one another to have the meaning as $R_L^{14}$, or the two of $R^4$ and $R^5$ radicals together being a 3- to 6-membered, saturated, unsaturated or aromatic heterocycle which, in addition to the ring nitrogen, may contain up to three other different or identical heteroatoms, O, N, S and optionally two radicals substituted or this heterocycle together are a fused, saturated, unsaturated or aromatic carbocyclic or heterocyclic system which may contain up to three different or identical heteroatoms, O, N, S, and it being possible for another cyclic system to be fused to this cyclic system;

or a physiologically tolerated salt, enantiomerically pure, diastereomerically pure or tautomeric form thereof.

2. A pharmaceutical preparation comprising at least one compound as claimed in claim 1 in addition to conventional pharmaceutical excipients.

* * * * *